US012503468B2

United States Patent
(12) United States Patent
Lou et al.

(10) Patent No.: US 12,503,468 B2
(45) Date of Patent: Dec. 23, 2025

(54) HETEROCYCLIC COMPOUND, INTERMEDIATE, PREPARATION METHOD THEREFOR AND APPLICATION THEREOF

(71) Applicant: WUHAN LL SCIENCE AND TECHNOLOGY DEVELOPMENT CO., LTD., Hubei (CN)

(72) Inventors: Jun Lou, Hubei (CN); Yongkai Chen, Hubei (CN); Junhua Liu, Hubei (CN); Yihan Zhang, Hubei (CN); Xiaodan Guo, Hubei (CN); Li Liu, Hubei (CN); Lina Qian, Hubei (CN); Chaodong Wang, Hubei (CN)

(73) Assignee: WUHAN LL SCIENCE AND TECHNOLOGY DEVELOPMENT CO., LTD., Hubei (CN)

( * ) Notice: Subject to any disclaimer, the term of this patent is extended or adjusted under 35 U.S.C. 154(b) by 1215 days.

(21) Appl. No.: 17/417,304

(22) PCT Filed: Dec. 27, 2019

(86) PCT No.: PCT/CN2019/129382
§ 371 (c)(1),
(2) Date: Jun. 22, 2021

(87) PCT Pub. No.: WO2020/135771
PCT Pub. Date: Jul. 2, 2020

(65) Prior Publication Data

US 2023/0068538 A1 Mar. 2, 2023
US 2024/0034729 A9 Feb. 1, 2024

(30) Foreign Application Priority Data

Dec. 29, 2018 (CN) ......................... 201811642319.9
May 24, 2019 (CN) ......................... 201910440214.3
Oct. 24, 2019 (CN) ......................... 201911016158.7

(51) Int. Cl.

| | |
|---|---|
| ***C07D 471/04*** | (2006.01) |
| ***A61P 11/14*** | (2006.01) |
| ***C07D 209/18*** | (2006.01) |
| ***C07D 413/06*** | (2006.01) |
| ***C07D 487/04*** | (2006.01) |
| ***C07D 491/048*** | (2006.01) |
| ***C07F 5/04*** | (2006.01) |

(52) U.S. Cl.
CPC ............ *C07D 471/04* (2013.01); *A61P 11/14* (2018.01); *C07D 209/18* (2013.01); *C07D 413/06* (2013.01); *C07D 487/04* (2013.01); *C07D 491/048* (2013.01); *C07F 5/04* (2013.01)

(58) Field of Classification Search
CPC .................................................... C07D 471/04
See application file for complete search history.

(56) References Cited

U.S. PATENT DOCUMENTS

| | | | |
|---|---|---|---|
| 9,598,409 | B2 | 3/2017 | Buon et al. |
| 9,814,725 | B2 | 11/2017 | Buon et al. |
| 9,937,185 | B2 | 4/2018 | Buon et al. |
| 10,111,883 | B1 | 10/2018 | Garceau et al. |
| 2013/0203754 | A1 | 8/2013 | Yang et al. |
| 2015/0045551 | A1 | 2/2015 | Yoshinaga et al. |
| 2015/0361078 | A1 | 12/2015 | Buon et al. |
| 2016/0120863 | A1 | 5/2016 | Cowley et al. |
| 2016/0376568 | A1 | 12/2016 | Duellman et al. |
| 2017/0143730 | A1 | 5/2017 | Buon et al. |
| 2017/0326141 | A1 | 11/2017 | Trower |
| 2018/0015099 | A1 | 1/2018 | Buon et al. |
| 2019/0030040 | A1 | 1/2019 | Buon et al. |
| 2019/0231789 | A1 | 8/2019 | Buon et al. |
| 2020/0063110 | A1 | 2/2020 | Duellman et al. |
| 2020/0138826 | A1 | 5/2020 | Buon et al. |

(Continued)

FOREIGN PATENT DOCUMENTS

| | | | |
|---|---|---|---|
| CN | 102803245 | A | 11/2012 |
| CN | 105237458 | A | 1/2016 |

(Continued)

OTHER PUBLICATIONS

Registry No. 727975-59-9; retrieved from CHEMCATS; entered in STN on Aug. 18, 2004.*

(Continued)

*Primary Examiner* — Shawquia Jackson
(74) *Attorney, Agent, or Firm* — NKL Law; Allen Xue

(57) ABSTRACT

Disclosed by the invention is a heterocyclic compound, an intermediate, and a preparation method therefor and an application thereof. Provided by the invention are a heterocyclic compound as shown in formula I, and a stereoisomer, a geometric isomer, a tautomer, a nitrogen oxide, a hydrate, a solvate, a metabolite, an ester, a pharmaceutically acceptable salt or a prodrug thereof. The heterocyclic compound has a high P2X3 antagonistic activity, and has good selectivity, low toxicity, good metabolic stability and little taste influence.

I

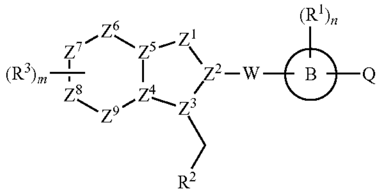

22 Claims, 4 Drawing Sheets

(56) References Cited

U.S. PATENT DOCUMENTS

| | | | |
|---|---|---|---|
| 2020/0390779 A1 | 12/2020 | Buon et al. |
| 2021/0228588 A1 | 7/2021 | Buon et al. |
| 2022/0062290 A1 | 3/2022 | Buon et al. |

FOREIGN PATENT DOCUMENTS

| | | | |
|---|---|---|---|
| CN | 105246888 A | 1/2016 |
| CN | 108904507 A | 11/2018 |
| EA | 023223 B1 | 5/2016 |
| EP | 2832722 A1 | 2/2015 |
| JP | 2013511517 A | 4/2013 |
| JP | 2015137266 A | 7/2015 |
| JP | 2016506935 A | 3/2016 |
| RU | 2656593 C2 | 6/2018 |
| WO | 0078726 A1 | 12/2000 |
| WO | 02092086 A1 | 11/2002 |
| WO | 2005086808 A2 | 9/2005 |
| WO | 2007019345 A1 | 2/2007 |
| WO | 2007034278 A2 | 3/2007 |
| WO | 2007034282 A2 | 3/2007 |
| WO | 2007047579 A2 | 4/2007 |
| WO | 2008003858 A2 | 1/2008 |
| WO | 2008029152 A2 | 3/2008 |
| WO | 2009075874 A1 | 6/2009 |
| WO | 2009089508 A1 | 7/2009 |
| WO | 2010034982 A1 | 4/2010 |
| WO | 2011137587 A1 | 11/2011 |
| WO | 2011160548 A1 | 12/2011 |
| WO | 2013040528 A1 | 3/2013 |
| WO | 2014017342 A1 | 1/2014 |
| WO | 2014117274 A1 | 8/2014 |
| WO | 2014187922 A1 | 11/2014 |
| WO | 2016054807 A1 | 4/2016 |
| WO | 2016210294 A1 | 12/2016 |
| WO | 2017097792 A1 | 6/2017 |

OTHER PUBLICATIONS

Registry No. 1176021-51-4; retrieved from CHEMCATS; entered in STN on Aug. 26, 2009.*
Registry No. 1176712-99-4; retrieved from CHEMCATS; entered in STN on Aug. 27, 2009.*
Registry No. 1176712-78-9; retrieved from CHEMCATS; entered in STN on Aug. 27, 2009.*
Registry No. 1176773-65-1; retrieved from CHEMCATS; entered in STN on Aug. 27, 2009.*
Asthma [online] retrieved from the internet on Nov. 10, 2024; URL: https://www.mayoclinic.org/diseases-conditions/asthma/symptoms-causes/syc-20369653.*
Pulmonary fibrosis can't be cured, but these tips can help mitigate the risk [online] retrieved from the internet on May 13, 2025; URL https://www.healthshots.com/preventative-care/self-care/pulmonary-fibrosis-tips-to-reduce-the-risk/.*
CAS Registry No. 1091449-15-8; Dec. 29, 2008.
CAS Registry No. 1091408-93-3; Dec. 29, 2008.
CAS Registry No. 1091373-63-5; Dec. 29, 2008.
CAS Registry No. 1091303-02-4; Dec. 29, 2008.
CAS Registry No. 1091202-31-1; Dec. 29, 2008.
CAS Registry No. 1091193-62-2; Dec. 29, 2008.
CAS Registry No. 1091185-55-5; Dec. 29, 2008.
CAS Registry No. 1091180-63-0; Dec. 29, 2008.
CAS Registry No. 1555688-50-0; Feb. 26, 2014.
CAS Registry No. 1664381-24-1; Mar. 18, 2016.
Akutsu, Eriko; "Notice of Reasons for Refusal (Japanese Patent Application No. 2021-538363)"; J-PlatPat; Jul. 26, 2022; pp. 1-6.
Akutsu, Eriko; "Notice of Reasons for Refusal (Japanese Patent Application No. 2021-538363)"; J-PlatPat; Feb. 14, 2023; pp. 1-4.
Shimkina H.G.; "RU2021114193 Office Acton 1"; Federal Intellectual Property Office, FIPS; Jul. 4, 2022; pp. 1-17.
Shimkina H. G.; "RU2021114193 Office Action 2"; Federal Intellectual Property Office, FIPS; Nov. 30, 2022; pp. 1-13.
Hariram K S; "Office Action for Application No. 202147033661"; Intellectual Property India; Aug. 13, 2021; pp. 1-7.
Sotoca Usina, E; "Annex To the European Search Report On European Patent Application No. EP19902183"; European Patent Office; Nov. 22, 2022; pp. 1-12.

* cited by examiner

HETEROCYCLIC COMPOUND, INTERMEDIATE, PREPARATION METHOD THEREFOR AND APPLICATION THEREOF

The present application claims priority to the Chinese Patent Application CN201811642319.9, filed on Dec. 29, 2018, the Chinese Patent Application CN201910440214.3, filed on May 24, 2019, and the Chinese Patent Application CN201911016158.7, filed on Oct. 24, 2019, which are incorporated herein by reference in their entirety.

TECHNICAL FIELD

The present invention relates to a heterocyclic compound, an intermediate, and a preparation method and use thereof.

BACKGROUND

ATP receptors are classified into two main families, the P2Y-purinoreceptors and P2X-purinoreceptors, according to the molecular structure, transduction mechanism and pharmacological properties. The P2X-purinoreceptors are a family of ATP-gated cation channels, and several subtypes have been cloned, including six homomeric receptors (P2X1, P2X2, P2X3, P2X4, P2X5 and P2X7) and three heteromeric receptors (P2X2/3, P2X4/6 and P2X1/5). The P2X3 receptor has been found to be expressed particularly in the primary afferent nerve fibers of "hollow viscera", such as the lower urinary tract and respiratory tract.

Cough is the main symptom of respiratory diseases, and is observed in 70-80% of patients in outpatients of the respiratory department. With increasing prevalence of COPD, IPF, etc., there's also an increasing demand for treatment of cough as it is the main manifestation of most respiratory tract diseases. Cough, as a defensive nervous reflex of the body, is beneficial to the removal of respiratory secretions and harmful factors. However, frequent and violent cough will seriously affect the work, life and social activities of patients.

Few P2X3 antagonists specifically targeting cough have been developed, and one project that advances rapidly at present is the Roche AF-219 project, which, in the newly completed phase II clinical trial, shows a relatively good efficacy for refractory cough but poses serious dysgeusia.

At present, no drug is available on the market that can treat various conditions including chronic cough via the P2X3-inhibiting route. Therefore, the development of new compounds capable of inhibiting the activity of P2X3 is of great significance for treating diseases.

SUMMARY

The present invention aims to solve the technical problem of the insufficiency of P2X3 antagonist in the prior art, and thus provides a heterocyclic compound, an intermediate, and a preparation method and use thereof. The heterocyclic compound disclosed herein has high antagonistic activity against P2X3, good selectivity, low toxicity, good metabolic stability and small influence on taste.

The present invention solves the above-mentioned problem by the following technical embodiments.

The present invention provides a heterocyclic compound of formula I, or a stereoisomer, a geometric isomer, a tautomer, a nitrogen oxide, a hydrate, a solvate, a metabolite, an ester, a pharmaceutically acceptable salt or a prodrug thereof,

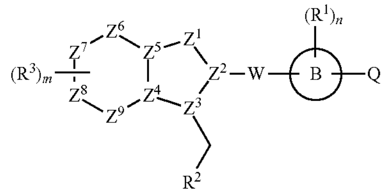

I wherein,

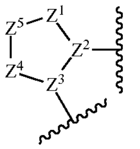

is a 5 membered heteroaryl or a 5 membered heterocycloalkenyl, wherein the 5 membered heteroaryl contains 1-2 heteroatoms selected from one or more of N, O and S; and the 5 membered heterocycloalkenyl contains 1-3 heteroatoms selected from one or more of N, O and S;

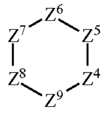

is phenyl, a 5-6 membered heterocycloalkyl, a 5-6 membered heterocycloalkenyl, or a 5-6 membered heteroaryl; wherein the 5-6 membered heterocycloalkyl contains 1-3 heteroatoms selected from one or more of N, O and S; the 5-6 membered heterocycloalkenyl contains 1-3 heteroatoms selected from one or more of N, O and S; and the 5-6 membered heteroaryl contains 1-3 heteroatoms selected from one or more of N, O and S;

$Z^1$, $Z^2$, $Z^3$, $Z^4$, $Z^5$, $Z^6$, $Z^7$, $Z^8$ and $Z^9$ independently represent a ring atom; and when

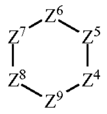

is a 5 membered heterocycloalkyl, a 5 membered heterocycloalkenyl or a 5 membered heteroaryl, $Z^6$ or $Z^9$ represents a single bond;

m is 1, 2, 3 or 4;

$R^3$ is H, halogen, —OH, a $C_1$-$C_6$ haloalkyl, —CN or a $C_1$-$C_6$ alkyl; when m is not 1, $R^3$ is independently the same or different; or when two adjacent $R^3$ are present, they, together with the ring atom to which they directly link, form a $C_3$-$C_6$ cycloalkyl, a $C_3$-$C_6$ cycloalkenyl, a $C_3$-$C_9$ heterocycloalkyl, a $C_3$-$C_9$ heterocycloalkenyl, phenyl or a 5-6 membered heteroaryl; wherein the $C_3$-$C_9$ heterocycloalkyl contains 1-3 heteroatoms selected from one or more of O, S and N; the $C_3$-$C_9$ heterocycloalkenyl contains 1-3 heteroatoms selected from one or more of O, S and N; and the 5-6 membered heteroaryl contains 1-3 heteroatoms selected from one or more of O, S and N;

W is a single bond or —C(═O)—NH—;

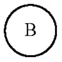

is phenyl, a 5-6 membered heteroaryl, or a $C_3$-$C_9$ heterocycloalkyl, wherein the 5-6 membered heteroaryl contains 1-3 heteroatoms selected from one or more of N, O and S, and the $C_3$-$C_9$ heterocycloalkyl contains 1-3 heteroatoms selected from one or more of O, S and N;

n is 1, 2, 3 or 4;

$R^1$ is independently H, halogen, —OH, —CN, an unsubstituted or substituted $C_1$-$C_6$ alkyl, or an unsubstituted or substituted $C_1$-$C_6$ alkyl-O—; wherein the substituted $C_1$-$C_6$ alkyl or the substituted $C_1$-$C_6$ alkyl-O— is substituted with one or more substituents independently selected from the following: halogen, —OH, —$CF_3$, —CN, —COOH, —C(═O)$NH_2$, a $C_1$-$C_6$ alkyl, a $C_1$-$C_6$ alkyl-O— or ═O (i.e., two geminal hydrogens on a carbon atom are substituted with the group O); when a plurality of substituents are present, they are the same or different; and when n is not 1, $R^1$ is independently the same or different;

Q is H, halogen, —OH, —$CF_3$, —CN, —NH—C(═O)—$R^{1-1}$, —C(═O)—$R^{1-2}$, —O—C(═O)—N($R^{13}R^{14}$), —C(═O)—N($R^{1-5}R^{1-6}$), —C(═NH)—N($R^{1-1}R^{1-3}$), —S(═O)$_2$—N($R^{1-9}R^{1-10}$), —S(═O)—N($R^{1-11}R^{1-12}$), —O—C(═O)—$R^{1-13}$, —N($R^{1-14}R^{1-15}$), —NH—S(═O)$_2$—$R^{1-16}$, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, an unsubstituted or substituted $C_6$-$C_{10}$ aryl, or an unsubstituted or substituted 5-10 membered heteroaryl; wherein the $C_3$-$C_9$ heterocycloalkyl contains 1-3 heteroatoms selected from one or more of O, S and N, the $C_3$-$C_9$ heterocycloalkenyl contains 1-3 heteroatoms selected from one or more of O, S and N, the 5-10 membered heteroaryl contains 1-3 heteroatoms selected from one or more of N, O and S; and the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_3$-$C_{10}$ cycloalkyl, the substituted $C_6$-$C_{10}$ aryl, the substituted $C_3$-$C_9$ heterocycloalkyl, the substituted $C_3$-$C_9$ heterocycloalkenyl or the substituted 5-10 membered heteroaryl is substituted with one or more substituents independently selected from the following: halogen, —OH, —$CF_3$, —CN, —COOH, —C(═O)$NH_2$, ═O (i.e., two geminal hydrogens on a carbon atom are substituted with the group O), —N($R^{1-21}R^{1-22}$), —C(═O)—N($R^{1-23}R^{1-24}$), —S(═O)$_2$—N($R^{1-25}R^{1-26}$), —C(═O)—O—$R^{1-27}$, and a $C_1$-$C_6$ alkyl, a $C_1$-$C_6$ alkyl-O— or a $C_3$-$C_9$ cycloalkyl that is unsubstituted or substituted with one or more $R^a$, wherein when a plurality of $R^a$ are present, they are the same or different, and each $R^a$ is halogen, —OH, ═O, —$CF_3$, —CN, —COOH or —C(═O)$NH_2$; and when a plurality of substituents are present, they are the same or different;

$R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each independently H, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_2$-$C_6$ alkynyl, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, an unsubstituted or substituted phenyl, or an unsubstituted or substituted 5-10 membered heteroaryl, wherein the $C_3$-$C_9$ heterocycloalkyl contains 1-3 heteroatoms selected from one or more of O, S and N, the $C_3$-$C_9$ heterocycloalkenyl contains 1-3 heteroatoms selected from one or more of O, S and N, the 5-10 membered heteroaryl contains 1-3 heteroatoms selected from one or more of N, O and S; and the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_2$-$C_6$ alkynyl, the substituted $C_3$-$C_{10}$ cycloalkyl, the substituted $C_3$-$C_9$ heterocycloalkyl, the substituted $C_3$-$C_9$ heterocycloalkenyl, the substituted phenyl or the substituted 5-10 membered heteroaryl is substituted with one or more substituents independently selected from the following: halogen, —OH, —$CF_3$, —CN, —COOH, —$COOCH_3$, —$NH_2$, ═O (i.e., two geminal hydrogens on a carbon atom are substituted with the group O), and a $C_1$-$C_6$ alkyl, a $C_1$-$C_6$ alkyl-O— or a $C_3$-$C_6$ cycloalkyl that is unsubstituted or substituted with one or more $R^d$, wherein when a plurality of $R^d$ are present, they are the same or different, and each $R^d$ is independently H, halogen, —OH, ═O, —$CF_3$, —CN, —COOH or —C(═O)$NH_2$; and when a plurality of substituents are present, they are the same or different; or $R^{1-3}$ and $R^{1-4}$, $R^{1-5}$ and $R^{1-6}$, $R^{1-7}$ and $R^{1-8}$, $R^{1-9}$ and $R^{1-10}$, $R^{1-11}$ and $R^{1-12}$, $R^{1-14}$ and $R^{1-15}$, $R^{1-21}$ and $R^{1-22}$, $R^{1-23}$ and $R^{1-24}$, or $R^{1-25}$ and $R^{1-26}$, independently together with the N atom to which they directly link, form an unsubstituted or substituted $C_3$-$C_9$ heterocycloalkyl, an unsubstituted or substituted $C_3$-$C_9$ heterocycloalkenyl, or an unsubstituted or substituted 5-10 membered heteroaryl; wherein the $C_3$-$C_9$ heterocycloalkyl contains no heteroatom or 1-2 heteroatoms selected from one or more of O, S and N in addition to the existing N atom, the $C_3$-$C_9$ heterocycloalkenyl contains no heteroatom or 1-2 heteroatoms selected from one or more of O, S and N in addition to the existing N atom, the 5-10 membered heteroaryl contains no heteroatom or 1-2 heteroatoms selected from one or more of O, S and N in addition to the existing N atom; and the substituted $C_3$-$C_9$ heterocycloalkyl, the substituted $C_3$-$C_9$ heterocycloalkenyl or the substituted 5-10 membered heteroaryl is substituted with one or more substituents independently selected from the following: halogen, —OH, —$CF_3$, —CN, a $C_1$-$C_6$ alkyl, a $C_1$-$C_6$ alkyl-O—, ═O (i.e., two geminal hydrogens on a carbon atom are substituted with the group O), and a $C_1$-$C_6$ alkyl, a $C_1$-$C_6$ alkyl-O— or a $C_3$-$C_6$ cycloalkyl that is unsubstituted or substituted with one or more $R^b$; wherein when a plurality of $R^b$ are present, they are the same or different, and each $R^b$ is halogen, —OH, ═O, —$CF_3$, —CN, —COOH or —C(═O)$NH_2$; and when a plurality of substituents are present, they are the same or different;

$R^2$ is independently

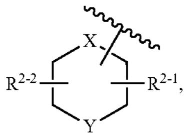

—C(═O)N($R^{2-5}R^{2-6}$) or an unsubstituted or substituted 5-6 membered heteroaryl; wherein the 5-6 membered heteroaryl contains 1-3 heteroatoms selected from one or more of N, O and S, and the substituted 5-6 membered heteroaryl is substituted with one or more substituents independently selected from the following: halogen, —OH, —CN, an unsubstituted or halogen-substituted $C_1$-$C_6$ alkyl, an unsubstituted or halogen-substituted $C_1$-$C_6$ alkyl-O—, —C(═O)$R^{2-7}$ or —C(═O)N($R^{2-8}R^{2-9}$); wherein when a plurality of substituents are present, they are the same or different;

$R^{2-1}$ and $R^{2-2}$ are each independently H, halogen, —OH, —CN, an unsubstituted or substituted $C_1$-$C_6$ alkyl, an unsubstituted or substituted $C_1$-$C_6$ alkyl-O—, or ═O (i.e., two geminal hydrogens on a carbon atom are substituted with the group O) wherein the substituted $C_1$-$C_6$ alkyl or the substituted $C_1$-$C_6$ alkyl-O— is substituted with one or more substituents independently selected from the following: halogen, —OH, —$CF_3$, —CN, a $C_1$-$C_6$ alkyl, a $C_1$-$C_6$ alkyl-O— or ═O (i.e., two geminal hydrogens on a carbon atom are substituted with the group O), and when a plurality of substituents are present, they are the same or different;

X and Y are each independently a single bond, methylene, —O—, —N($R^{2-3}$)— or

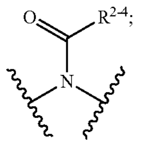

$R^{2-3}$, $R^{2-4}$, $R^{2-5}$ and $R^{2-6}$ are each independently H, an unsubstituted or substituted $C_1$-$C_6$ alkyl, an unsubstituted or substituted $C_3$-$C_8$ cycloalkyl, an unsubstituted or substituted $C_3$-$C_8$ cycloalkyl-O—, or an unsubstituted or substituted $C_1$-$C_6$ alkyl-O—; wherein the substituted $C_1$-$C_6$ alkyl, the substituted $C_3$-$C_8$cycloalkyl, the substituted $C_3$-$C_8$ cycloalkyl-O— or the substituted $C_1$-$C_6$ alkyl-O— is substituted with one or more substituents independently selected from the following: halogen, —OH, —$CF_3$, —CN, a $C_1$-$C_6$ alkyl, a $C_1$-$C_6$ alkyl-O— or ═O) (i.e., two geminal hydrogens on a carbon atom are substituted with the group O), and when a plurality of substituents are present, they are the same or different;

$R^{2-7}$ is independently H, halogen, —OH, —CN, an unsubstituted or halogen-substituted $C_1$-$C_6$ alkyl, or an unsubstituted or halogen-substituted $C_1$-$C_6$ alkyl-O—; and $R^{2-8}$ and $R^{2-9}$ are each independently H, or an unsubstituted or halogen-substituted $C_1$-$C_6$ alkyl.

In the present invention, some substituents in the heterocyclic compound of formula I may have the definitions below, and the substituents which are not mentioned have the definitions as described in any one of the above embodiments.

In a preferred embodiment of the present invention,

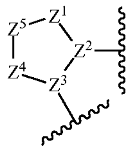

is a 5 membered heteroaryl or a 5 membered heterocycloalkenyl; wherein the 5 membered heteroaryl contains 1-2 heteroatoms selected from one or more of N, O and S, and the 5 membered heterocycloalkenyl contains 1-3 heteroatoms selected from one or more of N, O and S;

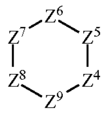

is phenyl, a 5-6 membered heterocycloalkyl, a 5-6 membered heterocycloalkenyl, or a 5-6 membered heteroaryl; wherein the 5-6 membered heterocycloalkyl contains 1-3 heteroatoms selected from one or more of N, O and S, the 5-6 membered heterocycloalkenyl contains 1-3 heteroatoms selected from one or more of N, O and S, and the 5-6 membered heteroaryl contains 1-3 heteroatoms selected from one or more of N, O and S;

$Z^1$, $Z^2$, $Z^3$, $Z^4$, $Z^5$, $Z^6$, $Z^7$, $Z^8$ and $Z^9$ independently represent a ring atom; and when

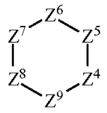

is a 5 membered heterocycloalkyl, a 5 membered heterocycloalkenyl or a 5 membered heteroaryl, $Z^6$ or $Z^9$ represents a single bond;

m is 1, 2, 3 or 4;

$R^3$ is H, halogen, —OH, a $C_1$-$C_6$ haloalkyl, —CN or a $C_1$-$C_6$ alkyl; when m is not 1, $R^3$ is independently the same or different; or when two adjacent $R^3$ are present, they, together with the ring atom to which they directly link, form a $C_3$-$C_6$ cycloalkyl, a $C_3$-$C_6$ cycloalkenyl, a $C_3$-$C_9$ heterocycloalkyl, a $C_3$-$C_9$ heterocycloalkenyl, phenyl or a 5-6 membered heteroaryl; wherein the $C_3$-$C_9$ heterocycloalkyl contains 1-3 heteroatoms selected from one or more of O, S and N, the $C_3$-$C_9$ heterocycloalkenyl contains 1-3 heteroatoms selected from one or more of O, S and N, and the 5-6 membered heteroaryl contains 1-3 heteroatoms selected from one or more of O, S and N;

W is a single bond or —C(═O)—NH—;

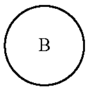

is phenyl, a 5-6 membered heteroaryl, or a $C_3$-$C_9$ heterocycloalkyl; wherein the 5-6 membered heteroaryl contains 1-3 heteroatoms selected from one or more of N, O and S, and the $C_3$-$C_9$ heterocycloalkyl contains 1-3 heteroatoms selected from one or more of O, S and N;

n is 1, 2, 3 or 4;

$R^1$ is independently H, halogen, —OH, —CN, an unsubstituted or substituted $C_1$-$C_6$ alkyl, or an unsubstituted or substituted $C_1$-$C_6$ alkyl-O—; wherein the substituted $C_1$-$C_6$ alkyl or the substituted $C_1$-$C_6$ alkyl-O— is substituted with one or more substituents independently selected from the following: halogen, —OH, —$CF_3$, —CN, —COOH, —C(═O)$NH_2$, a $C_1$-$C_6$ alkyl, a $C_1$-$C_6$ alkyl-O— or ═O (i.e., two geminal hydrogens on a carbon atom are substituted with the group O); when a plurality of substituents are present, they are the same or different; and when n is not 1, $R^1$ is independently the same or different;

Q is H, halogen, —OH, —$CF_3$, —CN, —NH—C(═O)—$R^{1-1}$, —C(═O)—$R^{1-2}$, —O—C(═O)—N($R^{1-3}R^{1-4}$), —C(═O)—N($R^{1-5}R^{1-6}$), —C(═NH)—N($R^{1-7}R^{1-8}$), —S(═O)$_2$—N($R^{1-9}R^{1-10}$), —S(═O)—N($R^{1-11}R^{1-12}$), —O—C(═O)—$R^{1-13}$, —N($R^{1-14}R^{1-15}$), —NH—S(═O)$_2$—$R^{1-16}$, an unsubstituted or substituted $C_1$-$C_6$ alkyl, an unsubstituted or substituted $C_1$-$C_6$ alkyl-O—, an unsubstituted or substituted $C_2$-$C_6$alkenyl, an unsubstituted or substituted $C_2$-$C_6$ alkenyl-O—, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, an unsubstituted or substituted $C_6$-$C_{10}$ aryl, or an unsubstituted or substituted 5-10 membered heteroaryl; wherein the $C_3$-$C_9$ heterocycloalkyl contains 1-3 heteroatoms selected from one or more of O, S and N, the $C_3$-$C_9$ heterocycloalkenyl contains 1-3 heteroatoms selected from one or more of O, S and N, the 5-10 membered heteroaryl contains 1-3 heteroatoms selected from one or more of O, S and N; and the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_3$-$C_{10}$ cycloalkyl, the substituted $C_6$-Cho aryl, the substituted $C_3$-$C_9$ heterocycloalkyl, the substituted $C_3$-$C_9$ heterocycloalkenyl or the substituted 5-10 membered heteroaryl is substituted with one or more substituents independently selected from the following: halogen, —OH, —$CF_3$, —CN, —COOH, —C(═O)$NH_2$, ═O (i.e., two geminal hydrogens on a carbon atom are substituted with the group O), —N($R^{1-21}R^{1-22}$), —C(═O)—N($R^{1-23}R^{1-24}$), —S(═O)$_2$—N($R^{1-25}R^{1-26}$), —C(═O)—O—$R^{1-27}$, and a $C_1$-$C_6$ alkyl, a $C_1$-$C_6$ alkyl-O— or a $C_3$-$C_6$ cycloalkyl that is unsubstituted or substituted with one or more $R^a$; wherein when a plurality of $R^a$ are present, they are the same or different, and each $R^a$ is halogen, —OH, ═O, —$CF_3$, —CN, —COOH or —C(═O)$NH_2$; and when a plurality of substituents are present, they are the same or different;

$R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each independently H, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_2$-$C_6$ alkynyl, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, an unsubstituted or substituted phenyl, or an unsubstituted or substituted 5-10 membered heteroaryl; wherein the $C_3$-$C_9$ heterocycloalkyl contains 1-3 heteroatoms selected from one or more of O, S and N, the $C_3$-$C_9$ heterocycloalkenyl contains 1-3 heteroatoms selected from one or more of O, S and N, the 5-10 membered heteroaryl contains 1-3 heteroatoms selected from one or more of N, O and S, and the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_2$-$C_6$ alkynyl, the substituted $C_3$-$C_{10}$ cycloalkyl, the substituted $C_3$-$C_9$ heterocycloalkyl, the substituted $C_3$-$C_9$ heterocycloalkenyl, the substituted phenyl or the substituted 5-10 membered heteroaryl is substituted with one or more substituents independently selected from the following: halogen, —OH, —$CF_3$, —CN, —COOH, —$COOCH_3$, —$NH_2$, ═O (i.e., two geminal hydrogens on a carbon atom are substituted with the group O), and a $C_1$-$C_6$ alkyl, a $C_1$-$C_6$ alkyl-O—or a $C_3$-$C_6$ cycloalkyl that is unsubstituted or substituted with one or more $R^d$, wherein when a plurality of $R^d$ are present, they are the same or different, and each $R^d$ is independently H, halogen, —OH, ═O, —$CF_3$, —CN, —COOH or —C(═O)$NH_2$; and when a plurality of substituents are present, they are the same or different; or $R^{1-3}$ and $R^{1-4}$, $R^{1-5}$ and $R^{1-6}$, $R^{1-7}$ and $R^{1-8}$, $R^{1-9}$ and $R^{1-10}$, $R^{1-11}$ and $R^{1-12}$, $R^{1-14}$ and $R^{1-15}$, $R^{1-21}$ and $R^{1-22}$, $R^{1-23}$ and $R^{1-24}$, or $R^{1-25}$ and $R^{1-26}$, independently together with the N atom to which they directly link, form an unsubstituted or substituted $C_3$-$C_9$ heterocycloalkyl, an unsubstituted or substituted $C_3$-$C_9$ heterocycloalkenyl, or an unsubstituted or substituted 5-10 membered heteroaryl; wherein the $C_3$-$C_9$ heterocycloalkyl contains no heteroatom or 1-2 heteroatoms selected from one or more of O, S and N in addition to the existing N atom, the $C_3$-$C_9$ heterocycloalkenyl contains no heteroatom or 1-2 heteroatoms selected from one or more of O, S and N in addition to the existing N atom, the 5-10 membered heteroaryl contains no heteroatom or 1-2 heteroatoms selected from one or more of O, S and N in addition to the existing N atom, and the substituted $C_3$-$C_9$ heterocycloalkyl, the substituted $C_3$-$C_9$ heterocycloalkenyl or the substituted 5-10 membered heteroaryl is substituted with one or more substituents independently selected from the following: halogen, —OH, —$CF_3$, —CN, a $C_1$-$C_6$ alkyl, a $C_1$-$C_6$ alkyl-O—, ═O (i.e., two geminal hydrogens on a carbon atom are substituted with the group O), and a $C_1$-$C_6$ alkyl, a $C_1$-$C_6$ alkyl-O— or a $C_3$-$C_6$ cycloalkyl that is unsubstituted or substituted with one or more $R^b$, wherein when a plurality of $R^b$ are present, they are the same or different, and each $R^b$ is halogen, —OH, ═O, —$CF_3$, —CN, —COOH or —C(═O)$NH_2$; and when a plurality of substituents are present, they are the same or different;

$R^2$ is

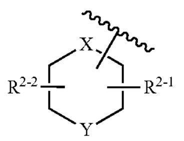

or —C(═O)N($R^{2-5}R^{2-6}$);

$R^{2-1}$ and $R^{2-2}$ are each independently H, halogen, —OH, —CN, an unsubstituted or substituted $C_1$-$C_6$ alkyl, an unsubstituted or substituted $C_1$-$C_6$ alkyl-O—, or =O (i.e., two geminal hydrogens on a carbon atom are substituted with the group O) wherein the substituted $C_1$-$C_6$ alkyl or the substituted $C_1$-$C_6$ alkyl-O— is substituted with one or more substituents independently selected from the following: halogen, —OH, —$CF_3$, —CN, a $C_1$-$C_6$ alkyl, a $C_1$-$C_6$ alkyl-O— or =O (i.e., two geminal hydrogens on a carbon atom are substituted with the group O), and when a plurality of substituents are present, they are the same or different;

X and Y are each independently a single bond, methylene, —O—, —N($R^{2-3}$)— or

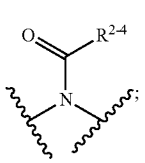

;

$R^{2-3}$, $R^{2-4}$, $R^{2-5}$ and $R^{2-6}$ are each independently H, an unsubstituted or substituted $C_1$-$C_6$ alkyl, an unsubstituted or substituted $C_3$-$C_8$ cycloalkyl, an unsubstituted or substituted $C_3$-$C_8$ cycloalkyl-O—, or an unsubstituted or substituted $C_1$-$C_6$ alkyl-O—; wherein the substituted $C_1$-$C_6$ alkyl, the substituted $C_3$-$C_8$ cycloalkyl, the substituted $C_3$-$C_8$ cycloalkyl-O— or the substituted $C_1$-$C_6$ alkyl-O— is substituted with one or more substituents independently selected from the following: halogen, —OH, —$CF_3$, —CN, a $C_1$-$C_6$ alkyl, a $C_1$-$C_6$ alkyl-O— or =O) (i.e., two geminal hydrogens on a carbon atom are substituted with the group O), and when a plurality of substituents are present, they are the same or different.

In the heterocyclic compound of formula I or the stereoisomer, the geometric isomer, the tautomer, the nitrogen oxide, the hydrate, the solvate, the metabolite, the ester, the pharmaceutically acceptable salt or the prodrug thereof disclosed herein, some substituents may have the definitions below, and the substituents which are not mentioned have the definitions as described in any one of the embodiments.

In a preferred embodiment of the present invention, $Z^6$ is a single bond and $Z^9$ is NH, O or S; or, $Z^9$ is a single bond and $Z^6$ is NH, O or S.

In a preferred embodiment of the present invention, when

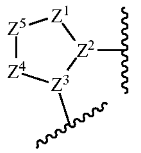

is a 5 membered heteroaryl the 5 membered heteroaryl is pyrrolyl (e.g.,

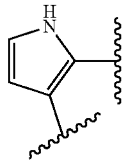

or

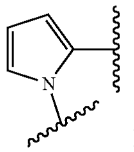

), furanyl (e.g.,

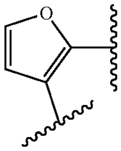

), pyrazolyl (e.g.,

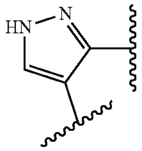

), thienyl (e.g.,

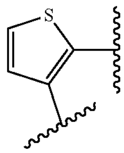

)

or imidazolyl (e.g.,

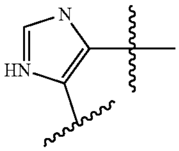

or

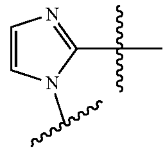

).

(In the structural formula, the right-side bond is linked to W)

In a preferred embodiment of the present invention, when

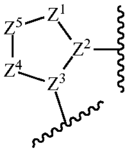

is a 5 membered heterocycloalkenyl, the 5 membered heterocycloalkenyl contains 1-2 heteroatoms selected from one or more of N, O and S, and is preferably 2,3-dihydro-1H-pyrazolyl (e.g., (e.g.,

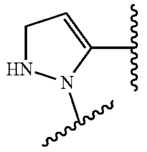

).

(In the structural formula, the right-side bond is linked to W)

In a preferred embodiment of the present invention, when

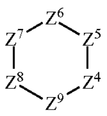

is a 5-6 membered heterocycloalkyl, the 5-6 membered heterocycloalkyl is a 6 membered heterocycloalkyl; wherein the 6 membered heterocycloalkyl contains 1-3 N heteroatoms; and the 5-6 membered heterocycloalkyl is preferably piperazinyl (e.g., 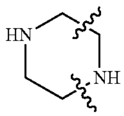 )

or piperidinyl (e.g., 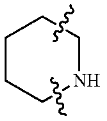 ).

(In the structural formula, the right-side carbon-nitrogen bond

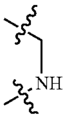

represents the position fusing to

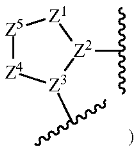 )

In a preferred embodiment of the present invention, when

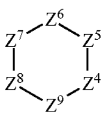

is a 5-6 membered heterocycloalkenyl, the 5-6 membered heterocycloalkenyl is a 6 membered heterocycloalkenyl; wherein the 6 membered heterocycloalkenyl contains 1-3 N heteroatoms; and the 5-6 membered heterocycloalkenyl is preferably 1,2-dihydropyridinyl (e.g.,

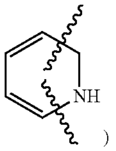 )

or 1,6-dihydropyrimidinyl (e.g.,

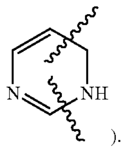 ).

(In the structural formula, the right-side carbon-nitrogen bond

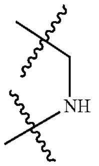

represents the position fusing to

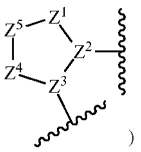 )

In a preferred embodiment of the present invention, when

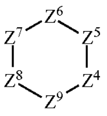

is a 5-6 membered heteroaryl, the 5-6 membered heteroaryl is a 6 membered heteroaryl; wherein the 6 membered heteroaryl contains 1-3 N heteroatoms (e.g., pyridinyl or pyrimidinyl); and the 5-6 membered heteroaryl is preferably pyridinyl (e.g.,

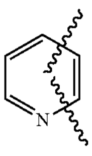 or 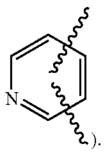 ).

(In the structural formula, the right-side carbon-carbon double bond

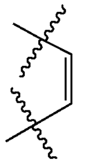 [SMILES: */C=C\*]

represents the position fusing to

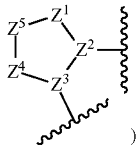
)

In a preferred embodiment of the present invention,

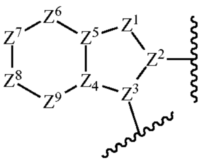
is

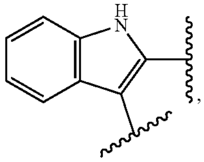, 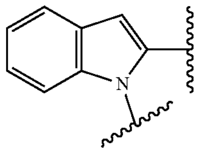,

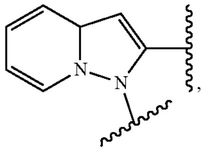, 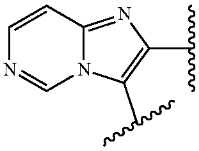,

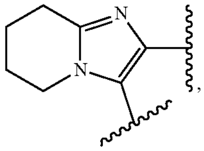, 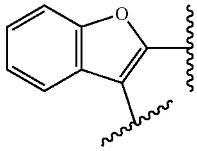,

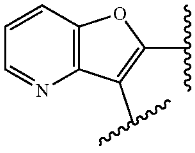, 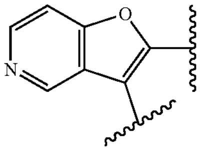,

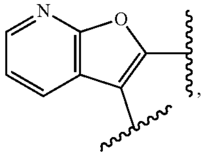, 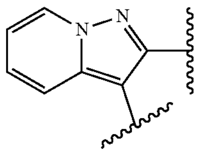,

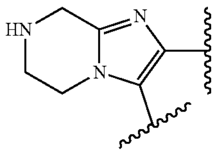 or 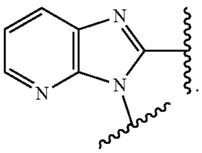.

In a preferred embodiment of the present invention,

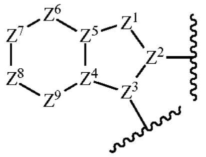 is 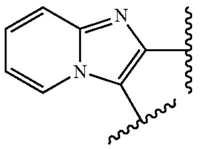.

In a preferred embodiment of the present invention, m is 1 or 2;

In a preferred embodiment of the present invention, $Z^7$ is substituted with $R^3$, $Z^8$ is unsubstituted or substituted with $R^3$, $Z^6$ and $Z^9$ are unsubstituted; when a plurality of $R^3$ are present, they are the same or different; and preferably, $Z^7$ is substituted with $R^3$, and $Z^6$, $Z^8$ and $Z^9$ are unsubstituted.

In a preferred embodiment of the present invention, when $R^3$ is halogen, the halogen is fluorine, chlorine, bromine or iodine.

In a preferred embodiment of the present invention, when $R^3$ is a $C_1$-$C_6$ alkyl (e.g., methyl, ethyl, propyl, butyl, pentyl or hexyl), the $C_1$-$C_6$ alkyl is a $C_1$-$C_4$alkyl (e.g., methyl, ethyl, n-propyl, isopropyl, n-butyl, isobutyl, sec-butyl or tert-butyl), and preferably methyl.

In a preferred embodiment of the present invention, when $R^3$ is a $C_1$-$C_6$ haloalkyl, the halogen is fluorine, chlorine, bromine or iodine, and preferably chlorine.

In a preferred embodiment of the present invention, when $R^3$ is a $C_1$-$C_6$ haloalkyl, it contains one or more (e.g., 1, 2, 3, 4 or 5) halogens, and preferably 1, 2 or 3 halogens.

In a preferred embodiment of the present invention, $R^3$ is $-CF_3$, $-CH_2F$ or $-CHF_2$.

In a preferred embodiment of the present invention, when two adjacent $R^3$ are present and they, together with the ring atom to which they directly link, form a $C_3$-$C_8$ cycloalkyl, the $C_3$-$C_6$ cycloalkyl is cyclopropyl, cyclobutyl, cyclopentyl or cyclohexyl.

In a preferred embodiment of the present invention, when two adjacent $R^3$ are present and they, together with the ring atom to which they directly link, form a $C_3$-$C_6$ cycloalkenyl, the $C_3$-$C_6$ cycloalkenyl is cyclopropenyl, cyclobutenyl, cyclopentenyl, cyclohexenyl or cyclohexadienyl.

In a preferred embodiment of the present invention, when two adjacent $R^3$ are present and they, together with the ring atom to which they directly link, form a $C_3$-$C_9$ heterocycloalkyl, the $C_3$-$C_9$ heterocycloalkyl is a $C_4$-$C_5$ heterocycloalkyl; wherein the $C_4$-$C_5$ heterocycloalkyl contains 1-2 heteroatoms selected from one or more of N, O and S.

In a preferred embodiment of the present invention, when two adjacent $R^3$ are present and they, together with the ring atom to which they directly link, form a $C_3$-$C_9$ heterocycloalkenyl, the $C_3$-$C_9$ heterocycloalkenyl is a $C_4$-$C_5$ heterocycloalkenyl; wherein the $C_4$-$C_5$ heterocycloalkenyl contains 1-2 heteroatoms selected from one or more of N, O and S.

In a preferred embodiment of the present invention, when two adjacent $R^3$ are present and they, together with the ring atom to which they directly link, form a 5-6 membered heteroaryl, the 5-6 membered heteroaryl contains 1-2 heteroatoms selected from one or more of N, O and S.

In a preferred embodiment of the present invention,
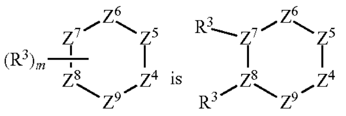
(as described above, $R^3$ is the same or different).
In a preferred embodiment of the present invention,
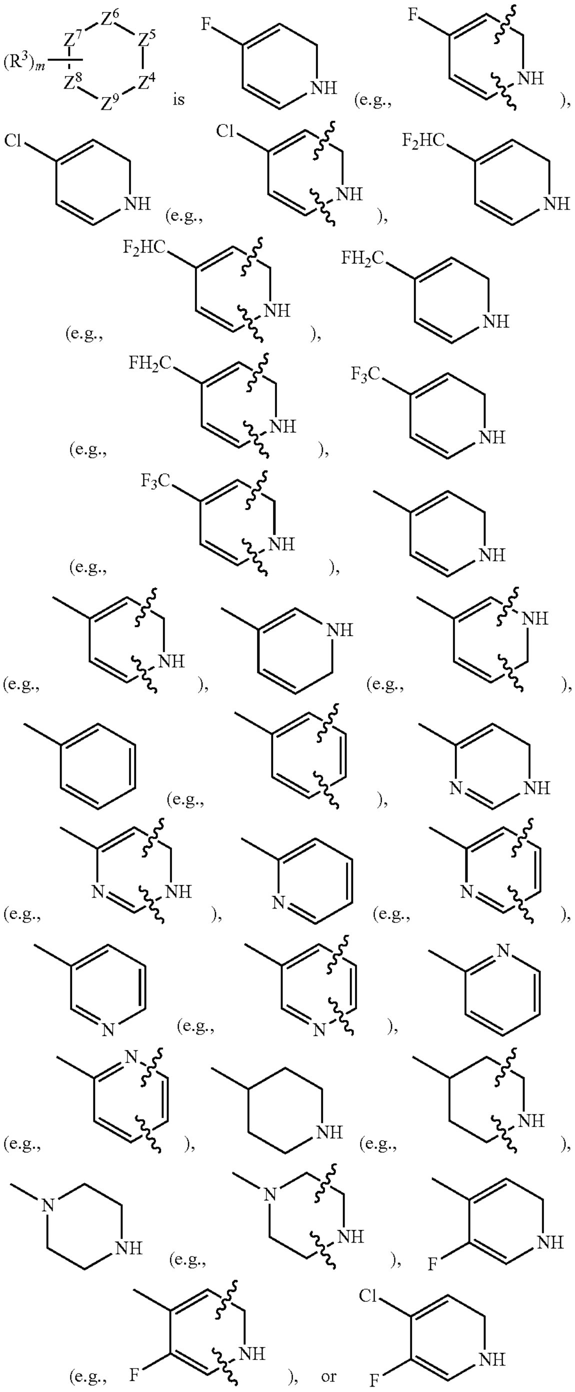
-continued
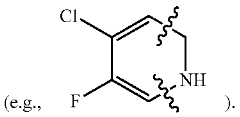
(In the structural formula, the right-side carbon-nitrogen bond
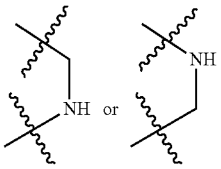
is fused to
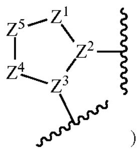
)
In a preferred embodiment of the present invention,
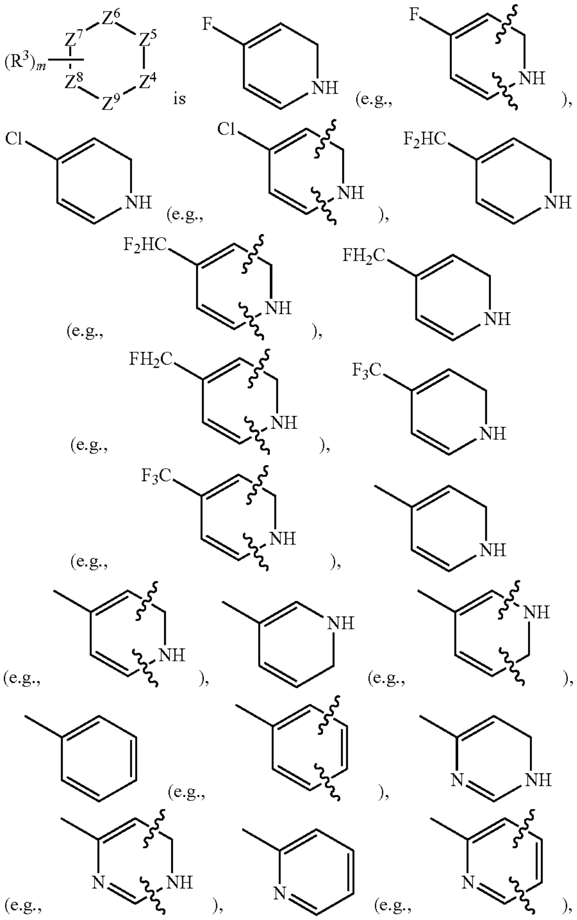

-continued
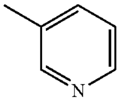 (e.g., 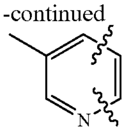), 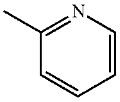 (e.g., 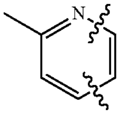), 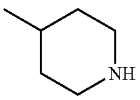 (e.g., 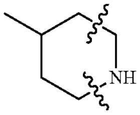), or 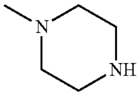 (e.g., 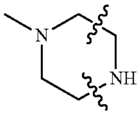).
(In the structural formula, the right-side carbon-nitrogen bond
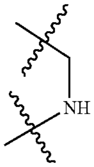 or 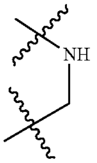
is fused to
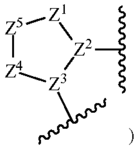
)
In a preferred embodiment of the present invention,
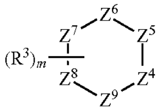 is
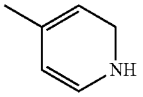 (e.g., 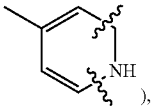), 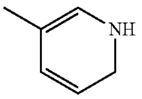 (e.g., 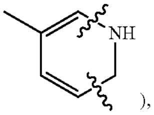), 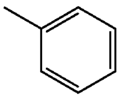 (e.g., 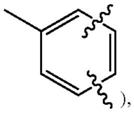), 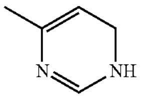 (e.g., 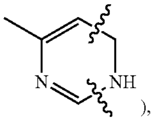),
-continued
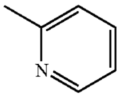 (e.g., 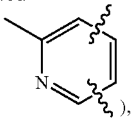), 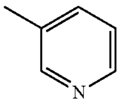 (e.g., 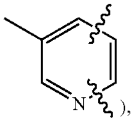), 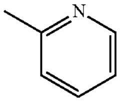 (e.g., 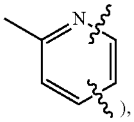), 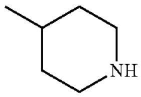 (e.g., 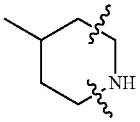), or 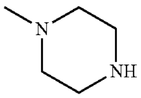 (e.g., 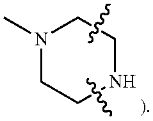).
(In the structural formula, the right-side carbon-nitrogen bond
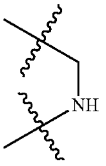 or 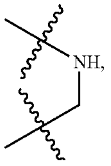
or the carbon-carbon double bond
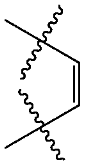 [SMILES: */C=C\*]
is fused to
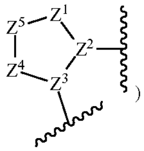)
In a preferred embodiment of the present invention,
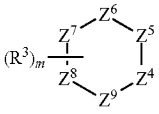 is -continued

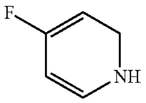 (e.g., 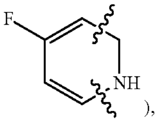 ),

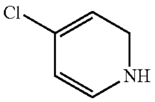 (e.g., 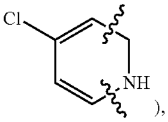 ),

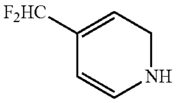 (e.g., 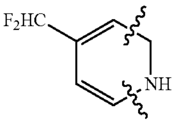 ),

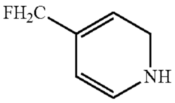 (e.g., 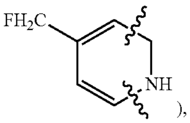 ), or

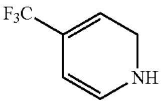 (e.g., 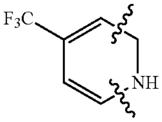 ).

(In the structural formula, the right-side carbon-nitrogen bond

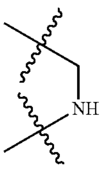 or 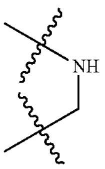

is fused to

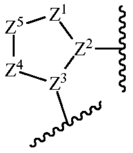 )

In a preferred embodiment of the present invention,

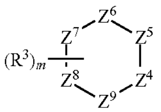 is 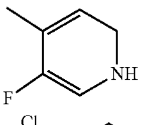

(e.g., 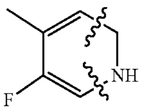 ) or 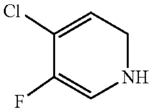

(e.g., 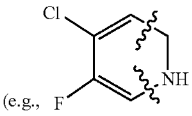 ).

(In the structural formula, the right-side carbon-nitrogen bond

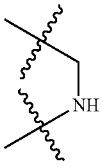 or 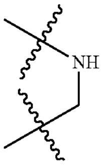

or the carbon-carbon double bond

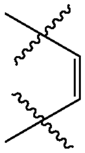 [SMILES: */C=C\*]

is fused to

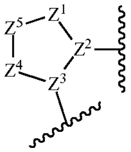 )

In a preferred embodiment of the present invention,

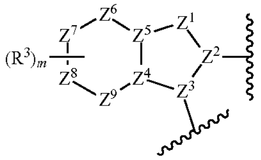 is

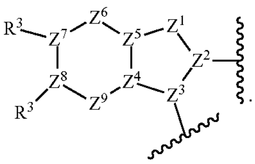.

In a preferred embodiment of the present invention,

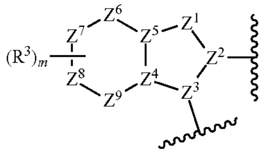 is 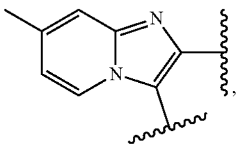,

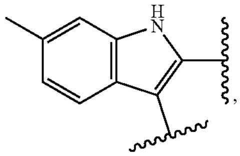, 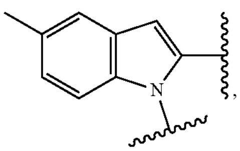,

-continued
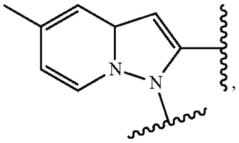
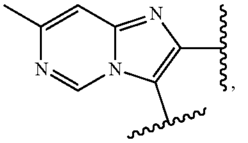
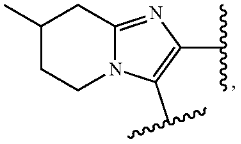
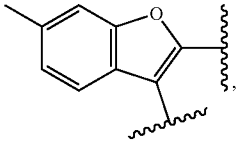
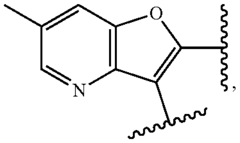
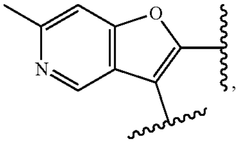
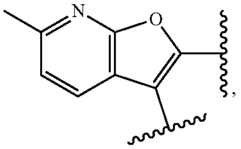
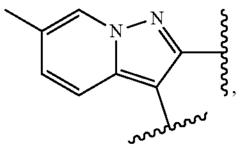
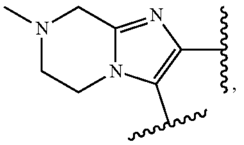
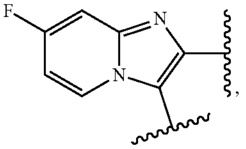
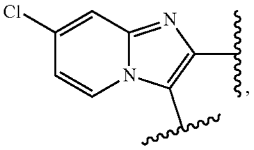
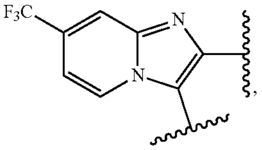
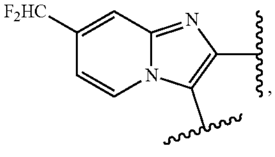
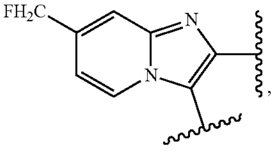
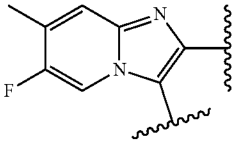
or
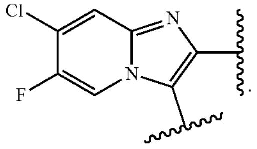
In a preferred embodiment of the present invention,
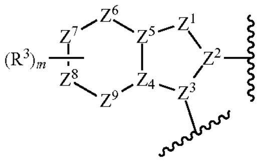
is
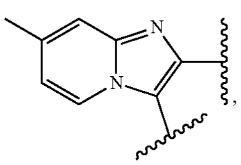
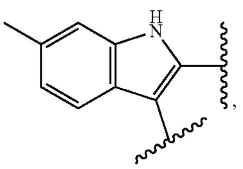
-continued
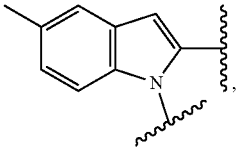
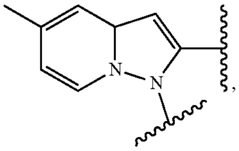
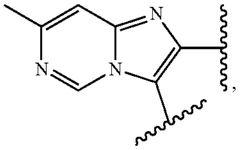
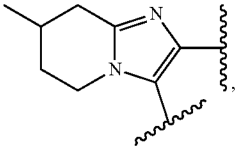
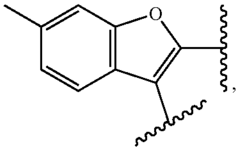
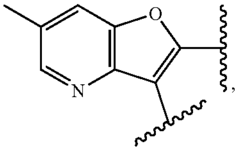
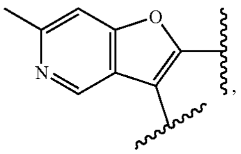
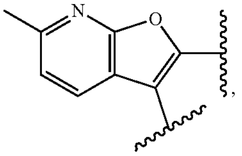
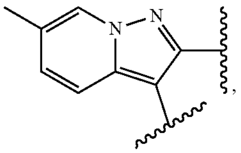
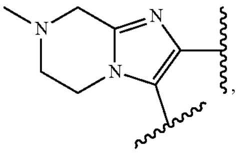
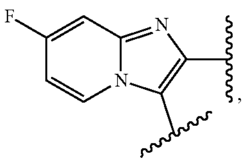
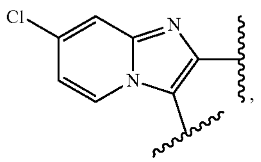
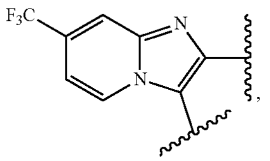
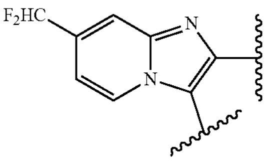
or
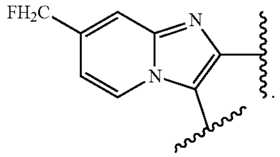
In a preferred embodiment of the present invention,
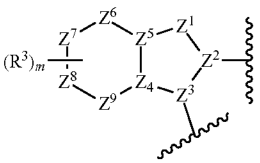
is
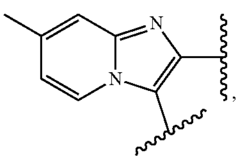
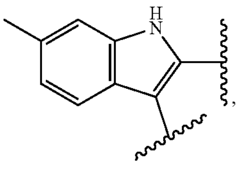

-continued

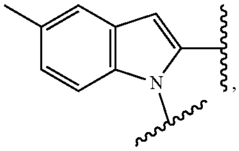,
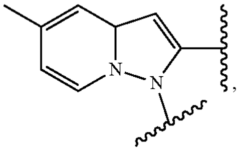,
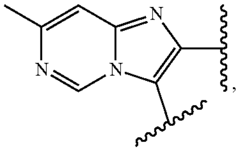,
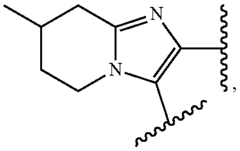,
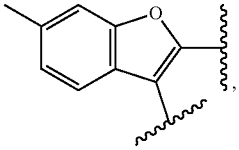,
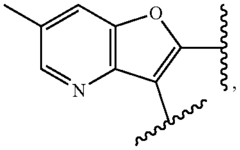,
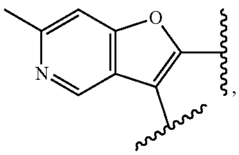,
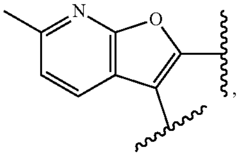,
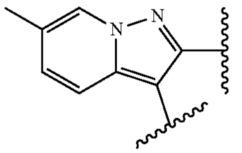 or
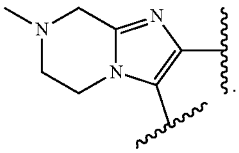.

In a preferred embodiment of the present invention,

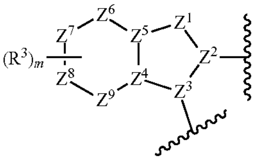 is

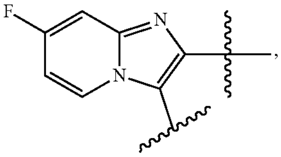,
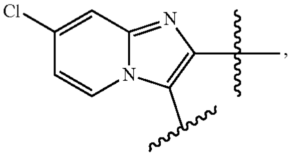,
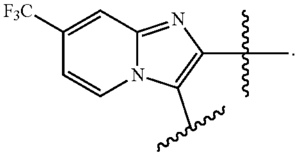,
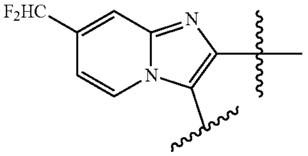 or

-continued

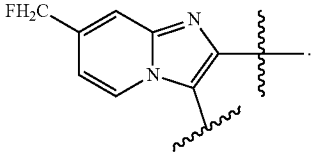.

In a preferred embodiment of the present invention,

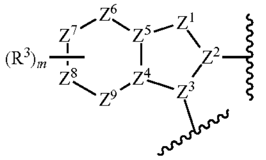 is

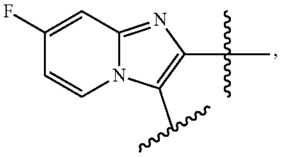,
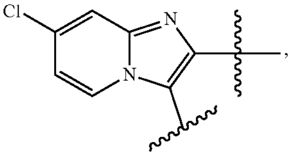,
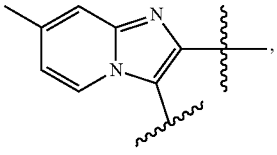,
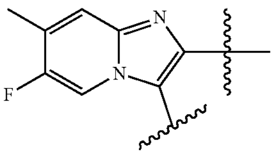 or
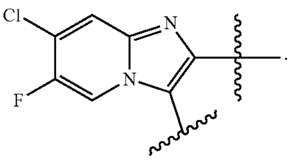.

In a preferred embodiment of the present invention, n is 1 or 2.

In a preferred embodiment of the present invention, each $R^1$ is independently located at position α (the ortho-position of $Z^2$) or position B (the meta-position of $Z^2$) of the linkage between

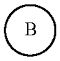

and $Z^2$.

In a preferred embodiment of the present invention, at least one $R^1$ is located at position α of the linkage between

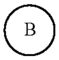

and $Z^2$; and preferably, when n is 2, each $R^1$ is independently located at position α of the linkage between

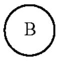

and $Z^2$.

In a preferred embodiment of the present invention, when $R^1$ is halogen, the halogen is fluorine, chlorine, bromine or iodine.

In a preferred embodiment of the present invention, when $R^1$ is an unsubstituted or substituted $C_1$-$C_6$ alkyl, or an unsubstituted or substituted $C_1$-$C_6$ alkyl-O—, the $C_1$-$C_6$ alkyl (e.g., methyl, ethyl, propyl, butyl, pentyl or hexyl) is independently a $C_1$-$C_4$ alkyl (e.g., methyl, ethyl, n-propyl, isopropyl, n-butyl, isobutyl, sec-butyl or tert-butyl), and preferably methyl.

In a preferred embodiment of the present invention, when $R^1$ is a substituted $C_1$-$C_6$ alkyl or a substituted $C_1$-$C_6$ alkyl-O—, and the substituent is each independently halogen, the halogen is fluorine, chlorine, bromine or iodine.

In a preferred embodiment of the present invention, when $R^1$ is a substituted $C_1$-$C_6$ alkyl or a substituted $C_1$-$C_6$ alkyl-O—, the substituent is independently a $C_1$-$C_6$ alkyl or a $C_1$-$C_6$ alkyl-O—, and the $C_1$-$C_6$ alkyl (e.g., methyl, ethyl, propyl, butyl, pentyl or hexyl) in the substituent is independently a $C_1$-$C_6$ alkyl (e.g., methyl, ethyl, n-propyl, isopropyl, n-butyl, isobutyl, sec-butyl or tert-butyl), and preferably methyl.

In a preferred embodiment of the present invention, when $R^1$ is a substituted $C_1$-$C_6$ alkyl or a substituted $C_1$-$C_6$ alkyl-O—, the number of the substituents is independently 1, 2 or 3.

In a preferred embodiment of the present invention, when $R^1$ is a substituted $C_1$-$C_6$ alkyl or a substituted $C_1$-$C_6$ alkyl-O— and the substituents are each independently halogen, the substituted $C_1$-$C_6$ alkyl in the substituted $C_1$-$C_6$ alkyl or the substituted $C_1$-$C_6$ alkyl-O— is independently-$CF_3$.

In a preferred embodiment of the present invention, Q is located at position β or γ of the linkage between

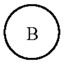

and W.

In a preferred embodiment of the present invention, when

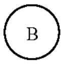

is a 5-6 membered heteroaryl, the 5-6 membered heteroaryl is a 5 membered heteroaryl, wherein the 5 membered heteroaryl contains 1-2 heteroatoms selected from one or more of N, O and S, and is preferably imidazolyl (e.g., 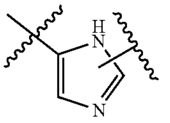 (e.g., 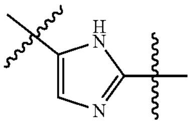 )), thienyl (e.g., 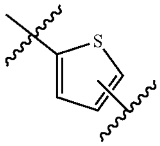 (e.g., 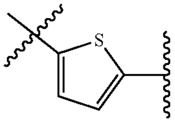 or 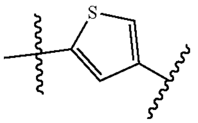 )), furanyl (e.g., 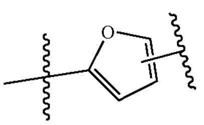 (e.g., 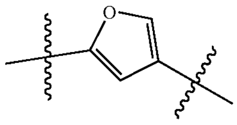 ))

or pyrrolyl (e.g., 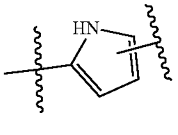 (e.g., 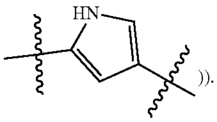 )).

(In the structural formula, the left-side bond is linked to W, and the right-side bond is linked to Q)

In a preferred embodiment of the present invention, when

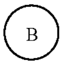

is a 5-6 membered heteroaryl, the 5-6 membered heteroaryl is a 6 membered heteroaryl; wherein the 6 membered heteroaryl contains 1-2 heteroatoms selected from one or more of N, O and S, and is preferably pyridinyl (e.g., 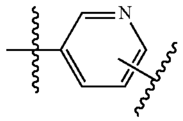 (e.g., 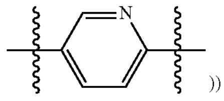 ))

or pyrazinyl (e.g., 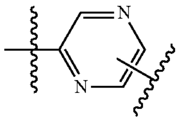 (e.g., 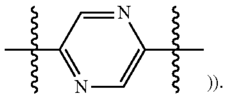 )).

(In the structural formula, the left-side bond is linked to W, and the right-side bond is linked to Q)

In a preferred embodiment of the present invention, when

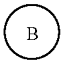

is a $C_3$-$C_9$ heterocycloalkyl, the $C_3$-$C_9$ heterocycloalkyl is a $C_3$-$C_5$ heterocycloalkyl, wherein the $C_3$-$C_5$ heterocycloalkyl contains 1-3 heteroatoms selected from one or more of N, O and S; the $C_3$-$C_9$ heterocycloalkyl is preferably a $C_4$-$C_5$ heterocycloalkyl, wherein the $C_4$-$C_5$ heterocycloalkyl contains 1-2 heteroatoms selected from one or more of N, O and S; and the $C_3$-$C_9$ heterocycloalkyl is preferably piperidinyl (e.g., 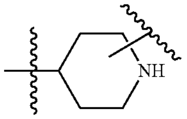 (e.g., 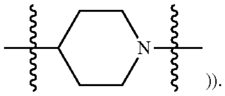 )).

(In the structural formula, the left-side bond is linked to W, and the right-side bond is linked to Q)

In a preferred embodiment of the present invention, $R^1$ is located at position B of the linkage between

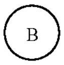

and $Z^2$. Preferably, when n is 2, each $R^1$ is independently located at position B of the linkage between

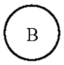

and $Z^2$.

In a preferred embodiment of the present invention, when

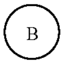

is phenyl,

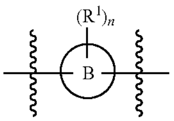

is

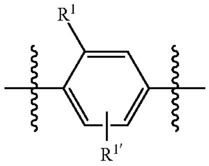 or 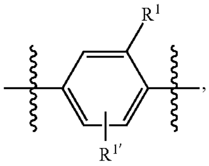, and is preferably

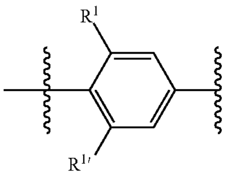 or 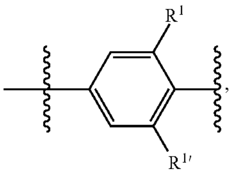, wherein $R^{1'}$ has the definition as described for $R^1$, and $R^{1'}$ is the same as or different from $R^1$. (In the structural formula, the left-side bond is linked to W, and the right-side bond is linked to Q)

In a preferred embodiment of the present invention, when

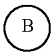

is phenyl,

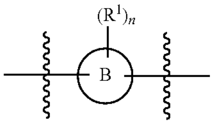 is 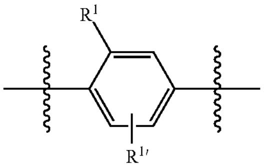 or

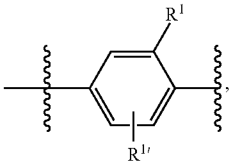, and is preferably

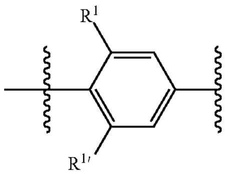 or

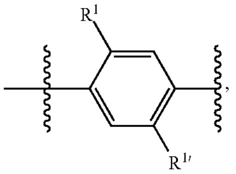, wherein $R^{1'}$ has the definition as described for $R^1$, and $R^{1'}$ is the same as or different from $R^1$. (In the structural formula, the left-side bond is linked to W, and the right-side bond is linked to Q)

In a preferred embodiment of the present invention, when the

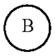

is phenyl,

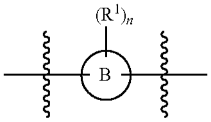

is

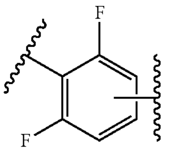

(e.g.,

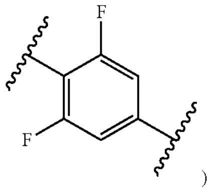

) or

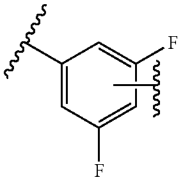

(e.g.,

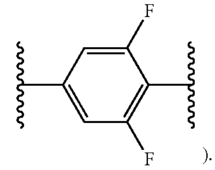

).

(In the structural formula, the left-side bond is linked to W, and the right-side bond is linked to Q)

In a preferred embodiment of the present invention, when the

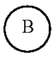

is phenyl,

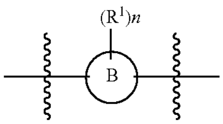

is

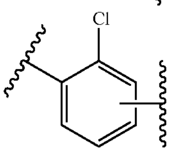

(e.g.,

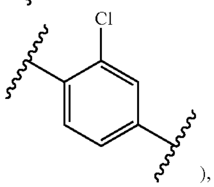

),

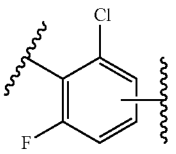

(e.g.,

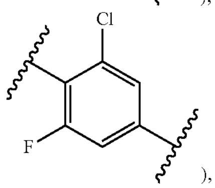

),

-continued

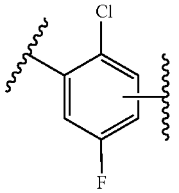

(e.g.,

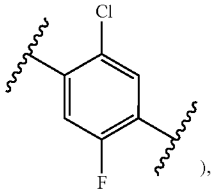

),

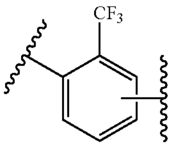

(e.g.,

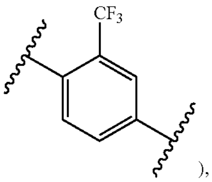

), or

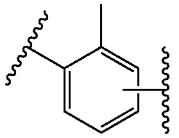

(e.g.,

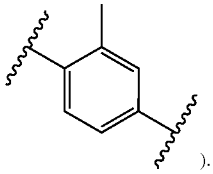

).

(In the structural formula, the left-side bond is linked to $Z^2$, and the right-side bond is linked to Q)

In a preferred embodiment of the present invention, when the

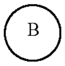

is phenyl,

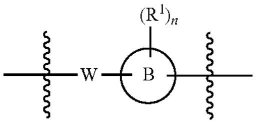

is

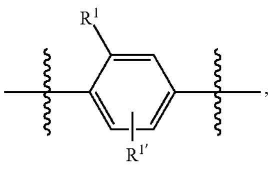

preferably

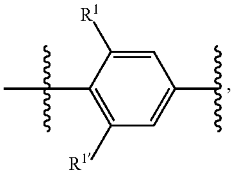

and more preferably

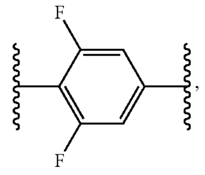

wherein $R^{1'}$ has the definition as described for $R^1$, and $R^{1'}$ is the same as or different from $R^1$. (In the structural formula, the left-side bond is linked to $Z^2$, and the right-side bond is linked to Q)

In a preferred embodiment of the present invention,

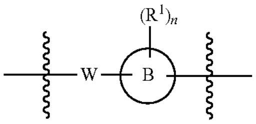

is

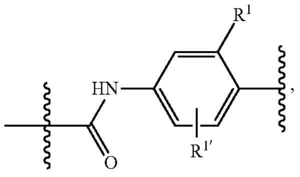

preferably

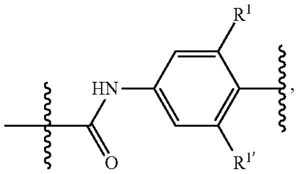

and more preferably

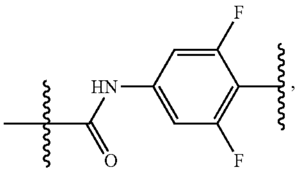 [SMILES: *C(=O)Nc1cc(F)c(*)c(F)c1]

wherein $R^{1'}$ has the definition as described for $R^1$, and $R^{1'}$ is the same as or different from $R^1$. (In the structural formula, the left-side bond is linked to $Z^2$, and the right-side bond is linked to Q)

In a preferred embodiment of the present invention,

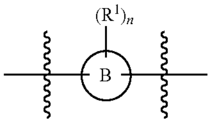

is

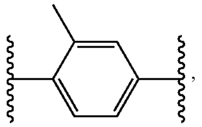

-continued

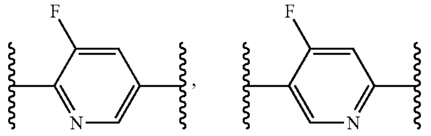

or

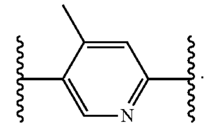

In a preferred embodiment of the present invention,

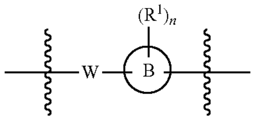

is

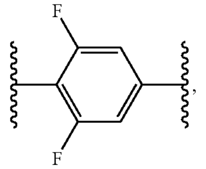

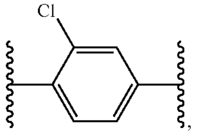

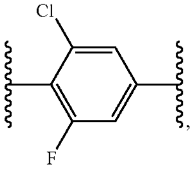

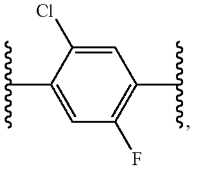

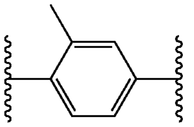

or

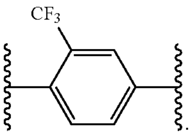

In a preferred embodiment of the present invention, when

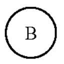

is a 5-6 membered heteroaryl,

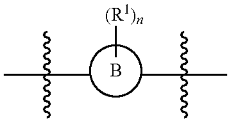

is

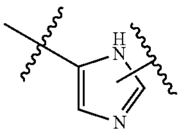

(e.g.,

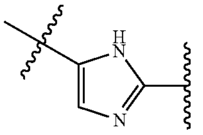

),

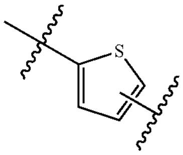

-continued (e.g., 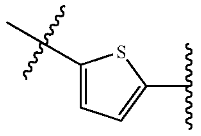 ), 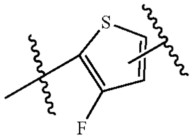

(e.g., 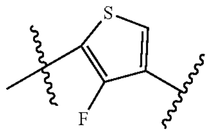 ), 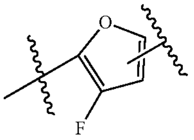

(e.g., 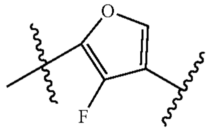 ), 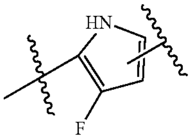

(e.g., 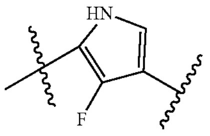 ), 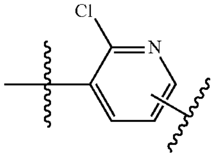

(e.g., 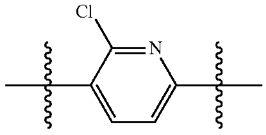 ), 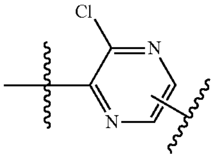

(e.g., 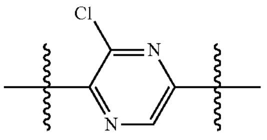 ) or 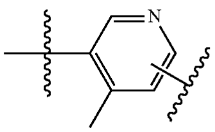

(e.g., 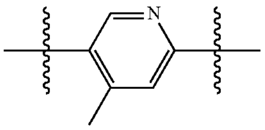 ).

(In the structural formula, the left-side bond is linked to W, and the right-side bond is linked to Q)

In a preferred embodiment of the present invention, when

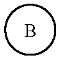

is a 5-6 membered heteroaryl,

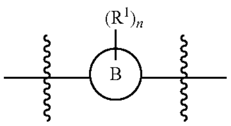 is 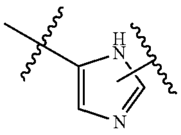

(e.g., 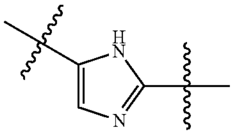 ), 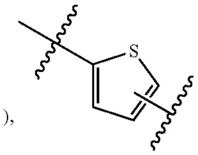

-continued (e.g., 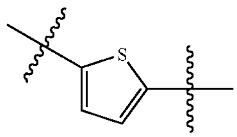 ), 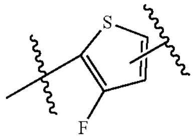

(e.g., 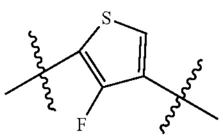 ), 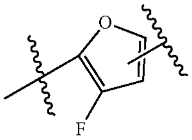

(e.g., 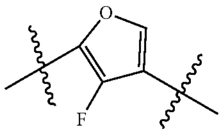 ), 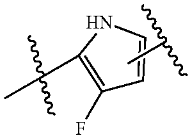

(e.g., 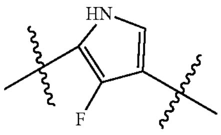 ), 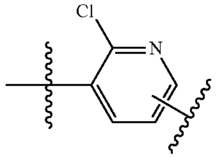

(e.g., 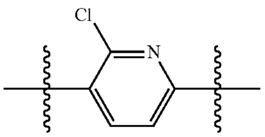 ), or

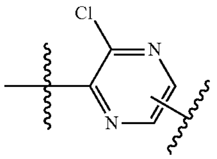 (e.g., 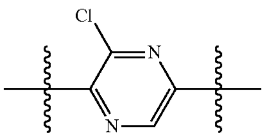 ).

(In the structural formula, the left-side bond is linked to W, and the right-side bond is linked to Q)

In a preferred embodiment of the present invention, when

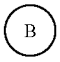

is a 5-6 membered heteroaryl,

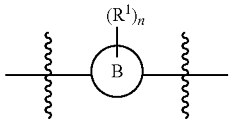 is 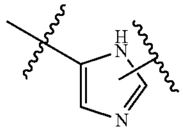

(e.g., 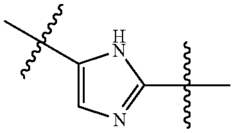 ), 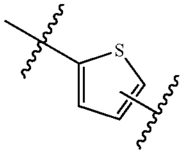

(e.g., 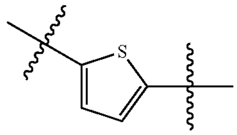 ), 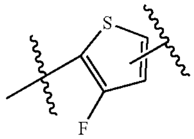

-continued (e.g., 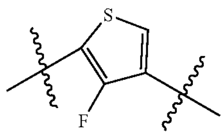),

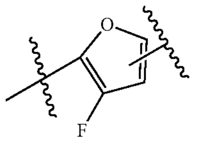

(e.g., 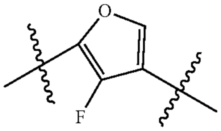), or

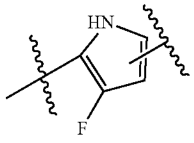

(e.g., 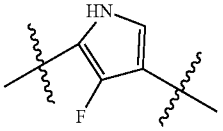).

(In the structural formula, the left-side bond is linked to W, and the right-side bond is linked to Q)

In a preferred embodiment of the present invention, when

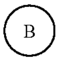

is a 5-6 membered heteroaryl,

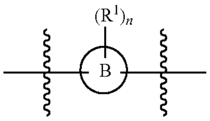 is 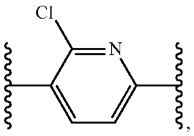, (e.g., 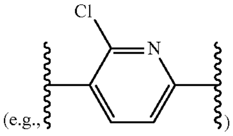) or 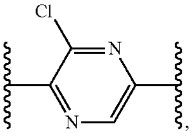, (e.g., 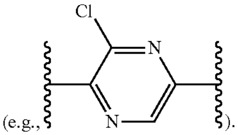).

(In the structural formula, the left-side bond is linked to W, and the right-side bond is linked to Q)

In a preferred embodiment of the present invention,

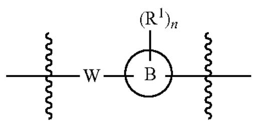 is 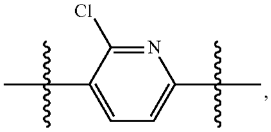,

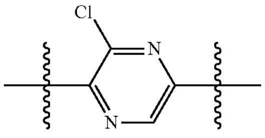 or 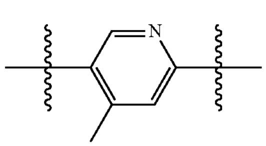.

In a preferred embodiment of the present invention,

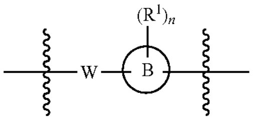 is 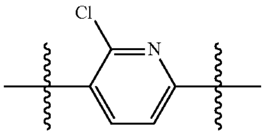 or

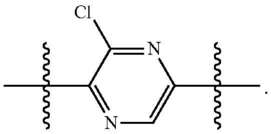.

In a preferred embodiment of the present invention, when

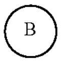

is a $C_3$-$C_5$ heterocycloalkyl,

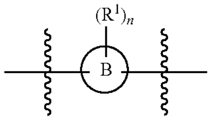 is 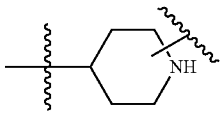

(e.g., 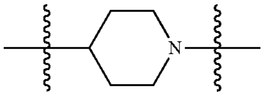).

(In the structural formula, the left-side bond is linked to W, and the right-side bond is linked to Q)

In a preferred embodiment of the present invention, when Q is halogen, the halogen is fluorine, chlorine, bromine or iodine.

In a preferred embodiment of the present invention, when Q is an unsubstituted or substituted $C_1$-$C_6$ alkyl, or an unsubstituted or substituted $C_1$-$C_6$ alkyl-O—, the $C_1$-$C_6$ alkyl (e.g., methyl, ethyl, propyl, butyl, pentyl or hexyl) is independently a $C_1$-$C_4$ alkyl (e.g., methyl, ethyl, n-propyl, isopropyl, n-butyl, isobutyl, sec-butyl or tert-butyl).

In a preferred embodiment of the present invention, when Q is an unsubstituted or substituted $C_2$-$C_6$ alkenyl, or an unsubstituted or substituted $C_2$-$C_6$ alkenyl-O—, the $C_2$-$C_6$ alkenyl is a $C_2$-$C_4$ alkenyl (e.g., ethenyl, propenyl (e.g., 1-propenyl or 2-propenyl), or butenyl (e.g., 2-butenyl, 1-butenyl, or butadienyl)).

In a preferred embodiment of the present invention, when Q is an unsubstituted or substituted $C_3$-$C_{10}$ cycloalkyl, the $C_3$-$C_{10}$ cycloalkyl is cyclopropyl, cyclobutyl, cyclopentyl, cyclohexyl, cycloheptyl or cyclooctyl.

In a preferred embodiment of the present invention, when Q is an unsubstituted or substituted $C_3$-$C_9$ heterocycloalkyl, the $C_3$-$C_9$ heterocycloalkyl is a $C_3$-$C_5$ heterocycloalkyl, wherein the $C_3$-$C_5$ heterocycloalkyl contains 1-3 heteroatoms selected from one or more of O, S and N; the $C_3$-$C_9$ heterocycloalkyl is preferably a $C_4$-$C_5$ heterocycloalkyl, wherein the $C_4$-$C_5$ heterocycloalkyl contains 1-2 heteroatoms selected from one or more of N, O and S; and the $C_3$-$C_9$ heterocycloalkyl is preferably oxetanyl (e.g., 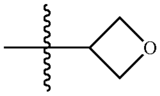 ), pyrrolidinyl (e.g., 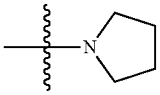 )

or piperazinyl (e.g., 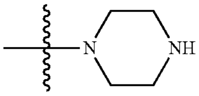 ).

In a preferred embodiment of the present invention, when Q is an unsubstituted or substituted $C_3$-$C_9$ heterocycloalkenyl, the $C_3$-$C_9$ heterocycloalkenyl is a $C_3$-$C_5$ heterocycloalkenyl, wherein the $C_3$-$C_5$ heterocycloalkenyl contains 1-3 heteroatoms selected from one or more of O, S and N; the $C_3$-$C_5$ heterocycloalkenyl is preferably a $C_4$-$C_5$ heterocycloalkenyl, wherein the $C_4$-$C_5$ heterocycloalkenyl contains 1-2 heteroatoms selected from one or more of N, O and S; and the $C_3$-$C_9$ heterocycloalkenyl is preferably

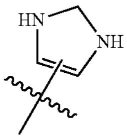 (e.g., 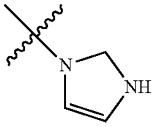 ),

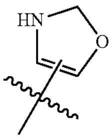 (e.g., 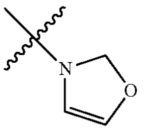 ),

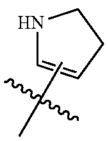 (e.g., 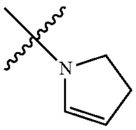 ) or

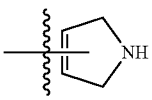 (e.g., 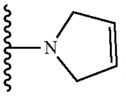 ).

In a preferred embodiment of the present invention, when Q is an unsubstituted or substituted $C_6$-$C_{10}$ aryl, the $C_6$-$C_{10}$ aryl is a phenyl.

In a preferred embodiment of the present invention, when Q is an unsubstituted or substituted 5-10 membered heteroaryl, the 5-10 membered heteroaryl is a 5-6 membered heteroaryl, and preferably imidazolyl (e.g., 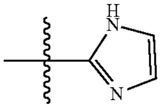 or 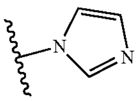 ).

oxazolyl (e.g., 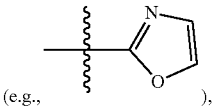 ), furanyl (e.g., 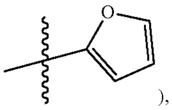 ), thienyl (e.g., 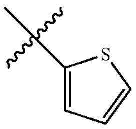 ), pyrrolyl (e.g., 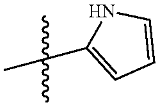 or 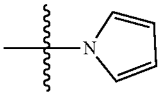 ), pyrazolyl (e.g., 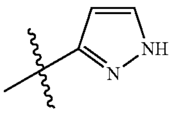 or 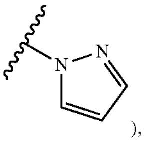 ), isoxazolyl (e.g., 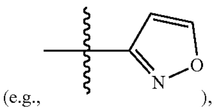 ), pyridinyl (e.g., 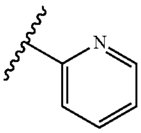 or 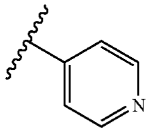), pyrimidinyl (e.g., 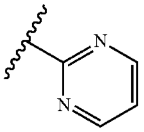), triazolyl (e.g., 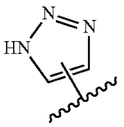 (e.g., 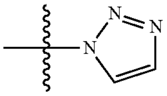), (e.g., 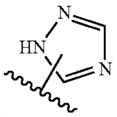 (e.g., 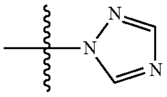), or

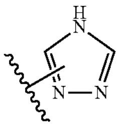 (e.g., 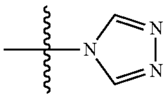 or

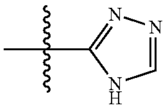)), or 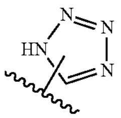

(e.g., 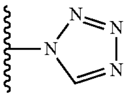 or 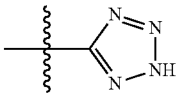).

In a preferred embodiment of the present invention, when Q is an unsubstituted or substituted 5-10 membered heteroaryl, the 5-10 membered heteroaryl is a 5-6 membered heteroaryl, and preferably imidazolyl (e.g., 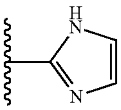 or 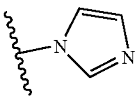), oxazolyl (e.g., 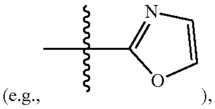 [SMILES: *c1ncco1]), furanyl (e.g., 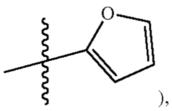), thienyl (e.g., 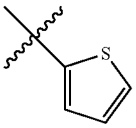), pyrrolyl (e.g., 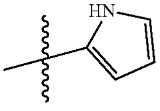 or 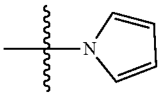), pyrazolyl (e.g., 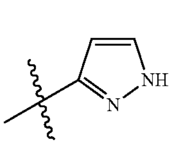 or 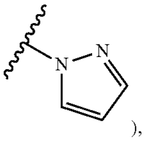), isoxazolyl (e.g., 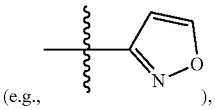), pyridinyl (e.g., 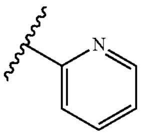 or 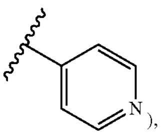), pyrimidinyl (e.g., 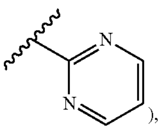), or triazolyl (e.g., 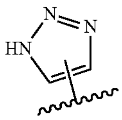 (e.g., 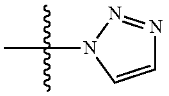), 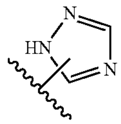 (e.g., 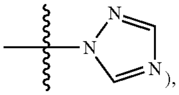), or 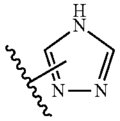 (e.g., 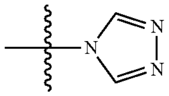 or 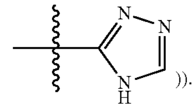)).

In a preferred embodiment of the present invention, when Q is an unsubstituted or substituted 5-10 membered heteroaryl, the 5-10 membered heteroaryl is a 5-6 membered heteroaryl, and preferably triazolyl (e.g., 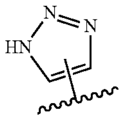 (e.g., 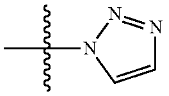), 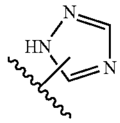 (e.g., 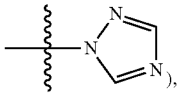), 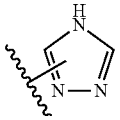 (e.g., 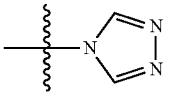 or 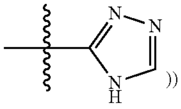)) or 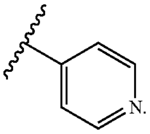.

In a preferred embodiment of the present invention, when Q is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted $C_3$-$C_{10}$ cycloalkyl, a substituted $C_6$-$C_{10}$ aryl, a substituted $C_3$-$C_9$ heterocycloalkyl, a substituted $C_3$-$C_9$ heterocycloalkenyl or a substituted 5-10 membered heteroaryl, the number of the substituents is independently 1, 2, 3 or 4.

In a preferred embodiment of the present invention, when Q is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted $C_3$-$C_{10}$ cycloalkyl, a substituted $C_6$-$C_{10}$ aryl, a substituted $C_3$-$C_9$ heterocycloalkyl, a substituted $C_3$-$C_9$ heterocycloalkenyl or a substituted 5-10 membered heteroaryl, and the substituent is halogen, the halogen is independently fluorine, chlorine, bromine, or iodine, and preferably fluorine.

In a preferred embodiment of the present invention, the $C_1$-$C_6$ alkyl (e.g., methyl, ethyl, propyl, butyl, pentyl or hexyl) in the $C_1$-$C_6$ alkyl or $C_1$-$C_6$ alkyl-O— that is unsubstituted or substituted with one or more $R^a$ is independently a $C_1$-$C_4$ alkyl (e.g., methyl, ethyl, n-propyl, isopropyl, n-butyl, isobutyl, sec-butyl or tert-butyl), and preferably methyl or isopropyl.

In a preferred embodiment of the present invention, the $C_3$-$C_6$ cycloalkyl in the $C_3$-$C_6$ cycloalkyl that is unsubstituted or substituted with one or more $R^a$ is independently cyclopropyl, cyclobutyl, cyclopentyl or cyclohexyl.

In a preferred embodiment of the present invention, when $R^a$ is halogen, the halogen is independently fluorine, chlorine, bromine or iodine.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each an unsubstituted or substituted $C_1$-$C_6$ alkyl, or an unsubstituted or substituted $C_1$-$C_6$ alkyl-O—, the $C_1$-$C_6$ alkyl (e.g., methyl, ethyl, propyl, butyl, pentyl or hexyl) is independently a $C_1$-$C_4$ alkyl (e.g., methyl, ethyl, n-propyl, isopropyl, n-butyl, isobutyl, sec-butyl or tert-butyl) or tert-pentyl(1,1-dimethyl-propyl).

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each an unsubstituted or substituted $C_2$-$C_6$ alkenyl, or an unsubstituted or substituted $C_2$-$C_6$ alkenyl-O—, the $C_2$-$C_6$ alkenyl is independently a $C_2$-$C_4$ alkenyl (e.g. ethenyl, propenyl (e.g., 1-propenyl or 2-propenyl), or butenyl (e.g., 2-butenyl 1-butenyl or butadienyl)), and preferably ethenyl.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each an unsubstituted or substituted $C_2$-$C_6$ alkynyl, the $C_2$-$C_6$ alkynyl is a $C_2$-$C_4$ alkynyl (e.g., ethynyl, propynyl (e.g., 1-propynyl or 2-propynyl), or butynyl (e.g., 2-butynyl, 1-butynyl or butadiynyl)), and preferably ethynyl.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each an unsubstituted or substituted $C_3$-$C_{10}$ cycloalkyl, the $C_3$-$C_{10}$ cycloalkyl is a $C_3$-$C_6$ cycloalkyl and preferably cyclopropyl, cyclobutyl, cyclopentyl and cyclohexyl.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each an unsubstituted or substituted $C_3$-$C_9$ heterocycloalkyl, the $C_3$-$C_9$ heterocycloalkyl is a $C_3$-$C_5$ heterocycloalkyl, wherein the $C_3$-$C_5$ heterocycloalkyl contains 1-3 heteroatoms selected from one or more of O, S and N; the $C_3$-$C_9$ heterocycloalkyl is preferably a $C_4$-$C_5$ heterocycloalkyl, wherein the $C_4$-$C_5$ heterocycloalkyl contains 1-2 heteroatoms selected from one or more of N, O and S; and the $C_3$-$C_9$ heterocycloalkyl is preferably oxetanyl (e.g., 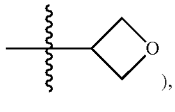), tetrahydrofuranyl (e.g., 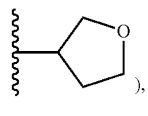), tetrahydropyranyl (e.g., 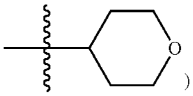)

or tetrahydrothienyl (e.g., 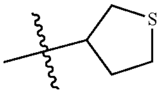).

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each an unsubstituted or substituted $C_3$-$C_9$ heterocycloalkenyl, the $C_3$-$C_9$ heterocycloalkenyl is a $C_3$-$C_5$ heterocycloalkenyl, wherein the $C_3$-$C_5$ heterocycloalkenyl contains 1-3 heteroatoms selected from one or more of O, S and N; and the $C_3$-$C_9$ heterocycloalkenyl is preferably a $C_4$-$C_5$ heterocycloalkenyl, wherein the $C_4$-$C_5$ heterocycloalkenyl contains 1-2 heteroatoms selected from one or more of N, O and S.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each an unsubstituted or substituted 5-10 membered heteroaryl, the 5-10 membered heteroaryl is a 5-6 membered heteroaryl, wherein the 5-6 membered heteroaryl contains 1-2 heteroatoms selected from one or two of N, O and S; and the 5-10 membered heteroaryl is preferably furanyl (e.g., 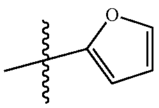 or 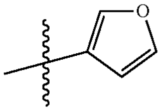)

or pyridinyl (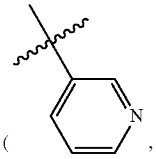, 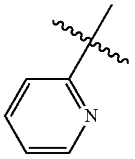 or 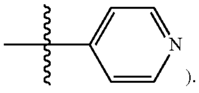).

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted $C_2$-$C_6$ alkynyl, a substituted $C_3$-$C_{10}$ cycloalkyl, a substituted phenyl, a substituted $C_3$-$C_9$ heterocycloalkyl, a substituted $C_3$-$C_5$ heterocycloalkenyl or a substituted 5-10 membered heteroaryl, and the substituent is halogen, the halogen is independently fluorine, chlorine, bromine or iodine, and preferably fluorine.

In a preferred embodiment of the present invention, when $R^d$ is independently halogen, the halogen is independently fluorine, chlorine, bromine or iodine, and preferably fluorine.

In a preferred embodiment of the present invention, the number of $R^d$ is independently 1, 2, 3, or 4, and preferably 1 or 2.

In a preferred embodiment of the present invention, the $C_1$-$C_6$ alkyl (e.g., methyl, ethyl, propyl, butyl, pentyl or hexyl) in the $C_1$-$C_6$ alkyl or $C_1$-$C_6$ alkyl-O— that is unsubstituted or substituted with one or more $R^d$ is independently a $C_1$-$C_4$ alkyl (e.g., methyl, ethyl, n-propyl, isopropyl, n-butyl, isobutyl, sec-butyl or tert-butyl).

In a preferred embodiment of the present invention, the $C_3$-$C_6$ cycloalkyl in the $C_3$-$C_6$ cycloalkyl that is unsubstituted or substituted with one or more $R^d$ is independently cyclopropyl, cyclobutyl, cyclopentyl or cyclohexyl.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted $C_2$-$C_6$ alkynyl, a substituted $C_3$-$C_{10}$ cycloalkyl, a substituted phenyl, a substituted $C_3$-$C_9$ heterocycloalkyl, a substituted $C_3$-$C_9$ heterocycloalkenyl or a substituted 5-10 membered heteroaryl, the number of the substituents is independently 1, 2, 3 or 4, and preferably 1 or 2.

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, $R^{1-11}$ and $R^{1-12}$, $R^{1-14}$ and $R^{1-15}$, $R^{1-21}$ and $R^{1-22}$, $R^{1-23}$ and $R^{1-24}$, or $R^{1-25}$ and $R^{1-26}$, each independently together with the N atom to which they directly link, form an unsubstituted or substituted $C_3$-$C_9$ heterocycloalkyl, the $C_3$-$C_9$ heterocycloalkyl contains no heteroatom or one heteroatom selected from one of O, S and N in addition to the existing N atom, and is preferably a $C_5$-$C_8$ heterocycloalkyl.

In a preferred embodiment of the present invention, when $R^{1-3}$ and $R^{1-4}$, $R^{1-5}$ and $R^{1-6}$, $R^{1-7}$ and $R^{1-3}$, $R^{1-9}$ and $R^{1-10}$, $R^{1-11}$ and $R^{1-12}$, $R^{1-14}$ and $R^{1-15}$, $R^{1-21}$ and $R^{1-22}$, $R^{1-23}$ and $R^{1-24}$, or $R^{1-25}$ and $R^{1-26}$, each independently together with the N atom to which they directly link, form an unsubstituted or substituted $C_3$-$C_9$ heterocycloalkenyl, the $C_3$-$C_9$ heterocycloalkenyl contains no heteroatom or one heteroatom selected from one of O, S and N in addition to the existing N atom, and is preferably a $C_3$-$C_5$ heterocycloalkenyl.

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, $R^{1-11}$ and $R^{1-12}$, $R^{1-14}$ and $R^{1-15}$, $R^{1-21}$ and $R^{1-22}$, $R^{1-23}$ and $R^{1-24}$, or $R^{1-25}$ and $R^{1-26}$, each independently together with the N atom to which they directly link, form an unsubstituted or substituted 5-10 membered heteroaryl, the 5-10 membered heteroaryl contains no heteroatom or one heteroatom selected from one of O, S and N in addition to the existing N atom, and is preferably a 5-6 membered heteroaryl.

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, $R^{1-11}$ and $R^{1-12}$, $R^{1-14}$ and $R^{1-15}$, $R^{1-21}$ and $R^{1-22}$, $R^{1-23}$ and $R^{1-24}$, or $R^{1-25}$ and $R^{1-26}$, each independently together with the N atom to which they directly link, form a substituted $C_3$-$C_9$ heterocycloalkyl, a substituted $C_3$-$C_5$ heterocycloalkenyl or a substituted 5-10 membered heteroaryl, and the substituent is halogen, the halogen is independently fluorine, chlorine, bromine or iodine.

In a preferred embodiment of the present invention, the $C_1$-$C_8$ alkyl (e.g., methyl, ethyl, propyl, butyl, pentyl or hexyl) in the $C_1$-$C_6$ alkyl or $C_1$-$C_6$ alkyl-O— that is unsubstituted or substituted with one or more RE is independently a $C_1$-$C_4$ alkyl (e.g., methyl, ethyl, n-propyl, isopropyl, n-butyl, isobutyl, sec-butyl or tert-butyl).

In a preferred embodiment of the present invention, the $C_3$-$C_6$ cycloalkyl in the $C_3$-$C_6$ cycloalkyl that is unsubstituted or substituted with one or more R$ is independently cyclopropyl, cyclobutyl, cyclopentyl and cyclohexyl.

In a preferred embodiment of the present invention, when $R^b$ is halogen, the halogen is independently fluorine, chlorine, bromine or iodine.

In a preferred embodiment of the present invention, when $R^{1-3}$ and $R^{1-4}$, $R^{1-5}$ and $R^{1-6}$, $R^{1-1}$ and $R^{1-8}$, $R^{1-9}$ and $R^{1-10}$, $R^{1-11}$ and $R^{1-12}$, $R^{1-14}$ and $R^{1-15}$, $R^{1-21}$ and $R^{1-22}$, $R^{1-23}$ and $R^{1-24}$, or $R^{1-25}$ and $R^{1-26}$, each independently together with the N atom to which they directly link, form a substituted $C_3$-$C_9$ heterocycloalkyl, a substituted $C_3$-$C_9$ heterocycloalkenyl or a substituted 5-10 membered heteroaryl, the number of the substituents is independently 1, 2, 3 or 4, and preferably 1 or 2.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each a substituted $C_1$-$C_6$ alkyl, the substituted $C_1$-$C_8$ alkyl is

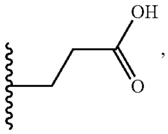 , 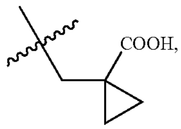

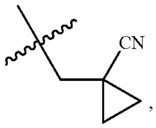 , 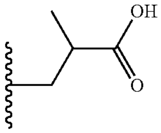 , 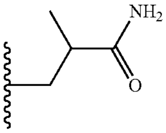 ,

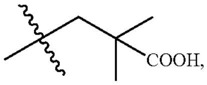 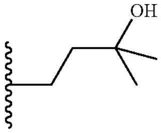 ,

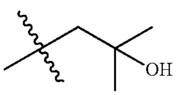 or 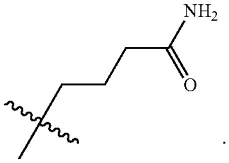 .

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each a substituted $C_1$-$C_6$ alkyl, the substituted $C_1$-$C_6$ alkyl is

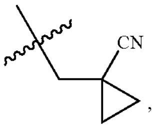 , 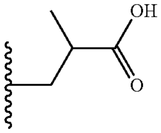 , 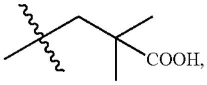

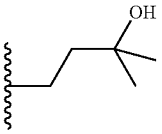 , 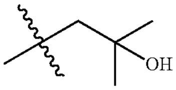 or

-continued

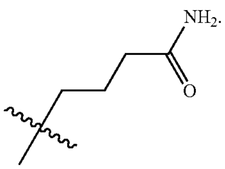

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each a substituted $C_2$-$C_6$ alkenyl, the substituted $C_2$-$C_6$ alkenyl is

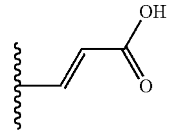 or 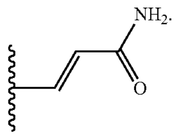

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each a substituted $C_2$-$C_6$ alkynyl, the substituted $C_2$-$C_6$ alkynyl is

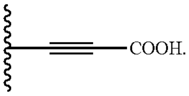 [SMILES: *C#CC(=O)O]

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each a substituted $C_3$-$C_{10}$ cycloalkyl, the substituted $C_3$-$C_{10}$ cycloalkyl is

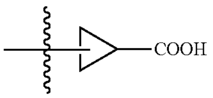 (e.g., 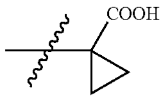 ),

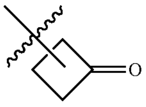 (e.g., 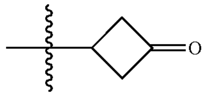 ),

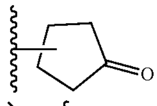 (e.g., 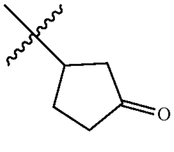 ),

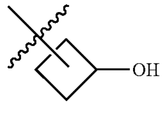 (e.g., 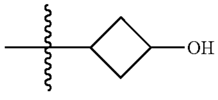 ),

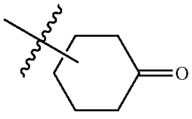 (e.g., 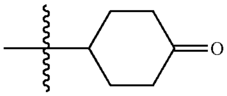 ),

-continued

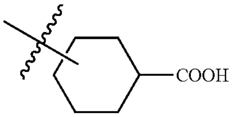

(e.g., 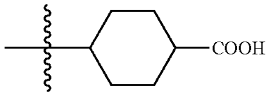 ) or

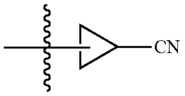

(e.g., 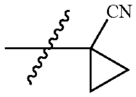 ).

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each a substituted $C_3$-$C_9$ heterocycloalkyl, the substituted $C_3$-$C_9$ heterocycloalkyl is

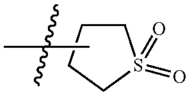 (e.g., 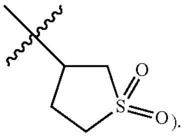).

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each an unsubstituted or substituted phenyl, the substituted phenyl is

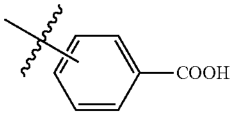 (e.g., 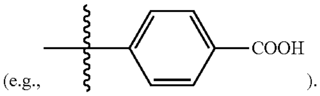 ).

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$, $R^{1-13}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each an unsubstituted or substituted 5-10 membered heteroaryl, the substituted 5-10 membered heteroaryl is

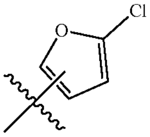 (e.g., 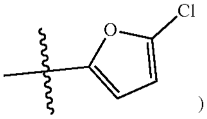 ) or

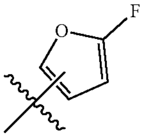 (e.g., 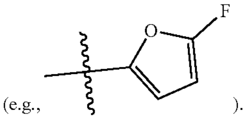 ).

In a preferred embodiment of the present invention, the $C_1$-$C_6$ alkyl substituted with one or more $R^a$ is

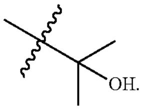 [SMILES: *C(C)(C)O]

In a preferred embodiment of the present invention, the $C_1$-$C_6$ alkyl substituted with one or more $R^a$ is

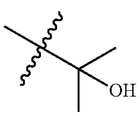 or 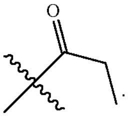.

In a preferred embodiment of the present invention, the $C_3$-$C_6$ cycloalkyl substituted with one or more $R^a$ is

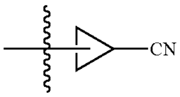 (e.g., 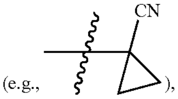),

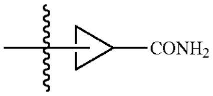 (e.g., 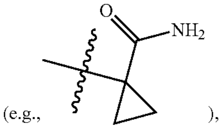 ),

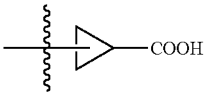 (e.g., 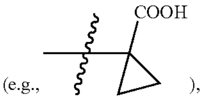 ), or

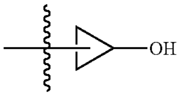 (e.g., 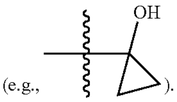).

In a preferred embodiment of the present invention, the $C_3$-$C_6$ cycloalkyl substituted with one or more $R^a$ is

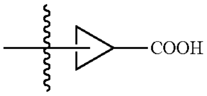 (e.g., 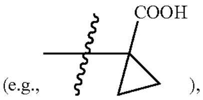 ), or

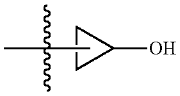 (e.g., 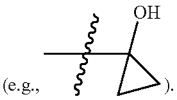).

In a preferred embodiment of the present invention, the $C_3$-$C_6$ cycloalkyl substituted with one or more $R^d$ is

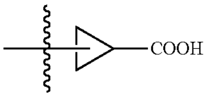 (e.g., 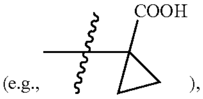 ), or

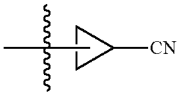 (e.g., 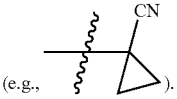).

In a preferred embodiment of the present invention, —N($R^{1-21}R^{1-22}$) is —$NHCH_3$ or —$NH_2$.

In a preferred embodiment of the present invention, —C(═O)—N($R^{1-23}R^{1-24}$) is —C(═O)—$NH_2$ or —C(═O)—$NHCH_3$.

In a preferred embodiment of the present invention, —S(═O)$_2$—N($R^{1-25}R^{1-26}$) is —S(═O)$_2$—$NH_2$.

In a preferred embodiment of the present invention, —C(═O)—O—$R^{1-27}$ is —COOH, —COOCH, or —$COOC_2H_5$.

In a preferred embodiment of the present invention, —C(═O)—O—$R^{1-27}$ is —COOH or —$COOCH_3$.

In a preferred embodiment of the present invention, —NH—C(═O)—$R^{1-1}$ is —NH—C(═O)—$CH_3$, —NH—C(═O)—O—$CH_3$,

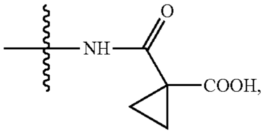
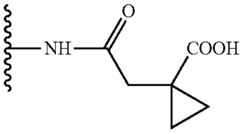
,
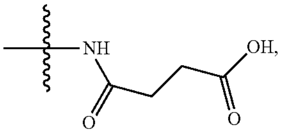
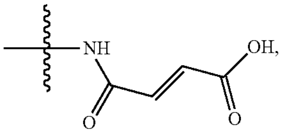
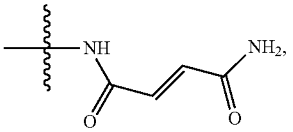
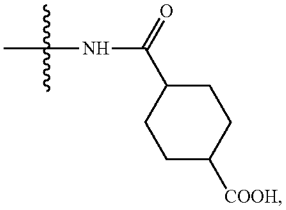
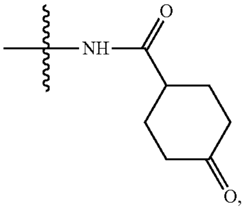
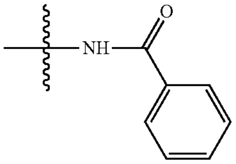
,
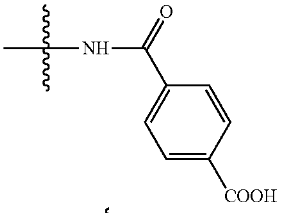
,
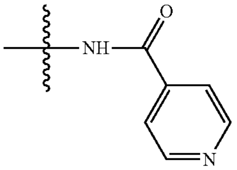
,
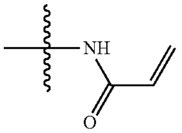
,
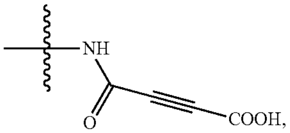
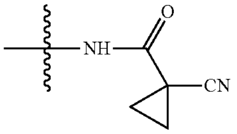
,
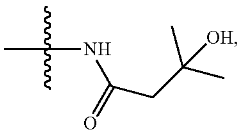
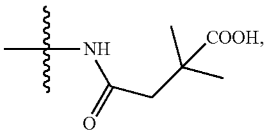

-continued

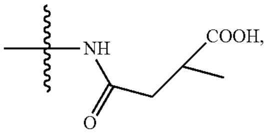
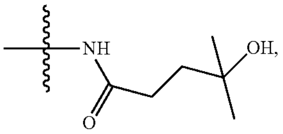
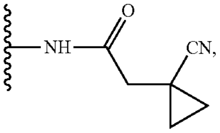
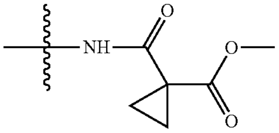
or
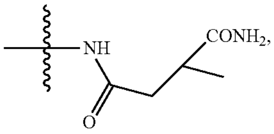

In a preferred embodiment of the present invention, —NH—C(═O)—$R^{1-1}$ is

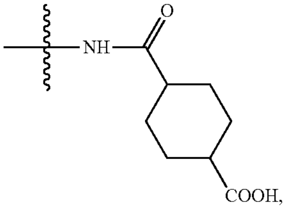
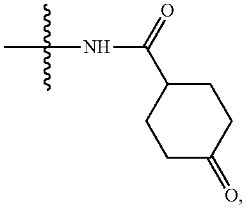
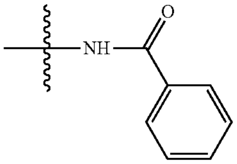
,
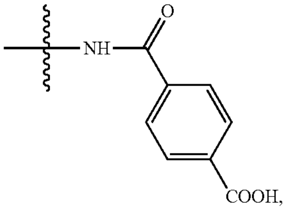
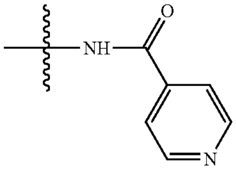
,
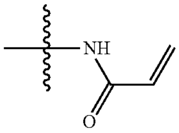
,
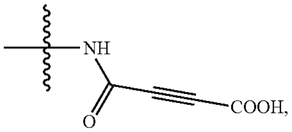
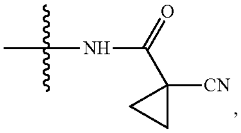
,
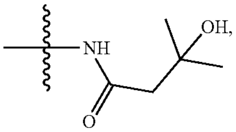
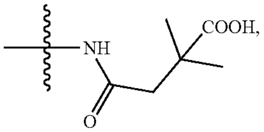
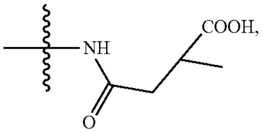
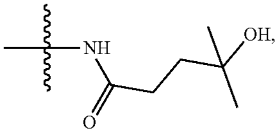
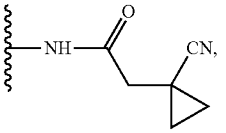
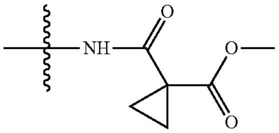
or -continued

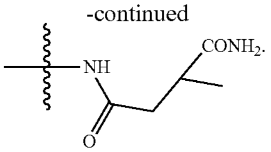

In a preferred embodiment of the present invention, —C(═O)—$R^{1-2}$ is —C(═O)—$CH_3$ or —C(═O)—O—$CH_3$.

In a preferred embodiment of the present invention, —O—C(═O)—N($R^{1-3}R^{1-4}$) is —O—C(═O)—NH—$CH_3$.

In a preferred embodiment of the present invention, —C(═O)—N($R^{1-5}R^{1-6}$) is —C(═O)—NH—$CH_3$.

In a preferred embodiment of the present invention, —C(═NH)—N($R^{1-7}R^{1-8}$) is —C(═NH)—NH—$CH_3$.

In a preferred embodiment of the present invention, —S(═O)$_2$—N($R^{1-9}R^{1-10}$) is —S(═O)$_2$—NH—$CH_3$ or —$SO_2NH_2$.

In a preferred embodiment of the present invention, —O—C(═O)—$R^{1-13}$ is —O—C(═O)—NH—$CH_3$.

In a preferred embodiment of the present invention, —N($R^{1-14}R^{1-15}$) is

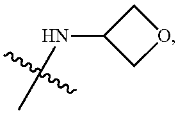 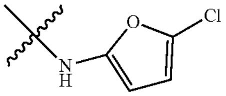 ,
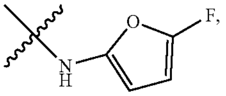 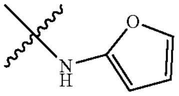 ,
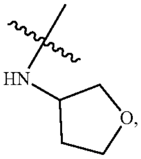 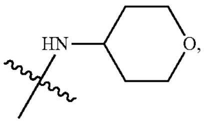
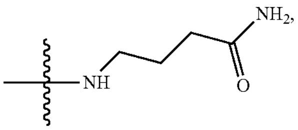 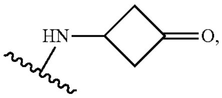
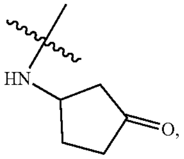 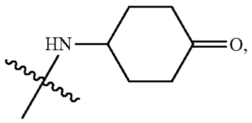
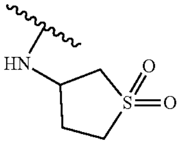 or 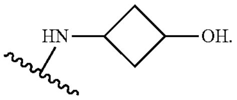

In a preferred embodiment of the present invention, Q is —N($R^{1-14}R^{1-15}$), e.g., ~$NH_2$.

In a preferred embodiment of the present invention, —NH—S(═O)$_2$—$R^{1-16}$ is —NH—S(═O)$_2$—$CH_3$.

In a preferred embodiment of the present invention, when Q is a substituted $C_1$-$C_6$ alkyl, the substituted $C_1$-$C_6$ alkyl is

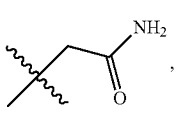 , 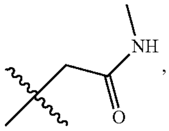 , or 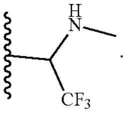 .

In a preferred embodiment of the present invention, when Q is a substituted $C_3$-$C_{10}$ cycloalkyl, the substituted $C_3$-$C_{10}$ cycloalkyl is

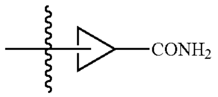 (e.g., 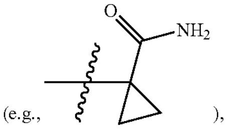 ),
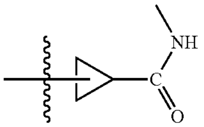 (e.g., 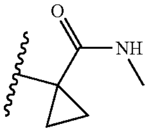 ) or
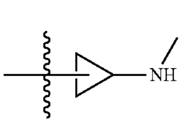 (e.g., 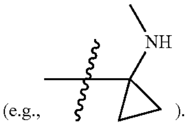 ).

In a preferred embodiment of the present invention, when Q is a substituted $C_3$-$C_9$ heterocycloalkyl, the substituted $C_3$-$C_9$ heterocycloalkyl is

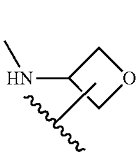 (e.g., 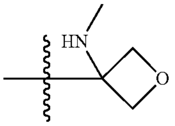 ),
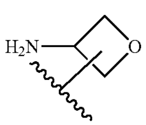 (e.g., 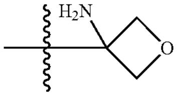 ),
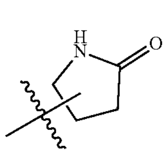 (e.g., 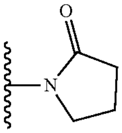 ),
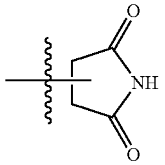 (e.g., 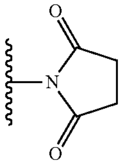 ) or
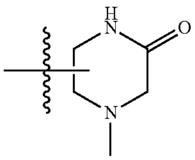 (e.g., 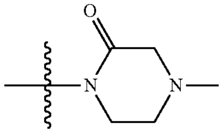 ).

In a preferred embodiment of the present invention, when Q is a substituted $C_3$-$C_9$ heterocycloalkyl, the substituted $C_3$-$C_9$ heterocycloalkyl is

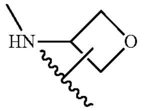
(e.g.,
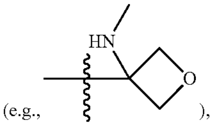
),
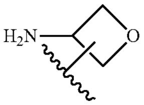
(e.g.,
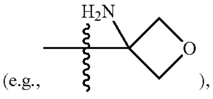
), or
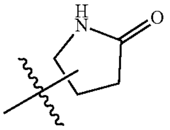
(e.g.,
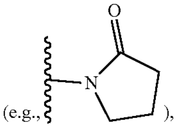
), In a preferred embodiment of the present invention, when Q is a substituted $C_3$-$C_9$ heterocycloalkenyl, the substituted $C_3$-$C_9$ heterocycloalkenyl is

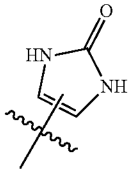
(e.g.,
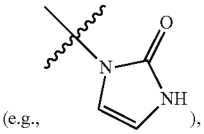
),
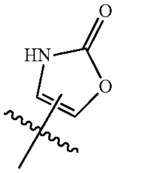
(e.g.,
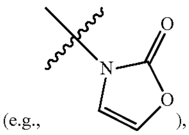
),
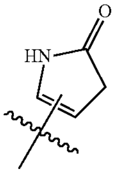
(e.g.,
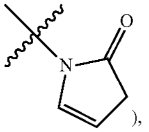
),
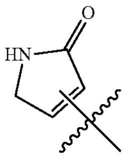
(e.g.,
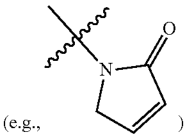
) or
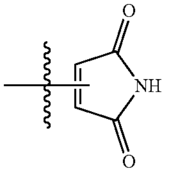
(e.g.,
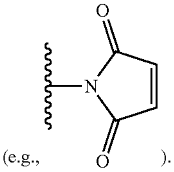
).

In a preferred embodiment of the present invention, when Q is a substituted 5-10 membered heteroaryl, the substituted 5-10 membered heteroaryl is

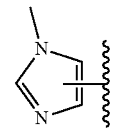
(e.g.,
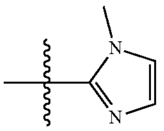
),

-continued

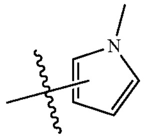
(e.g.,
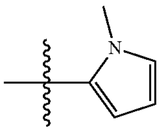
),
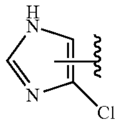
(e.g.,
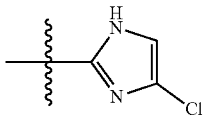
),
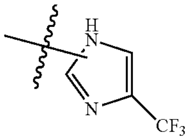
(e.g.,
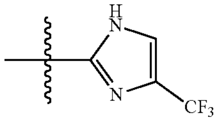
or
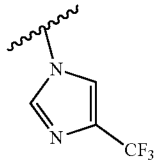
),
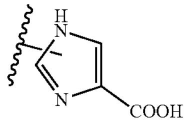
(e.g.,
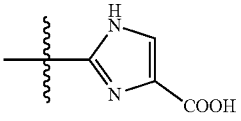
or
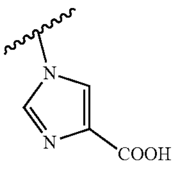
),
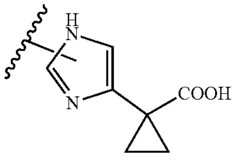
(e.g.,
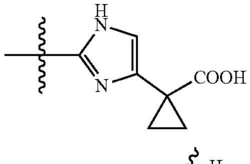
or
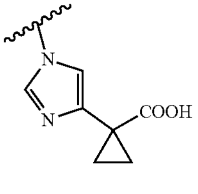
),
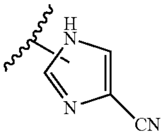
(e.g.,
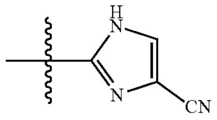
or
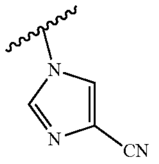
),
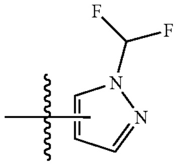
(e.g.,
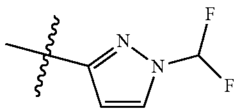
), -continued
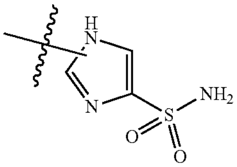
(e.g., 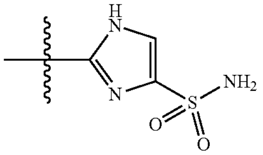 ),
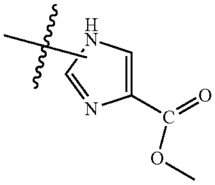
(e.g., 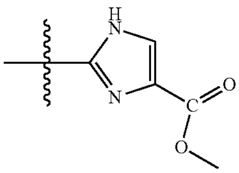 or 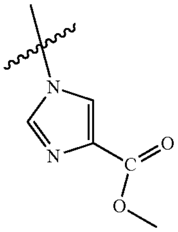 ),
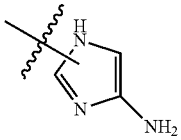
(e.g., 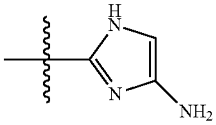 or 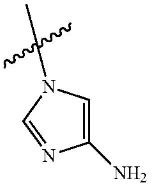 ),
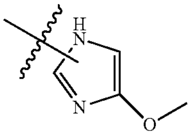
(e.g., 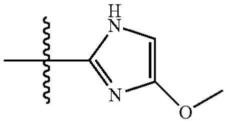 or 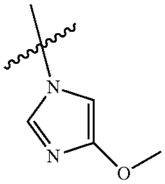 ),
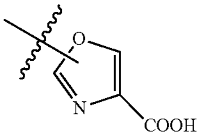 (e.g., 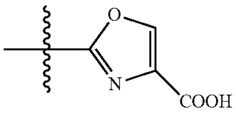 ),
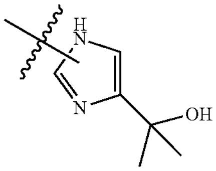
-continued
(e.g., 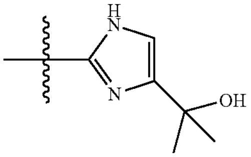 or 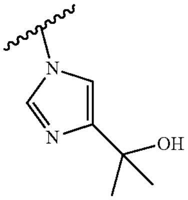 ),
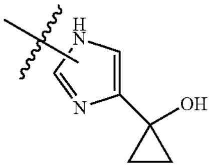
(e.g., 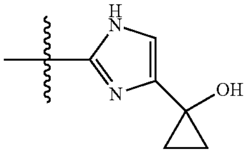 or 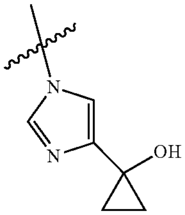 ),
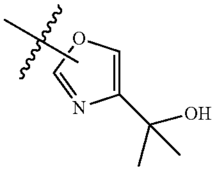 (e.g., 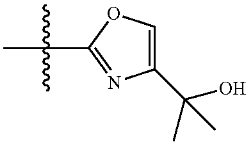 ),
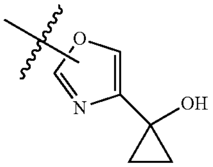 (e.g., 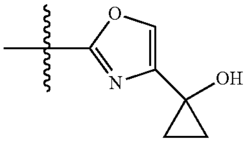 ),
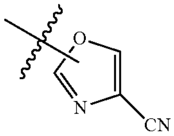 (e.g., 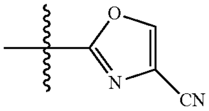 ),
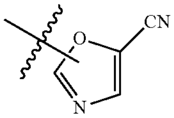 (e.g., 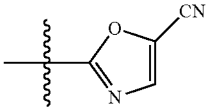 ),
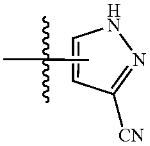 (e.g., 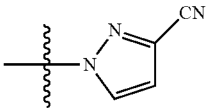 ),
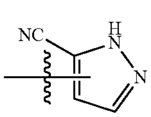 (e.g., 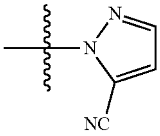 ),
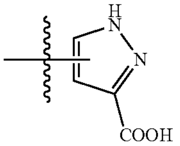 (e.g., 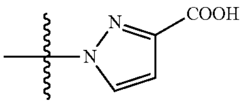 ), -continued
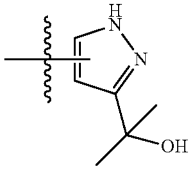 (e.g., 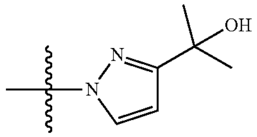),
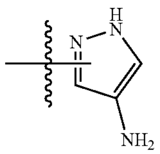 (e.g., 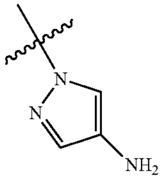),
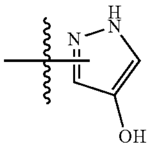 (e.g., 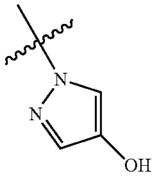),
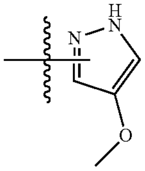 (e.g., 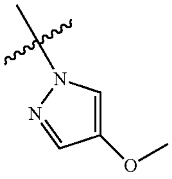),
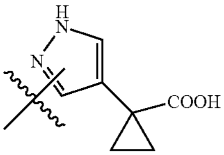 (e.g., 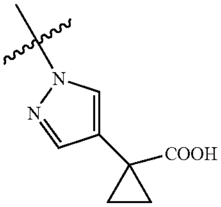),
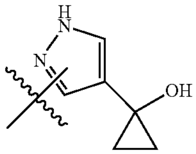 (e.g., 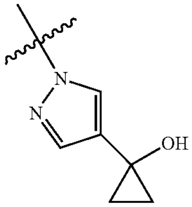),
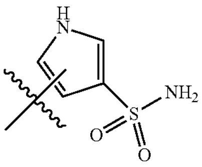 (e.g., 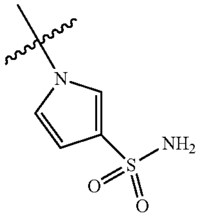),
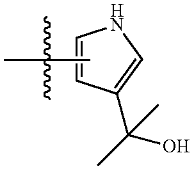 (e.g., 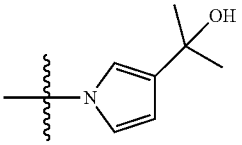),
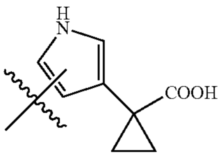 (e.g., 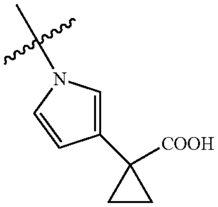),
-continued
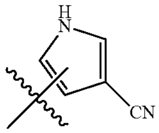 (e.g., 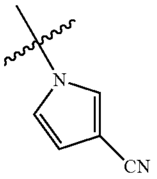),
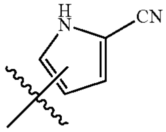 (e.g., 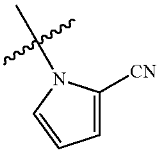),
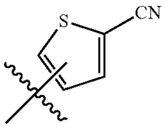 (e.g., 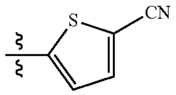),
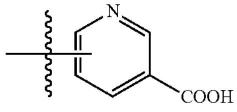 (e.g., 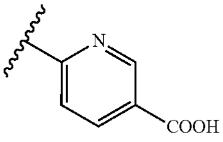),
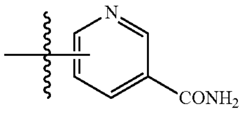 (e.g., 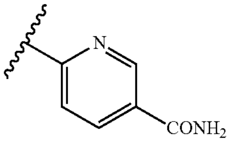),
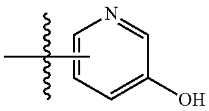 (e.g., 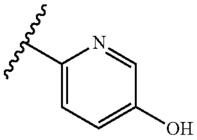),
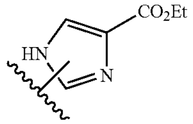 (e.g., 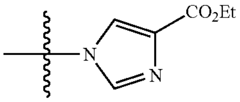),
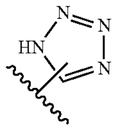 (e.g., 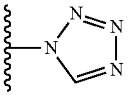 or 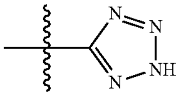),
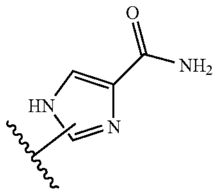 (e.g., 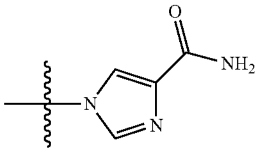),
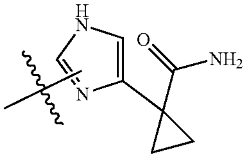 (e.g., 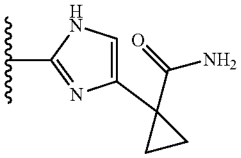), -continued
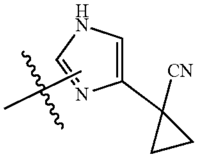
(e.g.,
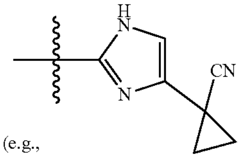
) or
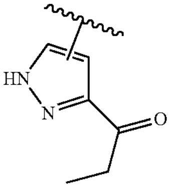
(e.g.,
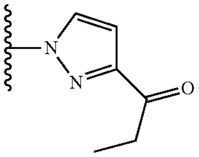
).
In a preferred embodiment of the present invention, when Q is a substituted 5-10 membered heteroaryl, the substituted 5-10 membered heteroaryl is
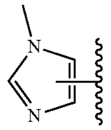
(e.g.,
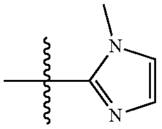
),
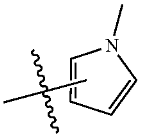
(e.g.,
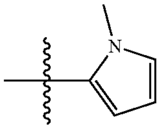
),
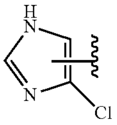
(e.g.,
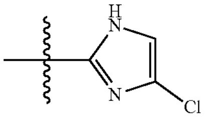
),
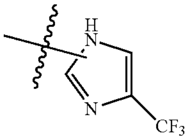
(e.g.,
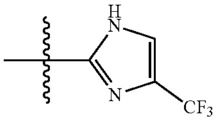
or
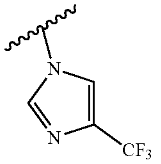
),
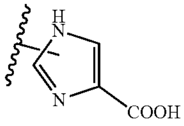
(e.g.,
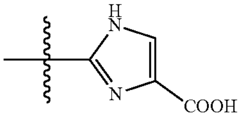
or
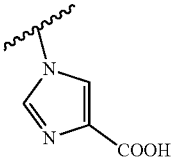
),
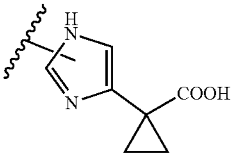
-continued
(e.g.,
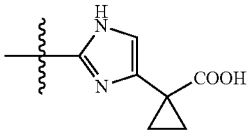
or
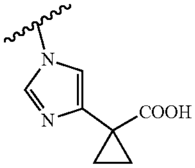
),
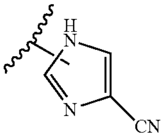
(e.g.,
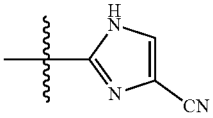
or
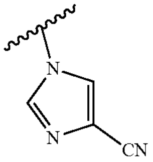
),
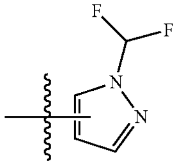
(e.g.,
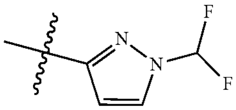
),
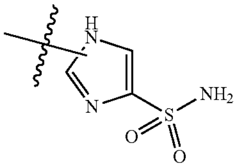
(e.g.,
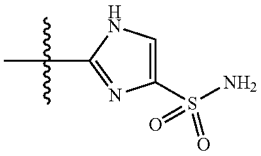
),
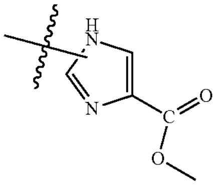
(e.g.,
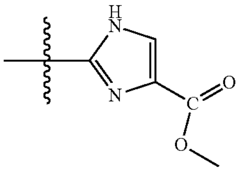
or
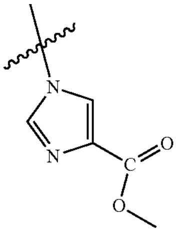
),
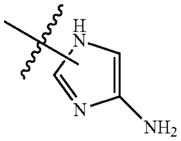
(e.g.,
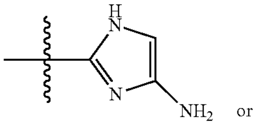
or
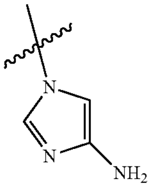
), -continued
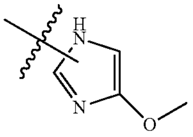
(e.g., 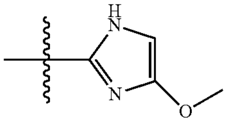 or 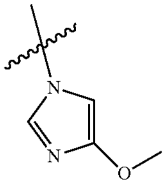 ),
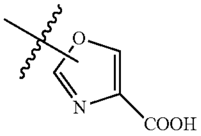 (e.g., 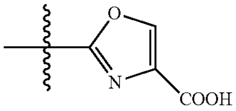 ),
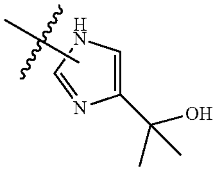
(e.g., 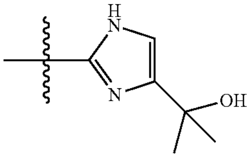 or 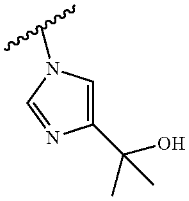 ),
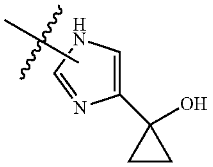
(e.g., 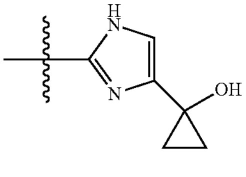 or 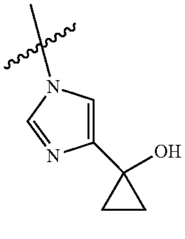 ),
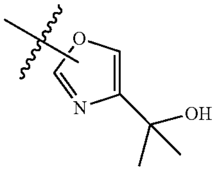 (e.g., 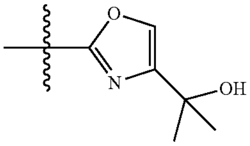 ),
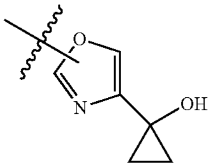 (e.g., 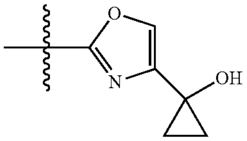 ),
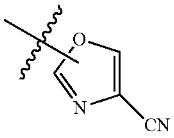 (e.g., 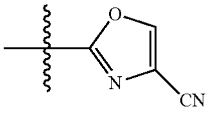 ),
-continued
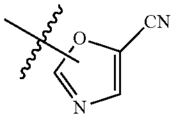 (e.g., 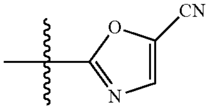 ),
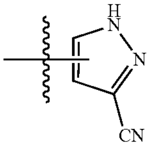 (e.g., 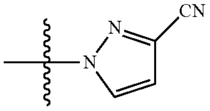 ),
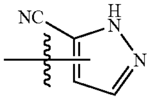 (e.g., 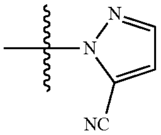 ),
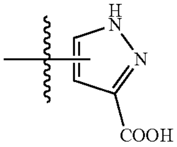 (e.g., 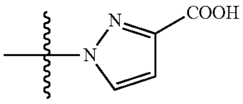 ),
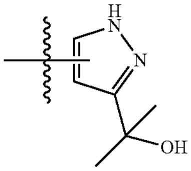 (e.g., 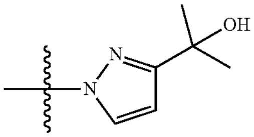 ),
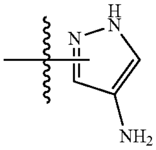 (e.g., 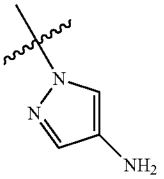 ),
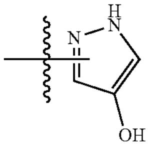 (e.g., 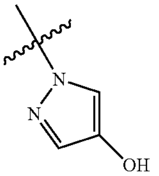 ),
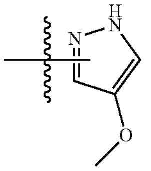 (e.g., 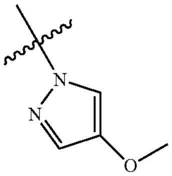 ),
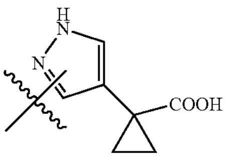 (e.g., 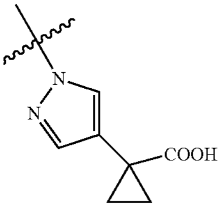 ),
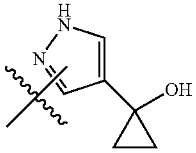 (e.g., 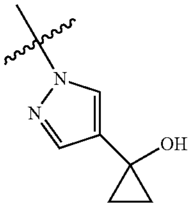 ), -continued
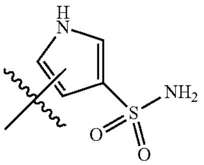 (e.g., 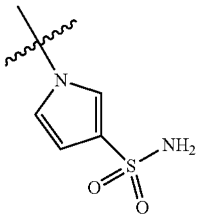 ),
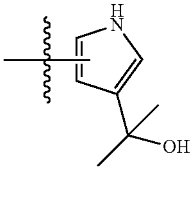 (e.g., 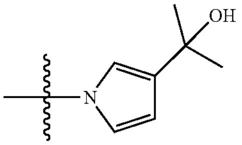 ),
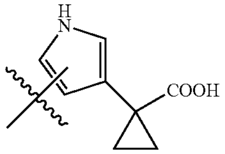 (e.g., 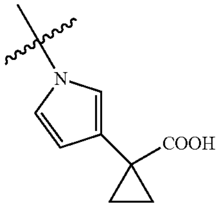 ),
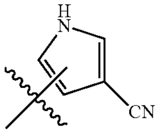 (e.g., 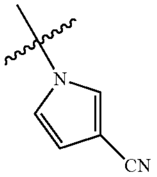 ),
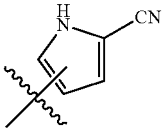 (e.g., 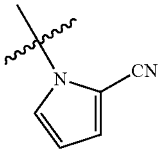 ),
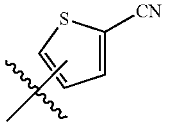 (e.g., 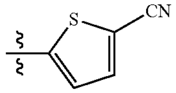 ),
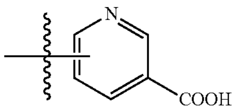 (e.g., 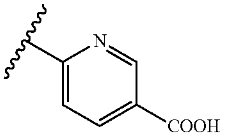 ),
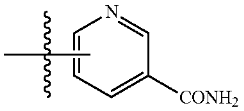 (e.g., 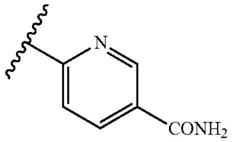 ) or
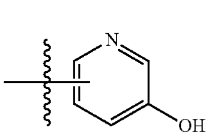 (e.g., 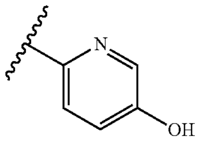 ).
In a preferred embodiment of the present invention, when Q is a substituted 5-10 membered heteroaryl, the substituted 5-10 membered heteroaryl is
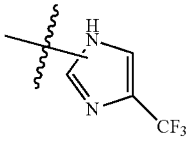
(e.g., 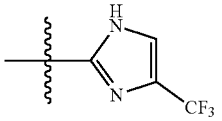 or 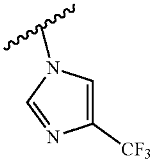 ),
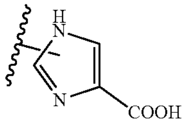
(e.g., 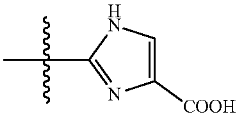 or 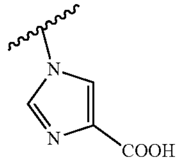 ),
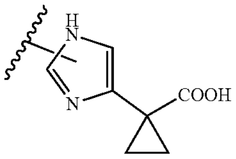
(e.g., 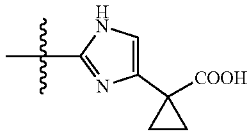 or 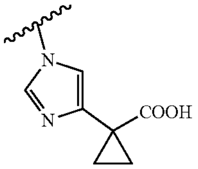 ),
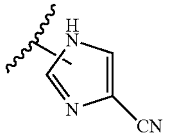
(e.g., 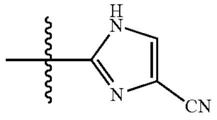 or 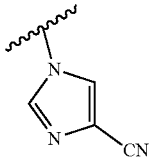 ),
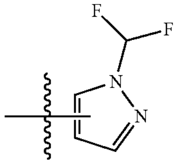 (e.g., 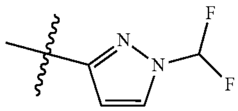 ),
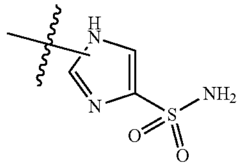
(e.g., 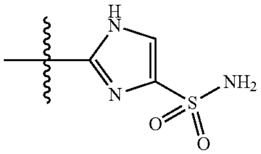 ), -continued
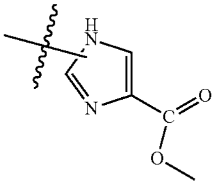
(e.g., 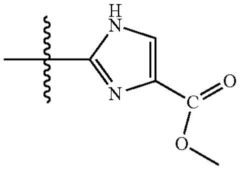 or 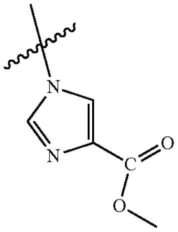 ),
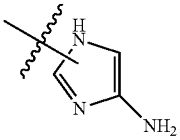
(e.g., 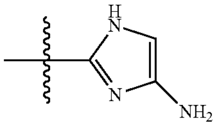 or 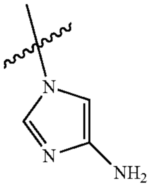 ),
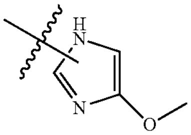
(e.g., 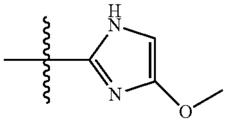 or 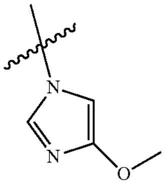 ),
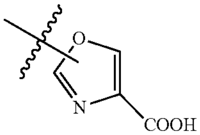 (e.g., 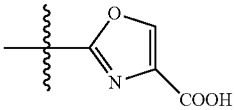 ),
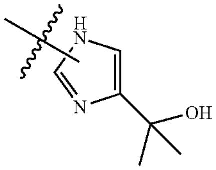
(e.g., 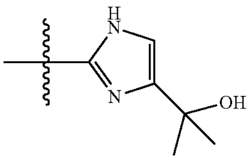 or 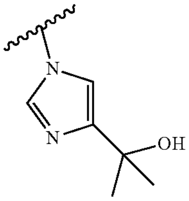 ),
-continued
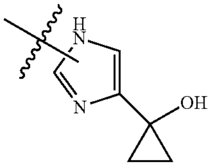
(e.g., 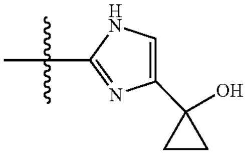 or 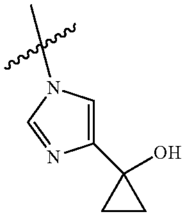 ),
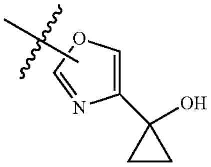 (e.g., 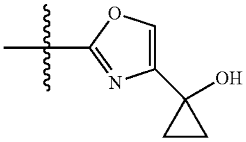 ),
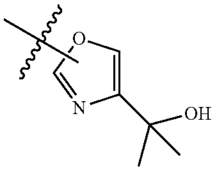 (e.g., 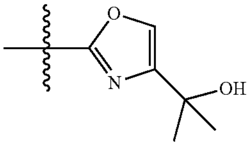 ),
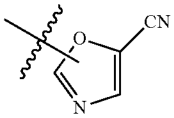 (e.g., 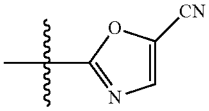 ),
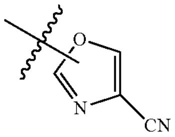 (e.g., 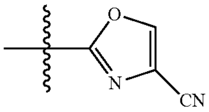 ),
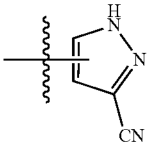 (e.g., 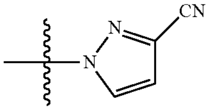 ),
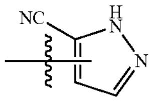 (e.g., 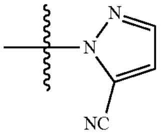 ),
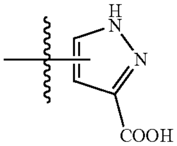 (e.g., 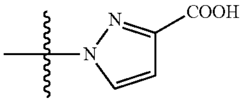 ),
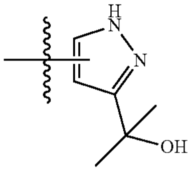 (e.g., 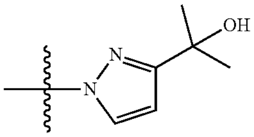 ), -continued
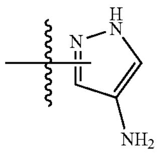
(e.g.,
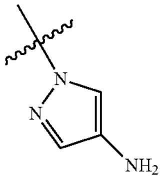
),
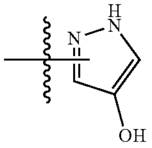
(e.g.,
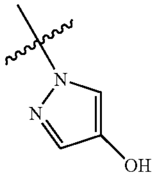
),
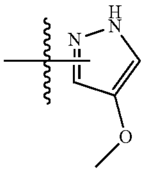
(e.g.,
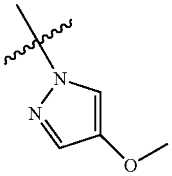
),
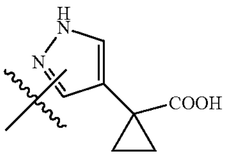
(e.g.,
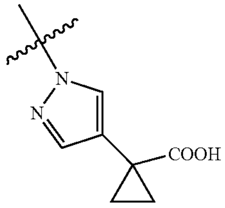
),
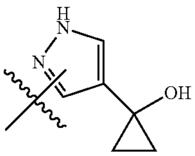
(e.g.,
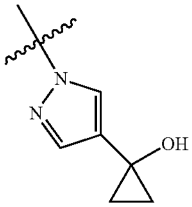
),
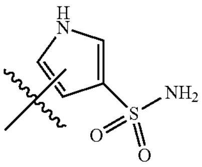
(e.g.,
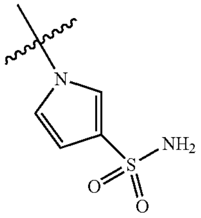
),
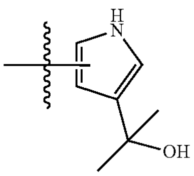
(e.g.,
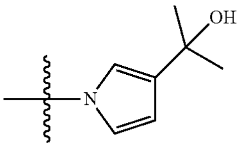
),
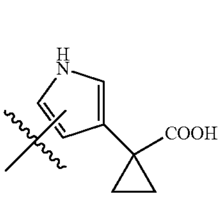
(e.g.,
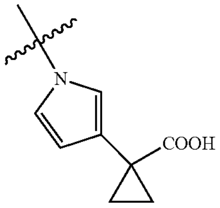
),
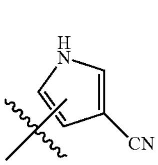
(e.g.,
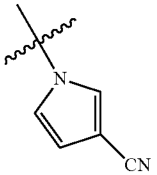
),
-continued
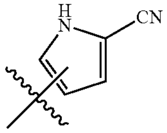
(e.g.,
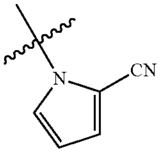
),
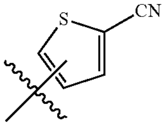
(e.g.,
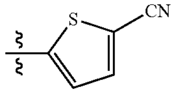
),
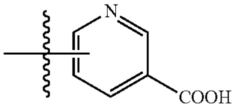
(e.g.,
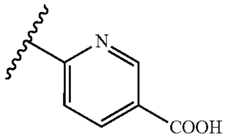
),
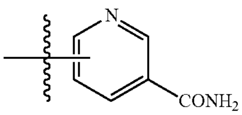
(e.g.,
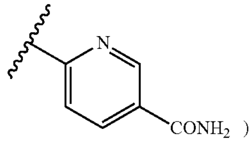
) or
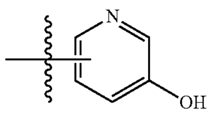
(e.g.,
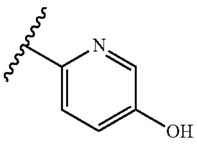
).
In a preferred embodiment of the present invention, Q is H, —OH, —$CF_3$, —CN, —$NH_2$, —NH—C(=O)—$CH_3$, —NH—C(=O)—O—$CH_3$,
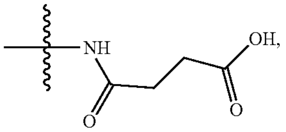
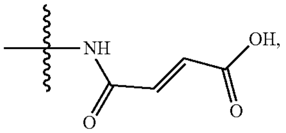
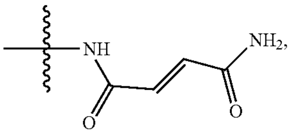
—C(=O)—$CH_3$, —C(=O)—$C_2H_5$, —C(=O)—O—$CH_3$, —O—C(=O)—NH—$CH_3$, —C(=O)—NH—$CH_3$, —C(=NH)—NH—$CH_3$, —S(=O)$_2$—NH—$CH_3$,
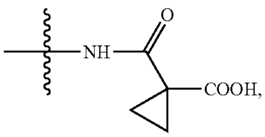
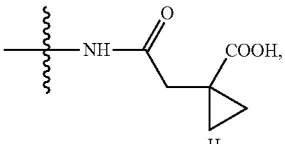
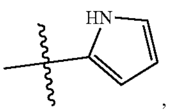
,
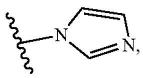
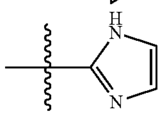
, -continued
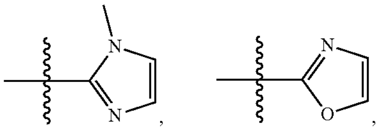
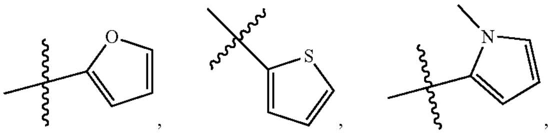
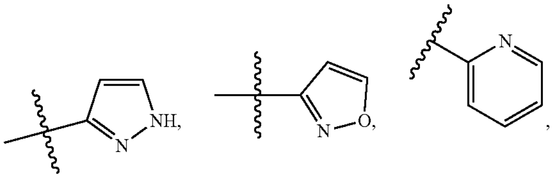
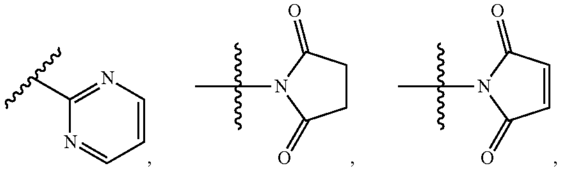
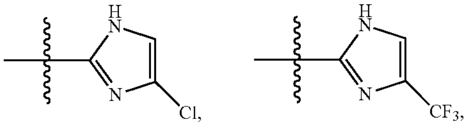
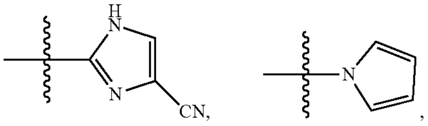
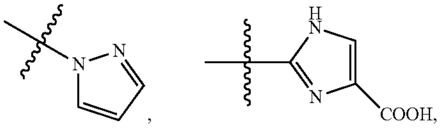
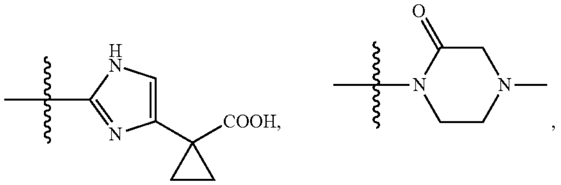
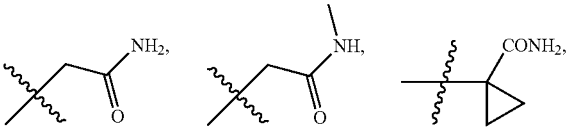
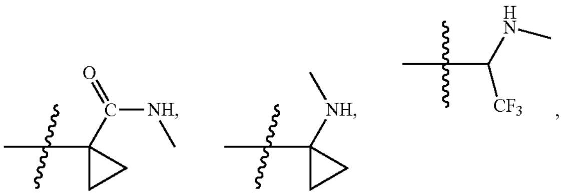
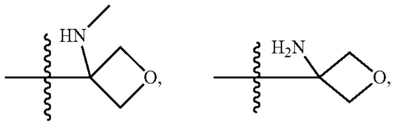
-continued
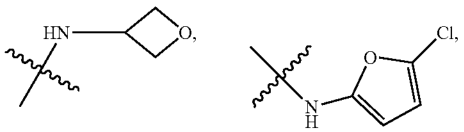
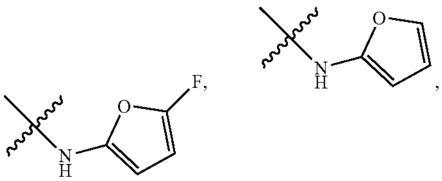
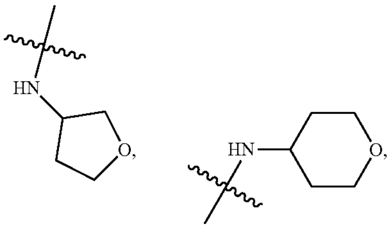
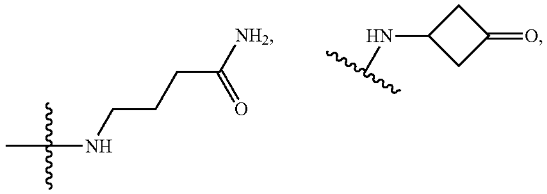
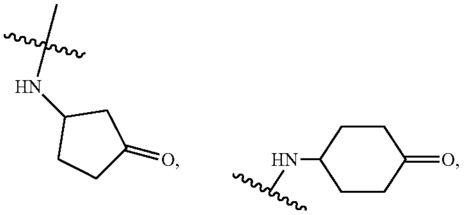
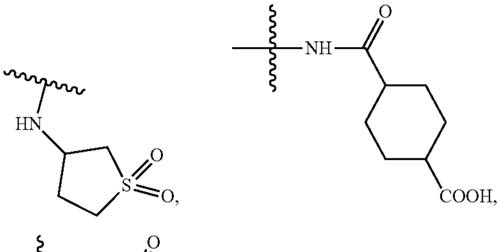
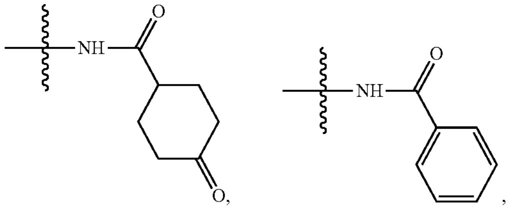
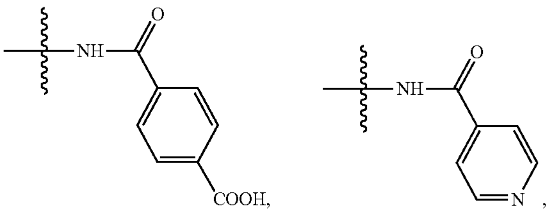

-continued
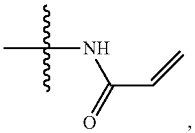
,
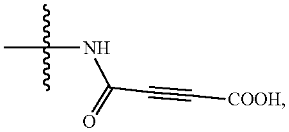
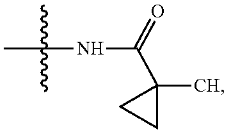
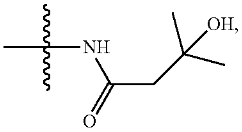
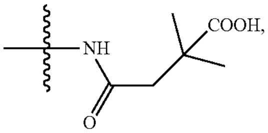
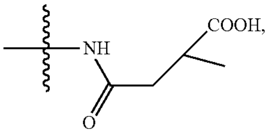
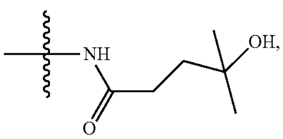
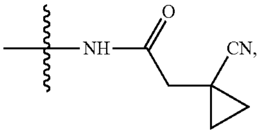
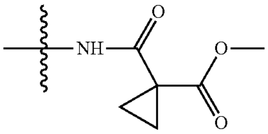
,
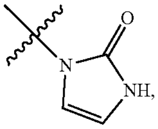
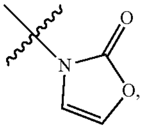
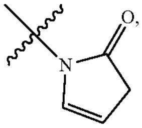
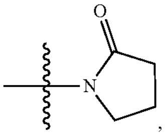
,
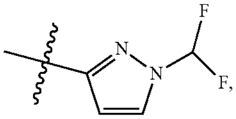
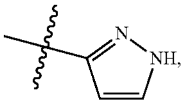
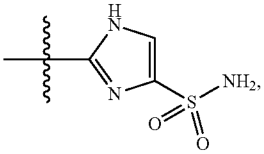
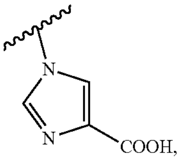
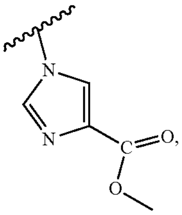
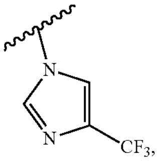
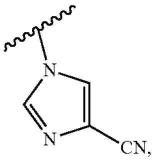
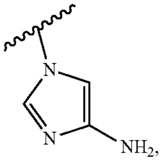
-continued
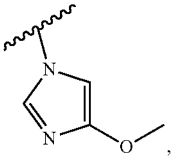
,
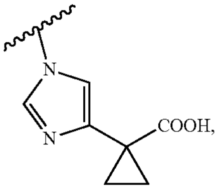
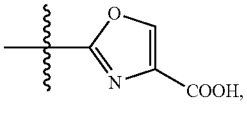
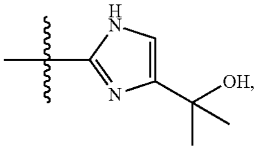
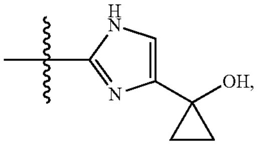
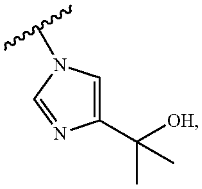
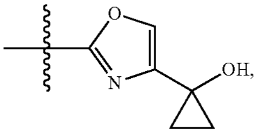
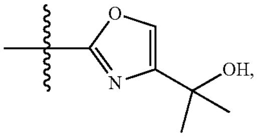
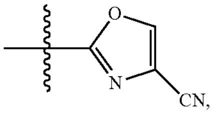
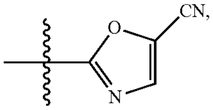
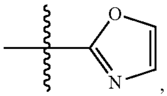
,
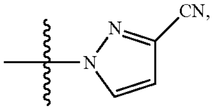
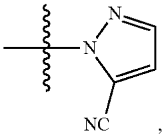
,
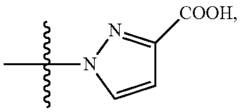
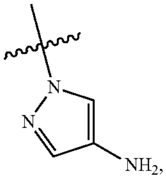
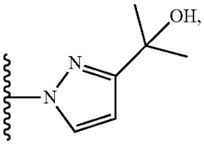

-continued
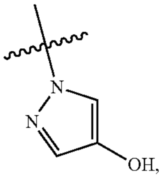
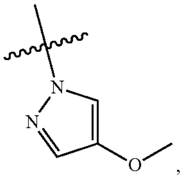
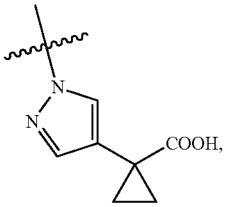
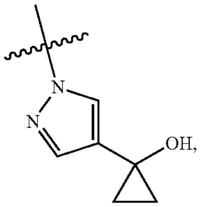
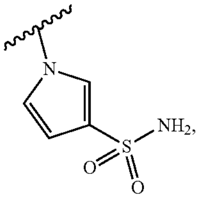
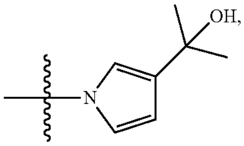
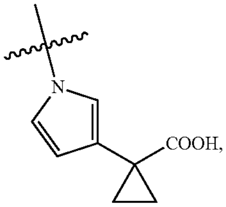
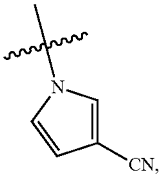
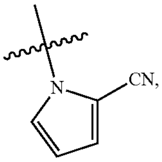
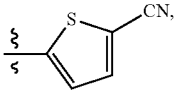
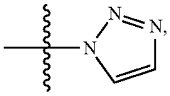
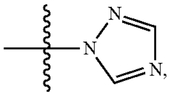
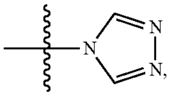
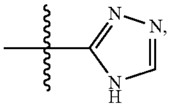
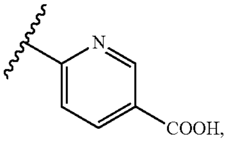
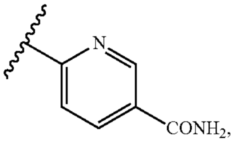
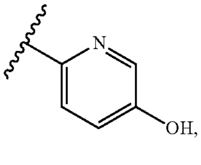
$—NH—S(=O)_2—CH_3$, $—S(=O)_2—NH_2$,
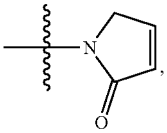
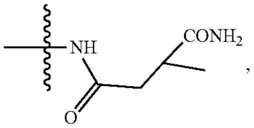
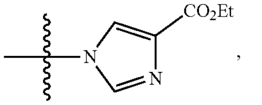
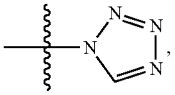
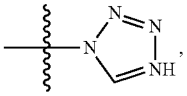
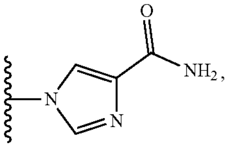
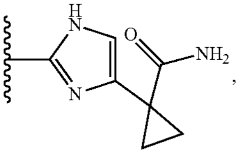
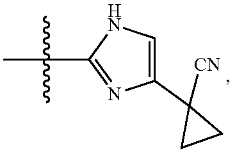
or
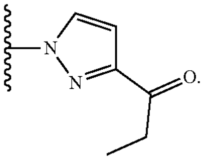
In a preferred embodiment of the present invention, Q is H, —OH, $—CF_3$, —CN, $—NH—C(=O)—CH_3$, $—NH—C(=O)—O—CH_3$,
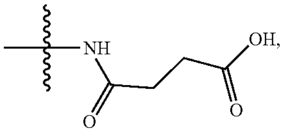
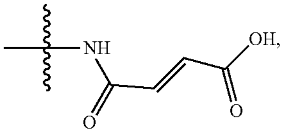
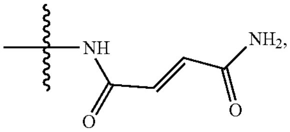
$—C(=O)—CH_3$, $—C(=O)—C_2H_5$, $—C(=O)—O—CH_3$, $—O—C(=O)—NH—CH_3$, $—C(=O)—NH—CH_3$, $—C(=NH)—NH—CH_3$, $—S(=O)_2—NH—CH_3$,
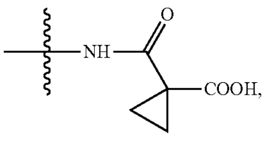
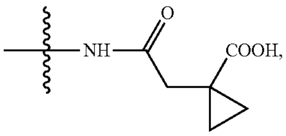

-continued
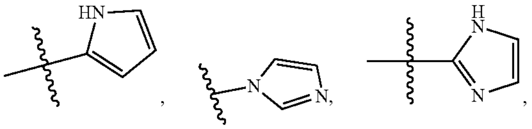
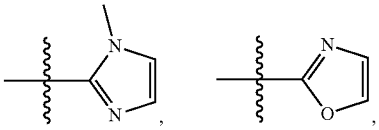
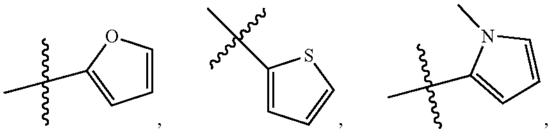
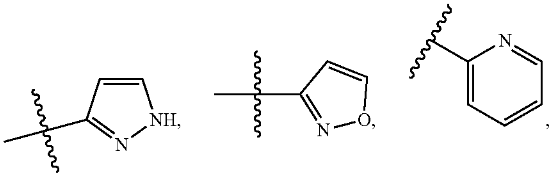
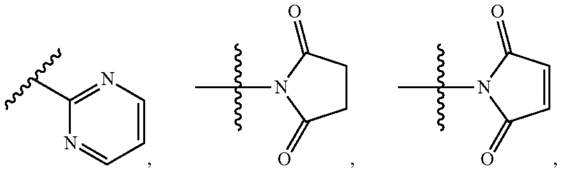
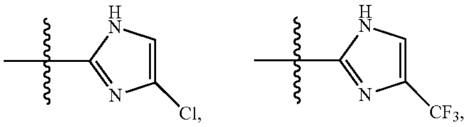
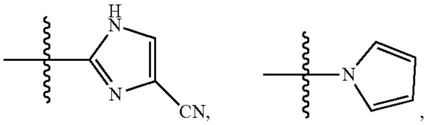
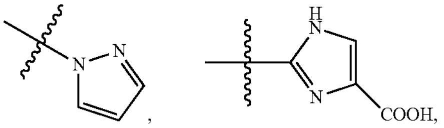
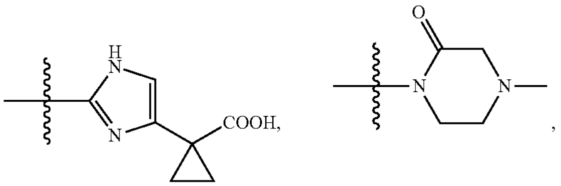
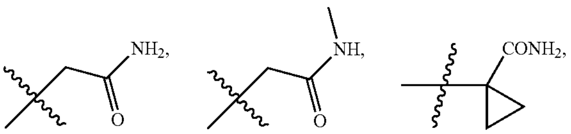
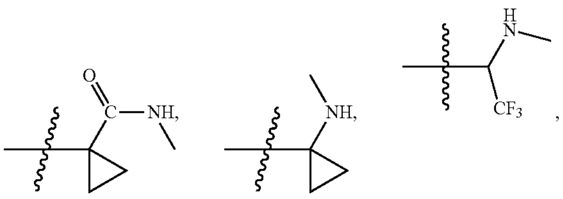
-continued
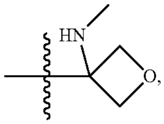
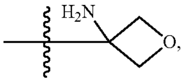
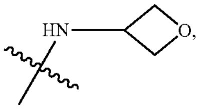
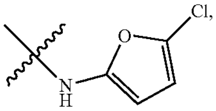
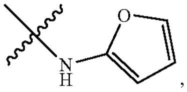
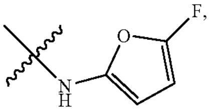
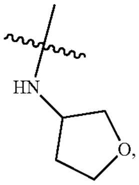
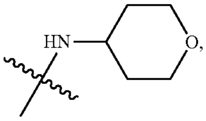
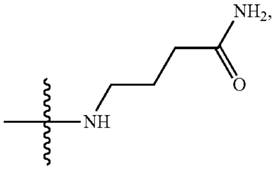
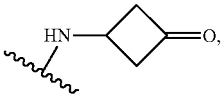
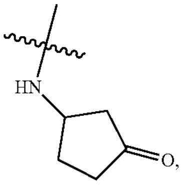
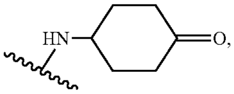
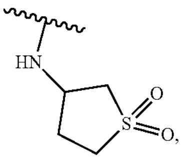
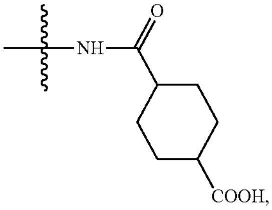
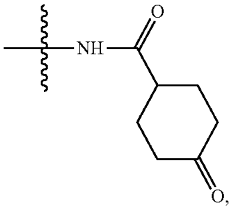
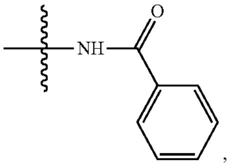
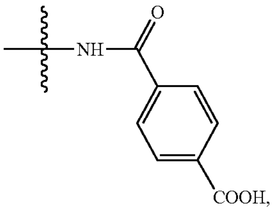
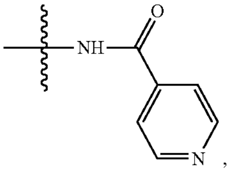

-continued
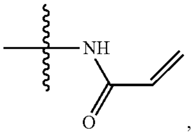
,
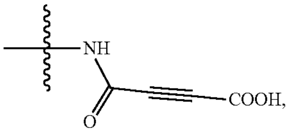
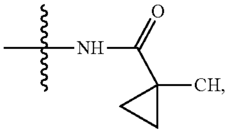
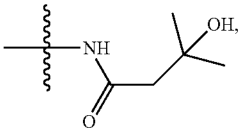
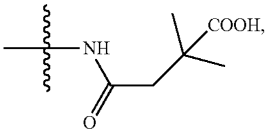
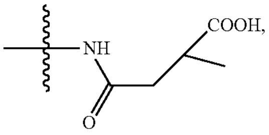
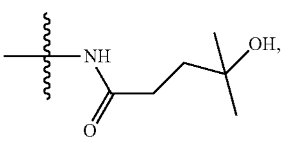
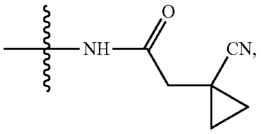
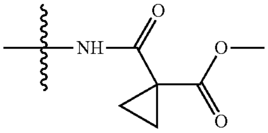
,
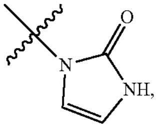
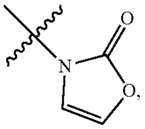
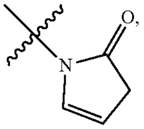
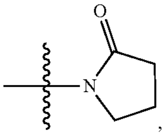
,
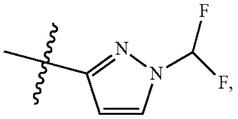
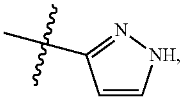
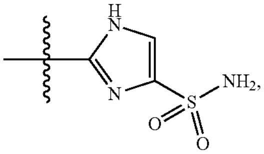
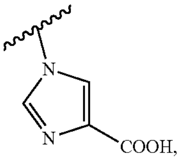
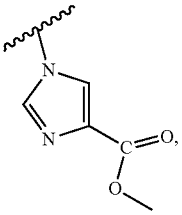
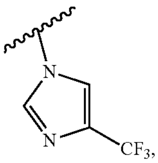
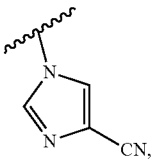
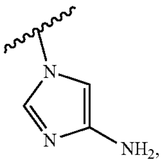
-continued
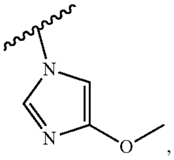
,
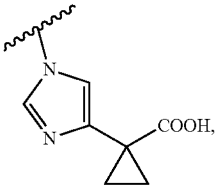
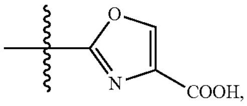
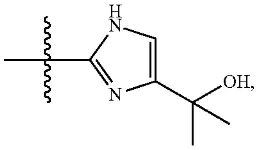
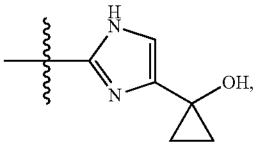
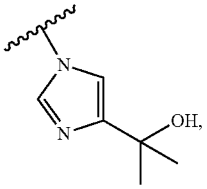
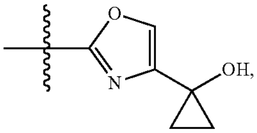
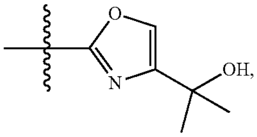
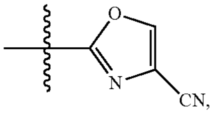
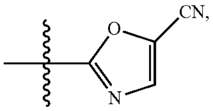
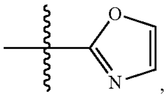
,
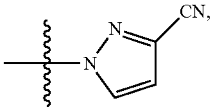
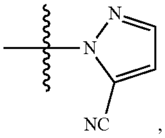
,
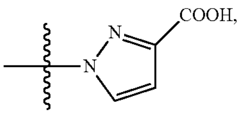
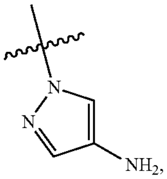
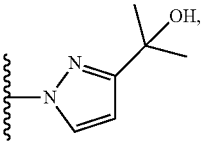

-continued
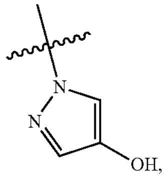
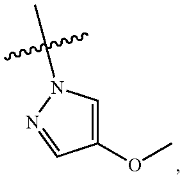
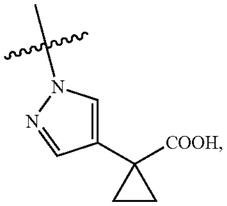
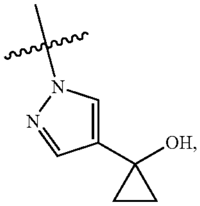
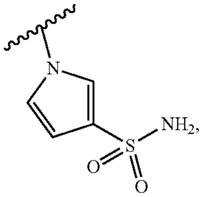
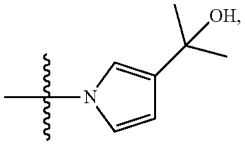
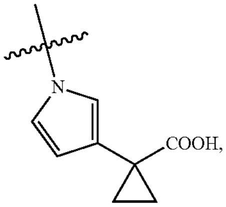
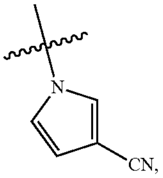
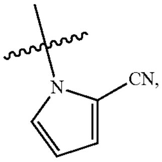
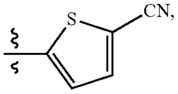
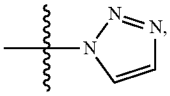
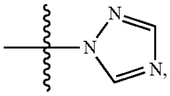
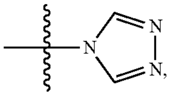
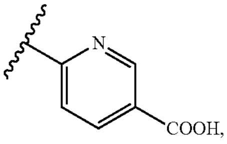
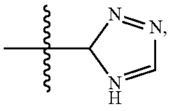
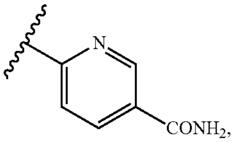
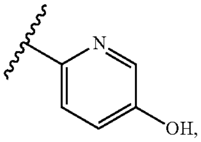
$-NH-S(=O)_2-CH_3$, $-S(=O)_2-NH_2$,
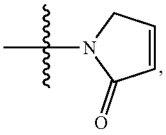
or
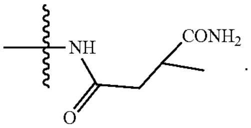
In a preferred embodiment of the present invention. Q is
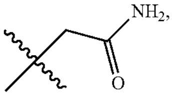
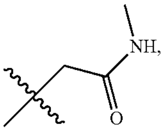
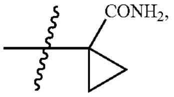
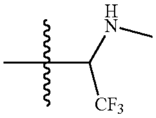
,
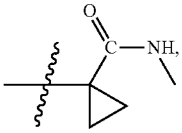
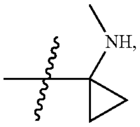
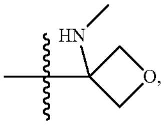
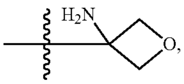
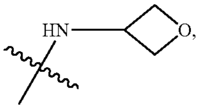
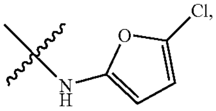
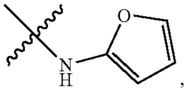
,
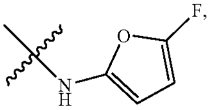
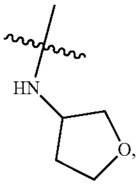
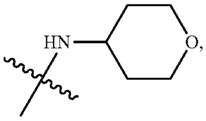
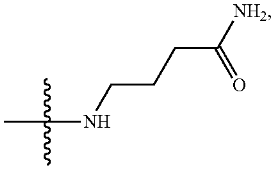
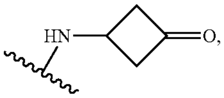
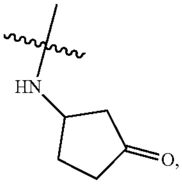
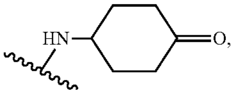

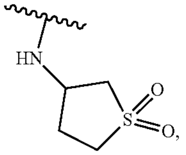
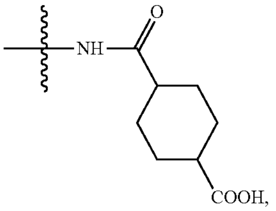
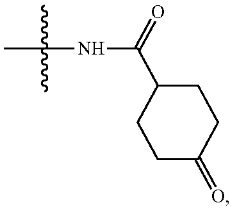
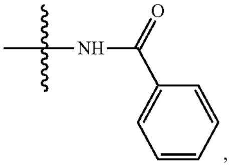
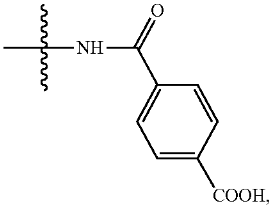
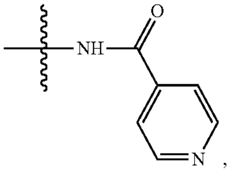
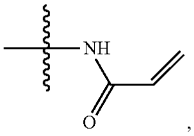
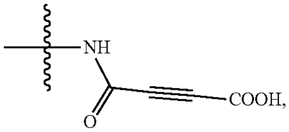
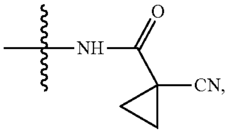
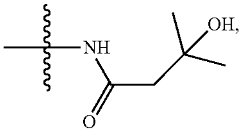
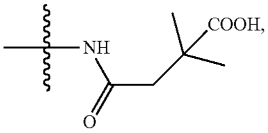
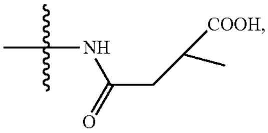
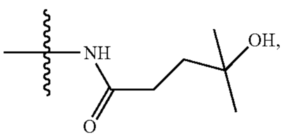
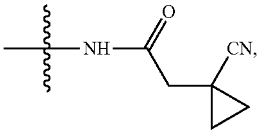
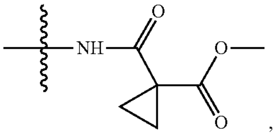
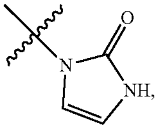
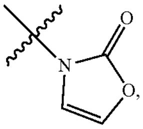
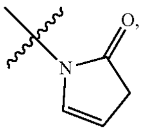
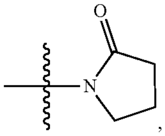
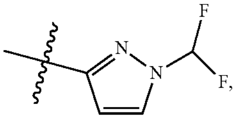
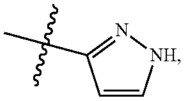
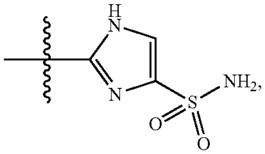
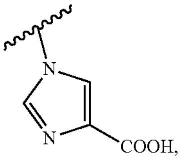
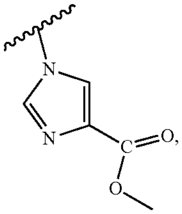
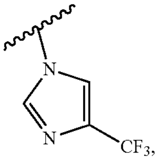
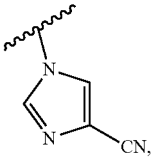
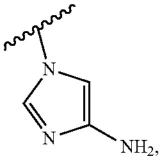
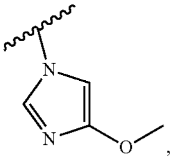
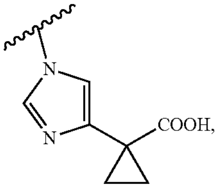
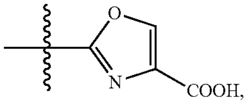
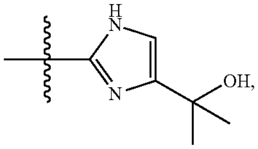
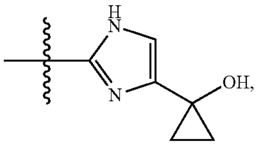
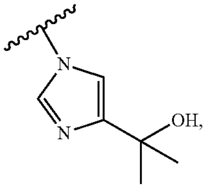
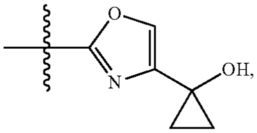
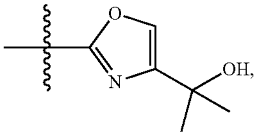
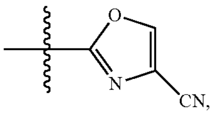
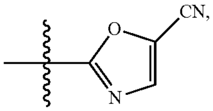

-continued

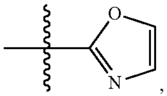,
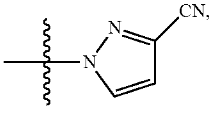
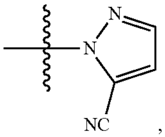,
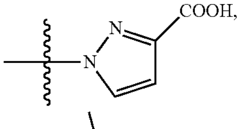
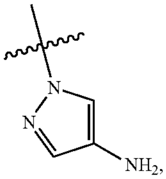
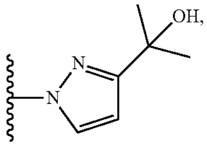
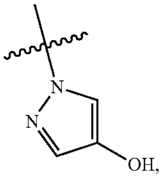
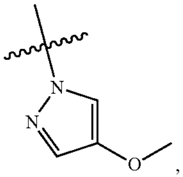,
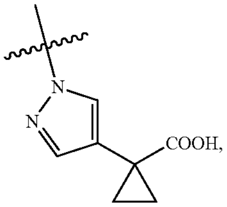
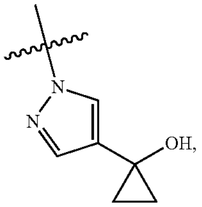
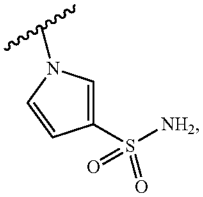
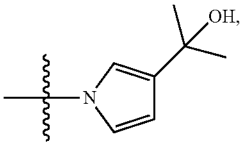
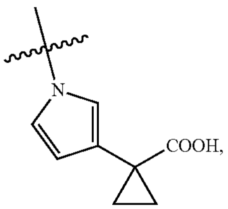
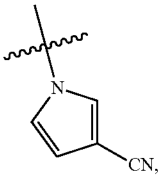
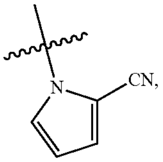
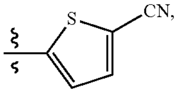

-continued

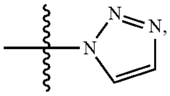
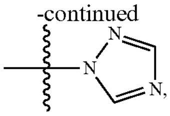
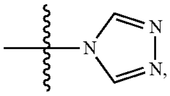
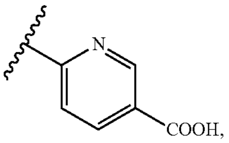
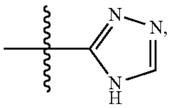
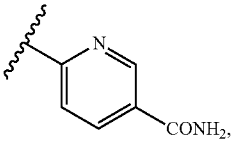
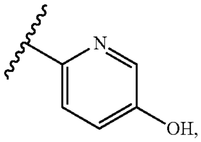

—NH—S(=O)$_2$—CH$_3$, —S(=O)$_2$—NH$_2$,

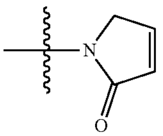 or 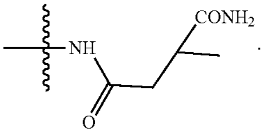.

In a preferred embodiment of the present invention, when $R^{2-1}$ or $R^{2-2}$ is halogen, the halogen is independently fluorine, chlorine, bromine or iodine.

In a preferred embodiment of the present invention, when $R^{2-1}$ or $R^{2-2}$ is an unsubstituted or substituted $C_1$-$C_6$ alkyl, or an unsubstituted or substituted $C_1$-$C_6$ alkyl-O—, the $C_1$-$C_6$ alkyl (e.g., methyl, ethyl, propyl, butyl, pentyl or hexyl) is independently a $C_1$-$C_4$ alkyl (e.g., methyl, ethyl, n-propyl, isopropyl, n-butyl, isobutyl, sec-butyl or tert-butyl).

In a preferred embodiment of the present invention, when $R^{2-1}$ or $R^{2-2}$ is a substituted $C_1$-$C_6$ alkyl or a substituted $C_1$-$C_6$ alkyl-O—, and the substituent is halogen, the halogen is independently fluorine, chlorine, bromine or iodine.

In a preferred embodiment of the present invention, when $R^{2-1}$ or $R^{2-2}$ is a substituted $C_1$-$C_6$ alkyl or a substituted $C_1$-$C_6$ alkyl-O—, and the substituent is a $C_1$-$C_6$ alkyl or a substituted $C_1$-$C_6$ alkyl-O—, the $C_1$-$C_6$ alkyl (e.g., methyl, ethyl, propyl, butyl, pentyl or hexyl) in the substituent is independently a $C_1$-$C_4$ alkyl (e.g., methyl, ethyl, n-propyl, isopropyl, n-butyl, isobutyl, sec-butyl or tert-butyl).

In a preferred embodiment of the present invention, when $R^{2-1}$ or $R^{2-2}$ is a substituted $C_1$-$C_6$ alkyl or a substituted $C_1$-$C_6$ alkyl-O—, the number of the substituents is independently 1, 2, 3 or 4, and preferably 1 or In a preferred embodiment of the present invention, when $R^{2-3}$, $R^{2-4}$, $R^{2-5}$ or $R^{2-6}$ is an unsubstituted or substituted $C_1$-$C_6$ alkyl, or an unsubstituted or substituted $C_1$-$C_6$ alkyl-O—, the $C_1$-$C_6$ alkyl (e.g., methyl, ethyl, propyl, butyl, pentyl or hexyl) is independently a $C_1$-$C_6$ alkyl (e.g., methyl, ethyl, n-propyl, isopropyl, n-butyl, isobutyl, sec-butyl or tert-butyl).

In a preferred embodiment of the present invention, when $R^{2-3}$, $R^{2-4}$, $R^{2-5}$ or $R^{2-6}$ is an unsubstituted or substituted $C_3$-$C_6$ cycloalkyl, or an unsubstituted or substituted $C_3$-$C_8$ cycloalkyl-O—, the $C_3$-$C_8$ cycloalkyl is a $C_3$-$C_6$ cycloalkyl (e.g., cyclopropyl, cyclobutyl, cyclopentyl and cyclohexyl).

In a preferred embodiment of the present invention, when $R^{2-3}$, $R^{2-4}$, $R^{2-5}$ or $R^{2-6}$ is a substituted $C_1$-$C_6$ alkyl, a substituted $C_3$-$C_8$ cycloalkyl, a substituted $C_3$-$C_8$ cycloalkyl-O—, or a substituted $C_1$-$C_6$ alkyl-O—, and the substituent is halogen, the halogen is independently fluorine, chlorine, bromine or iodine.

In a preferred embodiment of the present invention, when $R^{2-3}$, $R^{2-4}$, $R^{2-5}$ or $R^{2-6}$ is a substituted $C_1$-$C_6$ alkyl, a substituted $C_3$-$C_8$ cycloalkyl, a substituted $C_3$-$C_8$ cycloalkyl-O—, or a substituted $C_1$-$C_6$ alkyl-O—, and the substituent is a $C_1$-$C_6$ alkyl or a substituted $C_1$-$C_6$ alkyl-O—, the $C_1$-$C_6$ alkyl (e.g., methyl, ethyl, propyl, butyl, pentyl or hexyl) in the substituent is independently a $C_1$-$C_4$ alkyl (e.g., methyl, ethyl, n-propyl, isopropyl, n-butyl, isobutyl, sec-butyl or tert-butyl), and preferably methyl or ethyl.

In a preferred embodiment of the present invention, when $R^{2-3}$, $R^{2-4}$, $R^{2-5}$ or $R^{2-6}$ is a substituted $C_1$-$C_6$ alkyl, a substituted $C_3$-$C_8$ cycloalkyl, a substituted $C_3$-$C_8$ cycloalkyl-O— or a substituted $C_1$-$C_6$ alkyl-O—, and the substituent is a $C_1$-$C_6$ alkyl or a substituted $C_1$-$C_6$ alkyl-O—, the number of the substituents is independently 1, 2, 3 or 4, and preferably 1 or 2.

In a preferred embodiment of the present invention, when $R^{2-7}$ is independently halogen, $R^{2-7}$ is independently a halogen-substituted $C_1$-$C_6$ alkyl, or $R^{2-7}$ is independently a halogen-substituted $C_1$-$C_6$ alkyl-O—, the halogen therein is independently fluorine, chlorine, bromine or iodine.

In a preferred embodiment of the present invention, when $R^{2-7}$ is independently an unsubstituted or substituted $C_1$-$C_6$ alkyl, or $R^{2-7}$ is independently an unsubstituted or substituted $C_1$-$C_6$ alkyl-O—, the $C_1$-$C_6$ alkyl (e.g., methyl, ethyl, propyl, butyl, pentyl or hexyl) therein is independently a $C_1$-$C_4$ alkyl (e.g., methyl, ethyl, n-propyl, isopropyl, n-butyl, isobutyl, sec-butyl or tert-butyl).

In a preferred embodiment of the present invention, when $R^{2-8}$ or $R^{2-9}$ is independently a halogen-substituted $C_1$-$C_6$ alkyl, the halogen therein is independently fluorine, chlorine, bromine or iodine.

In a preferred embodiment of the present invention, when $R^{2-8}$ or $R^{2-9}$ is independently an unsubstituted or halogen-substituted $C_1$-$C_6$ alkyl, the $C_1$-$C_6$ alkyl (e.g., methyl, ethyl, propyl, butyl, pentyl or hexyl) therein is independently a $C_1$-$C_4$ alkyl (e.g., methyl, ethyl, n-propyl, isopropyl, n-butyl, isobutyl, sec-butyl or tert-butyl).

In a preferred embodiment of the present invention, —C(═O)N($R^{2-5}R^{2-6}$ is —C(═O)$NH_2$.

In a preferred embodiment of the present invention, —C(═O)N($R^{2-8}R^{2-9}$) is —C(═O)$NHCH_3$.

In a preferred embodiment of the present invention,

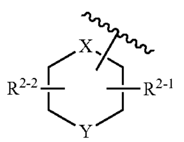

is

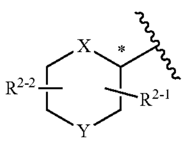

(e.g.,

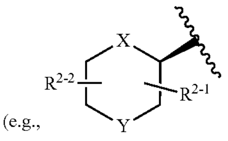

or

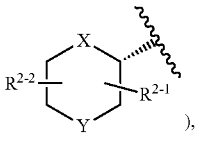

), wherein, the carbon atom labeled with "*" is a chiral carbon atom in S configuration, R configuration or a mixture thereof; and preferably, the carbon atom labeled with "*" is a chiral carbon atom in a form of a single (R) or(S) enantiomer or in a form enriched with one enantiomer.

In a preferred embodiment of the present invention,

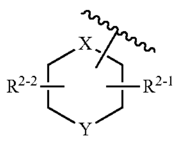

is

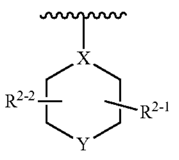

(wherein X is methylene or —NH—).

In a preferred embodiment of the present invention, when $R^2$ is

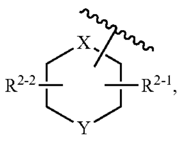

one of X and Y is

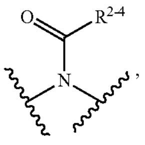

and the other is a single bond, methylene or —O— (e.g.,

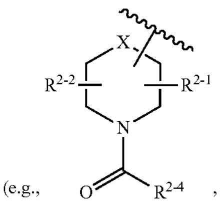

wherein X is a single bond, methylene or —O—); preferably X is —O—, namely, $R^2$ is

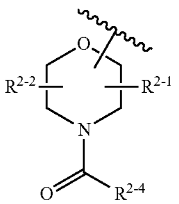

(e.g.,

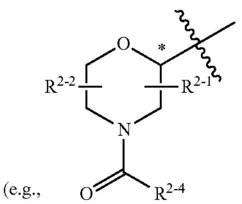

(e.g.,

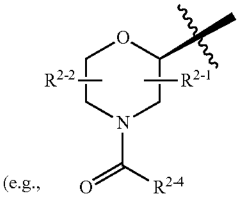

or

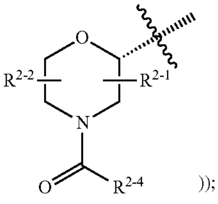

));

and more preferably, $R^2$ is
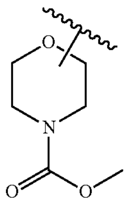
(e.g. 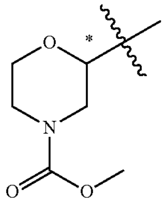
(e.g. 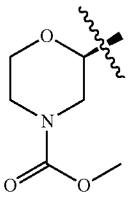 or 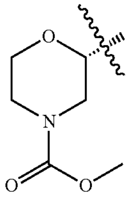)),
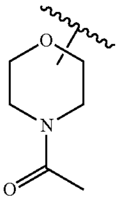
(e.g. 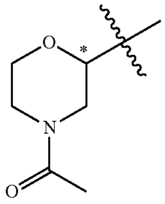) or
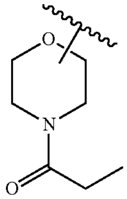
(e.g. 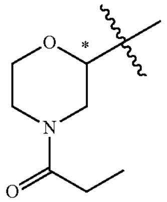
(e.g. 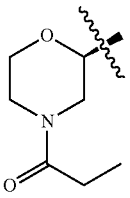 or 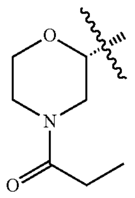)).
In a preferred embodiment of the present invention, when $R^2$ is
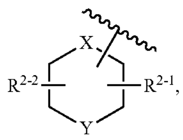
X or Y is —N($R^{2-3}$)—; preferably, one of X and Y is —N($R^{2-3}$)—, and the other is —O—, —N($R^{2-3}$)— or
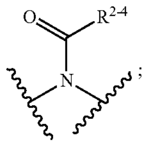;
more preferably,
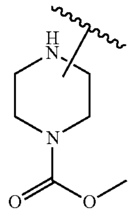
(e.g. 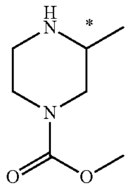
(e.g. 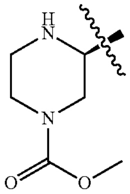 or 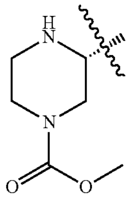) or
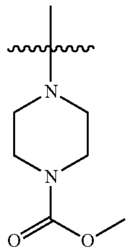),
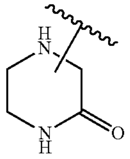
(e.g. 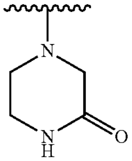 or 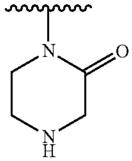),
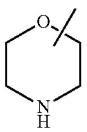
(e.g. 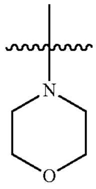) or
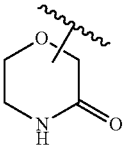
(e.g. 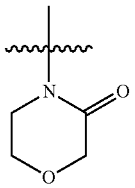).
In a preferred embodiment of the present invention, $R^2$ is
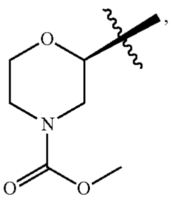, 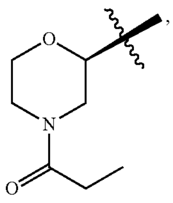, 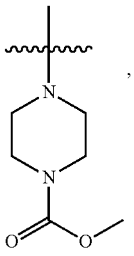, -continued

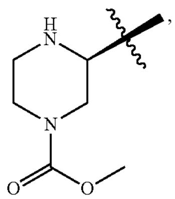,
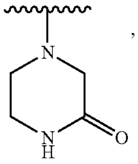,
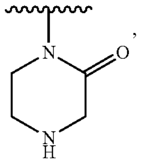,

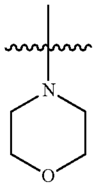 or 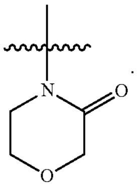.

In a preferred embodiment of the present invention, when $R^2$ is independently an unsubstituted or substituted 5-6 membered heteroaryl, the 5-6 membered heteroaryl is independently pyridinyl (e.g., 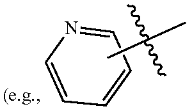 (e.g., 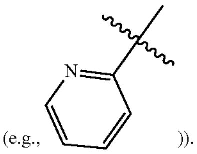)).

In a preferred embodiment of the present invention, when $R^2$ is independently a substituted 5-6 membered heteroaryl that may be substituted with halogen, a halogen-substituted $C_1$-$C_6$ alkyl or a halogen-substituted $C_1$-$C_6$ alkyl-O—, the halogen in the substituents is independently fluorine, chlorine, bromine or iodine.

In a preferred embodiment of the present invention, when $R^2$ is independently a substituted 5-6 membered heteroaryl that may be substituted with an unsubstituted or halogen-substituted $C_1$-$C_6$ alkyl, or an unsubstituted or halogen-substituted $C_1$-$C_6$ alkyl-O—, the $C_1$-$C_6$ alkyl (e.g., methyl, ethyl, propyl, butyl, pentyl or hexyl) in the substituents is independently a $C_1$-$C_4$ alkyl (e.g., methyl, ethyl, n-propyl, isopropyl, n-butyl, isobutyl, sec-butyl or tert-butyl).

In a preferred embodiment of the present invention, when $R^2$ is independently an unsubstituted or substituted 5-6 membered heteroaryl, the substituted 5-6 membered heteroaryl is independently

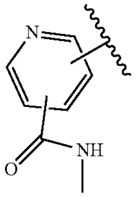 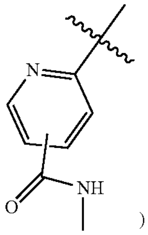 (e.g., ) or 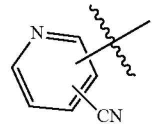

-continued (e.g., 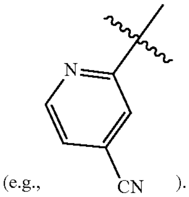).

In a preferred embodiment of the present invention,

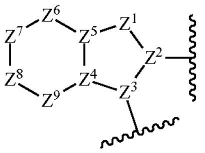

is not

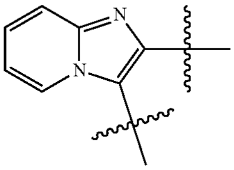 or 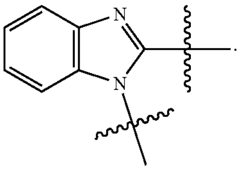.

In a preferred embodiment of the present invention,

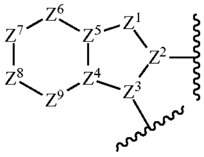 is 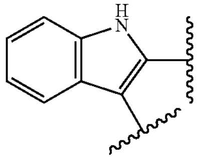,

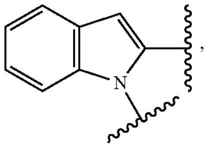, 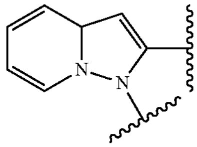,

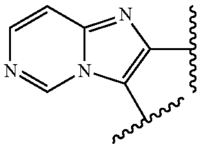, 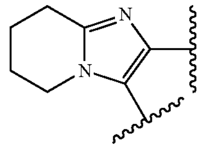,

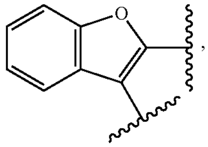, 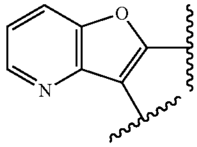,

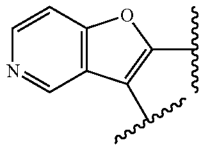, 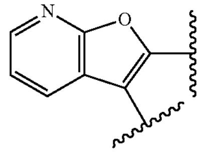,

-continued

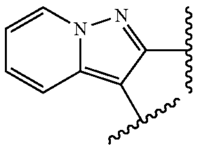 or 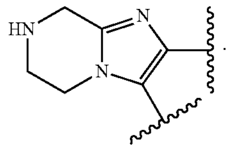.

In a preferred embodiment of the present invention, the heterocyclic compound of formula I is of formula I-A as shown below:

I-A

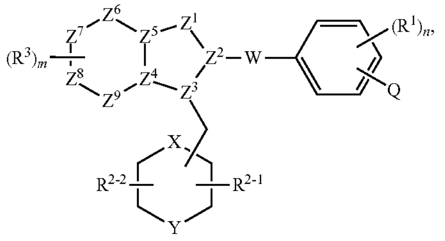

wherein

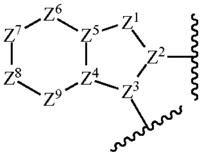 is 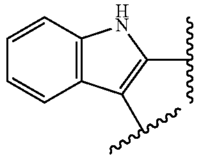,

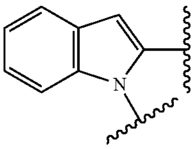, 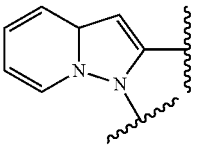,

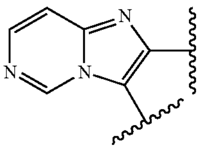, 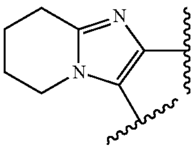,

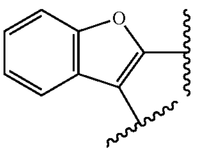, 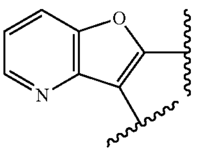,

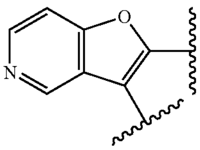, 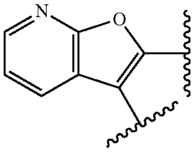,

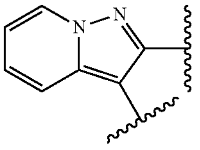 or 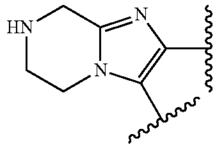;

preferably, the heterocyclic compound of formula I is of formula I-A-1 as shown below:

I-A-1

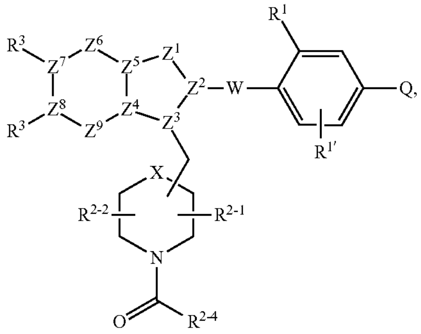

wherein $R^{1'}$ has the definition as described for $R^1$, and $R^{1'}$ is the same as or different from $R^1$; W is a single bond; and

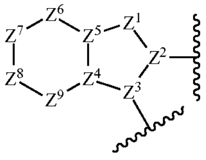 is 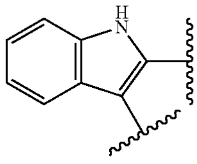,

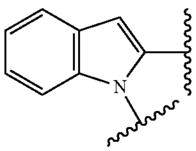, 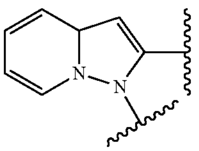,

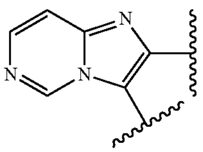, 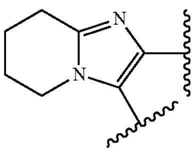,

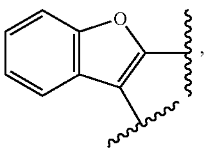, 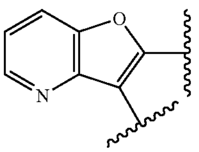,

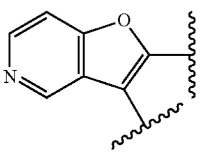, 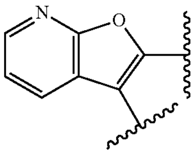,

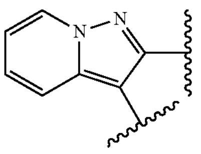 or 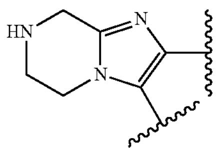;

more preferably, the heterocyclic compound of formula I is of formula I-A-2 as shown below:

I-A-2

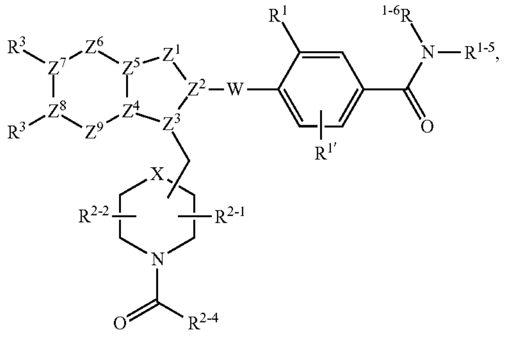

wherein R" has the definition as described for $R^1$, and $R^{1'}$ is the same as or different from $R^1$; W is a single bond; X is a single bond, methylene or —O—; and

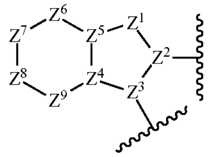

is

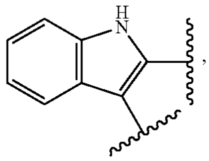

,

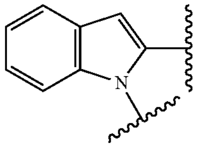

,

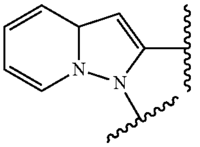

,

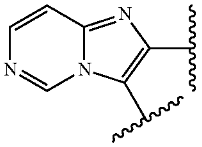

,

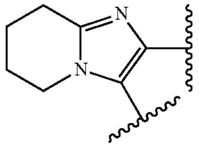

,

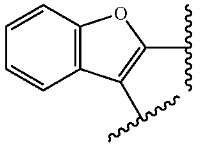

,

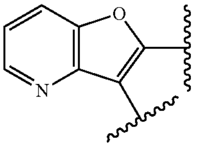

,

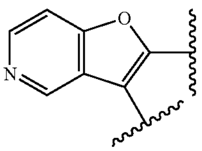

,

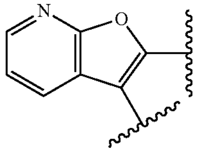

,

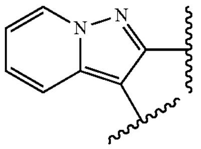

or

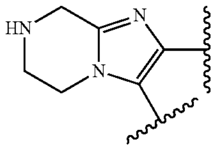

.

In a preferred embodiment of the present invention, the heterocyclic compound of formula I is of formula I-B as shown below:

I-B

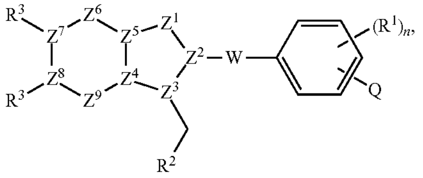

wherein $R^2$ is

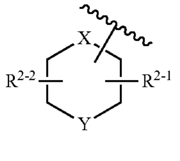

or —C(═O)N($R^{2-5}R^{2-6}$), X or Y is —N($R^{2-3}$)—;

preferably, the heterocyclic compound of formula I is of formula I-B-1 as shown below:

I-B-1

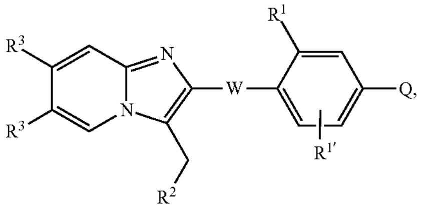

wherein $R^{1'}$ has the definition as described for $R^1$, and $R^{1'}$ is the same as or different from $R^1$; W is a single bond; and $R^2$ is

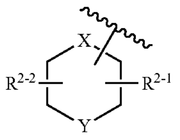

or —C(═O)N($R^{2-5}R^{2-6}$), wherein X or Y is —N($R^{2-3}$)—; and more preferably, the heterocyclic compound of formula I is of formula I-B-2 as shown below:

I-B-2

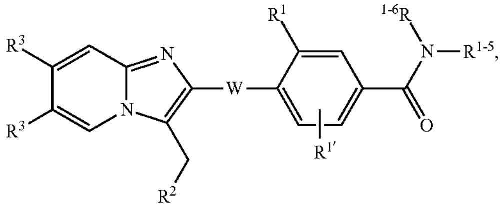

wherein $R^{1'}$ has the definition as described for $R^1$, and $R^{1'}$ is the same as or different from $R^1$; W is a single bond; and $R^2$ is

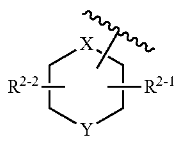

or —C(=O)N($R^{2-5}R^{2-6}$), wherein X or Y is —N($R^{2-3}$)—.

In a preferred embodiment of the present invention, in the heterocyclic compound of formula I, Q is H, halogen, —OH, —$CF_3$, —CN, —NH—C(=O)—$R^{1-1}$, —C(=O)—$R^{1-2}$, —O—C(=O)—N($R^{1-3}R^{1-4}$), —C(=NH)—N($R^{1-7}R^{1-8}$), —S(=O)$_2$—N($R^{1-9}R^{1-10}$), —S(=O)—N($R^{1-11}R^{1-12}$), —O—C(=O)—$R^{1-13}$, —N($R^{1-14}R^{1-15}$), —NH—S(=O)$_2$—$R^{1-16}$, an unsubstituted or substituted $C_1$-$C_6$ alkyl, an unsubstituted or substituted $C_1$-$C_6$ alkyl-O—, an unsubstituted or substituted $C_{2-6}$ alkenyl, an unsubstituted or substituted $C_2$-$C_6$ alkenyl-O—, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, an unsubstituted or substituted $C_6$-$C_{10}$ aryl, or an unsubstituted or substituted 5-10 membered heteroaryl.

In a preferred embodiment of the present invention, the heterocyclic compound of formula I is of formula I-C as shown below:

I-C

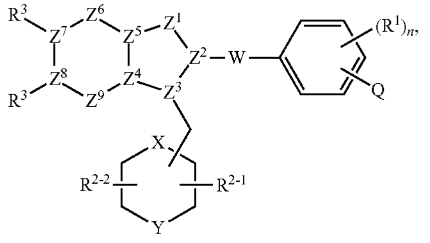

wherein Q is H, halogen, —OH, —$CF_3$, —CN, —NH—C(=O)—$R^{1-1}$, —C(=O)—$R^{12}$, —O—C(=O)—N($R^{1-3}R^{1-4}$), —C(=NH)—N($R^{1-7}R^{1-8}$), —S(=O)$_2$—N($R^{1-9}R^{1-10}$), —S(=O)—N($R^{1-11}R^{1-12}$), —O—C(=O)—$R^{1-13}$, —N($R^{1-14}R^{1-15}$), —NH—S(=O)$_2$—$R^{1-16}$, an unsubstituted or substituted $C_1$-$C_6$ alkyl, an unsubstituted or substituted $C_1$-$C_8$ alkyl-O—, an unsubstituted or substituted $C_{2-6}$ alkenyl, an unsubstituted or substituted $C_2$-$C_6$ alkenyl-O—, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, an unsubstituted or substituted $C_6$-$C_{10}$ aryl, or an unsubstituted or substituted 5-10 membered heteroaryl;

preferably, the heterocyclic compound of formula I is of formula I-C-1 as shown below:

I-C-1

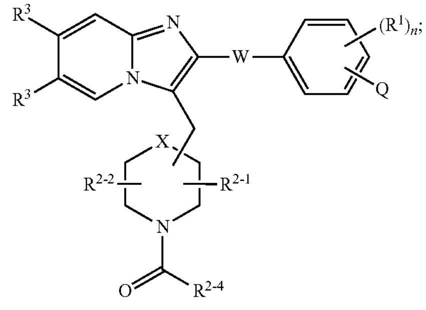

and more preferably, the heterocyclic compound of formula I is of formula I-C-2 as shown below:

I-C-2

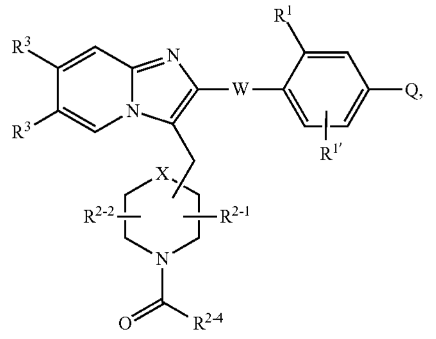

wherein $R^{1'}$ has the definition as described for $R^1$, $R^{1'}$ is the same as or different from $R^1$, and X is a single bond, methylene or —O—.

In a preferred embodiment of the present invention, the heterocyclic compound of formula I is of formula I-D as shown below:

I-D

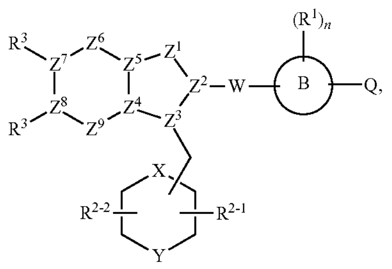

wherein

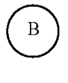

is a 5-6 membered heteroaryl or a $C_3$-$C_5$ heterocycloalkyl;

preferably, the heterocyclic compound of formula I is of formula I-D-1 as shown below:

I-D-1

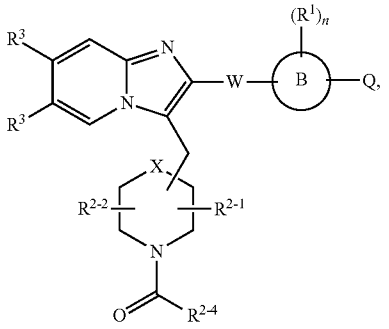

wherein

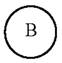

is a 5-6 membered heteroaryl or a $C_3$-$C_5$ heterocycloalkyl; and more preferably, the heterocyclic compound of formula I is of formula I-D-2 as shown below:

I-D-2

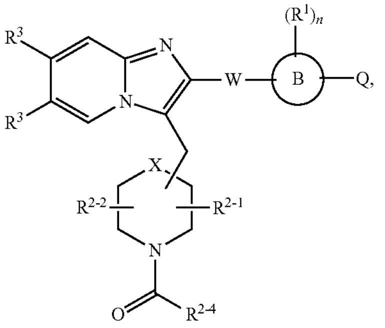

wherein X is a single bond, methylene or —O—; W is a single bond; and

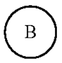

is a 5-6 membered heteroaryl or a $C_3$-$C_5$ heterocycloalkyl.

In a preferred embodiment of the present invention, the heterocyclic compound of formula I is of formula I-E as shown below:

I-E

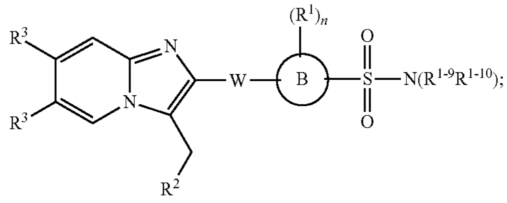

wherein $R^2$ is independently

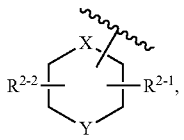

or an unsubstituted or substituted 5-6 membered heteroaryl; for example, W is a single bond;

preferably, the heterocyclic compound of formula I is of formula I-E-1 as shown below:

I-E-1

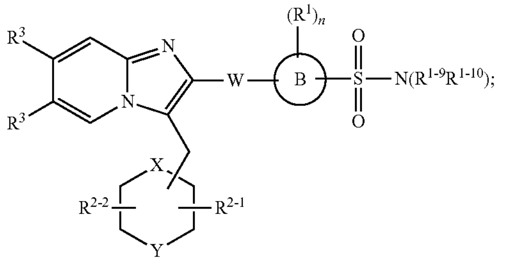

for example,

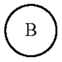

is phenyl or 6 membered heteroaryl; and more preferably, the heterocyclic compound of formula I of formula I-E-2 as shown below:

I-E-2

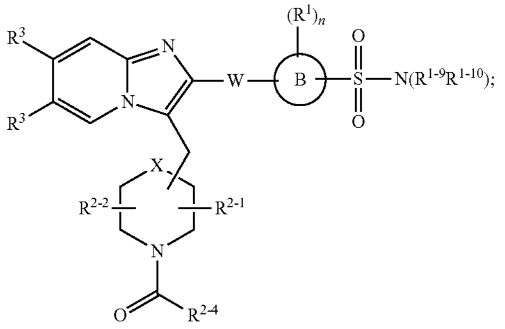

for example,

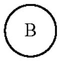

is phenyl.

In a preferred embodiment of the present invention,

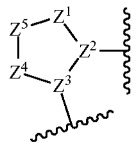

is a 5 membered heteroaryl;

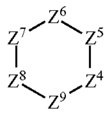

is phenyl, a 5-6 membered heterocycloalkyl, a 5-6 membered heterocycloalkenyl, or a 5-6 membered heteroaryl, wherein the 5-6 membered heterocycloalkyl contains 1-3 heteroatoms selected from one or more of N, O and S, the 5-6 membered heterocycloalkenyl contains 1-3 heteroatoms selected from one or more of N, O and S, and the 5-6 membered heteroaryl contains 1-3 heteroatoms selected from one or more of N, O and S;

$Z^1$, $Z^2$, $Z^3$, $Z^4$, $Z^5$, $Z^6$, $Z^7$, $Z^8$ and $Z^9$ independently represent a ring atom; and when

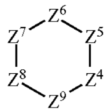

is a 5 membered heterocycloalkyl, a 5 membered heterocycloalkenyl or a 5 membered heteroaryl, $Z^6$ or $Z^9$ represents a single bond;

m is 1, 2, 3 or 4;

$R^3$ is H, halogen, —OH, a $C_1$-$C_6$ haloalkyl or a $C_1$-$C_6$ alkyl;

W is a single bond or —C(═O)—NH—;

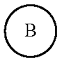

is phenyl, a 5-6 membered heteroaryl or a $C_3$-$C_9$ heterocycloalkyl;

n is 1, 2, 3 or 4;

$R^1$ is independently H, halogen, —OH, —CN or an unsubstituted or substituted $C_1$-$C_6$ alkyl;

Q is H, halogen, —OH, —CN, —NH—C(═O)—$R^{1-1}$, —C(═O)—$R^{1-2}$, —O—C(═O)—N($R^{1-3}R^{1-4}$), —C(═O)—N($R^{1-5}R^{1-6}$), —C(═NH)—N($R^{1-7}R^{1-8}$), —S(═O)$_2$—N($R^{1-9}R^{1-10}$), —N($R^{1-14}R^{1-15}$), —NH—S(═O)$_2$—$R^{1-16}$, an unsubstituted or substituted $C_1$-$C_6$ alkyl, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, or an unsubstituted or substituted 5-10 membered heteroaryl;

$R^2$ is independently

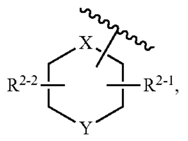

—C(═O)N($R^{2-5}R^{2-6}$) or an unsubstituted or substituted 5-6 membered heteroaryl;

preferably,

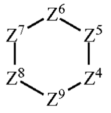

is phenyl, a 6 membered heterocycloalkyl, a 6 membered heterocycloalkenyl, or a 6 membered heteroaryl;

m is 1 or 2;

the substituent in $R^1$ is independently one or more selected from the following substituents: halogen, —OH, —CN or —C(═O)$NH_2$; and preferably halogen.

$R^3$ is H, halogen, —OH, —$CF_3$ or a $C_1$-$C_6$ alkyl;

$R^2$ is independently

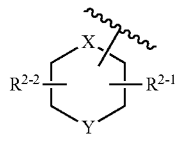

or —C(═O)N($R^{2-5}R^{2-6}$).

In a preferred embodiment of the present invention,

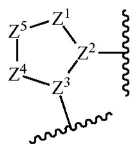

is a 5 membered heteroaryl.

In a preferred embodiment of the present invention,

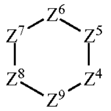

is phenyl, a 6 membered heterocycloalkyl, a 6 membered heterocycloalkenyl or a 6 membered heteroaryl.

In a preferred embodiment of the present invention, m is 1 or 2.

In a preferred embodiment of the present invention, $R^3$ is H, halogen, —OH, a $C_1$-$C_6$haloalkyl or a $C_1$-$C_6$ alkyl; and preferably, $R^3$ is H, halogen, —OH, —$CF_3$ or a $C_1$-$C_6$ alkyl.

In a preferred embodiment of the present invention, W is a single bond.

In a preferred embodiment of the present invention, n is 1 or 2.

In a preferred embodiment of the present invention, $R^1$ is independently H, halogen, —OH, —CN, or an unsubstituted or substituted $C_1$-$C_6$ alkyl, and preferably H, halogen, or an unsubstituted or substituted $C_1$-$C_6$ alkyl.

In a preferred embodiment of the present invention, the substituent in $R^1$ is independently one or more selected from the following substituents: halogen, —OH, —CN or —C(═O)$NH_2$; and preferably halogen.

In a preferred embodiment of the present invention, Q is H, halogen, —OH, —CN, —NH—C(═O)—$R^{1-1}$, —C(═O)—$R^{1-2}$, —O—C(═O)—N($R^{1-3}R^{1-4}$), —C(═O)—N($R^{1-5}R^{1-6}$), —C(═NH)—N($R^{1-7}R^{1-8}$), —S(═O)$_2$—N($R^{1-9}R^{1-10}$), —N($R^{1-14}R^{1-15}$), —NH—S(═O)$_2$—$R^{1-16}$, an unsubstituted or substituted $C_1$-$C_6$ alkyl, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, or an unsubstituted or substituted 5-10 membered heteroaryl.

In a preferred embodiment of the present invention, Q is H, halogen, —OH, —$CF_3$, —CN, —NH—C(═O)—$R^{1-1}$, —C(═O)—$R^{1-2}$, —O—C(═O)—N($R^{1-3}R^{1-4}$), —C(═O)—N($R^{1-5}R^{1-6}$), —C(═NH)—N($R^{1-7}R^{1-8}$), —S(═O)$_2$—N($R^{1-9}R^{1-10}$), —S(═O)—N($R^{1-11}R^{1-12}$), —O—C(═O)—$R^{1-13}$, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_3$-$C_9$ heterocycloalkyl, an unsubstituted or substituted $C_3$-$C_9$ heterocycloalkenyl, an unsubstituted or substituted $C_6$-$C_{10}$ aryl, or an unsubstituted or substituted 5-6 membered heteroaryl; and preferably, Q is H, halogen, —OH, —CN, —NH—C(═O)—$R^{1-1}$, —C(═O)—$R^{1-2}$, —O—C(═O)—N($R^{1-3}R^{1-4}$), —C(═O)—N($R^{1-5}R^{1-6}$), —C(═NH)—N($R^{1-7}R^{1-8}$), —S(═O)$_2$—N($R^{1-9}R^{1-10}$), an unsubstituted or substituted $C_1$-$C_6$ alkyl, an unsubstituted or substituted $C_3$-$C_9$ heterocycloalkyl, an unsubstituted or substituted $C_3$-$C_9$ heterocycloalkenyl, or an unsubstituted or substituted 5-10 membered heteroaryl.

In a preferred embodiment of the present invention, the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_6$-Cho aryl, the substituted $C_3$-$C_5$ heterocycloalkyl, the substituted $C_3$-$C_5$ heterocycloalkenyl or the substituted 5-6 membered heteroaryl is substituted with one or more substituents independently selected from the following: halogen, —OH, —$CF_3$, —CN, —COOH, —C(═O)$NH_2$, ═O (i.e., two geminal hydrogens on a carbon atom are substituted with the group O), and a $C_1$-$C_6$ alkyl, a $C_1$-$C_6$ alkyl-O— or a $C_3$-$C_6$ cycloalkyl that is unsubstituted or substituted with one or more $R^a$, wherein when a plurality of $R^a$ are present, they are the same or different, and each $R^a$ is halogen, —OH, ═O, —$CF_3$, —CN, —COOH or —C(═O)$NH_2$; and when a plurality of substituents are present, they are the same or different.

In a preferred embodiment of the present invention, $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ and $R^{1-13}$ are each independently H, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_3$-$C_6$ cycloalkyl, an unsubstituted or substituted $C_3$-$C_5$ heterocycloalkyl, an unsubstituted or substituted $C_3$-$C_5$ heterocycloalkenyl, an unsubstituted or substituted phenyl, or an unsubstituted or substituted 5-6 membered heteroaryl, wherein the $C_3$-$C_5$ heterocycloalkyl contains 1-3 heteroatoms selected from one or more of O, S and N, the $C_3$-$C_5$ heterocycloalkenyl contains 1-3 heteroatoms selected from one or more of O, S and N, the 5-6 membered heteroaryl contains 1-3 heteroatoms selected from one or more of N, O and S; and the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_3$-$C_6$ cycloalkyl, the substituted $C_3$-$C_5$ heterocycloalkyl, the substituted $C_3$-$C_5$ heterocycloalkenyl, the substituted phenyl or the substituted 5-6 membered heteroaryl is substituted with one or more substituents independently selected from the following: halogen, —OH, —$CF_3$, —CN, a $C_1$-$C_6$ alkyl, a $C_1$-$C_6$ alkyl-O—, a $C_3$-$C_6$ cycloalkyl, —COOH or ═O, wherein when a plurality of substituents are present, they are the same or different.

In a preferred embodiment of the present invention, $R^{1-3}$ and $R^{1-4}$, $R^{1-5}$ and $R^{1-6}$, $R^{1-7}$ and $R^{1-8}$, $R^{1-9}$ and $R^{1-10}$, or $R^{1-11}$ and $R^{1-12}$, independently together with the N atom to which they directly link, form an unsubstituted or substituted $C_3$-$C_5$ heterocycloalkyl, an unsubstituted or substituted $C_3$-$C_5$ heterocycloalkenyl, or an unsubstituted or substituted 5-6 membered heteroaryl, wherein the $C_3$-$C_5$ heterocycloalkyl contains no heteroatom or 1-2 heteroatoms selected from one or more of O, S and N in addition to the existing N atom, the $C_3$-$C_5$ heterocycloalkenyl contains no heteroatom or 1-2 heteroatoms selected from one or more of O, S and N in addition to the existing N atom, the 5-6 membered heteroaryl contains no heteroatom or 1-2 heteroatoms selected from one or more of O, S and N in addition to the existing N atom; and the substituted $C_3$-$C_5$ heterocycloalkyl, the substituted $C_3$-$C_5$ heterocycloalkenyl or the substituted 5-6 membered heteroaryl is substituted with one or more substituents independently selected from the following: halogen, —OH, —$CF_3$, —CN, a $C_1$-$C_6$ alkyl, a $C_1$-$C_6$ alkyl-O—, ═O (i.e., two geminal hydrogens on a carbon atom are substituted with the group O), and a $C_1$-$C_6$ alkyl, a $C_1$-$C_6$ alkyl-O— or a $C_3$-$C_6$ cycloalkyl that is unsubstituted or substituted with one or more $R^a$, wherein when a plurality of $R^b$ are present, they are the same or different, and each $R^b$ is halogen, —OH, ═O, —$CF_3$, —CN, —COOH or —C(═O)$NH_2$; and when a plurality of substituents are present, they are the same or different.

In a preferred embodiment of the present invention, $R^2$ is independently

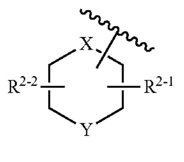

or —C(═O)N($R^{2-5}R^{2-6}$).

In a preferred embodiment of the present invention, when Q is H, halogen, —OH, —$CF_3$, —CN, —NH—C(═O)—$R^{1-1}$, —C(═O)—$R^{1-2}$, —O—C(═O)—N($R^{1-3}R^{1-4}$), —C(═NH)—N($R^{1-7}R^{1-8}$), —S(═O)$_2$—N($R^{1-9}R^{1-10}$), —S(═O)—N($R^{1-11}R^{1-13}$), —O—C(═O)—$R^{1-13}$, —N($R^{1-14}R^{1-15}$), —NH—S(═O)$_2$—$R^{1-16}$, an unsubstituted or substituted $C_1$-$C_6$ alkyl, an unsubstituted or substituted $C_1$-$C_6$ alkyl-O—, an unsubstituted or substituted $C_{2-6}$ alkenyl, an unsubstituted or substituted $C_2$-$C_6$ alkenyl-O—, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, an unsubstituted or substituted $C_6$-$C_{10}$ aryl, or an unsubstituted or substituted 5-10 membered heteroaryl,

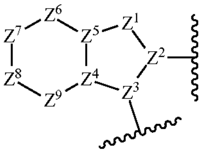

is

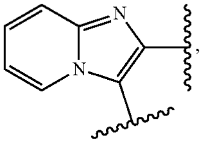

or $R^2$ is

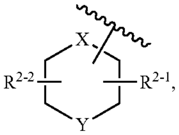

wherein X and Y are each independently a single bond, methylene, —O— or

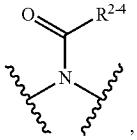

, e.g.,

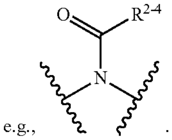

.

In a preferred embodiment of the present invention, when

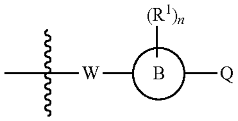

is

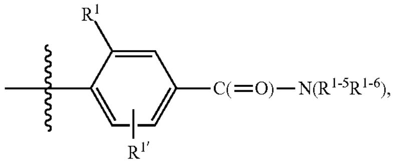

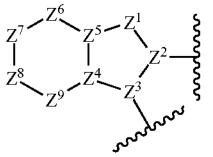

is

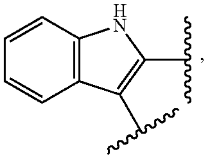

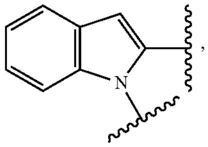

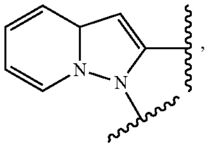

-continued

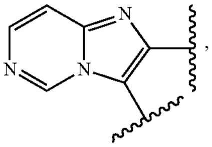

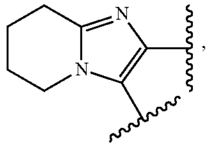

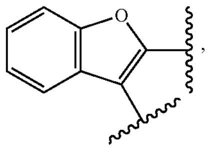

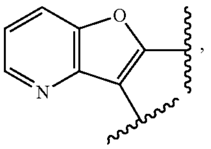

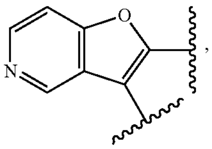

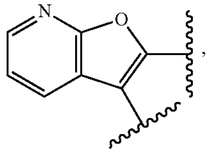

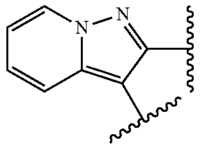

or

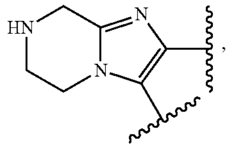

or $R^2$ is independently

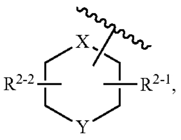

—C(=O)N($R^{2-5}R^{2-6}$) or an unsubstituted or substituted 5-6 membered heteroaryl, wherein X or Y is —N($R^{2-3}$)—.

In a preferred embodiment of the present invention, $R^2$ is independently

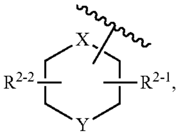

—C(=O)N($R^{2-5}R^{2-6}$), or an unsubstituted or substituted 5-6 membered heteroaryl, wherein X or Y is —N($R^{2-3}$)—.

In a preferred embodiment of the present invention, $R^2$ is independently

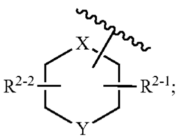

preferably, X and Y are each independently a single bond, methylene, —O—, or

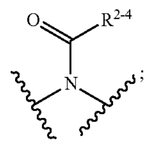

and more preferably, $R^2$ is

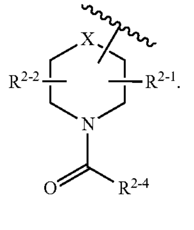

In a preferred embodiment of the present invention,

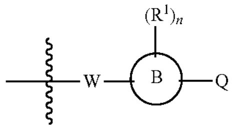

is

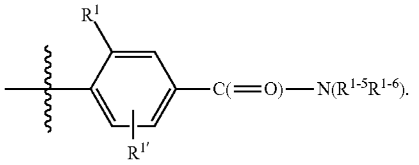

In a preferred embodiment of the present invention, $R^3$ is halogen, a $C_1$-$C_6$ haloalkyl or a $C_1$-$C_6$ alkyl;

Q is —NH—C(=O)—$R^{1-1}$, —C(=O)—N($R^{1-5}R^{1-6}$), —S(=O)$_2$—N($R^{1-9}R^{1-10}$), —N($R^{1-14}R^{1-15}$), —NH—S(=O)$_2$—$R^{1-16}$, an unsubstituted or substituted $C_1$-$C_6$ alkyl, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, or an unsubstituted or substituted 5-10 membered heteroaryl, wherein the $C_3$-$C_9$ heterocycloalkyl contains 1-3 heteroatoms selected from one or more of O, S and N, the $C_3$-$C_9$ heterocycloalkenyl contains 1-3 heteroatoms selected from one or more of O, S and N, the 5-10 membered heteroaryl contains 1-3 heteroatoms selected from one or more of N, O and S; and the substituted $C_1$-$C_6$ alkyl, the substituted $C_3$-$C_{10}$ cycloalkyl, the substituted $C_3$-$C_9$ heterocycloalkyl, the substituted $C_3$-$C_9$ heterocycloalkenyl or the substituted 5-10 membered heteroaryl is substituted with one or more substituents independently selected from the following:—OH, —$CF_3$, —CN, —N($R^{1-21}R^{1-22}$), —C(=O)—N($R^{1-23}R^{1-24}$), —S(=O)$_2$—N($R^{1-25}R^{1-26}$), —C(=O)—O—$R^{1-27}$, =O (i.e., two geminal hydrogens on a carbon atom are substituted with the group O), and a $C_1$-$C_6$ alkyl, a $C_1$-$C_6$ alkyl-O— or a $C_3$-$C_6$ cycloalkyl that is unsubstituted or substituted with one or more $R^a$, wherein when a plurality of $R^a$ are present, they are the same or different, and each $R^a$ is halogen, —OH or —COOH; and when a plurality of substituents are present, they are the same or different;

$R^2$ is independently

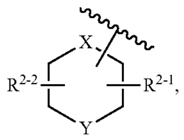

—C(=O)N($R^{2-5}R^{2-6}$) or an unsubstituted or substituted 5-6 membered heteroaryl; wherein the 5-6 membered heteroaryl contains 1-3 heteroatoms selected from one or more of N, O and S, and the substituted 5-6 membered heteroaryl is substituted with one or more substituents independently selected from the following: halogen, —OH, —CN, an unsubstituted or halogen-substituted $C_1$-$C_6$ alkyl, an unsubstituted or halogen-substituted $C_1$-$C_6$ alkyl-O—, —C(=O)$R^{2-7}$ or —C(=O)N($R^{2-8}R^{2-9}$), wherein when a plurality of substituents are present, they are the same or different;

preferably, Q is —S(=O)$_2$—N($R^{1-9}R^{1-10}$);

W is a single bond;

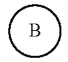

is phenyl; and $R^2$ is independently

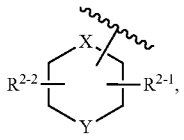

or an unsubstituted or substituted 5-6 membered heteroaryl.

In a preferred embodiment of the present invention, $R^3$ is halogen, a $C_1$-$C_6$ haloalkyl or a $C_1$-$C_6$ alkyl;

Q is —NH—C(=O)—$R^{1-1}$, —C(=O)—N($R^{1-5}R^{1-6}$), —N($R^{1-14}R^{1-15}$), —NH—S(=O)$_2$—$R^{1-16}$, an unsubstituted or substituted $C_1$-$C_6$ alkyl, an unsubstituted or substituted $C_3$-$C_{10}$ cycloalkyl, an unsubstituted or substituted $C_3$-$C_5$ heterocycloalkyl, an unsubstituted or substituted $C_3$-$C_9$ heterocycloalkenyl, or an unsubstituted or substituted 5-10 membered heteroaryl, wherein the $C_3$-$C_9$ heterocycloalkyl contains 1-3 heteroatoms selected from one or more of O, S and N, the $C_3$-$C_{10}$ heterocycloalkenyl contains 1-3 heteroatoms selected from one or more of O, S and N, and the 5-10 membered heteroaryl contains 1-3 heteroatoms selected from one or more of N, O and S; and the substituted $C_1$-$C_6$ alkyl, the substituted $C_3$-$C_{10}$ cycloalkyl, the substituted $C_3$-$C_9$ heterocycloalkyl, the substituted $C_3$-$C_9$ heterocycloalkenyl or the substituted 5-10 membered heteroaryl is substituted with one or more substituents independently selected from the following:—OH, —$CF_3$, ~CN, —N($R^{1-21}$, $R^{1-22}$), —C(=O)—N($R^{1-23}R^{1-24}$), —S(=O)$_2$—N($R^{1-25}R^{1-26}$), —C(=O)—O—$R^{1-27}$, =O (i.e., two geminal hydrogens on a carbon atom are substituted with the group O), and a $C_1$-$C_6$ alkyl, a $C_1$-$C_6$ alkyl-O—or a $C_3$-$C_6$ cycloalkyl that is unsubstituted or substituted with one or more $R^a$, wherein when a plurality of $R^a$ are present, they are the same or different, and each $R^a$ is halogen, —OH or —COOH; and when a plurality of substituents are present, they are the same or different;

$R^{1-1}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each independently H, an unsubstituted or substituted $C_1$-$C_6$ alkyl, an unsubstituted or substituted $C_2$-$C_6$ alkenyl, an unsubstituted or substituted $C_2$-$C_6$ alkynyl, an unsubstituted or substituted $C_3$-$C_{10}$ cycloalkyl, an unsubstituted or substituted $C_3$-$C_9$ heterocycloalkyl, an unsubstituted or substituted phenyl, or an unsubstituted or substituted 5-10 membered heteroaryl, wherein the $C_3$-$C_5$ heterocycloalkyl contains 1-3 heteroatoms selected from one or more of O, S and N, and the 5-10 membered heteroaryl contains 1-3 heteroatoms selected from one or more of N, O and S; and the substituted $C_1$-$C_6$ alkyl, the substituted $C_2$-$C_6$ alkenyl, the substituted $C_2$-$C_6$ alkynyl, the substituted $C_3$-$C_{10}$ cycloalkyl, the substituted $C_3$-$C_9$ heterocycloalkyl, the substituted phenyl, or the substituted 5-10 membered heteroaryl is substituted with one or more substituents independently selected from the following: halogen, —OH, —$CF_3$, —CN, —COOH, —C(═O)$NH_2$, —$COOCH_3$, —$NH_2$, —O, and a $C_1$-$C_6$ alkyl, a $C_1$-$C_6$ alkyl-O— or a $C_3$-$C_6$ cycloalkyl that is unsubstituted or substituted with one or more $R^d$, wherein when a plurality of $R^d$ are present, they are the same or different, and each $R^d$ is independently H, halogen, —OH, ═O, —$CF_3$, —CN, —COOH or —C(═O)$NH_2$; and when a plurality of substituents are present, they are the same or different.

In a preferred embodiment of the present invention, $R^3$ is halogen, —$CHF_2$, —$CH_2F$ or a $C_1$-$C_6$ alkyl;

Q is —NH—C(═O)—$R^{1-1}$, —N($R^{1-14}R^{1-15}$), —NH—S(═O)$_2$—$R^{1-16}$, an unsubstituted or substituted $C_1$-$C_6$ alkyl, an unsubstituted or substituted $C_3$-$C_{10}$ cycloalkyl, an unsubstituted or substituted $C_3$-$C_9$ heterocycloalkyl, or an unsubstituted or substituted 5-10 membered heteroaryl, wherein the $C_3$-$C_9$ heterocycloalkyl contains 1-3 heteroatoms selected from one or more of O, S and N, and the 5-10 membered heteroaryl contains 1-3 heteroatoms selected from one or more of N, O and S; and the substituted $C_1$-$C_6$ alkyl, the substituted $C_3$-$C_{10}$ cycloalkyl, the substituted $C_3$-$C_9$ heterocycloalkyl or the substituted 5-10 membered heteroaryl is substituted with one or more substituents independently selected from the following:—N($R^{1-21}R^{1-22}$), —C(═O)—N($R^{1-23}R^{1-24}$), —S(═O)$_2$—N($R^{1-25}R^{1-26}$) or —C(═O)—O—$R^{1-27}$, wherein when a plurality of substituents are present, they are the same or different;

$R^{1-1}$, $R^{1-14}$, $R^{1-15}$, $R^{1-16}$, $R^{1-21}$, $R^{1-22}$, $R^{1-23}$, $R^{1-24}$, $R^{1-25}$, $R^{1-26}$ and $R^{1-27}$ are each independently H, an unsubstituted or substituted $C_1$-$C_6$ alkyl, an unsubstituted or substituted $C_2$-$C_6$ alkynyl, an unsubstituted or substituted $C_3$-$C_{10}$ cycloalkyl, an unsubstituted or substituted $C_3$-$C_9$ heterocycloalkyl, or an unsubstituted or substituted 5-10 membered heteroaryl, wherein the $C_3$-$C_9$ heterocycloalkyl contains 1-3 heteroatoms selected from one or more of O, S and N, and the 5-10 membered heteroaryl contains 1-3 heteroatoms selected from one or more of N, O and S; and the substituted $C_1$-$C_6$ alkyl, the substituted $C_2$-$C_6$ alkynyl, the substituted $C_3$-$C_9$ heterocycloalkyl or the substituted 5-10 membered heteroaryl is substituted with one or more substituents independently selected from the following: halogen, —OH, —CN, ═O, —COOH, —C(═O)$NH_2$, —$COOCH_3$, —$NH_2$, and a $C_1$-$C_6$ alkyl, a $C_1$-$C_6$ alkyl-O— or a $C_3$-$C_6$ cycloalkyl that is unsubstituted or substituted with one or more $R^d$, wherein when a plurality of $R^d$ are present, they are the same or different, and each $R^d$ is independently H, halogen, —OH, ═O, —$CF_3$, —CN, —COOH or —C(═O)$NH_2$; and when a plurality of substituents are present, they are the same or different.

In a preferred embodiment of the present invention,

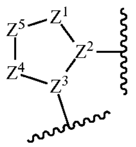

is a 5 membered heteroaryl or a 5 membered heterocycloalkenyl, wherein the 5 membered heteroaryl contains 1-2 heteroatoms selected from one or more of N, O and S, and the 5 membered heterocycloalkenyl contains 1-3 heteroatoms selected from one or more of N, O and S;

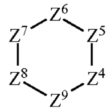

is phenyl, a 5-6 membered heterocycloalkyl, a 5-6 membered heterocycloalkenyl, or a 5-6 membered heteroaryl, wherein the 5-6 membered heterocycloalkyl contains 1-3 heteroatoms selected from one or more of N, O and S, the 5-6 membered heterocycloalkenyl contains 1-3 heteroatoms selected from one or more of N, O and S, and the 5-6 membered heteroaryl contains 1-3 heteroatoms selected from one or more of N, O and S;

$Z^1$, $Z^2$, $Z^3$, $Z^4$, $Z^5$, $Z^6$, $Z^7$, $Z^8$ and $Z^9$ independently represent a ring atom; and when

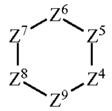

is a 5 membered heterocycloalkyl, a 5 membered heterocycloalkenyl or a 5 membered heteroaryl, $Z^6$ or $Z^9$ represents a single bond;

m is 1, 2, 3 or 4;

$R^3$ is H, halogen, —OH, —$CF_3$, —CN or a $C_1$-$C_6$ alkyl; when m is not 1, $R^3$ is independently the same or different; or when two adjacent $R^3$ are present, they, together with the ring atom to which they directly link, form a $C_3$-$C_6$ cycloalkyl, a $C_3$-$C_6$ cycloalkenyl, a $C_3$-$C_5$ heterocycloalkyl, a $C_3$-$C_5$ heterocycloalkenyl, phenyl or a 5-6 membered heteroaryl, wherein the $C_3$-$C_5$ heterocycloalkyl contains 1-3 heteroatoms selected from one or more of O, S and N, the $C_3$-$C_5$ heterocycloalkenyl contains 1-3 heteroatoms selected from one or more of O, S and N, and the 5-6 membered heteroaryl contains 1-3 heteroatoms selected from one or more of O, S and N;

W is a single bond or —C(═O)—NH—;

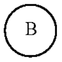

is phenyl, a 5-6 membered heteroaryl, or a $C_3$-$C_5$ heterocycloalkyl, wherein the 5-6 membered heteroaryl contains 1-3 heteroatoms selected from one or more of N, O and S, and the $C_3$-$C_5$ heterocycloalkyl contains 1-3 heteroatoms selected from one or more of O, S and N;

n is 1, 2, 3 or 4;

$R^1$ is independently H, halogen, —OH, —CN, an unsubstituted or substituted $C_1$-$C_6$ alkyl, or an unsubstituted or substituted $C_1$-$C_6$ alkyl-O—; wherein the substituted $C_1$-$C_6$ alkyl or the substituted $C_1$-$C_6$ alkyl-O— is substituted with one or more substituents independently selected from the following: halogen, —OH, —$CF_3$, —CN, —COOH, —C(═O)$NH_2$, a $C_1$-$C_6$ alkyl, a $C_1$-$C_6$ alkyl-O— or ═O (i.e., two geminal hydrogens on a carbon atom are substituted with the group O) when a plurality of substituents are present, they are the same or different; and when n is not 1, $R^1$ is independently the same or different;

Q is H, halogen, —OH, —$CF_3$, —CN, —$NH_2$, —NH—C(═O)—$R^{1-1}$, —C(═O)—$R^{1-2}$, —O—C(═O)—N($R^{1-3}R^{1-4}$), —C(═O)—N($R^{1-5}R^{1-6}$), —C(═NH)—N($R^{1-7}R^{1-8}$), —S(═O)$_2$—N($R^{1-9}R^{1-10}$), —S(═O)—N($R^{1-11}R^{1-12}$), —O—C(═O)—$R^{1-13}$, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_6$-$C_{10}$ aryl, an unsubstituted or substituted $C_3$-$C_5$ heterocycloalkyl, an unsubstituted or substituted $C_3$-$C_5$ heterocycloalkenyl, or an unsubstituted or substituted 5-6 membered heteroaryl; wherein the $C_3$-$C_5$ heterocycloalkyl contains 1-3 heteroatoms selected from one or more of O, S and N, the $C_3$-$C_5$ heterocycloalkenyl contains 1-3 heteroatoms selected from one or more of O, S and N, and the 5-6 membered heteroaryl contains 1-3 heteroatoms selected from one or more of N, O and S; and the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_6$-$C_{10}$ aryl, the substituted $C_3$-$C_5$ heterocycloalkyl, the substituted $C_3$-$C_5$ heterocycloalkenyl or the substituted 5-6 membered heteroaryl is substituted with one or more substituents independently selected from the following: halogen, —OH, —$CF_3$, —CN, —COOH, —C(═O)$NH_2$, ═O) (i.e., two geminal hydrogens on a carbon atom are substituted with the group O), and a $C_1$-$C_6$ alkyl, a $C_1$-$C_6$ alkyl-O— or a $C_3$-$C_6$ cycloalkyl that is unsubstituted or substituted with one or more $R^a$, wherein when a plurality of $R^a$ are present, they are the same or different, and each $R^a$ is halogen, —OH, ═O, —$CF_3$, —CN, —COOH or —C(═O)$NH_2$; and when a plurality of substituents are present, they are the same or different;

$R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ and $R^{1-13}$ are each independently H, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_3$-$C_6$ cycloalkyl, an unsubstituted or substituted $C_3$-$C_5$ heterocycloalkyl, an unsubstituted or substituted $C_3$-$C_5$ heterocycloalkenyl, an unsubstituted or substituted phenyl, or an unsubstituted or substituted 5-6 membered heteroaryl; wherein the $C_3$-$C_5$ heterocycloalkyl contains 1-3 heteroatoms selected from one or more of O, S and N, the $C_3$-$C_5$ heterocycloalkenyl contains 1-3 heteroatoms selected from one or more of O, S and N, and the 5-6 membered heteroaryl contains 1-3 heteroatoms selected from one or more of N, O and S; and the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_3$-$C_6$ cycloalkyl, the substituted $C_3$-$C_5$ heterocycloalkyl, the substituted $C_3$-$C_5$ heterocycloalkenyl, the substituted phenyl or the substituted 5-6 membered heteroaryl is substituted with one or more substituents independently selected from the following: halogen, —OH, —$CF_3$, —CN, a $C_1$-$C_6$ alkyl, a $C_1$-$C_6$ alkyl-O—, a $C_3$-$C_6$ cycloalkyl, —COOH or ═O (i.e., two geminal hydrogens on a carbon atom are substituted with the group O), wherein when a plurality of substituents are present, they are the same or different; or $R^{1-3}$ and $R^{1-4}$, $R^{1-5}$ and $R^{1-6}$, $R^{1-7}$ and $R^{1-8}$, $R^{1-2}$ and $R^{1-10}$, or $R^{1-11}$ and $R^{1-12}$, independently together with the N atom to which they directly link, form an unsubstituted or substituted $C_3$-$C_5$ heterocycloalkyl, an unsubstituted or substituted $C_3$-$C_5$ heterocycloalkenyl, or an unsubstituted or substituted 5-6 membered heteroaryl; wherein the $C_3$-$C_5$ heterocycloalkyl contains no heteroatom or 1-2 heteroatoms selected from one or more of O, S and N in addition to the existing N atom, the $C_3$-$C_5$ heterocycloalkenyl contains no heteroatom or 1-2 heteroatoms selected from one or more of O, S and N in addition to the existing N atom, and the 5-6 membered heteroaryl contains no heteroatom or 1-2 heteroatoms selected from one or more of O, S and N in addition to the existing N atom; and the substituted $C_3$-$C_5$ heterocycloalkyl, the substituted $C_3$-$C_5$ heterocycloalkenyl or the substituted 5-6 membered heteroaryl is substituted with one or more substituents independently selected from the following: halogen, —OH, —$CF_3$, —CN, a $C_1$-$C_6$ alkyl, a $C_1$-$C_6$ alkyl-O—, ═O (i.e., two geminal hydrogens on a carbon atom are substituted with the group O), and a $C_1$-$C_6$ alkyl, a $C_1$-$C_6$ alkyl-O— or a $C_3$-$C_6$ cycloalkyl that is unsubstituted or substituted with one or more $R^b$, wherein when a plurality of $R^b$ are present, they are the same or different and each $R^b$ is halogen, —OH, ═O, —$CF_3$, —CN, —COOH or —C(═O)$NH_2$; and when a plurality of substituents are present, they are the same or different;

$R^2$ is

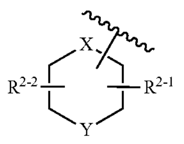

or —C(═O)N($R^{2-5}R^{2-6}$);

$R^{2-1}$ and $R^{2-2}$ are each independently H, halogen, —OH, —CN, an unsubstituted or substituted $C_1$-$C_6$ alkyl, an unsubstituted or substituted $C_1$-$C_8$ alkyl-O—, or ═O (i.e., two geminal hydrogens on a carbon atom are substituted with the group O); wherein the substituted $C_1$-$C_6$ alkyl or the substituted $C_1$-$C_6$ alkyl-O— is substituted with one or more substituents independently selected from the following: halogen, —OH, —$CF_3$, —CN, a $C_1$-$C_6$ alkyl, a $C_1$-$C_6$ alkyl-O— or =O) (i.e., two geminal hydrogens on a carbon atom are substituted with the group O), and when a plurality of substituents are present, they are the same or different;

X and Y are each independently a single bond, methylene, —O—, —N($R^{2-3}$)— or

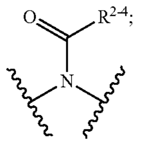

$R^{2-3}$, $R^{2-4}$, $R^{2-5}$ and $R^{2-6}$ are each independently H, an unsubstituted or substituted $C_1$-$C_6$ alkyl, an unsubstituted or substituted $C_3$-$C_8$ cycloalkyl, an unsubstituted or substituted $C_3$-$C_8$ cycloalkyl-O—, or an unsubstituted or substituted $C_1$-$C_6$ alkyl-O—; wherein the substituted $C_1$-$C_6$ alkyl, the substituted $C_3$-$C_8$ cycloalkyl, the substituted $C_3$-$C_8$ cycloalkyl-O— or the substituted $C_1$-$C_6$ alkyl-O— is substituted with one or more substituents independently selected from the following: halogen, —OH, —$CF_3$, —CN, a $C_1$-$C_6$ alkyl, a $C_1$-$C_6$ alkyl-O— or =O (i.e., two geminal hydrogens on a carbon atom are substituted with the group O), and when a plurality of substituents are present, they are the same or different.

In a preferred embodiment of the present invention, when

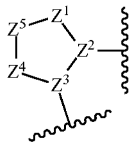

is a 5 membered heteroaryl, the 5 membered heteroaryl is pyrrolyl (e.g., 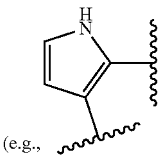 or 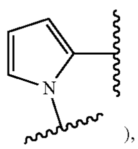), furanyl (e.g., 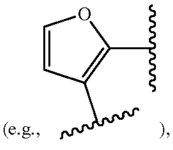), pyrazolyl (e.g., 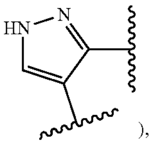), thienyl (e.g., 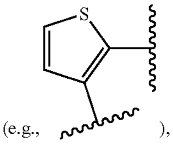), or imidazolyl (e.g., 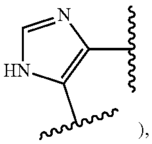), (In the structural formula, the right-side bond is linked to W)

In a preferred embodiment of the present invention,

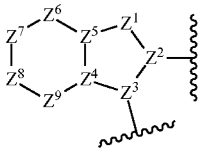

is

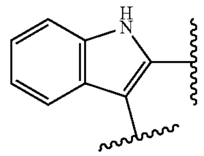,

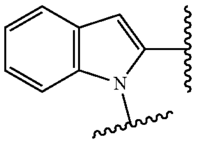,

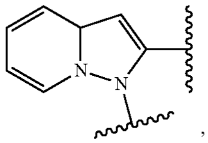,

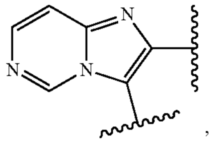,

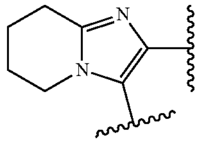,

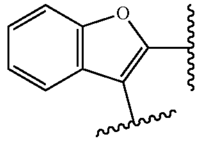,

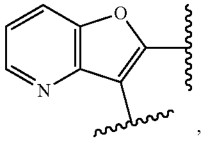,

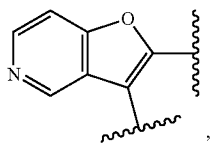,

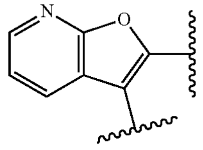,

-continued

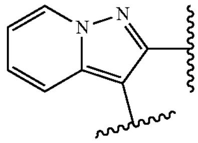

or

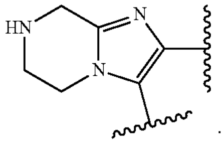

.

In a preferred embodiment of the present invention, when two adjacent $R^3$ are present and they, together with the ring atom to which they directly link, form a $C_3$-$C_5$ heterocycloalkyl, the $C_3$-$C_5$ heterocycloalkyl is a $C_4$-$C_5$ heterocycloalkyl, wherein the $C_4$-$C_5$ heterocycloalkyl contains 1-2 heteroatoms selected from one or more of N, O and S.

In a preferred embodiment of the present invention, when two adjacent $R^3$ are present and they, together with the ring atom to which they directly link, form a $C_3$-$C_5$ heterocycloalkenyl, the $C_3$-$C_5$ heterocycloalkenyl is a $C_4$-$C_5$ heterocycloalkenyl, wherein the $C_4$-$C_5$ heterocycloalkenyl contains 1-2 heteroatoms selected from one or more of N, O and S.

In a preferred embodiment of the present invention, when

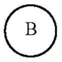

is a $C_3$-$C_5$ heterocycloalkyl, the $C_3$-$C_5$ heterocycloalkyl is a $C_4$-$C_5$ heterocycloalkyl, wherein the $C_4$-$C_5$ heterocycloalkyl contains 1-2 heteroatoms selected from one or more of N, O and S, and is preferably piperidinyl (e.g.,

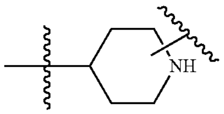

(e.g.,

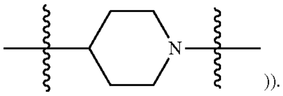

)).

(In the structural formula, the left-side bond is linked to W, and the right-side bond is linked to Q)

In a preferred embodiment of the present invention, when Q is an unsubstituted or substituted $C_3$-$C_5$ heterocycloalkyl, the $C_3$-$C_5$ heterocycloalkyl is a $C_4$-$C_5$ heterocycloalkyl, wherein the $C_4$-$C_5$ heterocycloalkyl contains 1-2 heteroatoms selected from one or more of N, O and S, and is preferably pyrrolidinyl (e.g.,

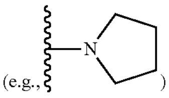 [SMILES: *N1CCCC1]

)

or piperazinyl (e.g.,

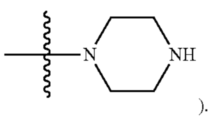

).

In a preferred embodiment of the present invention, when Q is an unsubstituted or substituted $C_3$-$C_5$ heterocycloalkenyl, the $C_3$-$C_5$ heterocycloalkenyl is a $C_4$-$C_5$ heterocycloalkenyl, wherein the $C_4$-$C_5$ heterocycloalkenyl contains 1-2 heteroatoms selected from one or more of N, O and S; and the $C_4$-$C_5$ heterocycloalkenyl is preferably 2,5-dihydro-1H-pyrrolyl (e.g.,

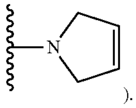

).

In a preferred embodiment of the present invention, when Q is an unsubstituted or substituted 5-6 membered heteroaryl, the 5-6 membered heteroaryl is imidazolyl (e.g.,

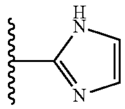

or

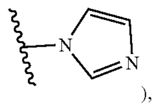

), oxazolyl (e.g.,

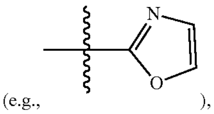

), furanyl (e.g.,

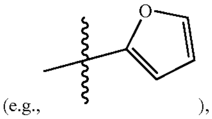 [SMILES: *c1ccco1]

), thienyl (e.g.,

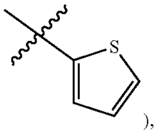

), pyrrolyl (e.g.,

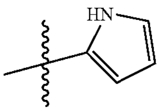

or

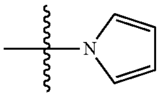

), pyrazolyl (e.g., 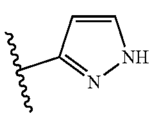 or 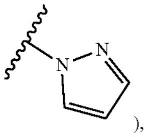), isoxazolyl (e.g., 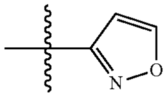), pyridinyl (e.g., 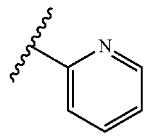)

or pyrimidinyl (e.g., 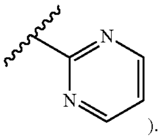).

In a preferred embodiment of the present invention, when Q is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted $C_6$-$C_{10}$ aryl, a substituted $C_3$-$C_5$ heterocycloalkyl, a substituted $C_3$-$C_5$ heterocycloalkenyl, or a substituted 5-6 membered heteroaryl, the number of the substituents is independently 1, 2, 3 or 4.

In a preferred embodiment of the present invention, when Q is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted $C_6$-$C_{10}$ aryl, a substituted $C_3$-$C_5$ heterocycloalkyl, a substituted $C_3$-$C_5$ heterocycloalkenyl, or a substituted 5-6 membered heteroaryl, and the substituent is halogen, the halogen is independently fluorine, chlorine, bromine or iodine, and preferably fluorine.

In a preferred embodiment of the present invention, when Q is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted $C_6$-$C_{10}$ aryl, a substituted $C_3$-$C_5$ heterocycloalkyl, a substituted $C_3$-$C_5$ heterocycloalkenyl, or a substituted 5-6 membered heteroaryl, and the substituent is a $C_2$-$C_6$ alkyl or a $C_1$-$C_8$ alkyl-O-substituted with one or more $R^a$, the $C_1$-$C_6$ alkyl (e.g., methyl, ethyl, propyl, butyl, pentyl or hexyl) in the substituent is independently a $C_1$-$C_4$ alkyl (e.g., methyl, ethyl, n-propyl, isopropyl, n-butyl, isobutyl, sec-butyl or tert-butyl), and preferably methyl.

In a preferred embodiment of the present invention, when Q is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted $C_6$-$C_{10}$ aryl, a substituted $C_3$-$C_5$ heterocycloalkyl, a substituted $C_3$-$C_5$ heterocycloalkenyl, or a substituted 5-6 membered heteroaryl, and the substituent is a $C_3$-$C_6$ cycloalkyl substituted with one or more $R^a$, the $C_3$-$C_8$ cycloalkyl in the substituent (e.g., cyclopropyl, cyclobutyl, cyclopentyl, and cyclohexyl) is cyclopropyl.

In a preferred embodiment of the present invention, when Q is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted $C_6$-$C_{10}$ aryl, a substituted $C_3$-$C_5$ heterocycloalkyl, a substituted $C_3$-$C_5$ heterocycloalkenyl, or a substituted 5-6 membered heteroaryl, the substituent is a $C_1$-$C_6$ alkyl, a $C_1$-$C_6$ alkyl-O—, or a $C_3$-$C_6$ cycloalkyl substituted with one or more $R^a$, and $R^a$ is halogen, the halogen is independently fluorine, chlorine, bromine or iodine.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ or $R^{1-13}$ is an unsubstituted or substituted $C_1$-$C_6$ alkyl, or an unsubstituted or substituted $C_1$-$C_6$ alkyl-O—, the $C_1$-$C_6$ alkyl (e.g., methyl, ethyl, propyl, butyl, pentyl or hexyl) is independently a $C_1$-$C_4$ alkyl (e.g., methyl, ethyl, n-propyl, isopropyl, n-butyl, isobutyl, sec-butyl or tert-butyl), and preferably methyl or ethyl.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ or $R^{1-13}$ is an unsubstituted or substituted $C_2$-$C_6$ alkenyl, or an unsubstituted or substituted $C_2$-$C_6$ alkenyl-O—, the $C_2$-$C_6$ alkenyl is a $C_2$-$C_4$ alkenyl {e.g., vinyl, propenyl (e.g., 1-propenyl or 2-propenyl), or butenyl (e.g., 2-butenyl, 1-butenyl or butadienyl)}, and preferably ethenyl.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ or $R^{1-13}$ is an unsubstituted or substituted $C_3$-$C_5$ heterocycloalkyl, the $C_3$-$C_5$ heterocycloalkyl is a $C_4$-$C_5$ heterocycloalkyl, wherein the $C_4$-$C_5$ heterocycloalkyl contains 1-2 heteroatoms selected from one or more of N, O and S.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ or $R^{1-13}$ is an unsubstituted or substituted $C_3$-$C_5$ heterocycloalkenyl, the $C_3$-$C_5$ heterocycloalkenyl is a $C_4$-$C_5$ heterocycloalkenyl, wherein the $C_4$-$C_5$ heterocycloalkenyl contains 1-2 heteroatoms selected from one or more of N, O and S.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ or $R^{1-13}$ is an unsubstituted or substituted 5-6 membered heteroaryl, the 5-6 membered heteroaryl contains 1-2 heteroatoms selected from one or two of N, O and S.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-4}$, $R^{1-9}$, $R^{1-10}$, $R^{1-11}$, $R^{1-12}$ or $R^{1-13}$ is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted phenyl, a substituted $C_3$-$C_5$ heterocycloalkyl, a substituted $C_3$-$C_5$ heterocycloalkenyl, or a substituted 5-6-membered heteroaryl, and the substituent is halogen, the halogen is independently fluorine, chlorine, bromine, or iodine, and preferably fluorine.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}R^{1-9}$, $R^{1-10}$, $R^{1-11}$, $R^{1-12}$ or $R^{1-13}$ is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted phenyl, a substituted $C_3$-$C_5$ heterocycloalkyl, a substituted $C_3$-$C_5$ heterocycloalkenyl, or a substituted 5-6 membered heteroaryl, and the substituent is a $C_1$-$C_6$ alkyl or $C_1$-$C_6$ alkyl-O—, the $C_1$-$C_6$ alkyl in the substituent (e.g., methyl, ethyl, propyl, butyl, pentyl or hexyl) is independently a $C_1$-$C_4$ alkyl (e.g., methyl, ethyl, n-propyl, isopropyl, n-butyl, isobutyl, sec-butyl or tert-butyl).

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ or $R^{1-13}$ is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted phenyl, a substituted $C_3$-$C_5$ heterocycloalkyl, a substituted $C_3$-$C_5$ heterocycloalkenyl or a substituted 5-6 membered heteroaryl, and the substituent is a $C_3$-$C_6$ cycloalkyl, the $C_3$-$C_6$ cycloalkyl in the substituent (e.g., cyclopropyl, cyclobutyl, cyclopentyl and cyclohexyl) is cyclopropyl.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ or $R^{1-13}$ is a substituted $C_1$-$C_6$ alkyl, a substituted $C_1$-$C_6$ alkyl-O—, a substituted $C_2$-$C_6$ alkenyl, a substituted $C_2$-$C_6$ alkenyl-O—, a substituted phenyl, a substituted $C_3$-$C_5$ heterocycloalkyl, a substituted $C_3$-$C_5$ heterocycloalkenyl or a substituted 5-6 membered heteroaryl, the number of the substituents is independently 1, 2, 3 or 4, and preferably 1 or 2.

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, or $R^{1-11}$ and $R^{1-12}$, independently together with the N atom to which they directly link, form an unsubstituted or substituted $C_3$-$C_5$ heterocycloalkyl, the $C_3$-$C_5$ heterocycloalkyl contains no heteroatom or one heteroatom selected from one of O, S and N in addition to the existing N atom.

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, or $R^{1-11}$ and $R^{1-12}$, independently together with the N atom to which they directly link, form an unsubstituted or substituted $C_3$-$C_5$ heterocycloalkenyl, the $C_3$-$C_5$ heterocycloalkenyl contains no heteroatom or one heteroatom selected from one of O, S and N in addition to the existing N atom.

In a preferred embodiment of the present invention, when $R^{13}$ and $R^{1-4}$, $R^{1-5}$ and $R^{1-6}$, $R^{1-7}$ and $R^{1-8}$, $R^{1-9}$ and $R^{1-10}$, or $R^{1-11}$ and $R^{1-12}$, independently together with the N atom to which they directly link, form an unsubstituted or substituted 5-6 membered heteroaryl, the unsubstituted or substituted 5-6 membered heteroaryl contains no heteroatom or one heteroatom selected from one of O, S and N in addition to the existing N atom.

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, or $R^{1-11}$ and $R^{1-12}$, independently together with the N atom to which they directly link, form a substituted $C_3$-$C_5$ heterocycloalkyl, a substituted $C_3$-$C_5$ heterocycloalkenyl, or a substituted 5-6 membered heteroaryl, and the substituent is halogen, the halogen is independently fluorine, chlorine, bromine, or iodine.

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, or $R^{1-11}$ and $R^{1-12}$, independently together with the N atom to which they directly link, form a substituted $C_3$-$C_5$ heterocycloalkyl, a substituted $C_3$-$C_5$ heterocycloalkenyl, or a substituted 5-6 membered heteroaryl, and the substituent is a $C_1$-$C_6$ alkyl or a $C_1$-$C_6$ alkyl-O-substituted with one or more $R^b$, the $C_1$-$C_6$ alkyl in the substituent (e.g., methyl, ethyl, propyl, butyl, pentyl or hexyl) is independently a $C_1$-$C_4$ alkyl (e.g., methyl, ethyl, n-propyl, isopropyl, n-butyl, isobutyl, sec-butyl or tert-butyl).

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, or $R^{1-11}$ and $R^{1-12}$, independently together with the N atom to which they directly link, form a substituted $C_3$-$C_5$ heterocycloalkyl, a substituted $C_3$-$C_5$ heterocycloalkenyl, or a substituted 5-6 membered heteroaryl, and the substituent is a $C_3$-$C_6$ cycloalkyl substituted with one or more $R^b$, the $C_3$-$C_6$ cycloalkyl in the substituent is cyclopropyl, cyclobutyl, cyclopentyl, and cyclohexyl.

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, or $R^{1-11}$ and $R^{1-12}$, independently together with the N atom to which they directly link, form a substituted $C_3$-$C_5$ heterocycloalkyl, a substituted $C_3$-$C_5$ heterocycloalkenyl, or a substituted 5-6 membered heteroaryl, the substituent is a $C_1$-$C_6$ alkyl, a $C_1$-$C_6$ alkyl-O— or a $C_3$-$C_6$ cycloalkyl substituted with one or more $R^b$, wherein when $R^b$ is halogen, the halogen is independently fluorine, chlorine, bromine or iodine.

In a preferred embodiment of the present invention, when $R^{1-3}$ and $R^{1-4}$, $R^{1-5}$ and $R^{1-6}$, $R^{1-7}$ and $R^{1-8}$, $R^{1-9}$ and $R^{1-10}$, or $R^{1-11}$ and $R^{1-12}$, independently together with the N atom to which they directly link, form a substituted $C_3$-$C_5$ heterocycloalkyl, a substituted $C_3$-$C_5$ heterocycloalkenyl or a substituted 5-6 membered heteroaryl, the number of the substituent is 1, 2, 3, or 4 independently, and preferably 1 or 2.

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$. $R^{1-11}$, $R^{1-12}$ or $R^{1-13}$ is a substituted $C_1$-$C_6$ alkyl, the substituted $C_1$-$C_6$ alkyl is

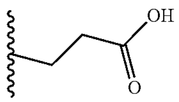

or

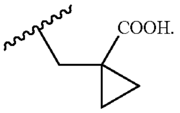

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ or $R^{1-13}$ is a substituted $C_2$-$C_6$ alkenyl, the substituted $C_2$-$C_6$ alkenyl may be

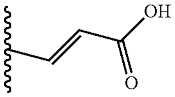

or

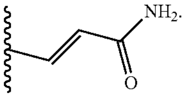

In a preferred embodiment of the present invention, when $R^{1-1}$, $R^{1-2}$, $R^{1-3}$, $R^{1-4}$, $R^{1-5}$, $R^{1-6}$, $R^{1-7}$, $R^{1-8}$, $R^{1-9}$, $R^{1-10}$, $R^{1-11}$, $R^{1-12}$ or $R^{1-13}$ is a substituted $C_3$-$C_6$ cycloalkyl, the substituted $C_3$-$C_6$ cycloalkyl is

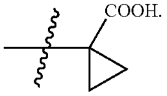 [SMILES: *C1(C(=O)O)CC1]

In a preferred embodiment of the present invention, when Q is a substituted $C_3$-$C_5$ heterocycloalkyl, the substituted $C_3$-$C_5$ heterocycloalkyl is

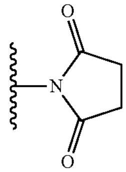
or
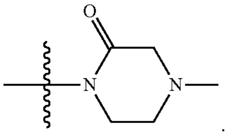
.

In a preferred embodiment of the present invention, when Q is a substituted $C_3$-$C_5$ heterocycloalkenyl, the substituted $C_3$-$C_5$ heterocycloalkenyl may be

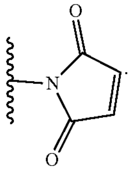

In a preferred embodiment of the present invention, when Q is a substituted 5-6 membered heteroaryl, the substituted 5-6 membered heteroaryl is

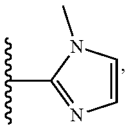
,
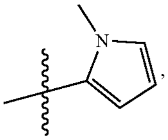
,
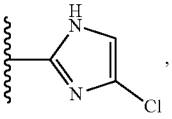
,
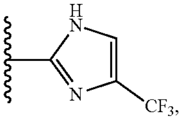
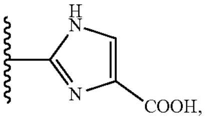
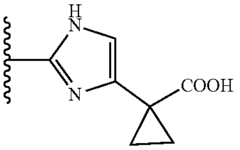
or
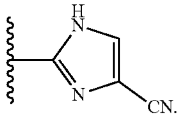

In a preferred embodiment of the present invention, when Q is —NH—C(═O)—$R^{1-1}$, the —NH—C(═O)—$R^{1-1}$ is —NH—C(═O)—$CH_3$, —NH—C(═O)—O—$CH_3$,

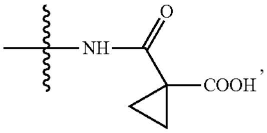
,
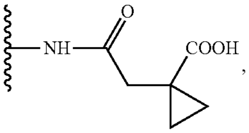
,
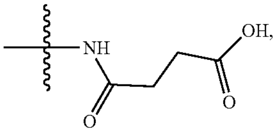
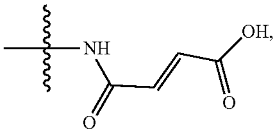
or

-continued

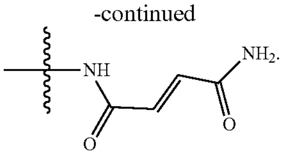

In a preferred embodiment of the present invention, when Q is —S(═O)$_2$—N($R^{1-9}R^{1-10}$), the —S(═O)$_2$—N($R^{1-9}R^{1-10}$) is —S(═O)$_2$—NH—$CH_3$.

In a preferred embodiment of the present invention, Q is H, —OH, —$CF_3$, —CN, —NH—C(═O)—$CH_3$, —NH—C(═O)—O—$CH_3$,

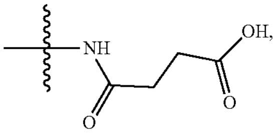
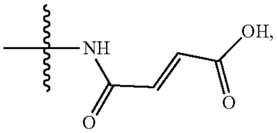
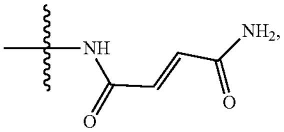

—C(═O)—$CH_3$, —C(═O)—$C_2H_5$, —C(═O)—O—$CH_3$, —O—C(═O)—NH—$CH_3$, —C(═O)—NH—$CH_3$, —C(═NH)—NH—$CH_3$, —S(═O)$_2$—NH—$CH_3$,

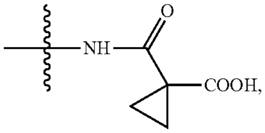
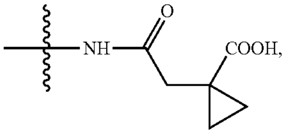
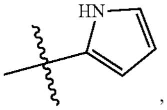
,
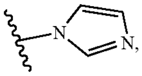
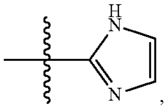
,
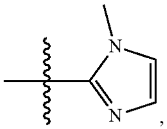
,
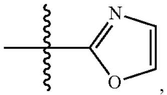
,
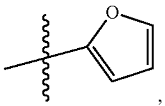
,
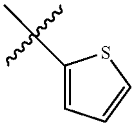
,
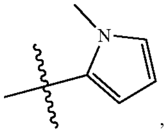
,
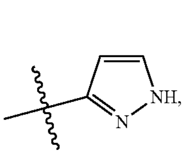
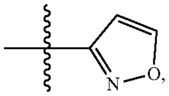
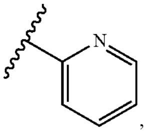
,
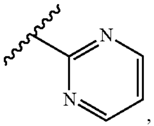
,
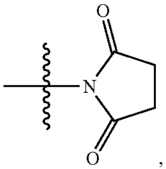
,
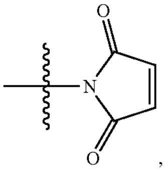
, -continued

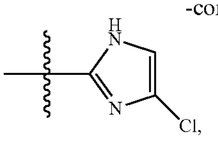
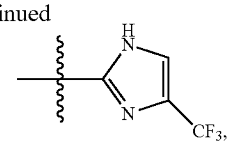
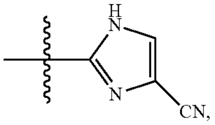
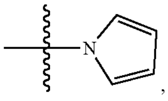
,
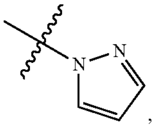
,
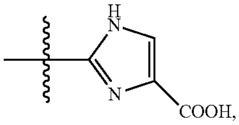
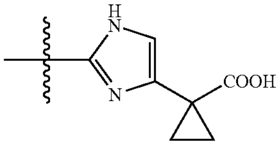
or
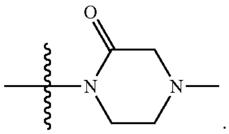
.

In a preferred embodiment of the present invention, when $R^2$ is

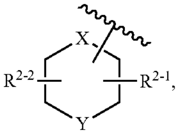

one of X and Y is

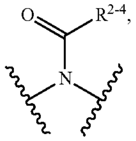

and the other is a single bond, methylene or —O— (e.g.,

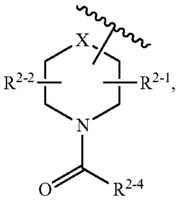

wherein X is a single bond, methylene or —O—); preferably X is —O—, i.e., $R^2$ is

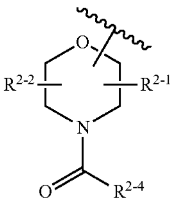
(e.g.,
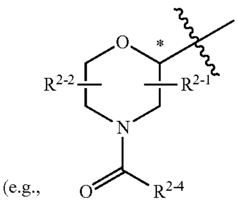

-continued

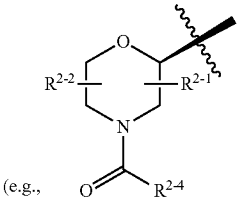
or
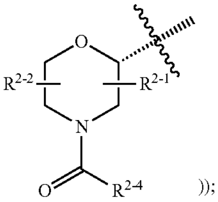
));

and more preferably, $R^2$ is

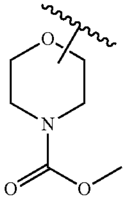
(e.g.,
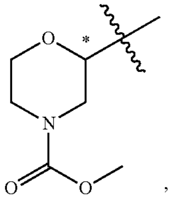
,
(e.g.,
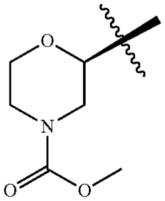
or
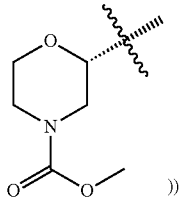
)) or
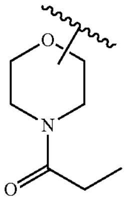
(e.g.,
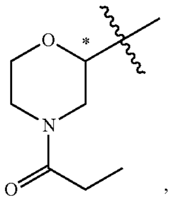
,
(e.g.,
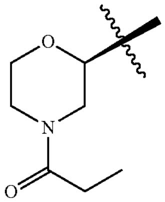
or
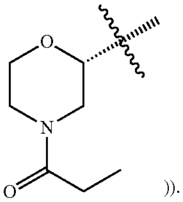
)).

In a preferred embodiment of the present invention, the heterocyclic compound of formula I is of formula I-C' as shown below:

I-C'

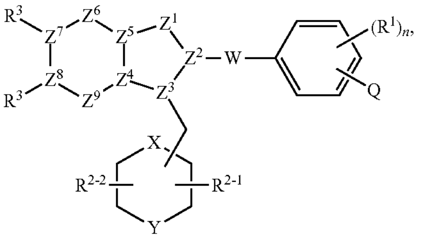

wherein Q is H, halogen, —OH, —$CF_3$, —CN, —$NH_2$, —NH—C(═O)—$R^{1-1}$, —C(═O)—$R^{1-2}$, —O—C(═O)—N($R^{1-3}R^{1-4}$), —C(═NH)—N($R^{1-7}R^{1-8}$), —$S(═O)_2$—N($R^{1-9}R^{1-1}$), ~S(═O)—N($R^{1-11}R^{1-12}$), —O—C(═O)—$R^{1-13}$, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_6$-$C_{10}$ aryl, an unsubstituted or substituted $C_3$-$C_5$ heterocycloalkyl, an unsubstituted or substituted $C_3$-$C_5$ heterocycloalkenyl, or an unsubstituted or substituted 5-6 membered heteroaryl;

preferably, the heterocyclic compound of formula I is of formula I-C'-1 as shown below:

I-C'-1

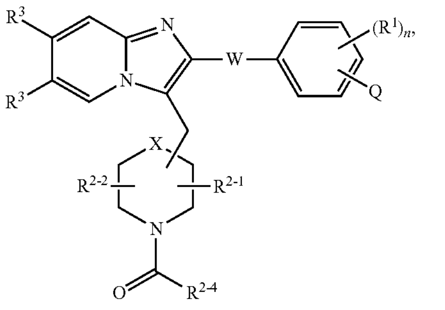

wherein Q is H, halogen, —OH, —$CF_3$, —CN, —$NH_2$, —NH—C(═O)—$R^{1-1}$, —C(═O)—$R^{1-2}$, —O—C(═O)—N($R^{1-3}R^{1-4}$), —C(═NH)—N($R^{1-7}R^{1-8}$), —S(═O)$_2$—N($R^{1-9}R^{1-10}$), —S(═O)—N($R^{1-11}R^{1-12}$), —O—C(═O)—$R^{1-13}$, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_6$-$C_{10}$ aryl, an unsubstituted or substituted $C_3$-$C_5$ heterocycloalkyl, an unsubstituted or substituted $C_3$-$C_5$ heterocycloalkenyl, or an unsubstituted or substituted 5-6 membered heteroaryl; and more preferably, the heterocyclic compound of formula I is of formula I-C'-2 as shown below:

I-C'-2

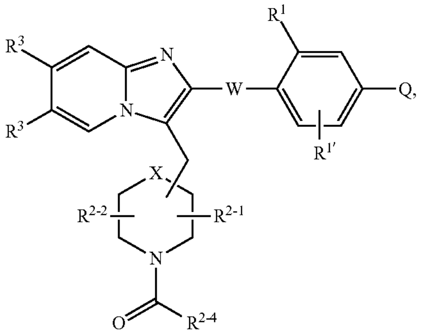

wherein $R^{1'}$ has the definition as described for $R^1$, $R^{1'}$ is the same as or different from $R^1$, and X is a single bond, methylene or —O—; Q is H, halogen, —OH, —$CF_3$, —CN, —$NH_2$, —NH—C(═O)—$R^{1-1}$, —C(═O)—$R^{1-2}$, —O—C(═O)—N($R^{1-3}R^{1-4}$), —C(═NH)—N($R^{1-7}R^{1-8}$), —S(═O)$_2$—N($R^{1-9}R^{1-10}$), —S(═O)—N($R^{1-11}R^{1-12}$), —O—C(═O)—$R^{1-13}$, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_6$-$C_{10}$ aryl, an unsubstituted or substituted $C_3$-$C_5$ heterocycloalkyl, an unsubstituted or substituted $C_3$-$C_5$ heterocycloalkenyl, or an unsubstituted or substituted 5-6 membered heteroaryl.

In a preferred embodiment of the present invention, the heterocyclic compound of formula I is preferably any one of the following compounds:

1

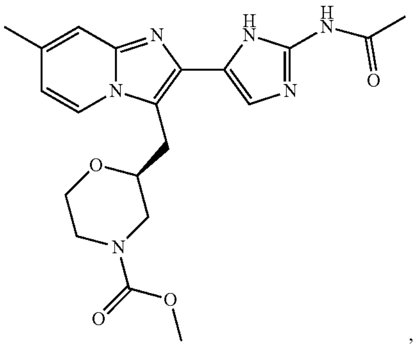

,

2

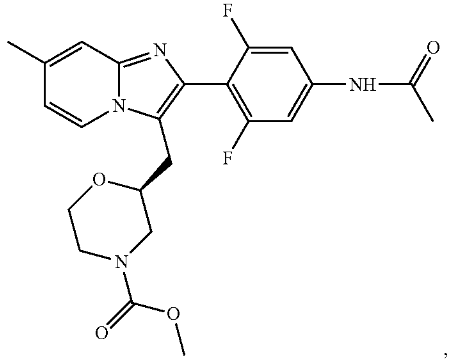

,

3

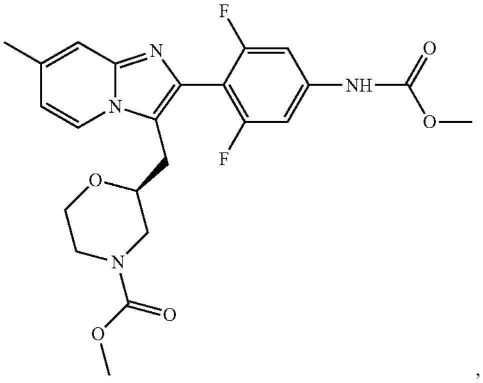

,

4

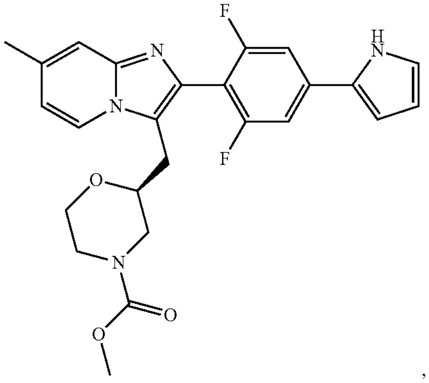

,

-continued
5
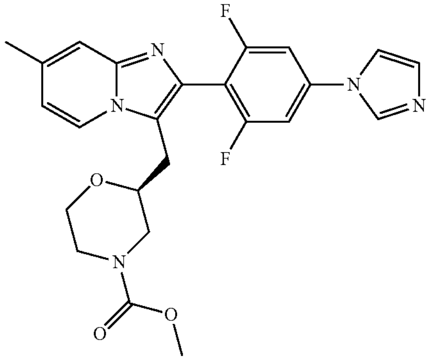
,
6
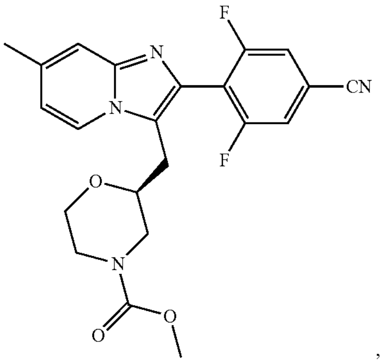
,
7
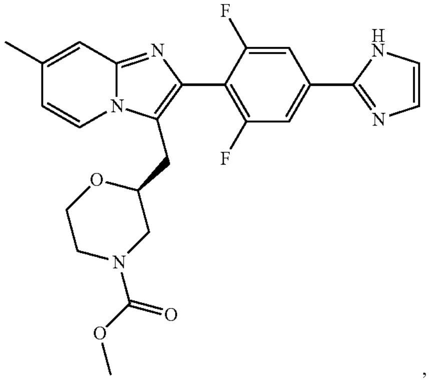
,
8
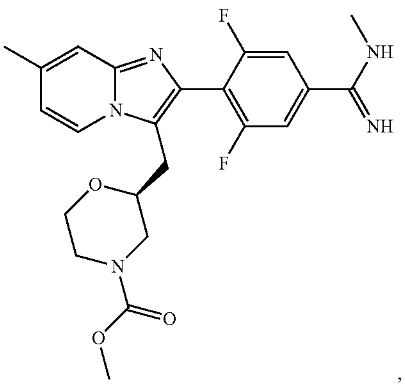
,
-continued
9
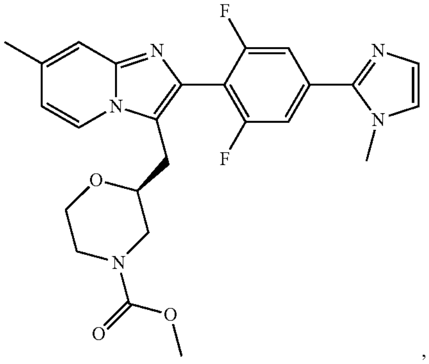
,
10
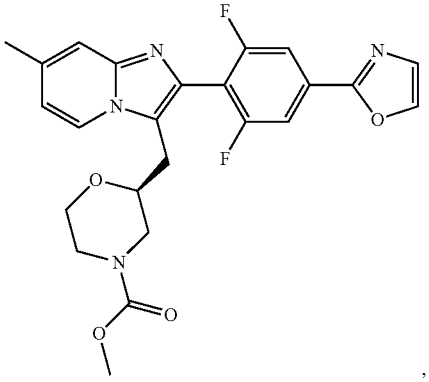
,
11
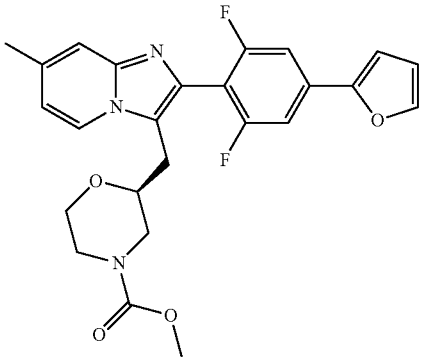
,
12
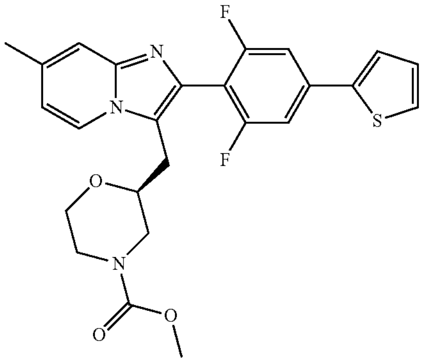
, -continued
13
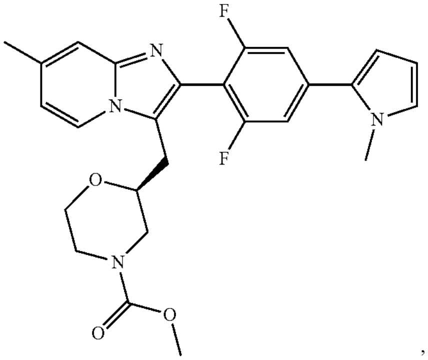
,
14
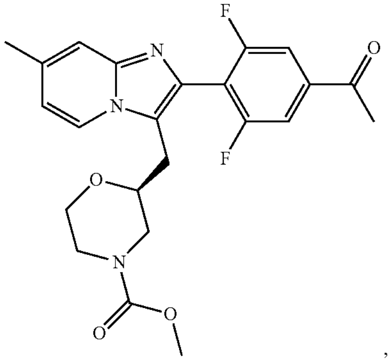
,
15
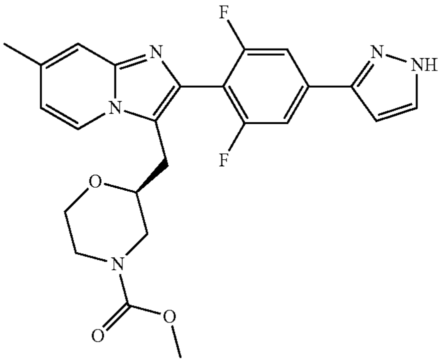
,
16
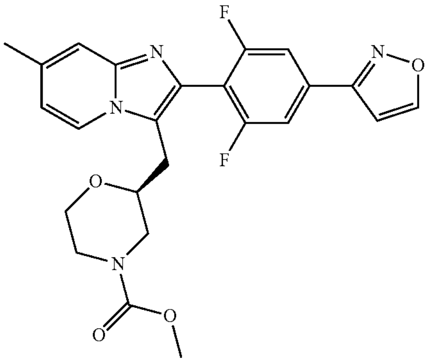
,
-continued
17
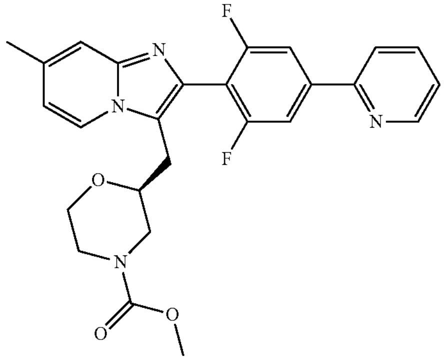
,
18
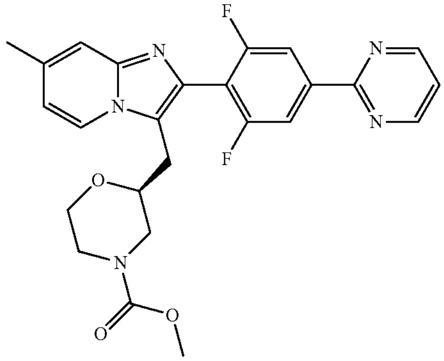
,
19
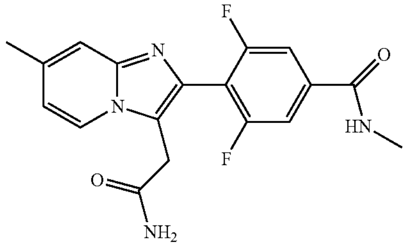
,
20
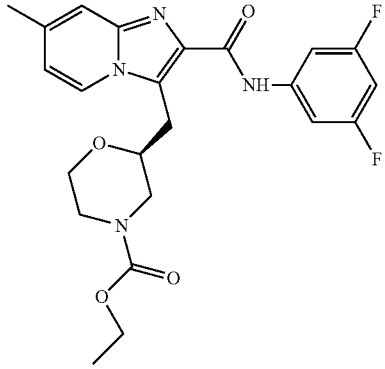
, -continued
21
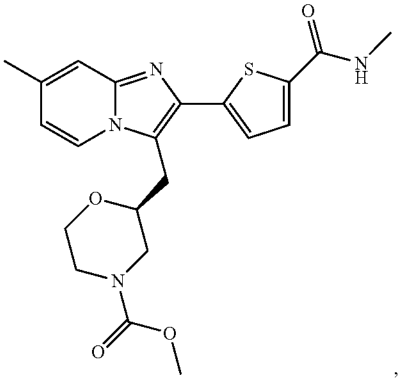
,
22
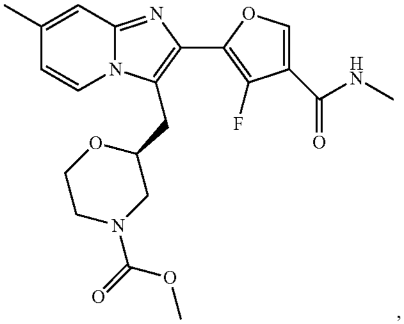
,
23
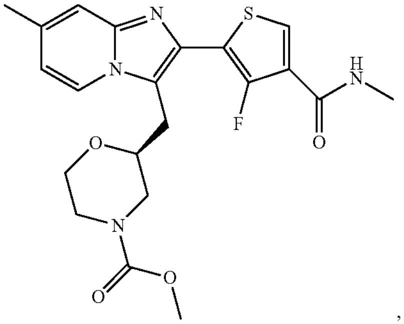
,
24
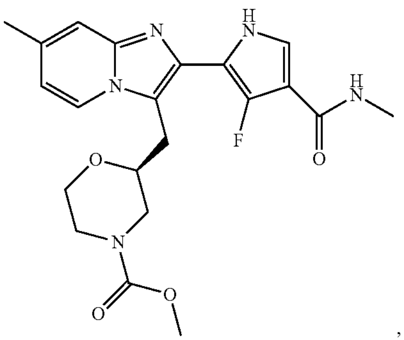
,
-continued
25
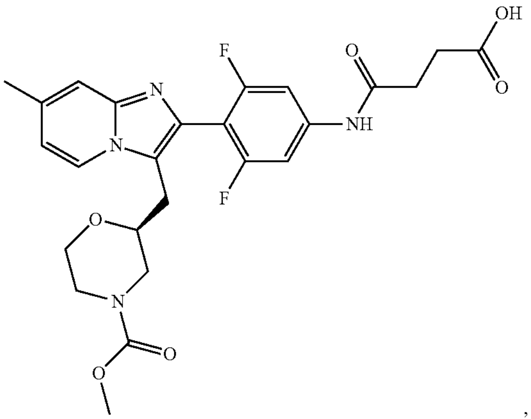
,
26
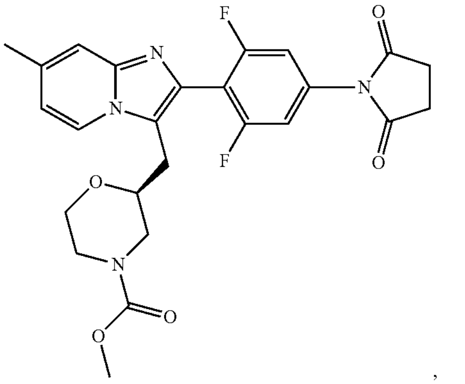
,
27
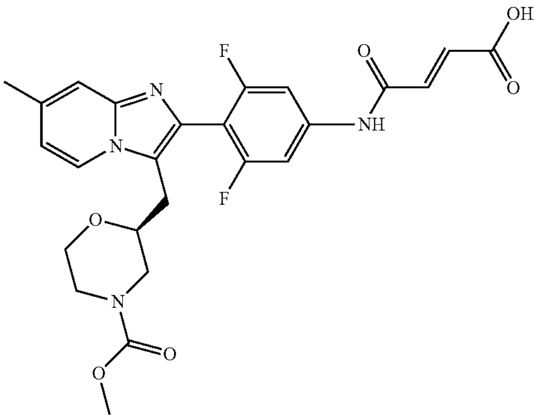
, -continued
28
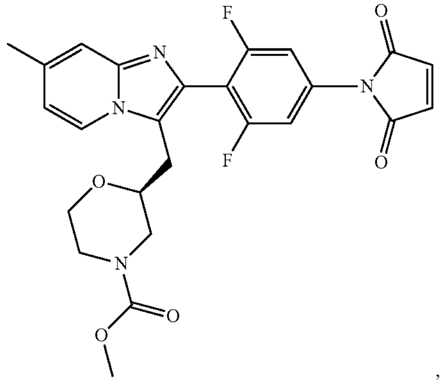
,
29
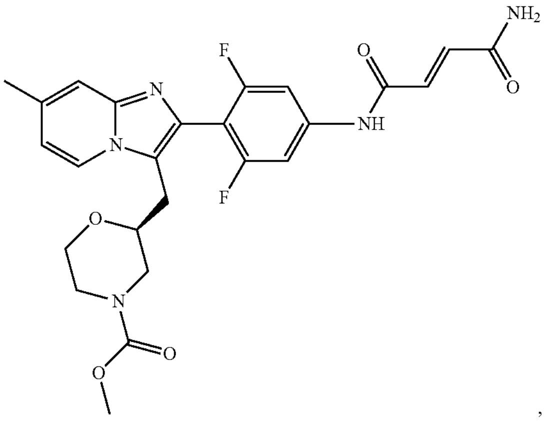
,
30
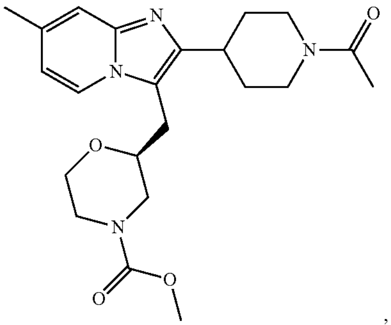
,
31
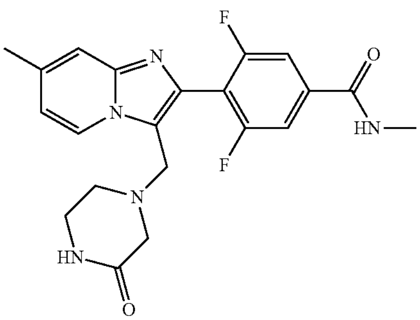
,
-continued
32
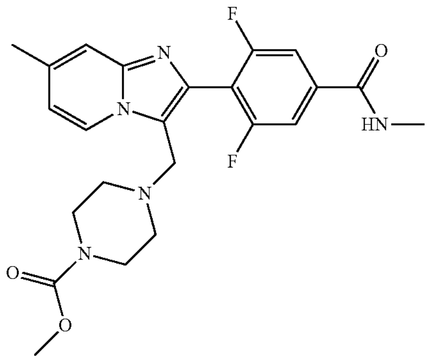
,
33
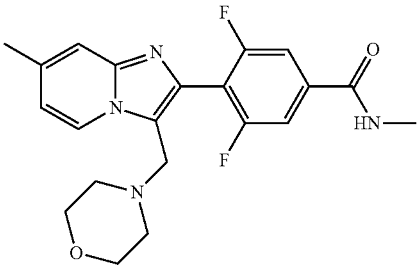
,
34
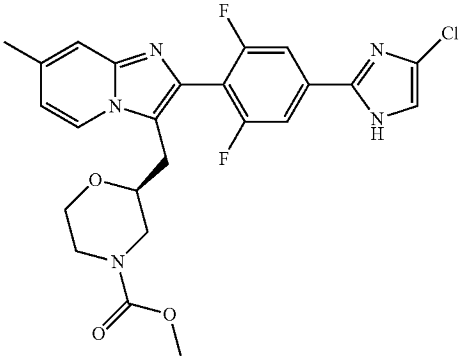
,
35
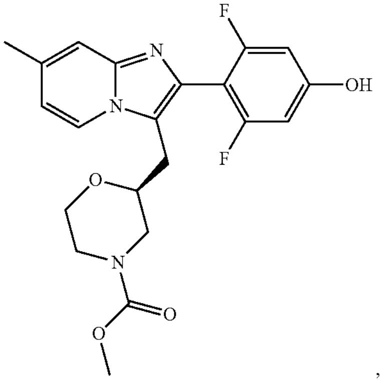
, -continued
36
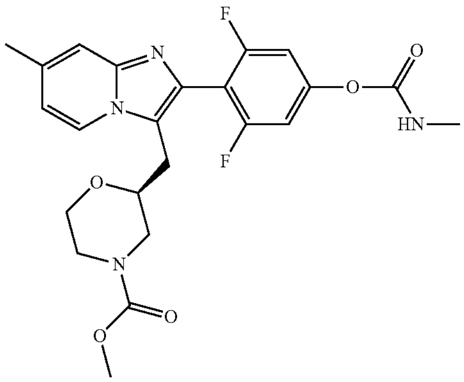
,
37
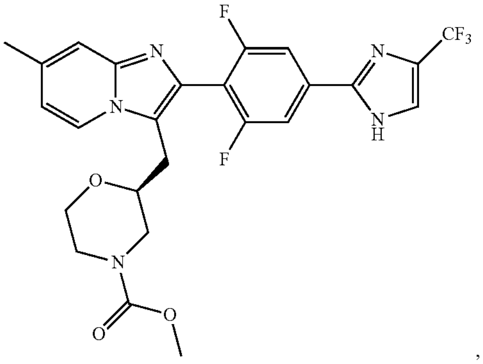
,
38
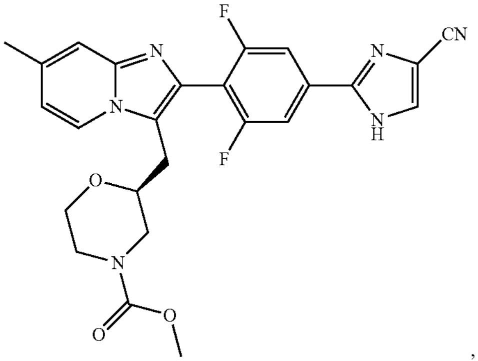
,
39
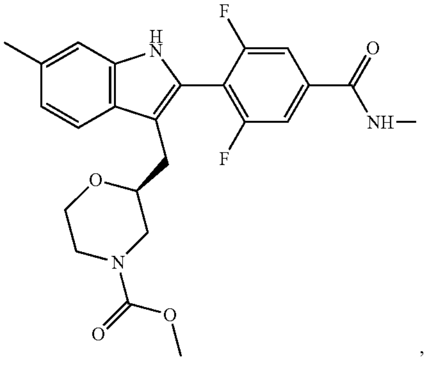
,
-continued
40
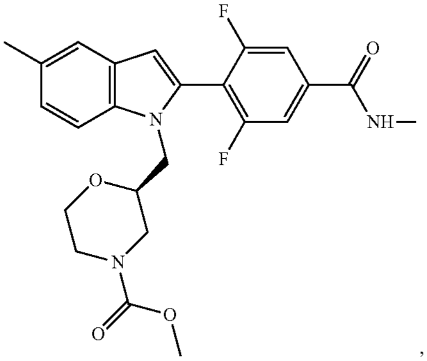
,
41
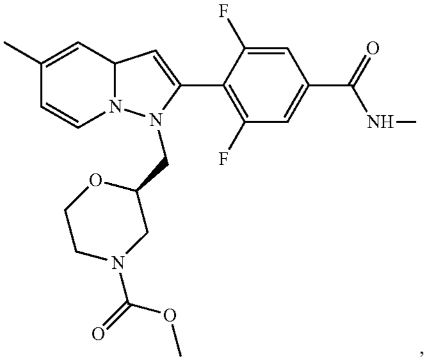
,
42
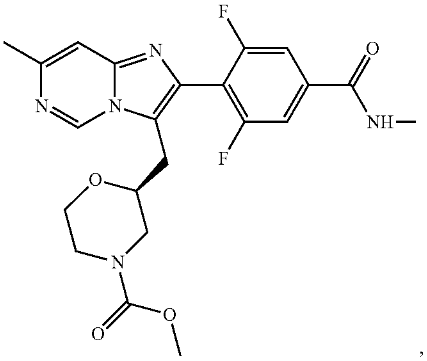
,
43
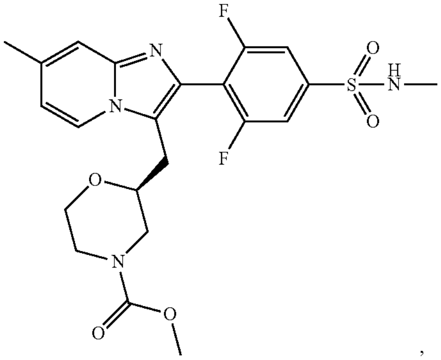
, -continued
44
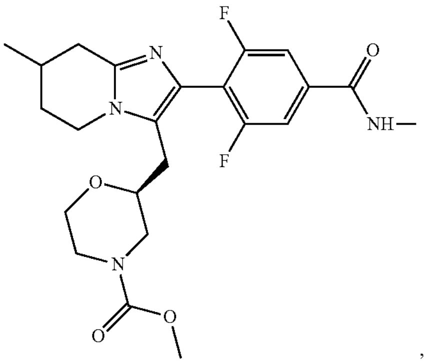
,
45
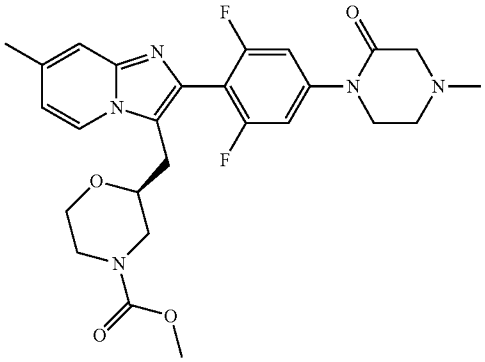
,
46
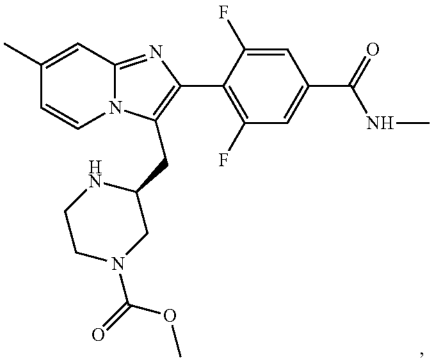
,
47
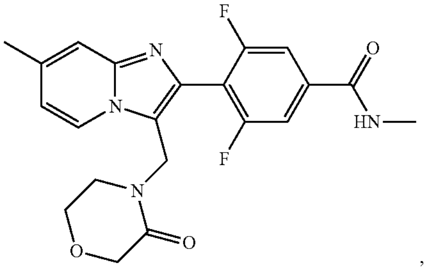
,
-continued
48
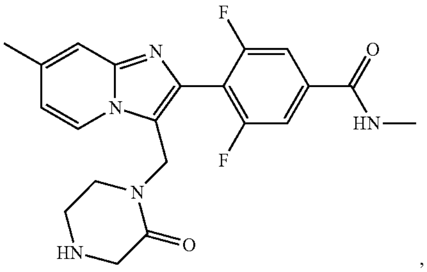
,
49
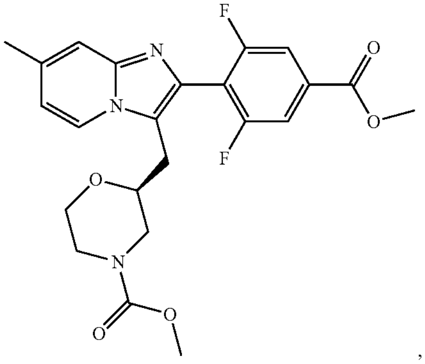
,
50
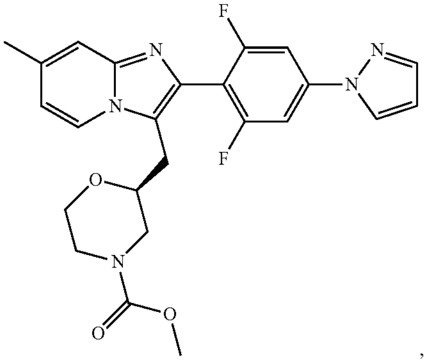
,
51
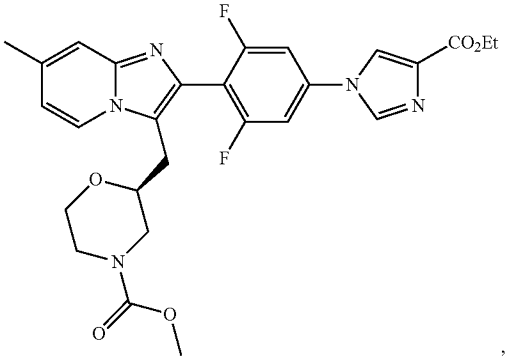
, -continued
52
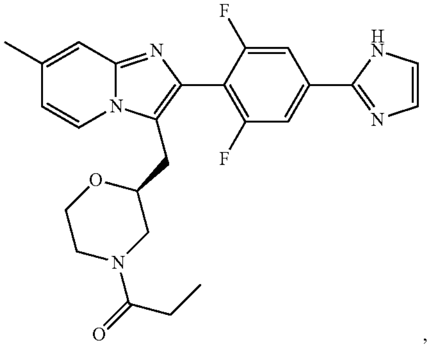
,
53
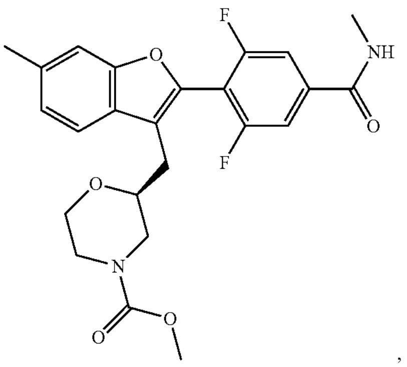
,
54
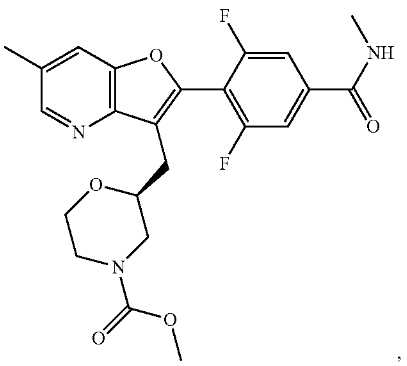
,
55
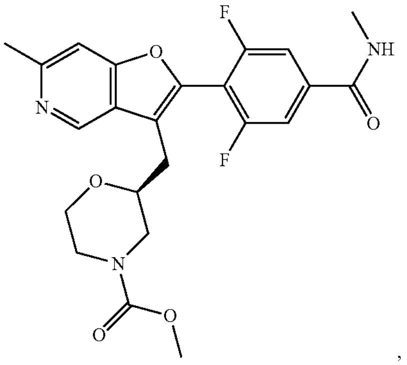
,
-continued
56
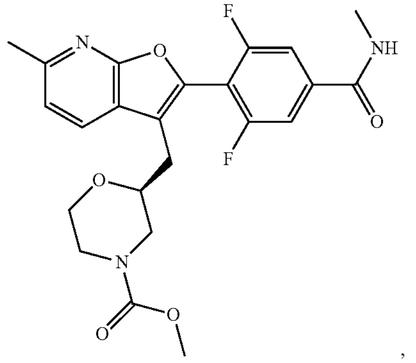
,
57
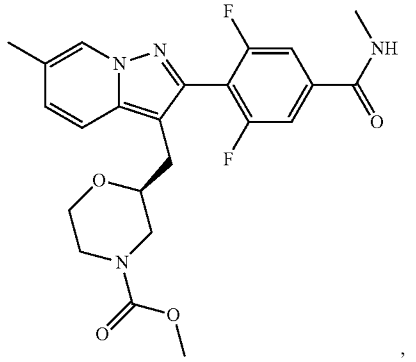
,
58
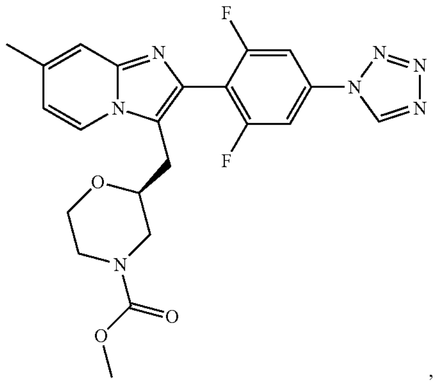
,
59
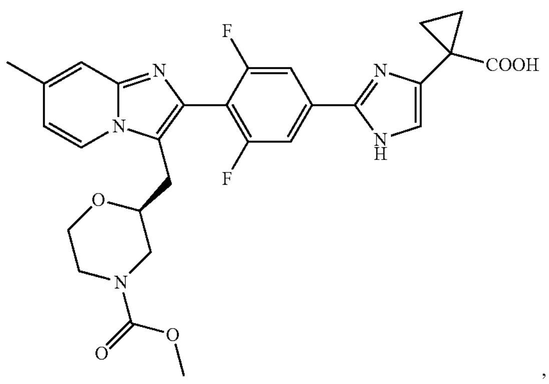
, 60
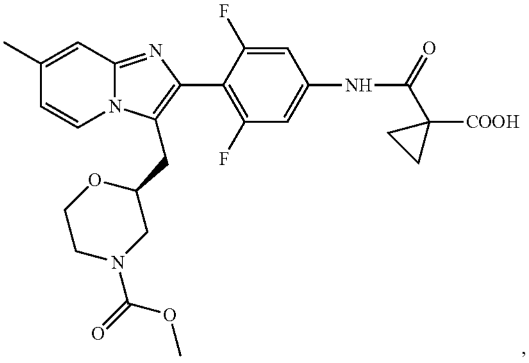
,
61
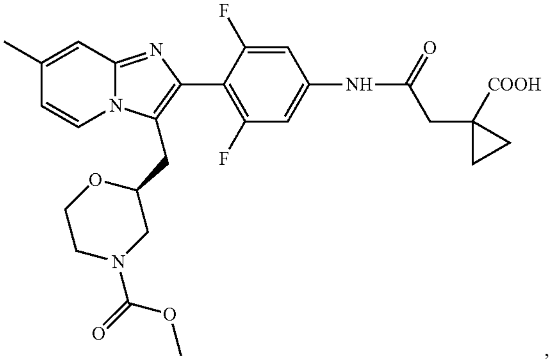
,
62
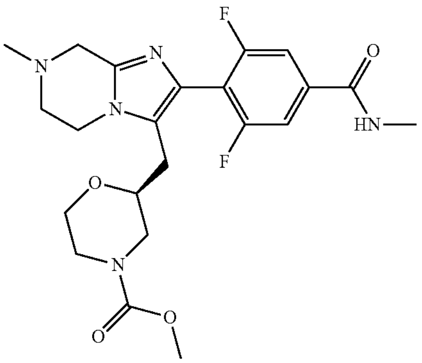
,
63
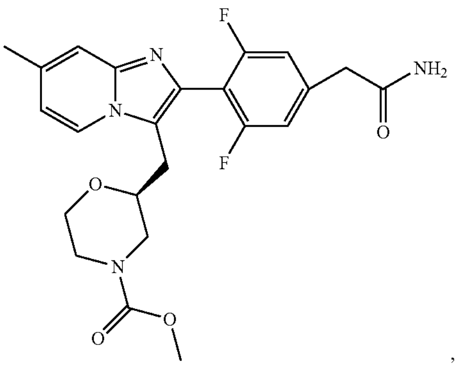
,
64
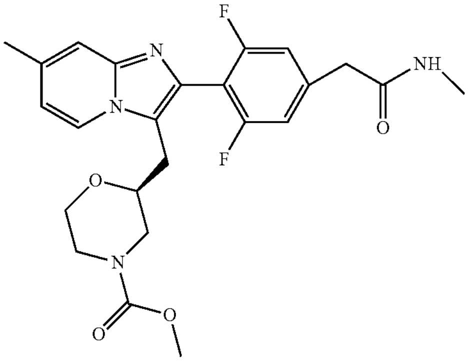
,
65
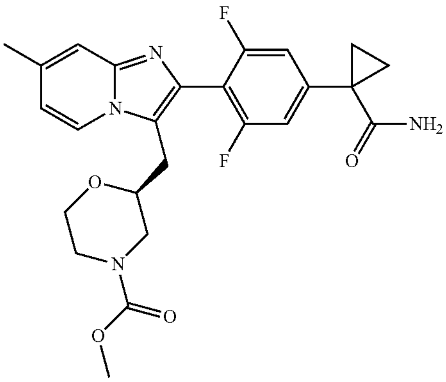
,
66
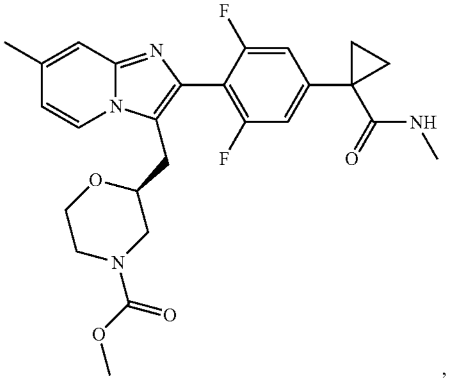
,
67
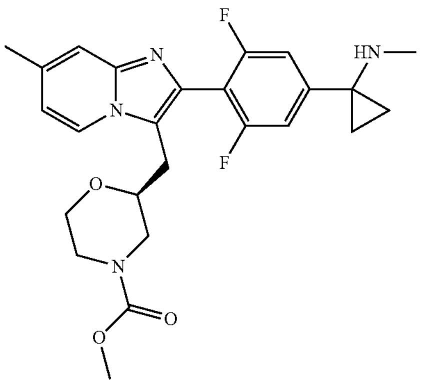
, -continued
68
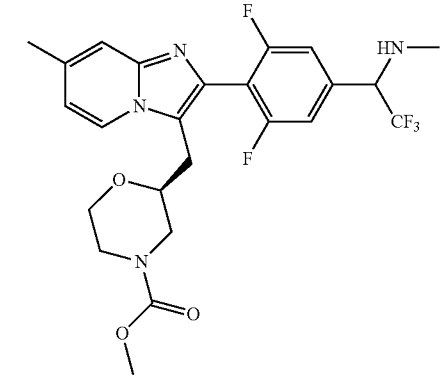
,
69
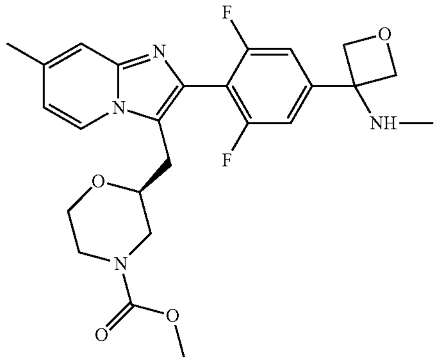
,
70
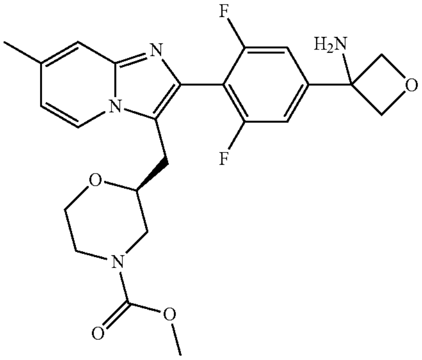
,
71
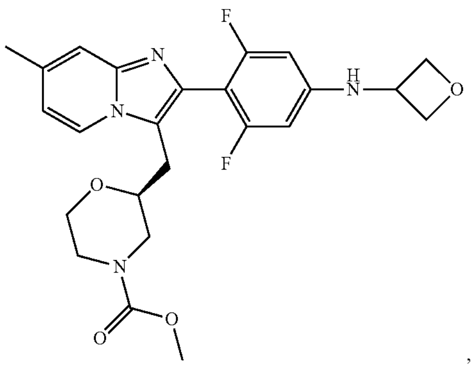
,
-continued
72
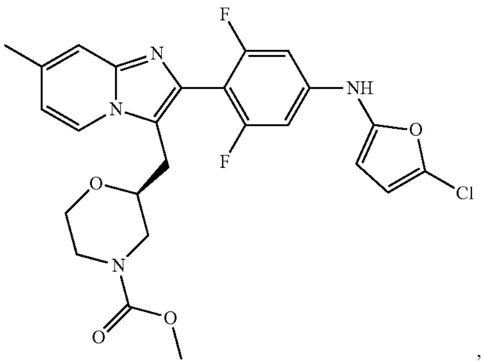
,
73
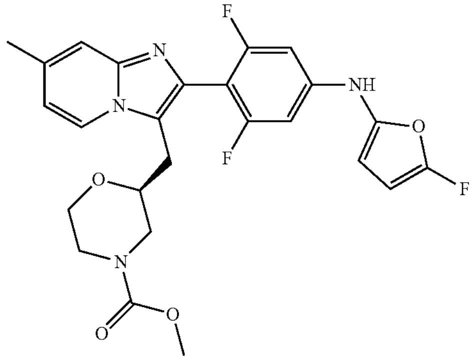
,
74
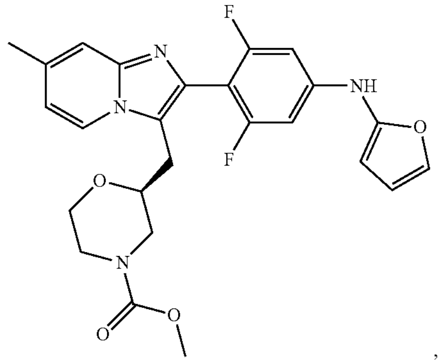
,
75
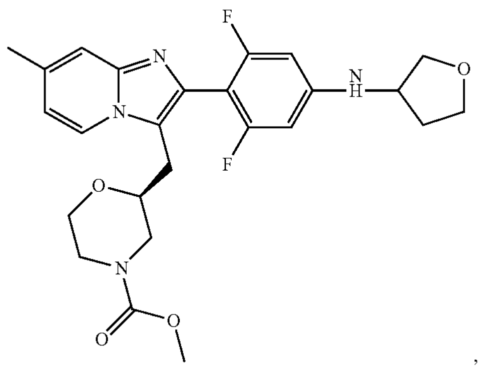
, -continued
76
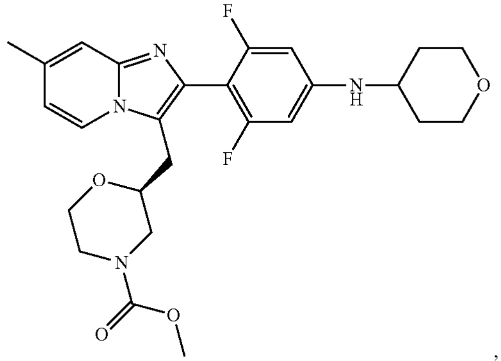
,
77
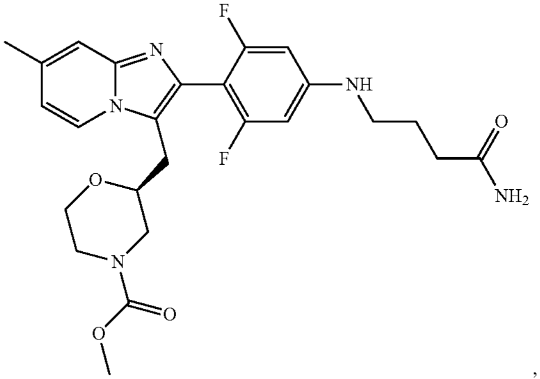
,
78
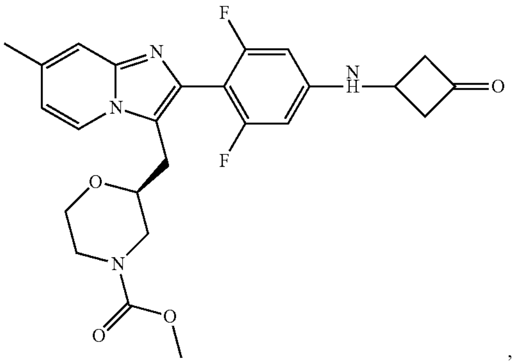
,
79
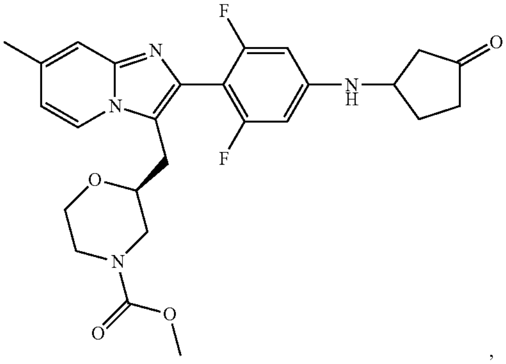
,
-continued
80
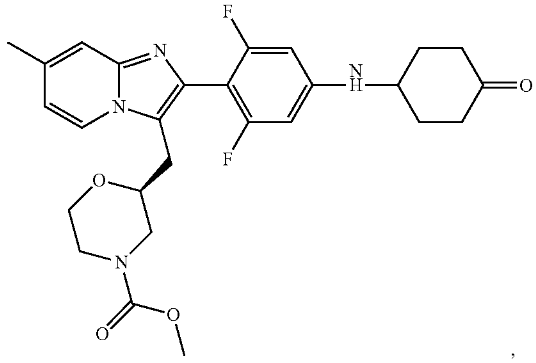
,
81
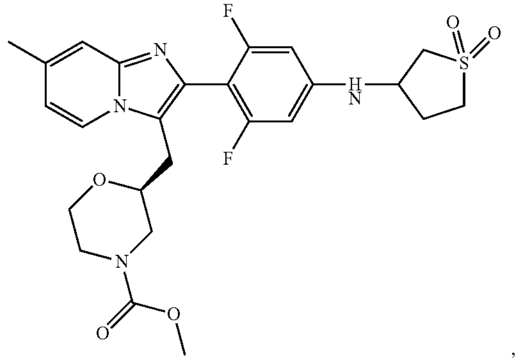
,
82
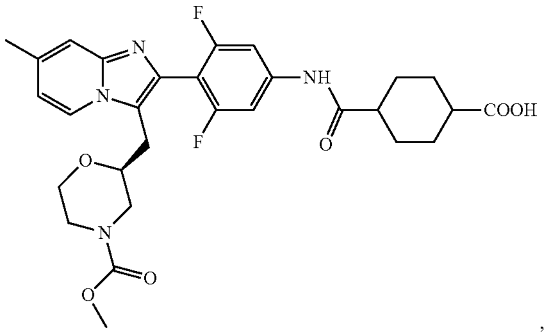
,
83
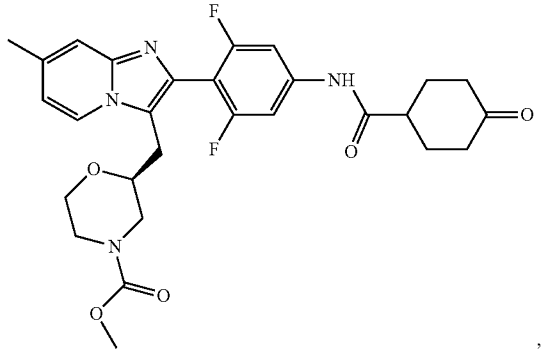
, 84
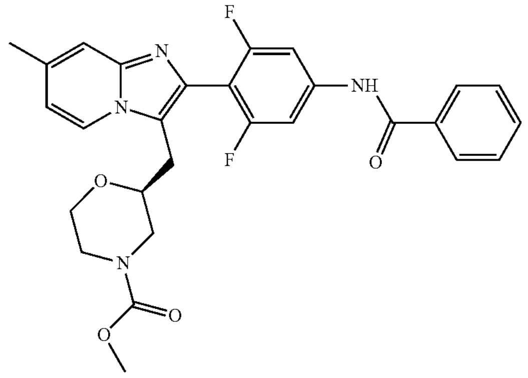
,
85
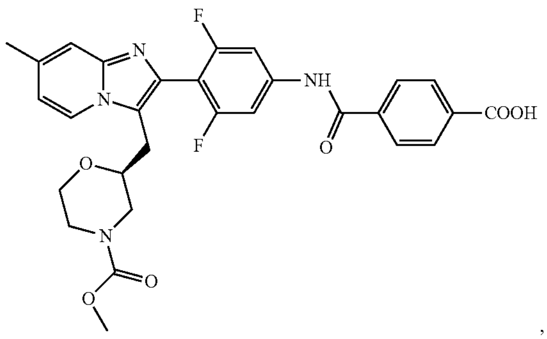
,
86
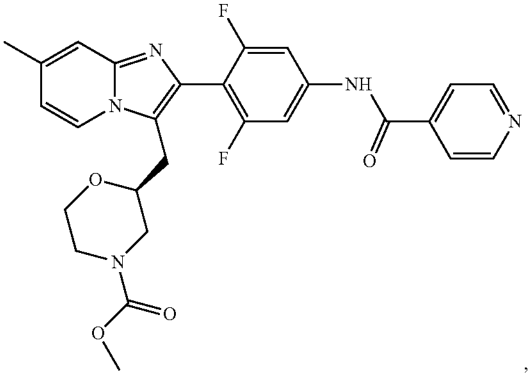
,
87
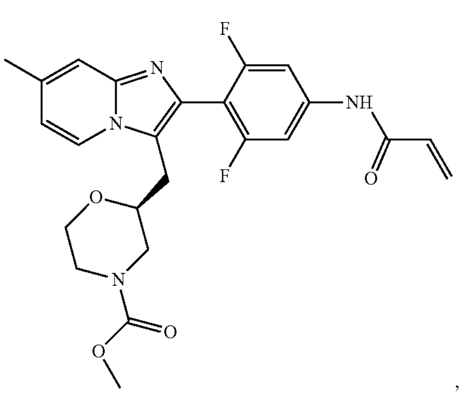
,
88
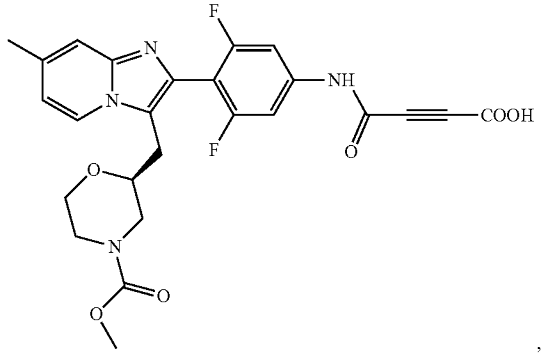
,
89
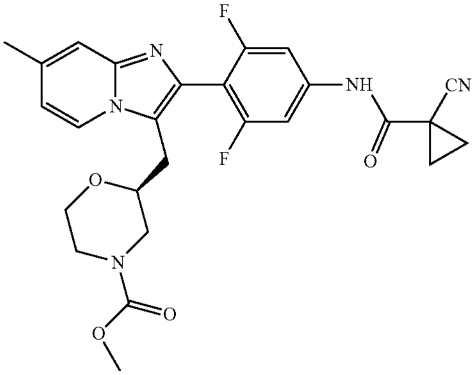
,
90
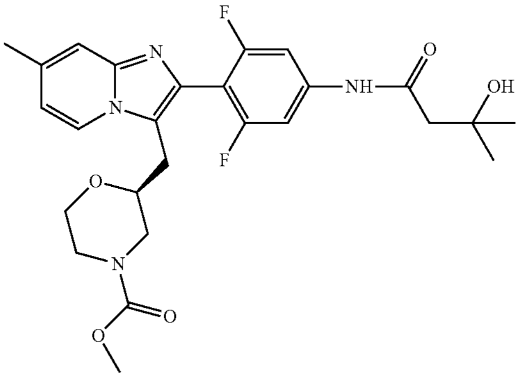
,
91
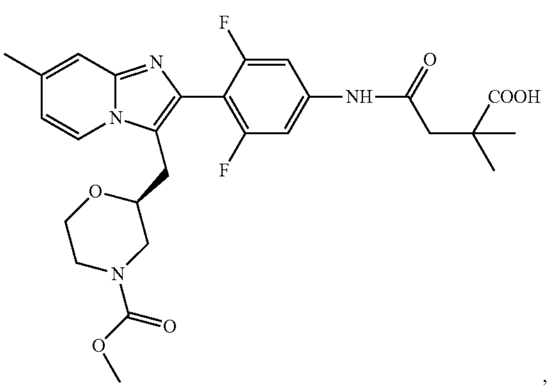
, -continued
92
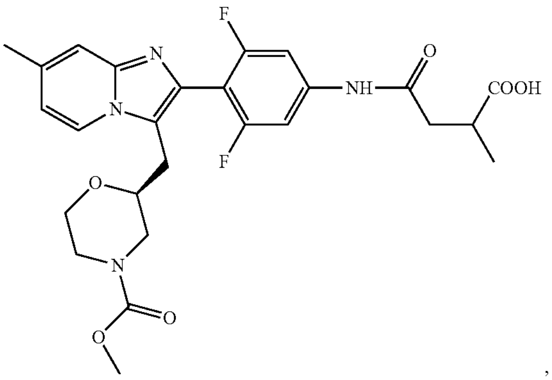
,
93
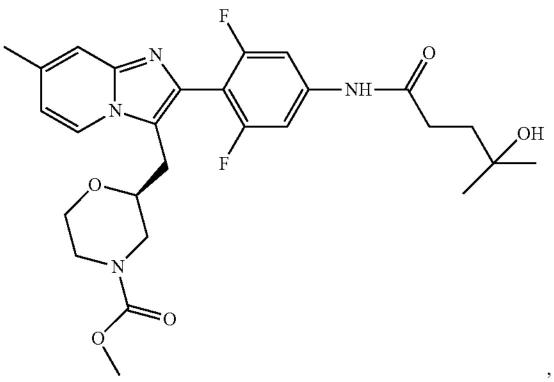
,
94
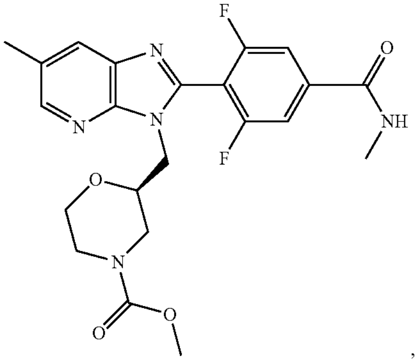
,
95
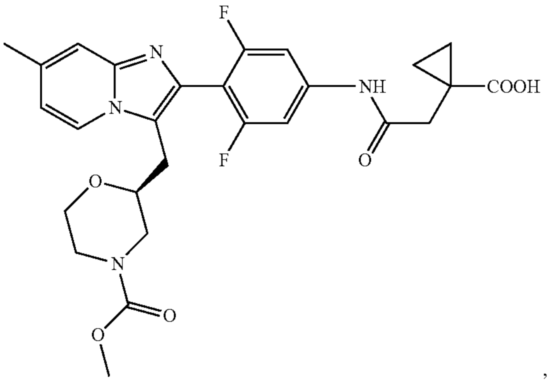
,
-continued
96
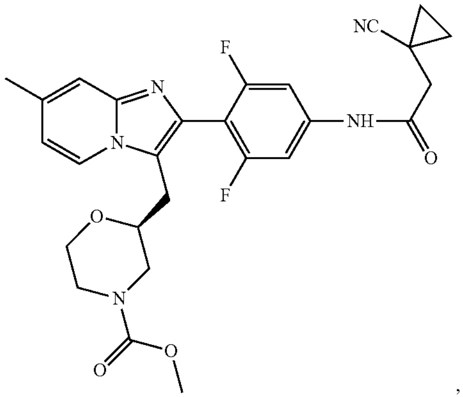
,
97
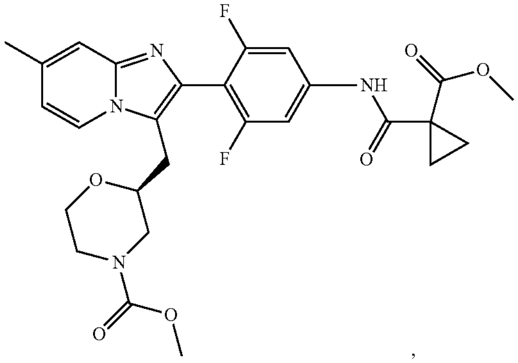
,
98
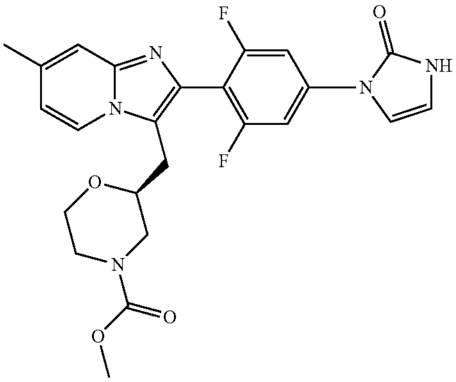
,
99
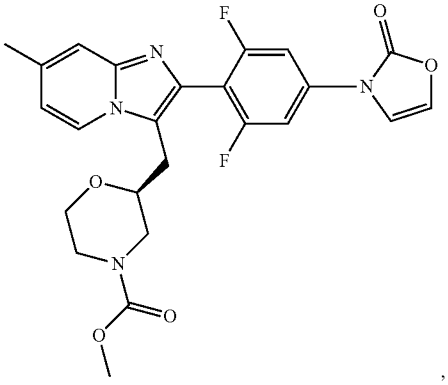
, -continued
100
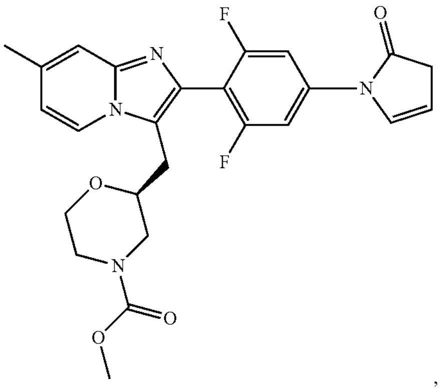
,
101
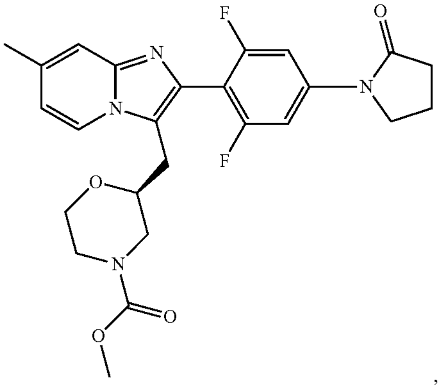
,
102
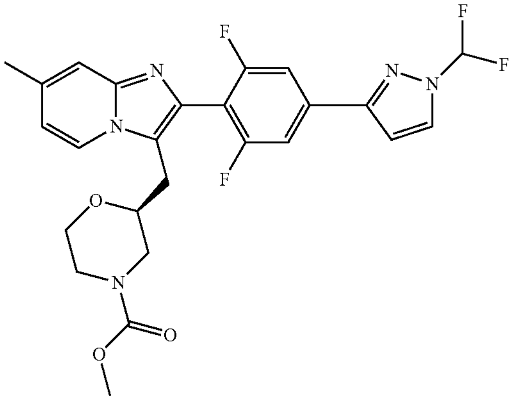
,
103
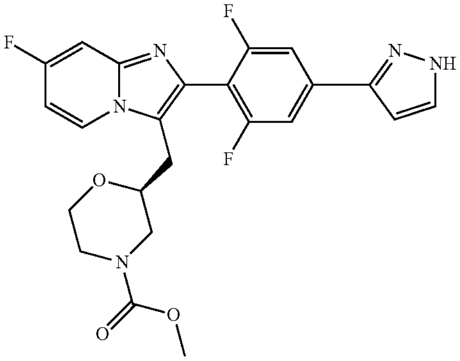
,
-continued
104
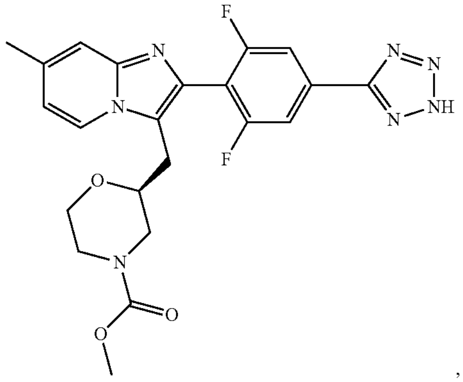
,
105
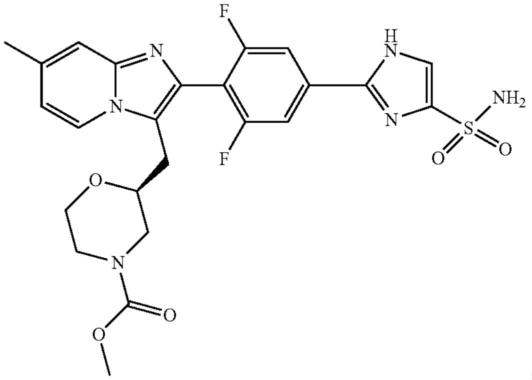
,
106
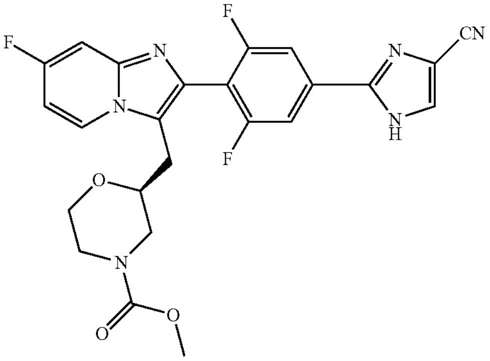
,
107
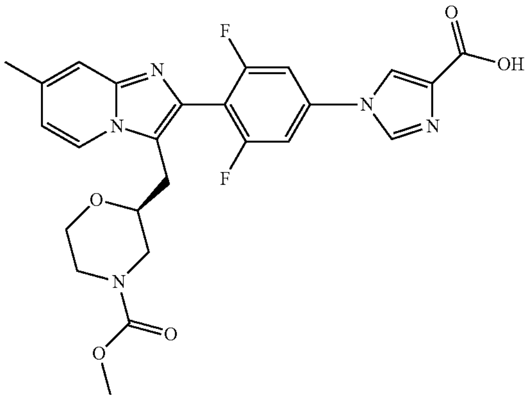
, -continued
108
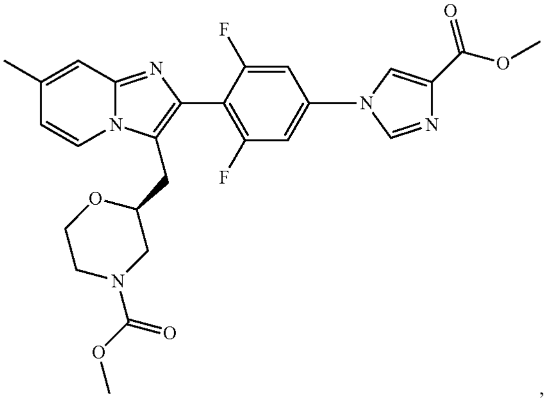
,
109
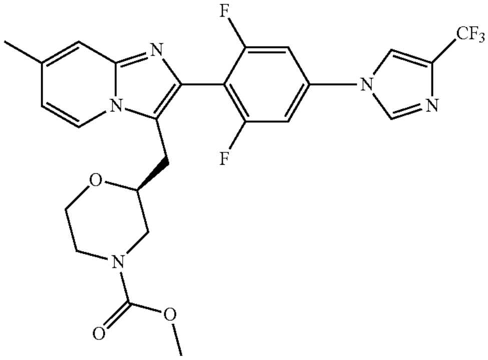
,
110
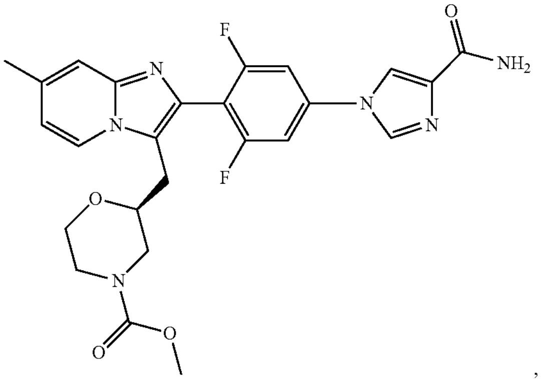
,
111
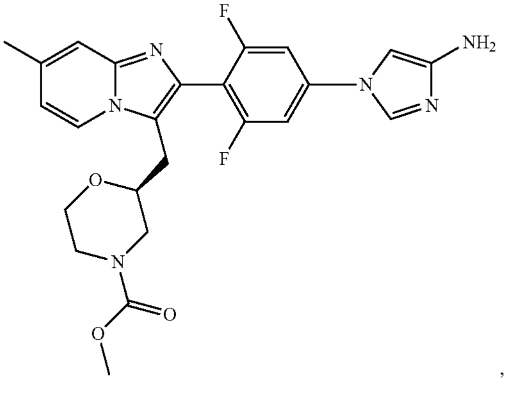
,
-continued
112
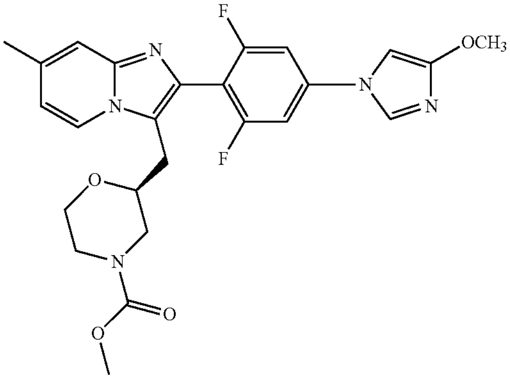
,
113
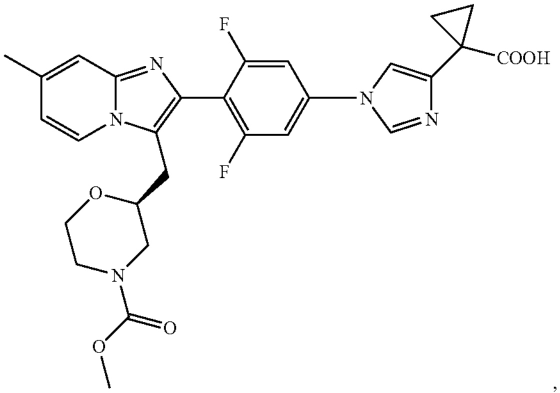
,
114
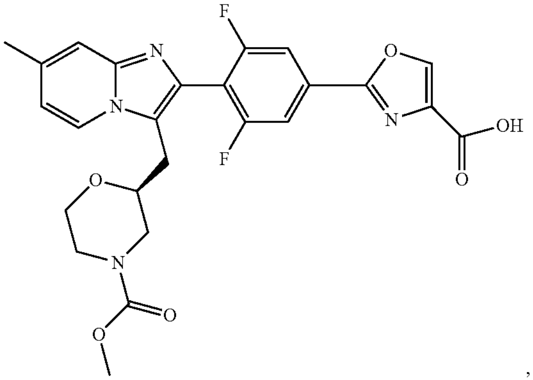
,
115
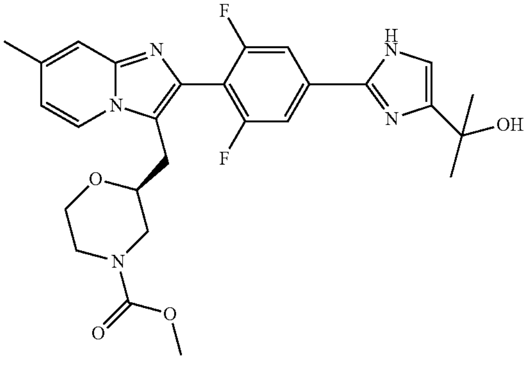
, -continued
116
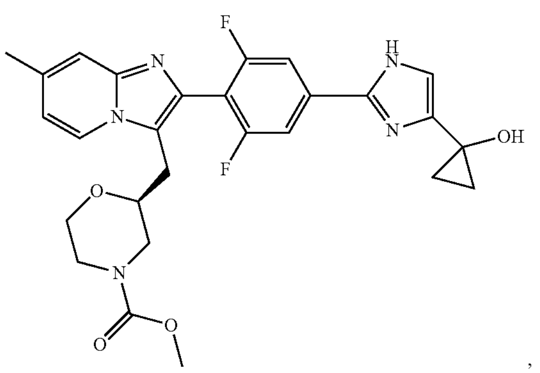
,
117
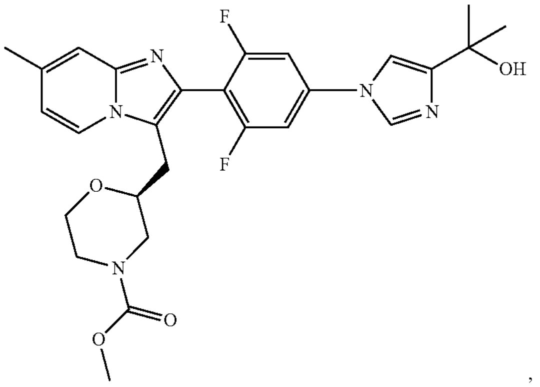
,
118
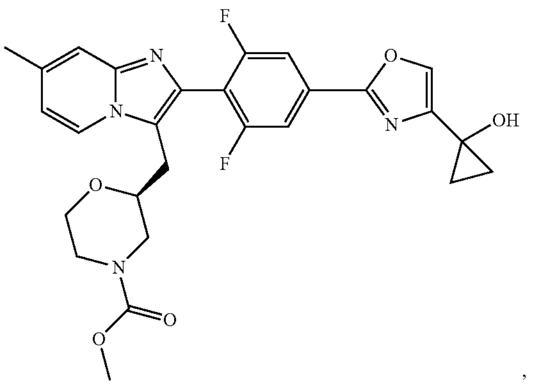
,
119
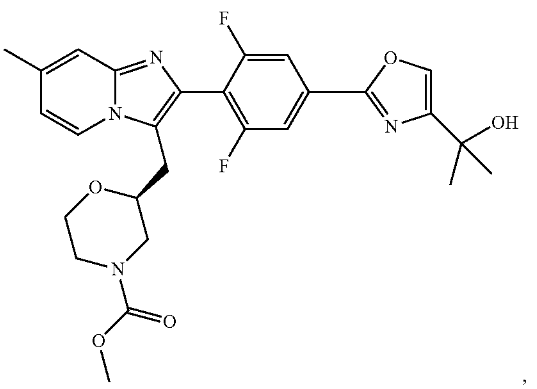
,
-continued
120
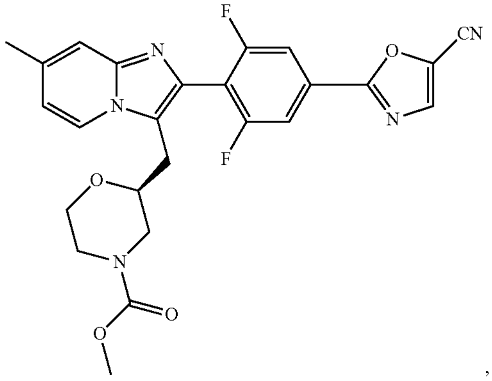
,
121
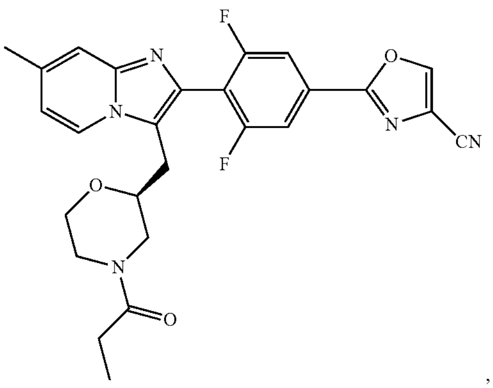
,
122
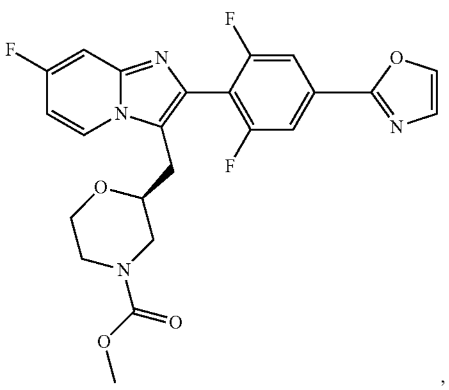
,
123
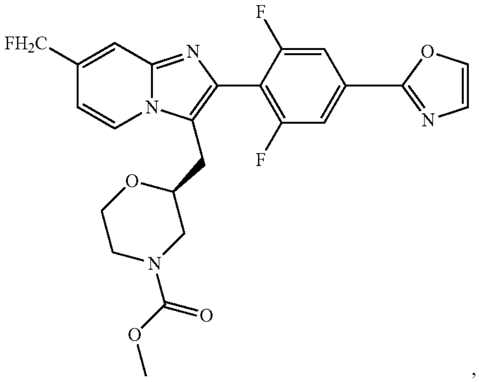
, 124
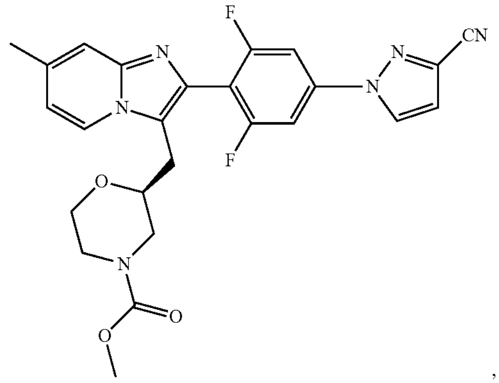
,
124-2
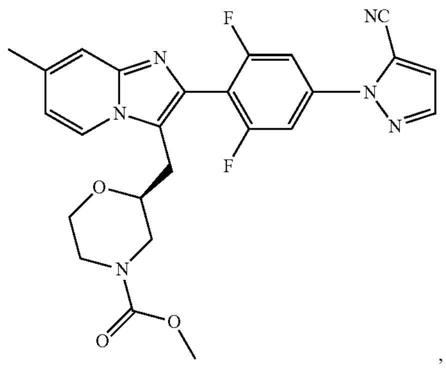
,
125
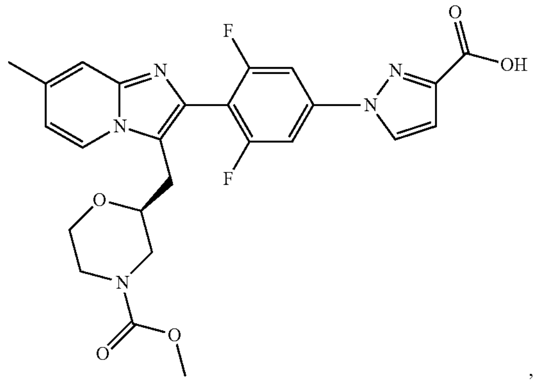
,
126
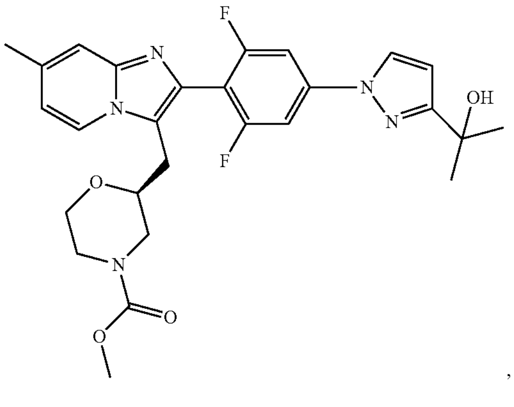
,
127
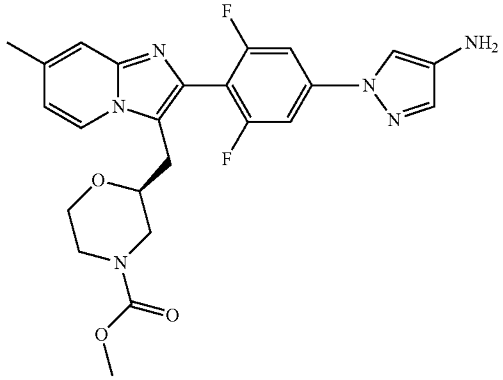
,
128
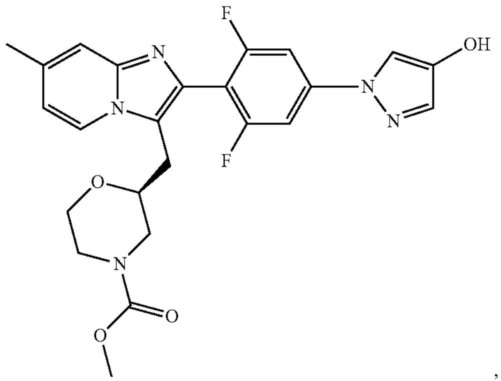
,
129
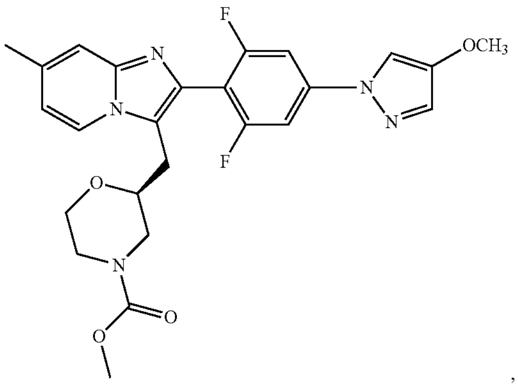
,
130
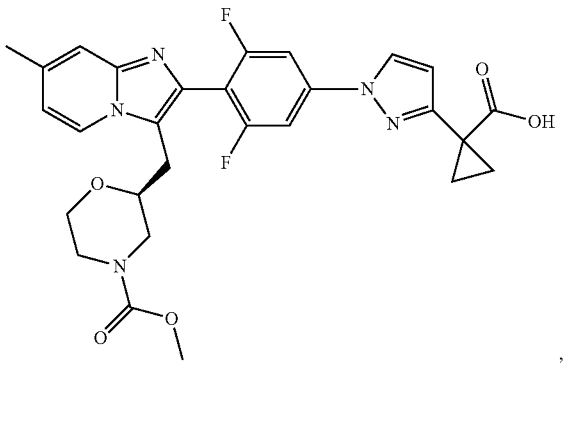
, -continued
131
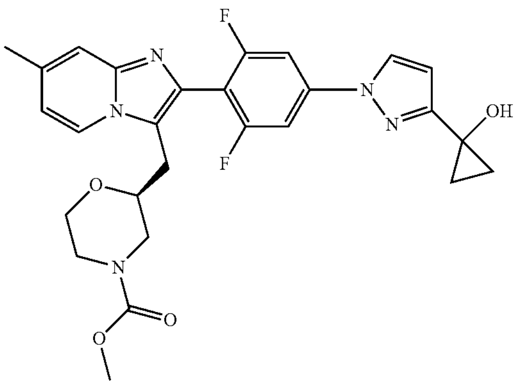
,
132
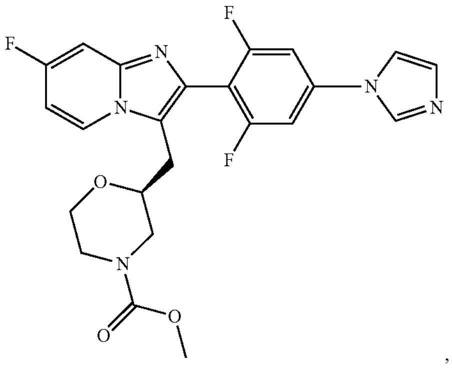
,
133
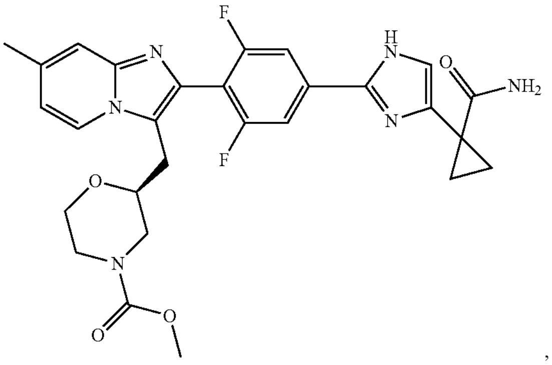
,
134
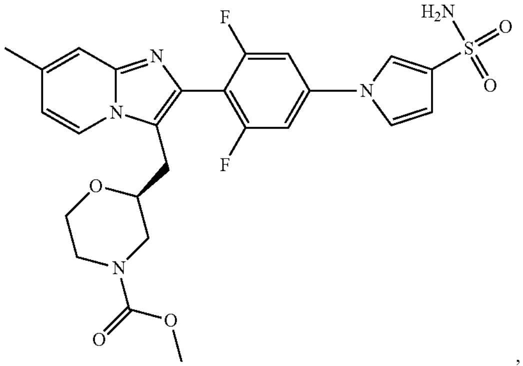
,
-continued
135
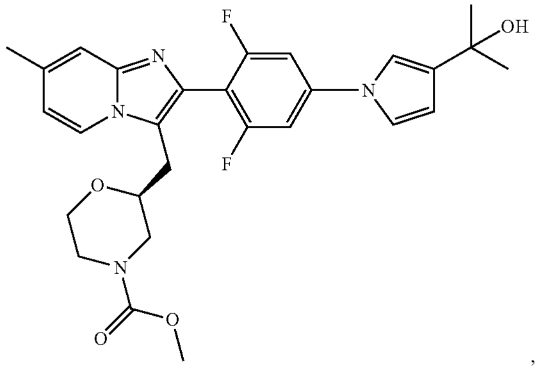
,
136
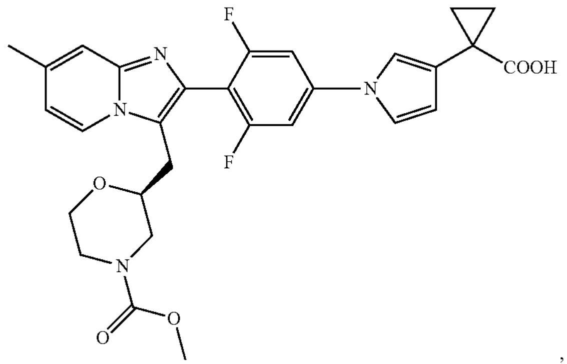
,
137
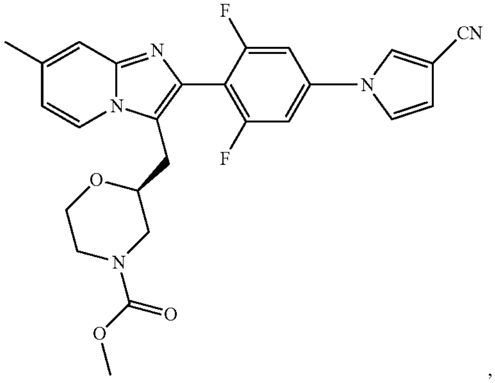
,
138
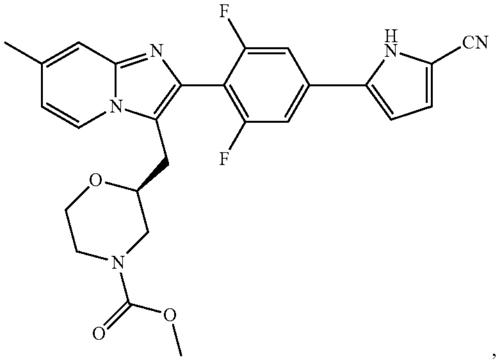
, -continued
139
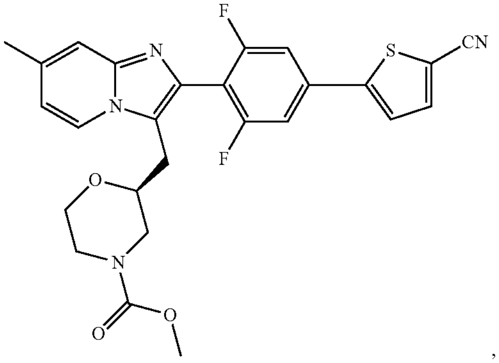
,
140
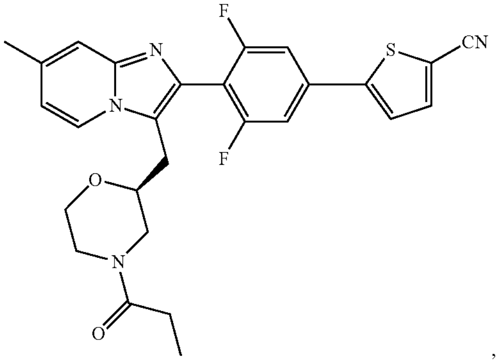
,
141
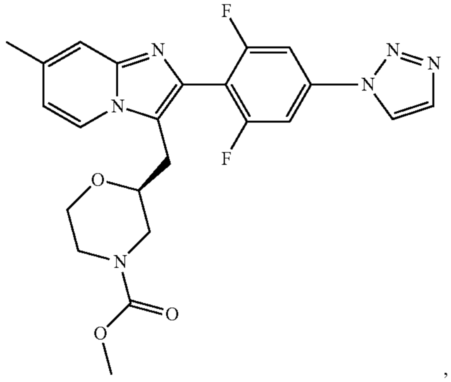
,
142
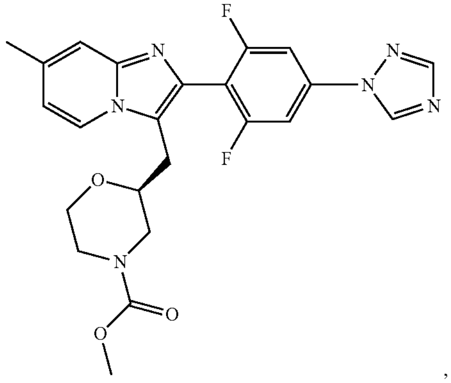
,
-continued
143
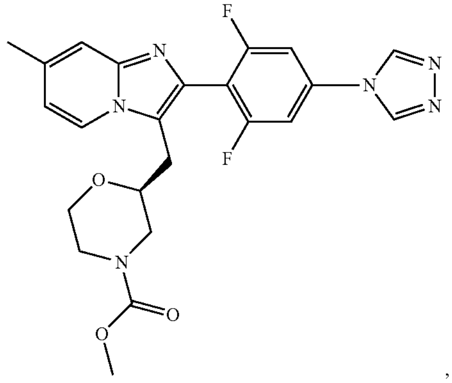
,
144
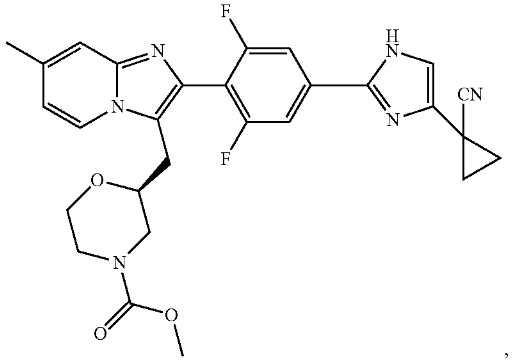
,
145
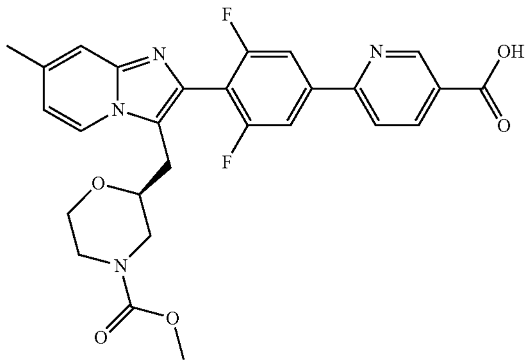
,
146
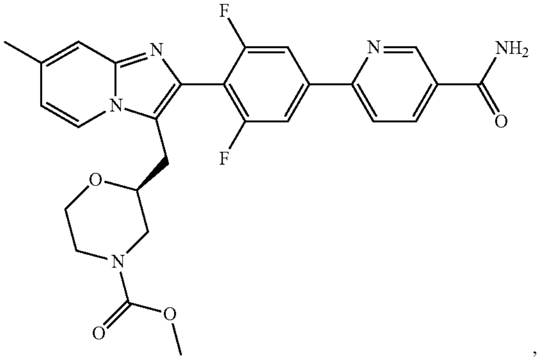
, -continued
147
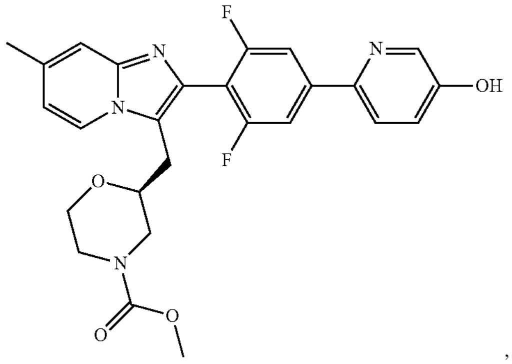
,
148
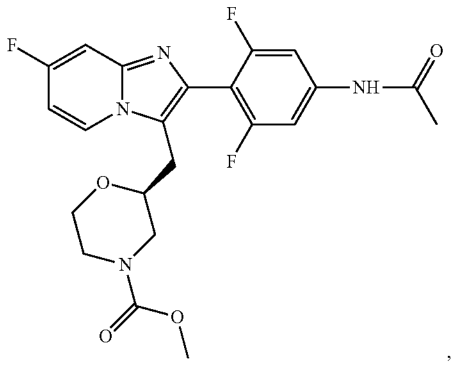
,
149
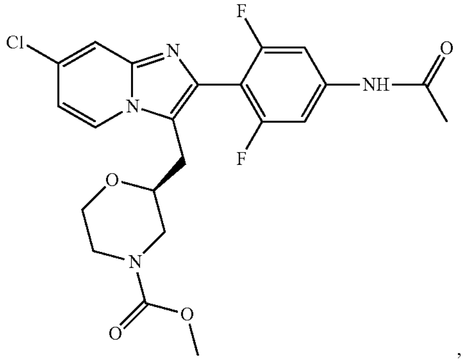
,
150
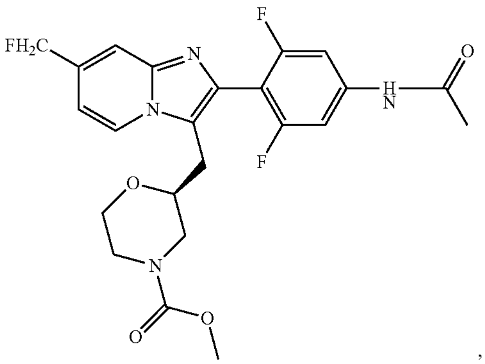
,
-continued
151
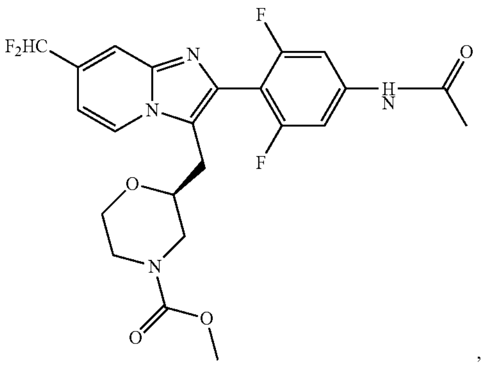
,
152
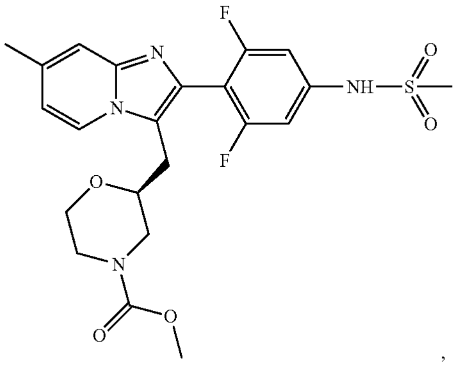
,
153
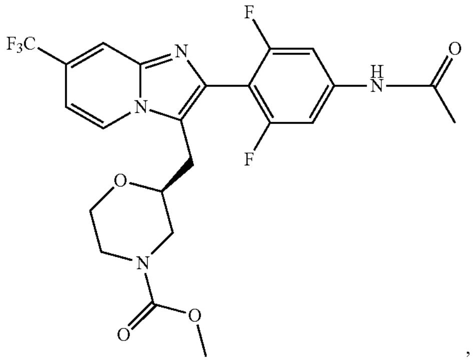
,
154
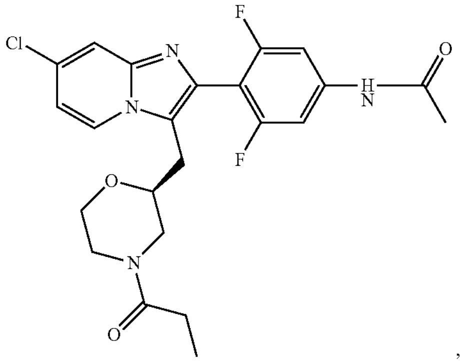
, -continued
155
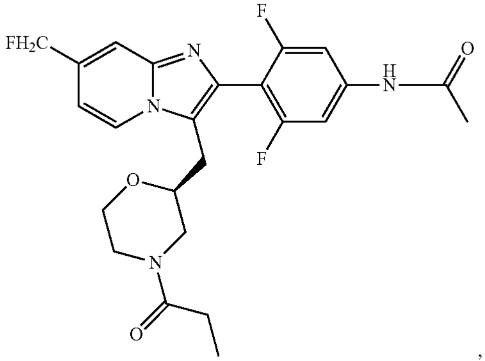
,
156
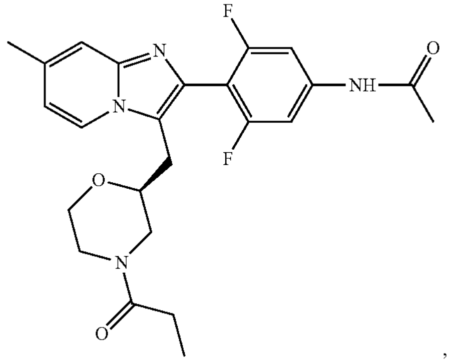
,
157
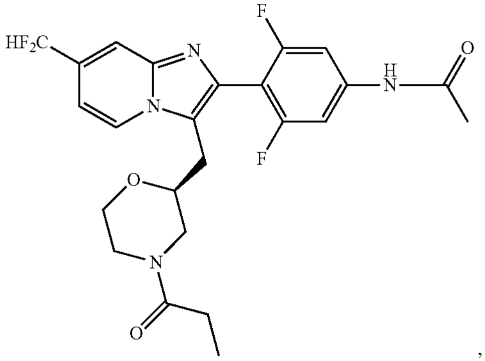
,
158
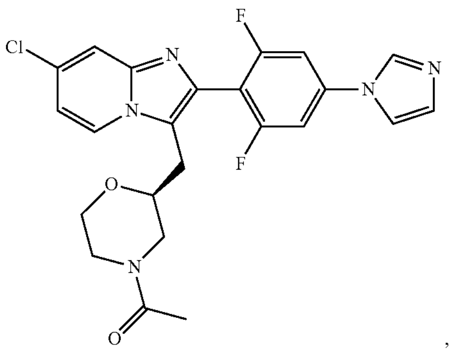
,
-continued
159
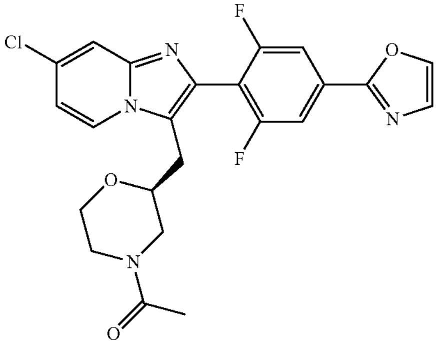
,
160
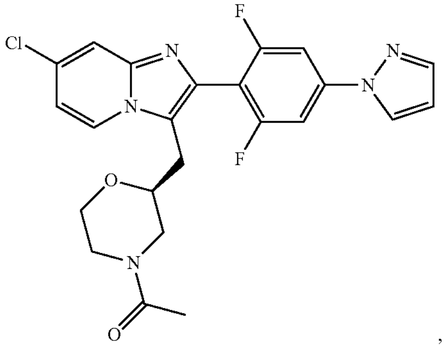
,
161
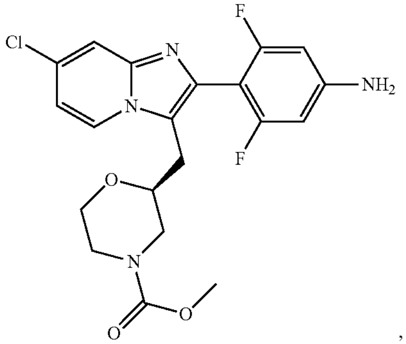
,
162
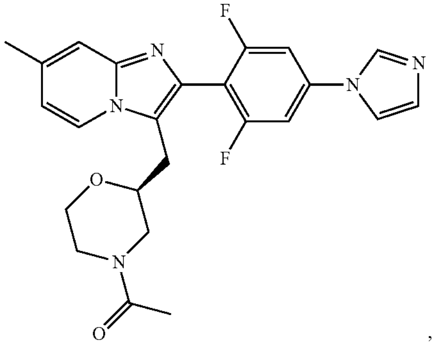
, -continued
163
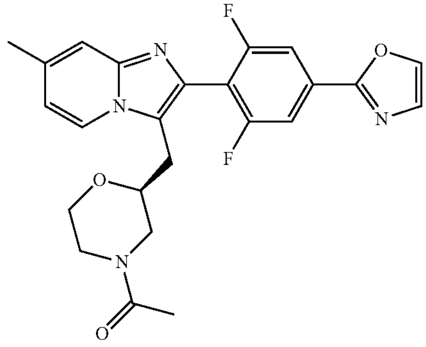
,
164
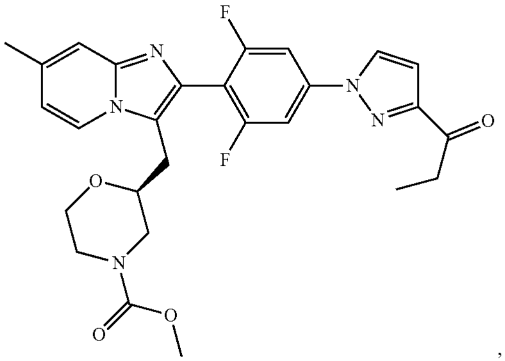
,
165
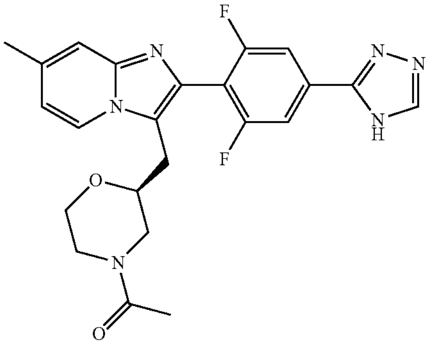
,
166
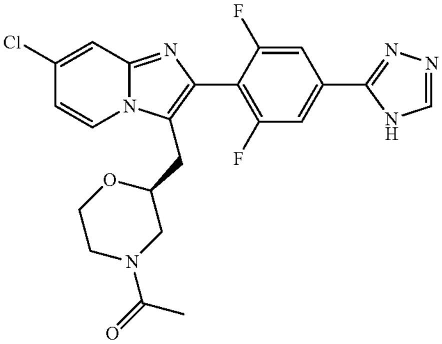
,
-continued
167
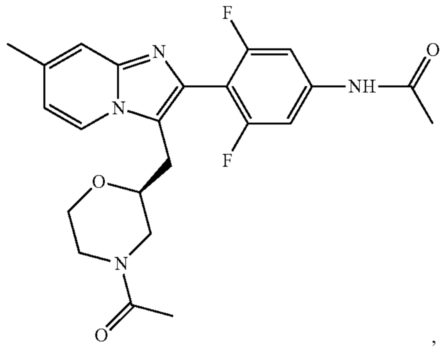
,
168
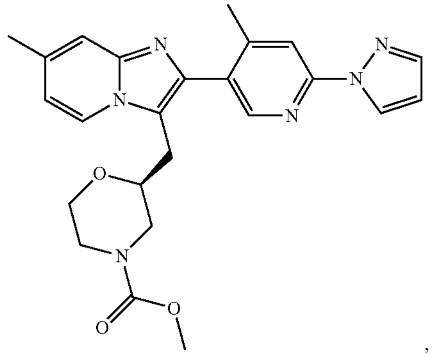
,
169
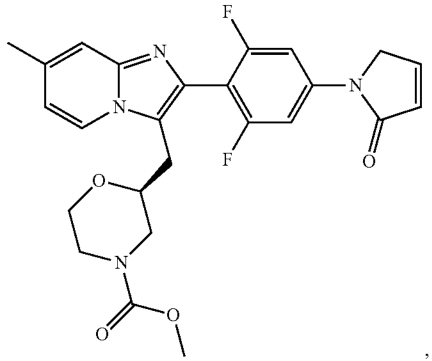
,
170
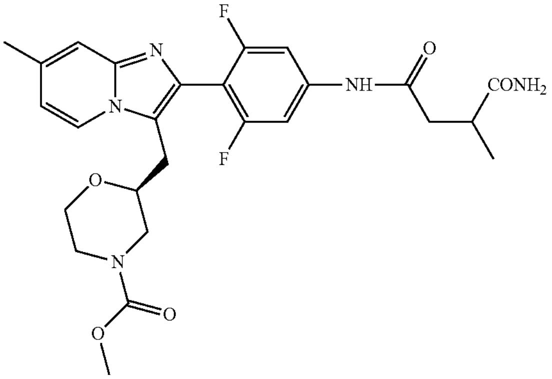
, 171
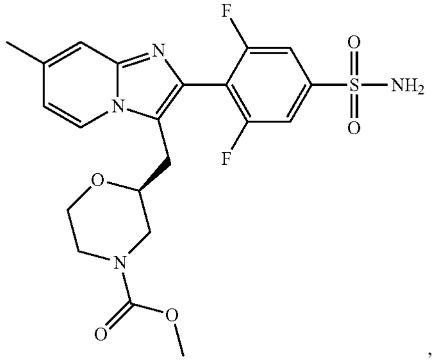
,
172
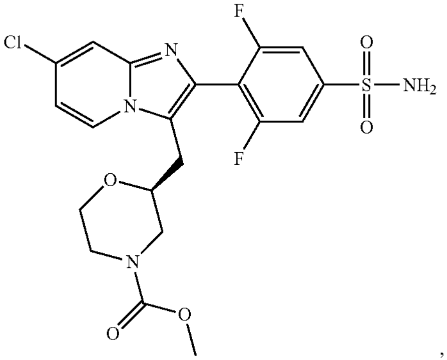
,
173
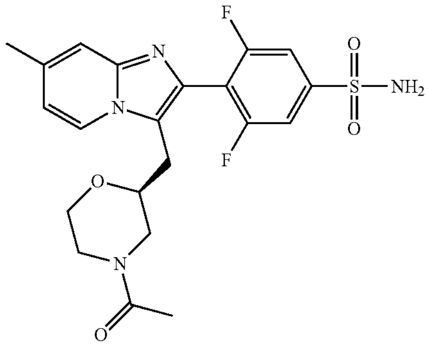
,
174
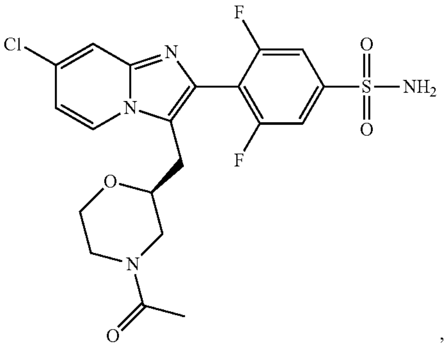
,
175
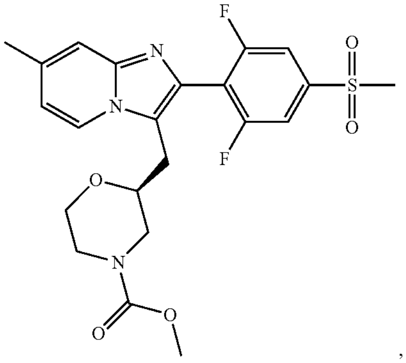
,
176
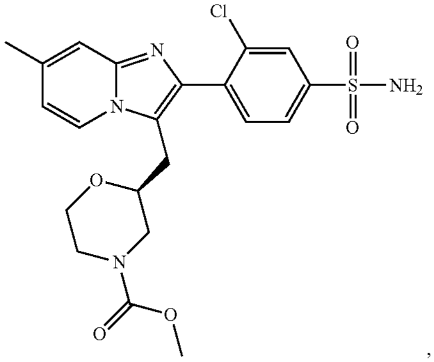
,
177
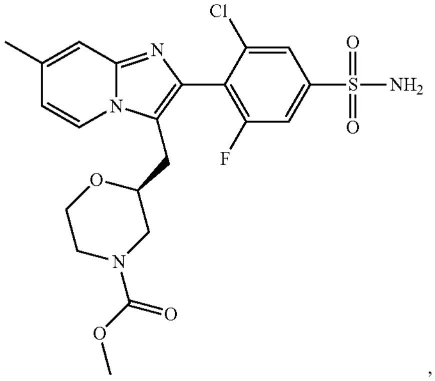
,
178
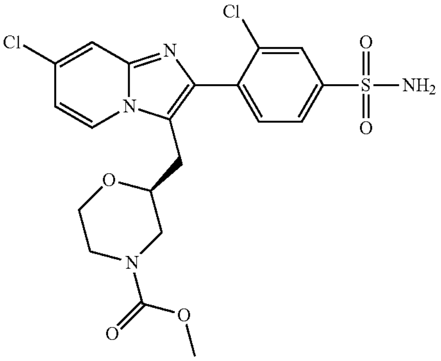
, -continued
179
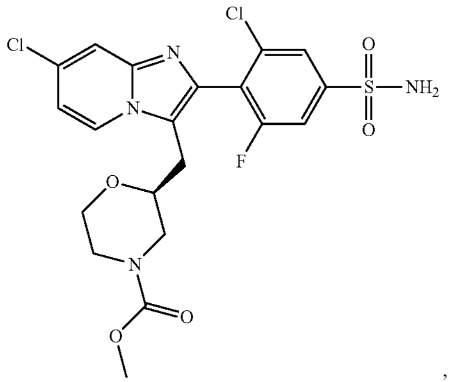
,
180
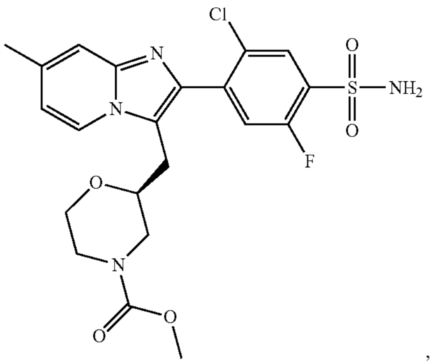
,
181
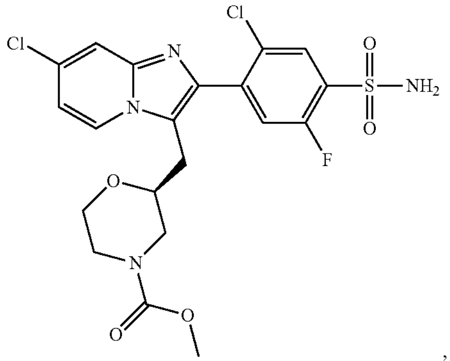
,
182
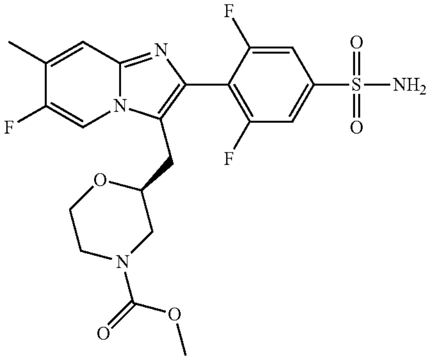
,
-continued
183
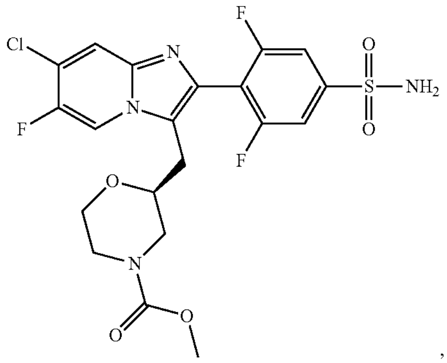
,
184
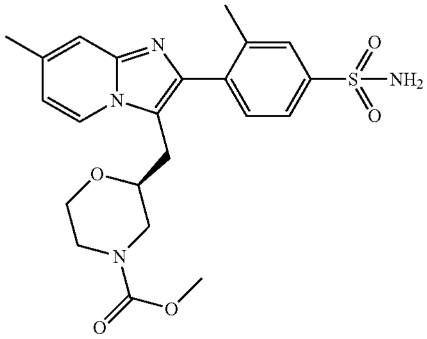
,
185
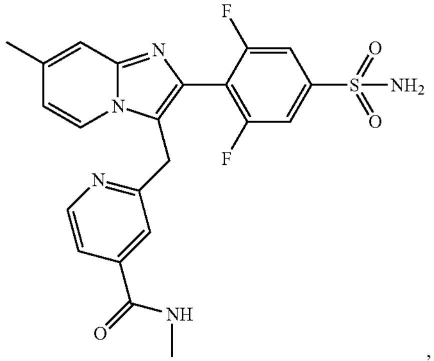
,
186
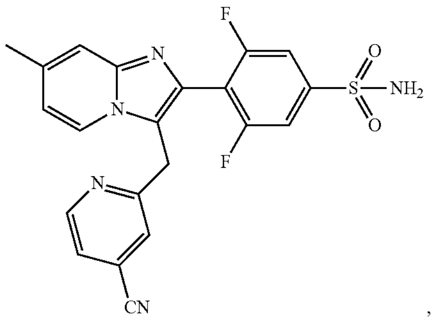
, -continued

187

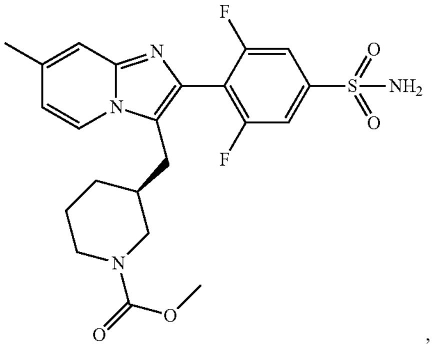

,

188

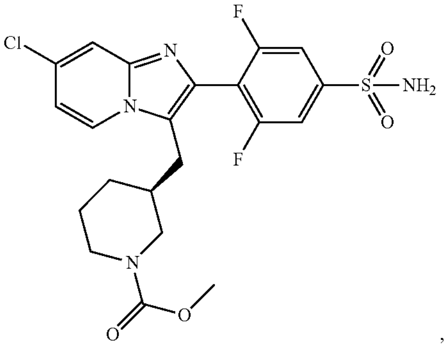

,

189

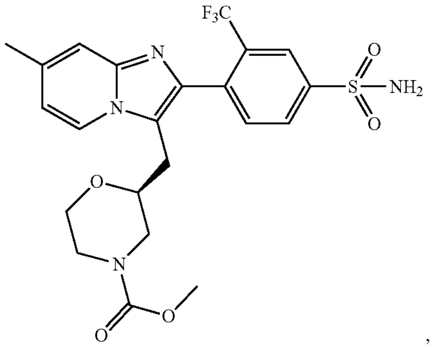

,

190

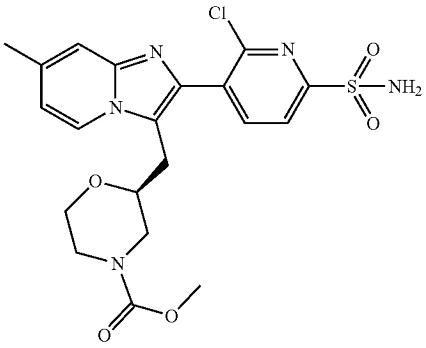

,

-continued

191

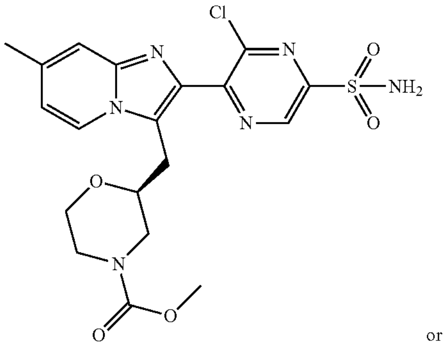

or

192

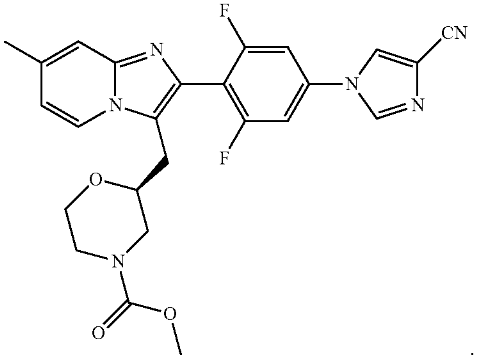

.

In a preferred embodiment of the present invention, the pharmaceutically acceptable salt of the heterocyclic compound of formula I is preferably the following compound:

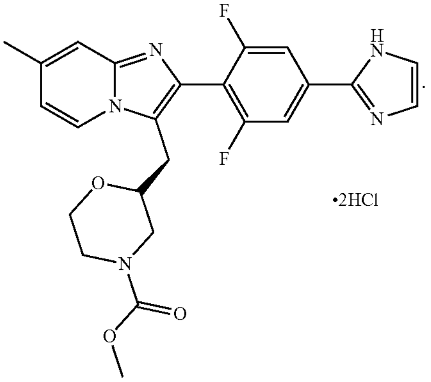

•2HCl

Thus, throughout the present specification, the groups and substituents thereof in the heterocyclic compound of formula I or the stereoisomer, the geometric isomer, the tautomer, the nitrogen oxide, the hydrate, the solvate, the metabolite, the ester, the pharmaceutically acceptable salt or the prodrug thereof can be selected by those skilled in the art, to provide a stable heterocyclic compound of formula I or a stereoisomer, a geometric isomer, a tautomer, a nitrogen oxide, a hydrate, a solvate, a metabolite, an ester, a pharmaceutically acceptable salt or a prodrug thereof, including but not limited to the compounds described in the examples of the present invention.

The present invention further includes the isotopically labeled heterocyclic compound of formula I or the stereoisomer, the geometric isomer, the tautomer, the nitrogen oxide, the hydrate, the solvate, the metabolite, the ester, the pharmaceutically acceptable salt or the prodrug thereof disclosed herein, wherein one or more atoms are substituted with one or more atoms having a specified atomic mass or mass number. Examples of isotopes that can be incorporated into the compound disclosed herein include, but are not limited to, isotopes of hydrogen, carbon, nitrogen, oxygen, fluorine, sulfur, and chlorine (e.g., $^2H$, $^3H$, $^{13}C$, $^{14}C$, $^{15}N$, $^{18}O$, $^{17}O$, $^{18}F$, $^{35}S$ and $^{36}Cl$). The isotopically labeled compound disclosed herein is useful in the assay of tissue distribution of the compound, the prodrug and the metabolite thereof; and preferred isotopes for such assays include $^3H$ and $^{14}C$. Furthermore, in some cases, substitution with heavier isotopes such as deuterium ($^2H$ or D) can afford increased metabolic stability, which provides therapeutic advantages such as increased in vivo half-life or reduced dosage requirements.

The isotopically labeled compound disclosed herein can generally be prepared by substituting an isotopically labeled reagent for a non-isotopically labeled reagent according to the methods described herein.

The heterocyclic compound of formula I or the stereoisomer, the geometric isomer, the tautomer, the nitrogen oxide, the hydrate, the solvate, the metabolite, the ester, the pharmaceutically acceptable salt or the prodrug thereof disclosed herein can be synthesized by methods similar to those known in the field of chemistry, with the steps and conditions that can be referred to those of similar reactions in the art, in particular according to the description herein. Starting materials are generally from commercial sources (e.g., Aldrich), or can be readily prepared using methods well known to those skilled in the art (obtained by SciFinder and Reaxys online databases).

The other heterocyclic compounds of formula I can also be obtained by peripherally modifying the heterocyclic compound of formula I disclosed herein using the prepared compounds by conventional methods known in the art.

In general, the compound disclosed herein may be prepared by the methods described herein, wherein the substituents are defined as in formula I, unless otherwise specified. The following schemes and examples serve to further illustrate the context of the present invention.

The present invention provides a preparation method of the heterocyclic compound of formula I, which comprises the following schemes.

Scheme I comprises the following step: performing Stille coupling reaction as shown below on a compound of formula II-1 and an organic tin reagent of formula III-1 in an organic solvent in the presence of a catalyst to give the heterocyclic compound of formula I:

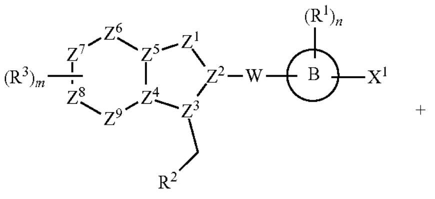

II-1

-continued

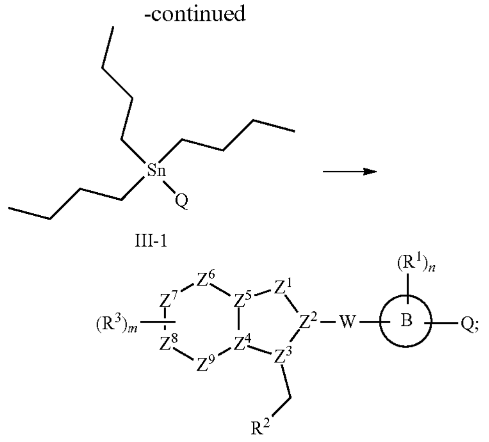

III-1

I wherein $X^1$ is Br or Cl.

The methods and conditions for the Stille coupling reaction are conventional in the art for such reactions. For example:

The organic solvent is preferably a cyclic ether solvent (e.g., tetrahydrofuran and/or dioxane) and/or an aromatic hydrocarbon solvent (e.g., toluene). The amount of the organic solvent is not particularly limited as long as the reaction proceeds.

The catalyst is preferably $Pd(PPh_3)_4$. The molar ratio of the catalyst to the compound of formula II-1 may be 1:5-1:20 (e.g., 1:10).

The molar ratio of the compound of formula II-1 to the organic tin reagent of formula III-1 may be a conventional molar ratio in the art, and the molar ratio of the compound of formula II-1 to the organic tin reagent of formula III-1 is preferably 1:3-1:4.

The temperature of the Stille coupling reaction may be 85-110° C. (e.g., 95-100° C.).

The progress of the reaction may be monitored by detection methods conventional in the art (e.g., TLC, GC, HNMR, or HPLC), and preferably by detecting the disappearance of the compound of formula II-1 as the end point of the reaction.

In a preferred embodiment of the present invention, in Scheme I, Q is an unsubstituted or substituted $C_1$-$C_6$ alkyl, an unsubstituted or substituted $C_2$-$C_6$ alkenyl, an unsubstituted or substituted $C_6$-$C_{10}$ aryl, an unsubstituted or substituted $C_3$-$C_5$ heterocycloalkyl, an unsubstituted or substituted $C_3$-$C_5$ heterocycloalkenyl, or an unsubstituted or substituted 5-6 membered heteroaryl.

Scheme II comprises the following step: performing Suzuki coupling reaction as shown below on a compound of formula II-2 and a compound of formula III-2 in a solvent in the presence of a catalyst and a basic reagent to give the heterocyclic compound of formula I:

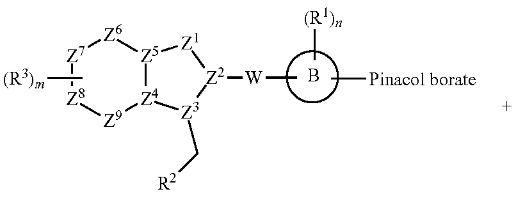

II-2

-continued

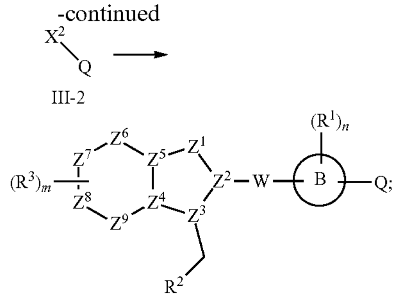

III-2

I wherein $X^2$ is Br or Cl.

The methods and conditions for the Suzuki coupling reaction are conventional in the art for such reactions. For example:

The solvent may be water and an organic solvent, and the organic solvent is preferably a cyclic ether solvent (e.g., tetrahydrofuran and/or dioxane). The amount of the organic solvent is not particularly limited as long as the reaction proceeds.

The catalyst is preferably $Pd(PPh_3)_4$. The molar ratio of the catalyst to the compound of formula II-2 may be 1:5-1:20 (e.g., 1:20).

The basic reagent may be $Na_2CO_3$, and the molar ratio of the basic reagent to the compound of formula II-2 may be 1:1-5:1 (e.g., 3:1).

The molar ratio of the compound of formula II-2 to the compound of formula III-2 may be a conventional molar ratio in the art, and the molar ratio of the compound of formula II-2 to the compound of formula III-2 is preferably 1:1-1:1.2.

The temperature of the Suzuki coupling reaction may be 90-100° C.

The progress of the reaction may be monitored by detection methods conventional in the art (e.g., TLC, GC, HNMR, or HPLC), and preferably by detecting the disappearance of the compound of formula II-2 as the end point of the reaction.

In a preferred embodiment of the present invention, in Scheme II, Q is an unsubstituted or substituted $C_1$-$C_6$ alkyl, an unsubstituted or substituted $C_2$-$C_6$ alkenyl, an unsubstituted or substituted $C_6$-$C_{10}$ aryl, an unsubstituted or substituted $C_3$-$C_5$ heterocycloalkyl, an unsubstituted or substituted $C_3$-$C_5$ heterocycloalkenyl, or an unsubstituted or substituted 5-6 membered heteroaryl.

Scheme III comprises the following step: performing the reaction as shown below on a compound of formula II-3, a compound of formula III-3 and formaldehyde in an organic solvent to give the heterocyclic compound of formula I:

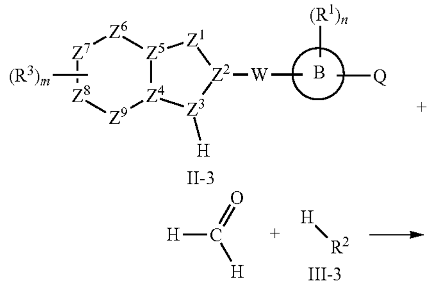

II-3

III-3

-continued

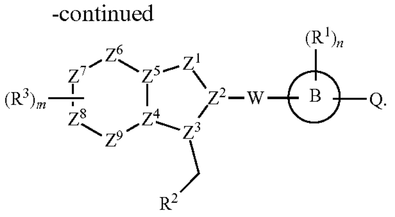

I

The methods and conditions for the reaction are conventional in the art for such reactions. For example:

The organic solvent is preferably a carboxylic acid solvent (e.g., acetic acid). The amount of the organic solvent is not particularly limited as long as the reaction proceeds.

The formaldehyde may be aqueous formaldehyde solution, and preferably the aqueous formaldehyde solution at 37 wt. %; and the molar ratio of the formaldehyde to the compound of formula II-2 may be 1:1.

The molar ratio of the compound of formula II-2 to the compound of formula III-2 may be a conventional molar ratio in the art, and the molar ratio of the compound of formula II-2 to the compound of formula III-2 is preferably 1.2:1-1:1.2.

The temperature of the reaction may be 40-60° C.

The progress of the reaction may be monitored by detection methods conventional in the art (e.g., TLC, GC, HNMR, or HPLC), and preferably by detecting the disappearance of the compound of formula II-3 as the end point of the reaction.

In a preferred embodiment of the present invention, in Scheme III, $Z^3$ is a carbon atom; $R^2$ is

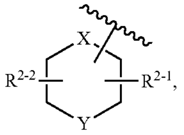

preferably

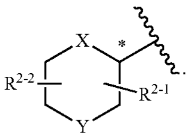

Scheme IV comprises the following step: performing the reaction as shown below on a compound of formula II-3 and a compound of formula III-4 in an organic solvent to give the heterocyclic compound of formula I:

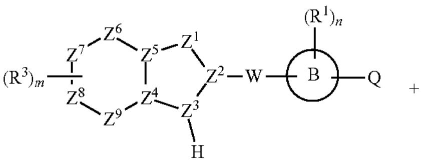

II-3

-continued

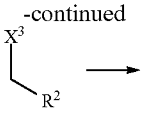

III-4

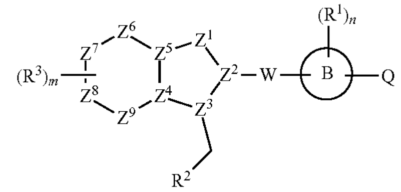

I wherein $X^3$ is a leaving group (e.g., —OMs, Br or Cl).

The methods and conditions for the reaction are conventional in the art for such reactions. For example:

The organic solvent is preferably an amide solvent (e.g., N,N-dimethylformamide). The amount of the organic solvent is not particularly limited as long as the reaction proceeds.

The basic reagent may be potassium tert-butoxide, and the molar ratio of the basic reagent to the compound of formula II-3 may be 2:1-3:1 (e.g., 2.2:1).

The molar ratio of the compound of formula II-3 to the compound of formula III-4 may be a conventional molar ratio in the art, and the molar ratio of the compound of formula II-3 to the compound of formula III-4 is preferably 1.2:1-1:1.2.

The temperature of the reaction may be 100-120° C.

The progress of the reaction may be monitored by detection methods conventional in the art (e.g., TLC, GC, HNMR, or HPLC), and preferably by detecting the disappearance of the compound of formula II-3 as the end point of the reaction.

In a preferred embodiment of the present invention, in Scheme IV, $R^2$ is

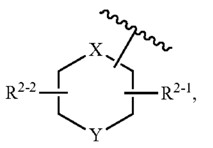

and preferably

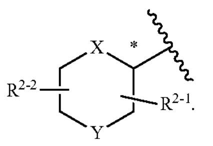

Scheme V comprises the following step: performing amidation reaction as shown below on a compound of formula I (wherein $R^2$ is

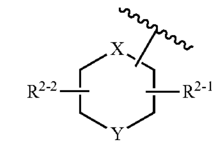

and Y is —NH—) and a compound of formula III-5 in an organic solvent in the presence of a basic reagent to give the heterocyclic compound of formula I (wherein Y is

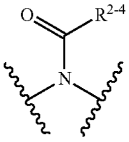

):

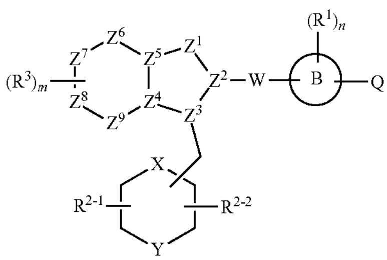

I

Y is

—NH—

+

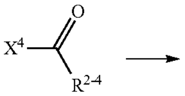

III-5

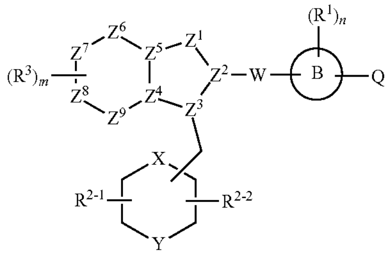

I

Y is

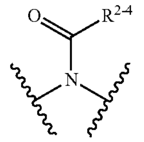

wherein $X^4$ is halogen (e.g., Br or Cl).

The methods and conditions for the amidation reaction are conventional in the art for such reactions. For example:

The organic solvent is preferably a halogenated alkane solvent (e.g., dichloromethane). The amount of the organic solvent is not particularly limited as long as the reaction proceeds.

The basic reagent may be N,N-diisopropylethylamine, and the molar ratio of the basic reagent to the compound of formula II-4 may be 2:1-4:1 (e.g., 3:1).

The molar ratio of the compound of formula II-4 to the compound of formula III-5 may be a conventional molar ratio in the art, and the molar ratio of the compound of formula II-4 to the compound of formula III-5 is preferably 1.2:1-1:1.2.

The temperature of the amidation reaction may be −10-20° C.

The progress of the amidation reaction may be monitored by detection methods conventional in the art (e.g., TLC, GC, HNMR, or HPLC), and preferably by detecting the disappearance of the compound of formula II-4 as the end point of the reaction.

Scheme VI comprises the following step: performing deprotection reaction as shown below on a compound of formula II-4 and a compound of formula III-5 in an organic solvent in the presence of an acid to give the heterocyclic compound of formula I:

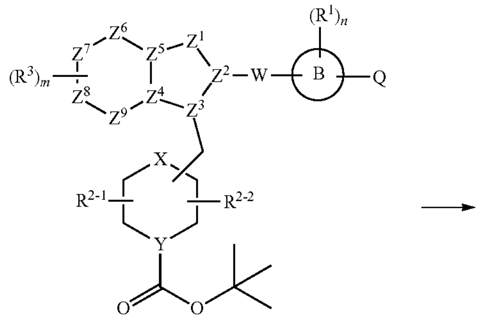

II-4

Y is —NH—

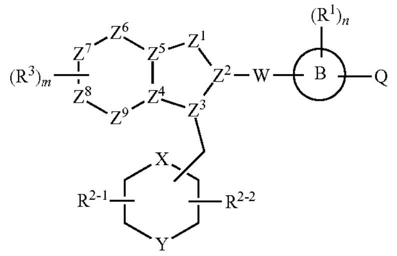

Y is —NH— wherein Y is —NH—.

The methods and conditions for the deprotection reaction are conventional in the art for such reactions. For example:

The organic solvent is preferably an alcohol solvent (e.g., ethanol). The amount of the organic solvent is not particularly limited as long as the reaction proceeds.

The acid may be hydrochloric acid, and the molar ratio of the acid to the compound of formula II-4 may be 1:1-4:1 (e.g., 1.5:1).

The temperature of the deprotection reaction may be −10-20° C.

The progress of the amidation reaction may be monitored by detection methods conventional in the art (e.g., TLC, GC, HNMR, or HPLC), and preferably by detecting the disappearance of the compound of formula II-4 as the end point of the reaction.

Scheme VII comprises the following step: performing substitution reaction as shown below on a compound of formula II-5 and $NH(R^{1-9}R^{1-10})$ in an organic solvent to give the heterocyclic compound of formula I (wherein Q is $—S(=O)_2—N(R^{1-9}R^{1-10})$);

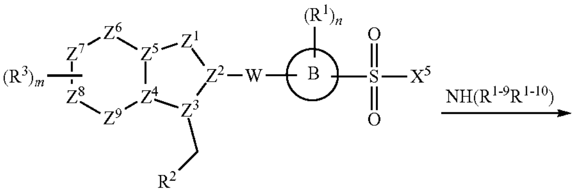

II-5

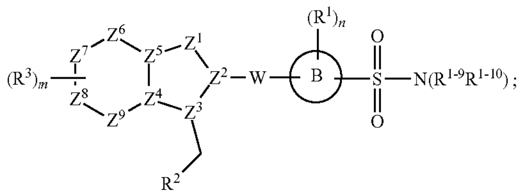

I wherein $X^5$ is Br or Cl.

The methods and conditions for the reaction are conventional in the art for such reactions. For example:

The organic solvent is preferably a nitrile solvent (e.g., acetonitrile). The amount of the organic solvent is not particularly limited as long as the reaction proceeds.

The molar ratio of the compound of formula II-5 to $NH(R^{1-9}R^{1-10})$ may be 1:1-1:5.

The $NH(R^{1-9}R^{1-10})$ may be in a form conventional in the art, for example in the form of aqueous ammonia when it is $NH_3$.

The temperature of the reaction may be −10-20° C. (e.g., 0° C.).

The progress of the reaction may be monitored by detection methods conventional in the art (e.g., TLC, GC, HNMR, or HPLC), and preferably by detecting the disappearance of the compound of formula II-3 as the end point of the reaction.

Scheme VIII comprises the following step: performing deprotection reaction as shown below on a compound of formula II-6 or formula II-6' in an organic solvent in the presence of an acid to give the heterocyclic compound of formula I:

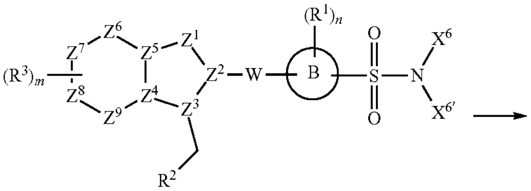

II-6

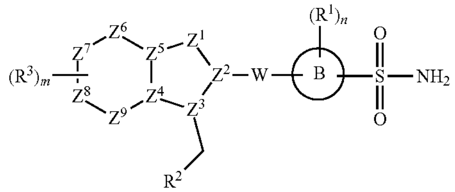

I

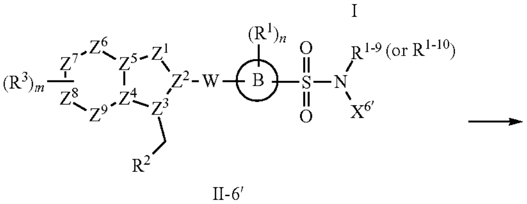

II-6'

-continued

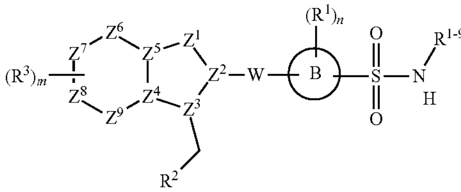

I wherein $X^6$, $X^6$ and $X^{6''}$ are N protecting groups.

In a preferred embodiment, when $X^6$, $X^6$ and $X^{6''}$ are N protecting groups, the N protecting groups may be 4-methoxybenzyl (PMB).

The methods and conditions for the reaction are conventional in the art for such reactions. For example:

The organic solvent is preferably a halogenated alkane solvent (e.g., dichloromethane). The amount of the organic solvent is not particularly limited as long as the reaction proceeds.

The acid may be trifluoromethanesulfonic acid, and the volume-to-mass ratio of the acid to the compound of formula II-6 or formula II-6' may be 1-5 mL/g (e.g., 3-4 mL/g).

The temperature of the reaction may be 0-100° C. (e.g., 30-50° C.).

The progress of the reaction may be monitored by detection methods conventional in the art (e.g., TLC, GC, HNMR, or HPLC), and preferably by detecting the disappearance of the compound of formula II-6 or formula II-6' as the end point of the reaction.

In the present invention, after the reaction is completed, conventional work-up methods can be adopted for a treatment. In the present invention, after work-up, if the heterocyclic compound crude product of formula I is obtained, conventional means such as preparative HPLC, preparative TLC or recrystallization can be adopted for separation and purification.

The present invention also provides a compound of formula II-1, II-2, II-3, II-4, II-5, II-6 or II-6':

II-1

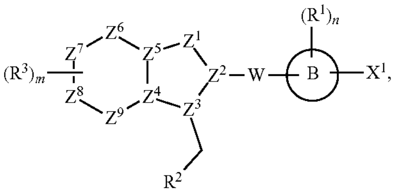

II-2

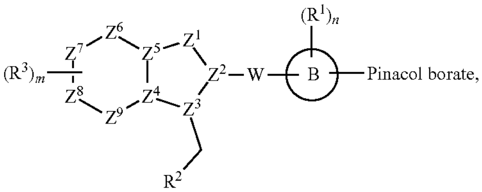

II-3

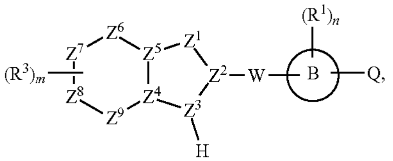

-continued

II-4

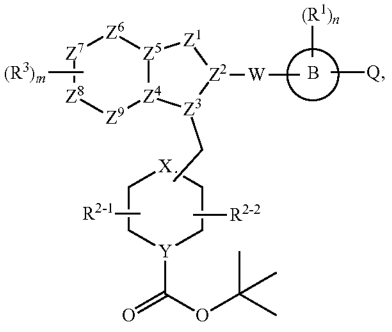

Y is —NH—

II-5

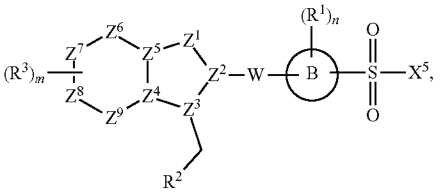

II-6

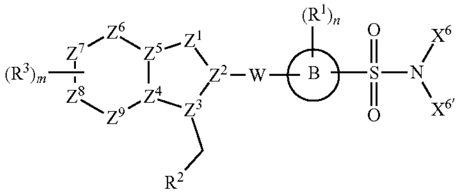

or

II-6'

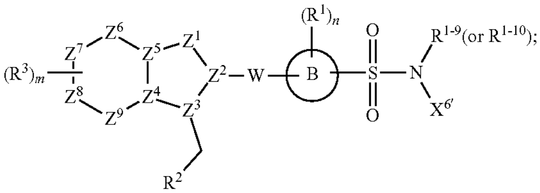

wherein the

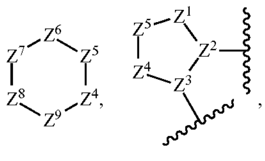

$R^3$, $R^2$, $R^1$, W, X, Y, $R^{2-1}$, $R^{2-2}$, n, m. $X^5$, $X^6$, $X^{6'}$, $X^{6''}$ and $X^1$ have the definitions as described above.

The present invention also provides compounds as shown below:
1-7
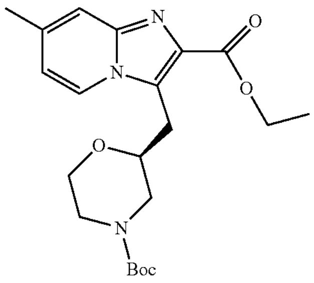
1-8
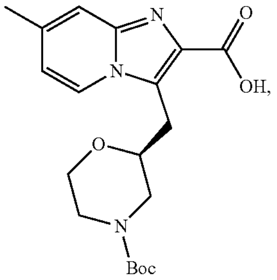
1-10
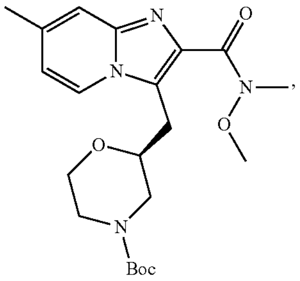
1-11
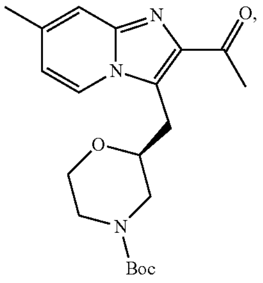
1-14
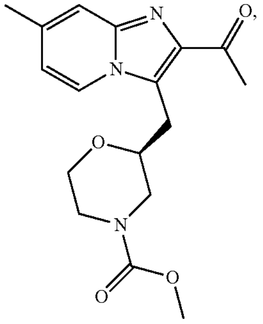
-continued
1-15
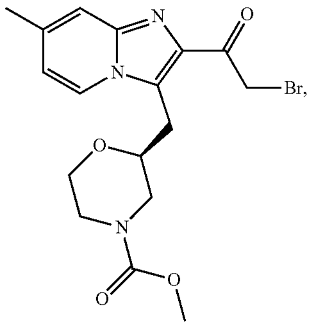
2-4
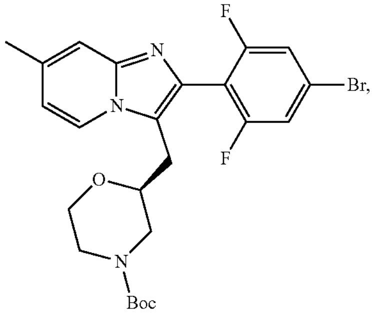
2-5
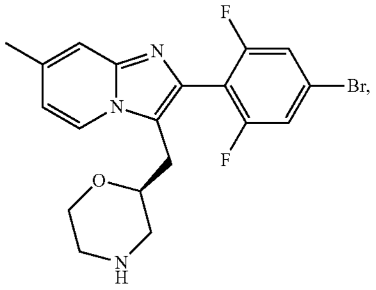
2-7
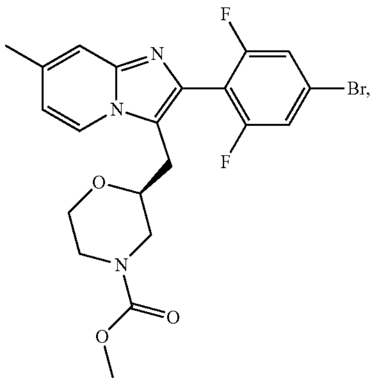

-continued
3-1
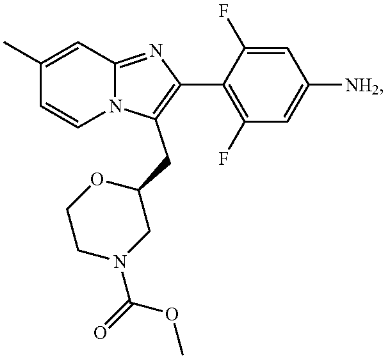
4-2
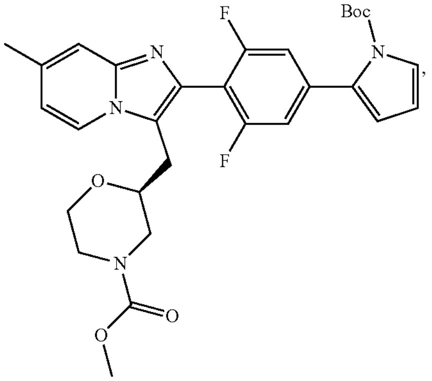
6-3
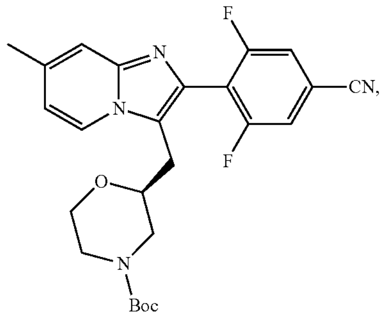
6-4
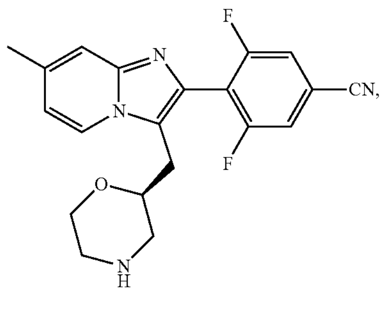
-continued
14-2
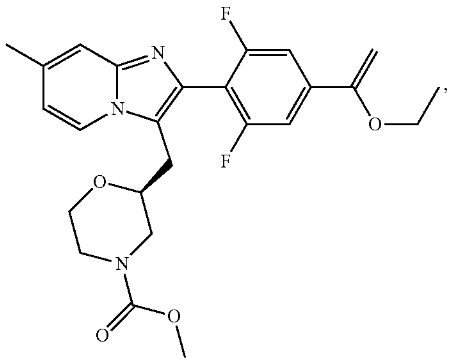
15-1
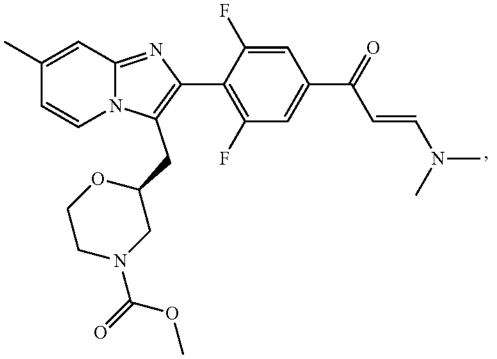
17-2
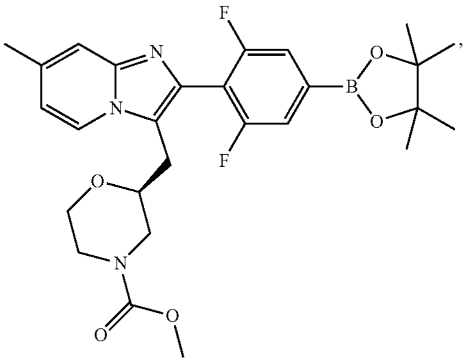
19-3
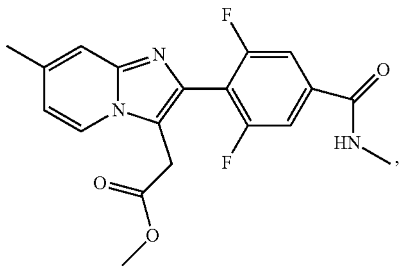
20-2
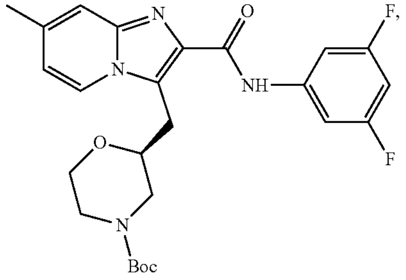

-continued
20-3
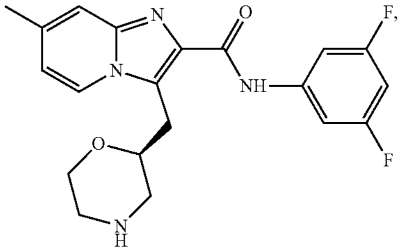
21-3
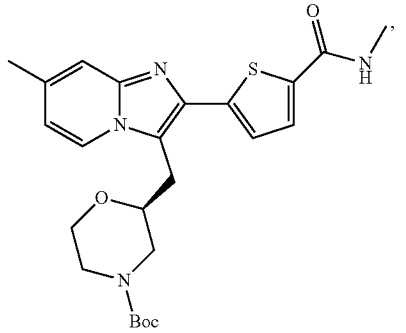
21-4
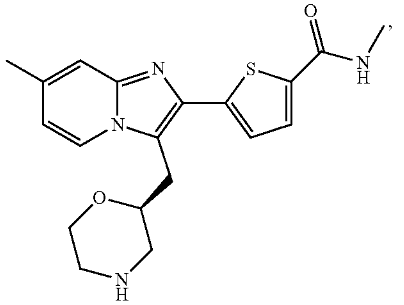
25-2
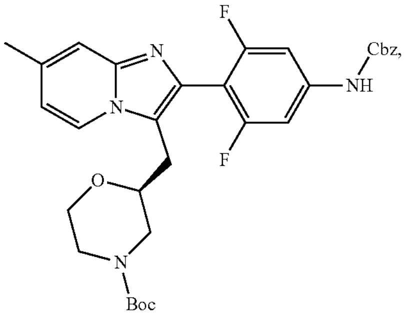
25-3
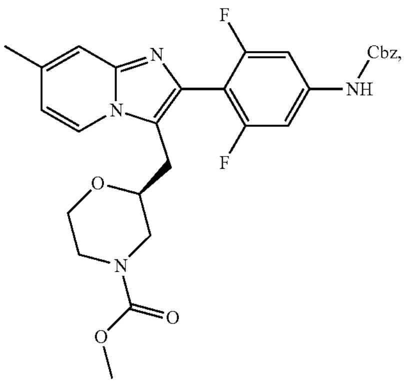
-continued
25-4
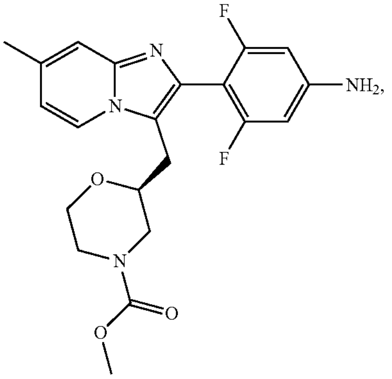
30-6
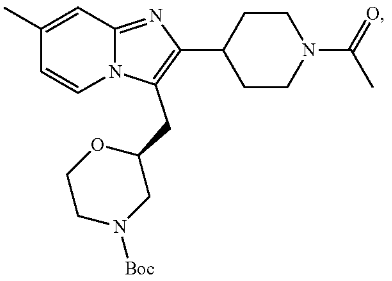
30-7
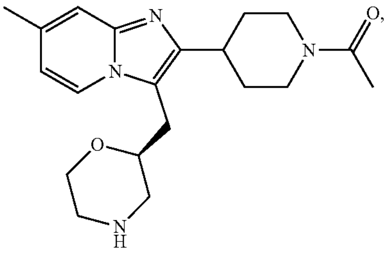
31-6
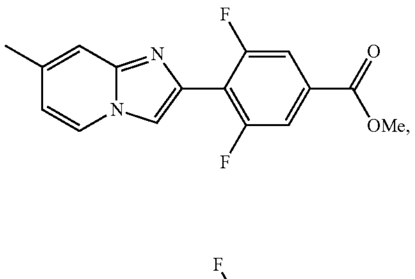
31-7
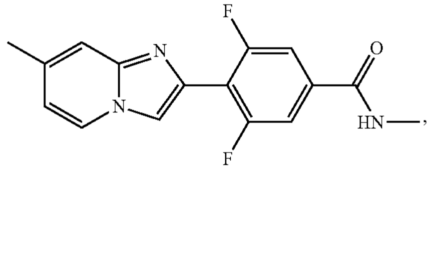

34-4
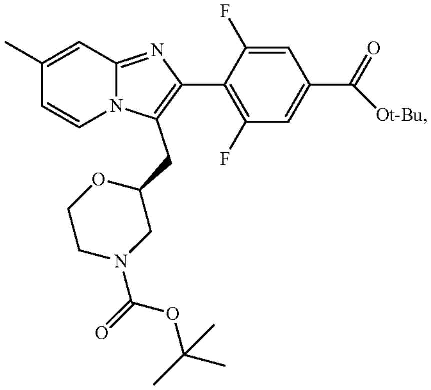
34-5
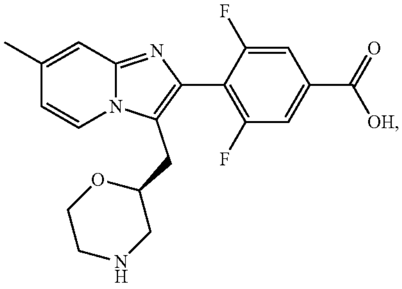
34-6
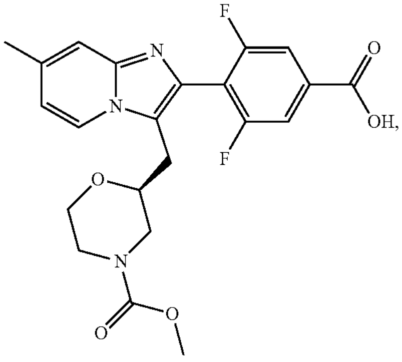
34-7
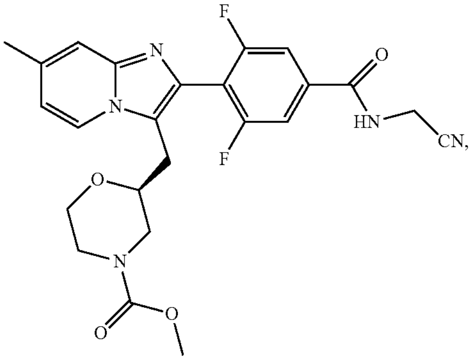
35-2
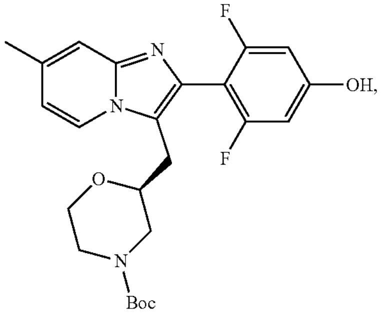
35-3
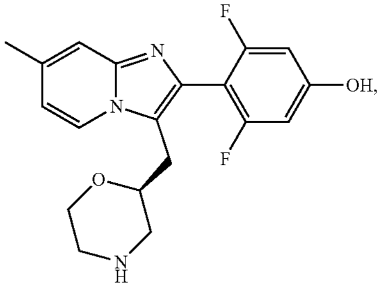
37-5
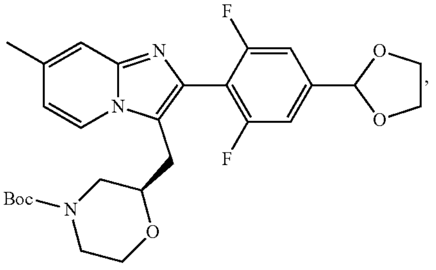
37-6
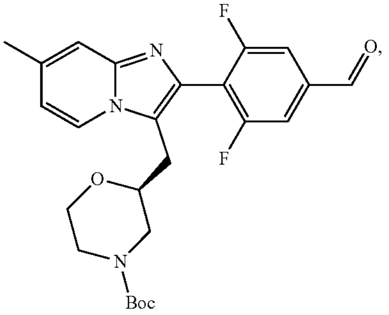
37-8
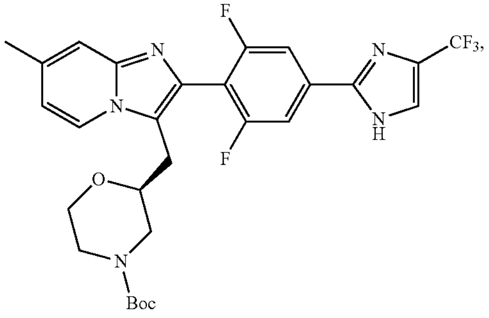

-continued
37-9
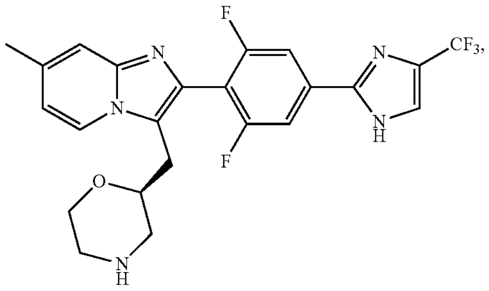
39-9
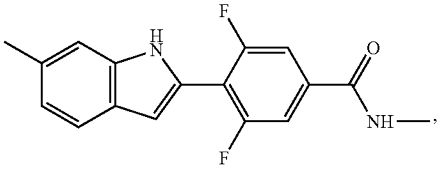
42-10
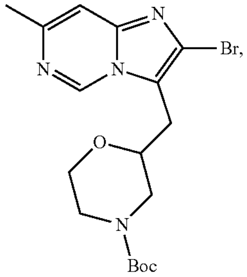
42-11
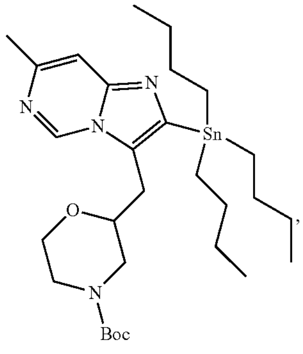
42-13
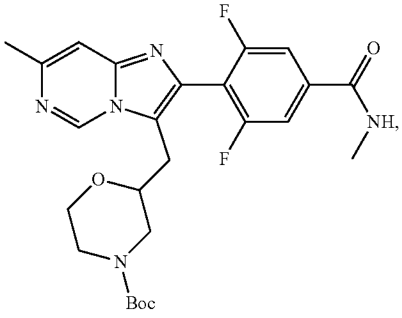
-continued
42-14
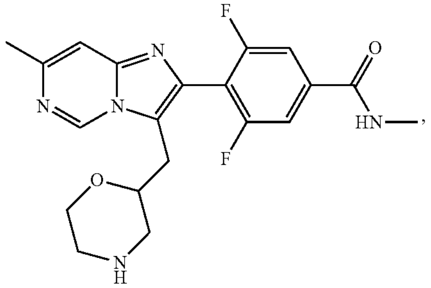
43-5
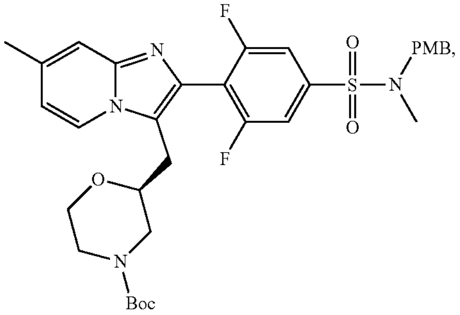
43-6
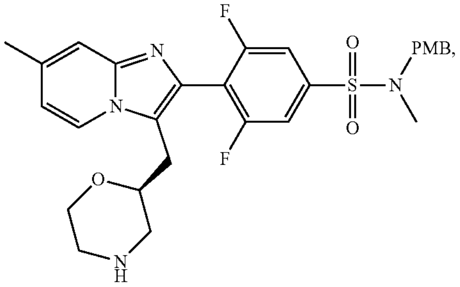
43-7
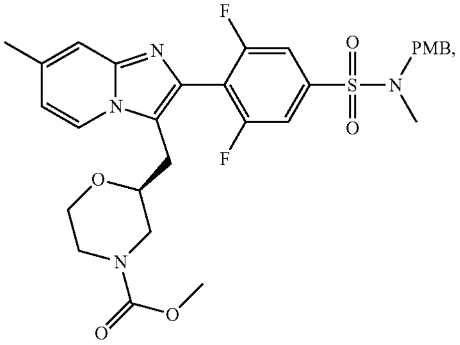
45-2
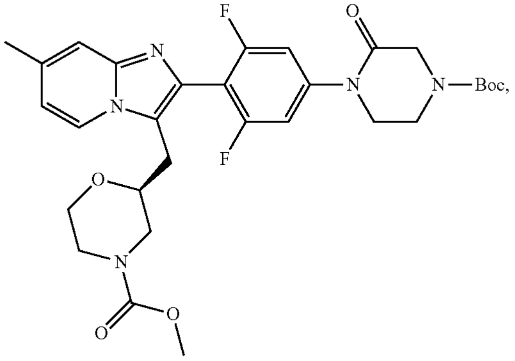

-continued
45-3
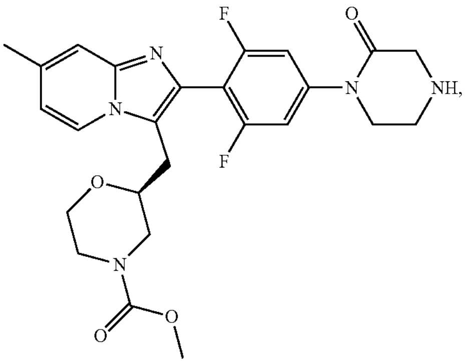
46-6
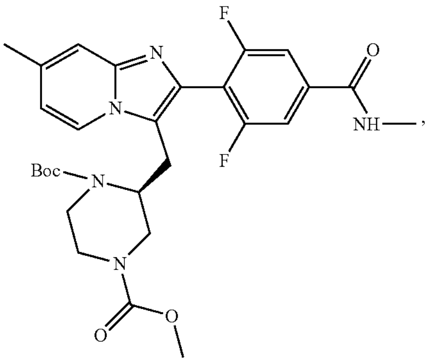
47-1
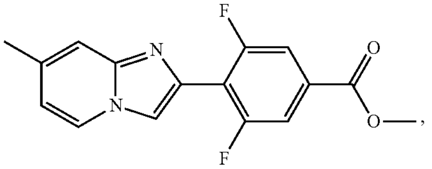
47-2
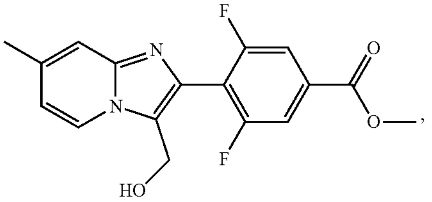
47-3
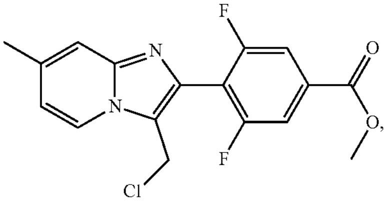
47-5
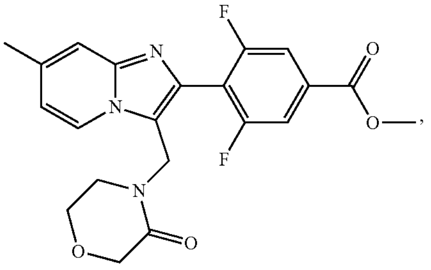
-continued
47-6
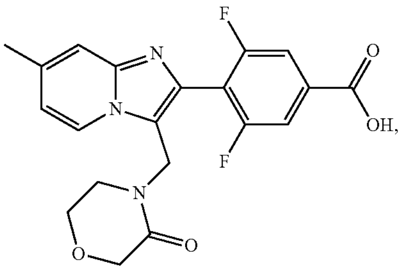
48-1
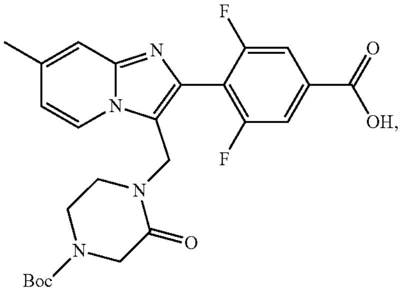
48-2
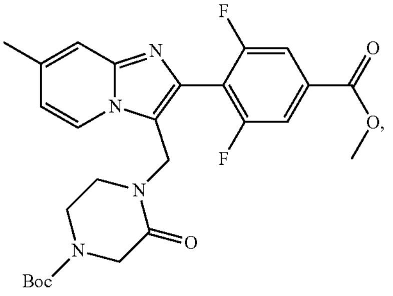
48-3
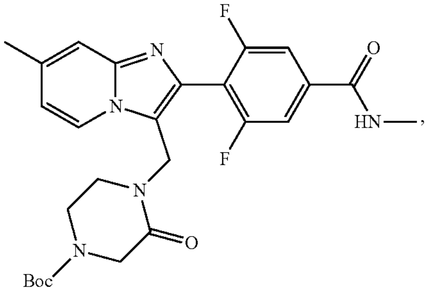
49-4
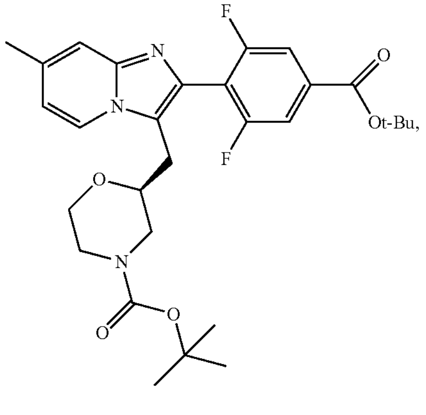

-continued
49-5
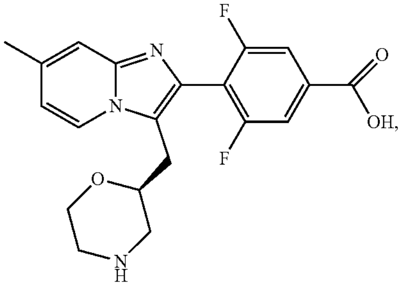
49-6
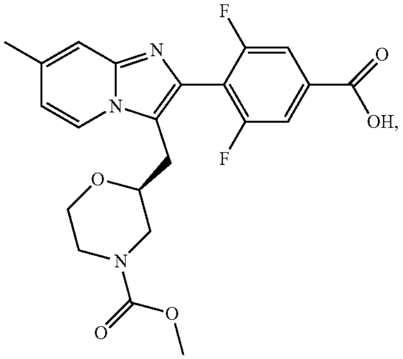
51-1
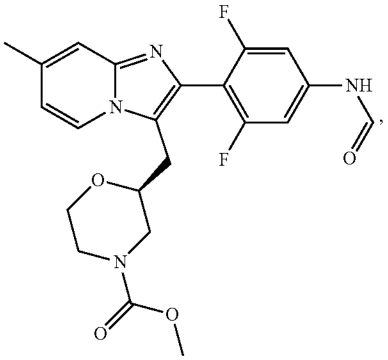
51-2
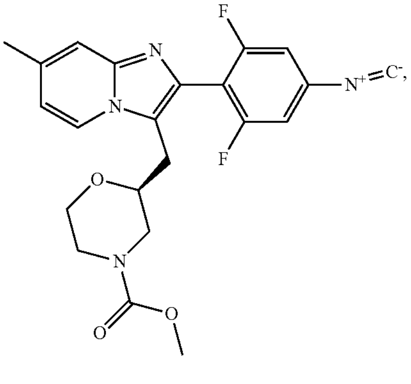
-continued
52-1
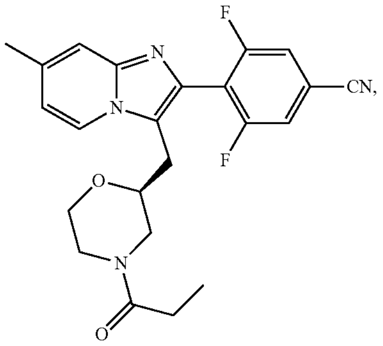
53-8
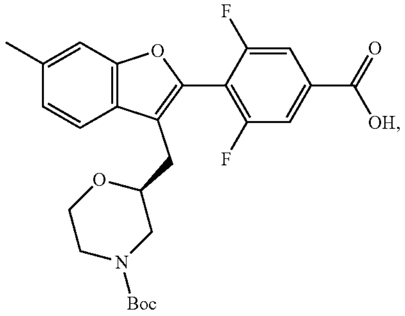
53-9
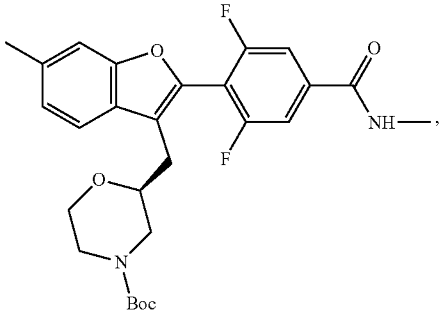
53-10
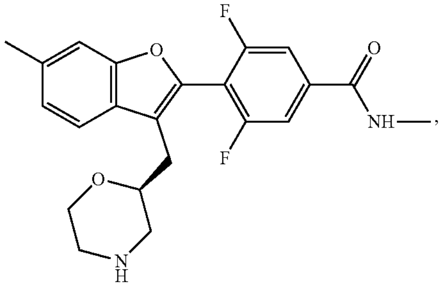
54-7
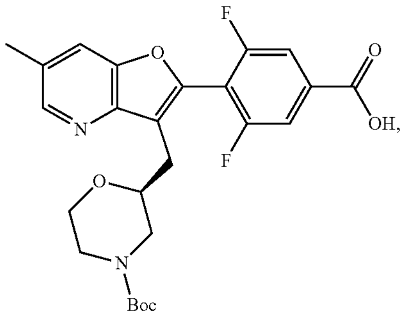

54-8
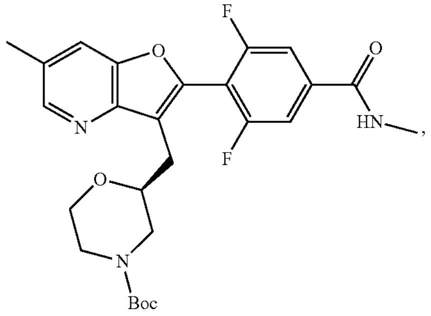
54-9
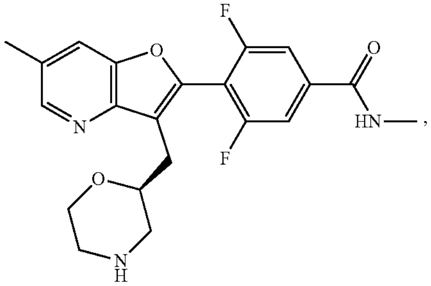
55-6
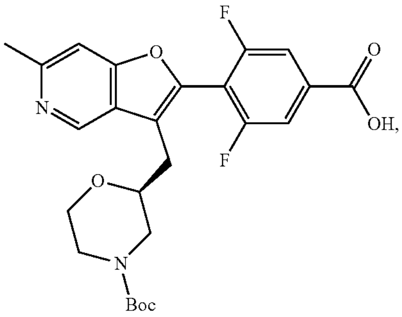
55-7
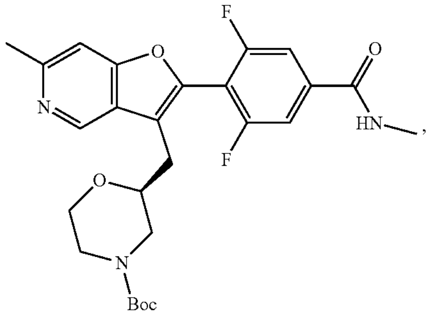
55-8
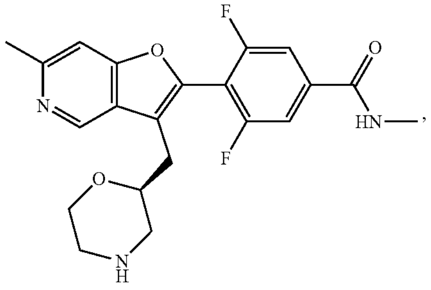
56-5
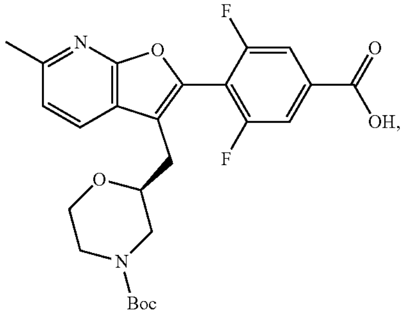
56-6
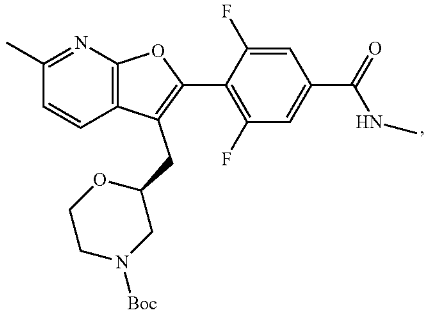
56-7
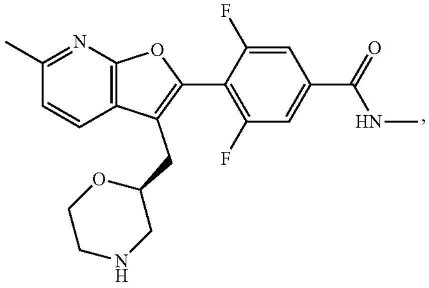
59-1
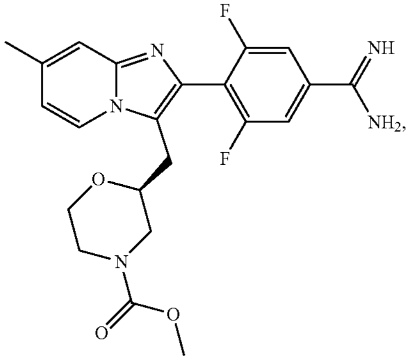

-continued
59-3
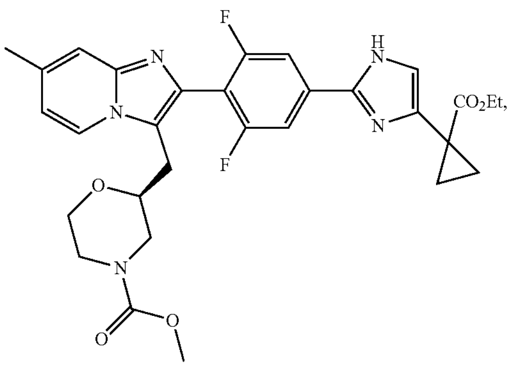
60-2
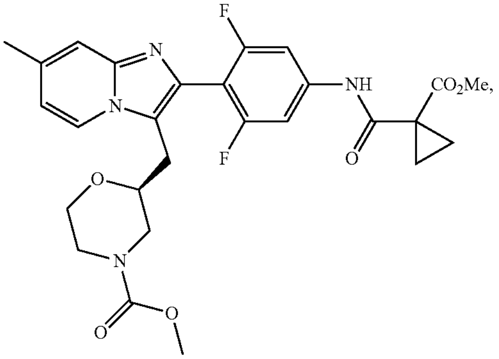
61-6
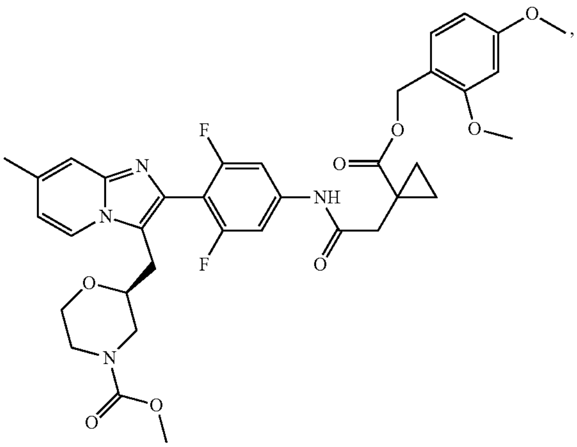
63-2
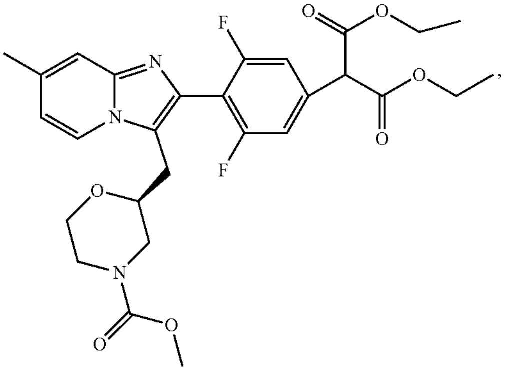
-continued
63-3
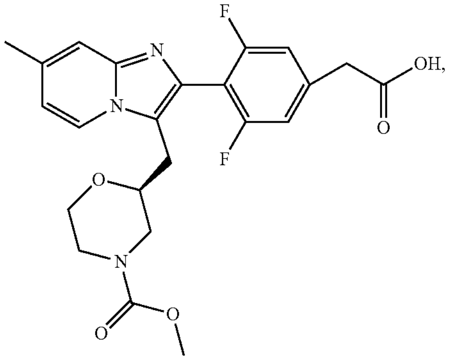
64-1
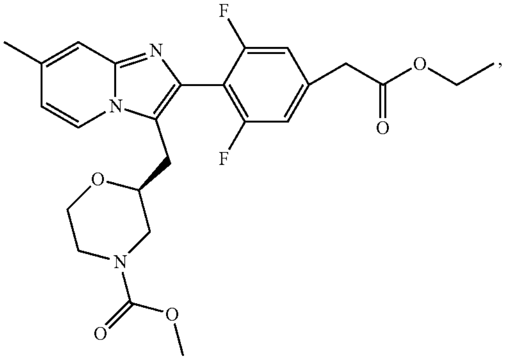
67-8
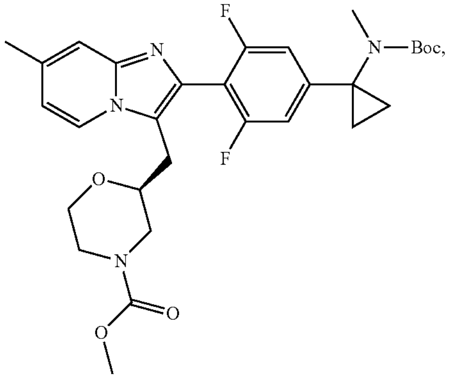
68-1
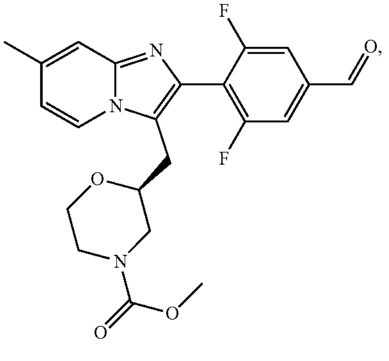

-continued
68-2
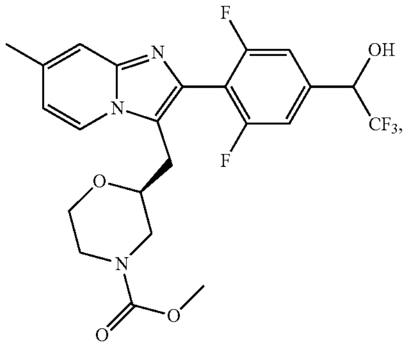
68-3
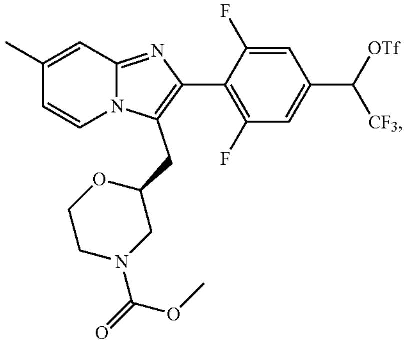
69-2
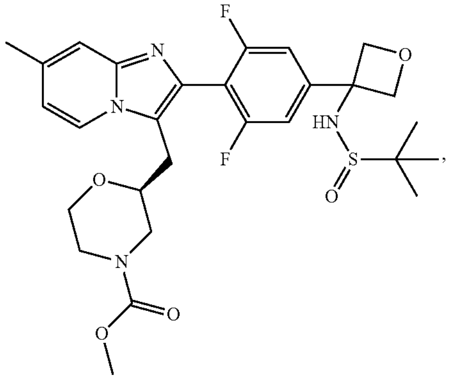
69-3
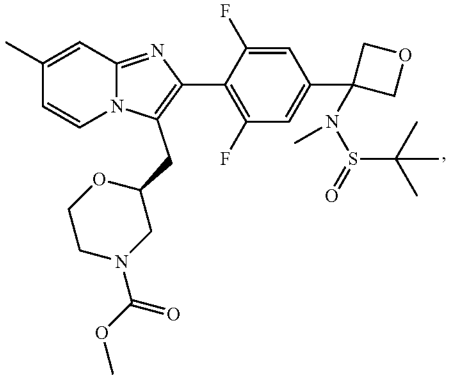
-continued
80-2
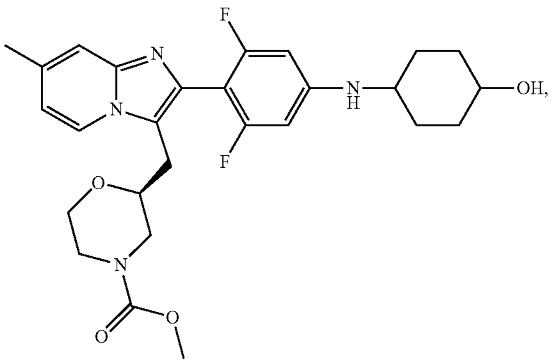
85-2
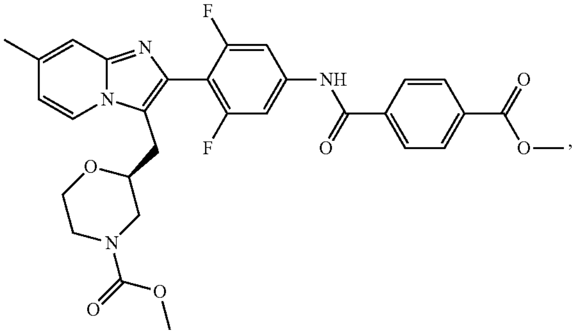
94-8
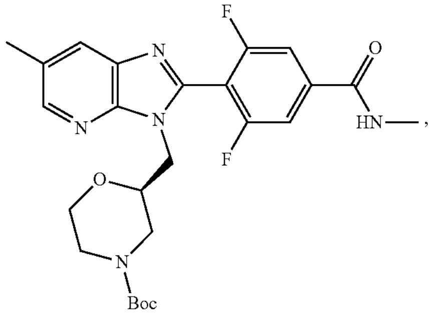
94-9
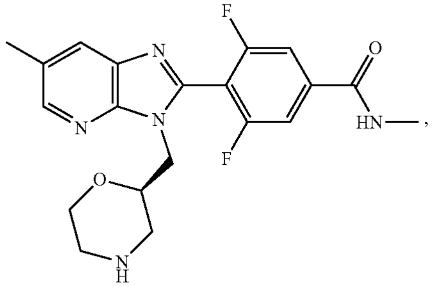
114-2
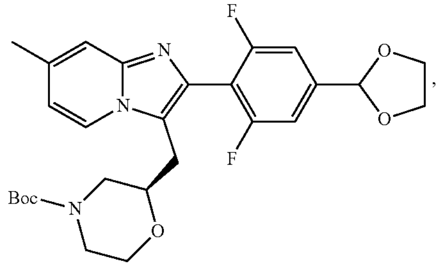

114-3
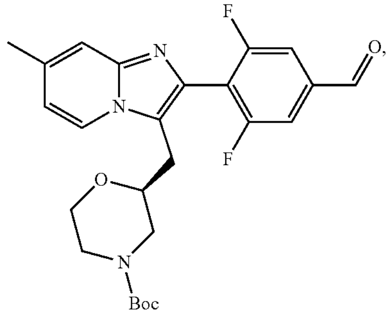
114-4
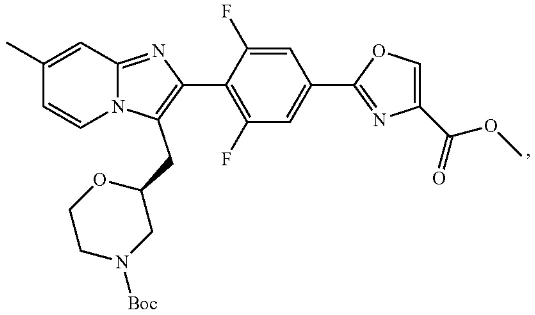
114-5
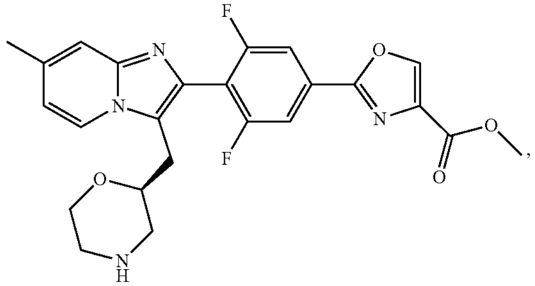
114-6
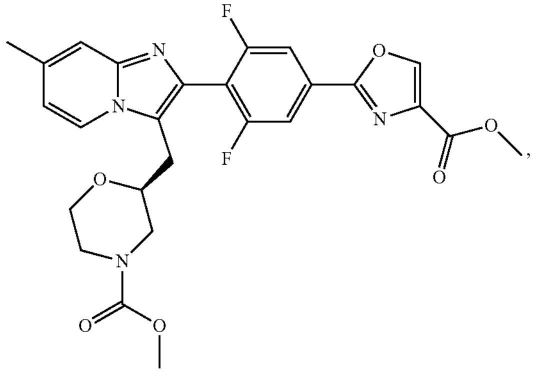
125-1
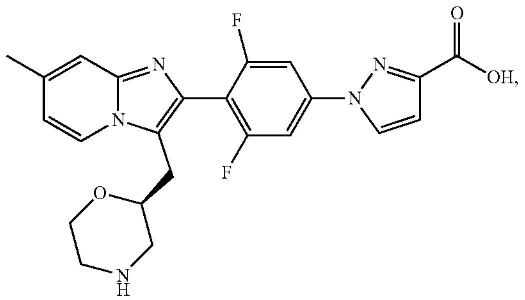
126-2
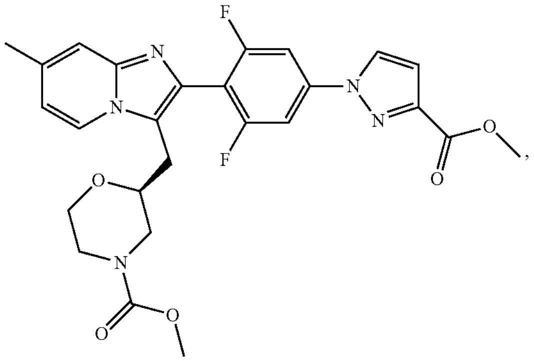
127-4
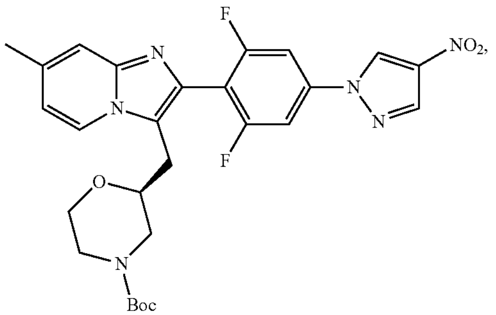
127-5
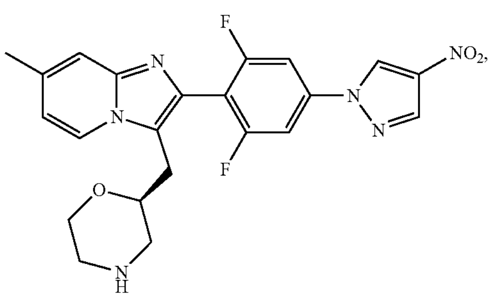

-continued
127-6
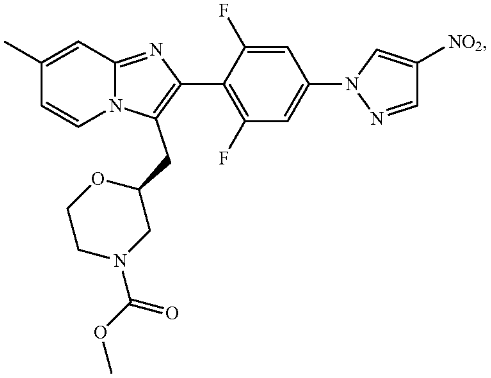
128-4
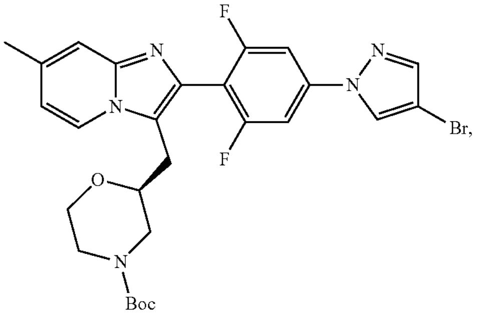
128-5
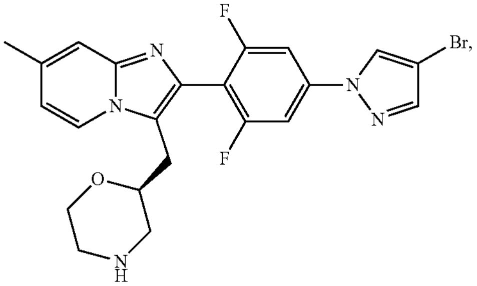
128-6
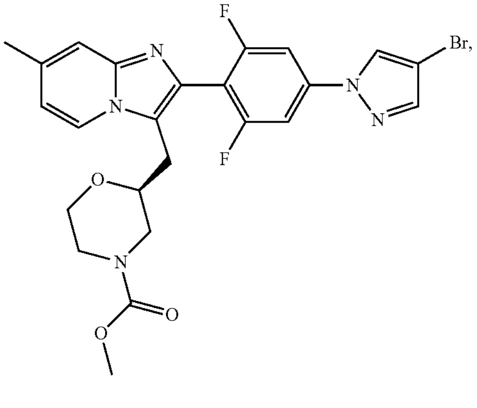
-continued
128-7
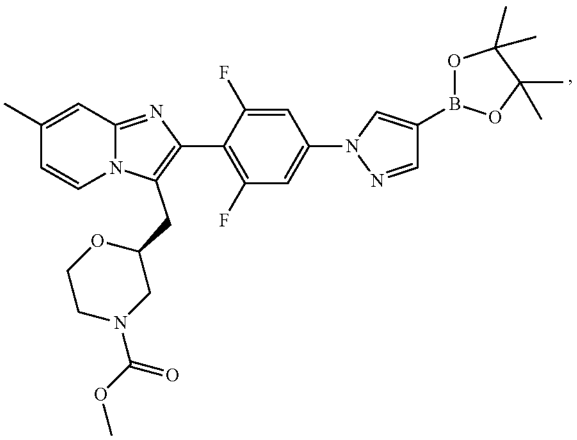
130-8
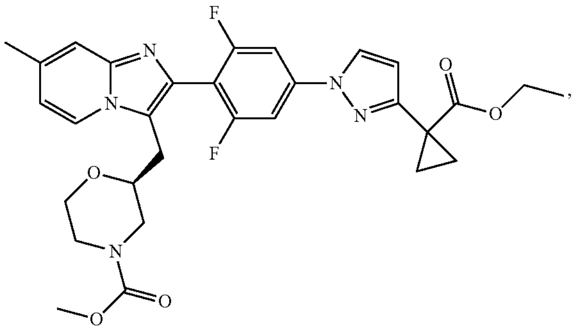
134-7
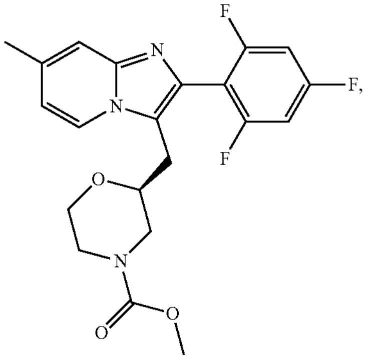
134-8
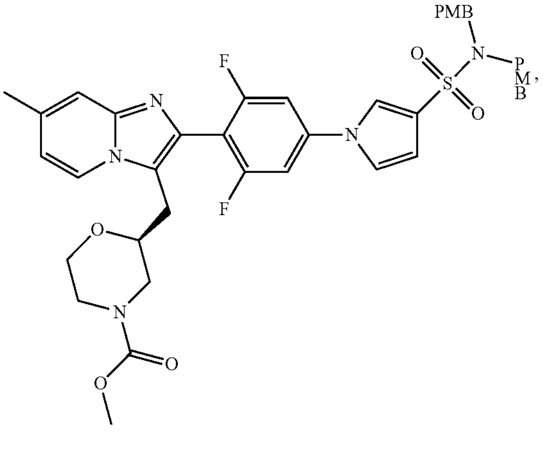

-continued
138-2
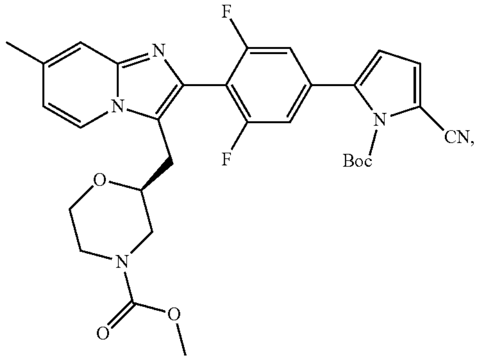
140-2
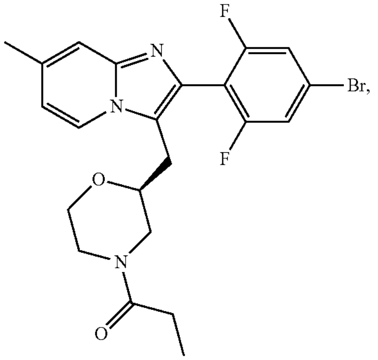
141-4
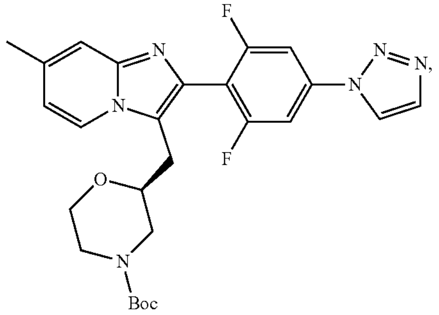
141-5
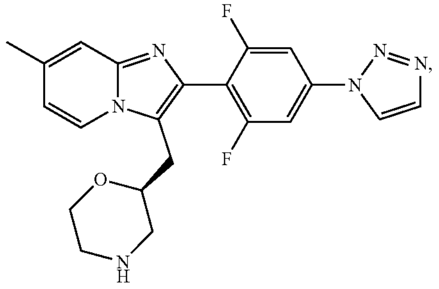
-continued
142-2
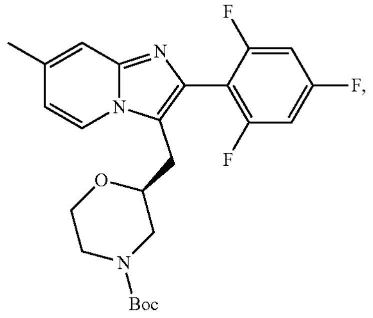
142-3
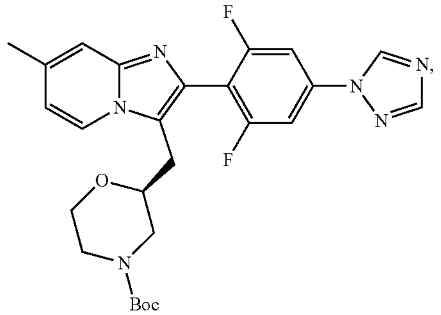
142-4
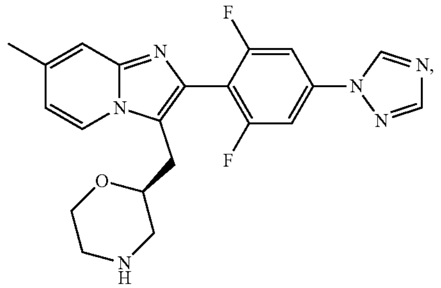
144-1
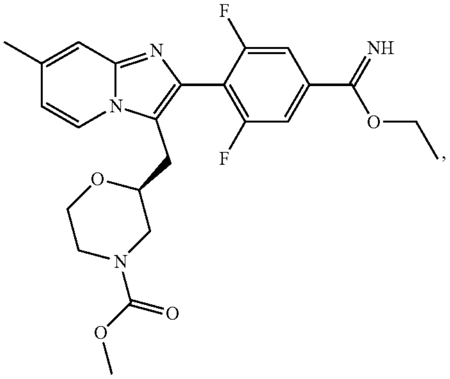

-continued
145-2
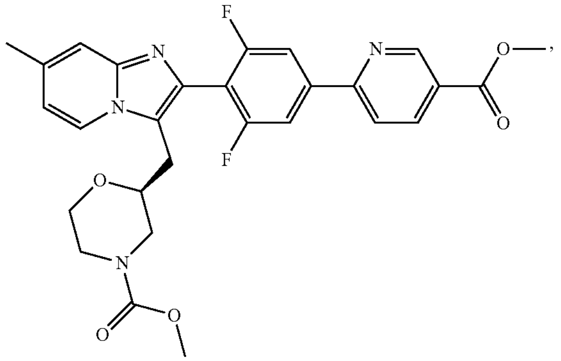
150-2
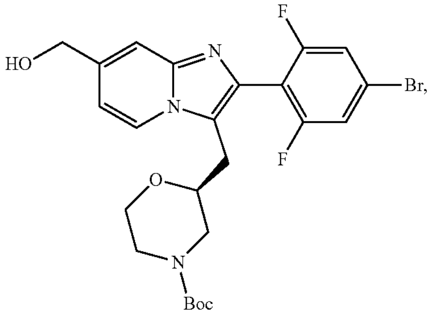
150-3
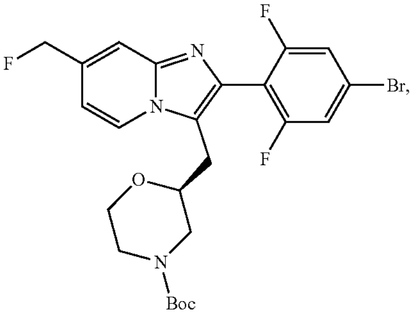
150-4
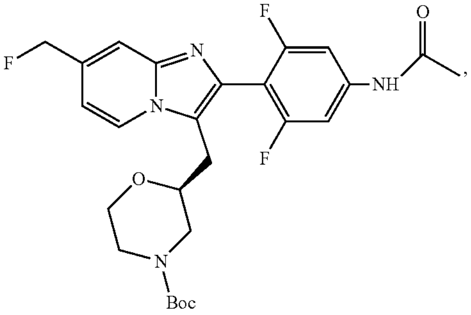
150-5
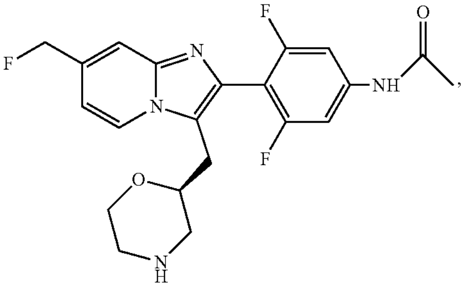
-continued
153-2
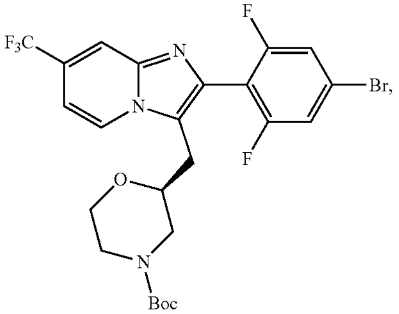
153-3
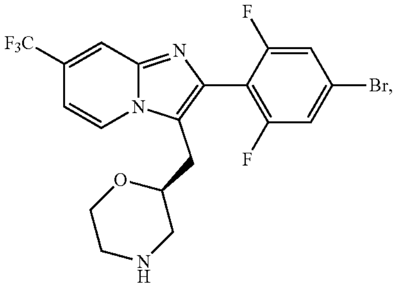
153-4
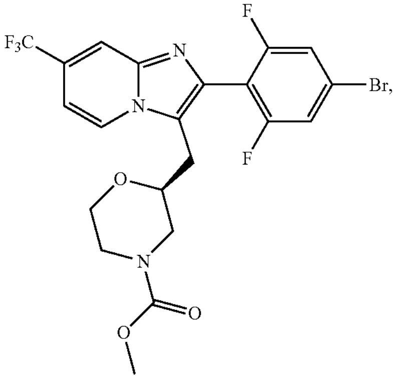
158-1
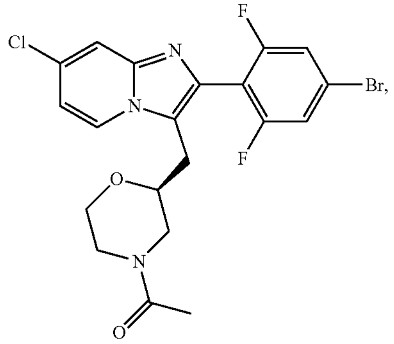

-continued
162-1
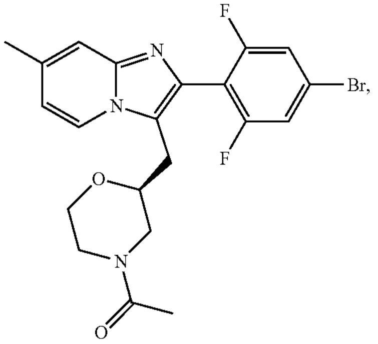
168-3
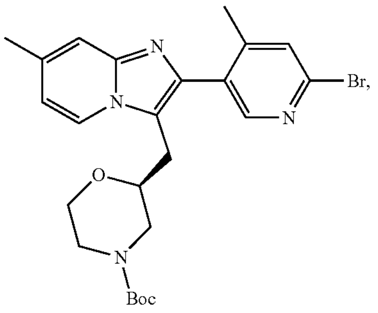
168-4
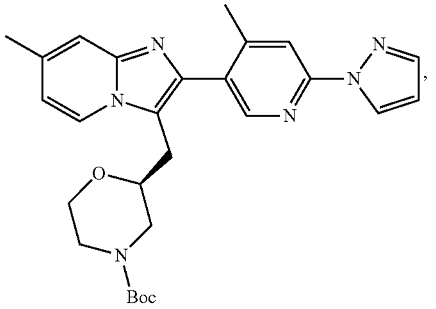
168-5
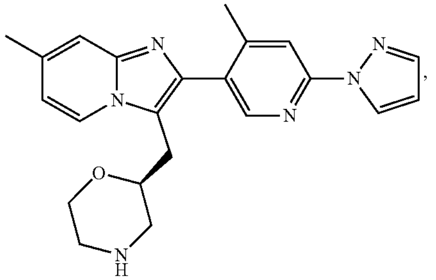
171-5
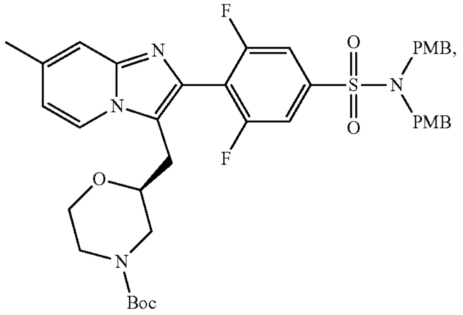
-continued
171-6
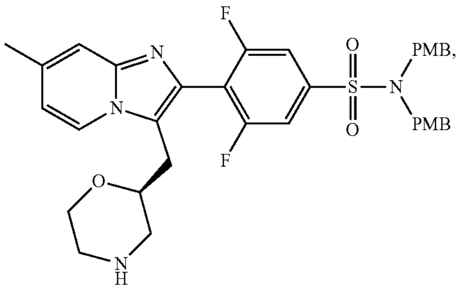
171-7
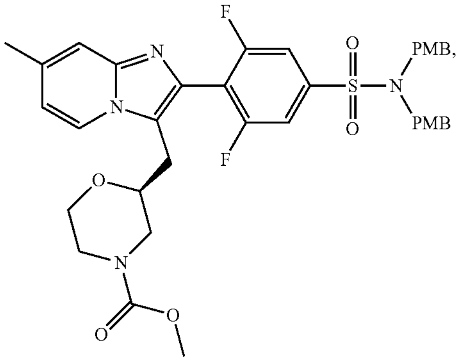
172-3
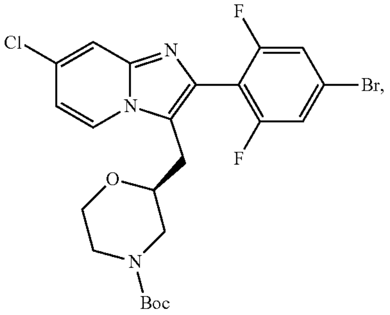
172-4
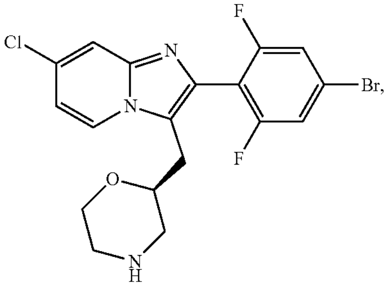

-continued
172-5
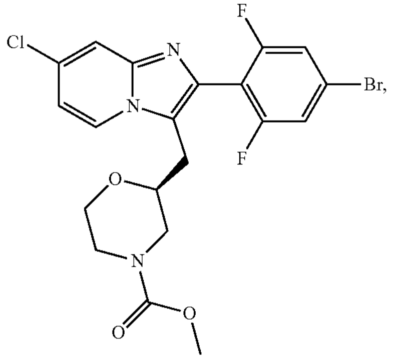
172-6
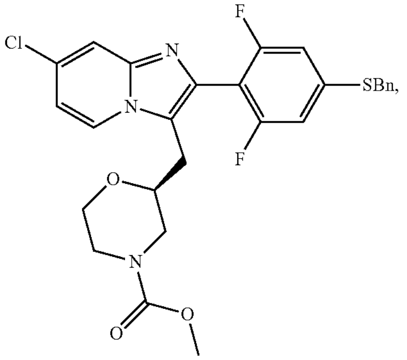
172-7
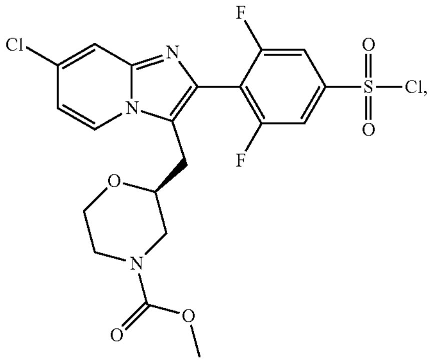
173-1
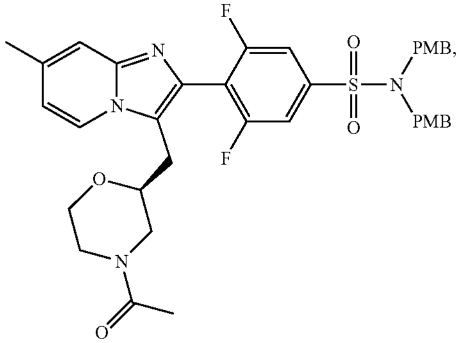
-continued
174-1
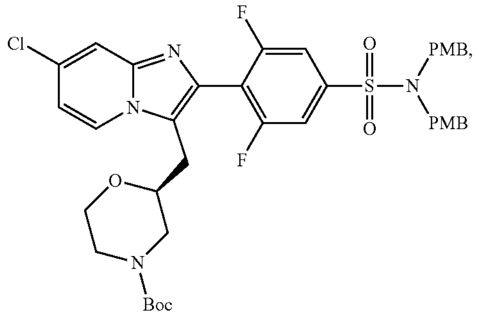
174-2
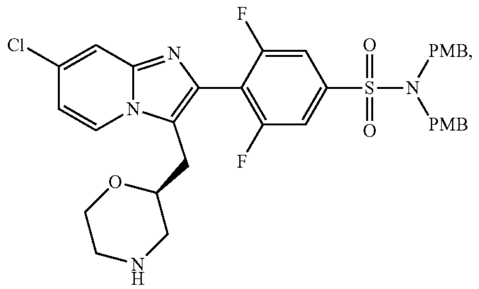
174-3
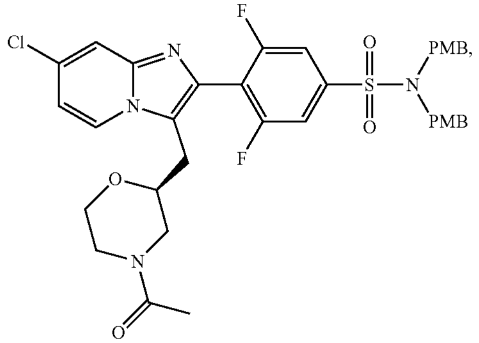
175-1
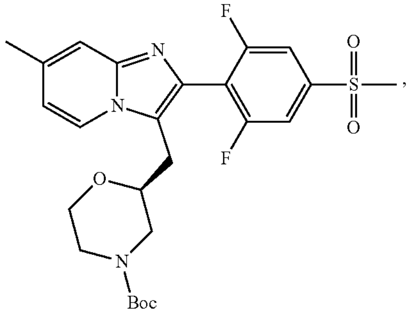
175-2
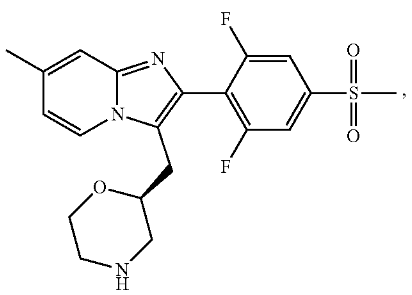

-continued
176-2
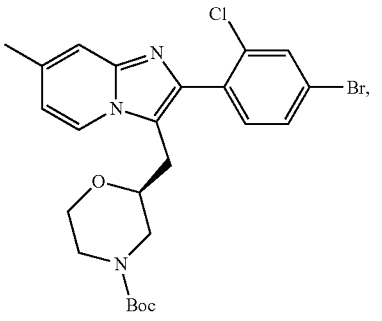
176-3
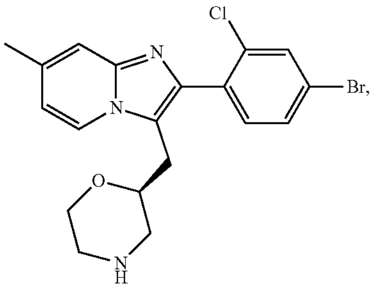
176-4
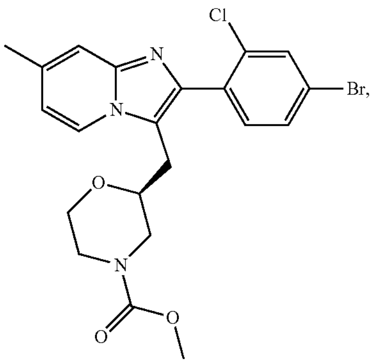
176-5
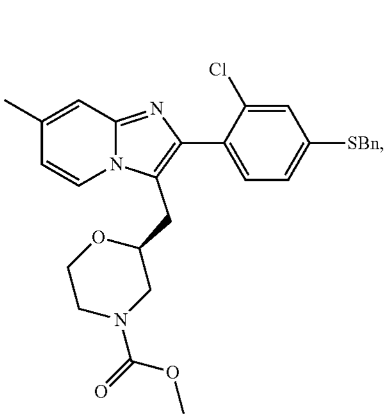
-continued
176-6
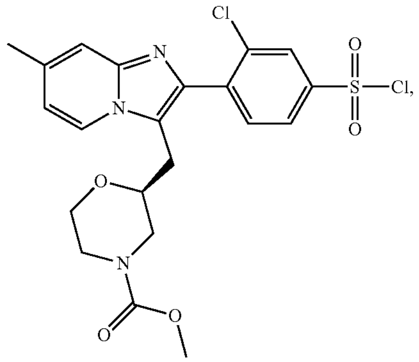
177-3
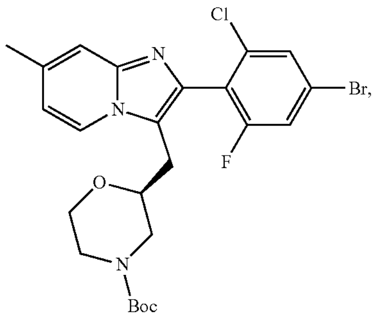
177-4
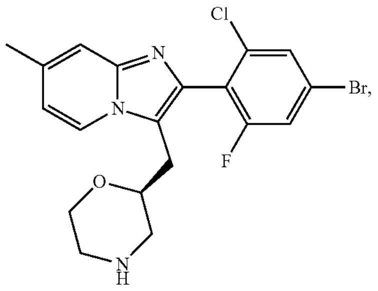
177-5
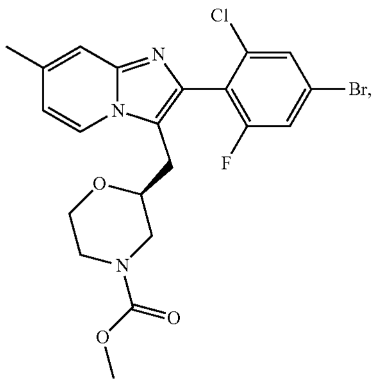

-continued
177-7
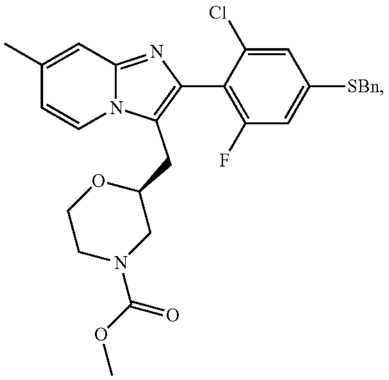
177-8
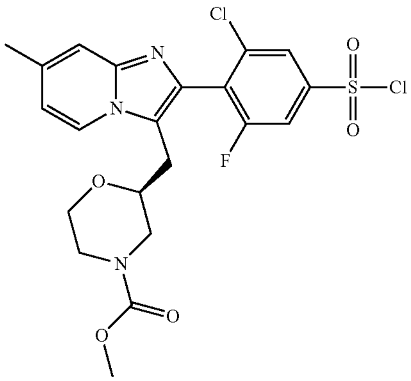
178-2
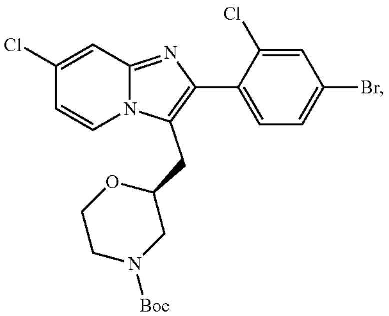
178-3
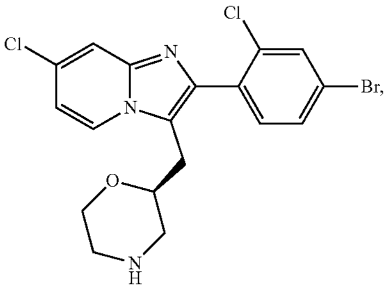
-continued
178-4
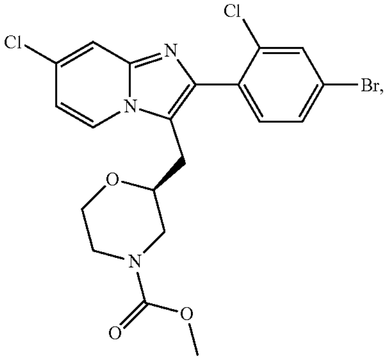
178-5
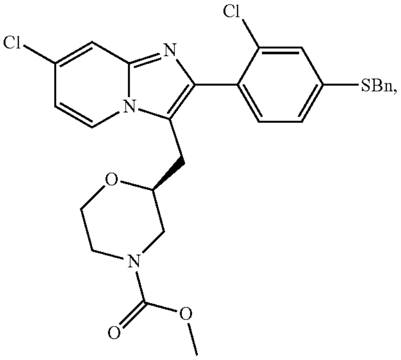
178-6
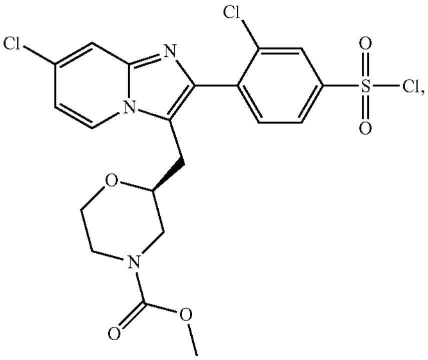
179-2
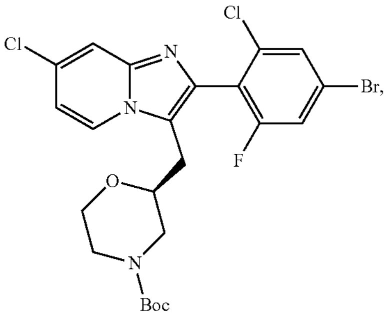

-continued
179-3
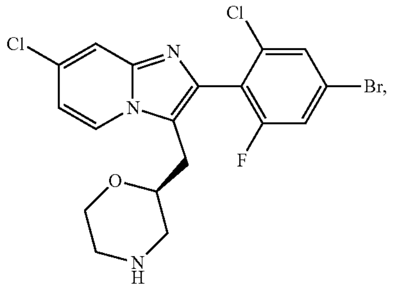
179-4
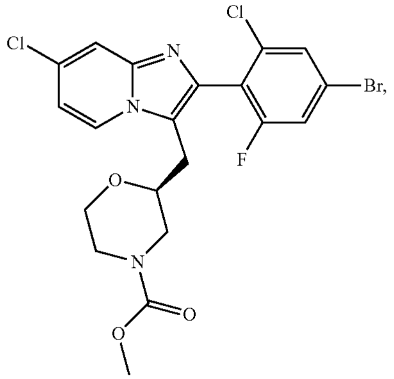
179-5
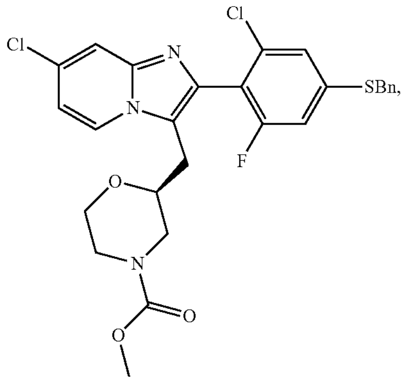
179-6
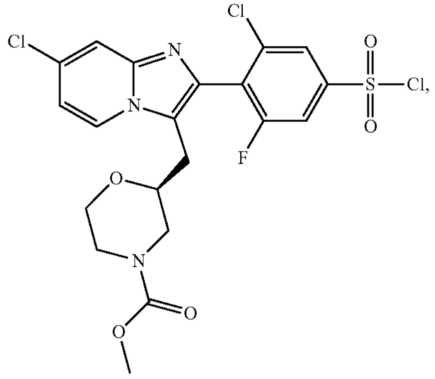
-continued
180-2
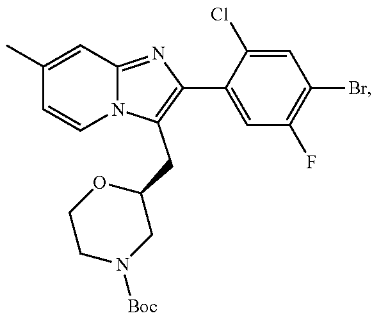
180-3
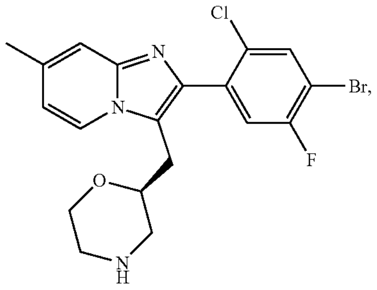
180-4
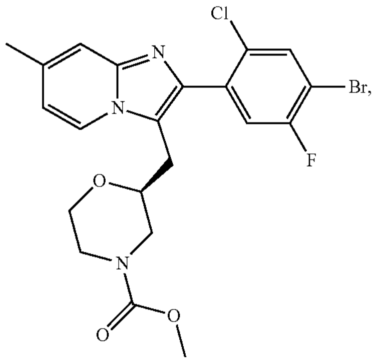
180-5
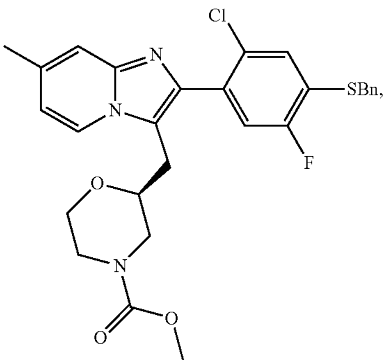

-continued
180-6
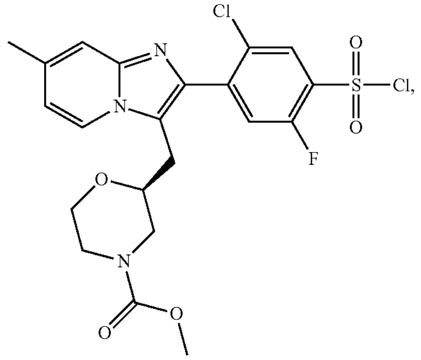
181-1
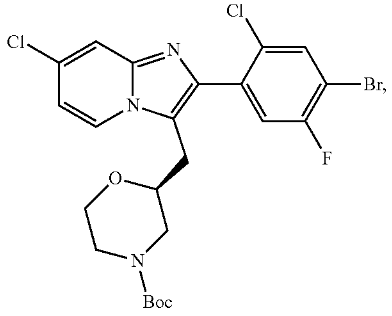
181-2
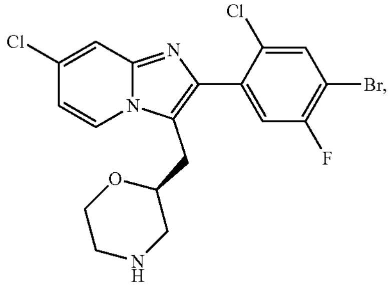
181-3
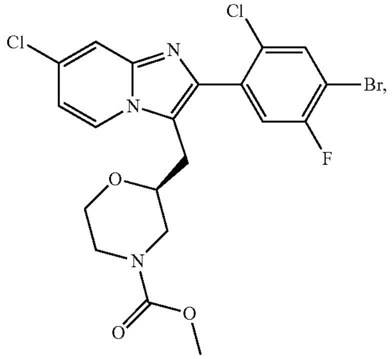
-continued
181-4
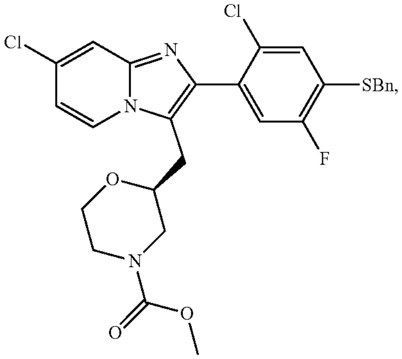
181-5
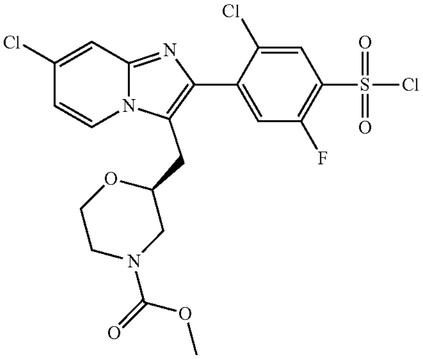
182-2
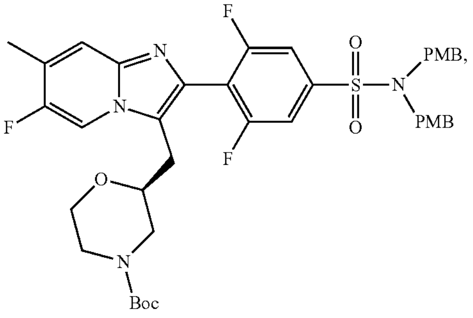
182-3
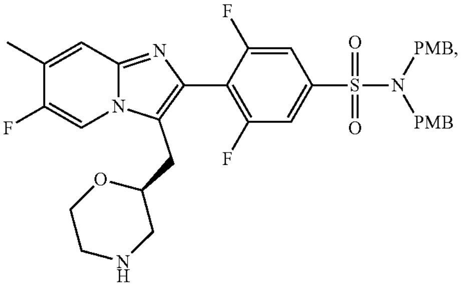

-continued
182-4
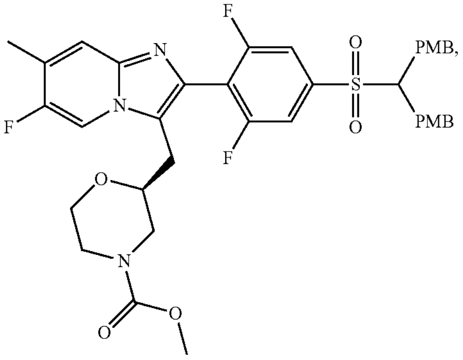
183-3
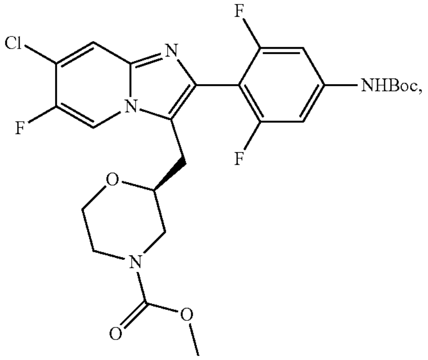
183-4
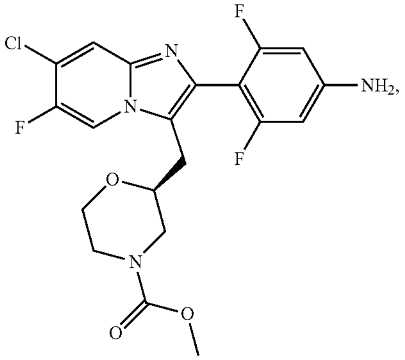
183-5
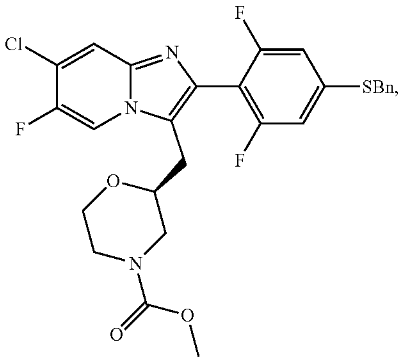
-continued
183-6
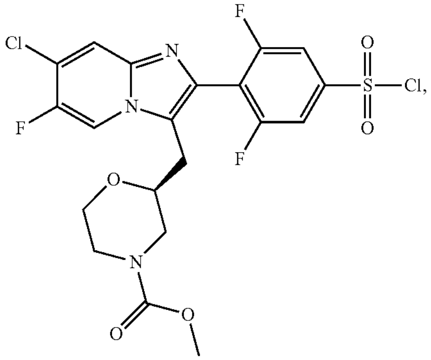
184-7
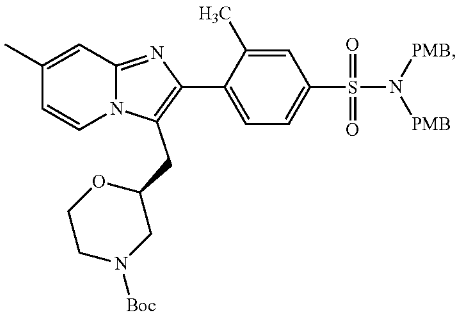
184-8
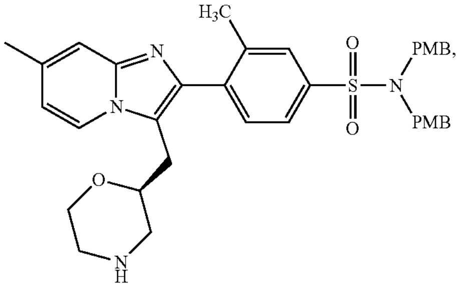
184-9
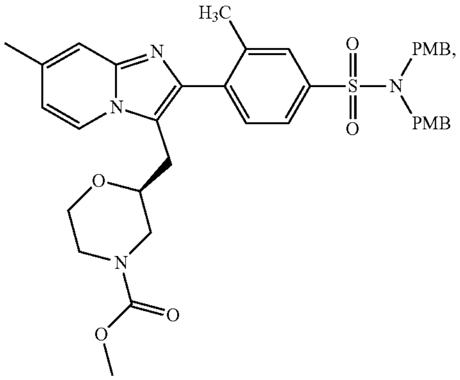

-continued 189-7

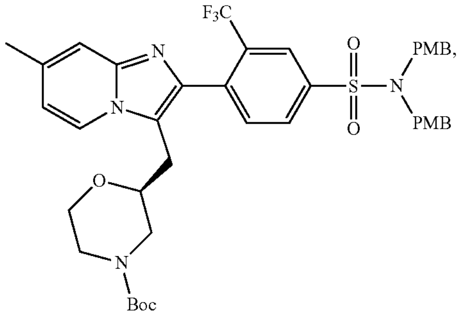

189-8

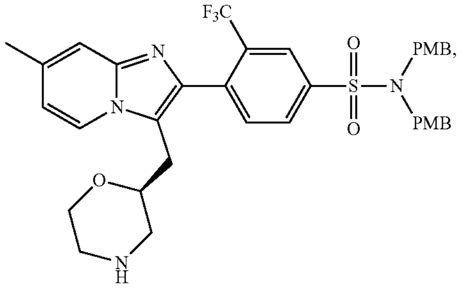

189-9

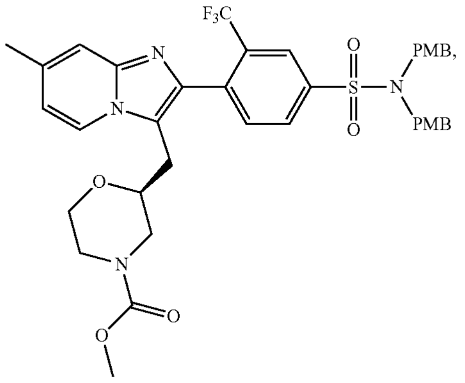

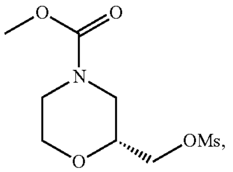

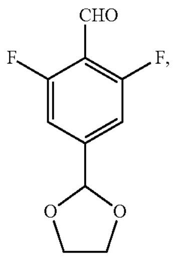

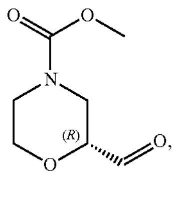

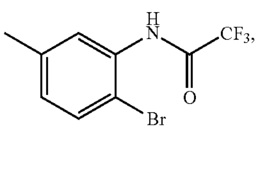

-continued

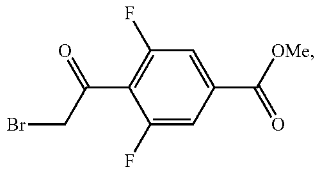

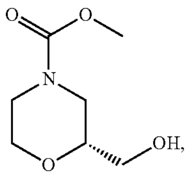

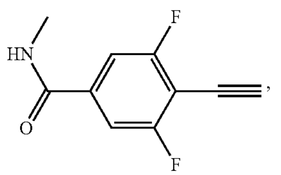

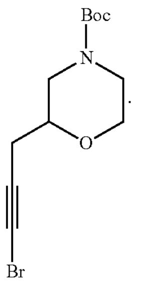

The present invention also provides a pharmaceutical composition comprising the heterocyclic compound of formula I or the pharmaceutically acceptable salt, the hydrate, the solvate, the metabolite, the stereoisomer, the tautomer or the prodrug thereof and at least one pharmaceutically acceptable excipient. The pharmaceutical composition may also comprise one or more additional active ingredients. For example, such pharmaceutical composition may comprise one or more additional heterocyclic compounds of formula I or pharmaceutically acceptable salts, hydrates, solvates, metabolites, stereoisomers, tautomers or prodrugs thereof. Alternatively or additionally, the pharmaceutical composition may, for example, comprise one or more active ingredients other than a heterocyclic compound of formula I or a pharmaceutically acceptable salt, a hydrate, a solvate, a metabolite, a stereoisomer, a tautomer or a prodrug thereof.

The pharmaceutical composition comprise an therapeutically effective amount of the heterocyclic compound of formula I or the pharmaceutically acceptable salt, the hydrate, the solvate, the metabolite, the stereoisomer, the tautomer or the prodrug thereof.

The effective amount of the compound, the pharmaceutical composition or the drug disclosed herein can be readily determined by routine experiments, and the most effective and convenient administration route and the most appropriate preparation can also be determined by routine experiments.

The pharmaceutically acceptable excipients may be those widely used in the field of pharmaceutical production. The excipients are primarily used to provide a safe, stable and functional pharmaceutical composition and may also provide methods for dissolving the active ingredients at a desired rate or for promoting effective absorption of the active ingredients after administration of the composition to a subject. The pharmaceutically acceptable excipients may be inert fillers or provide a function such as stabilizing the overall pH of the composition or preventing degradation of the active ingredients of the composition. The pharmaceutically acceptable excipients may include one or more of the following: binders, suspending agents, emulsifiers, diluents, fillers, granulating agents, gluing agents, disintegrants, lubricants, anti-adherents, glidants, wetting agents, gelling agents, absorption delaying agents, dissolution inhibitors, reinforcing agents, adsorbents, buffering agents, chelating agents, preservatives, colorants, flavoring agents and sweeteners.

Substances that may serve as pharmaceutically acceptable excipients include, but are not limited to, ion exchangers; aluminum; aluminum stearate; lecithin; serum proteins such as human serum protein; buffer substances such as phosphate; glycine; sorbic acid; potassium sorbate; partial glyceride mixture of saturated vegetable fatty acid; water; salts or electrolytes such as protamine sulfate, disodium hydrogen phosphate, potassium hydrogen phosphate, sodium chloride and zinc salt; colloidal silica; magnesium trisilicate; polyvinylpyrrolidone; polyacrylate; waxes; polyethylene-polyoxypropylene-blocking polymer; wool fat; sugars such as lactose, glucose and sucrose; starches such as corn starch and potato starch; cellulose and its derivatives such as sodium carboxymethyl cellulose, ethyl cellulose and cellulose acetate; gum powder; malt; gelatin; talc powder; adjuvants such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffers such as magnesium hydroxide and aluminum hydroxide; alginic acid; pyrogen-free water; isotonic salts; Ringer's solution; ethanol, phosphate buffered solution, and other non-toxic suitable lubricants such as sodium lauryl sulfate and magnesium stearate, coloring agents, releasing agents, coating agents, sweeteners, flavoring agents and perfumes, preservatives and antioxidants.

The pharmaceutical composition disclosed herein may be prepared in accordance with the disclosure by any method known to those skilled in the art, for example, conventional mixing, dissolving, granulating, emulsifying, levigating, encapsulating, embedding or lyophilizing processes.

The compound disclosed herein may be provided in pharmaceutical dosage forms including immediate release, controlled release, sustained release or targeted drug release systems. For example, common dosage forms include solutions and suspensions, (micro) emulsions, ointments, gels and patches, liposomes, tablets, dragees, soft or hard shell capsules, suppositories, ovules, implants, amorphous or crystalline powders, aerosols and lyophilized preparations. Depending on the administration route, special devices may be required to administer or deliver the drugs, such as syringes and needles, inhalers, pumps, injection pens, applicators or special flasks. Pharmaceutical dosage forms often comprises drugs, excipients, and containers/closure systems. One or more excipients (also known as inactive ingredients) may be added to the compound disclosed herein to improve or facilitate the manufacture, stability, administration and safety of drugs, and may provide a means to obtain a desired drug release profile. Thus, the types of the excipients to be added to a drug may depend on various factors, such as physical and chemical properties of the drug, administration route and preparation methods. Those pharmaceutical excipients in the art, including those listed in various pharmacopoeias, may be used. (See *U.S. Pharmacopeia* (USP), s (JP), *European Pharmacopoeia* (EP) and *British Pharmacopoeia* (BP); publications from the Center for Drug Evaluation and Research (CEDR) of U.S. Food and Drug Administration (www.fda.gov), for example, *Inactive Ingredient Guide,* 1996; and *Handbook of Pharmaceutical Additives,* 2002, edited by Ash & Ash, Synapse Information Resources, Inc., Endicott NY; etc.)

Pharmaceutical dosage forms of the compound disclosed herein may be prepared by any method well known in the art, for example, by conventional mixing, sieving, dissolving, melting, granulating, dragee-making, tabletting, suspending, extruding, spray-drying, grinding, emulsifying, (nano/micro) encapsulating, embedding or lyophilizing processes. As described above, the composition disclosed herein may include one or more physiologically acceptable inactive ingredients that facilitate the processing of active molecules into preparations for pharmaceutical use.

Appropriate preparations will be determined according to the desired administration route. For example, for intravenous injection, the composition may be prepared in aqueous solution and, if necessary, physiologically compatible buffers, including, for example, phosphate, histidine or citrate for adjusting the pH of the preparation, and tonicity agents such as sodium chloride or dextrose. For transmucosal or nasal administration, a semi-solid, liquid preparation or patch, possibly containing a penetration enhancer, may be preferred; and the penetration enhancer is generally known in the art. For oral administration, the compound may be prepared into liquid or solid dosage forms and used as immediate release or controlled/sustained release preparations. Suitable dosage forms for oral ingestion by an individual include tablets, pills, dragees, hard and soft shell capsules, liquids, gels, syrups, ointments, suspensions and emulsions. The compound may also be prepared in rectal compositions such as suppositories or retention enemas, e.g., containing conventional suppository matrices such as cocoa butter or other glycerides.

Oral solid dosage forms can be obtained using excipients including fillers, disintegrants, binders (dry and wet), dissolution retardants, lubricants, glidants, anti-adherents, cationic exchange resins, wetting agents, antioxidants, preservatives, colorants and flavoring agents. These excipients may be of synthetic or natural sources. Examples of such excipients include cellulose derivatives, citric acid, dicalcium phosphate, gelatin, magnesium carbonate, magnesium/sodium lauryl sulfate, mannitol, polyethylene glycol, polyvinylpyrrolidone, silicates, silica, sodium benzoate, sorbitol, starches, stearic acid or salts thereof, sugars (i.e., dextrose, sucrose, lactose, etc.), talc, tragacanth mucilage, vegetable oils (hydrogenated) and waxes. Ethanol and water may be used as adjuvants for granulation. In some cases, it is desirable to coat tablets with, for example, a taste-masking film, a gastric acid-resistant film or a sustained release film. Natural and synthetic polymers are often used to coat tablets in combination with colorants, sugars, and organic solvents or water to produce dragees. When capsules are superior to tablets, the pharmaceutical powders, suspensions or solutions may be delivered in the form of compatible hard or soft shell capsules.

In some embodiments, the compound disclosed herein may be administered topically, e.g. by means of a skin patch, a semi-solid or liquid preparation such as gels, (micro) emulsions, ointments, solutions, (nano/micro) suspensions or foams. Skin and underlying tissue penetration of drugs may be modulated by: for example, using penetration enhancers; using appropriate selection and combination of lipophilic, hydrophilic and amphiphilic excipients, including water, organic solvents, waxes, oils, synthetic and natural polymers, surfactants, and emulsifiers; by adjusting the pH value; and using complexing agents. Other techniques, such as iontophoresi, may also be used to modulate skin penetration of the compound disclosed herein. Transdermal or topical administration will be preferred, for example, in situations where topical administration with minimal systemic exposure is desired.

For inhalation administration or nasal administration, the compound used herein is conveniently administered in the form of solutions, suspensions, emulsions or semi-solid aerosols from pressurised packs or nebulisers, usually with the aid of propellants, such as halocarbons derived from methane and ethane, carbon dioxide or any other suitable gas. For topical aerosols, hydrocarbons such as butane, isobutene and pentane are suitable. In the case of a pressurized aerosol, the appropriate dosage unit may be determined by providing a valve delivery measurement. Capsules and cartridges having, for example, gelatin may be prepared for use in an inhaler or insufflator. These generally contain powder mixtures of compounds with suitable powder matrices such as lactose or starch.

Compositions prepared for parenteral administration by injection are generally sterile and may be presented in unit dosage form, for example, in ampoules, syringes, injection pens, or multiple-dose containers, the latter typically containing preservatives. The compositions may take such forms as suspensions, solutions, or emulsions in oily or aqueous carriers, and may contain preparations such as buffers, tonicity agents, viscosity enhancers, surfactants, suspending and dispersing agents, antioxidants, biocompatible polymers, chelating agents, and preservatives. Depending on the injection site, the carrier may contain water, synthetic or vegetable oils, and/or organic co-solvents. In some cases, e.g., for lyophilized products or concentrates, parenteral preparations will be reconstituted or diluted prior to administration. Depot preparations that provide controlled or sustained release of the compound disclosed herein may include injectable suspensions of nano/microparticles or nano/micro or non-micronized crystals. Other matrices well known in the art, polymers such as poly(lactic acid), poly (glycolic acid) or copolymers thereof, may be used as the controlled/sustained release matrices. Other depot administration systems may be presented in the form of implants and pumps requiring incisions.

Suitable carriers for the compound disclosed herein for intravenous injection are well known in the art and include water-based solutions containing a base (e.g., sodium hydroxide) for forming an ionic compound, sucrose or sodium chloride as a tonicity agent, and buffers, for example, containing phosphate or histidine. A co-solvent such as polyethylene glycol may be added. These water-based systems can effectively dissolve the compound disclosed herein and produce low toxicity after systemic administration. The proportion of components of the solution system can be varied considerably without destroying the solubility and toxicity characteristics. In addition, the properties of the components may be varied. For example, low toxicity surfactants such as polysorbate or poloxamer may be used, polyethylene glycol or other co-solvents may also be used, biocompatible polymers such as polyvinylbenzidine may be added, and other sugars and polyols may be used in place of dextrose.

The therapeutically effective dosage may first be estimated using various methods well known in the art. Initial dosage for animal studies may be based on established effective concentrations in cell culture assays. Dosage ranges suitable for human individuals may be determined, for example, using data obtained from animal studies and cell culture assays. In certain embodiments, the compound disclosed herein may be prepared as medicaments for oral administration.

An effective or therapeutically effective amount or dosage of a medicament (e.g., the compound disclosed herein) refers to the amount of the medicament or compound that causes improvement of symptoms or prolongation of survival in an individual. Toxicity and therapeutic efficacy of the molecule can be determined by standard pharmaceutical procedures in cell cultures or experimental animals, e.g., by measuring $LD_{50}$ (the dosage lethal to 50% of the population) and $ED_{50}$ (the dosage therapeutically effective in 50% of the population). The dose ratio of toxic to therapeutic effects is the therapeutic index and can be expressed as $LD_5/ED_{50}$. Medicaments that exhibit high therapeutic indexes are preferred.

An effective or therapeutically effective amount is the amount of the compound or pharmaceutical composition that will elicit the biological or medical response of a tissue, system, animal or human that is being sought by the researcher, veterinarian, physician or other clinicians. The dosage is preferably within a range of circulating concentrations that include $ED_{50}$ with minimal or no toxicity. The dosage may vary within this range depending on the dosage form employed and/or the administration route utilized. The correct preparation, administration route, dosage and time interval between administrations should be selected based on methods known in the art while taking the specificity of the individual condition into account.

The dosage and time interval may be adjusted individually to provide plasma levels of the active moiety sufficient to achieve the desired effect; i.e., the minimum effective concentration (MEC). The MEC for each compound will vary, but can be estimated, for example, from in vitro data and animal experiments. The dosage necessary to obtain MEC will depend on the individual characteristics and administration route. In the case of topical administration or selective uptake, the effective local concentration of drugs may not be related to the plasma concentration.

The amount of the medicament or composition administered may depend on various factors, including the gender, age and weight of a subject being treated, the severity of affliction, the administration route and the judgment of the prescribing physician.

When required, the composition disclosed herein may be presented in a package or with a dispensing device containing one or more unit dosage forms containing active ingredients. For example, the package or device may comprise a metal or plastic foil (such as a foaming package) or glass and a rubber stopper, such as in a vial. The package or dispensing device may be accompanied by instructions for administration. The composition comprising the compound disclosed herein formulated in a compatible pharmaceutical carrier may also be prepared, placed in an appropriate container, and labeled for treatment of a specified condition.

The present invention also provides use of the heterocyclic compound of formula I or the pharmaceutically acceptable salt, the hydrate, the solvate, the metabolite, the stereoisomer, the tautomer or the prodrug thereof or the pharmaceutical composition in the manufacture of a $P2X^3$ inhibitor.

The present invention also provides use of the heterocyclic compound of formula I or the pharmaceutically acceptable salt, the bydrate, the solvate, the metabolite, the stereoisomer, the tautomer or the prodrug thereof or the pharmaceutical composition in the manufacture of a medicament. The medicament is used for preventing, dealing with, treating or ameliorating diseases in an animal mediated at least in part by $P2X^3$ or associated with $P2X^3$ activity; alternatively, the medicament is used for treating pains, urinary tract diseases or respiratory diseases.

In some embodiments, the medicament may be used for treating urinary tract diseases in an animal (e.g., a human)

including, but not limited to: urinary incontinence, overactive bladder, dysuria, or cystitis.

In some embodiments, the medicament may be used for treating respiratory diseases in an animal (e.g., a human) including, but not limited to: respiratory disorders including idiopathic pulmonary fibrosis, chronic obstructive pulmonary disease, asthma, bronchospasm, or chronic cough.

In some embodiments, the medicament may be used for treating pains in an animal (e.g., a human) including, but not limited to: inflammatory pain, surgical pain, visceral pain, dental pain, premenstrual pain, central pain, pain caused by burns, migraine, cluster headache, or chronic pain.

The present invention also provides use of the heterocyclic compound of formula I or the pharmaceutically acceptable salt, the hydrate, the solvate, the metabolite, the stereoisomer, the tautomer or the prodrug thereof or the pharmaceutical composition in treating and preventing diseases.

The present invention also provides use of the heterocyclic compound of formula I or the pharmaceutically acceptable salt, the hydrate, the solvate, the metabolite, the stereoisomer, the tautomer or the prodrug thereof or the pharmaceutical composition in preventing, dealing with, treating or ameliorating diseases in an animal (e.g., a human) mediated at least in part by $P2X^3$ or associated with $P2X^3$ activity. The diseases include, but are not limited to: respiratory diseases, cough, chronic cough, idiopathic pulmonary fibrosis, chronic lung obstruction, asthma, pains, urinary incontinence, autoimmune diseases, overactive bladder, dysuria, inflammation, senile dementia, Parkinson's disease, sleep disorders, epilepsy, psychiatric diseases, arthritis, neurodegeneration, traumatic brain injury, myocardial infarction, rheumatoid arthritis, brain stroke, thrombosis, atherosclerosis, colon syndrome, inflammatory bowel diseases, digestive tract diseases, gastrointestinal dysfunction, respiratory failure, sexual dysfunction, cardiovascular system diseases, heart failure, hypertension, urinary incontinence, cystitis, arthritis, endometriosis, hematopathy, musculoskeletal and connective tissue development disorders, or systemic disorder diseases.

In some embodiments, the diseases include pains including, but not limited to: inflammatory pain, surgical pain, visceral pain, dental pain, premenstrual pain, central pain, pain caused by burns, migraine, or cluster headache.

In some embodiments, the diseases include urinary tract diseases.

In some embodiments, the diseases include respiratory diseases including, but not limited to: respiratory disorders including idiopathic pulmonary fibrosis, chronic obstructive pulmonary disease, asthma, bronchospasm, or chronic cough.

The present invention further provides a method for treating or preventing diseases, which comprises administering an effective dosage of the heterocyclic compound of formula I or the pharmaceutically acceptable salt, the hydrate, the solvate, the metabolite, the stereoisomer, the tautomer or the prodrug thereof or the pharmaceutical composition to a patient.

Definitions and General Terms

Unless otherwise stated, all technical and scientific terms used herein have the same meaning as commonly understood by those skilled in the art to which the present invention belongs. All patents and publications referred to herein are incorporated herein by reference in their entirety.

Unless otherwise stated, the following definitions used herein should be applied. For the purposes of the present invention, the chemical elements are in accordance with the Periodic Table of the Elements (CAS version), and the "Handbook of Chemistry and Physics", 75th edition, 1994. In addition, general principles of organic chemistry can be found in the descriptions of "Organic Chemistry", Thomas Sorrell, University Science Books, Sausalito: 1999, and "March's Advanced Organic Chemistry" by Michael B. Smith and Jerry March, John Wiley & Sons, New York: 2007, which are incorporated herein by reference in their entirety.

The term "include", "includes" or "including" is open-ended, i.e., including what is meant by the present invention, but not excluding other aspects.

The term "stereoisomer" refers to compounds having the same chemical structure, but different spatial arrangements of the atoms or groups. Stereoisomers include enantiomers, diastereomers, conformers (rotamers), geometric isomers (cis/trans), atropisomers, and the like.

The term "enantiomer" refers to two isomers of a compound that do mot overlap but are mirror images of each other.

The term "diastereoisomer" refers to stereoisomers having two or more chiral centers and whose molecules are not mirror images of each other. Diastereomers have different physical properties, such as melting points, boiling points, spectral properties, and reactivities. Mixtures of diastereomers can be separated by high resolution analytical procedures such as electrophoresis and chromatography (e.g., HPLC).

The stereochemical definitions and rules used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Any asymmetric atom (e.g., carbon, etc.) of the compound disclosed herein can exist in a racemate or enantiomer enriched form, e.g., the (R)-, (S)- or (R,S)-configuration. In certain embodiments, each asymmetric atom has at least 0% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Any resulting mixture of stereoisomers may be separated into pure or substantially pure geometric isomers, enantiomers and diastereomers depending on the differences in the physicochemical properties of the components, for example, by chromatography and/or fractional crystallization.

The term "tautomer" or "tautomeric form" refers to structural isomers having different energies that are interconvertible by a low energy barrier. If a tautomer is possible (e.g., in solution), the chemical equilibrium of the tautomer can be reached. For example, a proton tautomer, also known as a prototropic tautomer, includes the interconversion by proton transfer, such as keto-enol isomerization and imine-enamine isomerization. A valence tautomer includes the interconversion by recombination of some bonding electrons. A specific example of keto-enol tautomerization is the interconversion of the pentan-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4 (1H)-one tautomers. Unless otherwise indicated, all tautomeric forms of the compound disclosed herein are within the scope of the present invention.

In general, the term "substituted" means that one or more hydrogen atoms in a given structure are substituted with a particular substituent. Further, when the group is substituted with one or more substituents described above, the substituents are independent of each other, that is, the one or more substituents may be different from each other or the same. Unless otherwise indicated, the substitution of a substituent may occur at various substitutable positions of the substituted group. When more than one position in a given structure can be substituted with one or more substituents selected from particular groups, the substitution of the substituents may occur at various positions, identically or differently.

As will be understood by those skilled in the art,

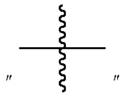

used in the structural formula describing groups herein means that the corresponding groups are connected with other fragments and groups in the compound through this site, according to conventions used in the art.

In each part of this specification, substituents for the disclosed compound are disclosed according to group types or ranges. It is specifically noted that each separate subcombination of the various members of these group types and ranges is encompassed by the present invention. For example, the term "$C_1$-$C_6$ alkyl" or "$C_{1-6}$ alkyl" may be linear or branched, and specifically refers to the independently disclosed methyl, ethyl, $C_3$ alkyl, $C_4$ alkyl, $C_5$ alkyl, and $C_6$ alkyl; "$C_{1-4}$ alkyl" specifically refers to the independently disclosed methyl, ethyl, $C_3$ alkyl (i.e., propyl, including n-propyl and isopropyl), and $C_4$ alkyl (i.e., butyl, including n-butyl, isobutyl, sec-butyl, and tert-butyl).

In each part of the present invention, connecting substituents are described. When a connecting group is clearly required to the structure, the Markush variables listed for that group should be considered as connecting groups. For example, if a connecting group is required to the structure and the "alkyl" or "aryl" is listed for the Markush group definition of the variable, it is to be understood that the "alkyl" or "aryl" represents a connected alkylene group or arylene group, respectively.

The term "alkyl" used herein refers to linear or branched saturated monovalent hydrocarbon radical containing 1-20 carbon atoms. Examples of alkyl groups include, but are not limited to, methyl, ethyl, n-propyl, isopropyl, n-butyl, isobutyl, sec-butyl, tert-butyl, n-pentyl, 2-pentyl, 3-pentyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-heptyl, n-octyl, and the like.

In some specific structures, when an alkyl group is explicitly indicated as a connecting group, the alkyl group represents a connected alkylene group, e.g., $C_1$-$C_6$ alkyl in the group "halogenated $C_1$-$C_6$ alkyl" should be considered as $C_1$-$C_6$ alkylene.

The term "alkylene" refers to a saturated divalent hydrocarbon radical resulting from the removal of two hydrogen atoms from a linear or branched saturated hydrocarbon radical. Examples of alkylene groups include methylene ($-CH_2-$), ethylidene (including $-CH_2CH_2-$ or $-CH(CH_3)-$), isopropylene (including $-CH(CH_3)CH_2-$ or $-C(CH_3)_2-$), and the like.

The term "alkenyl" refers to a linear or branched monovalent hydrocarbon radical containing 2-12 carbon atoms, wherein there is at least one unsaturated site, i.e., a carbon-carbon $sp^2$ double bond, which includes the positioning of "cis" and "tans", or the positioning of "E" and "Z". Examples of alkenyl groups include, but are not limited to, ethenyl ($-CH{=}CH_2$), allyl ($-CH_2CH{=}CH_2$), and the like.

The term "alkoxy" or "alkyl-O—" means that the alkyl group is connected with the rest of the molecule through an oxygen atom, wherein the alkyl group are described as herein. Examples of alkoxy groups include, but are not limited to, methoxy, ethoxy, 1-propoxy, 2-propoxy, 1-butoxy and the like.

The term "haloalkyl", "haloalkoxy" or "haloalkyl-O—" means that the alkyl or alkoxy group is substituted with one or more halogen atoms, examples of which include, but are not limited to, trifluoromethyl, trifluoromethoxy and the like.

The term "cycloalkyl" refers to a monovalent or polyvalent saturated monocyclic or bicyclic system containing 3-12 ring carbon atoms. Examples of cycloalkyl groups include, but are not limited to, cyclopropyl, cyclobutyl, cyclopentyl, cyclohexyl, cycloheptyl, cyclooctyl, and the like; wherein the $C_3$-$C_6$ cycloalkyl includes cyclopropyl, cyclobutyl, cyclopentyl and cyclohexyl.

The term "cycloalkenyl" refers to an unsaturated monocyclic carbocycloalkenyl group containing 3-6 ring carbon atoms ("$C_3$-$C_6$ cycloalkenyl"). Examples of cycloalkenyl groups include, but are not limited to, cyclopropenyl, cyclobutenyl, cyclopentenyl, cyclohexenyl or cyclohexadienyl, and the like.

The term "heterocycloalkyl" refers to a saturated monocyclic or bicyclic system containing 3-10 ring atoms, which can include fused, bridged, or spiro ring systems (e.g., bicyclic systems ("bicyclic heterocycloalkyl")); wherein the monocyclic or bicyclic system contains 3-9 ring carbon atoms and at least one ring heteroatom selected from nitrogen, sulfur, and oxygen ("$C_3$-$C_9$ heterocycloalkyl"). The bicyclic heterocycloalkyl system may include one or more heteroatoms in one or two rings, and is saturated. Unless otherwise stated, heterocycloalkyl may be carbon- or nitrogen-based, and the $-CH_2$-group may be optionally substituted with $-C({=}O)-$. The sulfur atom of the ring may be optionally oxidized to an S-oxide. The nitrogen atom of the ring may be optionally oxidized to an N-oxide. In some embodiments, heterocycloalkyl is $C_3$-$C_5$ heterocycloalkyl, meaning that heterocycloalkyl contains 3-5 ring carbon atoms and at least one ring heteroatom selected from O, S and N. Examples of heterocycloalkyl include, but are not limited to: oxiranyl, thietanyl, pyrrolidinyl, pyrazolinyl, pyrazolidinyl, imidazolinyl, imidazolidinyl, oxazolidinyl, tetrahydrofuranyl, piperidinyl, morpholinyl, tetrahydropyrimidinyl, oxazinanyl, thiomorpholinyl, piperazinyl, and the like. Examples of the substitution of the $-CH_2$-group with $-C({=}O)-$ in the heterocycloalkyl include, but are not limited to, 2-oxopyrrolidinyl, 2-piperidonyl, 3-morpholinonyl, 3-thiomorpholinonyl, and oxotetrahydropyrimidinyl, and the like, or isomers and stereoisomers thereof. In some embodiments, exemplary $C_3$-$C_9$ heterocycloalkyl groups include, but are not limited to, the $C_3$-$C_5$ heterocycloalkyl groups described above in conjunction with azepanyl, oxepanyl, thiepanyl, diazepanyl, azocanyl, oxecanyl, thiocanyl, quinuclidinyl, octahydroindolyl, octahydroisoindolyl, decahydroquinolinyl, decahydroisoquinolinyl, or isomers and stereoisomers thereof.

The term "heterocycloalkenyl" refers to a monocyclic or bicyclic system containing partially unsaturated alkenyl groups, which contains 3-9 ring carbon atoms and at least one ring atom selected from nitrogen, sulfur, and oxygen atoms ("$C_3$-$C_9$ heterocycloalkenyl"); wherein the heterocycloalkenyl is non-aromatic and does not contain any aromatic ring. Unless otherwise stated, heterocycloalkenyl may be carbon- or nitrogen-based, and the —$CH_2$-group may be optionally substituted with —C(═O)—. The sulfur atom of the ring may be optionally oxidized to an S-oxide. The nitrogen atom of the ring may be optionally oxidized to an N-oxide. In some embodiments, heterocycloalkenyl is preferably $C_3$-$C_5$ heterocycloalkenyl; examples of $C_3$-$C_5$ heterocycloalkenyl include, but are not limited to, dihydrofuranyl, dihydrothienyl, dihydropyrrolyl, dioxolyl, dihydroimidazolyl, dihydropyrazolyl, dihydrothiazolyl, dihydroisothiazolyl, dihydrooxadiazolyl, dihydrothiadiazolyl, dihydrotriazolyl, dihydrotetrazolyl, tetrahydropyridinyl, 3,4-dihydro-2H-pyran, pyranyl, thiopyranyl, dihydropyridinyl, dihydropyrazinyl, dihydropyrimidinyl, oxazinyl, and dihydrotetrazolyl, or isomers and stereoisomers thereof. In some embodiments, exemplary $C_3$-$C_9$ beterocycloalkenyl groups include, but are not limited to, the $C_3$-$C_5$ heterocycloalkenyl groups described above in conjunction with octahydroisoquinolinyl, 3H-indolyl, dihydroisoquinolinyl, dihydroquinolyl or 4H-quinolizinyl, or isomers and stereoisomers thereof.

The term "halogen" or "halo" refers to fluorine (F), chlorine (CI), bromine (Br), or iodine (I).

The term "aryl" refers to monocyclic, bicyclic and tricyclic carbon ring systems containing 6-14 ring atoms, or 6-10 ring atoms. Examples of aryl groups may include phenyl, naphthyl and anthryl. Unless otherwise stated, the group "$C_6$-$C_{10}$ aryl" refers to an aryl group containing 6-10 ring carbon atoms.

The term "heteroaryl" refers to monocyclic, bicyclic and tricyclic systems containing 5-6 ring atoms, or 5-10 ring atoms, or 5-12 ring atoms, wherein at least one ring contains one or more ring heteroatoms selected from nitrogen, oxygen, and sulfur. Unless otherwise stated, the heteroaryl group may be connected to the rest of the molecule (e.g., the host structure in the formula) via any reasonable site (which may be C in CH, or N in NH). Examples of heteroaryl groups include, but are not limited to, furanyl, imidazolyl, isoxazolyl, oxazolyl, pyrrolyl, pyrazolyl, pyridinyl, pyrimidinyl, pyridazinyl, pyrazinyl, thienyl, thiazolyl, and the like; and include, but are not limited to, the following bicyclic rings: benzimidazolyl, benzofuranyl, benzothienyl, indolyl, oxoindolyl, imidazopyridinyl, pyrazolopyridinyl, pyrazolopyrimidinyl, quinolinyl, isoquinolinyl, quinazolinyl, and the like.

In addition, it should be noted that, unless otherwise explicitly indicated, the description of " . . . is independently" used herein is to be understood broadly and means that each individual group described is independent from the others and may be independently the same or different specific groups. In more detail, the description of " . . . is independently" can mean that the specific options expressed by the same symbols in different groups do not affect each other; it can also mean that the specific options expressed by the same symbols in the same group do not affect each other.

The term "pharmaceutically acceptable" refers to molecular entities and compositions that are physiologically tolerable and do not typically produce an allergic or similar untoward reaction, such as gastrointestinal distress and dizziness, when administered to a human.

The term "carrier" refers to a diluent, adjuvant, excipient, or matrix with which the compound is administered. Such pharmaceutical carriers can be sterile liquid, such as water and oil, including those derived from petroleum, animals, plants or synthesis, such as peanut oil, soybean oil, mineral oil and sesame oil. Water or aqueous saline solutions and aqueous dextrose and glycerol solutions are preferably used as carriers, particularly injectable solutions. Suitable pharmaceutical carriers are described in "Remington's Pharmaceutical Sciences" by E. W. Martin.

The term "prodrug" used herein represents a compound that is converted in vivo to a compound of formula I. Such conversion is effected by hydrolysis of the prodrug in the blood or by enzymatic conversion of the prodrug into the parent structure in the blood or tissue. The prodrugs disclosed herein can be esters, and in the prior art, the esters that can be used as prodrugs include phenyl esters, aliphatic ($C_{1-24}$) esters, acyloxymethyl esters, carbonates, carbamates and amino acid esters. For example, a compound disclosed herein containing hydroxyl can be acylated to give a prodrug. Other prodrugs include phosphate esters, and those phosphate esters are obtained by phosphorylating via the hydroxyl on the parent structure. For a complete discussion of prodrugs, reference can be made to the following: T. Higuchiand V. Stella, Pro-drugs as Novel Delivery Systems, Vol. 14 of the *A.C.S. Symposium Series*; Edward B. Roche, ed., Bioreversible Carriersin Drug Design, American Pharmaceutical Association and Pergamon Press, 1987*, J. Rautioetal*; Prodrugs: Design and Clinical Applications, *Nature Review Drug Discovery,* 2008, 7, 255-270; and S. J. Heckeretal., Prodrugs of Phosphates and Phosphonates, *Journal of Medicinal Chemistry,* 2008, 51, 2328-2345.

The term "metabolite" used herein refers to a product obtained by the metabolism of a particular compound or salt thereof in vivo. Metabolites of a compound can be identified by techniques well known in the art, and their activities can be characterized by assays as described herein. Such products may be obtained by the oxidation, reduction, hydrolysis, amidation, deamidation, esterification, defatting, enzymatic cleavage, and the like of the administered compound. Accordingly, the present invention includes metabolites of the compound, including metabolites produced by contacting the compound disclosed herein with a mammal for a sufficient period of time.

The term "pharmaceutically acceptable salt" used herein refers to both organic and inorganic salts of the compound disclosed herein. Pharmaceutically acceptable salts are well known in the art. For example, S. M. Berge et al. describe pharmaceutically acceptable salts in detail in J. Pharmaceutical Sciences, 1977, 66:1-19. Pharmaceutically acceptable salts formed by non-toxic acids include, but are not limited to, inorganic acid salts such as hydrochloride, hydrobromide, phosphate, sulfate, perchlorate; organic acid salts such as acetate, oxalate, maleate, tartrate, citrate, succinate, malonate; or salts obtained by other methods described in the literature, such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentylpropionate, digluconate, dodecylsulfate, ethanesulfonate, formate, fumarate, glucoheptonate, glycerophosphate, gluconate, hemisulfate, heptanoate, hexanoate, hydriodate, 2-hydroxyethanesulfonate, lactobionate, lactate, laurate, lauryl sulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts formed by suitable bases include salts of alkali metal, alkaline earth metal, ammonium and $N^+(C_{1-4}\ alkyl)_4$. The present invention also contemplates quaternary ammonium salts formed by any compound containing an N group. Water-soluble or oil-soluble or dispersible products can be obtained by quaternization. Alkali metal or alkaline earth metal that can form salts include sodium, lithium, potassium, calcium, magnesium, and the like. Pharmaceutically acceptable salts further include suitable and non-toxic ammonium, quaternary ammonium salts and amine cations formed by counterions, such as halides, hydroxides, carboxylates, sulfates, phosphates, nitrates, $C_{1-8}$ sulfonates and aromatic sulfonates.

"Solvate" disclosed herein refers to an association compound of one or more solvent molecules with the compound disclosed herein. Solvents that form the solvate include, but are not limited to, water, isopropanol, ethanol, methanol, dimethyl sulfoxide, ethyl acetate, acetic acid and aminoethanol. The term "hydrate" refers to an association compound of solvent molecules with water.

"Ester" disclosed herein refers to an ester that is hydrolyzed in vivo and formed by a compound containing hydroxyl or carboxyl. Such esters are, for example, pharmaceutically acceptable esters that are hydrolyzed in human or animal to produce parent alcohol or acid. The compound of formula I disclosed herein contains carboxyl, which can form an ester that is hydrolyzed in vivo with appropriate groups including, but not limited to, alkyl, arylalkyl and the like.

"Nitrogen oxide" disclosed herein refers to an N-oxide formed by oxidizing one or more nitrogen atoms when the compound contains several amine functional groups. Specific examples of N-oxides are N-oxides of tertiary amines or N-oxides of nitrogen-containing heterocyclic nitrogen atoms. The corresponding amines can be treated with an oxidizing agent such as hydrogen peroxide or peracid (e.g., peroxycarboxylic acid) to form N-oxides (see Advanced Organic Chemistry, Wiley Interscience, 4th edition, Jerry March, pages). In particular, N-oxides may be prepared by the method of L. W. Deady (Syn. Comm. 1977, 7, 509-514) in which an amine compound is reacted with m-chloroperoxybenzoic acid (MCPBA), for example, in an inert solvent such as dichloromethane.

In some embodiments, the term "treat", "treating" or "treatment" used herein refers to ameliorating diseases or disorders (i.e., slowing or arresting or reducing the progression of the diseases or at least one clinical symptom thereof). In other embodiments, "treat", "treating" or "treatment" refers to mitigating or improving at least one physical parameter, including physical parameters that may not be perceived by a patient. In other embodiments, "treat", "treating" or "treatment" refers to modulating a disease or disorder, either physically (e.g., stabilizing a perceptible symptom) or physiologically (e.g., stabilizing a physical parameter), or both. In other embodiments, "treat", "treating" or "treatment" refers to preventing or delaying the onset, occurrence, or deterioration of a disease or disorder.

Unless otherwise indicated, abbreviations for any of protecting groups, amino acids and other compounds used herein are provided based on their commonly used and accepted abbreviations, or by referring to IUPAC-IUB Commission on Biochemical Nomenclature (see Biochem. 1972, 11: 942-944).

The biological activity of the compound disclosed herein can be assessed by using any conventionally known method. Appropriate detection methods are well known in the art. For example, the compound disclosed herein can be tested for $P2X^3$ inhibitory activity, pharmacokinetic activity, and/or liver microsomal stability, etc., by an appropriate conventional method. The detection methods provided by the present invention are presented as examples only and do not limit the present invention. The compound disclosed herein is active in at least one of the detection methods provided by the present invention.

In this specification, terms such as "some embodiments," "examples," or "a preferred embodiment" mean that a particular feature, structure, material or characteristic described in reference to the embodiment or example is included in at least one embodiment or example of the present invention. In this specification, the schematic descriptions of the terms used above do not necessarily refer to the same embodiment or example. Furthermore, the particular feature, structure, material or characteristic described may be combined in any one or more embodiments or examples in an appropriate manner. Moreover, various embodiments or examples and features of various embodiments or examples described in this specification can be combined by one skilled in the art to the extent that they do not contradict each other.

The above preferred conditions may be combined arbitrarily to obtain preferred embodiments of the present invention without departing from the general knowledge in the art.

The reagents and starting materials used in the present invention are commercially available.

The benefits of the present invention: the heterocyclic compound features high antagonistic activity against $P2X^3$, good selectivity, low toxicity, good metabolic stability and small influence on taste, showing a good prospect of drug development.

DETAILED DESCRIPTION

Figure 1:
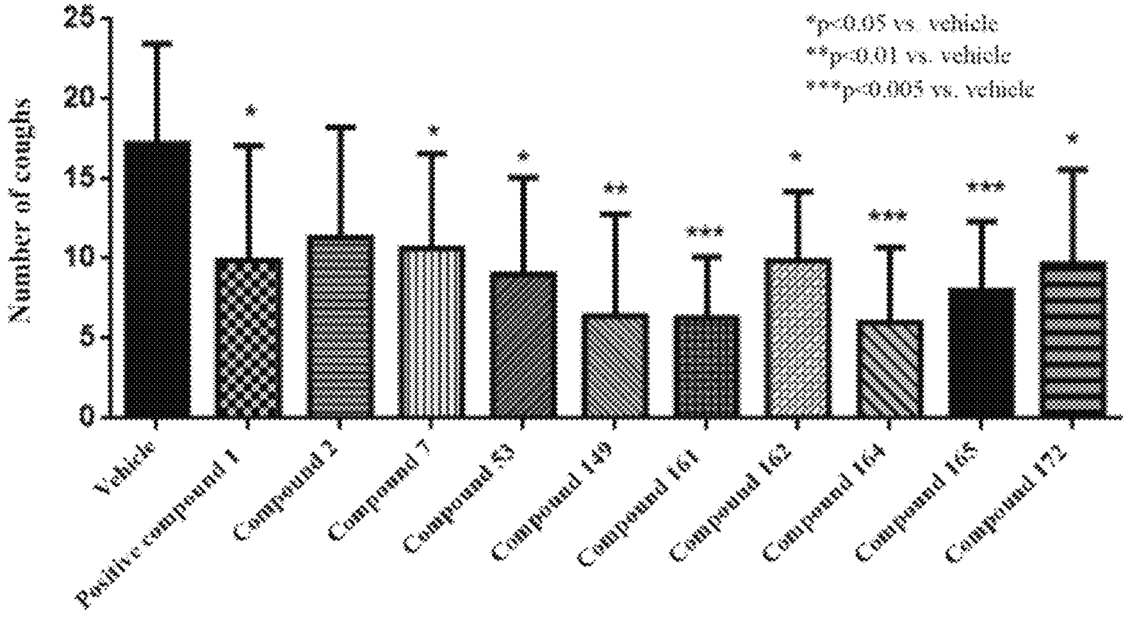
FIG. 1 shows the number of citric acid-induced coughs for the inventive compounds vs. vehicle.
Figure 2:
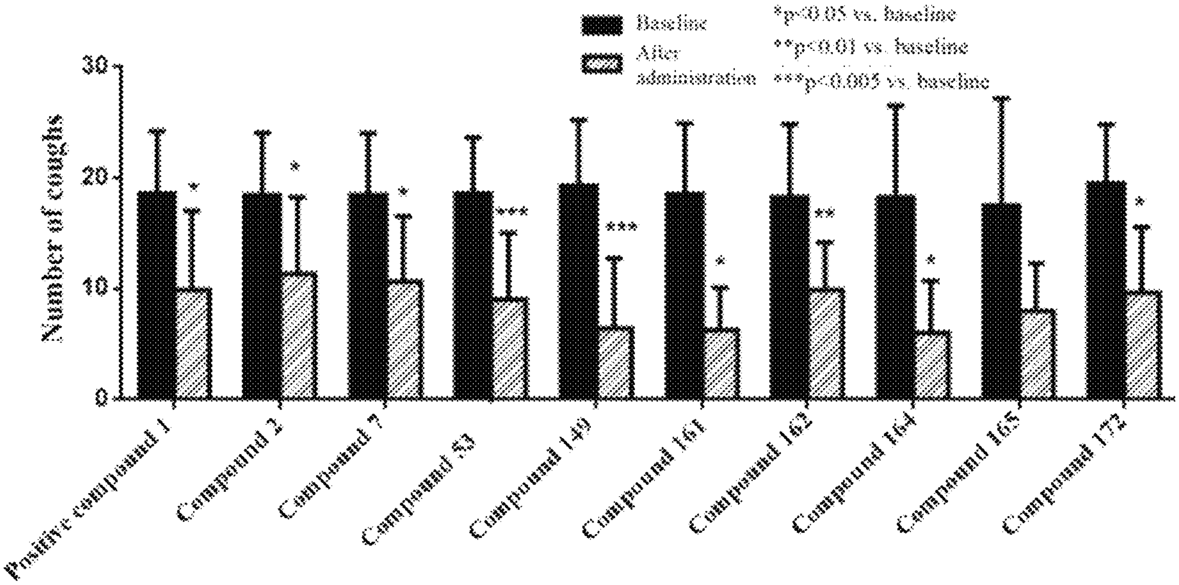
FIG. 2 shows the latency of citric acid-induced coughs for the inventive compounds vs. vehicle.
Figure 3:
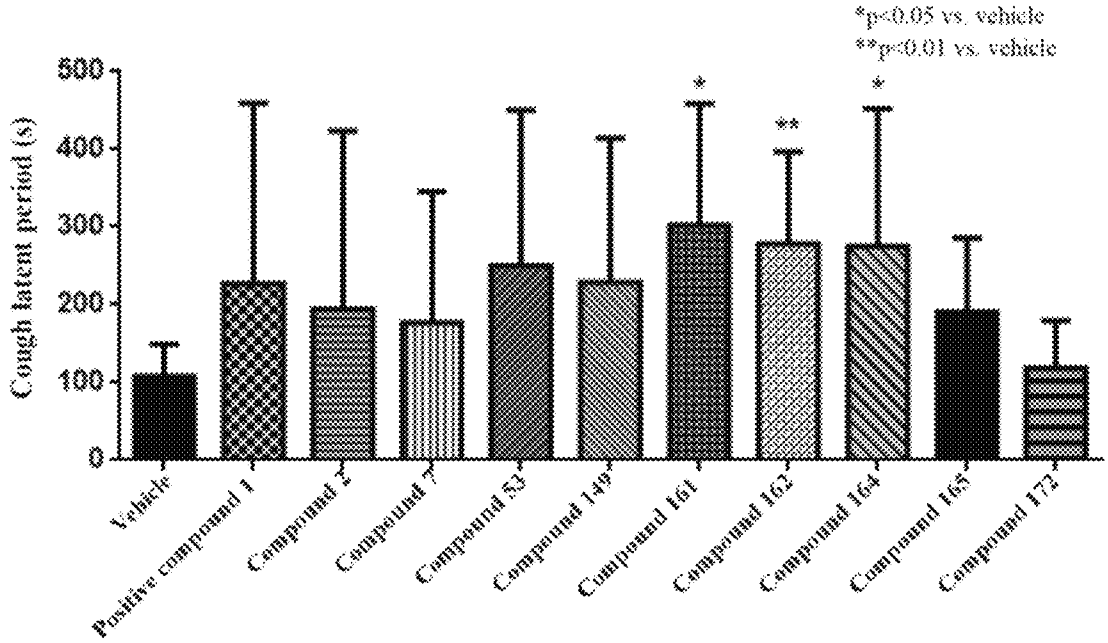
FIG. 3 shows the number of citric acid-induced coughs for the inventive compounds vs. their baseline.
Figure 4:
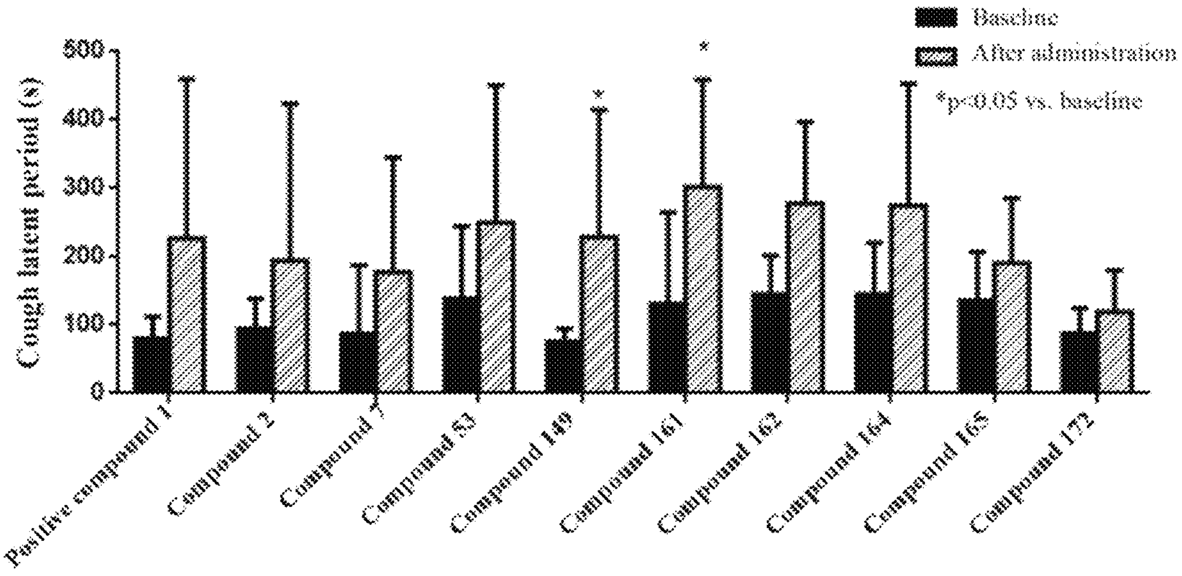
FIG. 4 shows the number of coughs, cough suppression rate and cough latency obtained in vivo for a portion of the inventive compounds.

The present invention is further illustrated by the following examples, which are not intended to limit the invention thereto. Experimental procedures without specifying specific conditions in the following examples are conducted in accordance with conventional procedures and conditions, or in accordance with commercial instructions.

The following abbreviations are used throughout the present invention:

TEMPO (2,2,6,6-tetramethyl-1-piperidone), LDA (lithium diisopropylamide), DMF (N,N-dimethylformamide), DMA (N,N-dimethylacetamide), DCM (dichloromethane), DME (dimethoxyethane), PE (petroleum ether), EA (ethyl acetate), DIPEA (N,N-diisopropylethylamine), THF (tetrahydrofuran), Ac (acetyl), MeOH (methanol), Boc (tert-butoxycarbonyl), B2Pin2 (bis(pinacolato)diboron), rt (room temperature), HATU (2-(7-azabenzotriazol-1-yl)-N, N,N',N'-tetramethyluronium hexafluorophosphate), reflux (refluxing conditions), eq (equivalent), Rf (retardation factor), g (gram), mg (milligram), mol (mole), mmol (millimole), h (hour), min (minute), mL (milliliter), μL (microliter).

Overnight refers to 8-15 h, for example 12 h; the room temperature refers to 10-30° C.; solvent ratio such as PE/EA refers to the volume ratio.

Unless otherwise indicated, all temperatures in the examples described below are given in Celsius degrees. Unless otherwise indicated, reagents are purchased from commercial suppliers such as Aldrich Chemical Company, Arco Chemical Company and Alfa Chemical Company, and used without further purification. General reagents are purchased from Shantou Xilong Chemical Plant Co. Ltd., Guangdong Guanghua Chemical Reagent Factory, Guangzhou Chemical Reagent Factory, Tianjin Haoyuyu Chemical Co., Ltd., Qingdao Tenglong Chemical Reagent Co., Ltd., and Qingdao Haiyang Chemical Co., Ltd.

Anhydrous tetrahydrofuran, dioxane, toluene and diethyl ether are obtained by refluxing and drying with metal sodium. Anhydrous dichloromethane and chloroform are obtained by refluxing and drying with calcium hydride. Ethyl acetate, petroleum ether, n-hexane, N,N-dimethylacetamide and N,N-dimethylformamide are pre-dried over anhydrous sodium sulfate.

The following reactions are generally conducted under a positive pressure of nitrogen or argon or by placing a drying tube over an anhydrous solvent (unless otherwise indicated), the reaction flask is stoppered with a suitable rubber stopper and the substrate is driven in by a syringe. Each piece of glassware is dried.

Chromatographic column is a silica gel column. Silica gel (300-400 mesh) is purchased from Qingdao Haiyang Chemical Co., Ltd. NMR spectral data are measured on a Bruker Avance 400 NMR spectrometer or a Bruker Avance IIIHD 600 NMR spectrometer using CDCl, DMSO-d6, CD3OD or Acetone-d6 as solvents (reported in ppm) and TMS (0 ppm) or chloroform (7.25 ppm) as reference standards. When multiple peaks are present, the following abbreviations will be used: s (singlet), d (doublet), t (triplet), m (multiplet), br (broadened), dd (doublet of doublets), dt (doublet of triplets), ddd (doublet of doublet of doublets), ddt (doublet of doublet of triplets), dddd (doublet of doublet of doublet of doublets). Coupling constants are expressed in hertz (Hz).

Low-Resolution Mass Spectrometry (MS) data are determined on an Agilent 6320 series LC-MS spectrometer equipped with a G1312A binary pump and an aG1316ATCC (column temperature maintained at 30° C.), with a G1329A autosampler and G1315BDAD detector applied to the analysis and an ESI source applied to the LC-MS spectrometer.

The above two spectrometers are equipped with an Agilent ZorbaxSB-$C_{18}$ column (2.1×30 mm, 5 μm). The injection volume is determined by the sample concentration; the flow rate is 0.6 mL/min; peak values of HPLC are recorded at UV-Vis wavelength of 210 nm and 254 nm.

Example 1

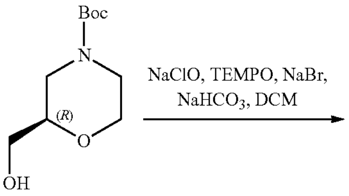

1-1

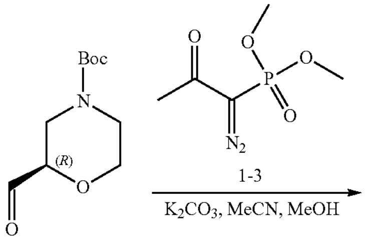

1-2

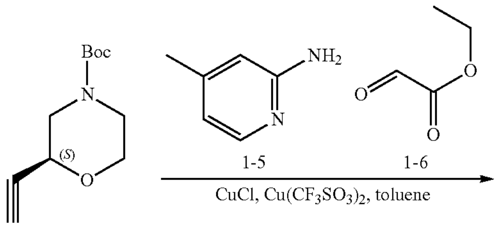

1-4

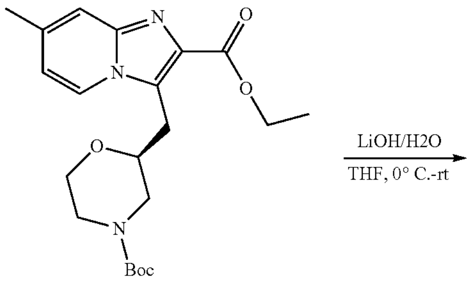

1-7

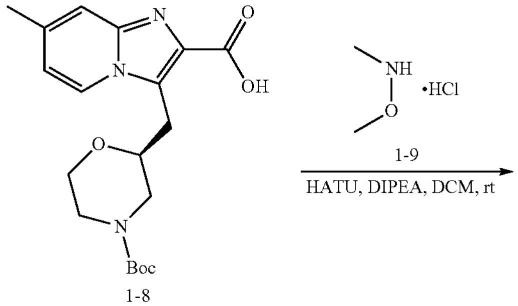

1-8

-continued

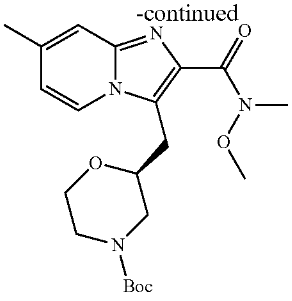

THF 1-10

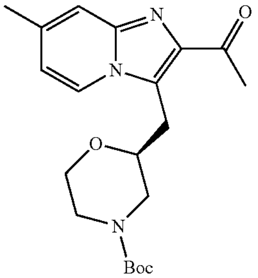

HCl/EtOH (g)
DCM, 0° C.-rt 1-11

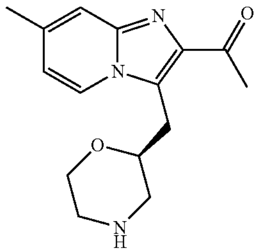

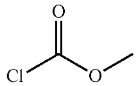

1-13
DIPEA, DCM, 0° C.

1-12

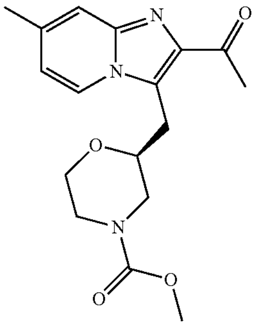

NBS
THF 1-14

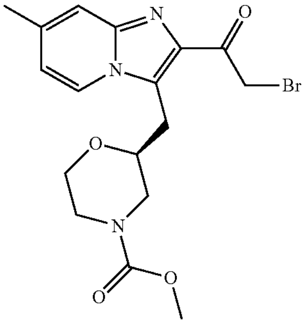

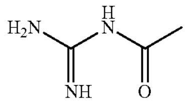

1-16

1-15

-continued

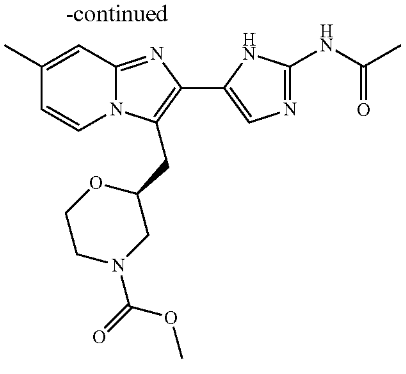

1

Step (1) Preparation of tert-butyl (R)-2-formyl-morpholine-4-carboxylate 1-2

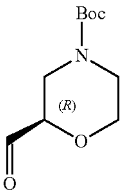

A mixture of compound 1-1 (10 g, 460 mmol), TEMPO (0.073 g, 0.44 mmol), aqueous sodium bromide solution (0.5 M, 10 mL, 41 mmol) and dichloromethane (100 mL) was cooled to 0-5° C. To a sodium hypochlorite solution (1.5 M, 34 mL, 58 mmol) was added sodium bicarbonate (2.3 g, 23 mmol), and the solution was adjusted to pH 9.3, and added dropwise to the reaction system over 30 min. After the completion of the dropwise addition, the reaction system was stirred for 0.5 h, heated to 20° C., and added with water (50 mL). The aqueous phase was extracted with dichloromethane multiple times. The organic phases were combined, dried over anhydrous sodium sulfate, filtered and concentrated under reduced pressure. The residue was purified by column chromatography to give compound 1-2 (6 g, 60% yield) in the form of an orange-yellow oily liquid. LC-MS: $[M+H]^+=216.4$.

Step (2) Preparation of tert-butyl (S)-2-ethynyl-morpholine-4-carboxylate 1-4

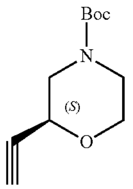

Dimethyl (1-diazo-2-oxopropyl)phosphonate (6 g, 31.3 mmol) was dissolved in a mixture of acetonitrile and methanol (5:1), and $K_2CO_3$ (59 mmol) was added. The reaction system was stirred at 20° C. for 15 min, and added dropwise with a dissolved solution of compound 1-2 (6 g, 28 mmol) in a mixed solvent (10 mL) of acetonitrile and methanol (5:1) slowly. After the completion of the dropwise addition, the reaction system was incubated at this temperature overnight. The suspension was filtered, and the filtrate was concentrated under reduced pressure to give an oil, which was then added to water (about 100 mL) to precipitate a solid. The mixture was filtered, and the filter cake was washed with water. The residue was purified by silica gel column chromatography to give compound 1-4 (3.4 g, 56.7% yield) in the form of a solid. LC-MS: $[M+H]^+$=212.1.

Step (3)

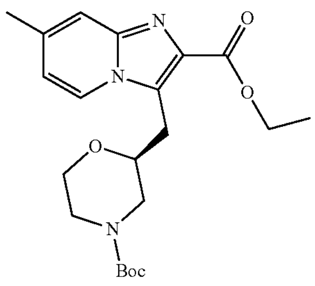

1-7

To a solution of compound 1-4 (300 mg, 1.4 mmol), compound 1-5 (145 mg, 1.4 mmol) and compound 1-6 (145 mg, 1.4 mmol) in toluene (3 mL) were added CuCl (42 mg, 0.4 mmol) and $Cu(CF_3SO_3)_2$ (154 mg, 0.4 mmol) at room temperature. Under nitrogen atmosphere, the reaction system was heated to 85° C., added with DME (0.1 mL), and reacted at this temperature for 5 h. After the reaction was completed, the reaction system was added with water (15 mL) to quench the reaction, extracted with dichloromethane (10 mL×3), washed with saturated sodium chloride solution (10 mL×2), dried over anhydrous sodium sulfate, and concentrated under reduced pressure. The residue was purified by silica gel column chromatography (PE/EA, 1/1) to give intermediate 1-7 (500 mg) in the form of a yellow oily liquid.

LC-MS: $[M+H]^+$=404.2.

Step (4)

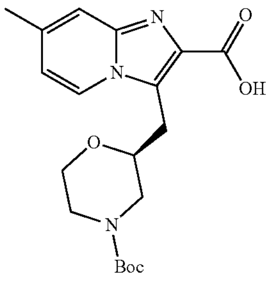

1-8

To a solution of intermediate 1-7 (3 g, 7.44 mmol) in THF (20 mL) was added LiOH (936 mg, 22.3 mmol) at 0° C. The reaction system was stirred at room temperature for 2 h. After the reaction was completed, the reaction system was adjusted to pH 6 with HCl (1 M) at 0° C., extracted with DCM (10 mL×3), washed with saturated sodium chloride solution (10 mL×2), dried over anhydrous sodium sulfate, and concentrated under reduced pressure to give intermediate 1-8 (2 g) in the form of a yellow oily liquid.

LC-MS: $[M+H]^+$=376.1.

Step (5)

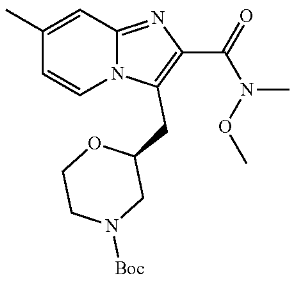

1-10

Intermediate 1-8 (375 mg) was dissolved in DCM (10 mL), and HATU (2 mmol) and DIPEA (4 mmol) were added. The reaction system was stirred at room temperature for 15 min, added with N,O-dimethylhydroxylamine hydrochloride (1.2 mmol), and stirred at room temperature for another 6-8 h. After the reaction was completed as monitored by TLC, the residue was purified by column chromatography to give intermediate 1-10 (275 mg, 65.8% yield), LC-MS: $[M+H]^+$=419.3.

Step (6)

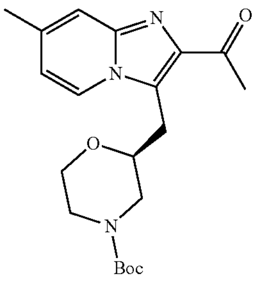

1-11

Intermediate 1-10 (418 mg, 1 mmol) was dissolved in anhydrous THF (10 mL), and methyl Grignard reagent was added dropwise at 0° C. After the completion of the dropwise addition, the reaction system was stirred overnight. After the reaction was completed, the reaction was quenched, and the reaction system was extracted with ethyl acetate, washed, dried, and purified by column chromatography to give intermediate 1-11 (236 mg, 63.3% yield). LC-MS: $[M+H]^+$=374.1.

Step (7)

1-12

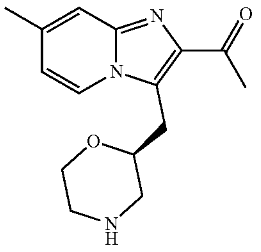

Intermediate 1-11 (373 mg) was dissolved in DCM (5 mL), and a solution of HCl in EtOH (1 N, 1.5 mL) was added dropwise at 0° C. After the completion of the dropwise addition, the reaction system was stirred for 2 h, and poured into $NaHCO_3$ solution to adjust the pH to 8. The aqueous phase was extracted with DCM. The organic phase was washed with NaCl solution, dried over anhydrous magnesium sulfate and filtered, and the filtrate was concentrated under reduced pressure. The residue was purified by column chromatography to give intermediate 1-12 (160 mg, 58.6% yield). LC-MS: $[M+H]^+$=274.6.

Step (8)

1-14

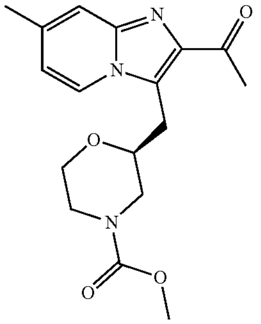

Intermediate 1-12 (273 mg, 1 mmol) and DIPEA (258 mg, 2 mmol) were dissolved in DCM (5 mL), and methyl chloroformate (compound 1-13) (282 mg, 3 mmol) was added. The reaction system was stirred at 0° C. for 3 h, poured into $H_2O$ and extracted with DCM. The organic phase was washed with NaCl solution, dried over anhydrous magnesium sulfate and filtered, and the filtrate was concentrated under reduced pressure. The residue was purified by column chromatography to give intermediate 1-14 (300 mg, 91% yield) in the form of a yellow oil. LC-MS: $[M+H]^+$=332.2.

Step (9)

1-15

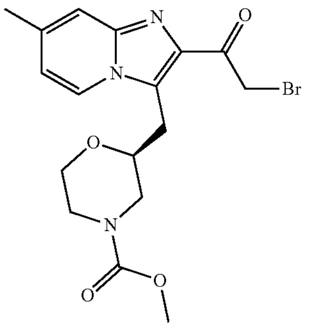

Intermediate 1-14 (331 mg, 1 mmol) was dissolved in tetrahydrofuran (5 mL) and water (2 mL), and N-bromosuccinimide (214 mg, 1.2 mmol) was added. The reaction system was reacted at room temperature for 1 h under nitrogen atmosphere. Then the reaction system was concentrated to half volume, diluted with water (10 mL), and extracted with ethyl acetate (10 mL×3). The ethyl acetate phases were combined, dried over anhydrous sodium sulfate, and concentrated to give intermediate 1-15 (300 mg, 73.3% yield) in the form of a solid. LC-MS: $[M+H]^+$=410.2.

Step (10)

1

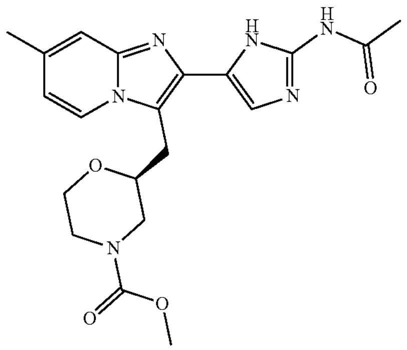

Intermediate 1-15 (0.82 g, 2 mmol) was dissolved in absolute ethanol (10 mL), and 1-acetylguanidine (242 mg, 2.4 mmol) and triethylamine (404 mg, 4 mmol) were added. The reaction system was heated to reflux. After the reaction was completed as detected by TLC, the reaction system was concentrated under reduced pressure, extracted with EA, and washed. The residue was purified by column chromatography to give compound 1 (531 mg, 64.4% yield).

LC-MS: $[M+H]^+$=413.2.

Example 2

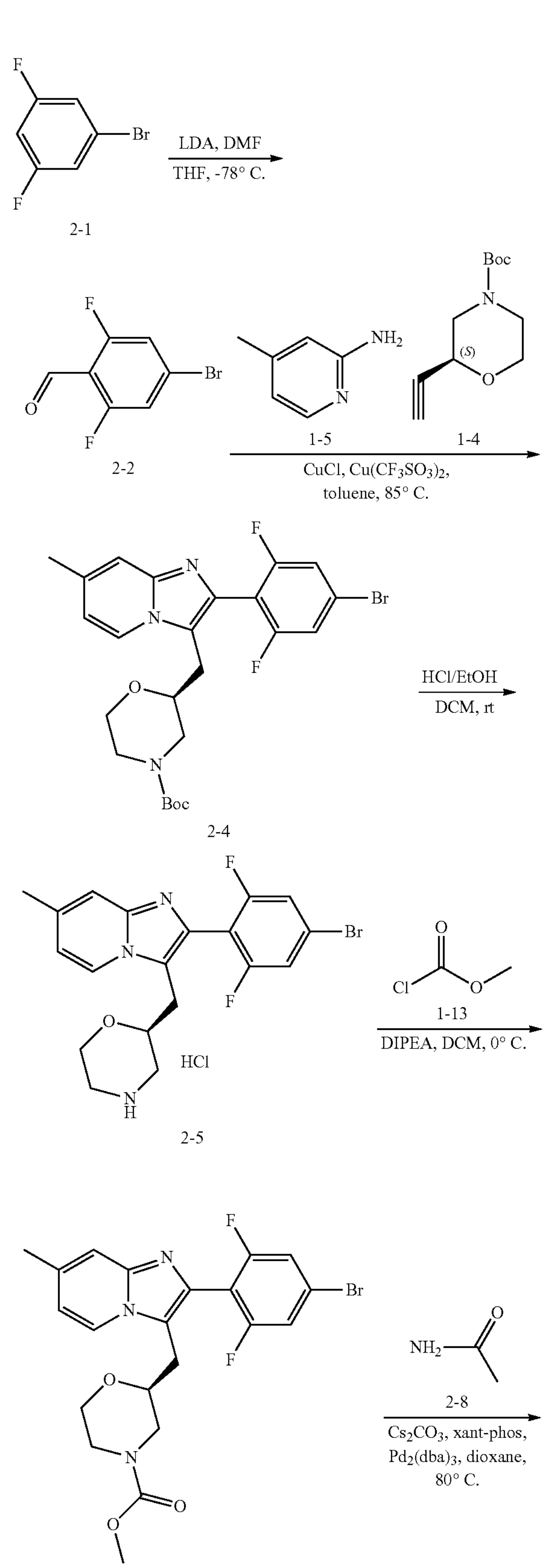

2-1, 2-2, 1-5, 1-4, 2-4, 2-5, 1-13, 2-8, 2-7

-continued

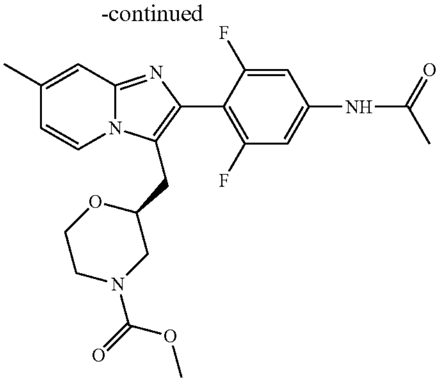

2

Step (1) Preparation of 2,6-difluoro-4-bromobenzaldehyde 2-2

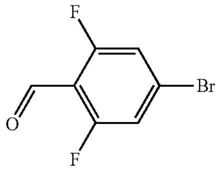

3,5-difluorobromobenzene (10 g, 51.8 mmol) was dissolved in anhydrous THF (80 mL), and LDA (31 mL, 62.5 mmol) was added dropwise at −78° C. under $N_2$ atmosphere. After the completion of the dropwise addition, the reaction system was stirred for 1 h, added with DMF (4 mL, 51.9 mmol), and stirred for another 30 min. The reaction system was poured into $NH_4Cl$ solution and extracted with ethyl acetate. The organic phase was washed with NaCl solution, dried over anhydrous magnesium sulfate and filtered, and the filtrate was concentrated under reduced pressure. The crude product was purified by column chromatography to give compound 2-2 (8 g, 70% yield) in the form of a yellow solid.

Step (2) Preparation of tert-butyl (S)-2-((2-(2,6-difluoro-4-bromophenyl)-7-methylimidazo[1,2-a]pyridin-3-yl)-methyl)morpholine-4-carboxylate 2-4

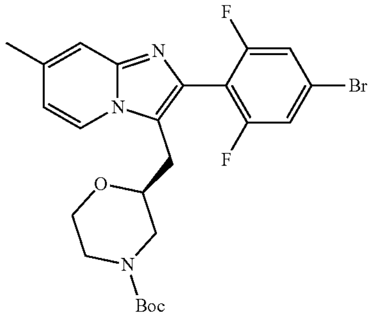

Compound 2-2 (200 mg, 0.9 mmol), 2-amino-4-methylpyridine (100 mg, 0.9 mmol), compound 1-4 (191 mg, 0.9 mmol), CuCl (27 mg, 0.27 mmol), and $Cu(CF_3SO_3)_2$ (100 mg, 0.27 mmol) were dissolved in toluene (3 mL). Under $N_2$ atmosphere, the reaction system was heated to 85° C., added with DMA (0.05 mL), and stirred for 5 h. Then the reaction system was cooled to room temperature, and incubated overnight. The resulting reaction system was poured into water (5 mL) and extracted with DCM (5 mL×3). The organic phase was washed with saturated NaCl solution, dried over $MgSO_4$ filtered, and concentrated under reduced pressure. The crude product was purified by column chromatography (PE:EA=1:1) to give intermediate 2-4 (100 mg, 21% yield) in the form of a yellow oil. LC-MS: $[M+H]^+$=522.3.

Step (3) Preparation of (S)-2-((2-(2,6-difluoro-4-bromophenyl)-7-methylimidazo[1,2-a]pyridin~3-yl)-methyl)morpholine 2-5

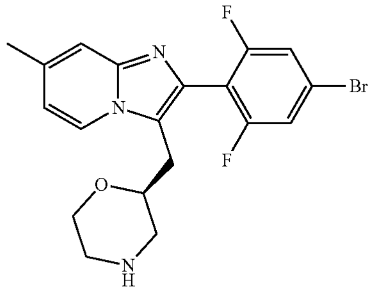

Intermediate 2-4 (100 mg) was dissolved in DCM (1 mL), and a solution of HCl in EtOH (0.5 mL) was added dropwise at 0° C. After the completion of the dropwise addition, the reaction system was stirred for 2 h, and poured into $NaHCO_3$ solution to adjust the pH to 8. The aqueous phase was extracted with DCM. The organic phase was washed with NaCl solution, dried over anhydrous magnesium sulfate and filtered, and the filtrate was concentrated under reduced pressure. The residue was purified by column chromatography to give intermediate 2-5 (60 mg, 75% yield) in the form of a yellow oil. LC-MS: $[M+H]^+$ 422.6.

Step (4) Preparation of methyl (S)-2-((2-(2,6-difluoro-4-bromophenyl)-7-methylimidazo[1,2-a]pyridin-3-yl)-methyl)morpholine-4-carboxylate 2-7

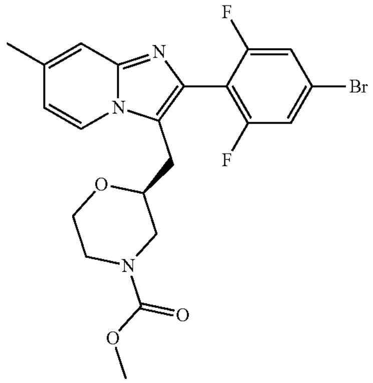

Intermediate 2-5 (320 mg, 0.76 mmol) and DIPEA (86 mg, 0.91 mmol) were dissolved in DCM (5 mL), and methyl chloroformate (compound 2-6) (86 mg, 0.91 mmol) was added. The reaction system was stirred at 0° C. for 3 h, poured into $H_2O$ and extracted with DCM. The organic phase was washed with NaCl solution, dried over anhydrous magnesium sulfate and filtered, and the filtrate was concentrated under reduced pressure. The residue was purified by column chromatography to give intermediate 2-7 (330 mg, 91% yield) in the form of a yellow oil. LC-MS: $[M+H]^+$=480.6.

Step (5) Preparation of methyl (S)-2-((2-(2,6-difluoro-4-acetamidophenyl)-7-methylimidazo[1,2-a]pyridin-3-yl)-methyl)morpholine-4-carboxylate

2

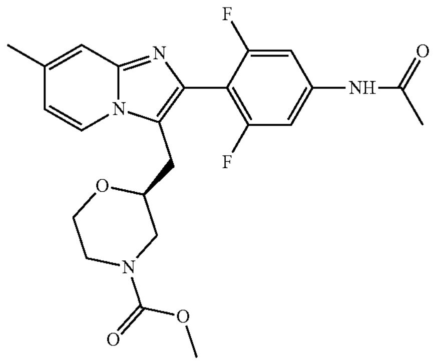

To a solution of intermediate 2-7 (50 mg, 0.10 mmol), acetamide (compound 2-8) (10 mg, 0.17 mmol) in 1,4-dioxane (2 mL) were added $CS_2CO_3$ (51 mg, 0.16 mmol), Xantphos (1.2 mg, 0.002 mmol) and Pd> (dba) 3 (2 mg, 0.002 mmol) at room temperature. Under nitrogen atmosphere, the reaction system was heated to 80° C. and reacted overnight. After the reaction was completed, the reaction system was cooled to room temperature, filtered, and concentrated under reduced pressure. The residue was purified by preparative HPLC to give compound 2 (18 mg, 38% yield) in the form of a white solid.

LC-MS: $[M+H]^+$=459.7. $^1$H NMR (400 MHZ, MeOD): δ 8.41 (d, J=7.1 Hz, 1H), 7.43 (d, J=9.7 Hz, 2H), 7.35 (s, 1H), 6.88 (dd, J=7.1, 1.5 Hz, 1H), 3.80 (d, J=12.3 Hz, 3H), 3.67 (s, 3H), 3.59 (m, 1H), 3.43-3.34 (m, 1H), 3.15-3.01 (m, 2H), 2.91 (m, 1H), 2.63 (m, 1H), 2.47 (s, 3H), 2.19 (s, 3H).

Example 3

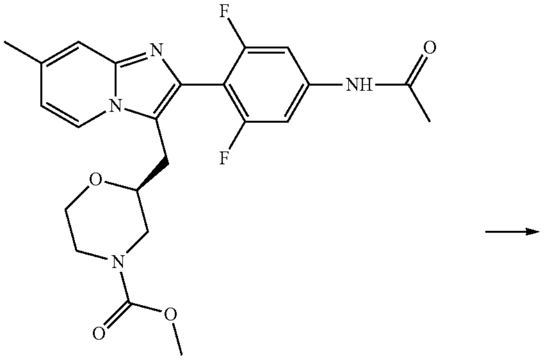

2

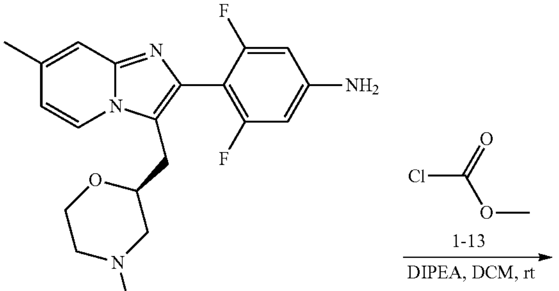

3-1

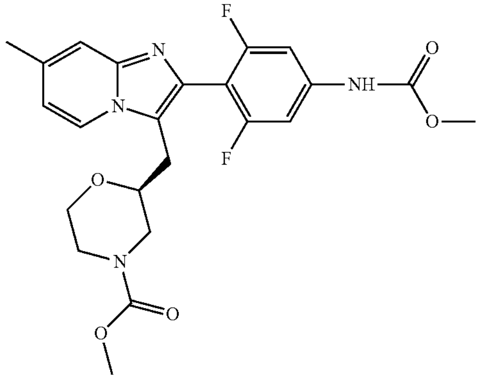

3

Step (1) Preparation of methyl (S)-2-((2-(2,6-difluoro-4-aminophenyl)-7-methylimidazo[1,2-a]pyridin-3-yl)-methyl)morpholine-4-carboxylate 3-1

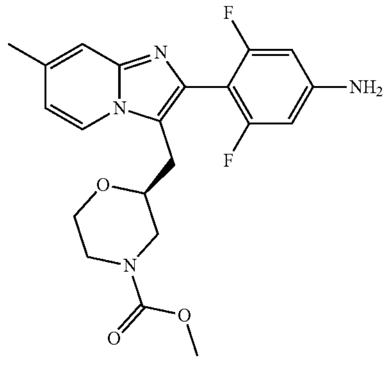

To a solution of compound 2 (145 mg, 0.32 mmol) in ethanol (3 mL) was added hydrochloric acid (1.5 mL) at room temperature. The reaction system was reacted at 100° C. for 1 h. After the reaction was completed, the reaction system was cooled to room temperature, added with $NaHCO_3$ solution (1 N) to quench the reaction, extracted with DCM (5 mL×3), washed with saturated sodium chloride solution (5 mL×2), dried over anhydrous sodium sulfate, and concentrated under reduced pressure to give a yellow oily liquid (90 mg). LC-MS: $[M+H]^+$=417.3.

Step (2) Preparation of methyl (S)-2-((2-(2,6-difluoro-4-(methoxycarbonylamino)phenyl)-7-methylimidazo[1,2-a]pyridin-3-yl)-methyl)morpholine-4-carboxylate

3

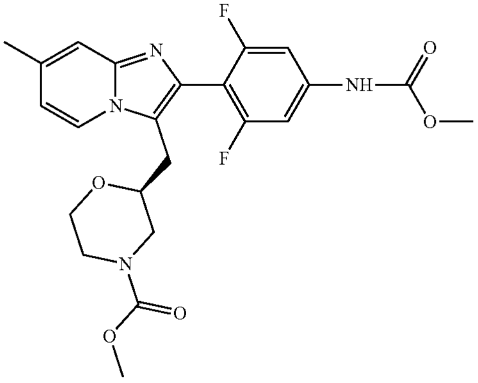

To a solution of intermediate 3-1 (70 mg, 0.17 mmol) and DIPEA (65 mg, 0.5 mmol) in DCM (5 mL) was added methyl chloroformate (20 mg, 0.21 mmol) at 0° C. The reaction system was reacted at this temperature for 3 h. After the reaction was completed, the reaction system was added with water (3 mL), extracted with DCM (3 mL×3), dried over anhydrous sodium sulfate, and concentrated under reduced pressure. The residue was purified by silica gel column chromatography (DCM/MeOH, 40/1) to give compound 3 (20 mg, 25% yield) in the form of a white solid.

LC-MS: $[M+H]^+$=475.6. $^1H$ NMR (400 MHZ, MeOD): δ 8.42 (d, J=7.1 Hz, 1H), 7.35 (s, 1H), 7.30 (d, J=9.9 Hz, 2H), 6.90 (d, J=7.1 Hz, 1H), 3.88-3.81 (m, 2H), 3.80 (s, 3H), 3.79-3.76 (m, 1H), 3.67 (s, 3H), 3.63-3.55 (m, 1H), 3.38 (t, J=10.8 Hz, 1H), 3.15-3.00 (m, 2H), 2.90 (dt, J=20.6, 7.7 Hz, 1H), 2.64 (t, J=11.5 Hz, 1H), 2.47 (s, 3H).

Example 4

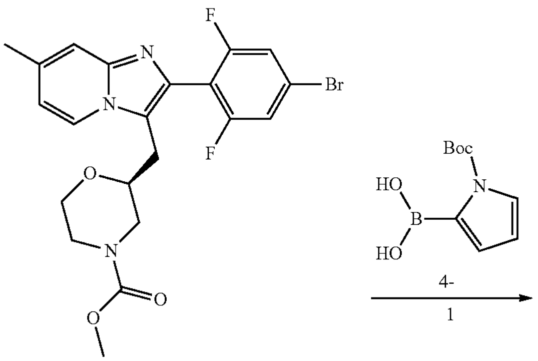

2-7

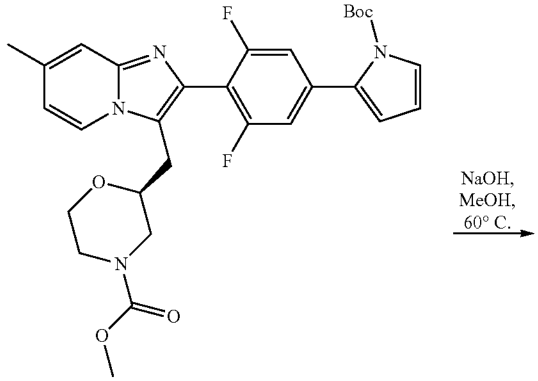

4-2

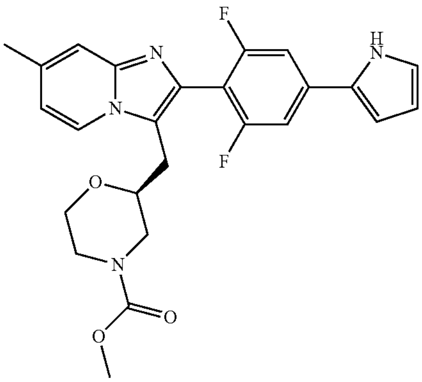

4

Step (1) Preparation of methyl (S)-2-((2-(4-(1-tert-butoxycarbonylpyrrol-2-yl)-2,6-difluorophenyl)-7-methylimidazo[1,2-a]pyridin-3-yl)-methyl)morpholine-4-carboxylate 4-2

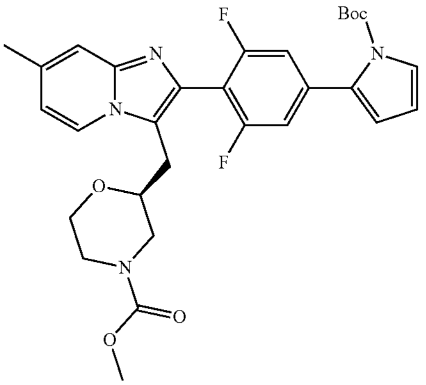

To a solution of intermediate 2-7 (50 mg, 0.1 mmol), N-tert-butoxycarbonylpyrrolidine-2-boronic acid (compound 4-1) (26 mg, 0.12 mmol) and $K_2CO_3$ (36 mg, 0.26 mmol) in $H_2O$ (0.3 mL) and 1,4-dioxane (2 mL) was added $Pd(dppf)Cl_2$ (2 mg, 0.016 mmol) at room temperature. Under nitrogen atmosphere, the mixture was heated to 80° C. and reacted for 3 h. After the reaction was completed, the reaction mixture was cooled to room temperature, filtered, added with water (3 mL), extracted with ethyl acetate (5 mL×3), washed with saturated sodium chloride solution (3 mL×2), dried over anhydrous sodium sulfate, and concentrated under reduced pressure. The residue was purified by silica gel column chromatography (PE/EA, 5/1) to give a yellow oily liquid (50 mg, 93% yield). LC-MS: $[M+H]^+$=567.4.

Step (2) Preparation of methyl (S)-2-((2-(2,6-difluoro-4-(1H-pyrrol-2-yl)phenyl)-7-methylimidazo[1,2-a]pyridin-3-yl)methyl)morpholine-4-carboxylate

4

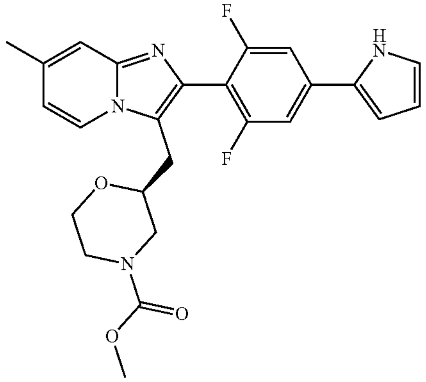

To a solution of intermediate 4-2 (20 mg, 0.035 mmol) in methanol (1 mL) was added 1 M NaOH (4 mg, 0.1 mmol). The reaction mixture was reacted at 60° C. for 2 h. After the reaction was completed, the reaction mixture was added with water (1 mL), extracted with DCM (1 mL×3), washed with saturated sodium chloride solution (1 mL×2), dried over anhydrous sodium sulfate, and concentrated under reduced pressure. The residue was purified by preparative HPLC to give compound 4 (17.3 mg, 92.9% yield) in the form of a white solid.

LC-MS: $[M+H]^+$=467.6. $^1H$ NMR (400 MHZ, MeOD): δ 8.41 (d, J=7.1 Hz, 1H), 7.34 (d, J=9.2 Hz, 3H), 6.91 (dd, J=2.6, 1.4 Hz, 1H), 6.88 (dd, J=7.1, 1.5 Hz, 1H), 6.69 (dd, J=3.6, 1.4 Hz, 1H), 6.24 (dd, J=3.5, 2.7 Hz, 1H), 3.81 (d, J=12.4 Hz, 3H), 3.66 (s, 3H), 3.63-3.56 (m, 1H), 3.39 (t, J=10.6 Hz, 1H), 3.17-3.04 (m, 2H), 2.96-2.85 (m, 1H), 2.71-2.59 (m, 1H), 2.47 (s, 3H).

Example 5

Preparation of methyl (S)-2-((2-(2,6-difluoro-4-(1H-imidazol-1-yl)phenyl)-7-methylimidazo[1,2-a]pyridin-3-yl)methyl)morpholine-4-carboxylate

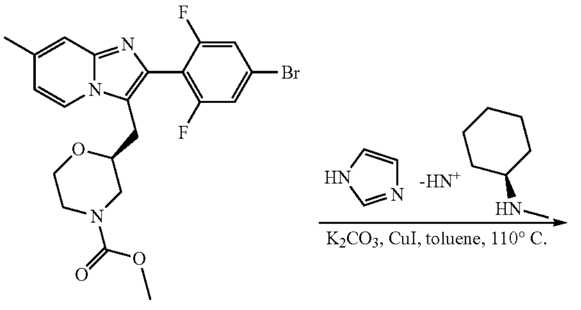

2-7

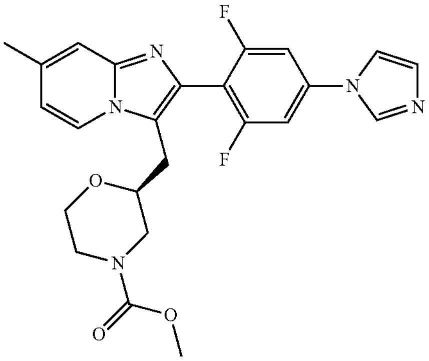

5

Intermediate 2-7 (50 mg, 0.1 mmol) was dissolved in toluene (2 mL), and imidazole (21 mg, 0.31 mmol), (1R, 2R)—N1,N2-dimethylcyclohexyl-1,2-diamine (1.5 mg, 0.01 mmol) and $K_2CO_3$ (15 mg, 0.11 mmol) was added. Under $N_2$ atmosphere, the reaction system was added with CuI (2 mg, 0.01 mmol), and heated to 110° C. overnight. Then the reaction system was filtered, and the filtrate was purified to give compound 5 (8.4 mg, 17.2% yield) in the form of a yellow solid.

LC-MS: $[M+H]^+$=468.6. $^1H$NMR (400 MHZ, MeOD): δ 8.44 (d, 1H), 8.42 (s, 1H), 7.78 (s, 1H), 7.56 (d, 2H), 7.36 (s, 1H), 7.22 (s, 1H), 6.91 (dd, 1H), 3.82 (m, 3H), 3.67 (s, 3H), 3.60 (m, 1H), 3.38 (m, 1H), 3.12 (m, 2H), 2.90 (m, 2H), 2.64 (s, 3H).

Example 6

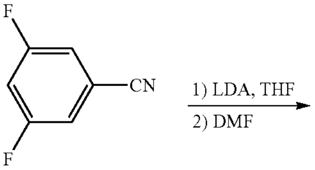

6-1

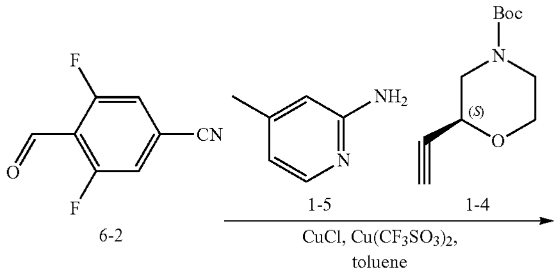

6-2

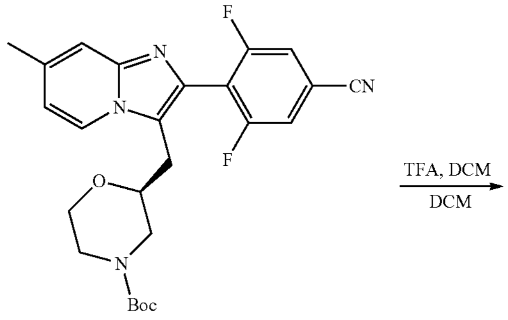

6-3

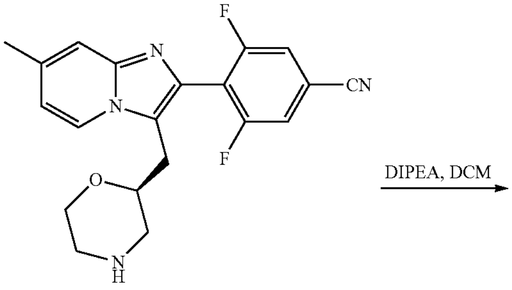

6-4

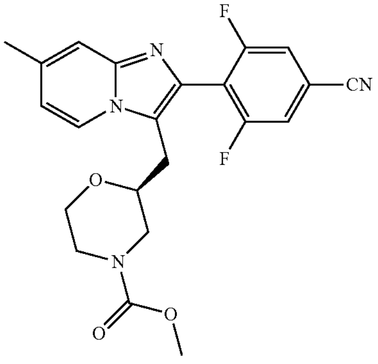

6

Step (1) Preparation of 2,6-difluoro-4-cyanobenzaldehyde 6-2

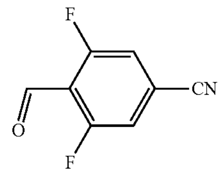

To a solution of compound 6-1 (2 g, 14 mmol) in THF (20 mL) was added LDA (8.6 mL, 17.2 mmol) dropwise at −78° C. under nitrogen atmosphere. Then the reaction system was stirred at −78° C. for 1 h under nitrogen atmosphere, and added dropwise with DMF (1.26 g, 17.2 mmol) over 30 min. After the reaction was completed, the reaction system was added with AcOH (10%) to quench the reaction, extracted with ethyl acetate (50 mL×3), washed with saturated sodium chloride solution (50 mL×2), dried over anhydrous sodium sulfate, and concentrated under reduced pressure. The residue was purified by silica gel column chromatography (PE/EA, 8/1) to give compound 6-2 (1.5 g, 60% yield) in the form of a yellow solid.

Step (2) Preparation of tert-butyl (S)-2-((2-(4-cyano-2,6-difluorophenyl)-7-methylimidazo[1,2-a]pyridin-3-yl)methyl)morpholine-4-carboxylate 6-3

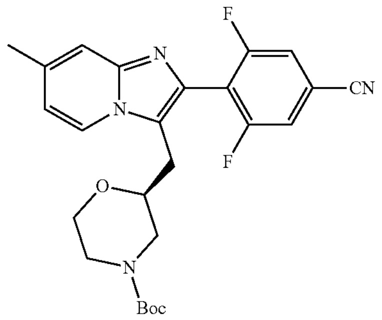

To a solution of compound 6-2 (500 mg, 3 mmol), compound 1-5 (330 mg, 3 mmol) and compound 1-4 (630 mg, 3 mmol) in toluene (15 mL) were added CuCl (90 mg, 0.9 mmol) and $Cu(CF_3SO_3)_2$ (330 mg, 0.9 mmol) at room temperature. Under nitrogen atmosphere, the reaction system was heated to 85° C., added with DME (0.1 mL), and reacted at this temperature for 5 h. After the reaction was completed, the reaction system was added with water (15 mL) to quench the reaction, extracted with dichloromethane (10 mL×3), washed with saturated sodium chloride solution (10 mL×2), dried over anhydrous sodium sulfate, and concentrated under reduced pressure. The residue was purified by silica gel column chromatography (PE/EA, 1/1) to give intermediate 6-3 (450 mg, 32% yield) in the form of a yellow oily liquid.

Step (3) Preparation of (S)-3,5-difluoro-4-(7-methyl-3-(morpholin-2-ylmethyl)imidazo[1,2-a]pyridin-2-yl)benzonitrile 6-4

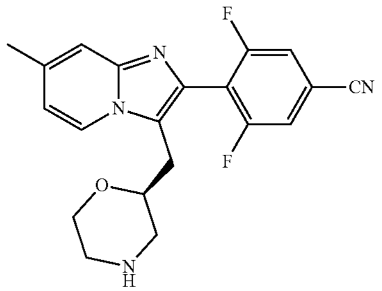

To a solution of intermediate 6-3 (400 mg, 1.1 mmol) in DCM (6 mL) was added TFA (2 mL) dropwise at 0° C. The reaction system was reacted at room temperature for 1 h. After the reaction was completed, the reaction system was added with saturated $NaHCO_3$ to quench the reaction at 0° C., extracted with dichloromethane (3 mL×3), washed with saturated sodium chloride solution (3 mL×2), dried over anhydrous sodium sulfate, and concentrated under reduced pressure. The residue was purified by silica gel column chromatography (DCM/MeOH, 40/1) to give intermediate 6-4 (280 mg, 79% yield) in the form of a brown solid.

Step (4) Preparation of methyl (S)-2-((2-(4-cyano-2,6-difluorophenyl)-7-methylimidazo[1,2-a]pyridin-3-yl)methyl)morpholine-4-carboxylate

6

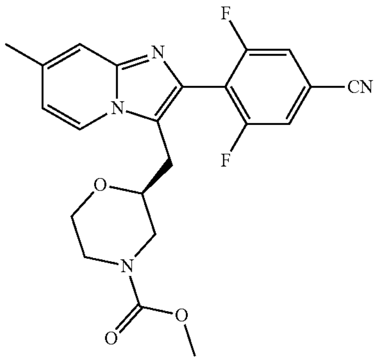

To a solution of intermediate 6-4 (230 mg, 0.6 mmol) and DIPEA (230 mg, 1.8 mmol) in DCM (2 mL) was added methyl chloroformate (66 mg, 0.72 mmol) at 0° C. The reaction system was reacted for 1 h. After the reaction was completed, the reaction system was added with water (3 mL), extracted with dichloromethane (3 mL×3), washed with saturated sodium chloride solution (3 mL×2), dried over anhydrous sodium sulfate, and concentrated under reduced pressure. The residue was purified by silica gel column chromatography (PE/EA, 2/1) to give compound 6 (230 mg, 83% yield) in the form of a yellow solid.

LC-MS: $[M+H]^+$=427.7. $^1H$ NMR (400 MHZ, $CDCl_3$): δ 8.19 (d, J=7.1 Hz, 1H), 7.41 (s, 1H), 7.37 (d, J=6.2 Hz, 2H), 6.72 (d, J=7.0 Hz, 1H), 4.03-3.74 (m, 3H), 3.71 (s, 3H), 3.61-3.51 (m, 1H), 3.38 (t, J=11.8 Hz, 1H), 3.09-2.82 (m, 3H), 2.68-2.53 (m, 1H), 2.44 (s, 3H).

Example 7

Preparation of methyl (S)-2-((2-(2,6-difluoro-4-(1H-imidazol-2-yl)phenyl)-7-methylimidazo[1,2-a]pyridin-3-yl)methyl)morpholine-4-carboxylate

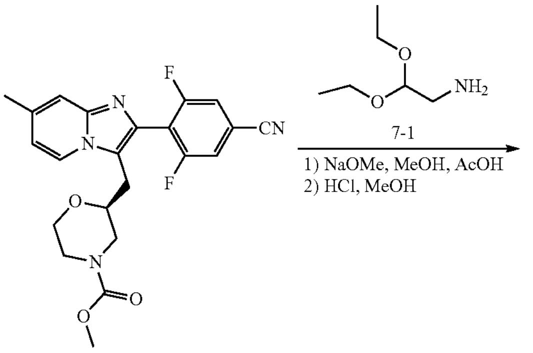

6

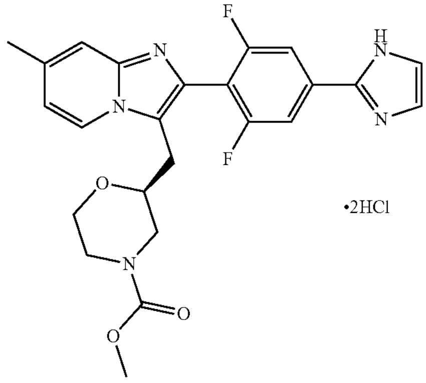

7

A solution of compound 6 (120 mg, 0.3 mmol) and NaOMe (3 mg, 0.05 mmol) in MeOH (2 mL) was stirred at room temperature for 15 min, and aminoacetaldehyde diethyl acetal (49 mg, 0.4 mmol) and AcOH (34 mg, 0.6 mmol) were added. The reaction system was reacted at 50° C. for 1 h, then cooled to room temperature, added with HCl (0.5 mL) and MeOH (2 mL), and reacted at 65° C. for 18 h. After the reaction was completed, the reaction system was concentrated under reduced pressure. The crude product was purified by preparative HPLC, added with 1 M hydrochloric acid, and lyophilized to give compound 7 (32 mg, 24% yield) in the form of a white solid.

LC-MS: $[M+H]^+$=468.1. $^1H$ NMR (400 MHZ, $CDCl_3$): δ 16.00 (s, 2H), 15.16 (s, 1H), 8.68 (s, 3H), 8.00 (s, 1H), 7.49 (s, 2H), 7.22 (s, 1H), 3.94 (s, 3H), 3.70 (m, 3H), 3.61 (m, 1H), 3.34 (m, 1H), 2.97 (m, 4H), 2.62 (s, 3H).

Example 8

Preparation of methyl (S)-2-((2-(2,6-difluoro-4-(N-methylcarbamimidoyl)phenyl)-7-methylimidazo[1,2-a]pyridin-3-yl)methyl)morpholine-4-carboxylate

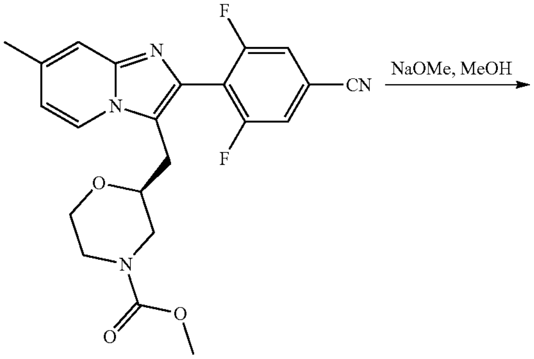

6

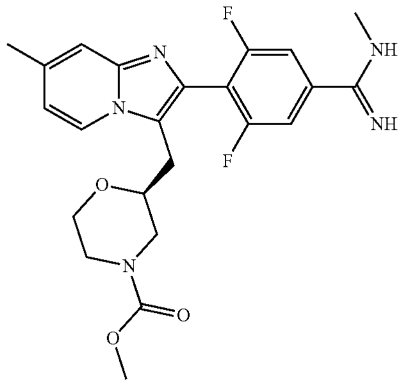

8

A solution of compound 6 (50 mg, 0.12 mmol) and NaOMe (2 mg, 0.03 mmol) in MeOH (2 mL) was stirred at room temperature for 30 min, then a solution of $MeNH_2$/THF (2 M, 0.1 mL, 0.15 mmol) and AcOH (14 mg, 0.24 mmol) were added at 50° C. The reaction system was reacted for 1 h. After the reaction was completed, the reaction system was concentrated under reduced pressure. The residue was purified by silica gel column chromatography to give compound 8 (17 mg, 31% yield) in the form of a white solid.

LC-MS: $[M+H]^+$=458.1. $^1H$ NMR (400 MHZ, $CDCl_3$): δ 8.54 (s, 1H), 8.25 (s, 1H), 7.57 (d, J=6.8 Hz, 2H), 7.39 (s, 1H), 6.74 (d, J=6.8 Hz, 1H), 3.82 (m, 3H), 3.68 (s, 3H), 3.56 (m, 1H), 3.36 (m, 1H), 3.22 (s, 2H), 3.07-2.75 (m, 4H), 2.61 (m, 1H), 2.45 (s, 3H).

Example 9

Preparation of methyl (S)-2-((2-(2,6-difluoro-4-(1-methyl-1H-imidazol-2-yl)phenyl)-7-methylimidazo[1,2-a]pyridin-3-yl)methyl)morpholine-4-carboxylate

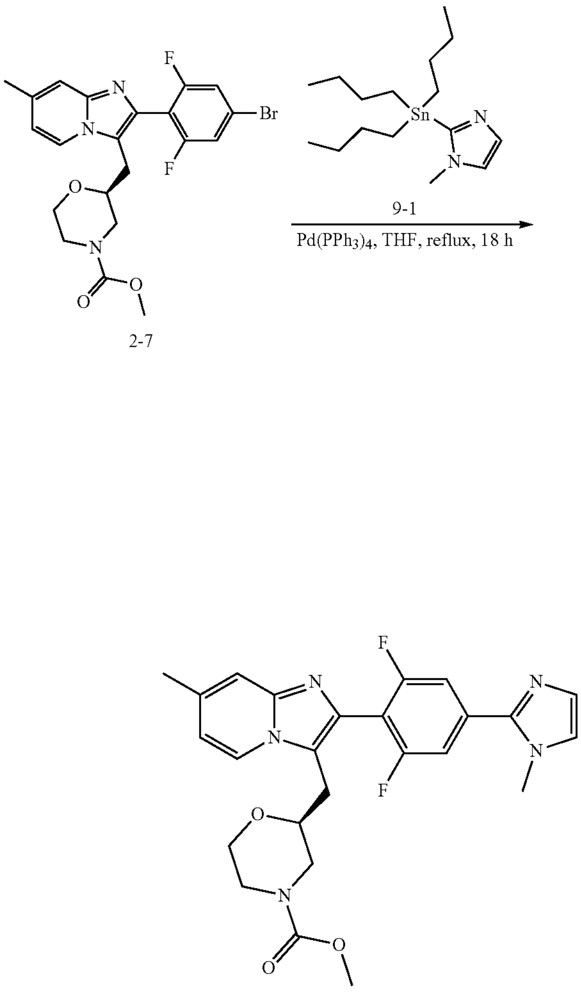

2-7

9-1

9

Intermediate 2-7 (50 mg, 0.1 mmol) was dissolved in toluene (3 mL), and the reaction system was added with $Pd(PPh_3)_4$ (12 mg, 0.01 mmol) and 1-methyl-2-(tri-n-butylstannyl)imidazole (78 mg, 0.2 mmol). Under $N_2$ atmosphere, the reaction system was heated to 85° C. and incubated at this temperature for 5 h. Then the reaction system was filtered, and the filtrate was concentrated under reduced pressure. The crude product was purified by column chromatography to give compound 9 (24 mg, 49% yield) in the form of a white solid.

LC-MS: $[M+H]^+$=482.2. $^1$HNMR (400 MHZ, MeOD): δ 8.69 (s, 1H), 8.55 (d, 1H), 7.99 (s, 1H), 7.55 (s, 1H), 7.22 (d, 2H), 7.15 (d, 1H), 4.06 (s, 1H), 3.96 (s, 3H), 3.86 (m, 2H), 3.73 (s, 3H), 3.68 (s, 1H), 3.43 (m, 1H), 3.09 (d, 2H), 2.99 (m, 1H), 2.73 (m, 1H), 2.61 (s, 3H).

Example 10

Preparation of methyl (S)-2-((2-(2,6-difluoro-4-(oxazol-2-yl)phenyl)-7-methylimidazo[1,2-a]pyridin-3-yl)methyl)morpholine-4-carboxylate

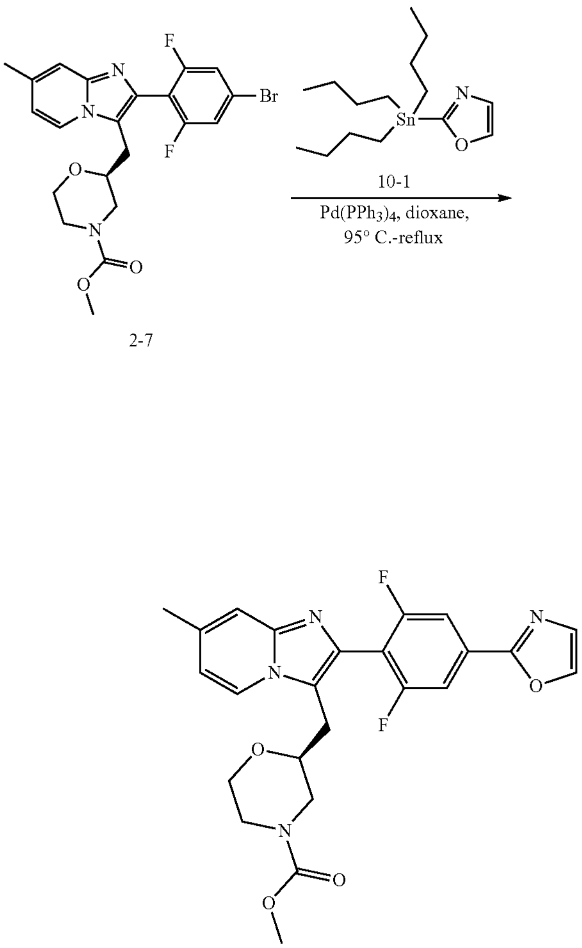

2-7

10-1

10

To a solution of intermediate 2-7 (50 mg, 0.1 mmol) in 1,4-dioxane (2 mL) were added $Pd(Ph_3P)_4$ (12 mg, 0.01 mmol) and 2-(tri-n-butylstannyl)oxazole (119 mg, 0.33 mmol) at room temperature. Under nitrogen atmosphere, the reaction system was heated to 95° C. and reacted for 3 h. After the reaction was completed, the reaction solution was cooled to room temperature, filtered, and concentrated under reduced pressure. The residue was purified by preparative HPLC to give compound 10 (12 mg, 25% yield) in the form of a white solid.

LC-MS: $[M+H]^+$=469.7. $^1$H NMR (400 MHZ, MeOD): δ 8.43 (d, J=7.1 Hz, 1H), 8.10 (d, J=0.8 Hz, 1H), 7.80 (d, J=8.0 Hz, 2H), 7.42 (d, J=0.8 Hz, 1H), 7.36 (s, 1H), 6.89 (dd, J=7.2, 1.6 Hz, 1H), 3.93-3.74 (m, 3H), 3.66 (s, 3H), 3.64-3.56 (m, 1H), 3.42-3.34 (m, 1H), 3.13 (d, J=6.3 Hz, 2H), 2.97-2.85 (m, 1H), 2.73-2.60 (m, 1H), 2.48 (s, 3H).

Example 11

Preparation of methyl (S)-2-((2-(2,6-difluoro-4-(furan-2-yl)phenyl)-7-methylimidazo[1,2-a]pyridin-3-yl)methyl)morpholine-4-carboxylate

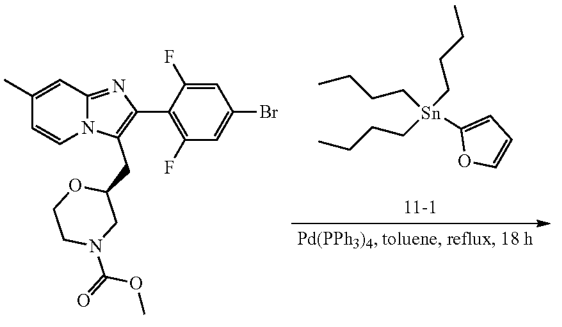

2-7

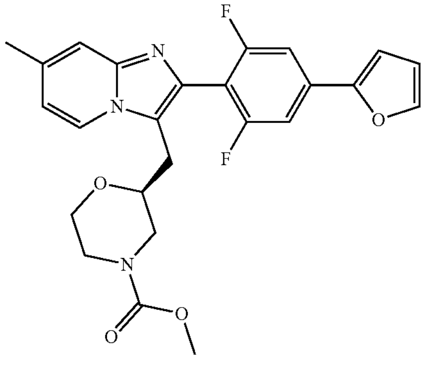

11

Intermediate 2-7 (50 mg, 0.1 mmol) was dissolved in toluene (3 mL), and the reaction system was added with $Pd(PPh_3)_4$ (12 mg, 0.01 mmol) and 2-(tri-n-butylstannyl) furan (37 mg, 0.1 mmol). Under $N_2$ atmosphere, the reaction system was heated to 110° C. and incubated at this temperature for 18 h. Then the reaction system was filtered, and the filtrate was concentrated under reduced pressure. The crude product was purified by column chromatography to give compound 11 (12 mg, 24% yield) in the form of a white solid.

LC-MS: $[M+H]^+$=468.1. $^1$HNMR (400 MHZ, $CDCl_3$): δ 8.55 (d, 1H), 8.08 (s, 1H), 7.58 (d, 1H), 7.40 (d, 2H), 7.14 (d, 1H), 6.86 (d, 1H), 6.58 (s, 1H), 3.82 (m, 3H), 3.73 (s, 3H), 3.68 (m, 1H), 3.43 (m, 1H), 3.05 (m, 2H), 2.96 (m, 1H), 2.71 (m, 1H), 2.61 (s, 3H).

Example 12

Preparation of methyl (S)-2-((2~ (2,6-difluoro-4-(thiophen-2-yl)phenyl)-7-methylimidazo[1,2-a]pyridin-3-yl)methyl)morpholine-4-carboxylate

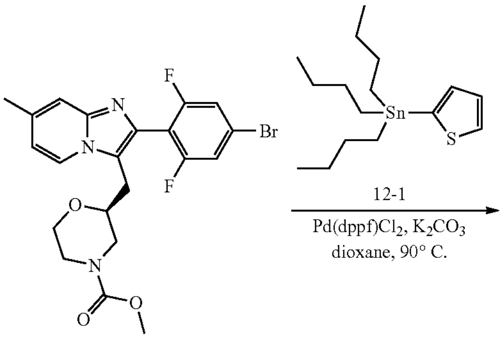

2-7

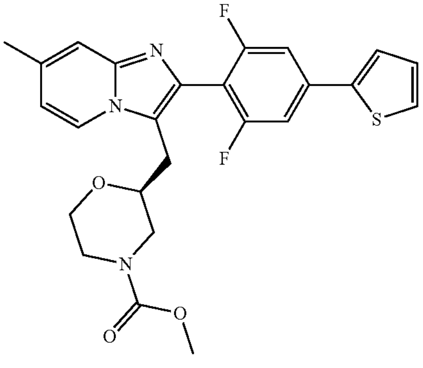

12

Intermediate 2-7 (50 mg, 0.1 mmol) was dissolved in dioxane (3 mL), and the reaction system was added with $Pd(PPh_3)_4$ (12 mg, 0.01 mmol) and 2-(tri-n-butylstannyl) thiophene (117 mg, 0.31 mmol). Under $N_2$ atmosphere, the reaction system was heated to 100° C. and incubated at this temperature for 8 h. Then the reaction system was filtered, and the filtrate was concentrated under reduced pressure. The crude product was purified by column chromatography to give compound 12 (18 mg, 35% yield) in the form of a white solid.

LC-MS: $[M+H]^+$=484.6. $^1$HNMR (400 MHZ, $CDCl_3$): δ 8.22 (d, 1H), 7.41 (m, 3H), 7.31 (m, 2H), 7.14 (dd, 1H), 6.71 (d, 1H), 3.82 (m, 3H), 3.68 (s, 3H), 3.62 (m, 1H), 3.41 (m, 1H), 3.03 (m, 2H), 2.92 (m, 1H), 2.64 (m, 1H), 2.46 (s, 3H).

Example 13

Preparation of methyl (S)-2-((2-(2,6-difluoro-4-(1-methyl-1H-pyrrol-2-yl)phenyl)-7-methylimidazo[1,2-a]pyridin-3-yl)methyl)morpholine-4-carboxylate

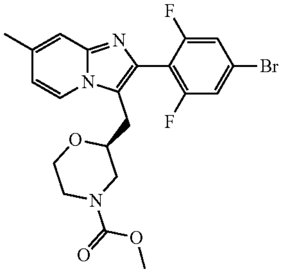

2-7

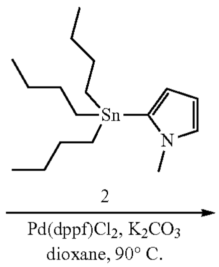

2

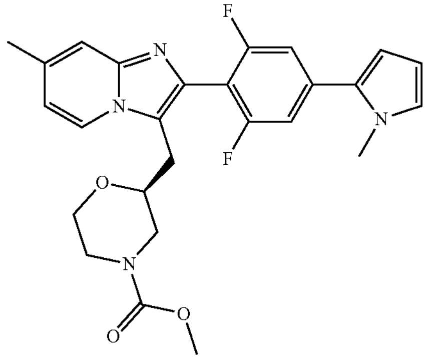

13

Intermediate 2-7 (50 mg, 0.1 mmol) was dissolved in dioxane (3 mL), and the reaction system was added with $Pd(PPh_3)_4$ (12 mg, 0.01 mmol) and 2-(tri-n-butylstannyl) methylpyrrole (115 mg, 0.31 mmol). Under $N_2$ atmosphere, the reaction system was heated to 100° C. and incubated at this temperature for 8 h. Then the reaction system was filtered, and the filtrate was concentrated under reduced pressure. The crude product was purified by column chromatography to give compound 13 (28 mg, 54% yield) in the form of a white solid.

LC-MS: $[M+H]^+$=481.4. $^1$HNMR (400 MHZ, $CD_3OD$): δ 8.86 (d, 1H), 7.72 (S, 1H), 7.42 (dd, 1H), 7.39 (d, 2H), 6.91 (t, 1H), 6.49 (dd, 1H), 6.20 (dd, 1H), 4.02 (d, 1H), 3.84 (s, 3H) 3.75 (m, 3H), 3.69 (s, 3H), 3.38 (m, 1H), 3.27 (m, 2H), 2.96 (m, 1H), 2.79 (m, 1H), 2.66 (s, 3H).

Example 14

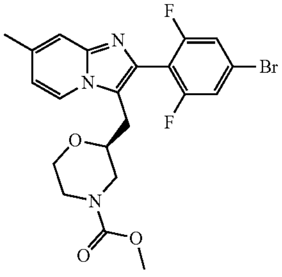

2-7

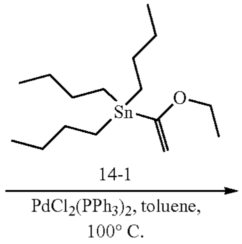

14-1

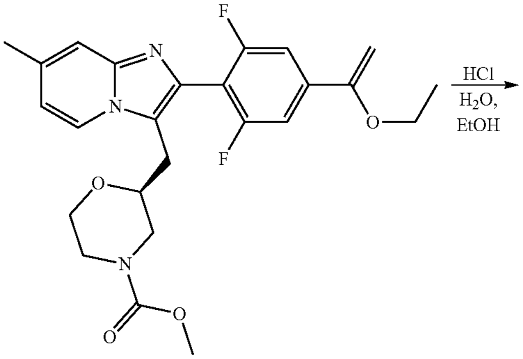

14-2

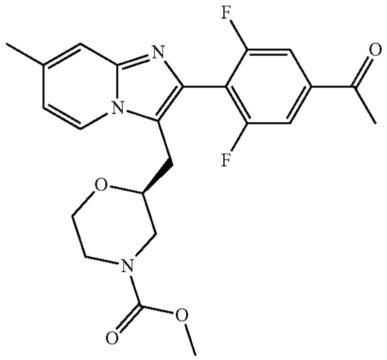

14

Step (1) Preparation of methyl (S)-2-((2-(4-(1-ethoxyethenyl)-2,6-difluorophenyl)-7-methylimidazo[1,2-a]pyridin-3-yl)methyl)morpholine-4-carboxylate 14-2

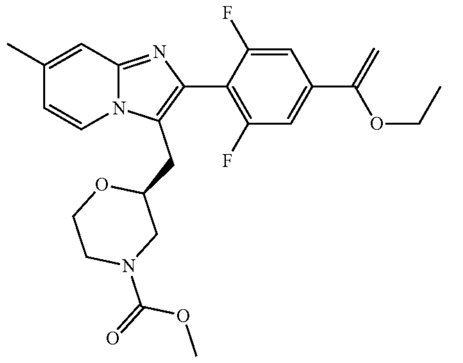

Intermediate 2-7 (300 mg, 0.62 mmol) was dissolved in toluene (3 mL), and the reaction system was added with $PdCl_2(PPh_3)_2$ (44 mg, 0.062 mmol), tri-tert-butyl (1-ethoxyethenyl) tin (680 mg, 1.88 mmol). Under $N_2$ atmosphere, the reaction system was heated to 95° C. and incubated at this temperature for 3 h. Then the reaction system was filtered, and the filtrate was concentrated under reduced pressure. The crude product was purified by column chromatography to give intermediate 14-2 (215 mg, 73% yield) in the form of a yellow oil. LC-MS: $[M+H]^+$=472.7.

Step (2) Preparation of methyl (S)-2-(2-(4-acetyl-2,6-difluorophenyl)-7-methylimidazo[1,2-a]pyridin-3-yl)methyl)morpholine-4-carboxylate

14

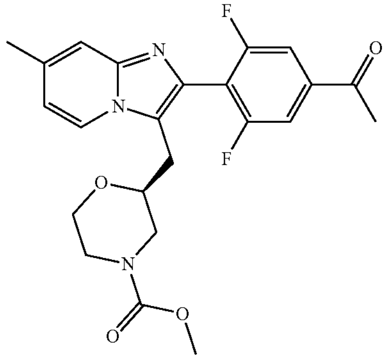

Intermediate 14-2 (250 mg, 0.53 mmol) was dissolved in EtOH (3 mL), and HCl (2 N, 1.7 mL) was added. The reaction system was stirred at room temperature for 2 h. After the reaction was completed, the reaction system was poured into $NaHCO_3$ solution to adjust the pH to 8. The aqueous phase was extracted with DCM. The organic phase was washed with NaCl solution 2-3 times, followed by liquid separation. The organic phase was dried over anhydrous magnesium sulfate and filtered, and the filtrate was concentrated under reduced pressure. The crude product was purified to give compound 14 (25 mg, 38% yield) in the form of a white solid.

LC-MS: $[M+H]^+$=444.7. $^1$HNMR (400 MHZ, MeOD): δ 8.43 (d, 1H), 7.76 (d, 2H), 7.36 (s, 1H), 6.90 (dd, 1H), 3.79 (m, 3H), 3.67 (s, 3H), 3.59 (m, 1H), 3.36 (m, 1H), 3.11 (m, 2H), 2.86 (m, 1H), 2.68 (s, 3H), 2.63 (m, 1H), 2.47 (s, 3H).

Example 15

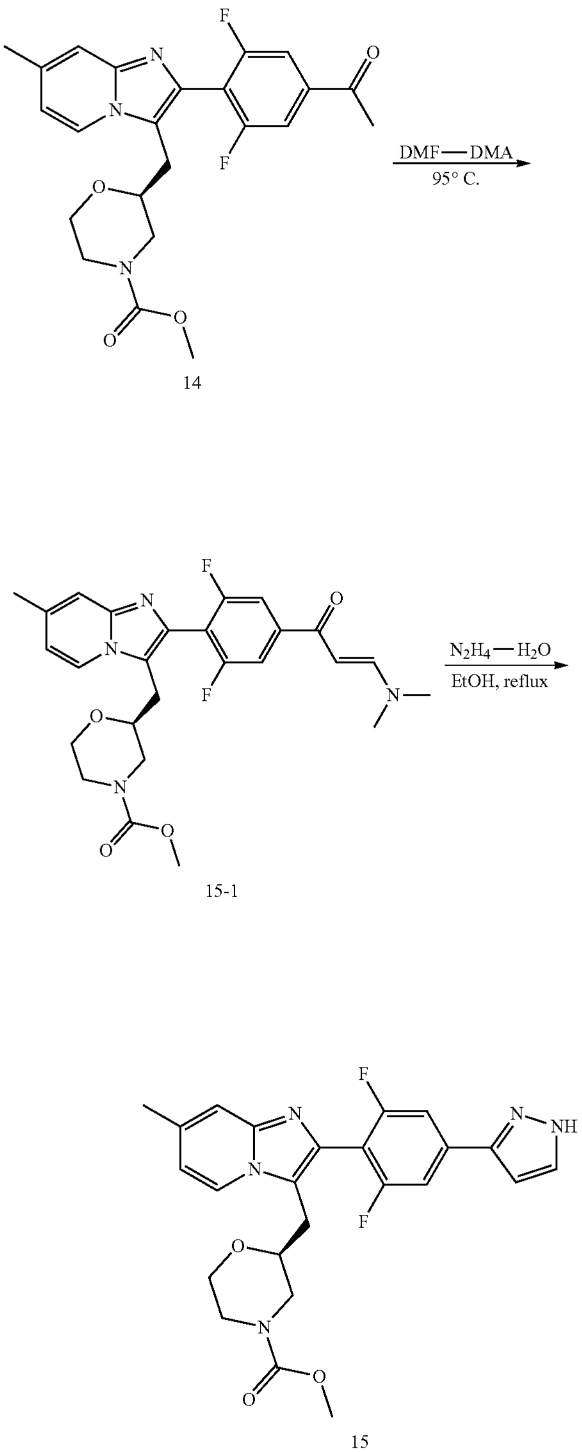

14

15-1

15

Step (1) Preparation of methyl (S,E)-2-((2-(4-(3-(dimethylamino)acryloyl)-2,6-difluorophenyl)-7-methylimidazo[1,2-a]pyridin-3-yl)-methyl)morpholine-4-carboxylate 15-1

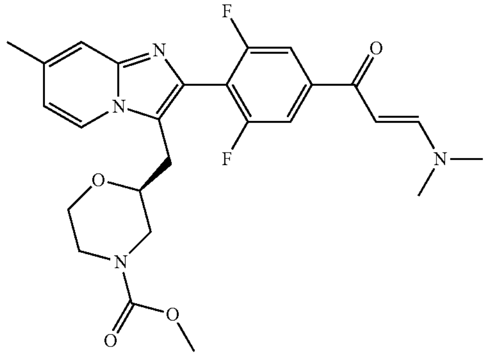

Compound 14 (180 mg, 0.41 mmol) was dissolved in DMF-DMA (2 mL). Under $N_2$ atmosphere, the reaction system was heated to 95° C. and reacted overnight. Then the reaction system was cooled to room temperature, and concentrated under reduced pressure. The residue was purified to give intermediate 15-1 (120 mg, 59.4% yield). LC-MS: $[M+H]^+$=499.7.

Step (2) Preparation of methyl (S)-2-((2-(2,6-difluoro-4-(1H-pyrazol-3-yl)phenyl)-7-methylimidazo[1,2-a]pyridin-3-yl)methyl)morpholine-4-carboxylate

15

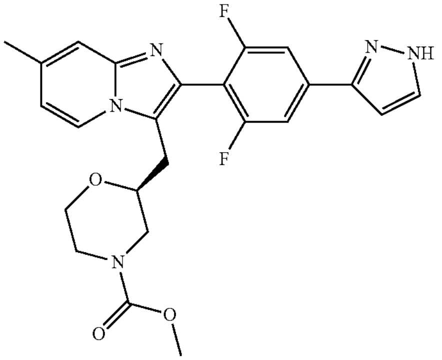

Intermediate 15-1 (80 mg, 0.12 mmol) was dissolved in ethanol (2 mL). The reaction system was added with $N_2H_4$-$H_2O$ (16 mg, 0.32 mg) dropwise, heated to 100° C. and incubated at this temperature for 2 h. Then the reaction system was concentrated under reduced pressure. The residue was purified to give compound 15 (49.8 mg, 66.4% yield) in the form of a white solid.

LC-MS: $[M+H]^+$=468.6. $^1H$ NMR (400 MHZ, MeOD): δ 8.86 (d, 1H), 7.81 (d, 1H), 7.76 (d, 2H), 7.73 (s, 1H), 7.43 (dd, 1H), 6.91 (d, 1H), 4.02 (m, 1H), 3.79 (m, 3H), 3.69 (s, 3H), 3.37 (m, 1H), 3.27 (m, 2H), 2.94 (m, 1H), 2.73 (m, 1H), 2.66 (s, 3H).

Example 16

Preparation of methyl (S)-2-((2-(2,6-difluoro-4-(isoxazol-3-yl)phenyl)-7-methylimidazo[1,2-a]pyridin-3-yl)methyl)morpholine-4-carboxylate

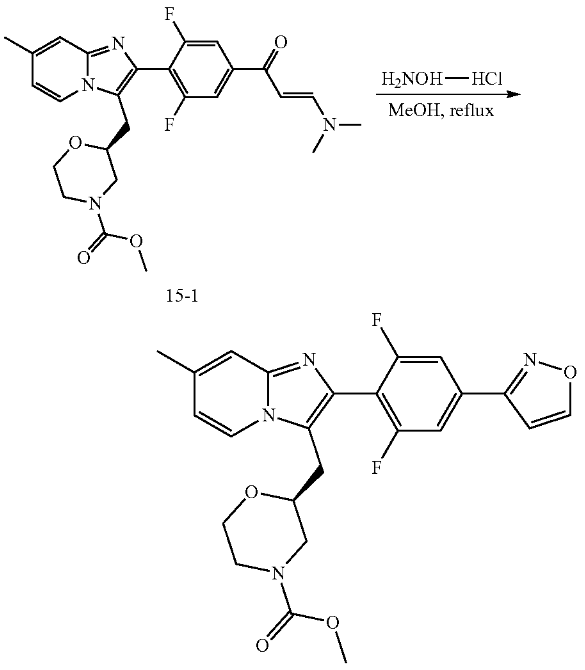

15-1

16

Intermediate 15-1 (80 mg, 0.12 mmol) was dissolved in methanol (2 mL). The reaction system was added with $N_2OH$—HCl (21 mg, 0.30 mg) dropwise, heated to 100° C. and incubated at this temperature for 2 h. Then the reaction system was concentrated under reduced pressure. The residue was purified to give compound 16 (34.2 mg, 45.4% yield) in the form of a white solid.

LC-MS: $[M+H]^+$=469.4. $^1H$ NMR (400 MHZ, $CDCl_3$): δ8.27 (d, 1H), 7.66 (m, 2H), 7.35 (s, 1H), 6.82 (dd, 1H), 3.78 (m, 3H), 3.61 (s, 3H), 3.54 (m, 1H), 3.30 (m, 1H), 3.10 (m, 2H), 2.88 (m, 1H), 2.63 (m, 1H), 2.47 (s, 3H).

Example 17

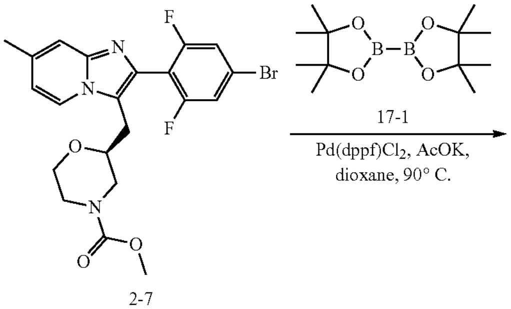

2-7

-continued

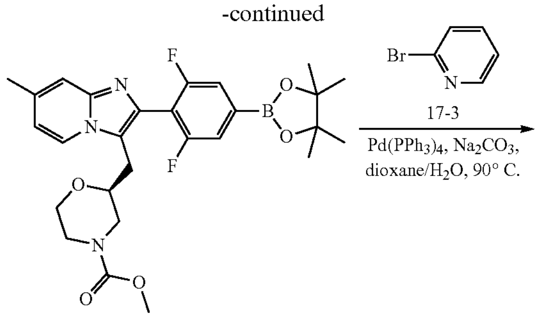

17-2

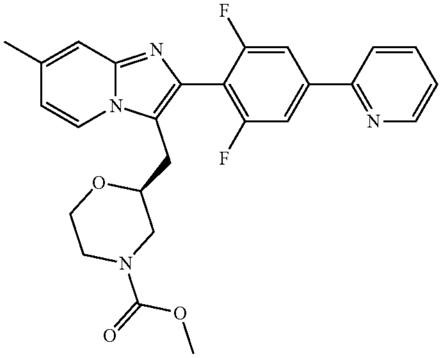

17

Step (1) Preparation of methyl (S)-2-((2-(2,6-difluoro-4-(4,4,5,5-tetramethyl-1,3,2-dioxaborolan-2-yl)phenyl)-7-methylimidazo[1,2-a]pyridin-3-yl)-methyl)morpholine-4-carboxylate 17-2

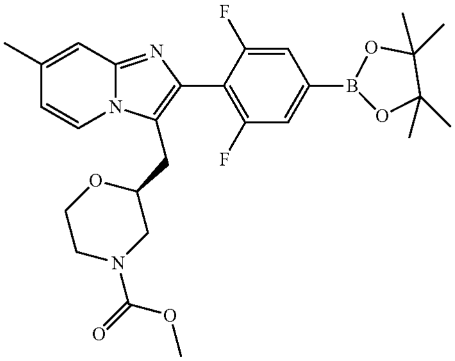

Intermediate 2-7 (100 mg, 0.21 mmol), boronate (64 mg, 0.25 mmol), Pd(dppf)$Cl_2$ (8 mg, 0.01 mmol) and AcOK (6.2 mg, 0.625 mmol) were dissolved in dioxane (3 mL). Under $N_2$ atmosphere, the reaction system was heated to 90° C. and reacted overnight. Then the reaction system was cooled to room temperature to give intermediate 17-2. LC-MS: $[M+H]^+$=528.2.

Step (2) Preparation of methyl (S)-2-((2-(2,6-difluoro-4-(pyridin-2-yl)phenyl)-7-methylimidazo[1,2-a]pyridin-3-yl)methyl)morpholine-4-carboxylate

17

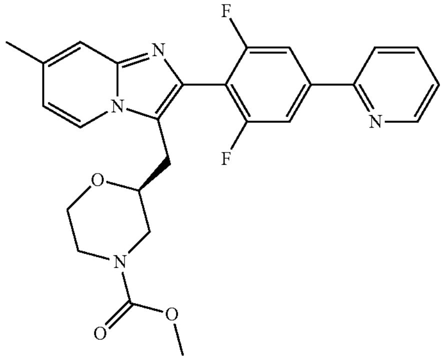

Intermediate 17-2 (55 mg, 0.1 mmol), 2-bromopyridine (18 mg, 0.11 mmol), $Na_2CO_3$ (33 mg, 0.31 mmol), $Pd(PPh_3)_4$ (6 mg, 0.005 mmol) were dissolved in dioxane (3 mL) and a small amount of water. Under $N_2$ atmosphere, the reaction system was heated to 100° C. After the reaction was completed, the reaction system was filtered, and the filtrate was diluted with water and extracted with EA. The organic phase was washed with NaCl, dried, filtered, and concentrated under reduced pressure. The residue was purified to give compound 17 (25 mg, 50% yield) in the form of a white solid.

LC-MS: $[M+H]^+$=479.7. $^1H$ NMR (400 MHz, $CDCl_3$): δ 8.75 (d, 1H), 8.27 (d, 1H), 7.85 (t, 1H), 7.76 (dd, 3H), 7.56 (m, 1H), 7.35 (m, 1H), 6.76 (d, 1H), 3.82 (s, 3H), 3.68 (s, 3H), 3.62 (s, 1H), 3.41 (s, 1H), 3.03 (dd, 2H), 2.92 (s, 1H), 2.64 (dd, 1H), 2.47 (s, 3H).

Example 18

Preparation of methyl (S)-2-((2-(2,6-difluoro-4-((pyrimidin-2-yl)phenyl)-7-methylimidazo[1,2-a]pyridin-3-yl)methyl)morpholine-4-carboxylate

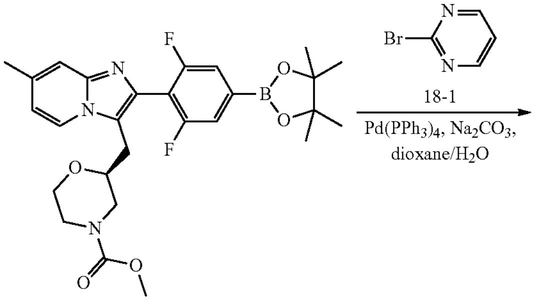

17-2

-continued

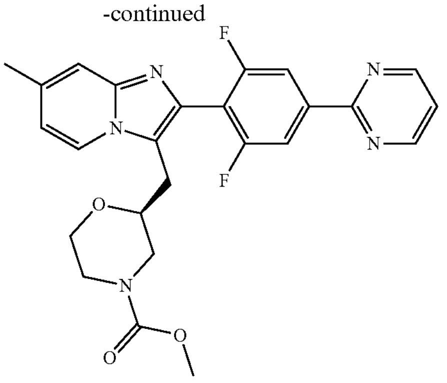

18

Intermediate 17-2 (55 mg, 0.1 mmol), 2-bromopyrimidine (19 mg, 0.11 mmol), $Na_2CO_3$ (27 mg, 0.31 mmol), $Pd(PPh_3)_4$ (4 mg, 0.005 mmol) were dissolved in dioxane (3 mL) and a small amount of water. Under $N_2$ atmosphere, the reaction system was heated to 90° C. After the reaction was completed, the reaction system was filtered, and the filtrate was diluted with water and extracted with EA. The organic phase was washed with NaCl, dried, filtered, and concentrated under reduced pressure. The residue was purified to give compound 18 (25 mg, 50% yield) in the form of a white solid.

LC-MS: $[M+H]^+$=480.2. $^1$HNMR (400 MHZ, $CDCl_3$): δ 8.87 (d, 2H), 8.24 (t, 1H), 8.18 (d, 2H), 7.54 (S, 1H), 7.30 (m, 1H), 6.76 (d, 1H), 3.82 (s, 3H), 3.72-3.77 (m, 3H), 3.68 (s, 3H), 3.62 (s, 1H), 3.41 (s, 1H), 3.03 (t, 2H), 2.92 (s, 1H), 2.64 (dd, 1H), 2.46 (s, 3H).

Example 19

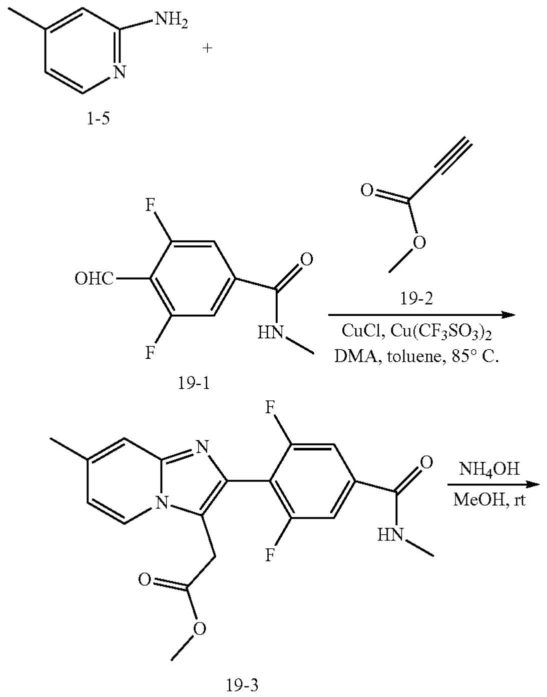

-continued

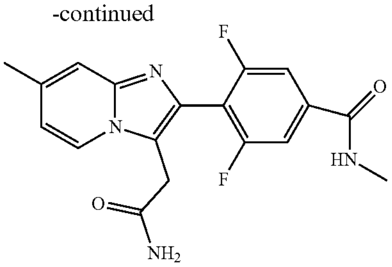

19

Step (1) Preparation of methyl 2-(2-((2,6-difluoro-4~ (methylcarbamoyl)phenyl)-7-methylimidazo[1,2-a]pyridin-3-yl)methyl)acetate 19-3

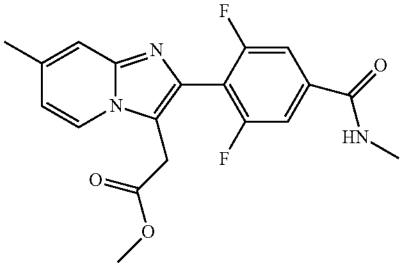

3,5-difluoro-4-formyl-N-methylbenzamide (200 mg, 1 mmol), 2-amino-4-methylpyridine (108 mg, 1 mmol), methyl propiolate (84 mg, 1 mmol), CuCl (30 mg, 0.3 mmol), and $Cu(CF_3SO_3)_2$ (109 mg, 0.3 mmol) were dissolved in toluene (3 mL). Under $N_2$ atmosphere, the reaction system was heated to 85° C., added with DMA (0.05 mL), and stirred for 5 h. Then the reaction system was cooled to room temperature, and incubated overnight. The resulting reaction system was poured into $H_2O$ (5 mL) and extracted with DCM (5 mL×3). The organic phase was washed with saturated NaCl, dried over $MgSO_4$, filtered, and concentrated under reduced pressure. The crude product was purified by column chromatography (PE:EA=1:1) to give intermediate 19-3 (172 mg, 25% yield) in the form of a yellow oil. LC-MS: $[M+H]^+$=374.4.

Step (2) Preparation of 4-(3-(2-amino-2-oxoethyl)-7-methylimidazo[1,2-a]pyridine)-3,5-difluorobenzoylmethylamine

19

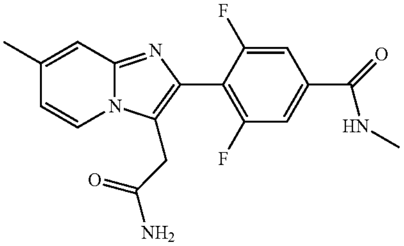

Intermediate 19-3 (82 mg, 0.22 mmol) was dissolved in methanol (2 mL). The reaction system was added with $NH_3H_2O$ (1 mL) and stirred overnight. Then the reaction system was concentrated under reduced pressure. The crude product was purified to give compound 19 (25 mg, 32% yield) in the form of a white solid.

LC-MS: $[M+H]^+$=359.8. $^1$HNMR (400 MHZ, $CD_3OD$): δ 8.36 (d, 1H), 7.63 (d, 2H), 7.46 (s, 1H), 7.02 (d, 1H), 3.93 (s, 2H), 2.97 (s, 3H), 2.52 (s, 3H).

Example 20

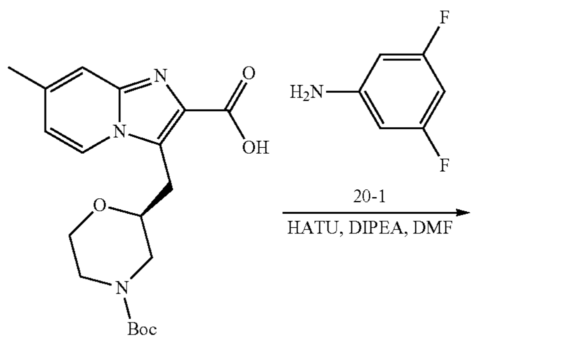

1-8

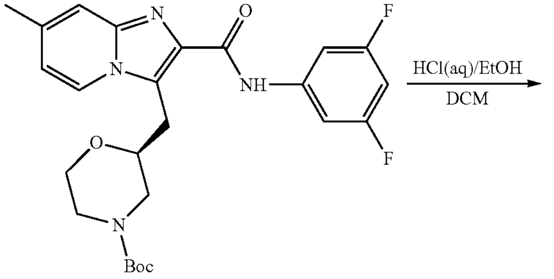

20-2

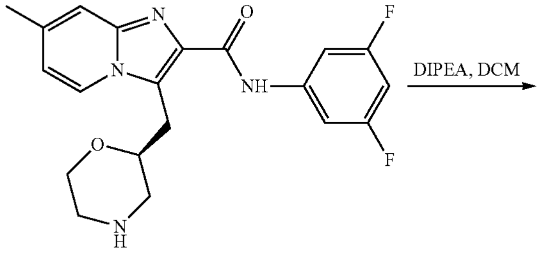

20-3

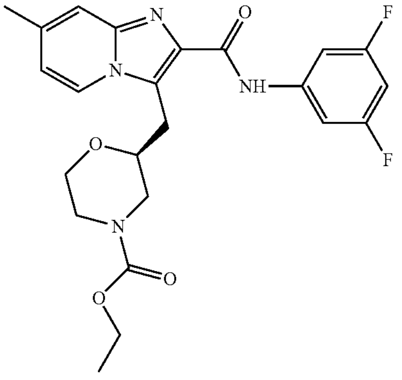

20

Step (1) Preparation of tert-butyl (S)-2-((2-(3,5-difluorophenyl)carbamoyl)-7-methylimidazo[1,2-a]pyridin-3-yl)-methyl)morpholine-4-carboxylate 20-2

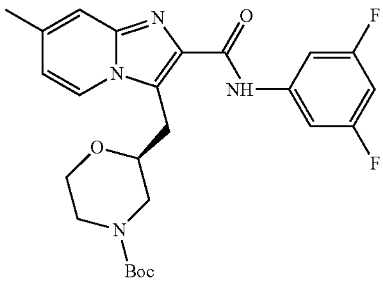

A solution of intermediate 1-8 (400 mg, 1.07 mmol) and HATU (608 mg, 1.6 mmol) in DMF (5 mL) was stirred at room temperature for 10 min, and DIPEA (418 mg, 3.24 mmol) and compound 20-1 (168 mg, 1.3 mmol) were added at room temperature. The reaction system was reacted for 1 h. After the reaction was completed, the reaction system was added with water (15 mL) to quench the reaction, extracted with dichloromethane (10 mL×3), washed with saturated sodium chloride solution (10 mL×2), dried over anhydrous sodium sulfate, and concentrated under reduced pressure. The residue was purified by silica gel column chromatography (DCM/MeOH, 10/1) to give intermediate 20-2 (450 mg) in the form of a yellow oily liquid.

Step (2) Preparation of (S)—N-(3,5-difluorophenyl)-7-methyl-3-(morpholin-2-ylmethyl)imidazo[1,2-a]pyridine-2-carboxamide 20-3

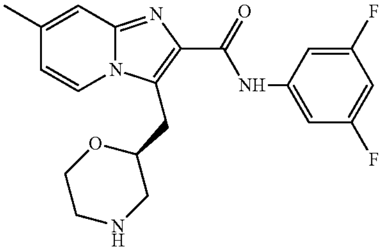

To a solution of intermediate 20-2 (330 mg, 0.7 mmol) in DCM (4 mL) was added a solution of HCl in ethanol (1 mL) dropwise at 0° C. The reaction system was reacted at room temperature for 1 h. After the reaction was completed, the reaction system was added with saturated $NaHCO_3$ to quench the reaction at 0° C., extracted with dichloromethane (3 mL×3), washed with saturated sodium chloride solution (3 mL×2), dried over anhydrous sodium sulfate, and concentrated under reduced pressure. The residue was purified by silica gel column chromatography (DCM/MeOH, 10/1) to give intermediate 20-3 (80 mg, 31% yield) in the form of a brown solid.

Step (3) Preparation of ethyl(S)-2-((2-(3,5-difluorophenyl)carbamoyl)-7-methylimidazo[1,2-a]pyridin-3-yl)methyl)morpholine-4-acetate

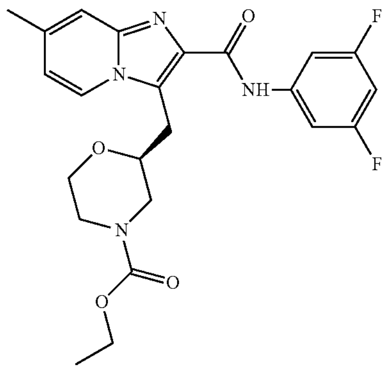

To a solution of intermediate 20-3 (80 mg, 0.2 mmol) and DIPEA (25 mg, 0.6 mmol) in DCM (2 mL) was added methyl chloroformate (1 mL) at 0° C. The reaction system was reacted for 1 h. After the reaction was completed, the reaction system was added with water (3 mL), extracted with dichloromethane (3 mL×3), washed with saturated sodium chloride solution (3 mL×2), dried over anhydrous sodium sulfate, and concentrated under reduced pressure. The residue was purified by preparative HPLC to give compound 20 (15 mg, 16% yield) in the form of a white solid.

LC-MS: $[M+H]^+$=459.7. $^1H$ NMR (400 MHZ, $CDCl_3$): δ 8.30 (s, 1H), 7.52 (s, 3H), 6.90 (s, 1H), 6.59 (t, J=8.7 Hz, 1H), 4.23 (d, J=9.8 Hz, 1H), 4.16 (dd, J=14.1, 7.1 Hz, 2H), 3.96-3.79 (m, 3H), 3.75 (d, J=12.2 Hz, 1H), 3.41 (dd, J=11.9, 9.2 Hz, 1H), 3.35-3.19 (m, 1H), 2.99-2.85 (m, 1H), 2.84-2.73 (m, 1H), 2.50 (s, 3H), 1.35-1.18 (m, 3H).

Example 21

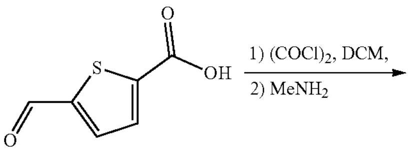

21-1

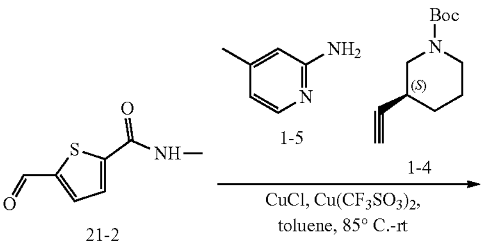

21-2 1-5 1-4

-continued

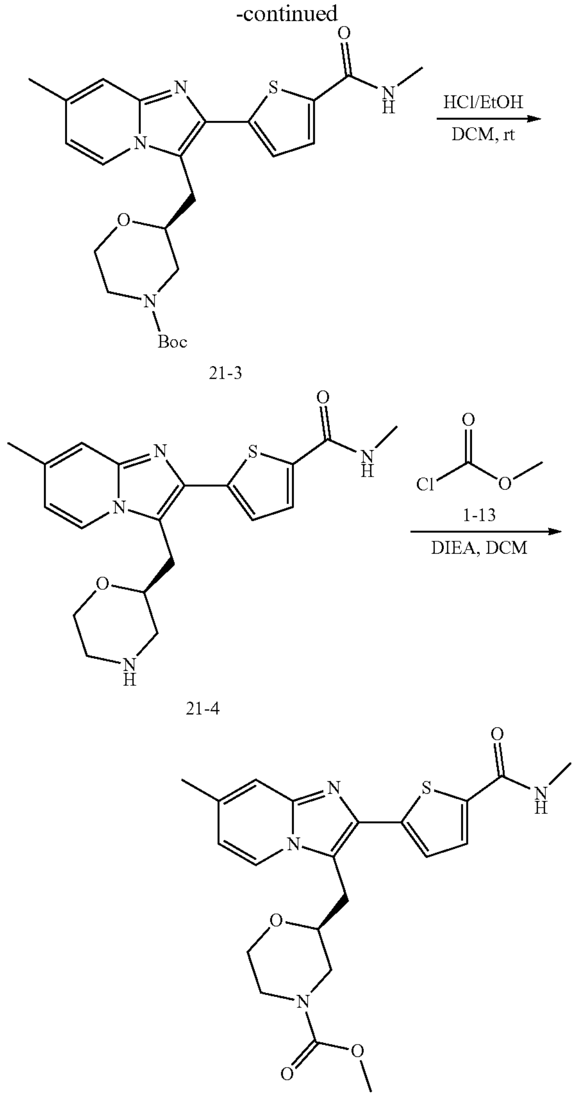

21-3 21-4 21

Step (1) Preparation of 5-formyl-N-methylthiophene-2-carboxamide 21-2

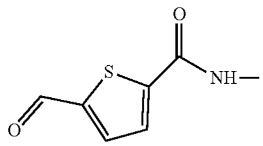

To a solution of 5-formylthiophene-2-carboxylic acid (500 mg, 3.2 mmol) and DMF (12 mg) was added oxalyl chloride (447 mg, 1.1 mmol) at 0° C. The reaction system was reacted at this temperature for 2 h, and added with aqueous methylamine solution (40%, 746 mg, 9.6 mmol) over 10 min. After the reaction was completed, the reaction system was added with water (3 mL) to quench the reaction, extracted with dichloromethane (5 mL×3), washed with saturated sodium chloride solution (5 mL×2), dried over anhydrous sodium sulfate and concentrated under reduced pressure. The residue was purified by silica gel column chromatography (PE/EA, 1/1) to give compound 21-2 in the form of a white solid (300 mg, 56% yield), LC-MS: $[M+H]^+$=170.9.

Step (2) Preparation of tert-butyl (S)-2-((7-methyl-2-(5-(methylcarbamoyl)thiophen-2-yl)imidazo[1,2-a]pyridin-3-yl)methyl)morpholine-4-carboxylate 21-3

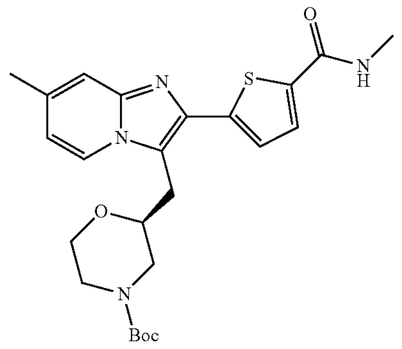

To a solution of compound 21-2 (500 mg, 2.96 mmol), 4-methylpyridin-2-amine (320 mg, 2.96 mmol) and compound 1-4 (625 mg, 2.96 mmol) in toluene (5 mL) were added copper(I) chloride (88 mg, 0.89 mmol) and copper(II) trifluoromethanesulfonate (321 mg, 0.89 mmol) at room temperature. Under nitrogen atmosphere, the reaction system was heated to 85° C., added with DMA (0.05 mL), and reacted at this temperature for 5 h. After the reaction was completed, the reaction system was added with water (5 mL) to quench the reaction, extracted with dichloromethane (5 mL×3), washed with saturated sodium chloride solution (5 mL×2), dried over anhydrous sodium sulfate, and concentrated under reduced pressure. The residue was purified by silica gel column chromatography (DCM/MeOH, 40/1) to give intermediate 21-3 (300 mg, 56% yield) in the form of a yellow oily liquid, LC-MS: $[M+H]^+$=471.7.

Step (3) Preparation of (S)-5-(7-methyl-3-(morpholin-2-yl-methyl)imidazo[1,2-a]pyridin-2-yl)thiophene-2-carboxamide 21-4

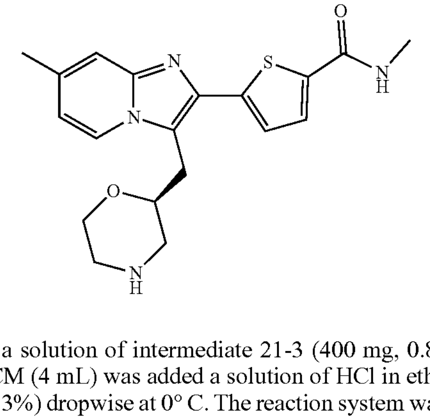

To a solution of intermediate 21-3 (400 mg, 0.85 mmol) in DCM (4 mL) was added a solution of HCl in ethanol (0.5 mL, 33%) dropwise at 0° C. The reaction system was reacted at room temperature for 1 h. After the reaction was completed, the reaction system was added with saturated $NaHCO_3$ to quench the reaction at 0° C., extracted with dichloromethane (5 mL×3), washed with saturated sodium chloride solution (5 mL×2), dried over anhydrous sodium sulfate, and concentrated under reduced pressure to give intermediate 21-4 (300 mg) in the form of a yellow oily liquid, LC-MS: $[M+H]^+$=371.8.

Step (4) Preparation of methyl (S)-2-((7-methyl-2-(5-(methylcarbamoyl)thiophen-2-yl)imidazo[1,2-a]pyridin-3-yl)methyl)morpholine-4-carboxylate

21

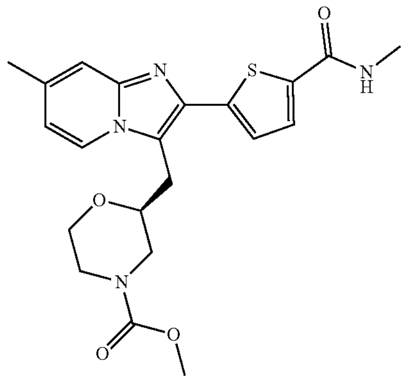

To a solution of intermediate 21-4 (100 mg, 0.27 mmol) and DIPEA (105 mg, 0.81 mmol) in DCM (2 mL) was added methyl chloroformate (31 mg, 0.33 mol) at 0° C. The reaction system was reacted for 3 h. After the reaction was completed, the reaction system was added with water (3 mL), extracted with dichloromethane (3 mL×2), washed with saturated sodium chloride solution (3 mL×2), dried over anhydrous sodium sulfate, and concentrated under reduced pressure. The residue was purified by preparative HPLC to give compound 21 (28.5 mg, 28% yield) in the form of a yellow solid.

LC-MS: $[M+H]^+$=429.7. $^1$H NMR (400 MHz, MeOD): δ 8.32 (d, J=7.0 Hz, 1H), 7.67 (d, J=3.9 Hz, 1H), 7.52 (d, J=3.8 Hz, 1H), 7.31 (s, 1H), 6.88-6.80 (m, 1H), 4.13 (d, J=12.8 Hz, 1H), 3.92-3.75 (m, 3H), 3.72 (s, 3H), 3.46-3.28 (m, 3H), 3.01 (m, 1H), 2.94 (s, 3H), 2.91 (m, 1H), 2.44 (s, 3H).

Examples 22-24

The compounds were prepared using the corresponding starting materials according to the method as described in Example 21.

| Number | Compound structure | LC-MC (RT, m/z) |
|---|---|---|
| Example 22 | 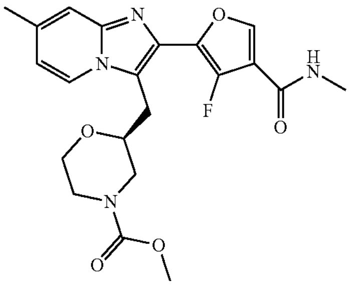 22 | 431.4 |
| Example 23 | 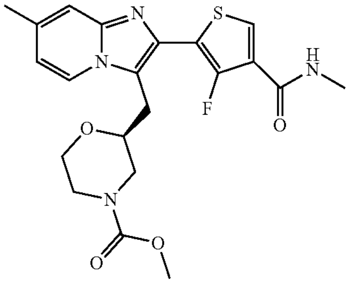 23 | 447.1 |
| Example 24 | 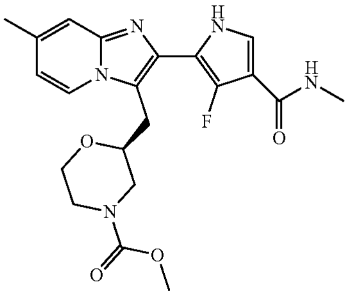 24 | 430.1 |
Example 25
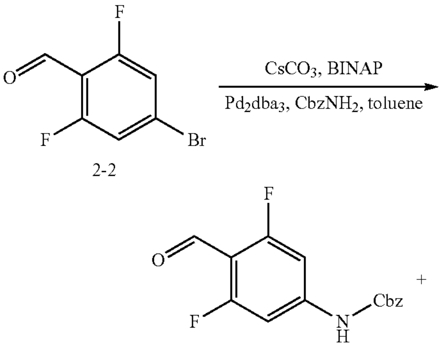
2-2
25-1
-continued
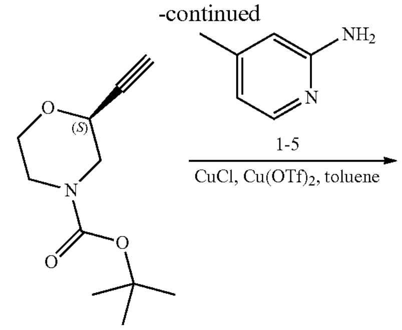
1-4
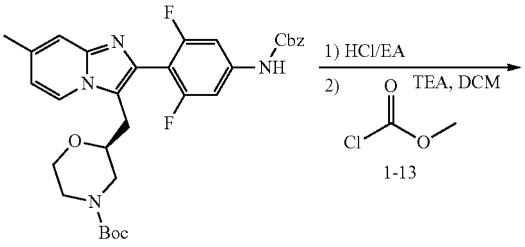
25-2
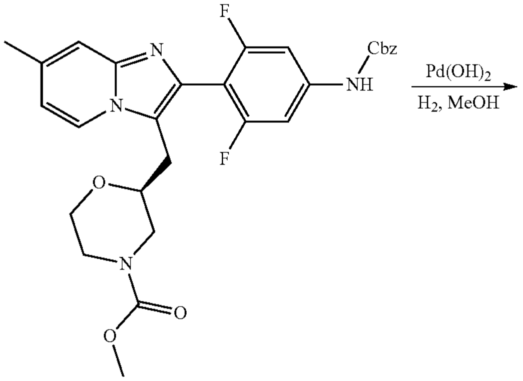
25-3
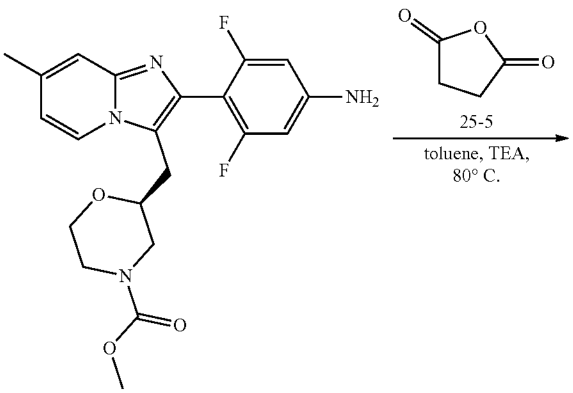
25-4

-continued

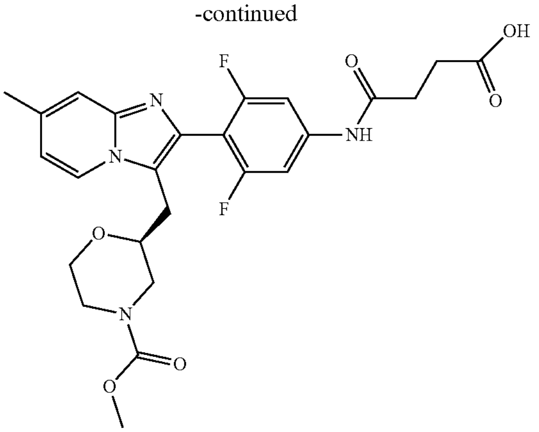

25

Step (1) Preparation of benzyl (3,5-difluoro-4-formylphenyl)-carbamate 25-1

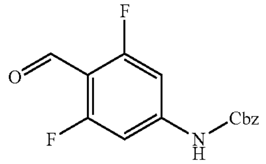

To a solution of compound 2-2 (1 g, 4.5 mmol) in toluene (20 mL) were added cesium carbonate (2 g, 6.3 mmol), benzyl carbamate (0.8 g, 5.4 mmol), (±)-2,2'-bis-(diphenylphosphino)-1,1'-binaphthalene (0.28 g, 0.45 mmol) and tris(dibenzylideneacetone) dipalladium (0.2 g, 0.2 mmol) at room temperature. After the addition, the reaction system was purged with nitrogen three times, heated to 100° C. and stirred overnight (16 h) under nitrogen atmosphere. Then the reaction system was filtered and concentrated under reduced pressure. The residue was purified by silica gel column chromatography (EA/PE=1/10) to give intermediate 25-1 (0.72 g, 55.2% yield) in the form of a yellow solid, LC-MS: $[M+H]^+$=292.1.

Step (2) Preparation of tert-butyl (S)-2-((2-(4~(((benzyloxy)-carbonyl)amino)-2,6-difluorophenyl)-7-methylimidazo[1,2-a]pyridin-3-yl)methyl)morpholine-4-carboxylate 25-2

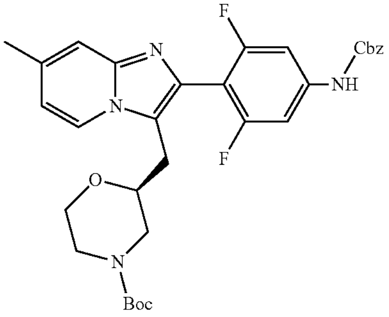

To a 20 mL microwave tube (Biotage) were added compound 25-1 (0.2 g, 0.68 mmol), compound 1-4 (0.22 g, 1.03 mmol) and compound 1-5 (74 mg, 0.68 mmol), copper (1) chloride (20 mg, 0.2 mmol), copper(II) trifluoromethanesulfonate (74 mg, 0.2 mmol) and toluene (6 mL). After the addition, the reaction system was purged with nitrogen for 2 min, and reacted at 120° C. overnight (16 h) after the tube was sealed. A new spot was generated by developing the TLC plate (PE/BA=1/1) with Rf value being about 0.3, and was identified as the target product by liquid chromatography. Then the reaction system was cooled to room temperature and concentrated under reduced pressure. The residue was mixed with silica gel and purified by silica gel column chromatography (EA/PE=1/1) to give intermediate 25-2 (184 mg, 45.5% yield) in the form of a yellow solid. LC-MS: $[M+H]^+$=593.6.

Step (3) Preparation of methyl (S)-2-((2-(4-(((benzyloxy)-carbonyl)amino)-2,6-difluorophenyl)-7-methylimidazo[1,2-a]pyridin-3-yl)methyl)morpholine-4-carboxylate 25-3

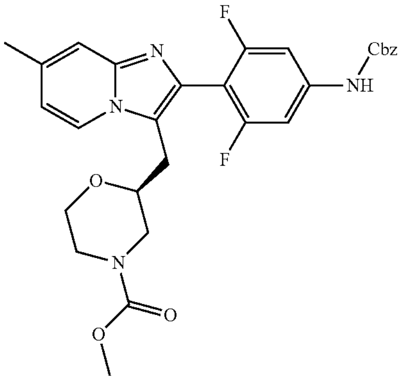

To intermediate 25-2 (0.8 g, 1.35 mmol) was added a solution of HCl in ethyl acetate (about 4 M, 5 mL) at room temperature. After the addition, the reaction system was stirred at room temperature for 2 h. After the reaction was completed as monitored by liquid chromatography, the reaction system was concentrated under reduced pressure to give a crude product, to which were added dichloromethane (5 mL), triethylamine (0.4 g, 4 mmol) and methyl chloroformate (0.19 g, 2 mmol). After the addition, the reaction system was stirred at room temperature for 3 h. After the reaction was completed as monitored by liquid chromatography, the reaction system was concentrated under reduced pressure. The residue was purified by silica gel column chromatography (EA) to give intermediate 25-3 (675 mg, 90.8% yield) in the form of a brown oil. LC-MS: $[M+H]^+$=551.2.

Step (4) Preparation of methyl (S)-2-((2-(4-amino-2,6-difluorophenyl)-7-methylimidazo[1,2-a]pyridin-3-yl)methyl)morpholine-4-carboxylate 25-4

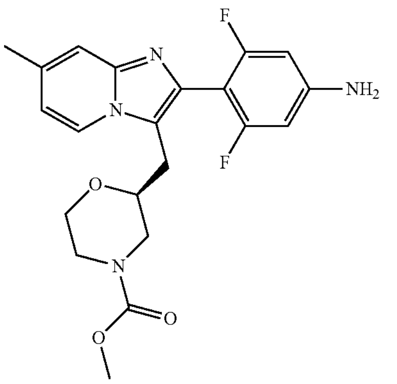

To a solution of intermediate 25-3 (200 mg, 0.363 mmol) in methanol (10 mL) was added palladium hydroxide (about 40 mg, 20% w/w) at room temperature. After the addition, the reaction system was purged with hydrogen balloon 3 times, and stirred at room temperature for 4 h under hydrogen atmosphere. After the reaction was completed as monitored by liquid chromatography, the reaction system was filtered and concentrated under reduced pressure. The residue was purified by silica gel column chromatography (EA) to give intermediate 25-4 (111 mg, 74% yield) in the form of a yellow solid. LC-MS: [M+H]$^+$=417.2.

Step (5) Preparation of (S)-4-((3,5-difluoro-4-(3-((4-(methoxycarbonyl)morpholin-2-yl)methyl)-7-methylimidazo[1,2-a]pyridin-2-yl)-phenyl)-amino)-4-oxobutanoic acid

25

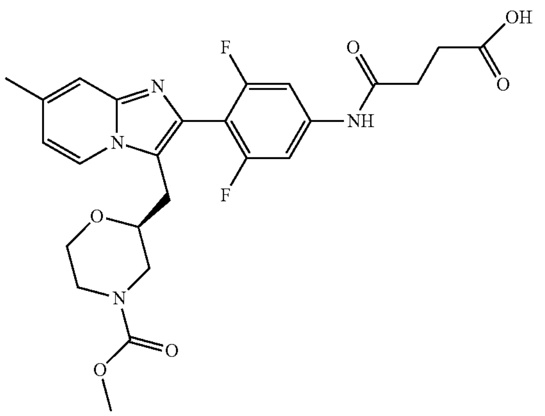

To a solution of intermediate 25-4 (100 mg, 0.24 mmol) in toluene (5 mL) were added triethylamine (24 mg, 0.24 mmol) and succinic anhydride (28.8 mg, 0.288 mmol) at room temperature. After the addition, the reaction system was heated to 80° C. and reacted for 4 h. After the reaction was completed as monitored by liquid chromatography, the reaction system was concentrated under reduced pressure.

The residue was purified by preparative high performance liquid chromatography (ammonium bicarbonate method), and lyophilized to give compound 25 (90 mg, 72.5% yield) in the form of a white solid.

LC-MS: [M+H]$^+$=517.1. $^1$H NMR (400 MHz, $CD_3OD$): δ 8.39 (d, J=7.2 Hz, 1H), 7.46-7.38 (m, 2H), 7.33 (s, 1H), 6.87-6.85 (m, 1H), 3.85-3.58 (m, 3H), 3.67 (s, 3H), 3.60-3.56 (m, 1H), 3.39-3.33 (m, 1H), 3.13-3.02 (m, 2H), 2.93-2.87 (m, 1H), 2.74-2.65 (m, 4H), 2.64-2.60 (m, 1H), 2.46 (s, 3H).

Example 26

Preparation of methyl (S)-2-((2-(4-(2,5-dioxopyrrolidin-1-yl)-2,6-difluorophenyl)-7-methylimidazo[1,2-a]pyridin-3-yl)methyl)morpholine-4-carboxylate

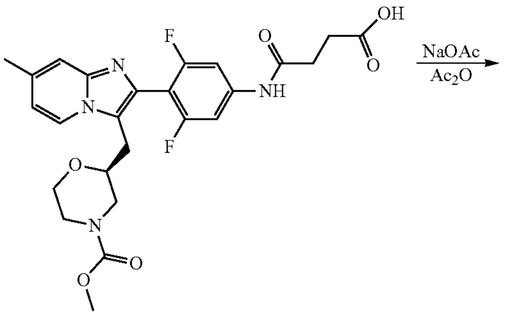

25

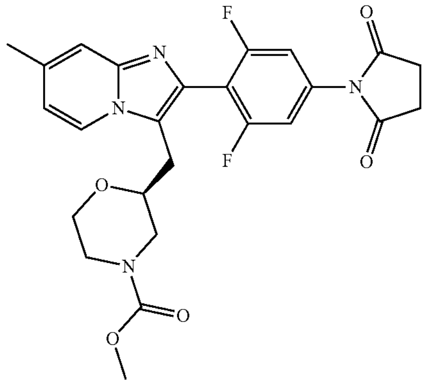

26

To a solution of compound 25 (77.6 mg, 0.15 mmol) in acetic anhydride (2 mL) was added sodium acetate (9.2 mg, 0.11 mmol) at room temperature. The reaction system was stirred at room temperature for 4 h. Then the reaction system was concentrated under reduced pressure. The residue was purified by preparative high performance liquid chromatography (trifluoroacetic acid method), and lyophilized to give compound 26 (30 mg, 40% yield) in the form of a white solid.

LC-MS: [M+H]$^+$=499.1. $^1$H NMR (400 MHZ, $CD_3OD$): δ 8.84 (d, J=6.8 Hz, 1H), 7.72 (s, 1H), 7.44-7.40 (m, 3H), 4.02-3.99 (m, 1H), 3.82-3.69 (m, 2H), 3.67 (s, 3H), 3.35-3.24 (m, 5H), 2.92-2.88 (m, 4H), 2.76-2.71 (m, 1H), 2.64 (s, 3H).

Example 27

(S,E)-4-((3,5-difluoro-4-(3-((4-(methoxycarbonyl)-morpholin-2-yl)-methyl)-7-methylimidazo[1,2-a]pyridin-2-yl)-phenyl)-amino)-4-oxobutyl-2-enoic acid

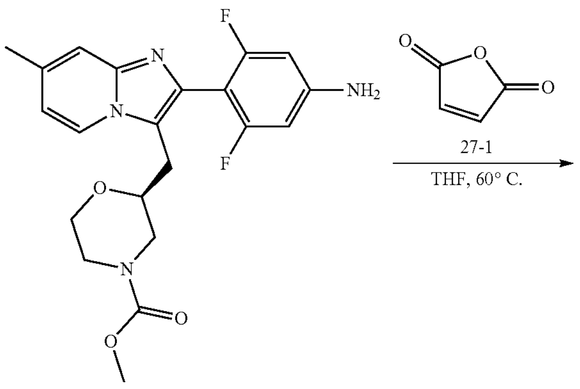

25-4

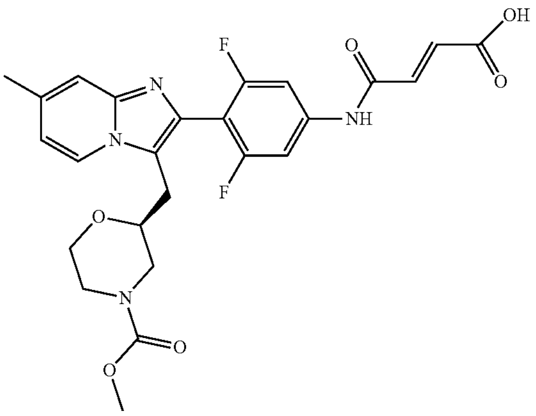

27

To a solution of intermediate 25-4 (20 mg, 0.048 mmol) in tetrahydrofuran (5 mL) was added maleic anhydride (7 mg, 0.071 mmol) at room temperature. After the addition, the reaction system was heated to 60° C. and reacted overnight (16 h). After the reaction was completed as monitored by liquid chromatography, the reaction system was concentrated under reduced pressure. The residue was purified by preparative high performance liquid chromatography (trifluoroacetic acid method), and lyophilized to give compound 27 (16 mg, 65% yield) in the form of a white solid.

LC-MS: $[M+H]^+$=515.9. $^1$H NMR (400 MHZ, DMSO-d6): δ 12.9 (br, 1H), 10.88 (s, 1H), 8.78 (d, J=2.8 Hz, 1H), 7.68 (s, 1H), 7.56 (d, J=10.4 Hz, 2H), 7.31-7.30 (m, 1H), 6.53 (d, J=12 Hz, 1H), 6.37 (d, J=12 Hz, 1H), 3.90-3.87 (m, 1H), 3.76-3.62 (m, 3H), 3.57-3.54 (m, 3H), 3.25-3.07 (m, 4H), 2.85-2.80 (m, 1H), 2.52 (overlap, 3H).

Example 28

Preparation of methyl (S)-2-((2-(2,6-difluoro-4-(2,5-dioxo-2,5-dihydropyrrol-1-yl)phenyl)-7-methylimidazo[1,2-a]pyridin-3-yl)methyl)morpholine-4-carboxylate

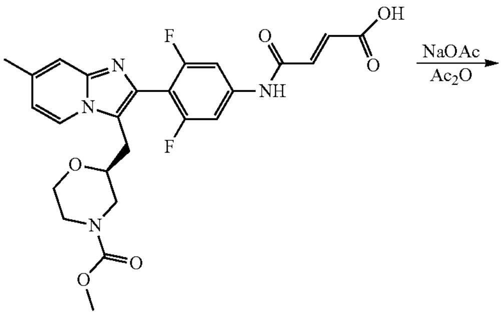

27

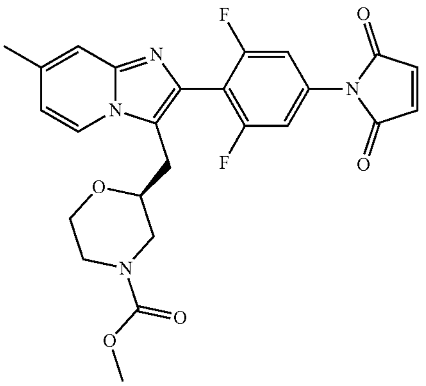

28

To a solution of compound 27 (100 mg, 0.25 mmol) in acetic anhydride (3 mL) was added sodium acetate (32.7 mg, 0.4 mmol) at room temperature. The reaction system was stirred at room temperature for 4 h. Then the reaction system was concentrated under reduced pressure. The residue was purified by preparative high performance liquid chromatography (trifluoroacetic acid method), and lyophilized to give compound 28 (40 mg, 30% yield) in the form of a white solid.

LC-MS: $[M+H]^+$=497.1. $^1$H NMR (400 MHZ, $CD_3OD$): δ8.83 (d, J=7.2 Hz, 1H), 7.71 (s, 1H), 7.56-7.52 (m, 2H), 7.43-7.39 (m, 1H), 7.68 (s, 2H), 4.02-3.99 (m, 1H), 3.83-3.69 (m, 3H), 3.67 (s, 3H), 3.36-3.33 (m, 1H), 3.30-3.22 (m, 2H), 2.92-2.90 (m, 1H), 2.87-2.73 (m, 1H), 2.64 (s, 3H).

Example 29

Preparation of methyl (S,E)-2-((2-(2,6-difluoro-4-(4-amino-4-oxobutyl-2-enamido)phenyl)-7-methylimidazo[1,2-a]pyridin-3-yl)methyl)morpholine-4-carboxylate

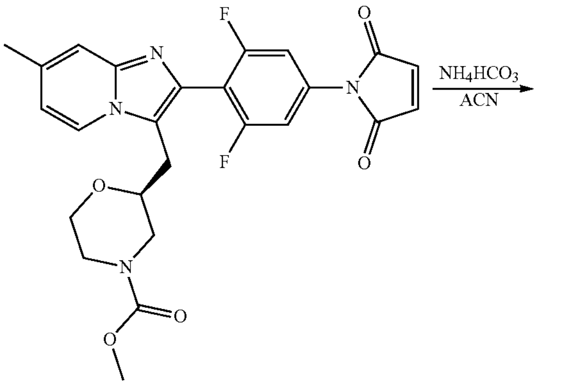

28

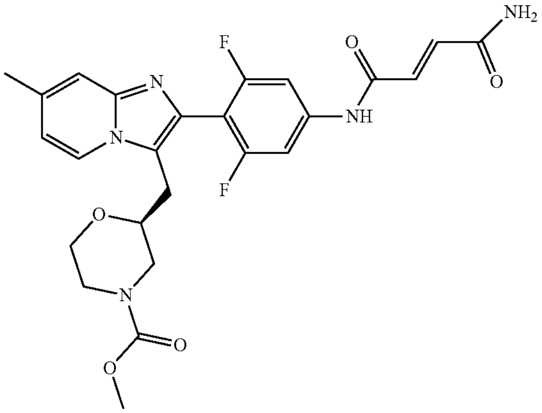

29

To a solution of compound 28 (20 mg, 0.04 mmol) in acetonitrile (3 mL) was added aqueous ammonium bicarbonate solution (5%, 2 mL) at room temperature. The reaction system was reacted at room temperature for 2 h. Then the reaction system was concentrated under reduced pressure. The residue was purified by preparative high performance liquid chromatography (ammonium bicarbonate method), and lyophilized to give compound 29 (10 mg, 40% yield) in the form of a white solid.

LC-MS: $[M+H]^+$=514.1. $^1H$ NMR (400 MHZ, DMSO-d6): δ 11.36 (s, 1H), 8.38 (d, J=7.2 Hz, 1H), 7.93 (s, 1H), 7.45-7.42 (m, 3H), 7.33 (s, 1H), 6.82-6.80 (m, 1H), 6.35-6.28 (m, 2H), 3.73-3.62 (m, 3H), 3.55 (s, 3H), 3.51-3.46 (m, 1H), 3.25-3.22 (m, 2H), 3.02-3.00 (m, 2H), 2.83-2.79 (m, 1H), 2.37 (s, 3H).

Example 30

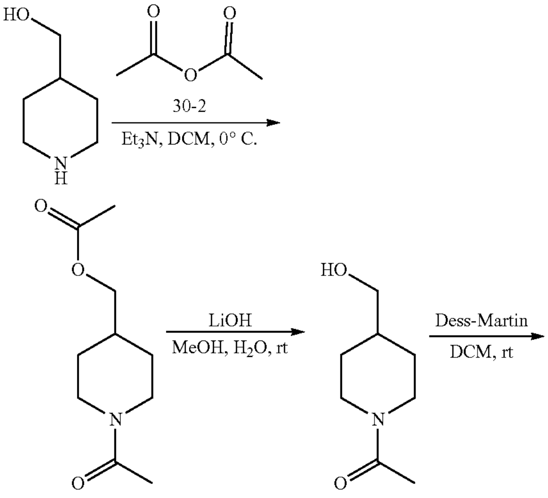

30-2

30-3

30-4

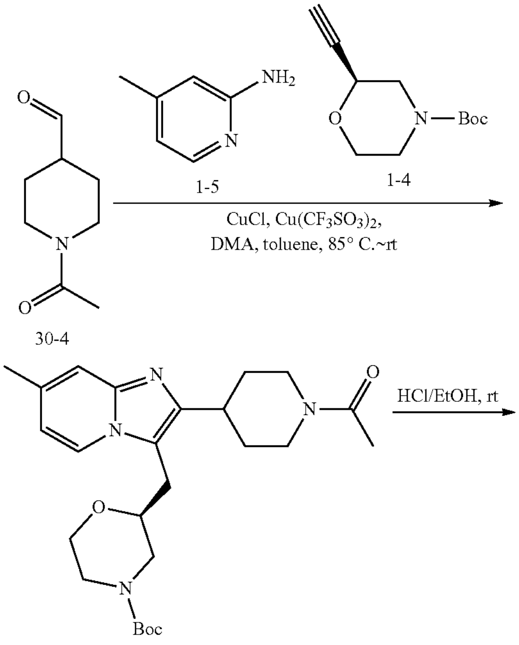

1-5

1-4

30-4

30-6

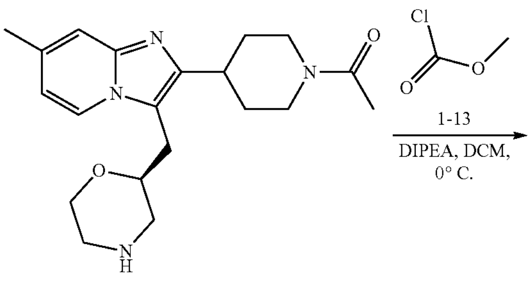

1-13

30-7

-continued

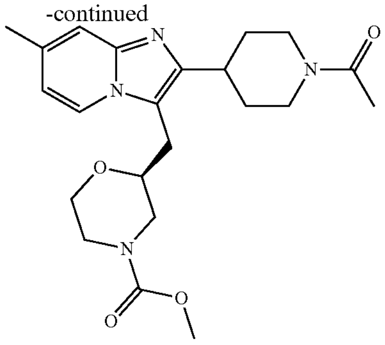

30

Step (1) Preparation of (1-acetylpiperidin-4-yl)methyl acetate 30-3

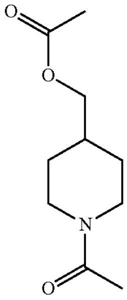

4-hydroxymethylpiperidine (5.2 g, 45.15 mmol) was dissolved in dichloromethane (60 mL), and triethylamine (13.5 g, 133.61 mmol) was added. The reaction system was cooled to 0° C., added with acetic anhydride (13.8 g, 135.4 mmol), and reacted at room temperature for 15 h. Then the reaction system was washed with diluted hydrochloric acid (1 N, 40 mL). The organic phase was dried over anhydrous sodium sulfate and concentrated to give compound 30-3 (6.2 g) in the form of a yellow oily liquid.

Step (2) Preparation of 1-(4-(hydroxymethyl)piperidin-1-yl)ethan-1-one 30-4

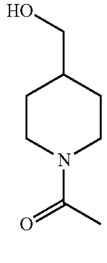

Compound 30-3 (6.2 g) was dissolved in methanol (50 mL), and aqueous lithium hydroxide solution (3.75 N, 25 mL) was added. The reaction system was stirred at room temperature for 12 h. Then the reaction system was concentrated. The residue was separated by column chromatography (EA/MeOH=50/1) to give compound 30-4 (7.5 g) in the form of a colorless oily liquid. LC-MS: $[M+H]^+=158.0$.

Step (3) Preparation of 1-acetylpiperidine-4-carbaldehyde 30-5

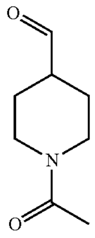

Compound 30-4 (3.2 g, 20.35 mmol) was dissolved in dichloromethane (40 mL), and Dess-Martin periodinane (12.9 g, 30.52 mmol) was added. The reaction system was reacted at room temperature for 1.5 h. Then the reaction system was added with saturated sodium thiosulfate solution (20 mL), diluted with water (40 mL), and extracted with dichloromethane (40 mL×2). The organic phase was dried over anhydrous sodium sulfate and concentrated. The residue was separated by column chromatography (EA-EA/MeOH=50/1) to give compound 30-5 (1.0 g, 31% yield) in the form of a white solid. LC-MS: $[M+H]^+=156.1$.

Step (4) Preparation of tert-butyl (S)-2-((2-(1-acetylpiperidin-4-yl)-7-methylimidazo[1,2-a]pyridin-3-yl)methyl)morpholine-4-carboxylate 30-6

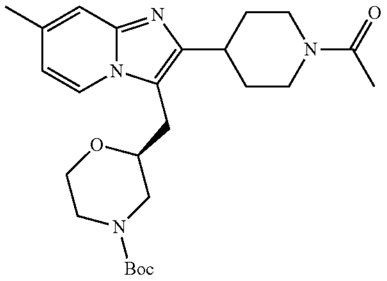

Compound 30-5 (200 mg, 1.29 mmol) was dissolved in anhydrous toluene (40 mL), and 4-methyl-2-aminopyridine (140 mg, 1.29 mmol), tert-butyl (S)-2-ethynylmorpholine-4-carboxylate (272 mg, 1.29 mmol), copper(I) chloride (40 mg, 0.4 mmol), and copper(II) trifluoromethanesulfonate (140 mg, 0.39 mmol) were added. Under nitrogen atmosphere, the reaction system was heated to 85° C., added with two drops of N,N-dimethylacetamide, heated and stirred for 6 h. Then the reaction system was cooled to room temperature and stirred overnight. The resulting reaction system was filtered, and the filtrate was concentrated. The residue was separated by column chromatography (DCM/MeOH=20/1) to give intermediate 30-6 (227 mg, 38% yield) in the form of a yellow solid. LC-MS: $[M+H]^+=456.8$.

Step (5) Preparation of (S)-1-(4-(7-methyl-3-(morpholin-2-ylmethyl)imidazo[1,2-a]pyridin-2-yl)piperidin-1-yl) acetamide 30-7

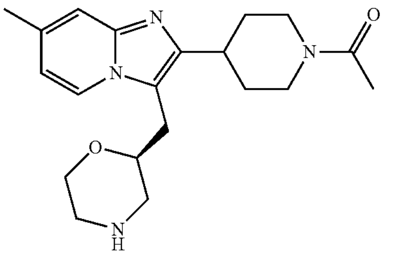

Intermediate 30-6 (227 mg, 0.49 mmol) was dissolved in ethanol (2 mL), and a solution of HCl in ethanol (1 mL, 33%) was added. The reaction system was stirred at room temperature for 1.5 h. Then the reaction system was concentrated to give intermediate 30-7 (250 mg, crude product), which was used directly in the next step. LC-MS $[M+H]^+$=357.8.

Step (6) Preparation of methyl (S)-2-((2-(1-acetylpiperidin-4-yl)-7-methylimidazo[1,2-a]pyridin-3-yl)methyl)morpholine-4-carboxylate

30

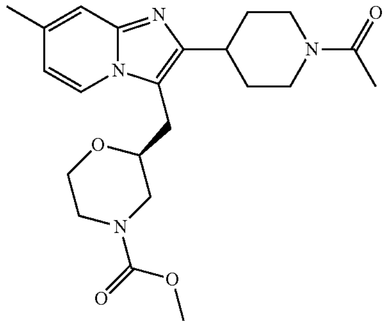

Intermediate 30-7 (356 mg) was dissolved in dichloromethane (5 mL), and pyridine (244 mg, 3.09 mmol) was added, followed by the addition of methyl chloroformate (62 mg, 0.65 mmol). The reaction system was stirred at room temperature for 1.5 h. Then the reaction system was concentrated to give compound 30 (360 mg, 87% yield).

LC-MS: $[M+H]^+$=415.6. $^1$HNMR (400 MHZ, MeOD): δ 8.42 (s, 1H), 7.56 (d, 1H), 6.91 (d, 1H), 3.82 (m, 3H), 3.67 (s, 3H), 3.60 (m, 1H), 3.54 (t, 4H) 3.38 (dd, 1H), 3.12 (m, 2H), 2.90 (m, 2H), 2.83 (m, 2H), 2.64 (m, 2H), 2.10 (s, 3H), 1.69 (m, 4H).

Example 31

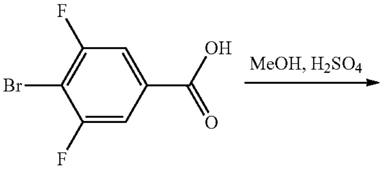

31-1

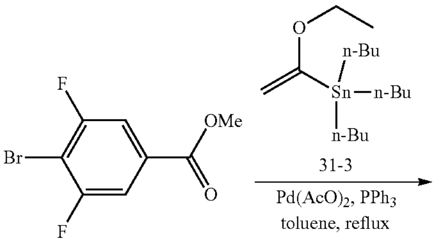

31-2

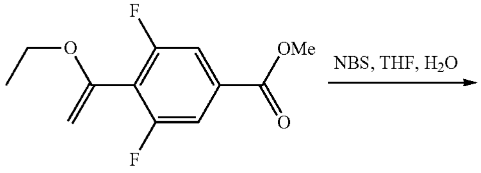

31-4

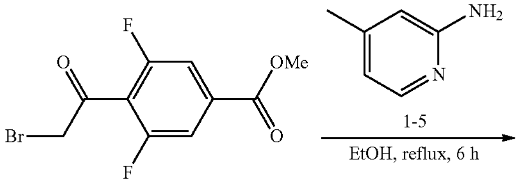

31-5

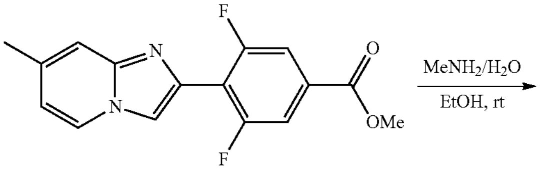

31-6

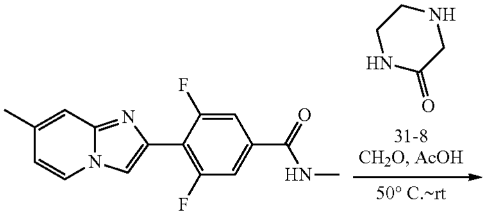

31-7

-continued

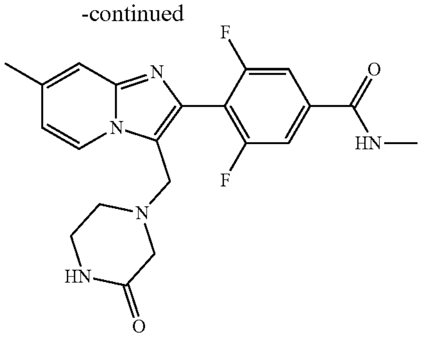

31

Step (1) Preparation of methyl 4-bromo-3,5-difluorobenzoate 31-2

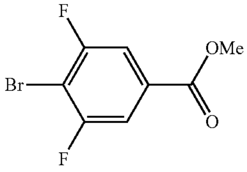

4-bromo-3,5-difluorobenzoic acid (11.5 g, 48.5 mmol) was dissolved in methanol (100 mL), and concentrated sulfuric acid (1.0 mL) was added. The reaction system was reacted under reflux for 15 h. Then the reaction system was concentrated, diluted with water (50 mL) and extracted with ethyl acetate (50 mL×2). The organic phase was dried over anhydrous sodium sulfate and concentrated. The residue was separated by column chromatography (PE) to give compound 31-2 (10 g, 82% yield) in the form of a colorless oily liquid.

Step (2) Preparation of methyl 4-(1-ethoxyethenyl)-3,5-difluorobenzoate 31-4

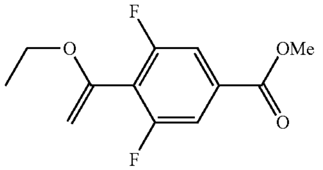

Compound 31-2 (10.0 g, 39.83 mmol) was dissolved in anhydrous toluene (90 mL), and palladium acetate (449 mg, 2 mmol), triphenylphosphine (2.0 g, 8.0 mmol) and tributyl (1-ethoxyethenyl) stannane (15.9 g, 44 mmol) were added. The reaction system was refluxed overnight under nitrogen atmosphere. Then the reaction system was concentrated, diluted with water (100 mL) and extracted with ethyl acetate (50 mL×3). The ethyl acetate phases were combined, dried over anhydrous sodium sulfate, and concentrated. The residue was separated by column chromatography (PE) to give compound 31-4 (7.4 g, 76% yield) in the form of a colorless liquid. LC-MS: $[M+H]^+$=214.8/242.8.

Step (3) Preparation of methyl 4-(2-bromoacetyl)-3,5-difluorobenzoate 31-5

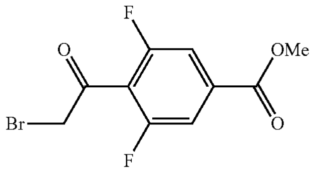

Compound 31-4 (7.4 g, 30.46 mmol) was dissolved in tetrahydrofuran (60 mL) and water (20 mL), and N-bromosuccinimide (5.4 g, 30.46 mmol) was added. The reaction system was reacted at room temperature for 1 h under nitrogen atmosphere. Then the reaction system was concentrated to half volume, diluted with water (60 mL), and extracted with ethyl acetate (30 mL×3). The ethyl acetate phases were combined, dried over anhydrous sodium sulfate, and concentrated to give intermediate 31-5 (9.0 g) in the form of a yellow solid. LC-MS: $[M+H]^+$=292.5.

Step (4) Preparation of methyl 3,5-difluoro-4-(7-methylimidazo[1,2-a]pyridin-2-yl)benzoate 31-6

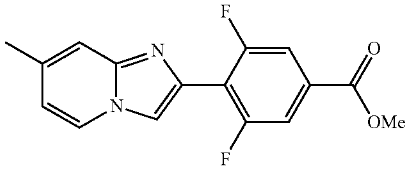

Intermediate 31-5 (9.0 g) was dissolved in ethanol (90 mL), and 4-methyl-2-aminopyridine (3.3 g, 30.47 mmol) was added. The reaction system was reacted under reflux for 12 h under nitrogen atmosphere. Then the reaction system was concentrated, diluted with water (60 mL), adjusted to pH 7-8 with saturated sodium bicarbonate solution, and extracted with ethyl acetate (40 mL×3). The ethyl acetate phases were combined, dried over anhydrous sodium sulfate, and concentrated. The residue was purified by column chromatography (PE/EA=1/1) to give intermediate 31-6 (4.2 g, 56% yield) in the form of a yellow solid.

LC-MS: $[M+H]^+$=303.8.

Step (5) Preparation of 3,5-difluoro-N-methyl-4-(7-methylimidazo[1,2-a]pyridin-2-yl)benzamide 31-7

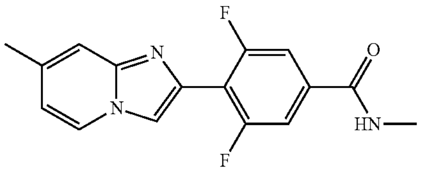

Intermediate 31-6 (1.5 g, 4.96 mmol) was dissolved in ethanol (15 mL), and aqueous methylamine solution (6 mL, 25-30%) was added. The reaction system was stirred at room temperature for 12 h. Then the reaction system was concentrated. The residue was separated by column chromatography (EA-EA/MeOH=50/1) to give intermediate 31-7 (1.1 g, 73% yield) in the form of a yellow solid. LC-MS: $[M+H]^+$=302.8.

Step (6) Preparation of 3,5-difluoro-4-(7-methyl-3-((3-oxopiperazin-1-yl)methyl)imidazo[1,2-a]pyridin-2-yl)benzamide

31

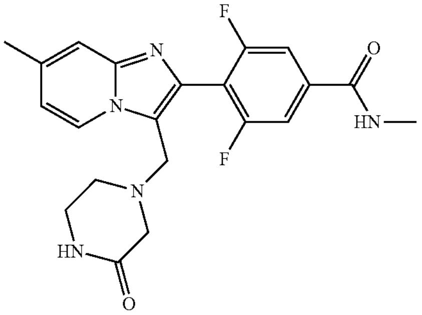

Intermediate 31-7 (150 mg, 0.49 mmol) and piperazin-2-one (50 mg, 0.49 mmol) were dissolved in acetic acid (1 mL), and aqueous formaldehyde solution (40 mg, 37%) was added. The reaction system was heated to 50° C. and reacted for 3 h. Then the reaction system was cooled to room temperature and stirred for 12 h. The resulting reaction system was diluted with dichloromethane (10 mL), and adjusted to pH 8 with aqueous sodium hydroxide solution (2 N). The aqueous phase was extracted with dichloromethane (10 mL×2). The organic phases were combined, dried over anhydrous sodium sulfate and concentrated. The residue was purified by preparative thin-layer chromatography (DCM/MeOH=20/1) to give compound 31 (39.2 mg, 19% yield) in the form of a white solid.

LC-MS: $[M+H]^+$=414.8. $^1H$ NMR (400 MHZ, MeOD): δ 8.52 (d, J=7.1 Hz, 1H), 7.62 (d, J=8.0 Hz, 2H), 7.40 (s, 1H), 6.94 (dd, J=7.1, 1.5 Hz, 1H), 3.90 (s, 2H), 3.21 (t, J=5.4 Hz, 2H), 3.05 (s, 2H), 2.97 (s, 3H), 2.66-2.54 (m, 2H), 2.48 (s, 3H).

Example 32

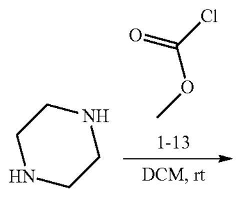

32-1

-continued

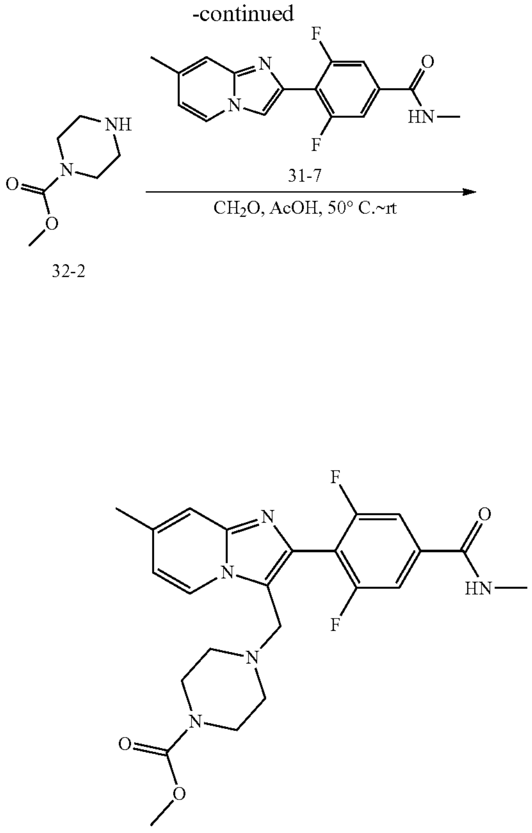

31-7

32-2

32

Step (1) Preparation of methyl piperazine-1-carboxylate 32-2

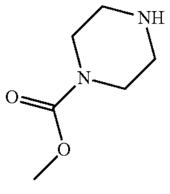

Piperazine (3 g, 34.8 mmol) was dissolved in dichloromethane (50 mL), and methyl chloroformate (658 mg, 6.96 mmol) was added in portions. The reaction system was reacted at room temperature for 30 min. Then the reaction system was added with aqueous potassium hydroxide solution (50 mL, 1 N) to quench the reaction, and extracted with dichloromethane (50 mL×3). The organic phases combined, dried over anhydrous sodium sulfate, and concentrated to give a white solid (1.8 g, 36% yield). LC-MS: $[M+H]^+$=145.7.

Step (2) Preparation of methyl (S)-2-((2-(2,6-difluoro-4-(methylcarbamoyl)phenyl)-7-methylimidazo [1,2-a]pyridin-3-yl)methyl)piperazine-4-carboxylate

32

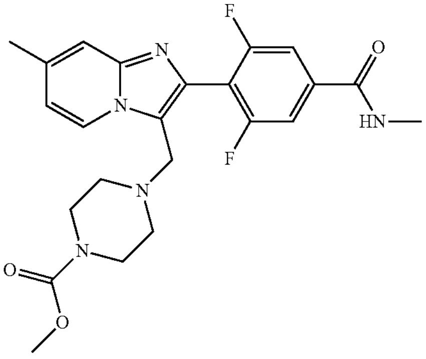

Intermediate 31-7 (150 mg, 0.49 mmol) and compound 32-2 (180 mg) were dissolved in acetic acid (1 mL), and aqueous formaldehyde solution (40 mg, 37%) was added. The reaction system was heated to 50° C. and reacted for 3 h. Then the reaction system was cooled to room temperature and stirred for 12 h. The resulting reaction system was diluted with dichloromethane (10 mL), and adjusted to pH 8 with aqueous sodium hydroxide solution (2 N). The aqueous phase was extracted with dichloromethane (15 mL×2). The organic phases were combined, dried over anhydrous sodium sulfate and concentrated. The residue was separated by HPLC to give compound 32 (98.2 mg, 43% yield) in the form of a white solid.

LC-MS: $[M+H]^+$=458.7. $^1$HNMR: $^1$H NMR (400 MHZ, MeOD): δ 8.55 (d, J=7.0 Hz, 1H), 7.60 (d, J=7.9 Hz, 2H), 7.39 (s, 1H), 6.94 (d, J=7.1 Hz, 1H), 3.80 (s, 2H), 3.66 (s, 3H), 3.47-3.36 (m, 4H), 2.97 (s, 3H), 2.49 (s, 3H), 2.37-2.29 (m, 4H).

Example 33

Preparation of 3,5-difluoro-N-methyl-4-(7-methyl-3-(morpholinomethyl)imidazo[1,2-a]pyridin-2-yl)-benzamide

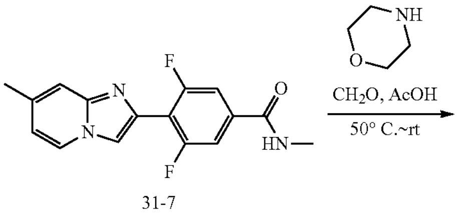

31-7

-continued

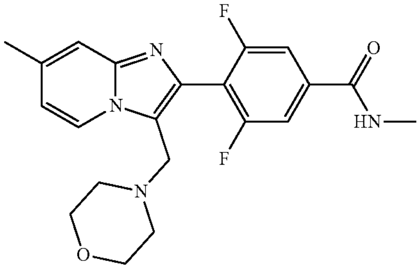

33

Intermediate 31-7 (100 mg, 0.33 mmol) and morpholine (29 mg, 0.33 mmol) were dissolved in acetic acid (0.5 mL), and aqueous formaldehyde solution (28 mg, 37%) was added. The reaction system was heated to 50° C. and reacted for 3 h. Then the reaction system was cooled to room temperature and stirred for 12 h. The resulting reaction system was diluted with dichloromethane (15 mL), and adjusted to pH & with aqueous sodium hydroxide solution (2 N). The aqueous phase was extracted with dichloromethane (10 mL×2). The organic phases were combined, dried over anhydrous sodium sulfate and concentrated. The residue was purified by HPLC to give compound 33 (50.2 mg, 38% yield) in the form of a white solid.

LC-MS: $[M+H]^+$=401.7. $^1$HNMR (400 MHZ, $CDCl_3$): δ 8.44 (d, J=7.0 Hz, 1H), 7.58-7.37 (m, 4H), 6.80 (d, J=6.9 Hz, 1H), 3.71 (s, 2H), 3.67-3.60 (m, 4H), 3.03 (d, J=4.6 Hz, 3H), 2.48 (s, 3H), 2.39-2.31 (m, 4H).

Example 34

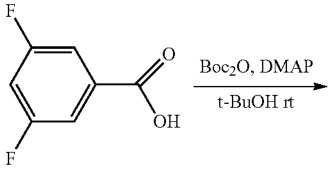

34-1

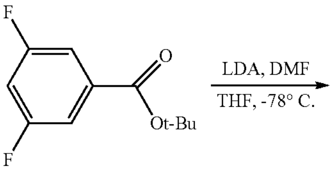

34-2

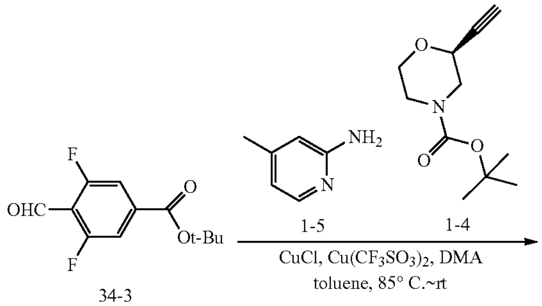

34-3

-continued

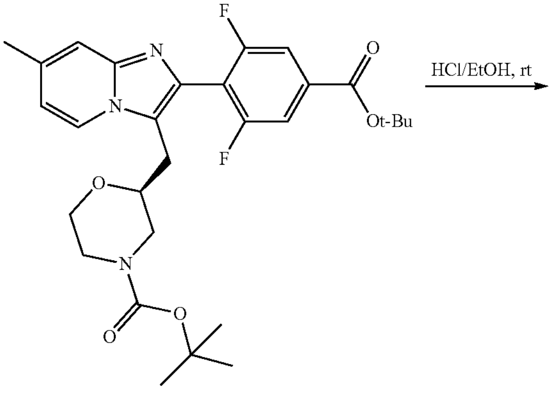

34-4

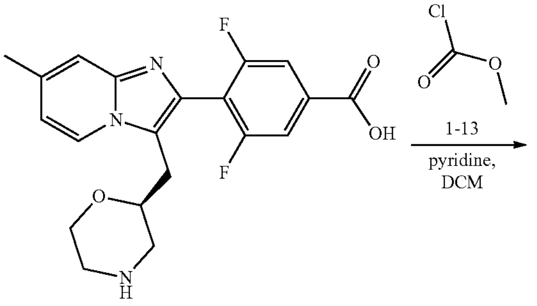

34-5

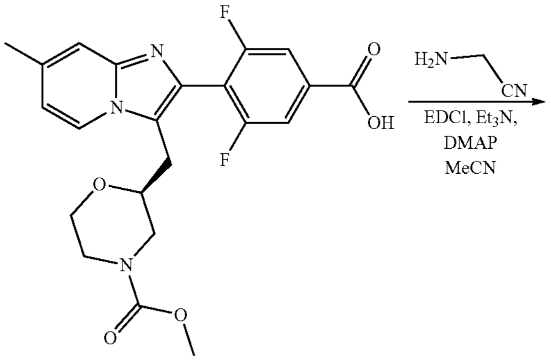

34-6

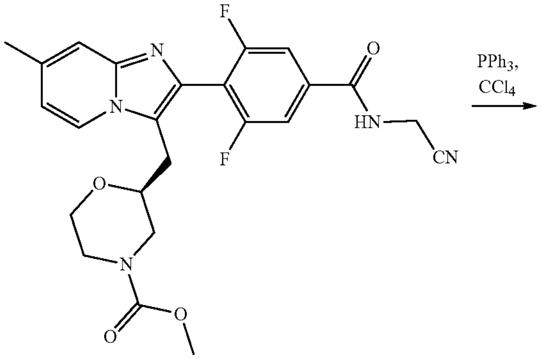

34-7

-continued

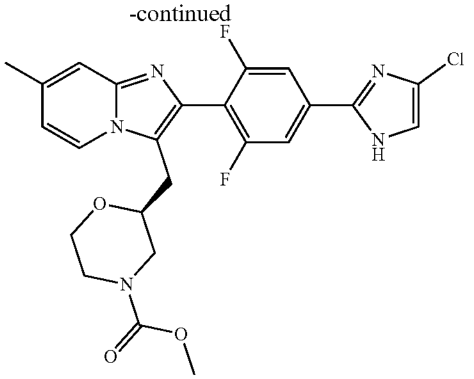

34

Step (1) Preparation of tert-butyl 3,5-difluorobenzoate 34-2

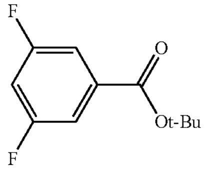

3,5-difluorobenzoic acid (10.0 g, 63.25 mmol) was dissolved in tert-butanol (100 mL), and DMAP (2.3 g, 18.98 mmol) and di-tert-butyl dicarbonate (27.6 g, 126.50 mmol) were added. The reaction system was reacted at room temperature for 15 h. Then the reaction system was concentrated, diluted with water (80 mL) and extracted with ethyl acetate (50 mL×2). The organic phase was dried over anhydrous sodium sulfate and concentrated. The residue was separated by column chromatography (PE/EA=20/1) to give compound 34-2 (12.0 g, 88% yield) in the form of a colorless oily liquid.

Step (2) Preparation of tert-butyl 3,5-difluoro-4-formylbenzoate 34-3

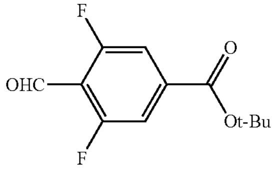

LDA (2 N, 8.4 mL) was dissolved in tetrahydrofuran (10 mL). The reaction system was cooled to −78° C. under nitrogen atmosphere. Compound 34-2 (3.0 g, 14.0 mmol) was dissolved in tetrahydrofuran (20 mL), and the solution was added to the reaction system. The reaction system was stirred at −78° C. for 1.5 h, added with DMF (1.2 g, 16.8 mmol), and stirred for another 1 h with the temperature maintained not higher than −70° C. Then the reaction system was added with saturated ammonium chloride solution (60 mL) to quench the reaction, and extracted with ethyl acetate (30 mL×3). The ethyl acetate phases were combined, dried over anhydrous sodium sulfate, and concentrated. The residue was separated by column chromatography (PE/EA=10/1) to give compound 34-3 (1.5 g, 44% yield) in the form of a yellow solid.

Step (3) Preparation of tert-butyl (S)-2-((2-(4-(tert-butoxycarbonyl)-2,6-difluorophenyl)-7-methylimidazo[1,2-a]pyridin-3-yl)methyl)morpholine-carboxylate 34-4

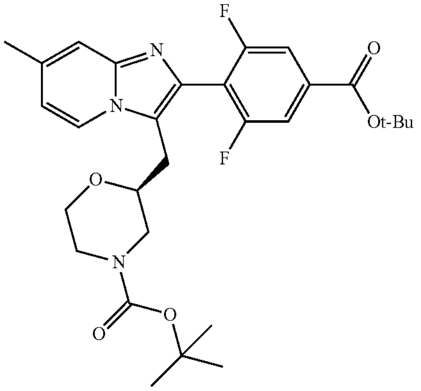

Compound 34-3 (480 mg, 1.98 mmol) was dissolved in anhydrous toluene (4 mL), and 4-methyl-2-aminopyridine (215 mg, 1.98 mmol), tert-butyl (S)-2-ethynylmorpholine-4-carboxylate (419 mg, 1.98 mmol), copper (1) chloride (62 mg, 0.63 mmol), and copper(II) trifluoromethanesulfonate (216 mg, 0.60 mmol) were added. Under nitrogen atmosphere, the reaction system was heated to 85° C., added with two drops of N,N-dimethylacetamide, heated and stirred for 6 h. Then the reaction system was cooled to room temperature and stirred overnight. The resulting reaction system was filtered, and the filtrate was concentrated. The residue was separated by column chromatography (PE/EA=2/1) to give intermediate 34-4 (340 mg, 31% yield) in the form of a brown solid. LC-MS: $[M+H]^+$=544.7.

Step (4) Preparation of (S)-3,5-difluoro-4-(7-methyl-3-(morpholinyl-2-methyl)imidazo[1,2-a]pyridin-2-yl)benzoic acid 34-5

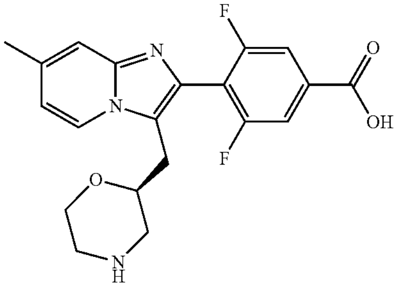

Intermediate 34-4 (340 mg, 0.62 mmol) was dissolved in ethanol (3 mL), and a solution of HCl in ethanol (1 mL, 33%) was added. The reaction system was stirred at room temperature for 1.5 h. Then the reaction system was concentrated to give intermediate 34-5 (400 mg) in the form of a yellow oily liquid.

LC-MS: $[M+H]^+$=388.7.

Step (5) Preparation of (S)-3,5-difluoro-4-(3-((4-(methoxycarbonyl)morpholin-2-yl)methyl)-7-methylimidazo[1,2-a]pyridin-2-yl)benzoic acid 34-6

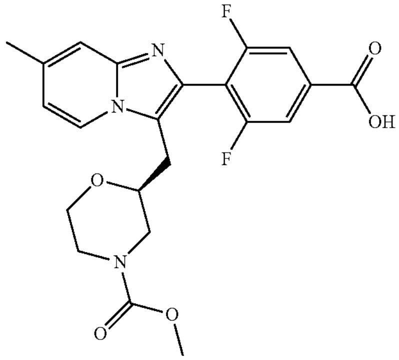

Intermediate 34-5 (400 mg) was dissolved in dichloromethane (5 mL), and pyridine (244 mg, 3.09 mmol) was added, followed by the addition of methyl chloroformate (62 mg, 0.65 mmol). The reaction system was stirred at room temperature for 1.5 h, and concentrated to give intermediate 34-6 (190 mg).

LC-MS: $[M+H]^+$=446.6.

Step (6) Preparation of methyl (S)-2-((2-(4-((cyanomethyl)carbamoyl)-2,6-difluorophenyl)-7-methylimidazo[1,2-a]pyridin-3-yl)methyl)morpholine-4-carboxylate 34-7

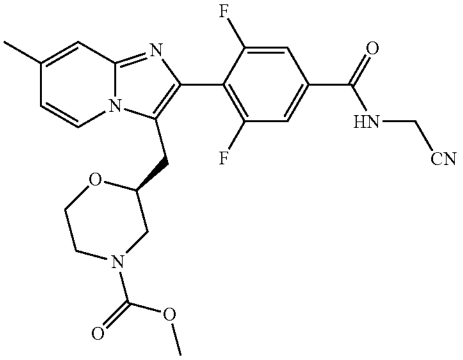

Intermediate 34-6 (445 mg, 1 mmol) was dissolved in $CH_3CN$ (10 mL), and triethylamine (1.2 mmol), DMAP (1.2 mmol) and EDCl (1.2 mmol) were added. The reaction system was stirred at room temperature overnight. After the reaction was completed, the reaction system was purified by column chromatography to give intermediate 34-7 (362 mg, 75% yield). LC-MS: $[M+H]^+$=484.6.

Step (7) Preparation of methyl (S)-2-((2-(4-(4-chloro-1H-imidazol-2-yl)-2,6-difluorophenyl)-7-methylimidazo[1,2-a]pyridin-3-yl)methyl)morpholine-4-carboxylate

34

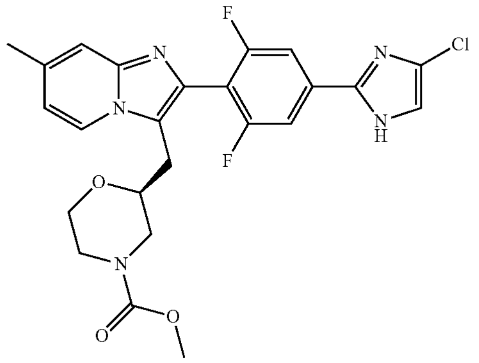

Intermediate 34-7 (483 mg, 1 mmol) was dissolved in THF (10 mL), and a certain amount of $CCl_4$ and $PPh_3$ was added. The reaction system was heated to 50° C., and detected by LC-MS for completion. After the reaction was completed, the reaction system was purified by column chromatography to give compound 34 (50 mg, 10% yield). LC-MS: $[M+H]^+$=502.1.

Example 35

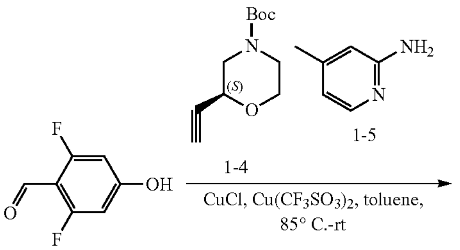

1-4

1-5

35-1

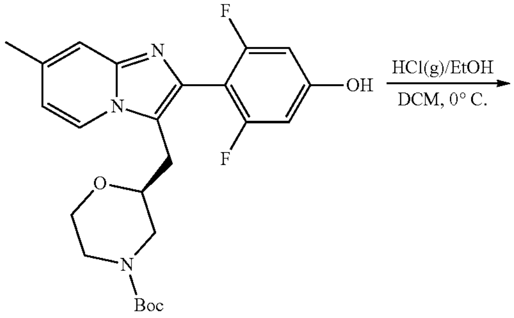

35-2

-continued

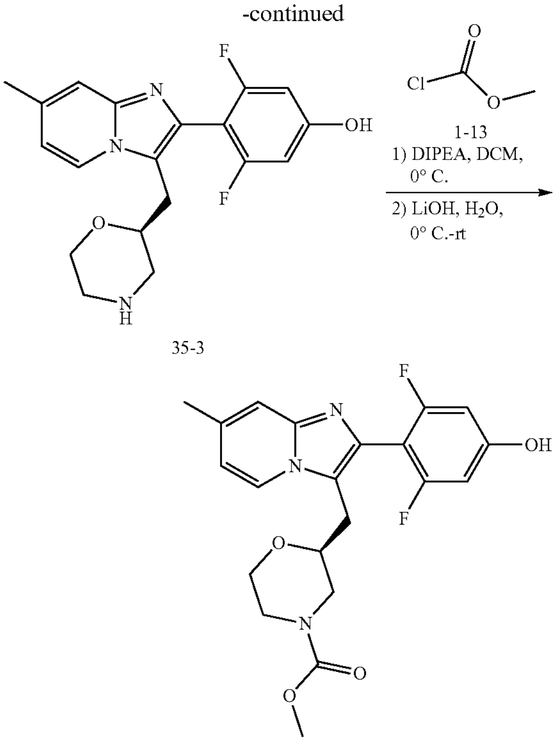

1-13

35-3

35

Step (1) Preparation of tert-butyl (S)-2-((2-(2,6-difluoro-4-hydroxyphenyl)-7-methylimidazo[1,2-a]pyridin-3-yl)methyl)morpholine-4-carboxylate 35-2

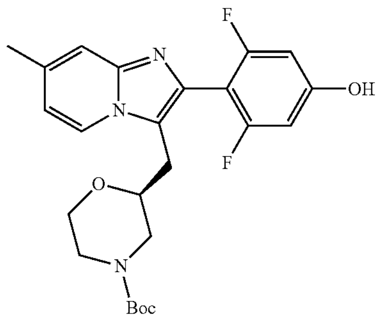

2,6-difluoro-4-hydroxybenzaldehyde (2.0 g, 9.05 mmol), 4-methylpyridin-2-amine (0.97 g, 9.05 mmol), compound 1-4 (1.9 g, 9.05 mmol), copper(I) chloride (0.27 g, 2.70 mmol) and copper(II) trifluoromethanesulfonate (0.98 g, 2.70 mmol) were dissolved in toluene solution (20 mL) under nitrogen atmosphere. The reaction system was reacted at 85° C. for 10 min, added with N,N-dimethylacetamide (0.5 mL), and reacted at 85° C. for another 5 h. Then the reaction system was reacted at room temperature overnight. After the reaction was completed, the reaction system was added with water (40 mL), and extracted with dichloromethane (50 mL×3). The organic phases were combined, washed with saturated brine (50 mL), dried over magnesium sulfate, filtered and concentrated by rotary evaporation. The crude product was purified by silica gel column chromatography (40 g of silica gel, petroleum ether:ethyl acetate=1:1) to give intermediate 35-2 (1.2 g, 29% yield) in the form of a yellow oil. LC-MS: $[M+H]^+$=460.1.

Step (2) Preparation of (S)-3,5-difluoro-4-(7-methyl-3-(morpholin-2-ylmethyl)imidazo[1,2-a]pyridin-2-yl) phenol 35-3

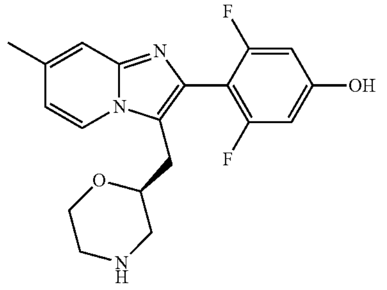

Intermediate 35-2 (1.0 g, 1.91 mmol) was dissolved in dichloromethane (10 mL), and a solution of HCl in ethanol (2 mL, 33%) was added dropwise. After the completion of the dropwise addition, the reaction system was reacted at room temperature for 2 h. After the reaction was completed, the reaction system was added dropwise with saturated sodium bicarbonate solution to adjust the pH to 8, added with water (30 mL), and extracted with dichloromethane (40 mL×3). The organic phases were combined, washed with saturated brine (40 mL), dried over magnesium sulfate, filtered and concentrated by rotary evaporation to give intermediate 35-3 (800 mg) in the form of a yellow oil. LC-MS $[M+H]^+$=360.7.

Step (3) Preparation of methyl (S)-2-((2-(2,6-difluoro-4-hydroxyphenyl)-7-methylimidazo[1,2-a]pyridin-3-yl)methyl)morpholine-4-carboxylate

35

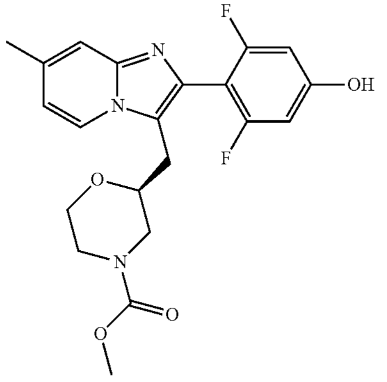

Intermediate 35-3 (350 mg, 0.97 mmol) and N,N-diisopropylethylamine (378 mg, 2.92 mmol) were dissolved in dichloromethane (10 mL), and methyl chloroformate (110 mg, 1.16 mmol) was added dropwise with the temperature maintained at 0° C. After the completion of the dropwise addition, the reaction system was reacted at 0° C. for 3 h. After the reaction was completed, the reaction system was added with lithium hydroxide (1.0 mL, 3 N) solution, and reacted at room temperature for 2 h. After the reaction was completed, the reaction system was adjusted to pH 5 with diluted hydrochloric acid, diluted with water (10 mL), and extracted with dichloromethane (15 mL×3). The organic phases were combined, washed with saturated brine (20 mL), dried over magnesium sulfate, and dried. The organic phase was filtered and concentrated by rotary evaporation. The residue was separated by HPLC to give compound 35 (150 mg, 37% yield) in the form of a yellow solid.

LC-MS: $[M+H]^+$=418.7. $^1H$ NMR (400 MHZ, MeOD): δ 8.57 (d, J=6.9 Hz, 1H), 7.47 (s, 1H), 7.08 (d, J=6.9 Hz, 1H), 6.60 (d, J=9.6 Hz, 2H), 3.92-3.76 (m, 3H), 3.68 (s, 3H), 3.69-3.57 (m, 1H), 3.39 (dd, J=11.9, 2.7 Hz, 1H). 3.16-3.10 (m, 2H), 2.98-2.86 (m, 1H), 2.74-2.63 (m, 1H), 2.53 (s, 3H).

Example 36

Preparation of methyl (S)-2-((2-(2,6-difluoro-4-(methylcarbamoyloxy)phenyl)-7-methylimidazo[1,2-a]pyridin-3-yl)methyl)morpholine-4-carboxylate

36

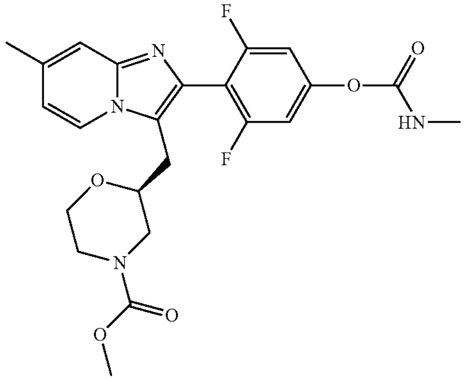

Compound 35 (359 mg, 1 mmol) was dissolved in $CH_2Cl$ (10 mL), and triethylamine (2 mmol) was added. Methylaminoformyl chloride (186 mg, 2 mmol) was dissolved in anhydrous $CH_2Cl_2$ (2 mL) and the solution was added dropwise to the reaction system. After the reaction was completed, the reaction system was neutralized and washed, dried, filtered, and purified by column chromatography to give compound 36 (62 mg, 13% yield). LC-MS $[M+H]^+$=475.1.

Example 37

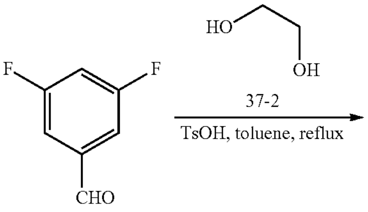

37-1

-continued

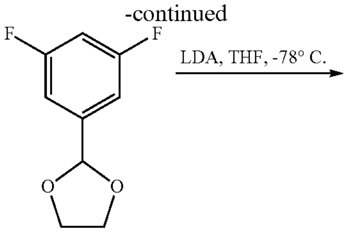

37-3

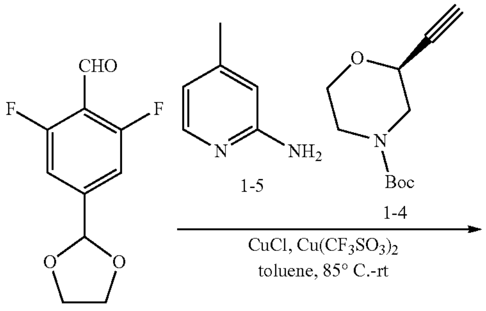

37-4

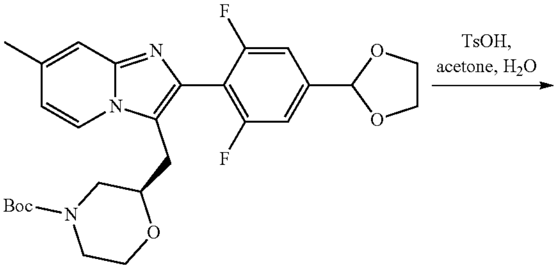

37-5

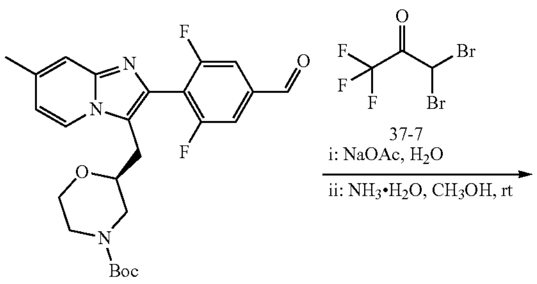

37-6

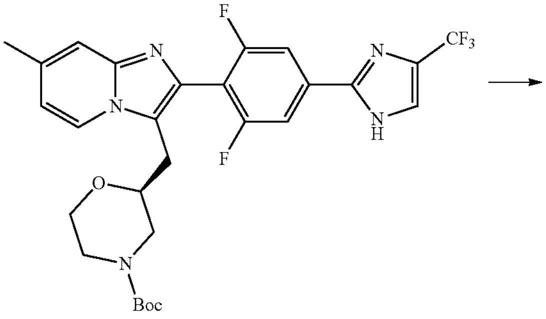

37-8

-continued

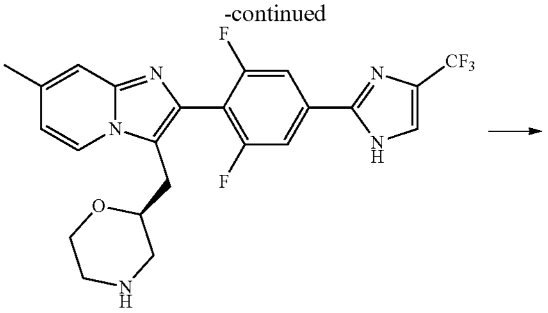

37-9

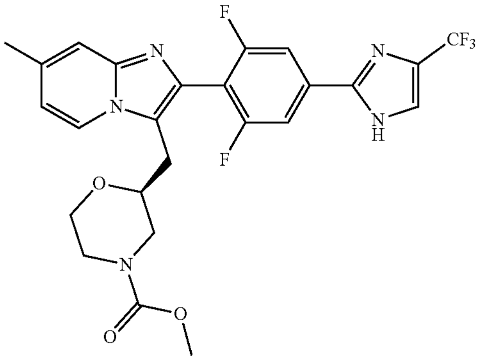

37

Step (1) Preparation of 2-(3,5-difluorophenyl)-1,3-dioxolane

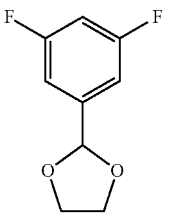

37-3

3,5-difluorobenzaldehyde (5.68 g, 40 mmol), p-toluenesulfonic acid (0.69 g, 4 mmol) and ethylene glycol (7.45 g, 120 mmol) were dissolved in toluene (80 mL). The reaction system was refluxed for separating water overnight. Then the reaction system was cooled to room temperature, diluted with ethyl acetate (40 mL) and washed with $NaHCO_3$ solution (40 mL×2). The organic phase was dried over $Na_2SO_4$ and filtered, and the filtrate was concentrated by rotary evaporation. The residue was purified by silica gel column chromatography (PE:EA=20:1) to give compound 37-3 (7.0 g, 94% yield) in the form of a white solid.

$^1H$ NMR (400 MHZ, $CDCl_3$): δ 7.03-7.00 (m, 2H), 6.82-6.76 (m, 1H), 5.79 (s, 1H), 4.09-4.05 (m, 2H), 4.07-3.99 (m, 2H).

Step (2) Preparation of 4-(1,3-dioxolan-2-yl)-2,6-difluorobenzaldehyde

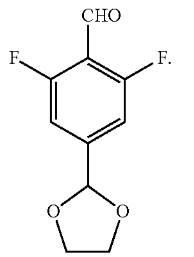

37-4

Compound 37-3 (7.0 g, 37.8 mmol) was dissolved in tetrahydrofuran (50 mL). The reaction system was cooled to −78° C. under nitrogen atmosphere, and added dropwise with LDA (22.4 mL, 44.8 mmol). After the completion of the dropwise addition, the reaction system was reacted at this temperature for 30 min, then added with anhydrous DMF (3.3 g, 44.3 mmol). After the completion of the dropwise addition, the reaction system was reacted at this temperature for 2.5 h. Then the reaction system was added with saturated $NH_4Cl$ (20 mL) to quench the reaction, diluted with water (50 mL), and extracted with ethyl acetate (50 mL×3). The organic phases were combined, washed with saturated sodium chloride solution (50 mL), dried over anhydrous sodium sulfate and filtered, and the filtrate was concentrated by rotary evaporation. The resulting crude product was purified by silica gel column chromatography (PE:EA=10:1) to give intermediate 37-4 (0.90 g, 12% yield) in the form of a white solid.

$^1$H NMR (300 MHz, DMSO): δ 10.18 (s, 1H), 7.28 (d, J=9.8 Hz, 2H), 5.82 (s, 1H), 4.06-4.00 (m, 2H), 4.01-3.93 (m, 2H).

Step (3) Preparation of tert-butyl (S)-2-((2-(4-(1,3-dioxolan-2-yl)-2,6-difluorophenyl)-7-methylimidazo[1,2-a]pyridin-3-yl)methyl)morpholine-4-carboxylate

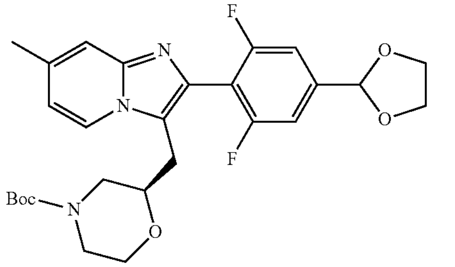

37-5

Intermediate 37-4 (100 mg, 0.47 mmol), compound 1-4 (100 mg, 0.47 mmol), 4-methylpyridin-2-amine (51 mg, 0.47 mmol), copper (1) chloride (25 mg, 0.14 mmol), and copper(II) trifluoromethanesulfonate (51 mg, 0.14 mmol) were dissolved in toluene (3 mL) in a single-necked flask. The reaction system was heated to 85° C. under nitrogen atmosphere, added dropwise with two drops of DMA and reacted at this temperature for 5 h. Then the reaction system was cooled to room temperature and stirred overnight. The resulting reaction system was diluted with water (20 mL) and extracted with ethyl acetate (20 mL×3). The organic phases were combined, washed with saturated brine (20 mL), dried over $Na_2SO_4$ and filtered, and the filtrate was concentrated by rotary evaporation. The resulting crude product was purified by silica gel column chromatography (PE:EA=5:1) to give intermediate 37-5 (150 mg, 62% yield). LC-MS: $[M+H]^+$=516.7.

Step (4) Preparation of tert-butyl (S)-2-((2-(2,6-difluoro-4-formylphenyl)-7-methylimidazo[1,2-a]pyridin-3-yl)methyl)morpholine-4-carboxylate

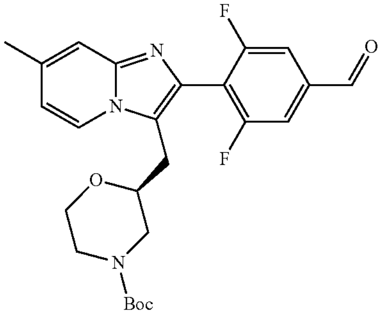

37-6

Intermediate 37-5 (150 mg, 0.29 mmol) was dissolved in acetone (10 mL) and water (1 mL), and TsOH (90 mg, 0.3 mmol) was added. The reaction system was heated to 50° C. and reacted overnight. Then the reaction system was diluted with water (50 mL), added with $Na_2CO_3$ (92 mg, 0.87 mmol) and $(Boc)_2O$ (75 mg, 0.35 mmol), stirred for 1.5 h and extracted with ethyl acetate (15 mL×2). The organic phases were combined, dried over anhydrous $Na_2SO_4$ and filtered, and the filtrate was concentrated by rotary evaporation. The resulting crude product was purified by silica gel column chromatography (PE:EA=5:1) to give intermediate 37-6 (60 mg, 44.8% yield) in the form of a white solid. LC-MS: $[M+H]^+$=472.7.

Step (5) Preparation of tert-butyl (S)-2-((2-(2,6-difluoro-4-(4-trifluoromethyl-1H-imidazol-2-yl)phenyl)-7-methylimidazo[1,2-a]pyridin-3-yl)methyl)morpholine-4-carboxylate

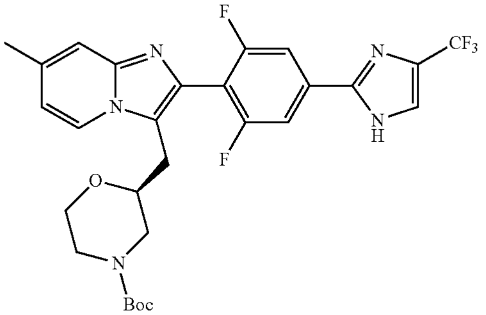

37-8

3,3-dibromo-1,1,1-trifluoropropan-2-one (35 mg, 0.13 mmol) was dissolved in sodium acetate (2 mL, 15 weight %) solution. The reaction system was stirred at 90° C. for 30 min and cooled to room temperature. Intermediate 37-6 (50 mg, 0.11 mmol) was dissolved in methanol (3 mL) and strong ammonia (0.6 mL), and the solution was added to the reaction system, and stirred at room temperature overnight. Then the reaction system was concentrated by rotary evaporation. The residual liquid was extracted with ethyl acetate (5 mL×3) and washed with saturated brine (10 mL). The organic phase was dried over $Na_2SO_4$ and filtered, and the filtrate was concentrated by rotary evaporation. The crude product was purified by silica gel column chromatography (dichloromethane:methanol=50:1) to give intermediate 37-8 (45 mg, 72.2% yield) in the form of a white solid. LC-MS: $[M+H]^+$=578.6.

Step (6) Preparation of (S)-2-((2-(2,6-difluoro-4-(4-trifluoromethyl-1H-imidazole)phenyl)-7-methylimidazo[1,2-a]pyridin-3-yl)methyl)morpholine 37-9

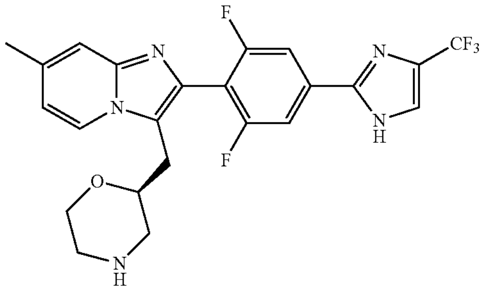

Intermediate 37-8 (45 mg, 0.08 mmol) was dissolved in dichloromethane (3 mL), and a solution of HCl in ethanol (0.5 mL) was added. The reaction system was stirred at room temperature for 3 h. Then the reaction system was concentrated by rotary evaporation to give intermediate 37-9 (80 mg, crude product).

LC-MS: $[M+H]^+$=478.7.

Step (7) Preparation of methyl (S)-2-((2-(2,6-difluoro-4-(4-trifluoromethyl-1H-imidazol-2-yl)phenyl)-7-methylimidazo[1,2-a]pyridin-3-yl)methyl) morpholine-4-carboxylate

37

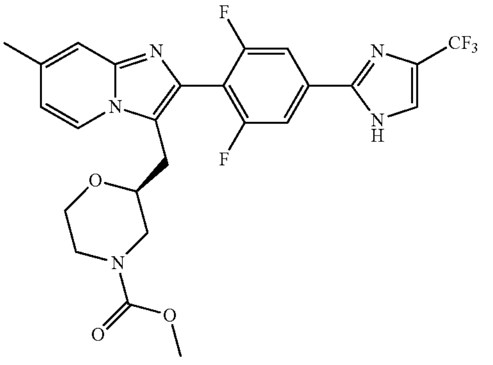

Intermediate 37-9 (80 mg, crude product) and DIPEA (30 mg, 0.23 mmol) were dissolved in dichloromethane (3 mL). The reaction system was cooled to 0° C. and stirred for 10 min. Then the reaction system was added dropwise with a solution of methyl chloroformate in dichloromethane (0.1 N, 0.8 mL), stirred for 3 h, added with water (10 mL) to quench the reaction and extracted with ethyl acetate (10 mL×3). The organic phase was dried over $Na_2SO_4$ and filtered, and the filtrate was concentrated by rotary evaporation. The crude product was purified by silica gel column chromatography (dichloromethane:methanol=20:1), prepared and lyophilized to give compound 37 (7.0 mg, 16.3% yield) in the form of a white solid product.

LC-MS: $[M+H]^+$=536.7. $^1$H NMR (400 MHZ, $CDCl_3$): δ 13.18 (s, 1H), 8.58 (brs, 1H), 7.97-7.93 (m, 3H), 7.53 (s, 1H), 7.16 (d, J=6.0 Hz, 1H), 4.05-3.70 (m, 3H), 3.71 (s, 3H), 3.64-3.56 (m, 1H), 3.45-3.30 (m, 1H), 3.09-2.85 (m, 3H), 2.74-2.64 (m, 1H), 2.60 (s, 3H).

Example 38

Preparation of methyl (S)-2-((2-(2,6-difluoro-4-(4-cyano-1H-imidazol-2-yl)phenyl)-7-methylimidazo[1,2-a]pyridin-3-yl)methyl)morpholine-4-carboxylate

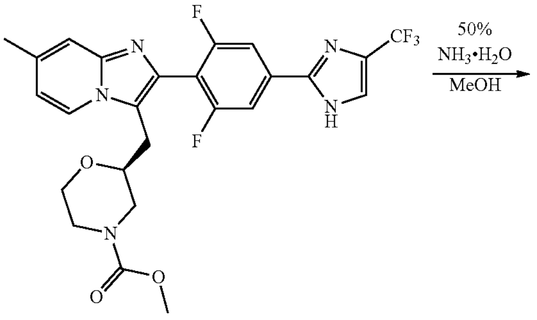

37

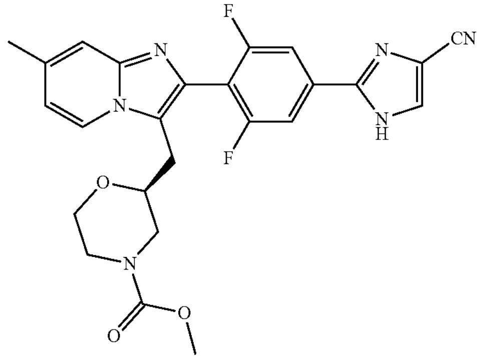

38

Compound 37 (30 mg, 0.05 mmol) was dissolved in methanol (2 mL), and strong ammonia (0.8 mL) and water (0.8 mL) were added. The reaction system was stirred at room temperature for 36 h. Then the reaction system was diluted with water (10 mL) and extracted with ethyl acetate (10 mL×3). The organic phase was dried over $Na_2SO_4$ and filtered, and the filtrate was concentrated by rotary evaporation. The crude product was purified by preparative thin-layer chromatography (dichloromethane:methanol=20:1) and lyophilized to give compound 38 (11 mg, 44.6% yield) in the form of a white solid product.

LC-MS: $[M+H]^+$=493.6. $^1$H NMR (400 MHZ, $CDCl_3$): δ 15.61 (brs, 1H), 8.31 (d, J=7.0 Hz, 1H), 7.74 (s, 1H), 7.47

(s, 1H), 7.33 (d, J=7.2 Hz, 2H), 6.85 (d, J=7.0 Hz, 1H), 3.97-3.72 (m, 3H), 3.66 (s, 3H), 3.62-3.52 (m, 1H), 3.42-3.30 (m, 1H), 3.03-2.85 (m, 3H), 2.65-2.55 (m, 1H), 2.54 (s, 3H).

Example 39

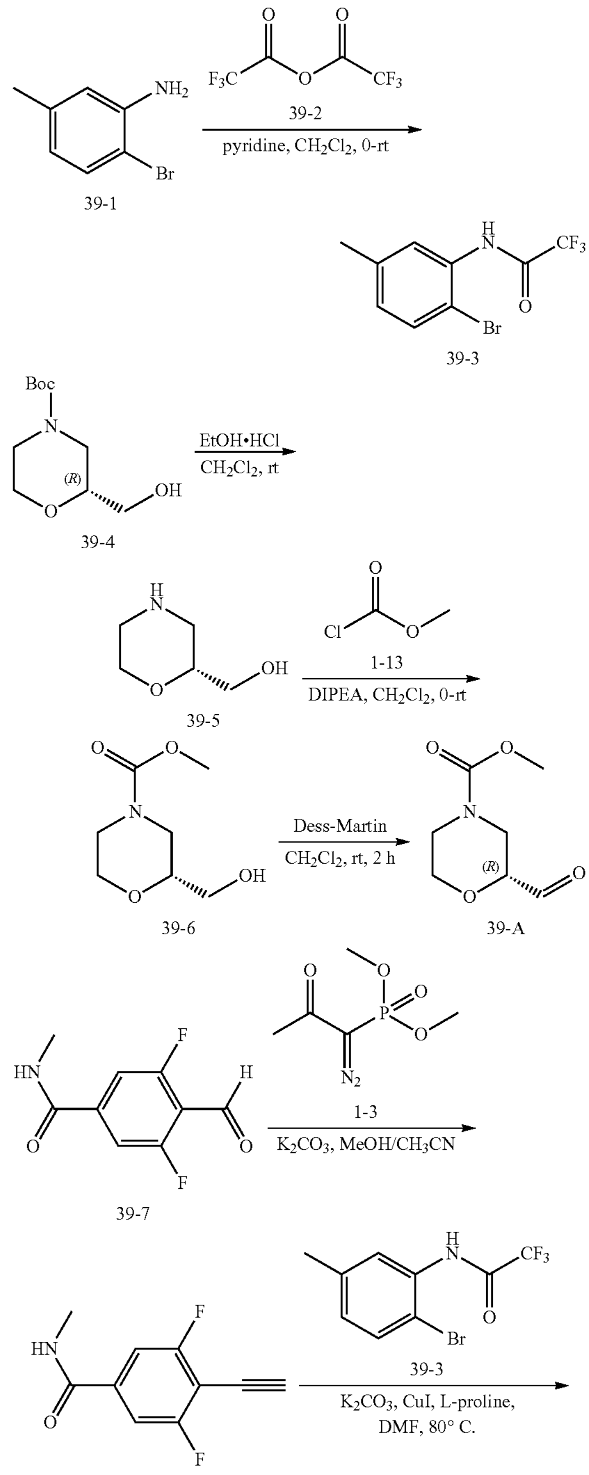

-continued

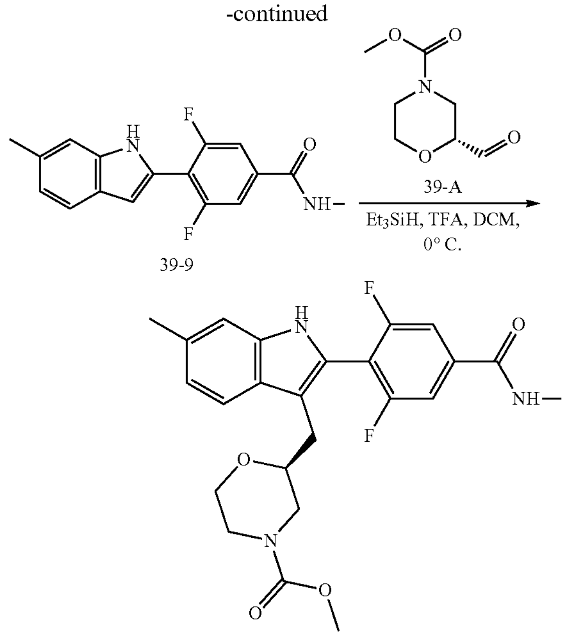

39

Step (1) Preparation of N-(2-bromo-5-methylphenyl)-2,2,2-trifluoroacetamide 39-3

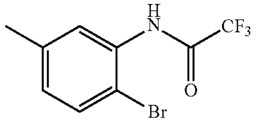

2-bromo-5-methylbenzenamine (2.5 g, 13.44 mmol) and pyridine (3.3 mL, 40.32 mmol) were dissolved in dichloromethane (30 mL). The reaction system was added dropwise with trifluoroacetic anhydride (3.4 g, 16.12 mmol) at 0° C. and reacted at room temperature overnight. The reaction mixture was washed with water (10 mL×2) and diluted hydrochloric acid (30 mL, 1 mol/L) sequentially, dried over anhydrous magnesium sulfate, filtered, and concentrated under reduced pressure to give compound 39-3 (3.4 g, 90% yield) in the form of a gray solid, LC-MS: $[M+H]^+$=281.7.

Step (2) Preparation of R-(morpholin-2-yl) methanol 39-5

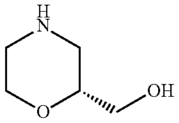

(R)—N-Boc-2-hydroxymethylmorpholine (3.5 g, 16.13 mmol) was dissolved in dichloromethane (20 mL), and a solution of HCl in ethanol (3.5 mL, 33%) was added dropwise at 0° C. The reaction system was stirred at room temperature overnight, and concentrated under reduced pressure to give compound 39-5 (1.8 g, 95% yield, crude product) in the form of a yellow oil. LC-MS: $[M+H]^+$=118.1.

Step (3) Preparation of methyl (R)-2-(hydroxymethyl)morpholine-4-carboxylate 39-6

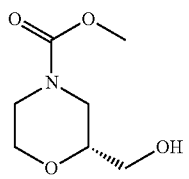

Compound 39-5 (4.0 g, 16.13 mmol) was dissolved in dichloromethane (40 mL), and DIPEA (12.5 g, 96.78 mmol) was added dropwise at 0° C. Then methyl chloroformate (1.97 g, 20.97 mmol) was dissolved in dichloromethane (10 mL) and added dropwise to the reaction system at 0° C. The reaction system was stirred at room temperature overnight, added with dichloromethane (100 mL), washed with brine (35 mL×2), and concentrated under reduced pressure. The residue was purified by silica gel column chromatography (20 g of silica gel, ethyl acetate:petroleum ether=1:2) to give intermediate 39-6 (1.0 g, 35% yield) in the form of a colorless oil. LC-MS: $[M+H]^+$=176.9.

Step (4) Preparation of methyl (R)-2-formylmorpholine-4-carboxylate

39-A

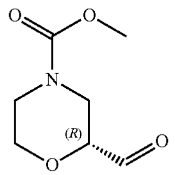

Intermediate 39-6 (600 mg, 3.43 mmol) was dissolved in dichloromethane (10 ml), and Dess-Martin periodinane (1.74 g, 4.11 mmol) was added. The reaction system was reacted at room temperature for 2 b, added with saturated sodium thiosulfate (2 mL) and stirred for 30 min. Then the reaction system was extracted with dichloromethane (30 mL×2), washed with brine (15 mL), and purified by silica gel column chromatography (12 g of silica gel, ethyl acetate: petroleum ether=1:1) to give intermediate 39-A (180 mg, 30% yield) in the form of a yellow oil. LC-MS: $[M+H]^+$=174.5.

Step (5) Preparation of 4-ethynyl-3,5-difluoro-N-methylbenzamide 39-8

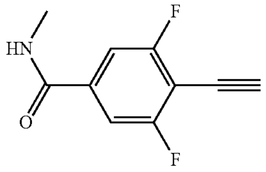

Dimethyl (1-diazo-2-oxopropyl)phosphonate (2.2 g, 11.3 mmol) was dissolved in acetonitrile (15 mL) and methanol (3 mL), then potassium carbonate (2.3 g, 16.56 mmol) was added. The reaction system was stirred at room temperature for 30 min, added with 3,5-difluoro-4-formyl-N-methylbenzamide (1.5 g, 7.53 mmol), and stirred at room temperature overnight. Then the reaction system was filtered and concentrated. The residue was purified by silica gel column chromatography (20 g of silica gel, ethyl acetate:petroleum ether=1:5) to give intermediate 39-8 (1.2 g, 81% yield) in the form of a yellow solid.

LC-MS: $[M+H]^+$=196.1.

Step (6) Preparation of 3,5-difluoro-N-methyl-4-(6-methyl-1H-indol-2-yl)benzamide 39-9

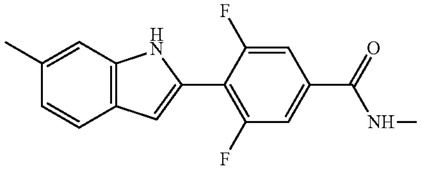

Intermediate 39-8 (1.4 g, 7.18 mmol), intermediate 39-3 (2.43 g, 8.61 mmol), potassium carbonate (1.97 g, 15.09 mmol), copper (1) iodide (0.14 g, 1.43 mmol) and L-proline (0.25 g, 2.87 mmol) were added to N,N-dimethylformamide (20 mL). The reaction system was reacted at 80° C. overnight under nitrogen atmosphere. Then the reaction system was cooled, poured into water (60 mL), extracted with ethyl acetate (50 mL×2), washed with saturated brine (30 mL×3), and purified by silica gel column chromatography (20 g of silica gel, developing agent: ethyl acetate:petroleum ether=1:2) to give intermediate 39-9 (800 mg, 44% yield) in the form of a yellow solid. LC-MS: $[M+H]^+$=301.8.

Step (7) Preparation of methyl (S)-2-((2-(2,6-difluoro-4-(methylcarbamoyl)phenyl)-7-methylindol-3-yl)methyl)morpholine-4-carboxylate

39

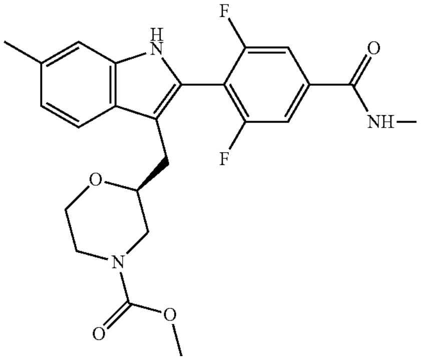

Trifluoroacetic acid (304 mg, 2.66 mmol) and triethylsilane (617 mg, 5.32 mmol) were dissolved in dichloromethane (3 mL) in a round-bottom flask (25 mL). Intermediate 39-9 (160 mg, 0.53 mmol) and intermediate 39-A (110 mg, 0.64 mmol) were then dissolved in dichloromethane (3 mL), and the solution was added dropwise to the reaction system at 0° C. The reaction system was stirred at room temperature overnight. Then the reaction system was added with water (20 mL), extracted with dichloromethane (20 mL×2), and separated by preparative reverse phase chromatography to give compound 39 (18 mg, 7.4% yield) in the form of a white solid.

LC-MS: $[M+H]^+$=458.2. $^1$H NMR (400 MHz, $CDCl_3$): δ 8.18 (brs, 1H), 7.62 (d, J=8.2 Hz, 1H), 7.43 (d, J=7.5 Hz, 2H), 7.21 (s, 1H), 7.02 (d, J=8.1 Hz, 1H), 6.29 (brs, 1H), 3.88-3.75 (m, 3H), 3.64 (s, 3H), 3.60-3.55 (m, 1H), 3.45-3.39 (m, 1H), 3.07 (d, J=3.6 Hz, 3H), 3.04-2.98 (m, 1H), 2.90-2.88 (m, 1H), 2.78 (dd, J=14.9, 6.6 Hz, 1H), 2.50 (s, 3H), 2.49-2.41 (m, 1H).

Example 40

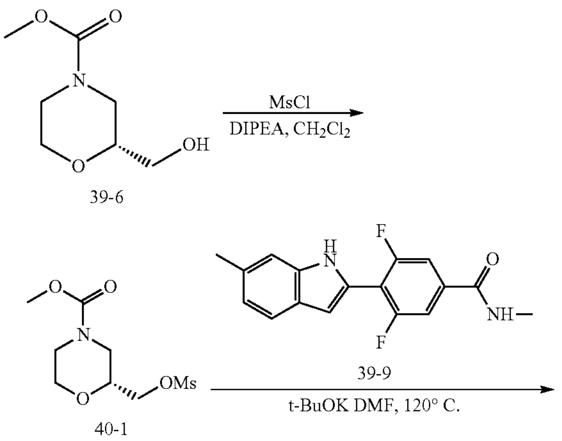

-continued

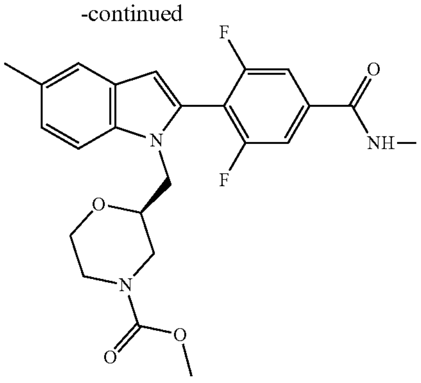

40

Step (1) Preparation of methyl (R)-2-(((methylsulfonyl)oxo)methyl)morpholine-4-carboxylate 40-1

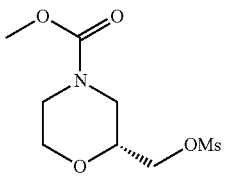

Intermediate 39-6 (400 mg, 2.28 mmol) and N,N-diisopropylethylamine (737 mg, 5.71 mmol) were dissolved in dichloromethane (10 mL), and methylsufonyl chloride (313 mg, 2.74 mmol) was added dropwise at 0° C. After the completion of the dropwise addition, the reaction system was reacted at room temperature overnight. Then the reaction system was added with dichloromethane (20 mL), washed with saturated brine (15 mL×2), dried over anhydrous magnesium sulfate, filtered, and concentrated under reduced pressure to give intermediate 40-1 (600 mg, crude product) in the form of a brown oil. LC-MS: $[M+H]^+$=254.9.

Step (2) Preparation of methyl (S)-2-((2-(2,6-difluoro-4-(methylcarbamoyl)phenyl)-5-methyl-1H-indol-1-yl)methyl)morpholine-4-carboxylate

40

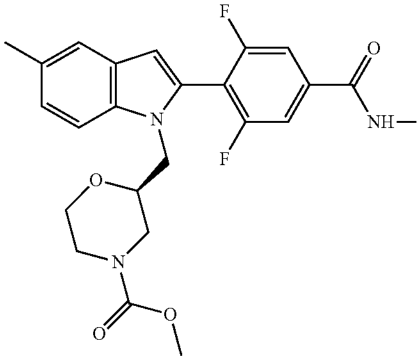

Intermediate 39-9 (250 mg, 0.83 mmol) was dissolved in N,N-dimethylformamide (5 mL), and intermediate 40-1

(421 mg, 1.67 mmol) and potassium tert-butoxide (205 mg, 1.83 mmol) were added at room temperature. The reaction system was stirred at 120° C. overnight under nitrogen atmosphere. Then the reaction system was cooled to room temperature, added with water (20 mL), and extracted with ethyl acetate (30 mL×2). The organic phases were combined, washed with saturated brine (15 mL), dried over anhydrous magnesium sulfate, filtered and concentrated. The crude product was purified by preparative reverse phase chromatography to give compound 40 (35 mg, 9.2% yield) in the form of a white solid.

LC-MS: $[M+H]^+$=458.8. $^1H$ NMR (400 MHZ, $CDCl_3$): δ 7.57 (d, J=8.1 Hz, 1H), 7.43 (d, J=7.7 Hz, 1H), 7.22 (s, 1H), 7.03 (d, J=8.1 Hz, 1H), 6.61 (s, 1H), 6.22 (brs, 1H), 4.15-3.99 (m, 2H), 3.85-3.60 (m, 3H), 3.67 (s, 3H), 3.60-3.50 (m, 1H), 3.32 (t, 1H), 3.08 (d, J=4.7 Hz, 3H), 2.81 (t, J=11.6 Hz, 1H), 2.54 (s, 3H), 2.39 (dd, J=13.0, 10.8 Hz, 1H).

Example 41

41

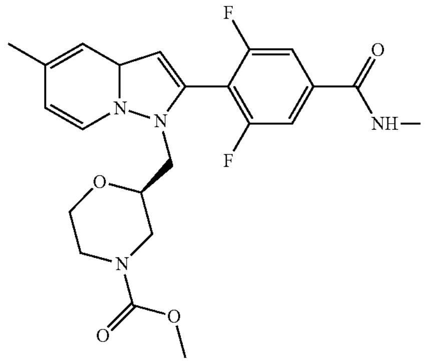

The compound was prepared according to the preparation method as described in Example 40.

LC-MS: $[M+H]^+$=461.2.

Example 42

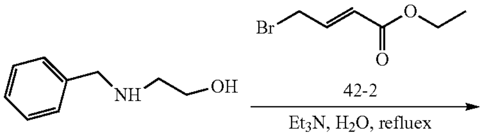

42-1

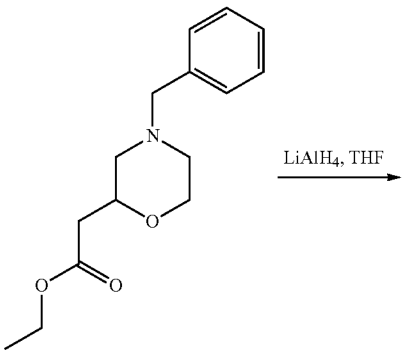

42-3

-continued

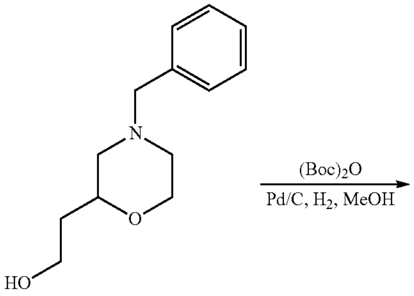

42-4

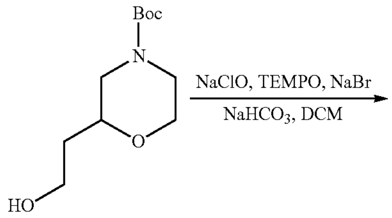

42-5

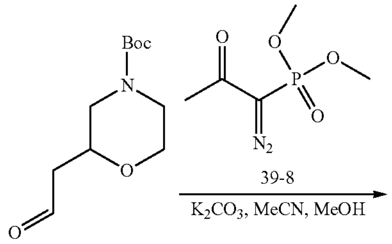

42-6

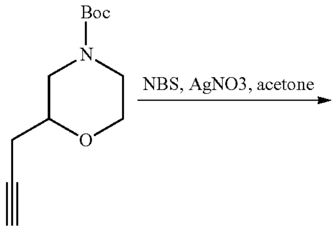

42-7

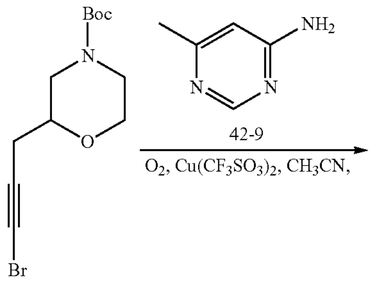

42-8

-continued

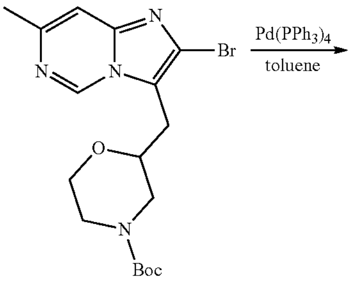

42-10

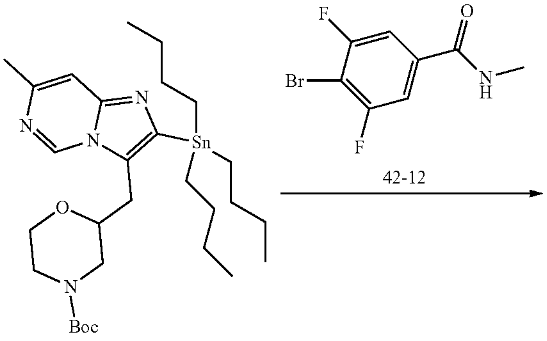

42-11

42-12

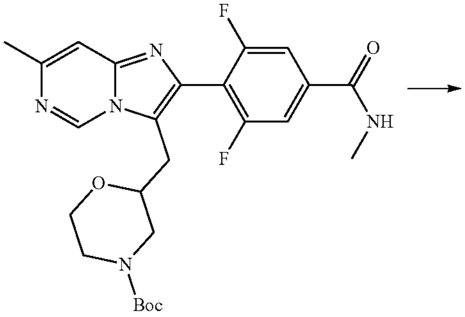

42-13

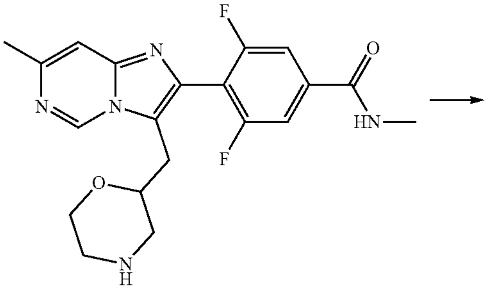

42-14

-continued

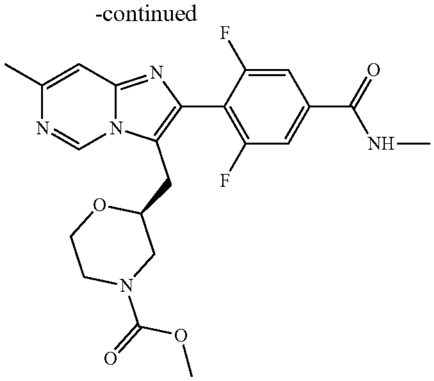

42

Step (1) Preparation of ethyl 2-(4-phenylmethylmorpholin-2-yl)acetate 42-3

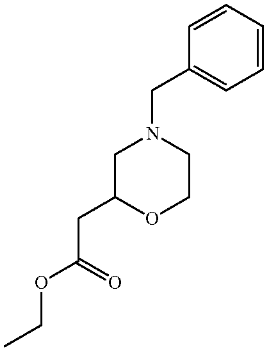

2-(phenylmethylamino) ethanol (45.0 g, 298 mmol) and triethylamine (30.0 g, 298 mmol) were dissolved in water (450 mL). The reaction system was heated to 100° C., added with (E)-ethyl-4-bromobut-2-enoate (57.5 g, 298 mmol), reacted overnight, and extracted with ethyl acetate (200 mL×3). The organic phase was dried over anhydrous sodium sulfate and concentrated. The residue was separated by column chromatography (PE/EA=10/1) to give compound 42-3 (27.0 g, 35% yield) in the form of a yellow oily liquid. LC-MS: $[M+H]^+$=264.2.

Step (2) Preparation of 2-(4-phenylmethylmorpholin-2-yl)ethanol 42-4

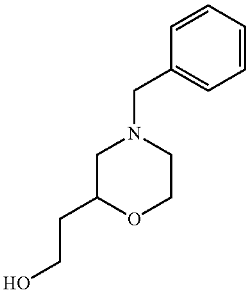

Compound 42-3 (27.0 g, 103 mmol) was dissolved in tetrahydrofuran (300 mL). The reaction system was cooled to 0° C. under nitrogen atmosphere. added with lithium aluminum hydride (3.9 g, 103 mmol) in portions, and warmed to room temperature and stirred for 3 h. Then the reaction system was added with sodium sulfate decahydrate to quench the reaction, filtered, and washed with ethyl acetate, and the filtrate was concentrated. The residue was separated by column chromatography (PE/EA=2/1) to give compound 42-4 (17.4 g, 76% yield) in the form of a colorless oily liquid. LC-MS: $[M+H]^+$=222.1.

Step (3) Preparation of tert-butyl 2-(2-hydroxyethyl)morpholine-4-carboxylate 42-5

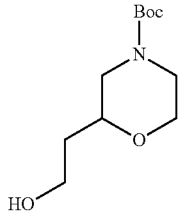

Compound 42-4 (17.6 g, 78.4 mmol) and di-ter-butyl dicarbonate (51.3 g, 235 mmol) were dissolved in absolute methanol (180 mL), and palladium on carbon (1.74 g, 10%) was added. The reaction system was purged with hydrogen and stirred at room temperature overnight. Then the reaction system was filtered, and the filtrate was concentrated. The residue was separated by column chromatography (PE/EA=3/1) to give compound 42-5 (12.5 g, 68% yield) in the form of a colorless oily liquid. LC-MS: $[M+H]^+$=232.3.

Step (4) Preparation of tert-butyl 2-(2-carbonylethyl)morpholine-4-carboxylate 42-6

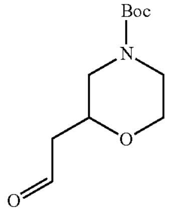

Compound 42-5 (2.0 g, 1.44 mmol) was dissolved in dichloromethane (40 mL), and Dess-Martin periodinane (5.5 g, 2.15 mmol) was added. The reaction system was stirred at room temperature for 2 h. Then the reaction system was added with sodium thiosulfate to quench the reaction, and extracted with dichloromethane (40 mL×3). The organic phases were combined, dried over anhydrous sodium sulfate and concentrated. The residue was separated by column chromatography (PE/EA=2/1) to give compound 42-6 (1.1 g, 67% yield) in the form of a colorless oily liquid. LC-MS: $[M+H]^+$=230.1.

Step (5) Preparation of tert-butyl 2-(prop-2-yn-1-yl) morpholine-4-carboxylate 42-7

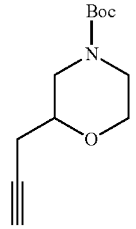

Dimethyl (1-diazo-2-oxopropyl)phosphonate (4.0 g, 20.9 mmol) was dissolved in dichloromethane (40 mL) and acetonitrile (8 mL). The reaction system was stirred at room temperature for 15 min, added with compound 42-6 (4.0 g, 17.5 mmol) and potassium carbonate (2.4 g, 17.5 mmol), and stirred at room temperature overnight. Then the reaction system was filtered, and the filtrate was concentrated. The residue was separated by column chromatography (PE/EA=10/1) to give compound 42-7 (2.1 g, 53% yield) in the form of a colorless oily liquid. LC-MS: $[M-55]^+$=226.2.

Step (6) Preparation of tert-butyl 2-(3-bromoprop-2-yn-1-yl)morpholine-4-carboxylate 42-8

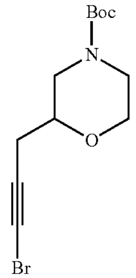

Compound 42-7 (2.1 g, 9.3 mmol) and silver nitrate (1.9 g, 11.1 mmol) were dissolved in acetone (20 mL), and N-bromosuccinimide (1.8 g, 10.2 mmol) was added. The reaction system was stirred at room temperature for 4 h, and extracted with ethyl acetate (60 mL×3). The organic phases were combined, dried over anhydrous sodium sulfate and concentrated. The residue was separated by column chromatography (PE/EA=20/1) to give intermediate 42-8 (2.0 g, 71% yield) in the form of a colorless oily liquid. LC-MS: $[M+H]^+$=304.2.

Step (7) Preparation of tert-butyl 2-((2-bromo-7-methylimidazo[1,2-c]pyrimidin-3-yl)methyl)morpholine-4-carboxylate

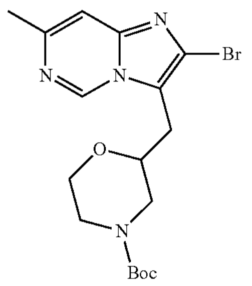

42-10

Intermediate 42-8 (2.0 g, 6.5 mmol), 6-methylpyrimidin-4-amine (0.85 g, 7.9 mmol) and copper(II) trifluoromethanesulfonate (0.24 g, 0.65 mmol) were dissolved in acetonitrile (20 mL). The reaction system was stirred at room temperature overnight under oxygen atmosphere, diluted with water (50 mL) and extracted with ethyl acetate (30 mL×3). The organic phases were combined, dried over anhydrous sodium sulfate and concentrated. The residue was separated by column chromatography (PE/EA=2/1) to give intermediate 42-10 (400 mg, 15% yield) in the form of a colorless oily liquid. LC-MS: $[M+H]^+$=411.1.

Step (8) Preparation of tert-butyl 2-((7-methyl-2-(tributylstannyl)imidazo[1,2-c]pyrimidin-3-yl)methyl)morpholine-4-carboxylate

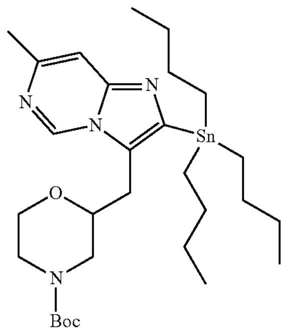

42-11

Intermediate 42-10 (40 mg, 0.1 mmol), 1,1,1,2,2,2-hexabutyldistannane (170 mg, 0.3 mmol) and tetrakis (triphenylphosphine)palladium (11 mg, 0.01 mmol) were dissolved in 1,4-dioxane (2 mL). The reaction system was stirred at 100° C. overnight under nitrogen atmosphere, and detected by LC-MS for completion to give intermediate 42-11 (5% yield). LC-MS: $[M+H]^+$=623.5.

Step (9))) Preparation of tert-butyl (S)-2-((2-(2,6-difluoro-4-(methylcarbamoyl)phenyl)-7-methylimidazo[1,2-c]pyrimidin-3-yl)methyl)morpholine-4-carboxylate

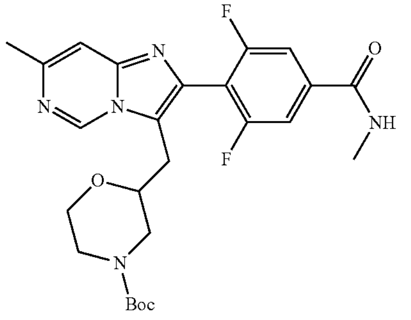

42-13

The compound was prepared according to the preparation method for compound 37-9.

Step (10) Preparation of (S)-2-((2-(2,6-difluoro-4~(methylcarbamoyl)phenyl)-7-methylimidazo[1,2-c]pyrimidin-3-yl)methyl)morpholine

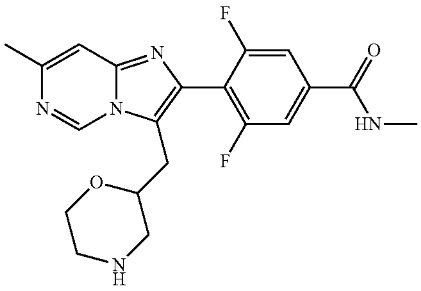

42-14

The compound was prepared according to the preparation method as described in step (6) of Example 37.

Step (11) Preparation of methyl (S)-2-((2-(2,6-difluoro-4-(methylcarbamoyl)phenyl)-7-methylimidazo[1,2-c]pyrimidin-3-yl)methyl)morpholine-4-carboxylate

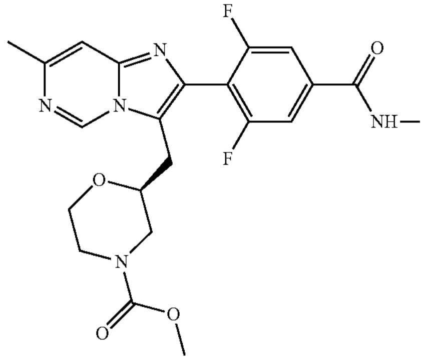

42

The compound was prepared according to the preparation method as described in step (7) of Example 37.

LC-MS: $[M+H]^+=460.2$.

Example 43

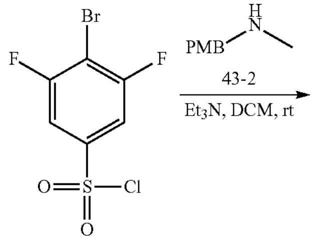

43-1

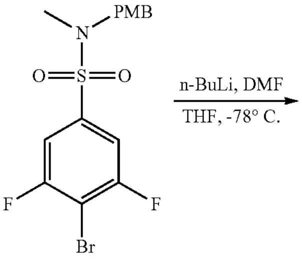

43-3

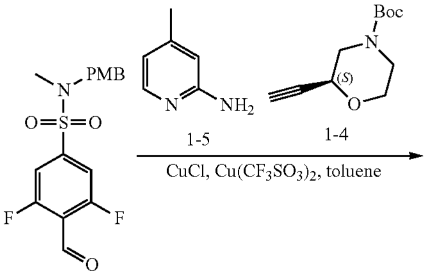

43-4

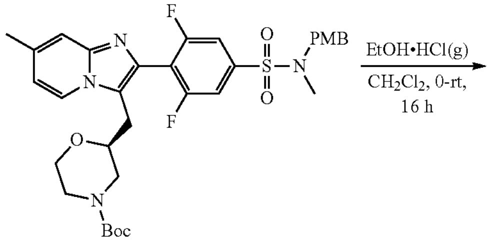

43-5

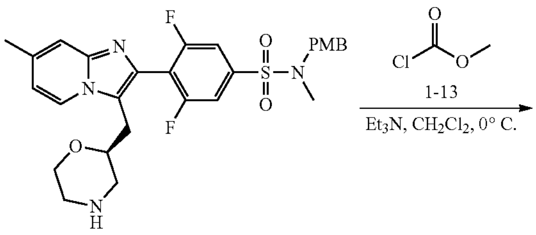

43-6

-continued

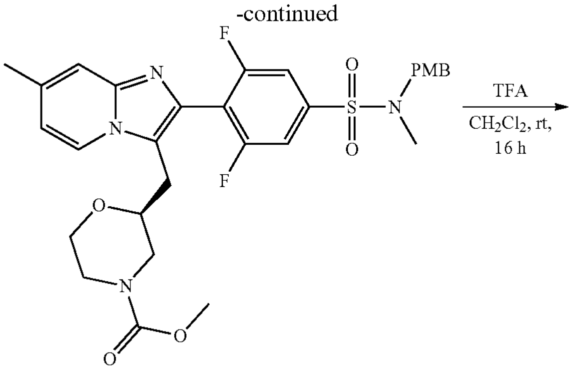

43-7

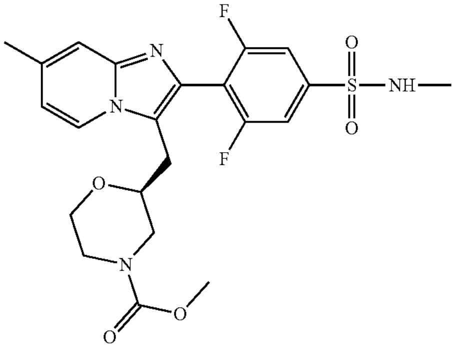

43

Step (1) Preparation of 4-bromo-3,5-difluoro-N-(4-methoxybenzyl)-N-methylbenzenesulfonamide 43-3

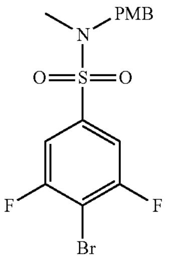

1-(4-methoxyphenyl)-N-methylmethylamine (1.30 g, 8.24 mmol) and triethylamine (2.10 g, 20.61 mmol) were dissolved in dichloromethane (16 mL), and a solution of 4-bromo-3,5-difluorobenzenesulfonyl chloride (2.00 g, 6.87 mmol) in dichloromethane (4 mL) was added dropwise at 0° C. The reaction system was warmed to room temperature and reacted for 4 h. Then the reaction system was added with water (50 mL) to quench the reaction, extracted with dichloromethane (50 mL×2), washed with saturated brine (30 mL), dried over anhydrous sodium sulfate, filtered and concentrated. The crude product was purified by silica gel column chromatography to give intermediate 43-3 (2.30 g, 78% yield) in the form of a white solid. MS [M+Na]=427.6, 429.6.

Step (2) Preparation of 3,5-difluoro-4-formyl-N-(4-methoxybenzyl)-N-methylbenzenesulfonamide 43-4

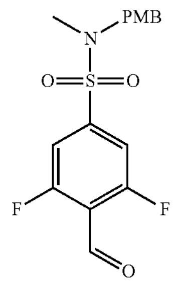

Intermediate 43-3 (1.70 g, 4.19 mmol) was dissolved in anhydrous tetrahydrofuran (17 mL) under nitrogen atmosphere, and n-butyllithium (2.4 mol/L, 1.75 mL) was added dropwise at 78° C. After the completion of the dropwise addition, the reaction system was stirred at this temperature for 0.5 h, added dropwise with N,N-dimethylformamide (367 mg, 5.03 mmol), and reacted for 3 h. Then the reaction system was added with diluted hydrochloric acid (0.5 mol/L, 10 mL) to quench the reaction, diluted with water (50 mL) and extracted with ethyl acetate (30 mL×2). The organic phases were combined, washed with saturated brine (30 mL), dried over anhydrous sodium sulfate, filtered and concentrated. The crude product was purified by silica gel column chromatography to give intermediate 43-4 (600 mg, 32% yield) in the form of a white solid. MS [M+Na]=377.8.

Step (3) Preparation of tert-butyl (S)-2-((2-(2,6-difluoro-4-(N-(4-methoxybenzyl)-N-methylsulfamoyl)phenyl)-7-methylimidazo[1,2-a]pyridin-3-yl)methyl)morpholine-4-carboxylate 43-5

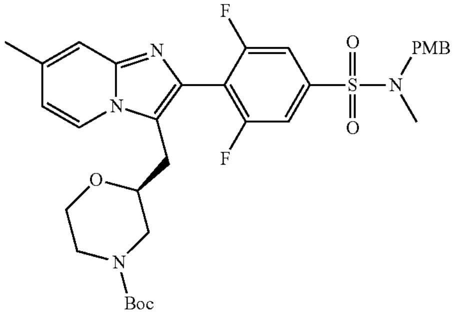

Intermediate 43-4 (600 mg, 1.69 mmol), 4-methylpyridin-2-amine (183 mg, 1.69 mmol) and tert-butyl (S)-2-ethynylmorpholine-4-carboxylate (359 mg, 1.69 mmol) were dissolved in toluene (6 mL) under nitrogen atmosphere, and copper (1) chloride (50 mg, 0.51 mmol) and copper(II) trifluoromethanesulfonate (183 mg, 0.51 mmol) were added. The reaction system was reacted at 85° C. for 10 min, added with dimethylacetamide (0.1 mL), and reacted at 85° C. for another 5 h. Then the reaction system was stirred at room temperature overnight. The resulting reaction system was filtered, and the filtrate was added with water (30 mL) and extracted with dichloromethane (30 mL×3). The organic phases were combined, washed with saturated brine (20 mL), dried over anhydrous sodium sulfate, filtered and concentrated. The crude product was purified by silica gel column chromatography to give intermediate 43-5 (298 mg, 27% yield) in the form of a light yellow solid. MS [M+H]$^+$=656.7.

Step (4) Preparation of (S)-3,5-difluoro-N-(4-methoxybenzyl)-N-methyl-4-(7-methyl-3-(morpholin-2-ylmethyl)imidazo[1,2-a]pyridin-2-yl)benzenesulfonamide hydrochloride 43-6

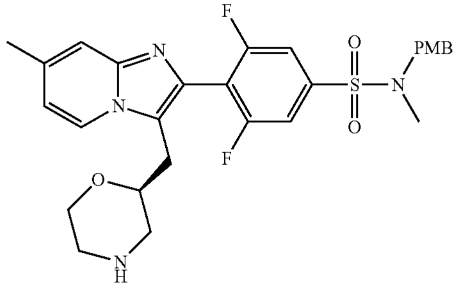

Intermediate 43-5 (298 mg, 0.45 mmol) was dissolved in dichloromethane (5 mL), and a solution of HCl in ethanol (33%, 0.45 mL) was added dropwise. The reaction system was reacted at room temperature for 16 h. Then the reaction system was concentrated under reduced pressure to give intermediate 43-6 (300 mg, crude product as a hydrochloride) in the form of a light yellow solid. MS [M+H]$^+$=556.8.

Step (5) Preparation of methyl (S)-2-((2-(2,6-difluoro-4-(N-(4-methoxybenzyl)-N-methylsulfamoyl)phenyl)-7-methylimidazo[1,2-a]pyridin-3-yl)methyl)morpholine-4-carboxylate 43-7

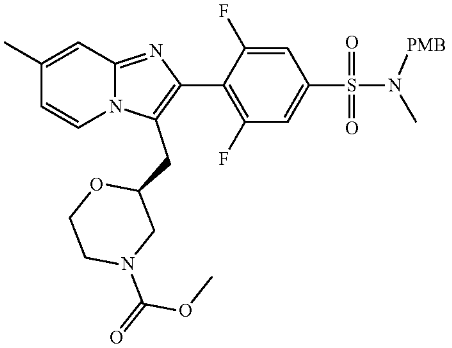

Intermediate 43-6 (300 mg, 0.50 mmol) was dissolved in dichloromethane (5 mL) under nitrogen atmosphere, and triethylamine (202 mg, 2.00 mmol) was added at 0° C., followed by the dropwise addition of a solution of methyl chloroformate (57 mg, 0.60 mmol) in dichloromethane (1 mL). The reaction system was reacted at 0° C. for 4 h. Then the reaction system was added with water (20 mL) to quench the reaction, and extracted with dichloromethane (20 mL×2). The organic phases were combined, washed with saturated brine (20 mL×2), dried over anhydrous sodium sulfate, filtered and concentrated. The crude product was purified by silica gel column chromatography to give intermediate 43-7 (200 mg, 88% purity, 64.5% yield) in the form of a brown solid. MS $[M+H]^+$=615.2.

Step (6) Preparation of methyl (S)-2-((2-(2,6-difluoro-4-(N-methylsulfamoyl)phenyl)-7-methylimidazo[1,2-a]pyridin-3-yl)methyl)morpholine-4-carboxylate

43

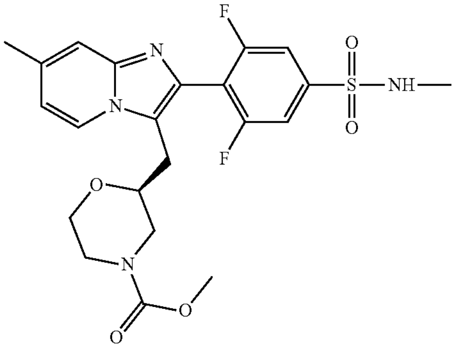

Intermediate 43-7 (200 mg, 0.32 mmol) was dissolved in dichloromethane (3 mL), and trifluoroacetic acid (1 mL) was added at 0° C. The reaction system was reacted at room temperature for 16 h. Then the reaction system was concentrated under reduced pressure. The residue was dissolved in dichloromethane (40 mL), washed with aqueous sodium bicarbonate solution (10%, 15 mL×2) and saturated brine (15 mL) sequentially, dried over anhydrous sodium sulfate, filtered and concentrated. The crude product was purified by preparative chromatography to give compound 43 (80.2 mg, 49.8% yield) in the form of a white solid.

MS [M+H]+=494.7. $^1$H NMR (400 MHZ, $CDCl_3$) δ 8.58 (d, J=5.2 Hz, 1H), 7.93 (s, 1H), 7.61 (d, J=6.7 Hz, 2H), 7.20 (d, J=7.1 Hz, 1H), 5.11-4.95 (m, 1H), 4.22-4.06 (m, 1H), 3.96-3.90 (m, 1H), 3.86-3.77 (m, 1H), 3.74 (s, 3H), 3.69-3.63 (m, 1H), 3.45-3.39 (m, 1H), 3.13-3.02 (m, 2H), 3.01-2.92 (m, 1H), 2.79 (s, 3H), 2.75-2.70 (m, 1H), 2.63 (s, 3H).

Example 44

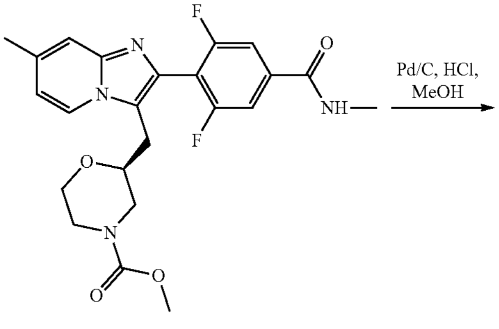

Positive compound 1

-continued

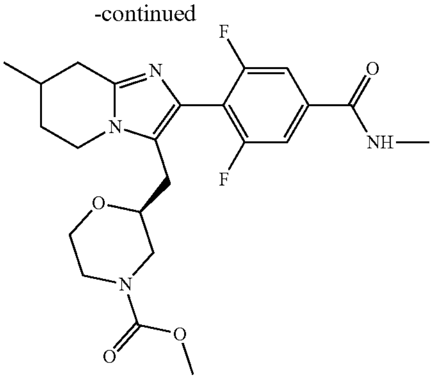

44

Step (1) Preparation of methyl (S)-2-((2-(2,6-difluoro-4-(4-methylcarbamoyl)phenyl)-7-methylimidazo[1,2-a]pyridin-3-yl)methyl)morpholine-4-carboxylate Positive Compound 1

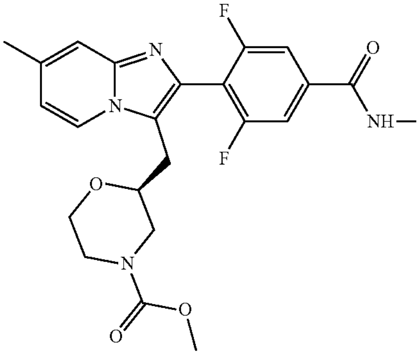

The compound was prepared according to patent literature CN105246888A.

Step (2) Preparation of methyl (2S)-2-((2-(2,6-difluoro-4-(methylcarbamoyl)phenyl)-7-methyl-5,6,7,8-tetrahydroimidazo[1,2-a]pyridin-3-yl)methyl)morpholine-4-carboxylate

44

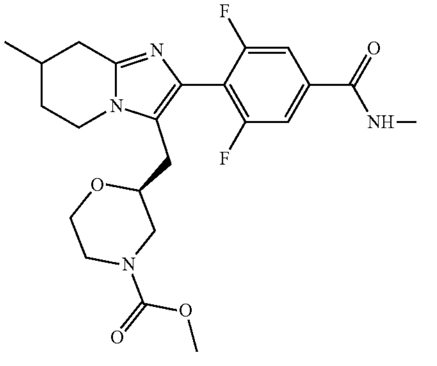

Positive compound 1 (120 mg, 0.3 mmol) and concentrated hydrochloric acid (0.1 mL) were dissolved in absolute methanol (3 mL). The reaction system was purged with hydrogen and stirred at room temperature for 6 h. Then the reaction system was filtered and concentrated. The residue was diluted with ethyl acetate (50 mL), washed with saturated sodium bicarbonate (15 mL) and saturated brine (15 mL) sequentially, dried over anhydrous sodium sulfate, filtered and concentrated. The residue was purified by silica gel column chromatography (DCM/MeOH=40/1) to give compound 44 (61 mg, 50% yield) in the form of a white solid.

LC-MS: $[M+H]^+$=463.2. $^1H$ NMR (400 MHz, $CDCl_3$): δ 7.48 (brs, 2H), 4.30-4.23 (m, 1H), 4.12-4.04 (m, 1H), 3.99-3.69 (m, 4H), 3.68 (s, 3H), 3.40-3.30 (s, 2H), 3.20-3.10 (m, 1H), 3.03 (d, J=3.5 Hz, 3H), 2.92-2.80 (m, 1H), 2.74-2.62 (m, 2H), 2.60-2.44 (m, 2H), 2.18-2.06 (m, 2H), 1.80-1.68 (m, 1H), 1.20 (d, J=5.8 Hz, 3H).

Example 45

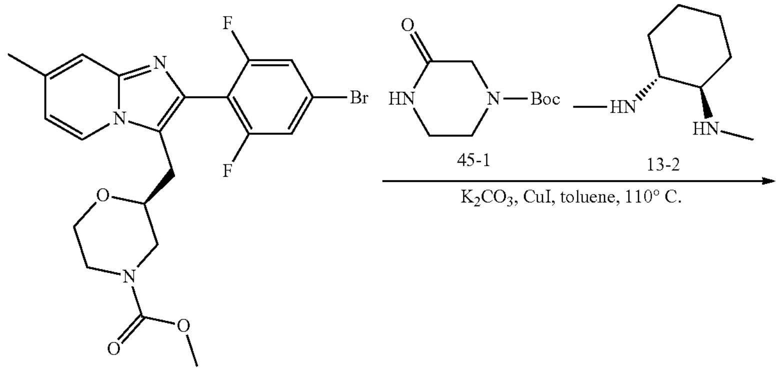

2-7

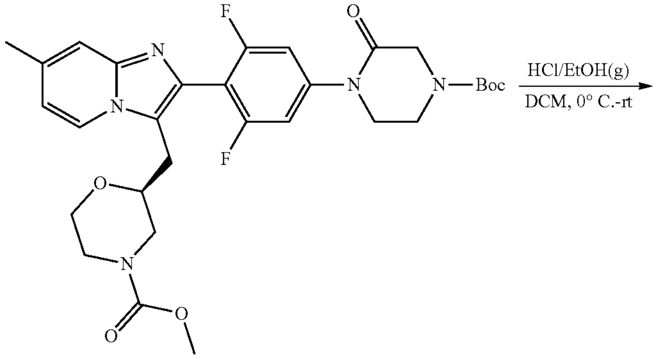

45-2

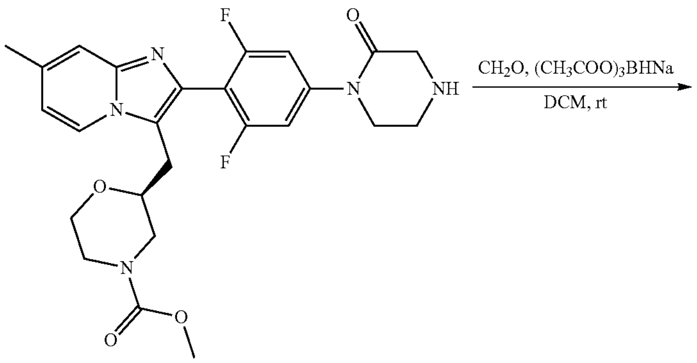

45-3

-continued

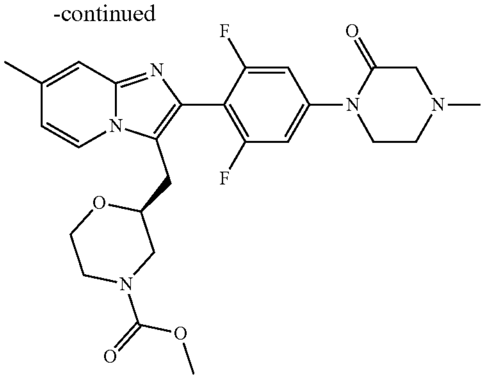

45

Step (1) Preparation of methyl (S)-2-((2-(4-(4-(tert-butoxycarbonyl)-2-oxopiperazin-1-yl)-2,6-difluorophenyl)-7-methylimidazo[1,2-a]pyridin-3-yl)methyl)morpholine-4-carboxylate 45-2

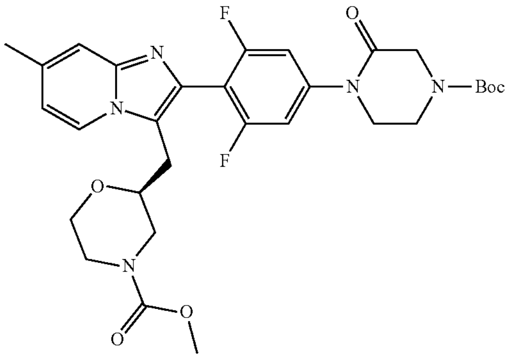

Intermediate 2-7 (250 mg, 0.52 mmol) was dissolved in anhydrous toluene (3 mL) and tert-butyl 3-carbonylpiperazine-1-carboxylate (125 mg, 0.62 mmol), potassium carbonate (216 mg, 1.56 mmol), trans-(1R,2R)—N,N'-dimethyl-1,2-cyclohexanediamine (7.4 mg, 0.052 mmol) and copper(I) iodide (10 mg, 0.052 mmol) were added under nitrogen atmosphere. The reaction system was reacted at 110° C. overnight. After the reaction was completed, the reaction system was cooled to room temperature, and filtered, and the filtrate was added with water (10 mL), and extracted with dichloromethane (30 mL×3). The organic phases were combined, washed with saturated brine (30 mL×1), dried over magnesium sulfate, filtered and concentrated by rotary evaporation to give a crude product. The crude product was purified by column chromatography (4 g of silica gel column, petroleum ether:ethyl acetate=1:1) to give intermediate 45-2 in the form of a yellow oil (200 mg, 64% yield), LC-MS: $[M+H]^+$=600.9.

Step (2) Preparation of methyl (S)-2-((2-(2,6-difluoro-4-(2-oxopiperazin-1-yl)phenyl)-7-methylimidazo[1,2-a]pyridin-3-yl)methyl)morpholine-4-carboxylate 45-3

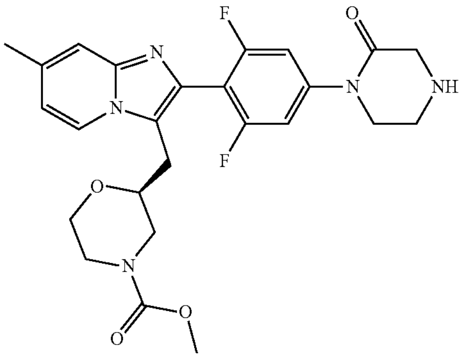

Intermediate 45-2 (200 mg, 0.33 mmol) was dissolved in dichloromethane (5 mL), and a solution of HCl in ethanol (33%, 0.5 mL) was added dropwise with the temperature maintained at 0° C. After the completion of the dropwise addition, the reaction system was reacted at room temperature for 2 h. After the reaction was completed, the reaction system was added dropwise with saturated sodium bicarbonate solution to adjust the pH to 8 with the temperature maintained at 0° C., added with water (10 mL), and extracted with dichloromethane (20 mL×3). The organic phases were combined, washed with saturated brine (20 mL×1), dried over magnesium sulfate, filtered and concentrated by rotary evaporation to give intermediate 45-3 (175 mg) in the form of a yellow oil, LC-MS: $[M+H]^+$=500.9.

Step (3) Preparation of methyl (S)-2-((2-(2,6-difluoro-4-(4-methyl-2-oxopiperazin-1-yl)phenyl)-7-methylimidazo[1,2-a]pyridin-3-yl)methyl)morpholine-4-carboxylate

45

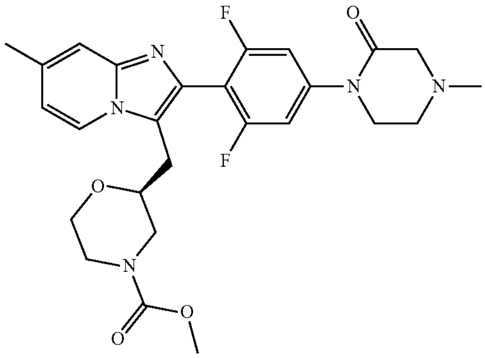

Intermediate 45-3 (175 mg, 0.35 mmol) and aqueous formaldehyde solution (37%, 30 mg, 0.364 mmol) were dissolved in dichloromethane (3 mL), and sodium triacetoxyborohydride (287 mg, 1.36 mmol) was slowly added. The reaction system was reacted at room temperature for 3 h. After the reaction was completed, the reaction system was added with water (10 mL) and extracted with dichloromethane (15 mL×3). The organic phases were combined, washed with saturated brine (20 mL×1), dried over magnesium sulfate, filtered and concentrated by rotary evaporation to give a crude product. The crude product was purified by column chromatography to give compound 45 (74 mg, 41% yield) in the form of a yellow solid.

LC-MS: $[M+H]^+$=514.7. $^1H$ NMR (400 MHZ, MeOD): δ 8.86 (d, J=7.1 Hz, 1H), 7.73 (s, 1H), 7.51 (d, J=9.0 Hz, 2H), 7.43 (dd, J=7.1, 1.4 Hz, 1H), 4.18 (m, 3H), 4.18-4.11 (m, 1H), 4.01 (d, J=13.0 Hz, 1H), 3.88-3.74 (m, 4H), 3.70 (s, 3H), 3.69-3.65 (m, 1H), 3.40-3.32 (m, 1H), 3.26 (d, J=5.7 Hz, 2H), 3.10 (s, 3H), 2.00-2.86 (m, 1H), 2.82-2.70 (m, 1H), 2.65 (s, 3H).

Example 46

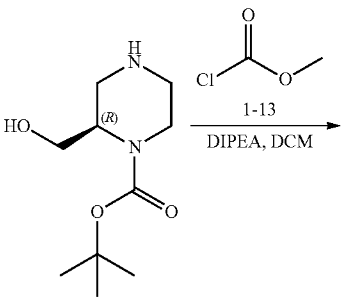

46-1

-continued

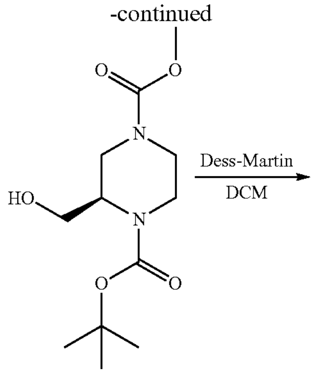

46-2

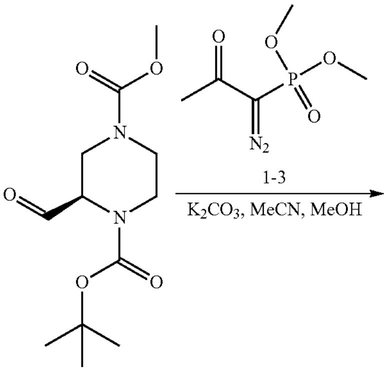

46-3

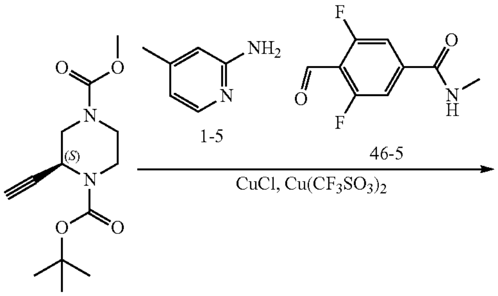

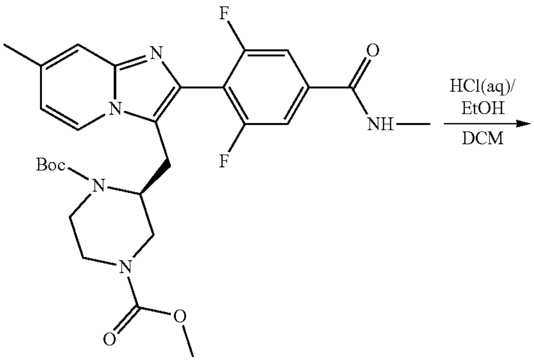

46-6

-continued

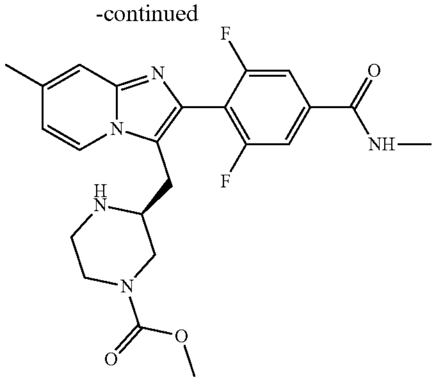

46

Step (1) Preparation of 1-tert-butyl-4-methyl (R)-2-(hydroxymethyl)piperazine-1,4-dicarboxylate 46-2

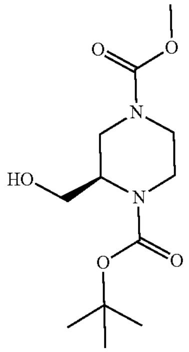

Tert-butyl (R)-2-(hydroxymethyl)piperazine-1-carboxylate (2.0 g, 9.0 mmol) and N,N-diisopropylethylamine (3.6 g, 27.0 mmol) were dissolved in dichloromethane (20 mL). Under nitrogen atmosphere, the reaction system was cooled to 0° C., added with methyl chloroformate (1.0 g, 11.0 mmol), and warmed to room temperature and reacted for 1 h. Then the reaction system was extracted with ethyl acetate (25 mL×3). The organic phase was washed with saturated brine (30 mL×2), dried over anhydrous sodium sulfate and concentrated. The residue was separated by column chromatography (PE/EA=2/1) to give intermediate 46-2 (1.7 g, 68% yield) in the form of a colorless oily liquid. LC-MS: $[M+H]^+$=275.2.

Step (2) Preparation of 1-tert-butyl-4-methyl (R)-2-formylpiperazine-1,4-dicarboxylate 46-3

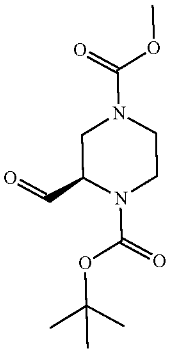

Intermediate 46-2 (1.7 g, 6.0 mmol) was dissolved in dichloromethane (30 mL). Under nitrogen atmosphere, the reaction system was cooled to 0° C., added with Dess-Martin periodinane (3.9 g, 9.0 mmol), and warmed to room temperature and stirred for 2 h. Then the reaction system was extracted with dichloromethane (30 mL×3). The organic phase was washed with saturated brine (50 mL×2), dried over anhydrous sodium sulfate and concentrated. The residue was separated by column chromatography (PE/EA=2/1) to give intermediate 46-3 (360 mg, 21% yield) in the form of a colorless oily liquid. LC-MS: [M-55]=217.1.

Step (3) Preparation of 1-tert-butyl-4-methyl (S)-2-ethynylpiperazine-1,4-dicarboxylate 46-4

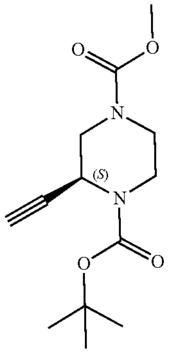

Compound 1-3 (305 mg, 1.6 mmol) and potassium carbonate (365 mg, 2.6 mmol) were dissolved in acetonitrile (2.5 mL) and absolute methanol (0.5 mL). The reaction system was stirred at room temperature for 15 min, added with a dissolved solution of intermediate 46-3 (360 mg, 1.3 mmol) in acetonitrile (2.5 mL) and absolute methanol (0.5 mL), and stirred at room temperature overnight. Then the reaction system was filtered and concentrated. The residue was separated by column chromatography (PE/EA=10/1) to give intermediate 46-4 (165 mg, 46% yield) in the form of a white oily liquid. LC-MS: $[M-55]^+$=213.7.

Step (4) Preparation of methyl (S)-2-((2-(2-(2,6-difluoro-4-(methylcarbamoyl)phenyl)-7-methylimidazo[1,2-a]pyridin-3-yl)methyl)-1-tert-butyl carboxylate-piperazine-4-carboxylate 46-6

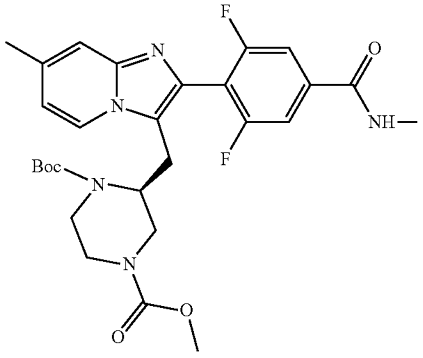

Intermediate 46-4 (165 mg, 0.6 mmol), 4-methylpyridin-2-amine (66 mg, 0.6 mmol), 3,5-difluoro-4-formyl-N-methylbenzamide (123 mg, 0.6 mmol), copper (1) chloride (18 mg, 0.2 mmol) and copper(II) trifluoromethanesulfonate (67 g, 0.2 mmol) were dissolved in anhydrous toluene (3 mL). The reaction system was heated to 85° C., added with N,N-dimethylacetamide (0.2 mL), and reacted at 85° C. for 5 h. Then the reaction system was cooled to room temperature and reacted overnight, and extracted with dichloromethane (15 mL×3). The organic phase was washed with saturated brine (20 mL×2), dried over anhydrous sodium sulfate and concentrated. The residue was separated by column chromatography (DCM/MeOH=40/1) to give intermediate 46-6 (105 mg) in the form of a brown solid. LC-MS: $[M+H]^+$=558.2.

Step (5) of methyl (S)-2-((2-(2-(2,6-difluoro-4-(methylcarbamoyl)phenyl)-7-Preparation methylimidazo[1,2-a]pyridin-3-yl)methyl)piperazine-4-carboxylate

46

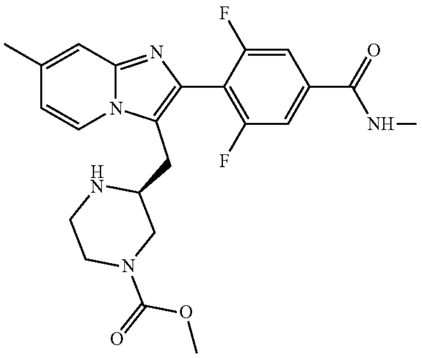

Intermediate 46-6 (105 mg, 0.2 mmol) was dissolved in anhydrous dichloromethane (2 mL). The reaction system was cooled to 0° C., added dropwise with a solution of HCl in ethanol (0.5 mL), and warmed to room temperature and stirred for 1 h. Then the reaction system was concentrated. The residue was separated by preparative reverse phase chromatography to give compound 46 (3.5 mg) in the form of a white solid.

LC-MS: $[M+H]^+$=458.5. $^1$H NMR (400 MHz, MeOD): δ 8.75 (brs, 1H), 7.84 (m, 3H), 7.42 (brs, 1H), 4.10-4.02 (m, 2H), 3.70-3.66 (m, 1H), 3.66 (s, 3H), 3.57-3.37 (m, 3H), 3.20-3.10 (m, 2H), 2.98 (s, 3H), 2.95-2.85 (m, 1H), 2.64 (s, 3H).

Example 47

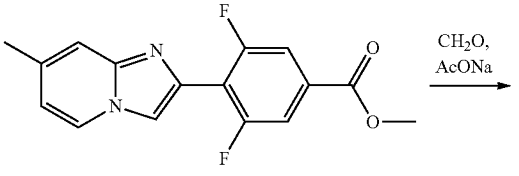

47-1

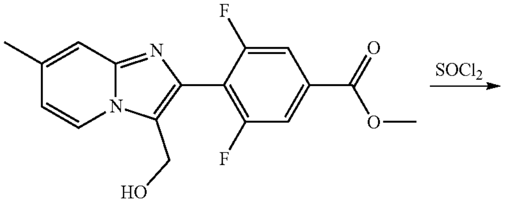

47-2

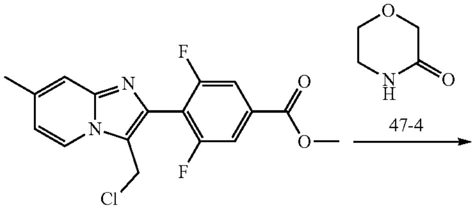

47-3

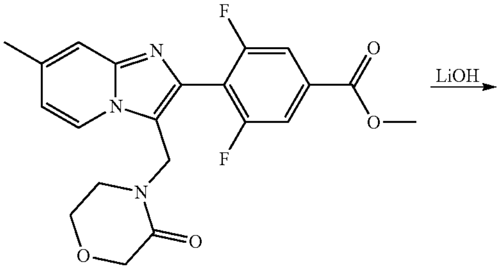

47-5

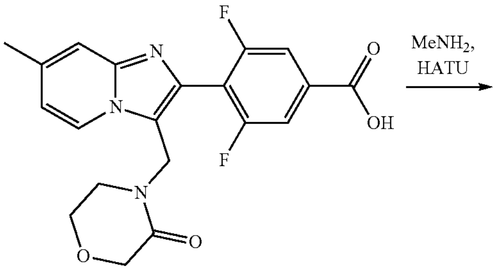

47-6

-continued

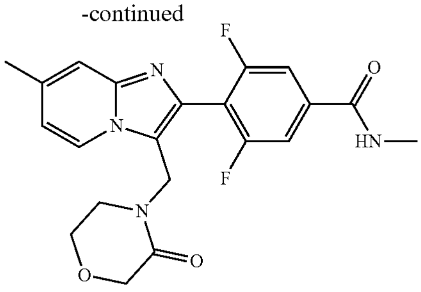

47

Step (1) Preparation of methyl 3,5-difluoro-4-(3-(hydroxymethyl)-7-methylimidazo[1,2-a]pyridin-2-yl)benzoate 47-2

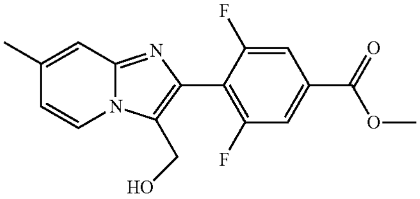

Intermediate 47-1 (synthesized according to the preparation method for intermediate 31-7, LC-MS $[M+H]^+$: 303.18) (1.2 g, 4.0 mmol) was dissolved in acetonitrile (8 mL), and acetic acid (8 mL), aqueous formaldehyde solution (0.25 mL, 24 mmol) and sodium acetate (1.31 g, 16 mmol) were added. The reaction system was heated to 50° C. and reacted for 16 h. Then the reaction system was concentrated by rotary evaporation to remove the solvent. The residue was diluted with dichloromethane (50 mL), and washed with saturated aqueous sodium bicarbonate solution (20 mL×2). The organic phases were combined, dried over anhydrous sodium sulfate and concentrated. The residue was separated by column chromatography (DCM/MeOH=50/1) to give intermediate 47-2 (945 mg, 71% yield) in the form of a yellow solid. LC-MS: $[M+H]^+$=333.2.

Step (2) Preparation of methyl 4-(3-(chloromethyl)-7-methylimidazo[1,2-a]pyridin-2-yl)-3,5-difluorobenzoate 47-3

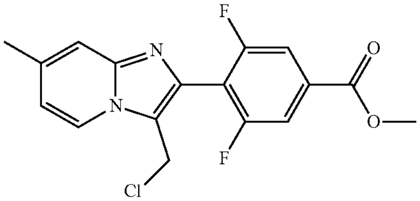

Intermediate 47-2 (1.2 g, 4.0 mmol) was dissolved in dichloromethane (15 mL), and thionyl chloride (4 mL) was added at 0° C. The reaction system was reacted at 0° C. for 3 h. Then the reaction system was concentrated by rotary evaporation to remove the solvent to give intermediate 47-2 (900 mg) in the form of a yellow solid. LC-MS: $[M+H]^+$=336.1.

Step (3) Preparation of methyl 3,5-difluoro-4-(7-methyl-3-((3-oxo-4-morpholinyl)methyl)imidazo[1,2-a]pyridin-2-yl)benzoate 47-5

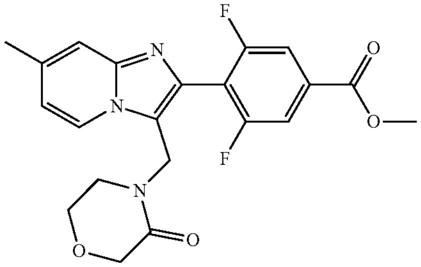

Morpholin-3-one (101 mg, 1.0 mmol) was dissolved in DMF (5 mL), and sodium hydride (80 mg, 2 mol) was added in an ice bath. The reaction system was reacted for 0.5 h, added with methyl intermediate 47-4 (351 mg, 1 mmol), and reacted at room temperature for 16 h. Then the reaction system was poured into ice water (10 mL), extracted with dichloromethane (10 mL×2), washed with saturated brine (10 mL), dried over anhydrous sodium sulfate, and filtered, and the filtrate was concentrated by rotary evaporation to give intermediate 47-5 (120 mg) in the form of a yellow solid. LC-MS: $[M+H]^+$=416.4.

Step (4) Preparation of 3,5-difluoro-4-(7-methyl-3-((3-oxo-4-morpholinyl)methyl)imidazo[1,2-a]pyridin-2-yl)benzoic acid 47-6

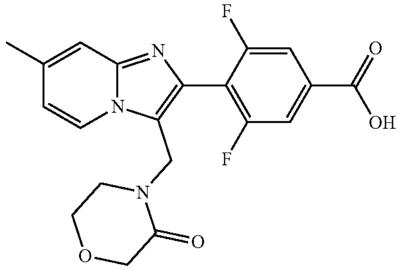

Intermediate 47-5 (120 mg, 0.29 mmol) was dissolved in THF (9 mL), and MeOH (3 mL), $H_2O$ (3 mL), and lithium hydroxide (61 mg, 1.45 mmol) were added sequentially. The reaction system was stirred at room temperature overnight, then diluted with water (10 mL), and concentrated by rotary evaporation under reduced pressure to remove the organic solvent. The aqueous phase was adjusted to pH 5-6 with hydrochloric acid (1 N), and extracted with dichloromethane (10 mL×2). The organic phase was dried over anhydrous sodium sulfate, and filtered, and the filtrate was concentrated by rotary evaporation. The residue was purified by silica gel column chromatography (DCM/MeOH=15:1) to give intermediate 47-6 (85 mg, 72.4% yield) in the form of a white solid. LC-MS: $[M+H]^+$=402.3.

Step (5) Preparation of 3,5-difluoro-N-methyl-4-(7-methyl-3-((3-oxo-4-morpholinyl)methyl)imidazo[1,2-a]pyridin-2-yl)benzamide

47

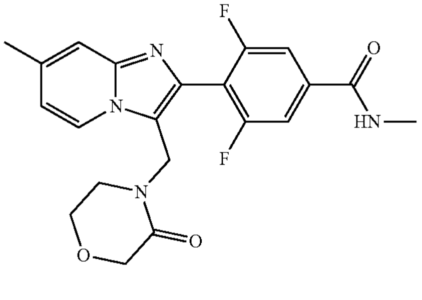

Intermediate 47-6 (80 mg, 0.2 mmol) was dissolved in DMF (5 mL), and methylamine hydrochloride (20 mg, 0.3 mmol), 2-(7-azabenzotriazol-1-yl)-N,N,N',N'-tetramethyluronium hexafluorophosphate (114 mg, 0.3 mmol) and triethylamine (44 mg, 0.4 mmol) were added sequentially. The reaction system was stirred at room temperature overnight. Then the reaction system was diluted with water (15 mL), extracted with ethyl acetate (10 mL×2), washed with saturated brine (10 mL), dried over anhydrous sodium sulfate and filtered, and the filtrate was concentrated by rotary evaporation. The residue was purified by silica gel column chromatography (DCM/MeOH=30:1) to give compound 47 (21 mg, 20% yield) in the form of a white solid.

LC-MS: $[M+H]^+$=415.1. $^1H$ NMR (400 MHZ, MeOD): δ 8.44 (d, J=6.9 Hz, 1H), 7.64 (d, J=7.8 Hz, 2H), 7.43 (s, 1H), 6.96 (d, J=6.9 Hz, 1H), 5.00 (s, 2H), 4.14-4.12 (m, 2H), 3.75-3.71 (m, 2H), 3.04-3.01 (m, 2H), 2.98 (s, 3H), 2.47 (s, 3H).

Example 48

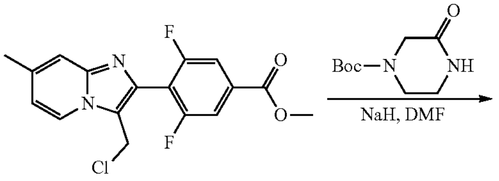

47-3

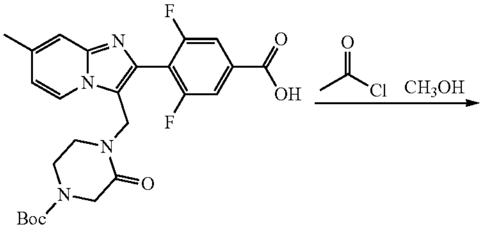

48-1

-continued

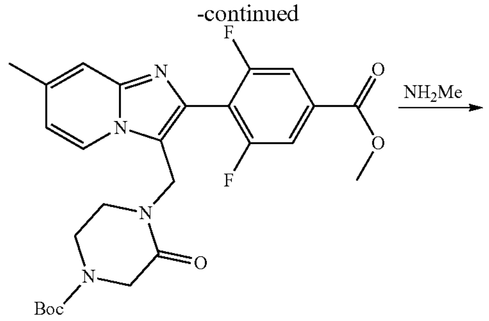

48-2

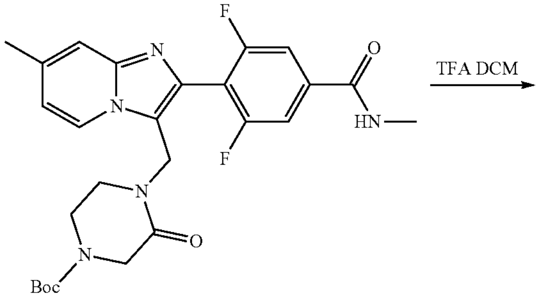

48-3

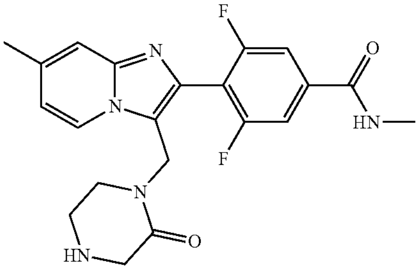

48

Step (1) Preparation of 4~ (3-((4-(tert-butoxycarbonyl)-2-oxopiperazin-1-yl)methyl)-7-methylimidazo[1,2-a]pyridin-2-yl)-3,5-difluorobenzoic acid 48-1

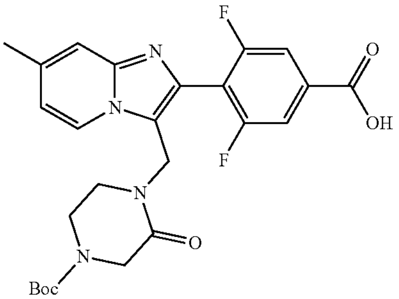

Tert-butyl 3-carbonylpiperazine-carboxylate (400 mg, 2.0 mmol) was dissolved in N,N-dimethylformamide (10 mL). The reaction system was cooled in an ice water bath for 5 min, added with sodium hydride (120 mg, 3.0 mmol) slowly, and reacted for 30 min. Then the reaction system was added with intermediate 47-3 (350 mg, 1.0 mmol) (60% purity shown on LC-MS) and stirred overnight. After the reaction was quenched with saturated ammonium chloride solution (5 mL), the reaction system was added dropwise with hydrochloric acid (1 N) to adjust the pH to 3-4, diluted with water (20 mL), and extracted with dichloromethane extraction (45 mL×3). The organic phases were combined, dried over anhydrous sodium sulfate, filtered and concentrated. The residue was separated by column chromatography (DCM/$CH_3OH$=10/1) to give intermediate 48-1 (300 mg, 50% purity shown on LC-MS) in the form of a light yellow solid. LC-MS: $[M+H]^+$=501.2.

Step (2) Preparation of tert-butyl (S)-2-((2-(2,6-difluoro-4-carbomethoxyphenyl)-7-methylimidazo [1,2-a]pyridin-3-yl)methyl)-2-carbonylpiperazine-carboxylate 48-2

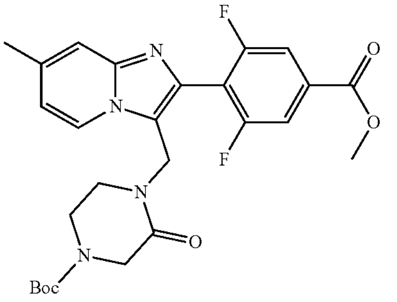

Intermediate 48-1 (300 mg, 0.69 mmol) was dissolved in methanol (5 mL). The reaction system was added dropwise with acetyl chloride (0.5 mL), and stirred overnight. Then the reaction system was concentrated, diluted with dichloromethane (25 mL), and washed with saturated sodium bicarbonate solution (15 mL). The aqueous phase was extracted with dichloromethane (20 mL×2). The organic phases were combined, washed with saturated brine (20 mL), dried over anhydrous sodium sulfate, filtered and concentrated. The residue was separated by column chromatography (PE/EA=1/1) to give intermediate 48-2 (70 mg, 60% purity shown on LC-MS) in the form of a colorless oily liquid, LC-MS: $[M+H]^+$=515.1.

Step (3) Preparation of tert-butyl (S)-2-((2-(2,6-difluoro-4-(methylcarbamoyl)phenyl)-7-methylimidazo[1,2-a]pyridin-3-yl)methyl)-2-carbonylpiperazine-carboxylate 48-3

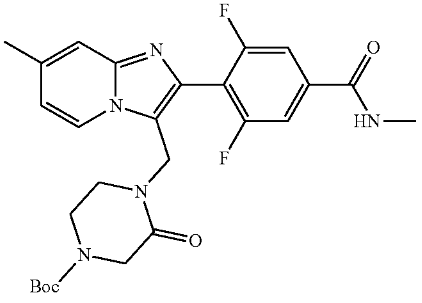

Intermediate 48-2 (70 mg, 0.13 mmol) was dissolved in ethanol (5 mL), and aqueous methylamine solution (2 mL, 25-30% w/w) was added. The reaction system was stirred at room temperature overnight. Then the reaction system was added with $H_2O$ (15 mL) to quench the reaction, and extracted with ethyl acetate (15 mL×2). The organic phases were combined, washed with saturated brine (15 mL), dried over anhydrous sodium sulfate, filtered and concentrated to give intermediate 48-3 (60 mg, 60% purity shown on LC-MS) in the form of a colorless oily liquid. LC-MS: $[M+H]^+$=514.1.

Step (4) Preparation of (S)-2-((2-(2,6-difluoro-4-(methylcarbamoyl)phenyl)-7-methylimidazo[1,2-a] pyridin-3-yl)methyl)-2-carbonyl-piperazine

48

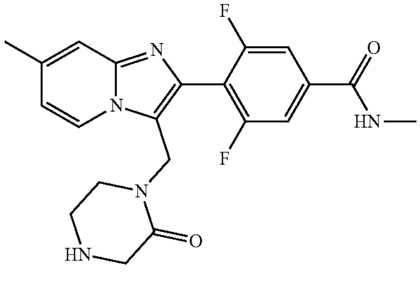

Intermediate 48-3 (60 mg, 0.12 mmol) was dissolved in dichloromethane (3 mL), and trifluoroacetic acid (3 mL) was added. The reaction system was stirred overnight at room temperature, concentrated by rotary evaporation, diluted with dichloromethane (40 mL), washed with saturated sodium bicarbonate solution (10 mL), washed with saturated brine (10 mL), and dried over anhydrous sodium sulfate. The residue was purified by preparative chromatography, and lyophilized to give compound 48 (3 mg) in the form of a white solid.

LC-MS: $[M+H]^+$=414.1. $^1H$ NMR (400 MHZ, MeOD): δ 8.47 (d, J=7.2 Hz, 1H), 7.64 (d, J=7.8 Hz, 2H), 7.42 (s, 1H), 6.95 (d, J=7.2 Hz, 2H), 4.99 (s, 2H), 3.42 (s, 2H), 3.00-2.95 (m, 5H), 2.87 (t, J=5.2 Hz, 2H), 2.49 (s, 3H).

Example 49

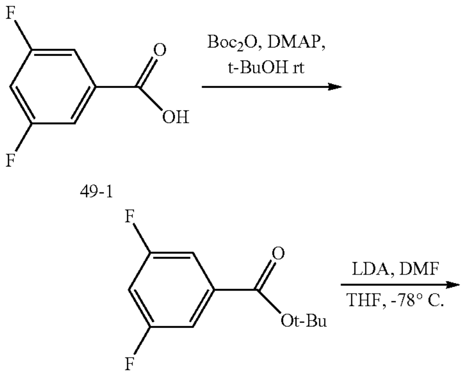

49-1

49-2

-continued

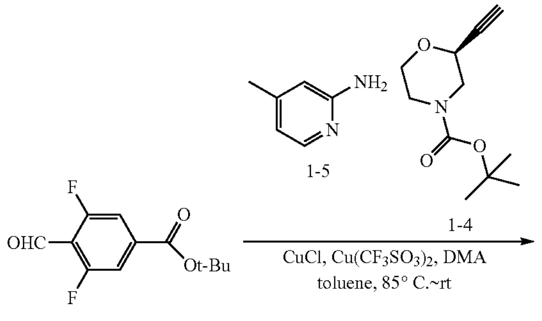

49-3

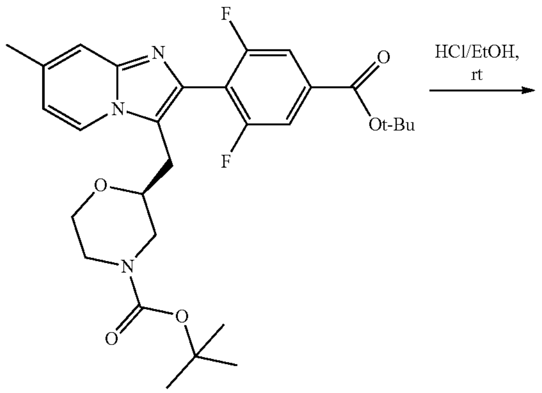

49-4

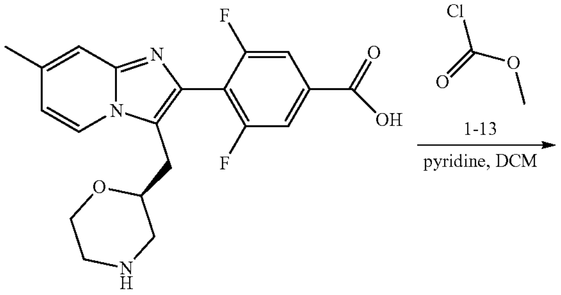

49-5

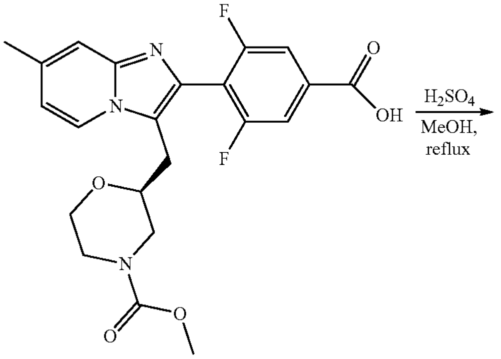

49-6

-continued

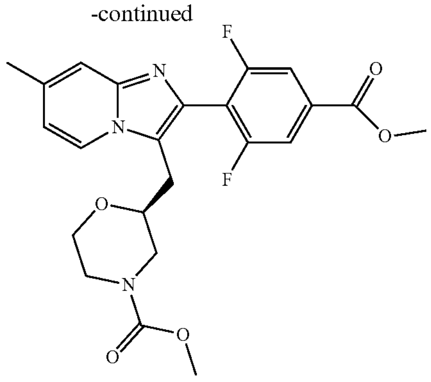

49

Step (1) Preparation of tert-butyl 3,5-difluorobenzoate 49-2

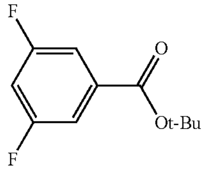

3,5-difluorobenzoic acid (10 g, 63.25 mmol) was dissolved in tert-butanol (100 mL), and DMAP (12.3 g, 18.975 mmol) and Boc-anhydride (27.6 g, 126.5 mmol) were added. The reaction system was reacted at room temperature for 15 h. Then the reaction system was concentrated, diluted with water (150 mL) and extracted with ethyl acetate (50 mL×3). The organic phase was dried over anhydrous sodium sulfate and concentrated. The residue was separated by column chromatography (PE/EA=20/1) to give compound 49-2 (12 g, 88% yield) in the form of a colorless oily liquid.

Step (2) Preparation of tert-butyl 3,5-difluoro-4-formylbenzoate 49-3

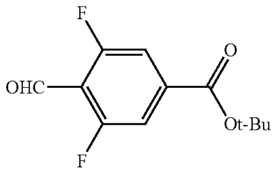

LDA (2 M, 8.4 mL) was dissolved in tetrahydrofuran (10 mL). The reaction system was cooled to −78° C. under nitrogen atmosphere. Compound 49-2 (3 g, 14 mmol) was dissolved in tetrahydrofuran (20 mL), and the solution was added to the reaction system. The reaction system was stirred at −78° C. for 1.5 h, added with DMF (1.228 g, 16.8 mmol), and stirred for another 1 h with the temperature maintained not higher than −70° C. Then the reaction system was added with saturated aqueous ammonium chloride solution (60 mL) to quench the reaction, and extracted with ethyl acetate (30 mL×3). The ethyl acetate phases were combined, dried over anhydrous sodium sulfate, and concentrated. The residue was separated by column chromatography (PE/EA=10/1) to give compound 49-3 (1.5 g, 44% yield) in the form of a yellow solid.

Step (3) Preparation of tert-butyl (S)-2-((2-(4-(tert-butoxycarbonyl)-2,6-difluorophenyl)-7-methylimidazo[1,2-a]pyridin-3-yl)methyl)morpholine-4-carboxylate 49-4

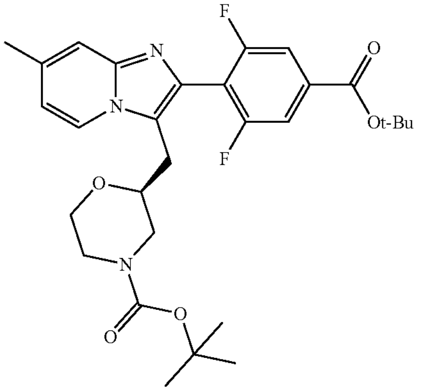

Compound 49-3 (480 mg, 1.98 mmol) was dissolved in anhydrous toluene (4 mL), and compound 1-4 (419 mg, 1.98 mmol), compound 1-5 (215 mg, 1.98 mmol), copper (1) chloride (62 mg, 0.63 mmol), and copper(II) trifluoromethanesulfonate (216 mg, 0.60 mmol) were added. Under nitrogen atmosphere, the reaction system was heated to 85° C., added with two drops of N,N-dimethylacetamide, heated and stirred for 6 h. Then the reaction system was cooled to room temperature and stirred overnight. Then the reaction system was filtered, and the filtrate was concentrated. The residue was separated by column chromatography (PE/EA=2/1) to give intermediate 49-4 (340 mg, 31% yield) in the form of a brown solid. LC-MS: $[M+H]^+$=544.7.

Step (4) Preparation of (S)-3,5-difluoro-4-(7-methyl-3-(morpholin-2-ylmethyl)imidazo[1,2-a]pyridin-2-yl)benzoic acid 49-5

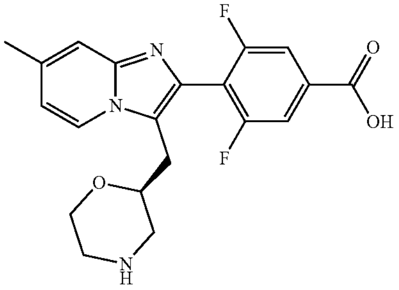

Intermediate 49-4 (340 mg, 0.62 mmol) was dissolved in ethanol (3 mL), and a solution of HCl in ethanol (1 mL, 33%) was added. The reaction system was stirred at room temperature for 1.5 h. Then the reaction system was concentrated to give intermediate 49-5 (400 mg) in the form of a yellow oily liquid.

LC-MS: $[M+H]^+$=388.7.

Step (5) Preparation of (S)-3,5-difluoro-4-(3-((4-(methoxycarbonyl)morpholin-2-yl)methyl)-7-methylimidazo[1,2-a]pyridin-2-yl)benzoic acid 49-6

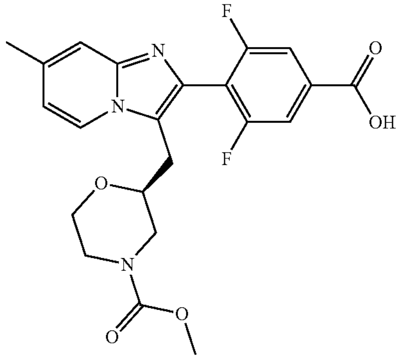

Intermediate 49-5 (400 mg) was dissolved in dichloromethane (5 mL), and pyridine (244 mg, 3.09 mmol) was added, followed by the addition of methyl chloroformate (62 mg, 0.65 mmol). The reaction system was stirred at room temperature for 1.5 h, and concentrated to give intermediate 49-6 (190 mg).

LC-MS: $[M+H]^+$=446.6.

Step (6) Preparation of methyl (S)-2-((2-(2,6-difluoro-4-carbomethoxyphenyl)-7-methylimidazo[1,2-a]pyridin-3-yl)-methyl)morpholine-4-carboxylate

49

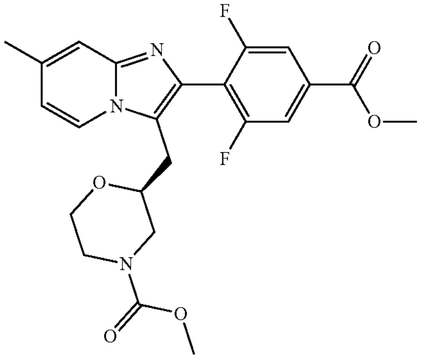

Intermediate 49-6 (50 mg, 0.1124 mmol) was dissolved in absolute methanol (5 mL), and concentrated sulfuric acid (0.1 mL) was added. The reaction system was stirred under reflux overnight. Then the reaction system was concentrated, diluted with water (10 mL), and extracted with ethyl acetate (10 mL×2). The organic phase was dried over anhydrous sodium sulfate and concentrated. The residue was separated by thin-layer chromatography (PE/EA=3/1) to give compound 49 (20.8 mg, 40% yield) in the form of a white solid.

LC-MS: $[M+H]^+$=460.7. $^1$H NMR (400 MHZ, $CDCl_3$): δ 8.27 (brs, 1H), 7.73 (d, J=7.1 Hz, 2H), 7.54 (brs, 1H), 6.80 (brs, 1H), 4.00 (s, 3H), 3.99-3.75 (m, 3H), 3.70 (s, 3H), 3.65-3.56 (m, 1H), 3.45-3.35 (m, 1H), 3.10-3.85 (m, 3H), 2.67-2.57 (m, 1H), 2.48 (s, 3H).

Example 50

Preparation of methyl (S)-2-((2-(2,6-difluoro-4-(1H-parazole)phenyl)-7-methylimidazo[1,2-a]pyridin-3-yl)methyl)morpholine-4-carboxylate

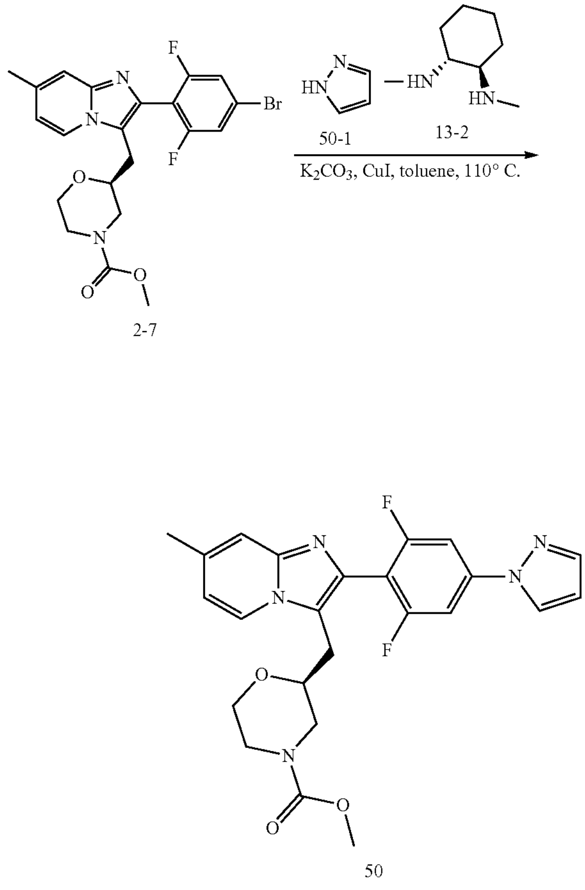

2-7

50

Intermediate 2-7 (120 mg, 0.25 mmol) was dissolved in anhydrous toluene (3 mL), and potassium carbonate (104 mg, 0.75 mmol), copper (1) iodide (4.8 mg, 0.025 mmol), 1H-pyrazole (34 mg, 0.50 mmol) and trans-(1R,2R)—N,N'-dimethyl-1,2-cyclohexanediamine (3.6 mg, 0.025 mmol) were added under nitrogen atmosphere. The reaction system was reacted at 110° C. overnight. After the reaction was completed, the reaction system was cooled to room temperature and filtered, and the filtrate was added with water (10 mL) and extracted with dichloromethane (20 mL×3). The organic phases were combined, washed with saturated brine (20 ml×1), dried over magnesium sulfate, filtered and concentrated by rotary evaporation to give a crude product. The crude product was purified by high performance liquid chromatography to give compound 50 (18.7 mg, 16% yield) in the form of a yellow solid.

LC-MS: $[M+H]^+$=468.7. $^1$H NMR (400 MHZ, MeOD): δ 8.44-8.40 (m, 2H), 7.80 (s, 1H), 7.67 (d, J=8.1 Hz, 2H), 7.35 (s, 1H), 6.88 (d, J=7.0 Hz, 1H), 6.61 (s, 1H), 3.89-3.76 (m, 3H), 3.66 (s, 3H), 3.65-3.56 (m, 1H), 3.42-3.36 (m, 1H), 3.15-3.06 (m, 2H), 2.96-2.80 (m, 1H), 2.72-2.60 (m, 1H), 2.47 (s, 3H).

Example 51

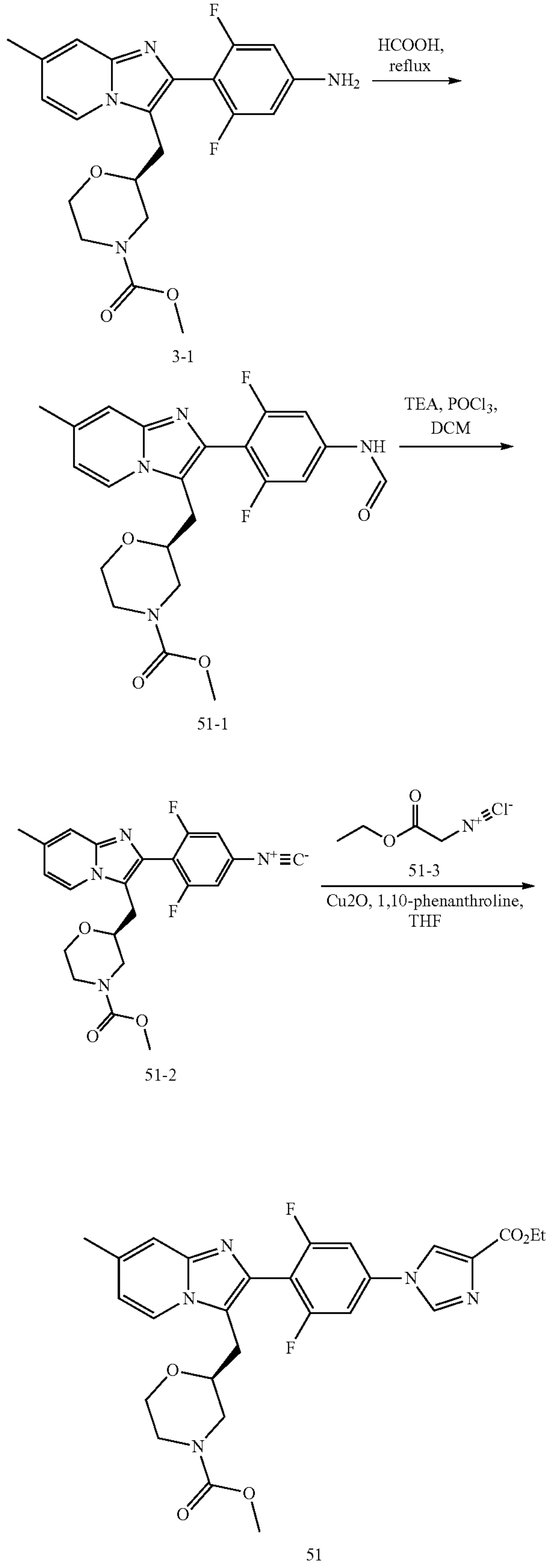

3-1

51-1

51-2

51

Step (1) Preparation of methyl (S)-2-((2-(2,6-difluoro-4-formylaminophenyl)-7-methylimidazo[1,2-a]pyridin-3-yl)methyl)morpholine-4-carboxylate 51-1

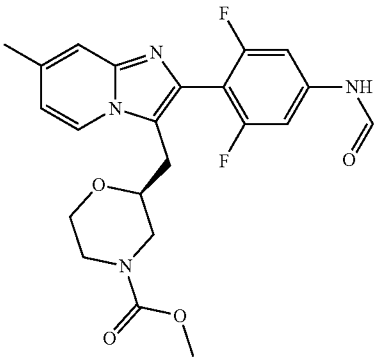

Intermediate 3-1 (360 mg, 0.86 mmol) was dissolved in formic acid (5 mL). The reaction system was reacted at 90° C. for 2 h. After the reaction was completed as monitored by TLC, the reaction system was concentrated under reduced pressure, added with saturated brine (10 mL), adjusted to pH 7-8 with saturated sodium bicarbonate solution, and extracted with DCM (10 mL×3). The organic phases were combined, dried over anhydrous sodium sulfate, filtered and concentrated. The crude product was purified by silica gel column chromatography to give intermediate 51-1 (220 mg, 52% yield) in the form of a yellow solid. MS $[M+H]^+$=445.1.

Step (2) Preparation of methyl (S)-2-((2-(2,6-difluoro-4-isocyanophenyl)-7-methylimidazo[1,2-a]pyridin-3-yl)methyl)morpholine-4-carboxylate 51-2

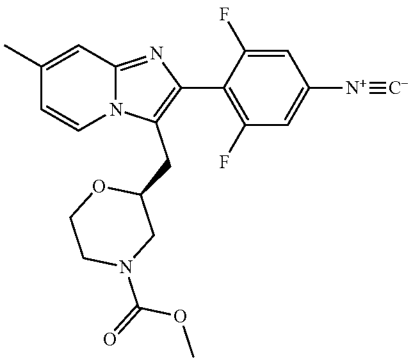

Intermediate 51-1 (220 mg, 0.49 mmol) and triethylamine (149 mg, 1.5 mmol) were dissolved in dichloromethane (25 mL) and phosphorus oxychloride (115 mg, 0.75 mmol) was added dropwise slowly at 0° C. After the completion of the dropwise addition, the reaction system was reacted at 0° C. for 2 h. After the reaction was completed as monitored by LCMS, the reaction system was added with water at 0° C. to quench the reaction, with the temperature maintained at 25° C. below. Then the reaction system was adjusted to pH 7-8 with saturated sodium bicarbonate solution, and washed with saturated saline (10 mL). The organic phase was dried, and concentrated to give intermediate 51-2 (210 mg, 84% yield, crude product) in the form of a yellow oily liquid, which was used directly in the next step without purification. MS $[M+H]^+$=427.0.

Step (3) Preparation of methyl (S)-2-((2-(4-(4-(carbethoxy<ethoxycarbonyl>)-1H-imidazol-1-yl)-2,6-difluorophenyl)-7-methylimidazo[1,2-a]pyridin-3-yl)methyl)morpholine-4-carboxylate

51

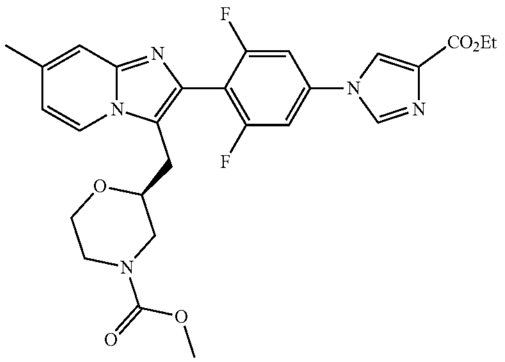

Intermediate 51-2 (170 mg, 0.4 mmol), ethyl isocyanoacetate (45 mg, 0.4 mmol), copper(I) chloride (8.6 mg, 0.06 mmol) and 1,10-phenanthroline (22 mg, 0.12 mmol) were dissolved in tetrahydrofuran (15 mL). The reaction system was reacted at 60° C. for 3 h under nitrogen atmosphere, and reacted at room temperature overnight. Then the reaction system was added with saturated brine (20 mL), and extracted with ethyl acetate (10 mL×3). The organic phases were combined, dried over anhydrous sodium sulfate, filtered and concentrated by rotary evaporation to give a crude product. The crude product was purified by FCC to give compound 51 (160 mg, 70% yield) in the form of a white solid. MS $[M+H]^+$=540.1.

1H NMR (400 MHz, d6-DMSO) δ 8.70 (d, J=1.3 Hz, 1H), 8.60 (d, J=1.3 Hz, 1H), 8.44 (d, J=7.1 Hz, 1H), 7.89 (d, J=8.6 Hz, 2H), 7.37 (s, 1H), 6.85 (dd, J=7.1, 1.5 Hz, 1H), 4.30 (q, J=7.1 Hz, 2H), 3.77 (d, J=12.2 Hz, 1H), 3.66 (t, J=12.1 Hz, 2H), 3.56 (s, 3H), 3.53-3.47 (m, 1H), 3.29-3.21 (m, 1H), 3.10-3.00 (m, 2H), 2.90-2.74 (m, 1H), 2.60-2.45 (m, 1H), 2.40 (s, 3H), 1.32 (t, J=7.1 Hz, 3H).

Example 52

Step (1)

Compound 52-1 was prepared by replacing methyl chloroformate with acetyl chloride, according to the preparation method for compound 6 in Example 6.

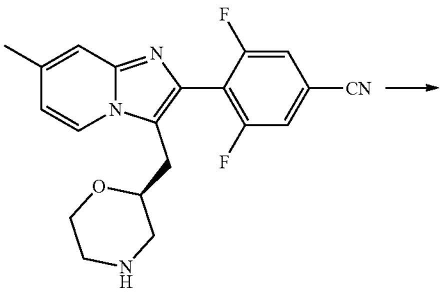
6-4
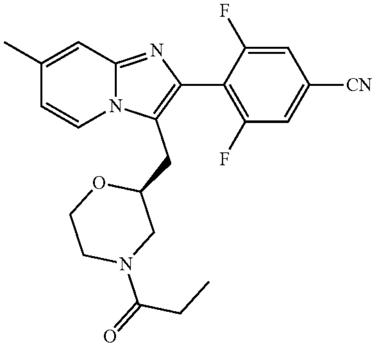
52-1
Step (2)
Compound 52 was prepared by using compound 52-1 as the starting material, according to the preparation method as described in Example 7.
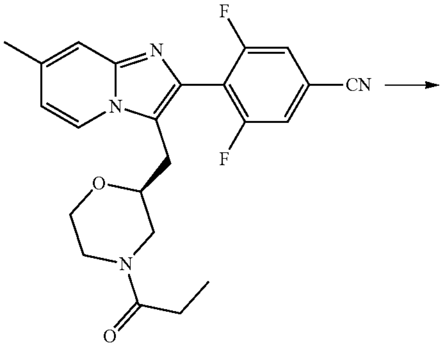
52-1
-continued
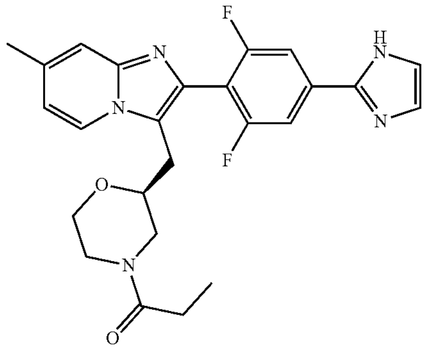
52
LC-MS: $[M+H]^+$=466.1.
Example 53
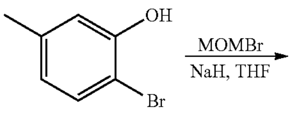
53-1
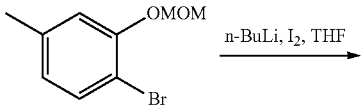
53-2
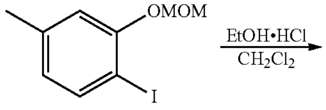
53-3
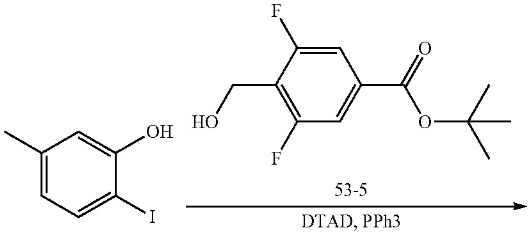
53-4
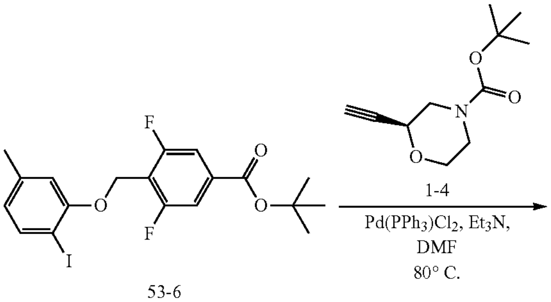
53-6

-continued

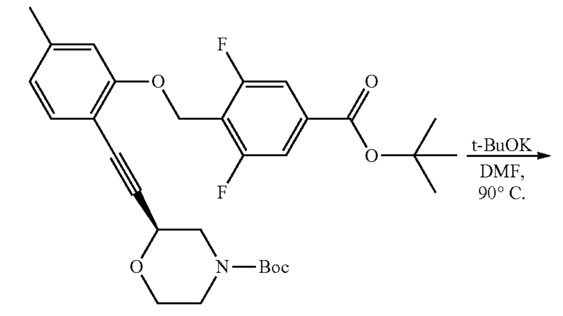

53-7

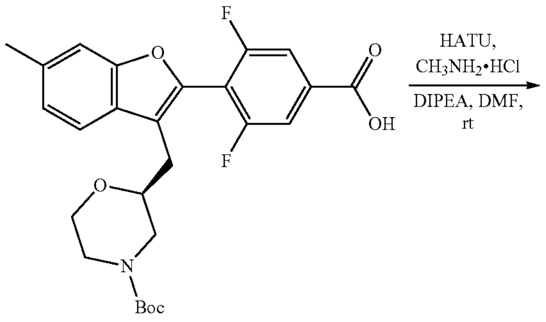

53-8

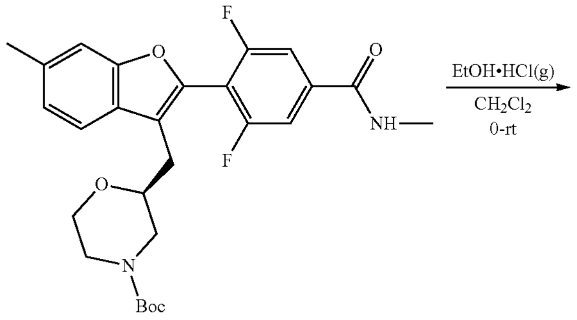

53-9

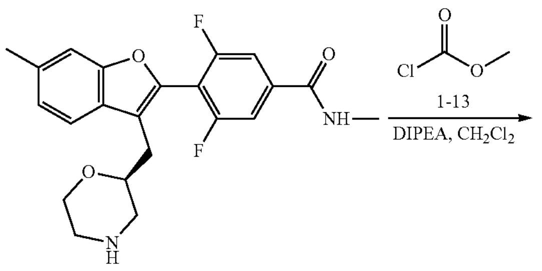

53-10

-continued

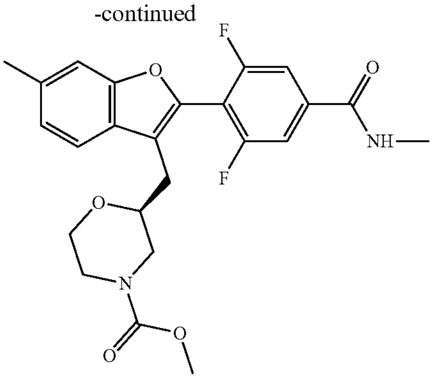

53

Step (1) Preparation of 1-bromo-2-(methoxymethoxy)-4-methylbenzene 53-2

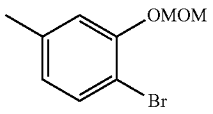

2-bromo-5-methylphenol (1.6 g, 8.55 mmol) was dissolved in tetrahydrofuran (20 mL), and sodium hydride (855 mg, 21.37 mmol) was added in portions under nitrogen atmosphere in an ice water bath. The reaction system was reacted at 0° C. for 30 min, added dropwise with bromomethyl methyl ether (1.4 g, 11.12 mmol), and stirred at room temperature overnight. Then the reaction system was poured into ice water (20 mL), and extracted with ethyl acetate (20 mL×2). The organic phases were combined, washed with saturated brine (30 mL), dried over anhydrous sodium sulfate, filtered and concentrated. The residue was purified by silica gel column chromatography to give intermediate 53-2 (1.7 g, 68% yield) in the form of a colorless oil.

Step (2) Preparation of 1-iodo-2-(methoxymethoxy)-4-methylbenzene 53-3

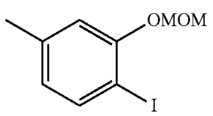

Intermediate 53-2 (528 mg, 2.29 mmol) was dissolved in tetrahydrofuran (10 mL) under nitrogen atmosphere, and n-butyllithium (1.2 mL, 2.75 mmol) was added dropwise at −78° C. The reaction system was reacted at this temperature for 20 min, added dropwise with a solution of iodine (874 mg, 3.44 mmol) in tetrahydrofuran (5 mL), and reacted for 2 h. Then the reaction system added with ice water (20 mL) to quench the reaction, added with saturated sodium thiosulfate solution (2 mL), stirred at room temperature for 5 min, and extracted with ethyl acetate (25 mL×2). The organic phases were combined, washed with saturated brine (20 mL), dried over anhydrous sodium sulfate, filtered and concentrated to give intermediate 53-3 (570 mg, 80% purity, 72% yield, crude product) in the form of a brown oil.

Step (3) Preparation of 2-iodo-5-methylphenol 53-4

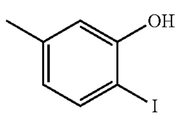

Intermediate 53-3 (570 mg, 2.05 mmol) was dissolved in tetrahydrofuran (8 mL), and a solution of HCl in ethanol (1.03 mL, 4.1 mmol) was added dropwise at 0° C. The reaction system was stirred at room temperature for 2 h and concentrated under reduced pressure. The residue was purified by silica gel column chromatography to give intermediate 53-4 (400 mg, 70% purity, 58% yield) in the form of a colorless oil.

Step (4) Preparation of tert-butyl 3,5-difluoro-4-((2-iodo-5-methylphenoxy)methyl)benzoate 53-6

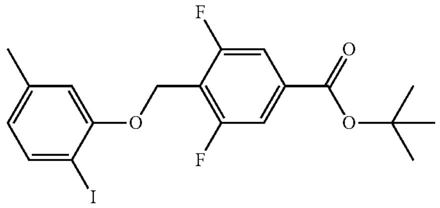

Intermediate 53-4 (400 mg, 1.71 mmol), triphenylphosphine (673 mg, 2.57 mmol) and tert-butyl 3,5-difluoro-4-(hydroxymethyl)benzoate (418 mg, 1.71 mmol) were dissolved in tetrahydrofuran (6 mL) under nitrogen atmosphere, and di-tert-butyl azodicarboxylate (591 mg, 2.57 mmol) was added. The reaction system was reacted at room temperature overnight. Then the reaction system was concentrated under reduced pressure, added with ethyl acetate (30 mL), washed with saturated brine (20 mL×2), dried over anhydrous sodium sulfate, filtered and concentrated. The crude product was purified by silica gel column chromatography to give intermediate 53-6 (375 mg, 75% purity, 37% yield) in the form of a yellow oil. ESI-MS [M+Na]$^+$: 462.5.

Step (5) Preparation of tert-butyl (S)-2-((2-((4-(tert-butoxycarbonyl)-2,6-difluorobenzyl)oxo)-4-methylphenyl)ethynyl)morpholine-4-carboxylate 53-7

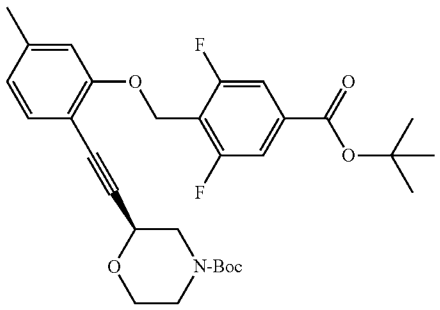

Intermediate 53-6 (290 mg, 0.63 mmol) and tert-butyl (S)-2-ethynylmorpholine-4-carboxylate (146 mg, 0.69 mmol) were dissolved in N,N-dimethylformamide (1.5 mL) under nitrogen atmosphere, and copper(I) iodide (12 mg, 0.063 mmol), bis(triphenylphosphine)palladium(II) chloride (91 mg, 0.13 mmol) and triethylamine (4 mL) were added. The reaction system was reacted at 80° C. for 8 h, cooled to room temperature, added with water (40 mL), and extracted with ethyl acetate (30 mL×2). The organic phases were combined, washed with saturated brine (20 mL×2), dried over anhydrous sodium sulfate, filtered and concentrated. The residue was purified by silica gel column chromatography to give intermediate 53-7 (132 mg, 75% purity, 29% yield) in the form of a brown solid. ESI-MS [M+Na]$^+$: 565.6.

Step (6) Preparation of (S)-4-(3-((4-(tert-butoxycarbonyl)morpholin-2-yl)methyl)-6-methylbenzofuran-2-yl)-3,5-difluorobenzoic acid 53-8

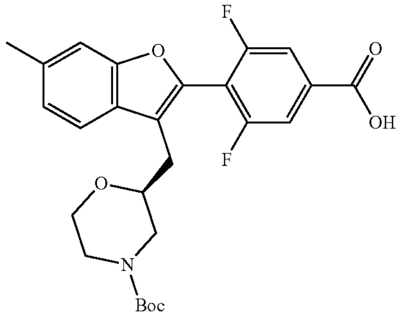

Intermediate 53-7 (132 mg, 0.24 mmol) was dissolved in N,N-dimethylformamide (3 mL) under nitrogen atmosphere, and potassium tert-butoxide (96 mg, 0.72 mmol) was added. The reaction system was reacted at 80° C. for 3 h. Then the reaction system was cooled to room temperature, poured into water (10 mL), adjusted to pH 4 with diluted hydrochloric acid (1 N), and extracted with ethyl acetate (20 mL×2). The organic phases were combined, washed with saturated brine (15 mL×2), dried over anhydrous magnesium sulfate, filtered and concentrated. The crude product was purified by silica gel column chromatography to give intermediate 53-8 (100 mg, 70% purity, 55% yield) in the form of a brown solid.

ESI-MS $[M+Na]^+$: 510.1.

Step (7) Preparation of tert-butyl (S)-2-((2-(2,6-difluoro-4-(methylcarbamoyl)phenyl)-6-methylbenzofuran-3-yl)methyl)morpholine-4-carboxylate

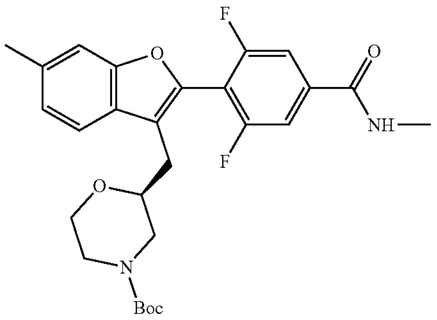

53-9

Intermediate 53-8 (100 mg, 0.20 mmol) and 2-(7-azabenzotriazol-1-yl)-N,N,N',N'-tetramethyluronium hexafluorophosphate (114 mg, 0.30 mmol) were dissolved in N,N-dimethylformamide (3 mL) under nitrogen atmosphere. The reaction system was stirred at room temperature for 10 min, added with N,N-diisopropylethylamine (1.79 mL, 1.40 mmol) and methylamine hydrochloride (68 mg, 1.00 mmol), and stirred at room temperature for another 4 h. Then the reaction system was added with water (20 mL) and extracted with ethyl acetate (20 mL×2). The organic phases were combined and washed with saturated brine (15 mL×2). The crude product was purified by silica gel column chromatography to give intermediate 53-9 (65 mg, 63% yield) in the form of a light yellow solid. ESI-MS $[M+Na]^+$: 522.7.

Step (8) Preparation of (S)-3,5-difluoro-N-methyl-4-(6-methyl-3-(morpholin-2-ylmethyl)benzofuran-2-yl)benzamide hydrochloride

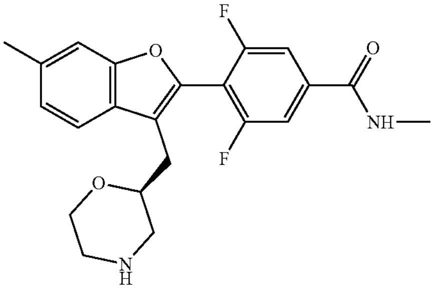

53-10

Intermediate 53-9 (65 mg, 0.13 mmol) was dissolved in dichloromethane (2 mL) and a solution of HCl in ethanol (0.5 mL, 0.52 mmol) was added dropwise. The reaction system was stirred at room temperature for 4 h and concentrated under reduced pressure to give intermediate 53-10 in the form of a light yellow solid (70 mg, crude product), ESI-MS $[M+H]^+$: 400.7.

Step (9) Preparation of methyl (S)-2-((2-(2,6-difluoro-4-(methylcarbamoyl)phenyl)-6-methylbenzofuran-3-yl)methyl)morpholine-4-carboxylate

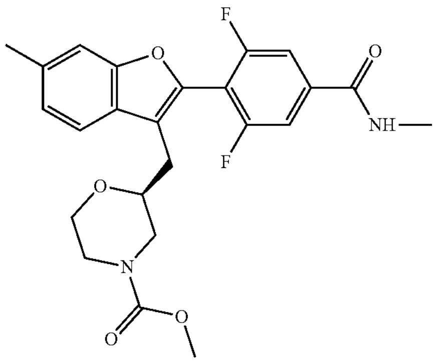

53

Intermediate 53-10 (70 mg, 0.18 mmol) and triethylamine (0.99 mL, 0.72 mmol) were dissolved in dichloromethane (2 mL), and methyl chloroformate (21 mg, 0.22 mmol) was added dropwise at 0° C. The reaction system was reacted at this temperature for 4 h. Then the reaction system was poured into ice water (10 mL), and extracted with dichloromethane (15 mL×2). The organic phases were combined, washed with saturated brine (10 mL×2), dried over anhydrous sodium sulfate, filtered and concentrated. The crude product was purified by preparative high performance liquid chromatography to give compound 53 (22 mg, 22% yield) in the form of a white solid.

ESI-MS $[M+H]^+$: 458.8. 1H NMR (400 MHZ, MeOD) δ 7.63 (d, J=8.0 Hz, 1H), 7.62 (d, J=8.4 Hz, 2H), 7.35 (s, 1H), 7.17 (d, J=8.0 Hz, 1H), 3.81-3.78 (m, 3H), 3.65 (s, 3H), 3.63-3.58 (m, 1H), 3.39-3.38 (m, 1H), 2.97 (s, 3H), 2.95-2.86 (m, 2H), 2.83-2.76 (m, 1H), 2.62-2.58 (m, 1H), 2.51 (s, 3H).

Example 54

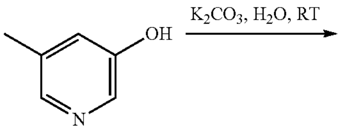

54-1

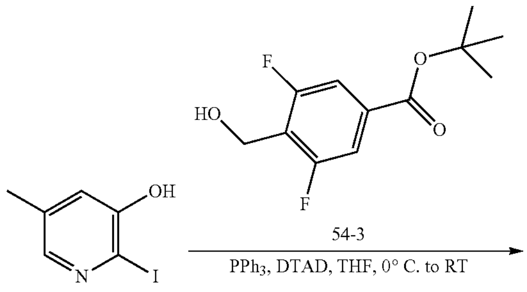

-continued

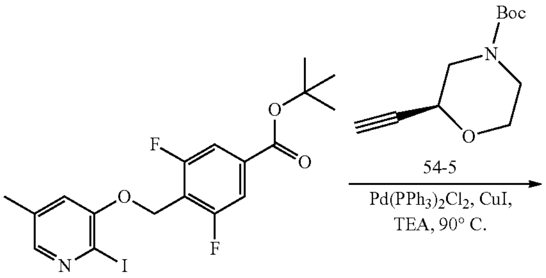

54-4

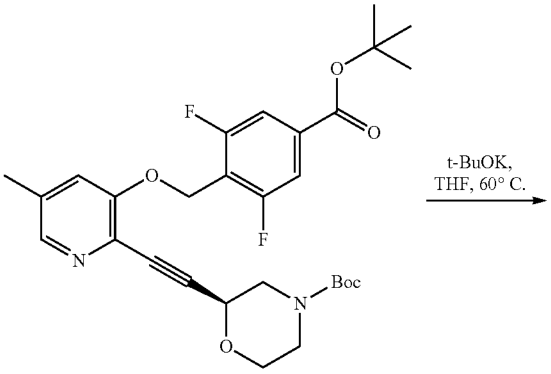

54-6

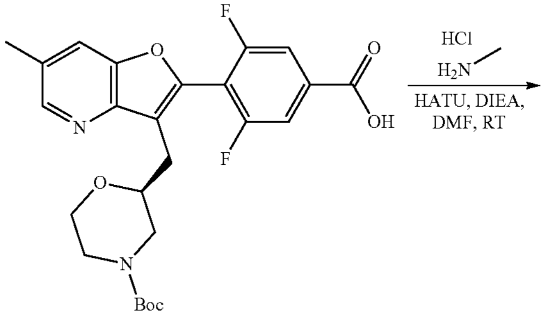

54-7

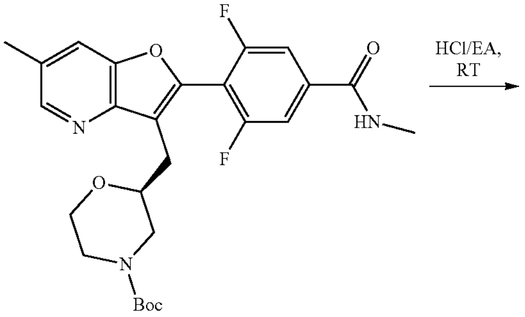

54-8

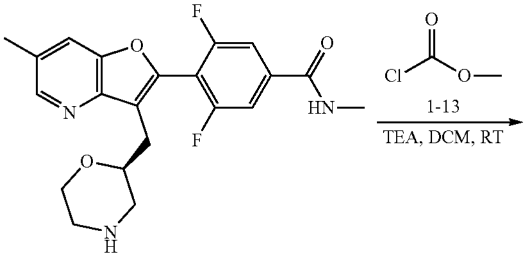

54-9

-continued

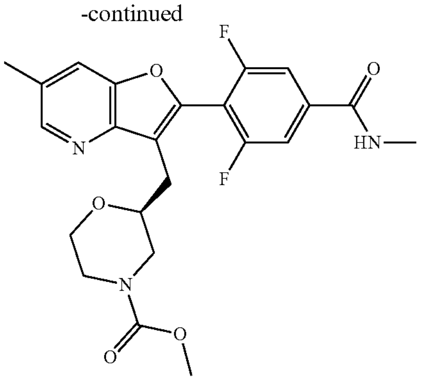

54

Step (1) Preparation of 2-iodo-5-methylpyridin-3-ol 54-2

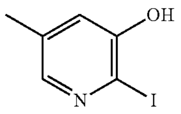

Iodine (2.56 g, 10.08 mmol) was added to a solution of 5-methylpyridin-3-ol (1.10 g, 10.08 mmol) and potassium carbonate (4.18 g, 30.24 mmol) in water (100 mL) while stirring at room temperature. The reaction mixture was stirred at room temperature for 3 h. Then the reaction system was adjusted to pH 6 with diluted hydrochloric acid and extracted with DCM (100 mL×3). The organic phases were combined, dried over anhydrous sodium sulfate, and evaporated to dryness. The crude product was purified by silica gel column chromatography to give intermediate 54-2 (1.9 g, 79.4% yield) in the form of a white solid.

LC-MS: $[M+H]^+$=235.9.

Step (2) Preparation of tert-butyl 3,5-difluoro-4-(((2-iodo-5-methylpyridin-3-yl)oxy)methyl)benzoate 54-4

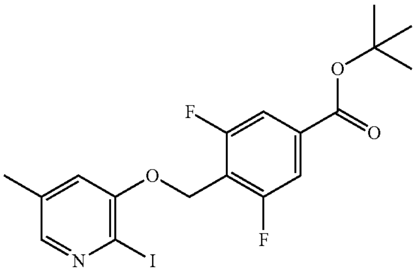

Intermediate 54-2 (773 mg, 3.29 mmol), tert-butyl 3,5-difluoro-4-(hydroxymethyl)benzoate (884 mg, 3.62 mmol) and triphenylphosphine (949 mg, 3.62 mmol) were dissolved in THF (15 mL) at 0° C. under nitrogen atmosphere, and a solution of DTAD (833 mg, 3.619 mmol) in THF (5 mL) was added dropwise. After the completion of the dropwise addition, the reaction system was slowly warmed to room temperature and stirred for 4 h. Then the reaction system was added with water (50 mL) to quench the reaction, and extracted with dichloromethane (30 mL×3). The organic phases were combined, washed with saturated brine (40 mL), dried over anhydrous sodium sulfate, filtered and concentrated by rotary evaporation to give a crude product. The crude product was purified by column chromatography to give intermediate 54-4 (1.5 g, 97.9% yield) in the form of a white solid. LC-MS: [M+H]$^+$=462.0.

Step (3) Preparation of tert-butyl (S)-2-((3-((4-(tert-butoxycarbonyl)-2,6-difluorobenzyl)oxy)-5-methylpyridin-2-yl)ethynyl)morpholine-4-carboxylate 54-6

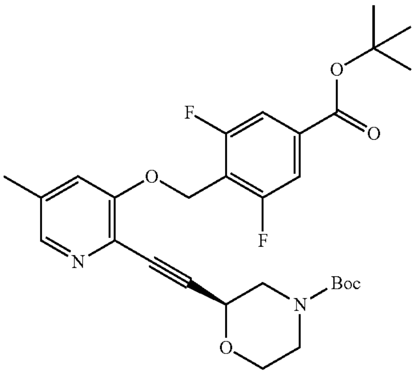

To a solution of intermediate 54-4 (500 mg, 1.08 mmol) and tert-butyl (2S)-2-ethynylmorpholin-4-yl formate (344 mg, 1.62 mmol) in TEA (30 mL) were added copper(I) iodide (21 mg, 0.11 mmol) and bis(triphenylphosphine) palladium(II) chloride (38 mg, 0.054 mmol) under nitrogen atmosphere. The reaction system was stirred at 90° C. overnight. Then the reaction system was evaporated to dryness to remove the solvent. The crude product was purified by silica gel column chromatography (petroleum ether/ethyl acetate=10/1) to give intermediate 54-6 (452 mg, 73.2% yield) in the form of a yellow oil.

LC-MS: [M+H]$^+$=545.2.

Step (4) Preparation of (S)-4-(3-((4~ (tert-butoxycarbonyl)morpholin-2-yl)methyl)-6-methylfurano[3,2-b]pyridin-2-yl)-3,5-difluorobenzoic acid 54-7

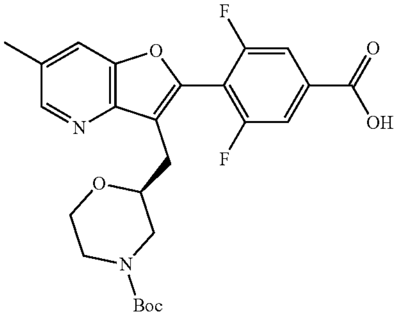

To a solution of intermediate 54-6 (453 mg, 0.83 mmol) in THF (20 mL) was added t-BuOK (232 mg, 2.08 mmol) at room temperature. The reaction system was reacted at 60° C. for 2 h. Then the reaction system was cooled to room temperature, added with water (50 mL), adjusted to pH 6 with formic acid, and extracted with EA (30 mL×3). The organic phases were combined, washed with saturated brine (30 mL), dried over anhydrous sodium sulfate, filtered and concentrated by rotary evaporation. The crude product was purified by silica gel column chromatography to give intermediate 54-7 (230 mg, 56.7% yield) in the form of a yellow solid. LC-MS: [M+H]$^+$=489.2.

Step (5) Preparation of tert-butyl (S)-2-((2-(2,6-difluoro-4-(methylcarbamoyl)phenyl)-6-methylfurano[3,2-b]pyridin-3-yl)methyl)morpholine-4-carboxylate 54-8

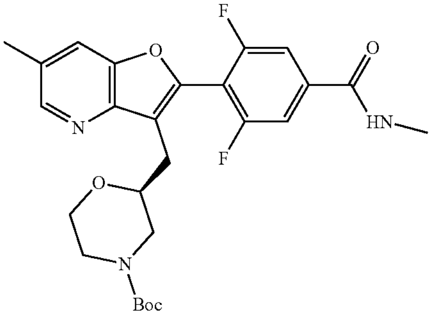

To a solution of intermediate 54-7 (230 mg, 0.47 mmol) and HATU (268 mg, 0.71 mmol) in DMF (10 mL) was added DIEA (243 mg, 1.88 mmol) at room temperature under nitrogen atmosphere. The reaction system was stirred for 10 min, added with methylamine hydrochloride (63 mg, 0.94 mmol), and stirred at room temperature overnight. Then the reaction system was added with water (50 mL) to quench the reaction and extracted with EA (30 mL×3). The organic phases were combined, dried over anhydrous sodium sulfate, filtered and concentrated by rotary evaporation. The crude product was purified by silica gel column chromatography to give intermediate 54-8 (162 mg, 68.1% yield) in the form of a yellow solid.

LC-MS: [M+H]$^+$=502.2.

Step (6) Preparation of (S)-3,5-difluoro-N-methyl-4-(6-methyl-3-(morpholin-2-ylmethyl)furano[3,2-b]pyridin-2-yl)benzamide 54-9

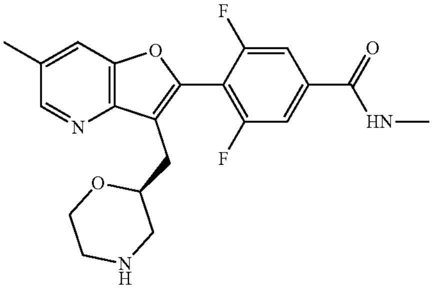

A solution of HCl in EA (3 M, 2 mL) was added dropwise to a solution of intermediate 54-8 (162 mg, 0.32 mmol) in EA (1 mL). The reaction system was stirred at room temperature for 2 h, and concentrated by rotary evaporation to give(S)-3,5-difluoro-N-methyl-4-(6-methyl-3-(morpholin-2-ylmethyl)furano[3,2-b]pyridin-2-yl)benzamide hydrochloride in the form of a yellow solid (130 mg, crude product), LC-MS: $[M+H]^+$=402.1.

Step (7) Preparation of methyl (S)-2-((2-(2,6-difluoro-4-(methylcarbamoyl)phenyl)-6-methylfurano [3,2-b]pyridin-3-yl)methyl)morpholine-4-carboxylate

54

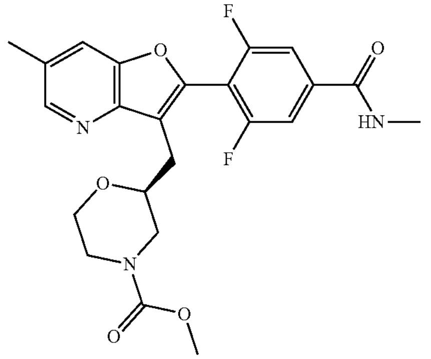

To a solution of intermediate 54-8 (130 mg, 0.32 mmol) and TEA (100 mg, 0.96 mmol) in DCM (10 mL) was added methyl chloroformate (61 mg, 0.64 mmol) dropwise while stirring at room temperature. After the completion of the dropwise addition, the reaction system was reacted at room temperature for 2 h, and concentrated by rotary evaporation. The crude product was purified by silica gel column chromatography, and lyophilized to give compound 54 (110 mg, 74.3% yield over two steps) in the form of a white solid.

LC-MS: $[M+H]^+$=460.1. $^1H$ NMR (400 MHz, MeOD): δ8.45 (s, 1H), 7.84 (s, 1H), 7.64 (d, J=8.3 Hz, 2H), 3.93 (d, J=13.6 Hz, 1H), 3.77 (d, J=13.2 Hz, 2H), 3.71-3.63 (m, 4H), 3.38-3.29 (m, 1H), 3.03-2.92 (m, 5H), 2.90-2.80 (m, 1H), 2.67-2.56 (m, 1H), 2.55 (s, 3H).

Example 55

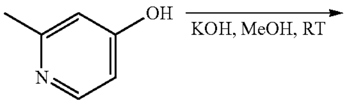

55-1

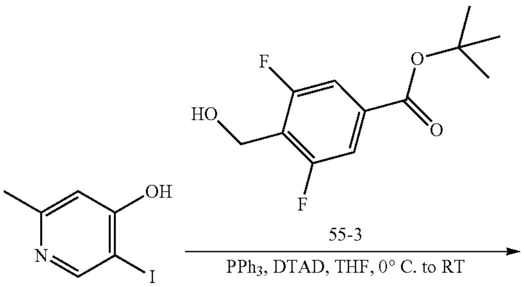

55-3

55-2

-continued

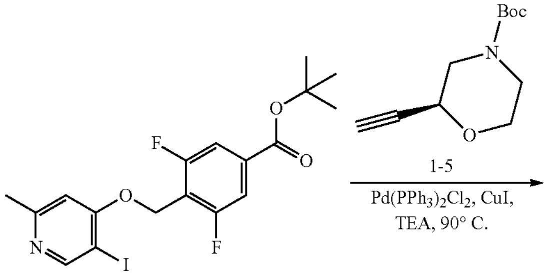

55-4

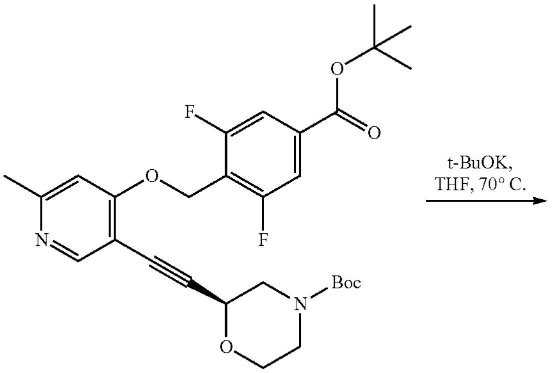

55-6

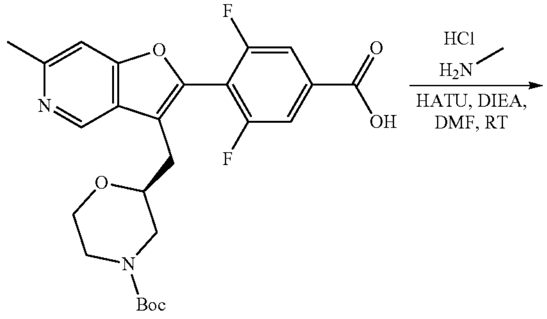

55-6

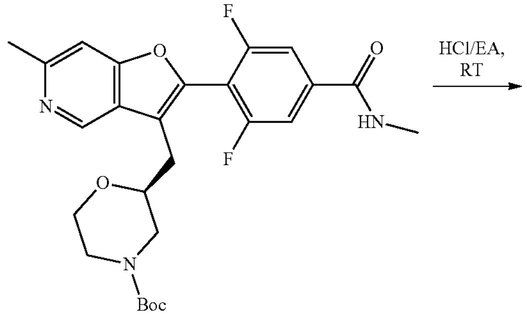

55-7

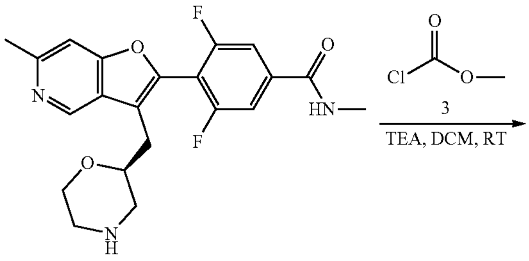

55-8

-continued

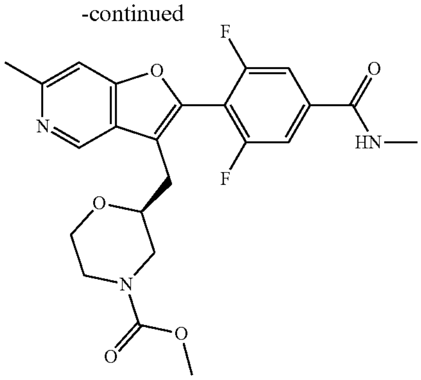

55

Step (1) Preparation of 5-iodo-2-methylpyridin-4-ol 55-2

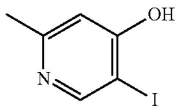

Iodine (7.8 g, 31 mmol) was added to a solution of 6-methylpyridin-2-ol (3.0 g, 28 mmol) and potassium hydroxide (6.3 g, 112 mmol) in methanol (200 mL) in portions while stirring at room temperature. The reaction system was stirred at room temperature overnight. Then the reaction system was adjusted to pH 6 with concentrated hydrochloric acid, and concentrated under reduced pressure. The crude product was purified by silica gel column chromatography to give intermediate 55-2 (1.2 g, 18.6% yield) in the form of an off-white solid. LC-MS: $[M+H]^+=235.8$.

Step (2) Preparation of tert-butyl 3,5-difluoro-4-(((5-iodo-2-methylpyridin-4-yl)oxy)methyl)benzoate 55-4

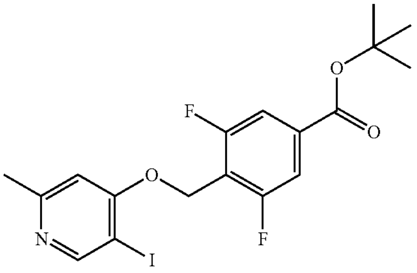

Intermediate 55-2 (470 mg, 2.0 mmol), tert-butyl 3,5-difluoro-4-(hydroxymethyl)benzoate (733 mg, 3.0 mmol) and triphenylphosphine (1049 mg, 4.0 mmol) were added to THF (25 mL) at 0° C. under nitrogen atmosphere, and a solution of DTAD (1382 mg, 6.0 mmol) in THF (5 mL) was added dropwise. After the completion of the dropwise addition, the reaction system was slowly warmed to room temperature and stirred for 2 h. Then the reaction system was added with water (50 mL) to quench the reaction, and extracted with dichloromethane (30 mL×3). The organic phases were combined, and dried over anhydrous sodium sulfate, filtered and concentrated by rotary evaporation. The crude product was purified by silica gel column chromatography to give intermediate 55-4 (620 mg, 66.5% yield) in the form of a white solid. LC-MS $[M+H]^+=461.6$.

Step (3) Preparation of tert-butyl (S)-2-((4-((4-(tert-butoxycarbonyl)-2,6-difluorobenzyl)oxy)-6-methylpyridin-3-yl)ethynyl)morpholine-4-carboxylate 55-5

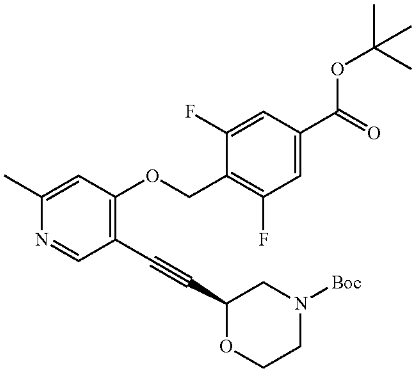

To a solution of intermediate 55-4 (620 mg, 1.35 mmol) and tert-butyl (2S)-2-ethynylmorpholin-4-yl formate (436 mg, 2.06 mmol) in TEA (20 mL) were added copper(I) iodide (26 mg, 0.14 mmol) and bis(triphenylphosphine) palladium(II) chloride (48 mg, 0.07 mmol) under nitrogen atmosphere. The reaction system was heated to 90° C. and reacted overnight. Then the reaction system was concentrated under reduced pressure. The crude product was purified by silica gel column chromatography to give intermediate 55-5 (520 mg, 68.6% yield) in the form of a yellow solid. LC-MS: $[M+H]^+=544.8$.

Step (4) Preparation of (S)-4-(3-((4-(tert-butoxycarbonyl)morpholin-2-yl)methyl)-6-methylfurano[3,2-c]pyridin-2-yl)-3,5-difluorobenzoic acid 55-6

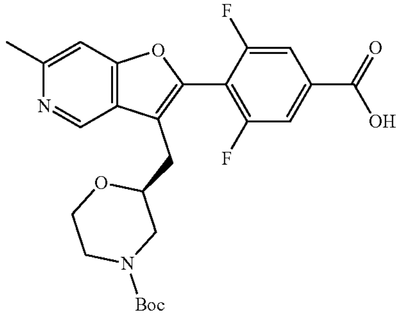

To a solution of intermediate 55-5 (500 mg, 0.92 mmol) in THF (15 mL) was added t-BuOK (258 mg, 2.30 mmol) under nitrogen atmosphere. The reaction system was stirred at 70° C. for 2 h. Then the reaction system was cooled to room temperature, adjusted to pH 6 with formic acid, and concentrated under reduced pressure. The crude product was purified by silica gel column chromatography to give intermediate 55-6 (250 mg, 53.3% yield) in the form of a yellow solid. LC-MS: $[M+H]^+$=488.7.

Step (5) Preparation of tert-butyl 1 (S)-2-((2-(2,6-difluoro-4-(methylcarbamoyl)phenyl)-6-methyl-furano[3,2-c]pyridin-3-yl)methyl)morpholine-4-carboxylate 55-7

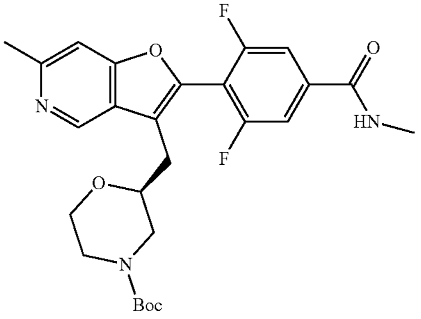

To a solution of intermediate 55-6 (250 mg, 0.51 mmol) and HATU (233 mg, 0.61 mmol) in DMF (4 mL) was added DIEA (264 mg, 2.04 mmol) under nitrogen atmosphere. The reaction system was stirred at room temperature for 10 min, added with methylamine hydrochloride (52 mg, 0.77 mmol), and stirred at room temperature overnight. Then the reaction system was added with water (30 mL), and extracted with ethyl acetate (10 mL×3). The organic phases were combined, dried over anhydrous sodium sulfate, filtered and concentrated. The crude product was purified by silica gel column chromatography to give intermediate 55-7 (250 mg, 94.12% yield) in the form of a yellow oil. LC-MS: $[M+H]^+$=502.2.

Step (6) Preparation of (S)-3,5-difluoro-N-methyl-4-(6-methyl-3-(morpholin-2-ylmethyl)furano[3,2-c]pyridin-2-yl)benzamide 55-8

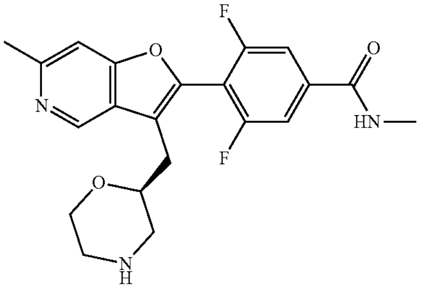

To a solution of intermediate 55-7 (250 mg, 0.50 mmol) in EA (5 mL) was added a solution of HCl (g) in EA (3 M, 10 mL) at room temperature. The reaction system was stirred at room temperature for 2 h, and concentrated under reduced pressure to give intermediate 55-8 (250 mg, crude product). LC-MS: $[M+H]^+$=402.1.

Step (7) Preparation of methyl (S)-2-((2-(2,6-difluoro-4-(methylcarbamoyl)phenyl)-6-methylfurano[3,2-c]pyridin-3-yl)methyl)morpholine-4-carboxylate

55

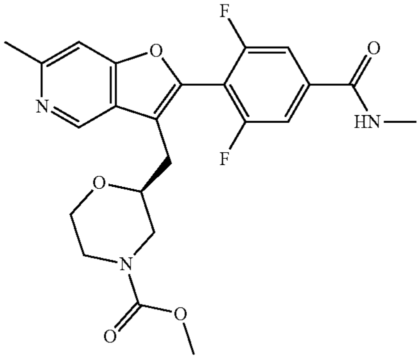

To a solution of intermediate 55-8 (300 mg, 0.75 mmol) and TEA (228 mg, 2.25 mmol) in DCM (10 mL) was added methyl chloroformate (142 mg, 1.50 mmol) dropwise under nitrogen atmosphere in an ice water bath. After the completion of the dropwise addition, the reaction system was warmed to room temperature and stirred for 2 h. Then the reaction system was concentrated under reduced pressure. The crude product was purified by silica gel column chromatography to give compound 55 (70 mg, 20.0% yield) in the form of a white solid. LC-MS: $[M+H]^+$=460.2.

$^1$H NMR (400 MHZ, MeOD) δ 8.93 (s, 1H), 7.63 (d, J=8.4 Hz, 2H), 7.48 (s, 1H), 3.90 (d, J=13.0 Hz, 1H), 3.83-3.77 (m, 2H), 3.65 (s, 3H), 3.64-3.58 (m, 1H), 3.39 (dt, J=11.8, 2.8 Hz, 1H), 2.95 (s, 3H), 2.94-2.81 (m, 3H), 2.70-2.63 (m, 1H), 2.69 (s, 3H).

Example 56

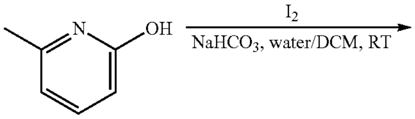

56-1

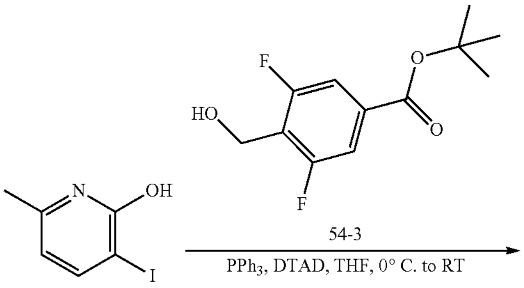

56-2

-continued

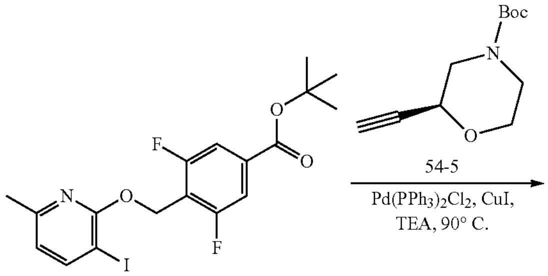

56-3

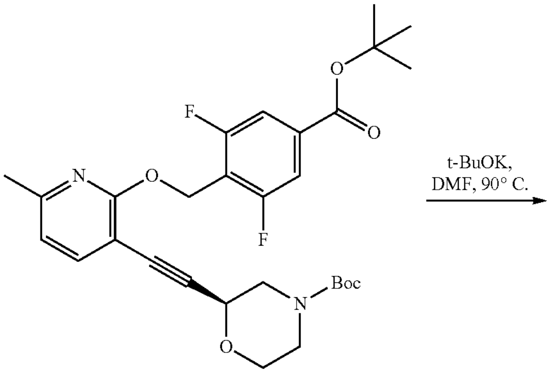

56-4

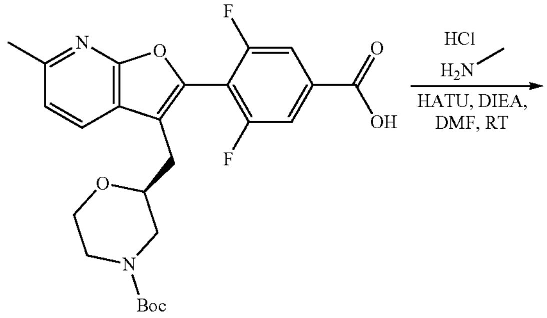

56-5

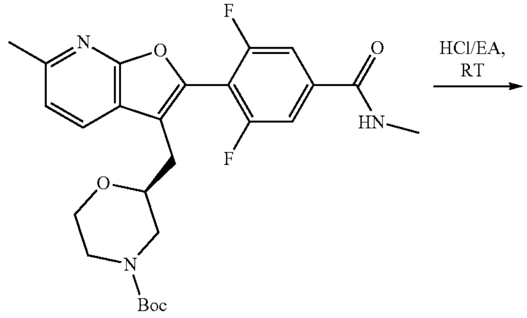

56-6

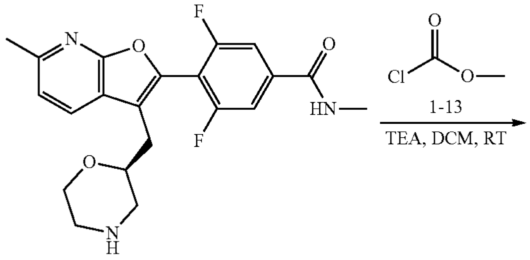

56-7

-continued

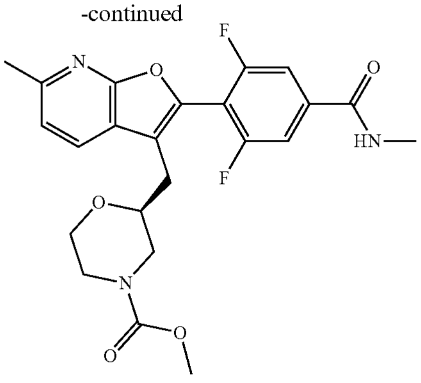

56

Step (1) Preparation of 3-iodo-6-methylpyridin-2-ol 56-2

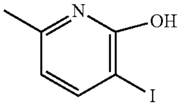

6-methylpyridin-2-ol (5 g, 46 mmol) and sodium hydrogen carbonate (7.73 g, 92 mmol) were added to a mixture of water and dichloromethane (500 mL, 3/2) while stirring at room temperature, and iodine (11.68 g, 46 mmol) was added. The reaction mixture was stirred at room temperature overnight. Then the reaction system was extracted with dichloromethane (200 mL×2). The organic phases were combined, washed with saturated brine (100 mL), dried over anhydrous sodium sulfate, filtered and concentrated. The crude product was purified by silica gel column chromatography to give intermediate 56-2 (2.5 g, 21.74% yield) in the form of an off-white solid. LC-MS: $[M+H]^+=235.0$.

Step (2) Preparation of tert-butyl 3,5-difluoro-4-(((3-iodo-6-methylpyridin-2-yl)oxy)methyl)benzoate 56-3

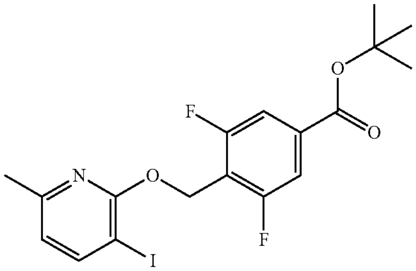

Intermediate 56-2 (510 mg, 2.17 mmol), tert-butyl 3,5-difluoro-4-(hydroxymethyl)benzoate (583 mg, 2.39 mmol) and triphenylphosphine (626 mg, 2.39 mmol) were dissolved in THF (15 mL) at 0° C. under nitrogen atmosphere, and a solution of DTAD (550 mg, 2.39 mmol) in THF (5 mL) was added dropwise. After the completion of the dropwise addition, the reaction system was reacted at room temperature for 2 h. Then the reaction system was added with water (50 mL), and extracted with dichloromethane (30 mL×3). The organic phases were combined, washed with saturated brine (30 mL), dried over anhydrous sodium sulfate and filtered, and the filtrate was concentrated by rotary evaporation to give a crude product. The crude product was purified by silica gel column chromatography to give intermediate 56-3 (860 mg, 94.84% yield) in the form of a white solid. LC-MS: $[M+H]^+$=462.1.

Step (3) Preparation of tert-butyl (S)-2-((2-((4-(tert-butoxycarbonyl)-2,6-difluorobenzyl)oxy)-6-methylpyridin-3-yl)ethynyl)morpholine-4-carboxylate 56-4

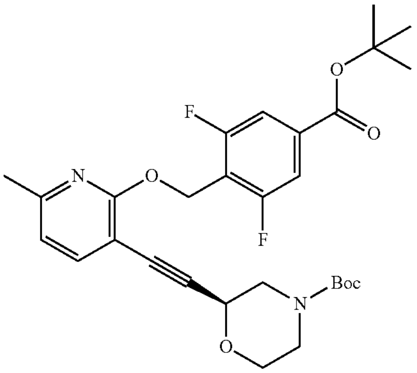

To a solution of intermediate 56-3 (500 mg, 1.08 mmol) and tert-butyl (2S)-2-ethynylmorpholin-4-yl formate (344 mg, 1.62 mmol) in triethylamine (20 mL) were added copper(I) iodide (21 mg, 0.11 mmol) and bis(triphenylphosphine)palladium(II) chloride (38 mg, 0.05 mmol) under nitrogen atmosphere. The reaction mixture was stirred at 90° C. for 12 h. Then the reaction system was concentrated under reduced pressure. The crude product was purified by silica gel column chromatography to give intermediate 56-4 (570 mg, 91.67% yield) in the form of a brownish-yellow solid. LC-MS: $[M+H]^+$=567.1.

Step (4) Preparation of (S)-4-(3-((4-(tert-butoxycarbonyl)morpholin-2-yl)methyl)-6-methylfurano[2,3-b]pyridin-2-yl)-3,5-difluorobenzoic acid 56-5

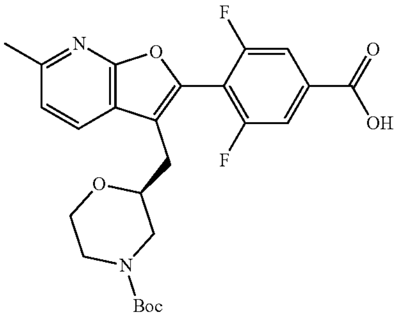

To a solution of intermediate 56-4 (502 mg, 0.92 mmol) in DMF (20 mL) was added potassium tert-butoxide (310 mg, 2.76 mmol) under nitrogen atmosphere. The reaction system was stirred at 90° C. for 2 h. After the reaction was completed, the reaction system was cooled to room temperature, adjusted to pH 6 with formic acid, and concentrated by rotary evaporation (oil pump) to remove the solvent. The crude product was purified by silica gel column chromatography to give intermediate 56-5 (108 mg, 39.13% yield) in the form of a yellow solid. LC-MS: $[M+H]^+$=489.8.

Step (5) Preparation of tert-butyl (S)-2-((2-(2,6-difluoro-4-(methylcarbamoyl)phenyl)-6-methylfurano[2,3-b]pyridin-3-yl)methyl)morpholine-4-carboxylate 56-6

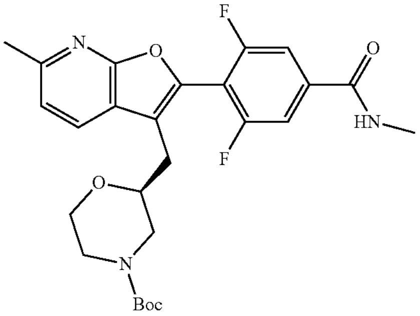

To a solution of intermediate 56-5 (180 mg, 0.37 mmol) in DMF (5 mL) were added HATU (211.06 mg, 0.56 mmol) and DIEA (143 mg, 1.11 mmol) under nitrogen atmosphere. The reaction system was stirred at room temperature for 10 min, added with methylamine hydrochloride (50 mg, 0.74 mmol), and stirred at room temperature overnight. Then the reaction system was added with water (20 mL), and extracted with ethyl acetate (10 mL×3). The organic phases were combined, washed with saturated brine (15 mL), dried over anhydrous sodium sulfate, filtered and concentrated. The crude product was purified by silica gel column chromatography to give intermediate 56-6 (90 mg, 48.65% yield) in the form of a yellow solid. LC-MS: $[M+H]^+$=502.8.

Step (6) Preparation of (S)-3,5-difluoro-N-methyl-4-(6-methyl-3-(morpholin-2-ylmethyl)furano[2,3-b]pyridin-2-yl)benzamide 56-7

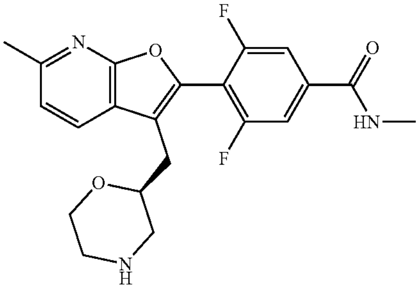

To a solution of intermediate 56-6 (100 mg, 0.20 mmol) in EA (1 mL) was added a solution of HCl (g) in EA (3 M, 2 mL) at room temperature. The reaction system was stirred at room temperature for 2 h. Then the reaction system was concentrated to give intermediate 56-7 hydrochloride (100 mg, crude product), LC-MS: $[M+H]^+$=401.9.

Step (7) Preparation of methyl (S)-2-((2-(2,6-difluoro-4-(methylcarbamoyl)phenyl)-6-methylfurano [2,3-b]pyridin-3-yl)methyl)morpholine-4-carboxylate

56

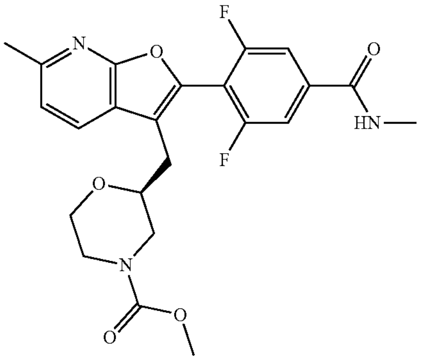

To a solution of intermediate 56-7 hydrochloride (100 mg, 0.20 mmol) and TEA (101 mg, 1.0 mmol) in DCM (10 mL) was added a solution of methyl chloroformate (47.25 mg, 0.50 mmol) in dichloromethane (1 mL) dropwise in an ice water bath. The reaction system was stirred at room temperature for 2 h. Then the reaction system was added with water (10 mL) to quench the reaction, and extracted with dichloromethane (10 mL×2). The organic phases were combined, washed with saturated brine (10 mL), filtered and concentrated. The crude product was purified by silica gel column chromatography, and lyophilized to give compound 56 (45 mg, 49.01% yield) in the form of an off-white solid.

LC-MS: $[M+H]^+$=460.8. $^1H$ NMR (400 MHz, MeOD): δ 8.19 (d, J=7.9 Hz, 1H), 7.65 (d, J=8.4 Hz, 2H), 7.31 (d, J=7.9 Hz, 1H), 3.89 (d, J=12.9 Hz, 1H), 3.85-3.75 (m, 2H), 3.67 (s, 3H), 3.66-3.58 (m, 1H), 3.44-3.35 (m, 1H), 2.97 (s, 3H), 2.92-2.82 (m, 3H), 2.73-2.58 (m, 1H), 2.65 (s, 3H).

Example 57

57

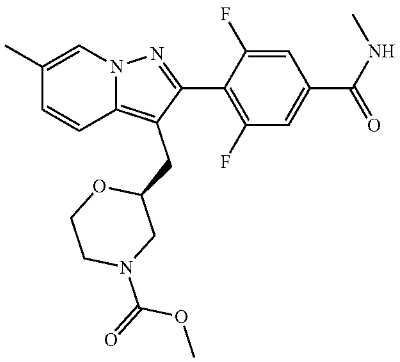

The compound was prepared according to the preparation method as described in Example 39. LC-MS: $[M+H]^+$=459.4.

Example 58

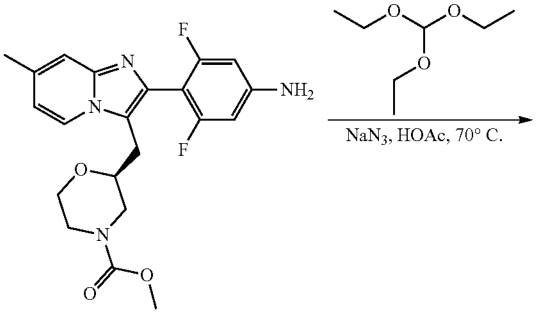

3-1

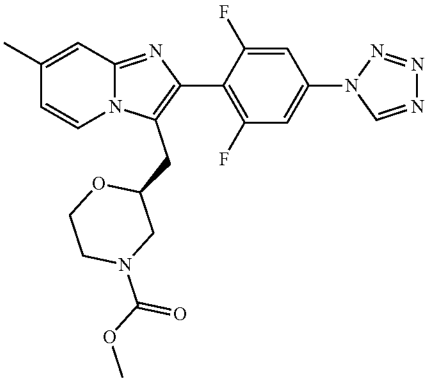

58

Intermediate 3-1 (400 mg, 0.96 mmol), triethyl orthoformate (456 mg, 3.07 mmol), sodium azide (78 mg, 1.20 mmol) and acetic acid (923 mg, 15.37 mmol) were sequentially added. The reaction system was stirred at room temperature for 10 min, and then stirred at 70° C. for 3 days. Then the reaction system was adjusted to pH 9, and extracted with ethyl acetate three times. The organic phases were combined, dried and concentrated by rotary evaporation. The crude product was purified by column chromatography to give a product (270 mg) in the form of a white solid, which was then purified by preparative HPLC to give compound 58 (109 mg, 99% purity, 24% yield) in the form of a white solid.

LCMS $[M+H]^+$=470. $^1H$ NMR (400 MHZ, DMSO-d6) δ 10.18 (s, 1H), 8.39 (dd, J=24.5, 7.3 Hz, 1H), 8.01-7.83 (m, 2H), 7.41-7.28 (m, 1H), 6.82 (dd, J=7.1, 1.6 Hz, 1H), 3.79-3.71 (m, 1H), 3.61 (t, J=9.8 Hz, 2H), 3.52 (s, 3H), 3.46 (dd, J=7.5, 2.8 Hz, 1H), 3.20 (m, 2.8 Hz, 1H), 3.10-2.93 (m, 2H), 2.77 (s, 1H), 2.51 (s, 1H), 2.35 (s, 3H).

Example 59

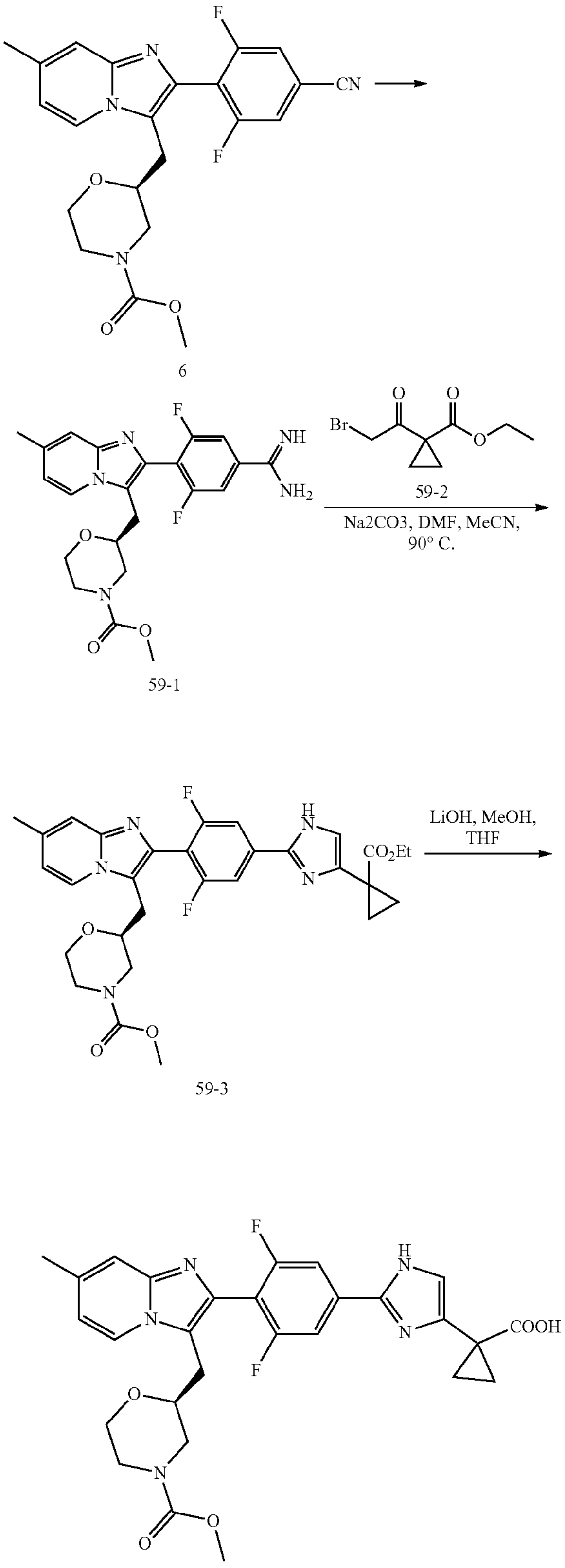

6

59-1

59-3

59

Step (1) Preparation of methyl (S)-2-((2-(4-carbamimidoyl-2,6-difluorophenyl)-7-methylimidazo[1,2-a]pyridin-3-yl)methyl)morpholine-4-carboxylate 59-1

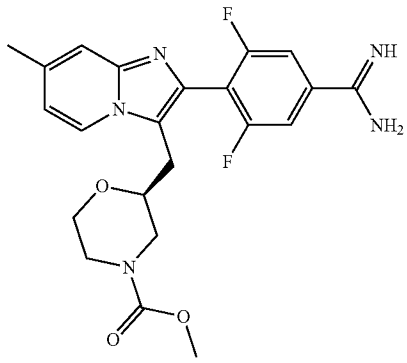

Compound 6 (800 mg, 1.88 mmol) and sodium methoxide (51 mg, 0.94 mmol) were dissolved in methanol (8 mL) under nitrogen atmosphere. The reaction system was stirred at room temperature overnight, added with $NH_4Cl$ solid (152 mg, 2.80 mmol), and stirred at room temperature overnight. Then the reaction system was adjusted to pH 8 with saturated sodium bicarbonate solution (10 mL), concentrated under reduced pressure to 1/2 volume, and extracted with dichloromethane (20 mL×3). The organic phases were combined, washed with saturated brine (20 mL×2), dried over anhydrous sodium sulfate, filtered and concentrated to give intermediate 59-1 (760 mg, crude product) in the form of a brown solid. LC-MS $[M+H]^+$: 444.

Step (2) Preparation of methyl (S)-2-(2-(4-(4-(1-(ethoxycarbonyl)cyclopropyl)-1H-imidazol-2-y)-2,6-difluorophenyl)-7-methylimidazo[1,2-a]pyridin-3-yl)methyl)morpholine-4-carboxylate 59-3

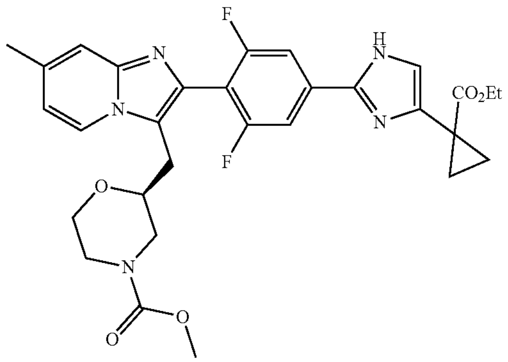

Intermediate 59-1 (800 mg, 1.80 mmol) and ethyl 1-(2-bromoacetyl)cyclopropane-1-carboxylate (329 mg, 1.4 mmol) were dissolved in N,N-dimethylformamide (8 mL) under nitrogen atmosphere, and potassium bicarbonate (360 mg, 3.6 mmol) was added. The reaction system was stirred at 70° C. overnight. Then the reaction system was added with water (30 mL) to quench the reaction, and extracted with dichloromethane (20 mL×3). The organic phases were combined, washed with saturated brine (20 mL×2), dried over anhydrous sodium sulfate, filtered and concentrated. The residue was separated by silica gel column chromatography to give intermediate 59-3 (600 mg, 57% yield) in the form of a brown solid. LC-MS $[M+H]^+$: 580.

Step (3) Preparation of (S)-1-(2-(3,5-difluoro-4-(3-((4-(methoxycarbonyl)morpholin-2-yl)methyl)-7-methylimidazo[1,2-a]pyridin-2-yl)phenyl)-1H-imidazol-4-yl)cyclopropane-1-carboxylic acid

59

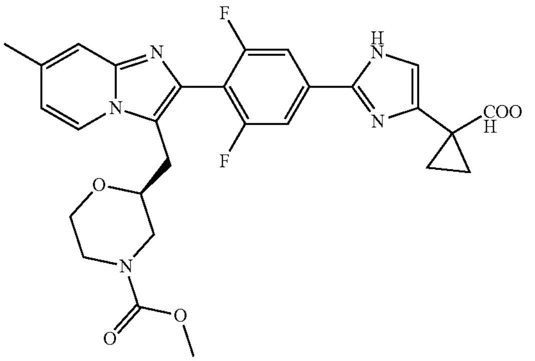

Intermediate 59-3 (600 mg, 1.1 mmol) was dissolved in tetrahydrofuran (4 mL) and absolute methanol (2 mL), and lithium hydroxide solution (1.5 mL, 3 M) was added dropwise at 0° C. The reaction system was warmed to room temperature and stirred for 3 h. Then the reaction system was adjusted to pH 4 with diluted hydrochloric acid (1 N), and concentrated to give a crude product (450 mg) in the from of a yellow solid. The crude product (50 mg) was purified by preparative chromatography to give compound 59 (4.6 mg) in the form of a white solid.

LC-MS $[M+H]^+$: 552. $^1H$ NMR (400 MHZ, $CDCl_3$) δ 8.28 (d, J=8.0 Hz, 1H), 7.47 (s, 1H), 7.30 (d, J=8.3 Hz, 2H), 6.81 (d, J=7.7 Hz, 1H), 6.75 (s, 1H), 4.00-3.81 (m, 3H), 3.67 (s, 3H), 3.63-3.57 (m, 1H), 3.45-3.35 (m, 1H), 3.05-2.85 (m, 3H), 2.66-2.57 (m, 1H), 2.52 (s, 3H), 1.92-1.86 (m, 2H), 1.25-1.19 (m, 2H).

Example 60

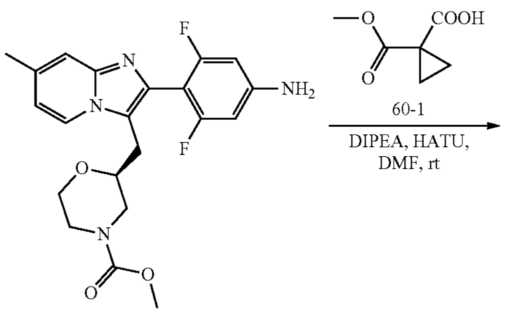

3-1

-continued

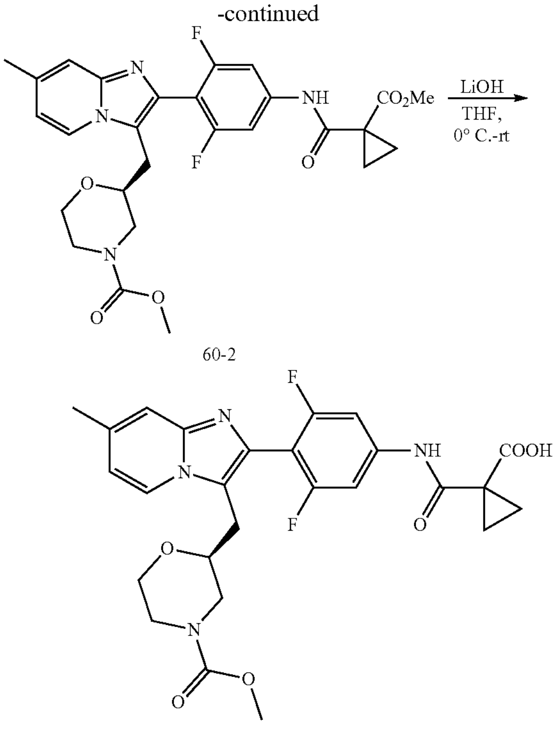

60-2

60

Step (1) Preparation of methyl (S)-2-((2-(2,6-difluoro-4-(1-(methoxycarbonyl)cyclopropane-1-carboxamido)phenyl)-7-methylimidazo[1,2-a]pyridin-3-yl)methyl)morpholine-4-carboxylate 60-2

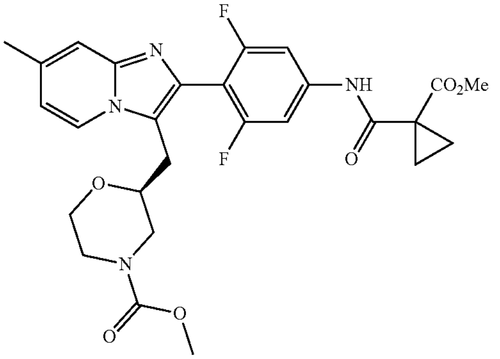

1-(methoxycarbonyl)cyclopropane-1-carboxylic acid (104 mg, 0.72 mmol) and 2-(7-azabenzotriazol-1-yl)-N,N,N',N'-tetramethyluronium hexafluorophosphate (275 mg, 0.72 mmol) were dissolved in anhydrous N,N-dimethylformamide (2 mL) under nitrogen atmosphere. The reaction system was reacted at room temperature for 10 min, added with N,N-diisopropylethylamine (252 mg, 1.95 mmol) and intermediate 3-1 (200 mg, 0.48 mmol), and reacted at room temperature overnight. Then the reaction system was added with water (20 mL), and extracted with ethyl acetate (20 mL×3). The organic phases were combined, washed with saturated brine (30 mL×2), dried over anhydrous sodium sulfate, filtered and concentrated by rotary evaporation to give a crude product. The crude product was purified by high performance liquid chromatography to give intermediate 60-2 (100 mg, 51.3% yield) in the form of a white solid. LC-MS: $[M+H]^+$=543.7.

Step (2) Preparation of (S)-2-((2-(2,6-difluoro-4-(1-(methoxycarbonyl)cyclopropane-1-carboxamido)phenyl)-7-methylimidazo[1,2-a]pyridin-3-yl)methyl)morpholine-4-carboxylic acid

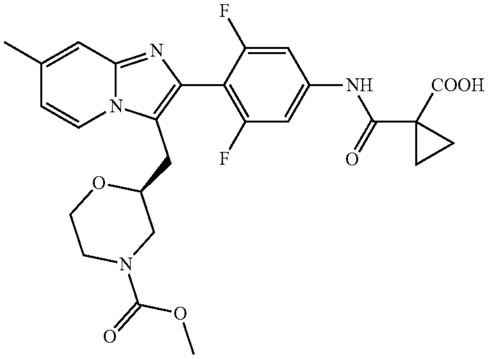

60

Intermediate 60-2 (100 mg, 0.18 mmol) was dissolved in tetrahydrofuran (1.5 mL), and lithium hydroxide solution (0.18 mL, 3 M) was added dropwise. The reaction system was reacted at room temperature for 1 h. After the reaction was completed, the reaction system was added dropwise with diluted hydrochloric acid (1 M) to adjust the pH to 6, added with water (10 mL), and extracted with dichloromethane (20 mL×3). The organic phases were combined, washed with saturated brine (20 mL), dried over magnesium sulfate, filtered and concentrated by rotary evaporation to give a crude product. The crude product was purified by high performance liquid chromatography to give compound 60 (65.9 mg, 67.6% yield) in the form of a white solid.

LC-MS: $[M+H]^+$=529.6. $^1$H NMR (400 MHZ, MeOD): δ 8.84 (d, J=7.1 Hz, 1H), 7.70 (s, 1H), 7.64 (d, J=7.4 Hz, 2H), 7.41 (dd, J=7.1, 1.5 Hz, 1H), 4.01-3.97 (m, 1H), 3.86-3.74 (m, 2H), 3.70 (s, 3H), 3.69-3.65 (m, 1H), 3.39-3.36 (m, 1H), 3.25-3.24 (m, J=5.2 Hz, 2H), 2.99-2.85 (m, 1H), 2.81-2.67 (m, 1H), 2.65 (s, 3H), 1.75-1.72 (m, 2H), 1.71-1.68 (m, 2H).

Example 61

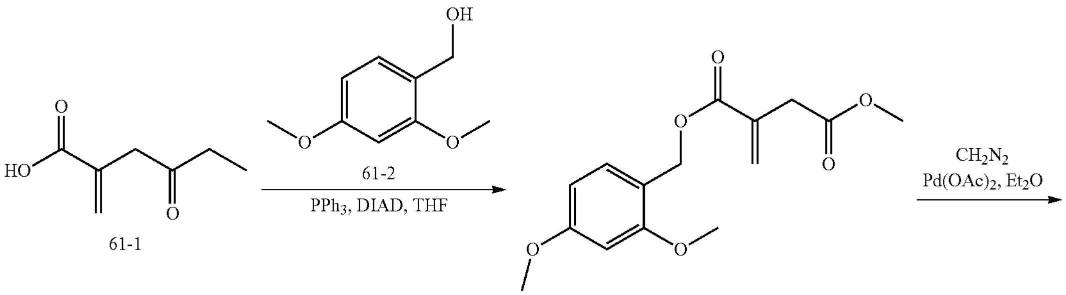

61-1

61-3

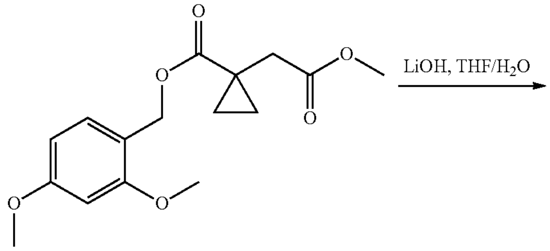

61-4

-continued

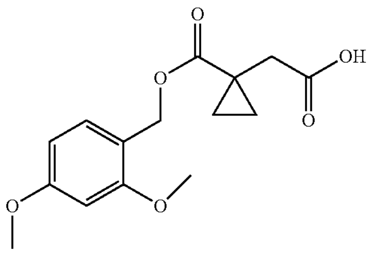

61-5

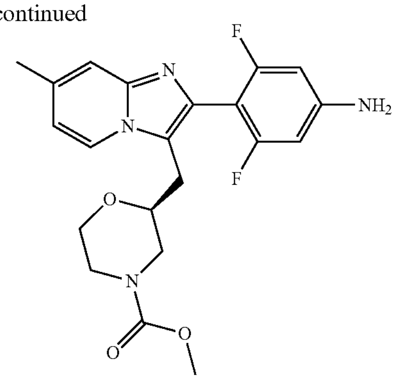

3-1

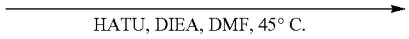

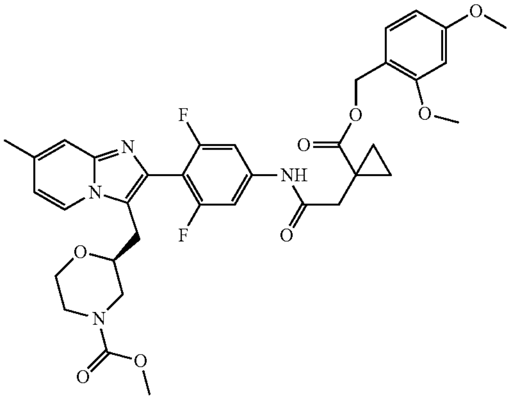

61-6

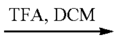

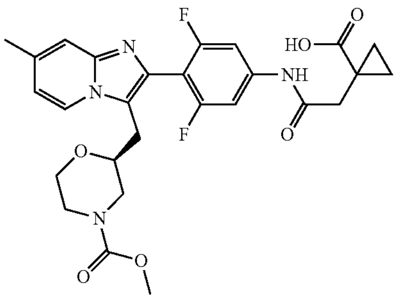

61

Step (1) Preparation of 1-(2,4-dimethoxybenzyl)-4-methyl 2-methylenesuccinate 61-3

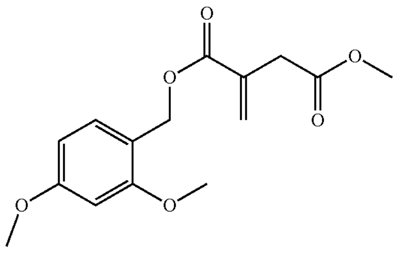

Monomethyl itaconate (3.00 g, 21.10 mmol), (2,4-dimethoxy)benzyl alcohol (3.90 g, 23.21 mmol) and triphenylphosphine (6.65 g, 25.33 mmol) were dissolved in THF (50 mL) at 0° C. under nitrogen atmosphere, and a solution of DIAD (5.12 g, 25.33 mmol) in THF (10 mL) was added dropwise. After the completion of the dropwise addition, the reaction system was warmed to room temperature and stirred overnight. Then the reaction system was added with water (60 mL) to quench the reaction, and extracted with ethyl acetate (40 mL×3). The organic phases were combined, washed with saturated brine (40 mL), dried over anhydrous sodium sulfate, filtered and concentrated to give a crude product. The crude product was purified by silica gel column chromatography to give intermediate 61-3 (4.5 g, 72.2% yield) in the form of a white solid. MS $[M+Na]^+$=316.8.

Step (2) Preparation of 2,4-dimethoxybenzyl 1-(2-methoxy-2-carbonylethyl)cyclopropanecarboxylate 61-4

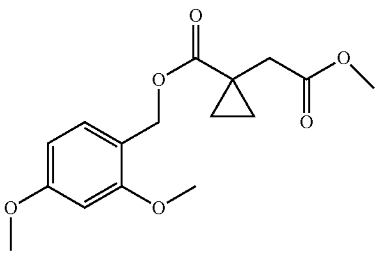

To a mixture of potassium hydroxide (30 mL, 40% aq) and diethyl ether (20 mL) was added 1-methyl-3-nitro-1-nitrosoguanidine (4.0 g, 13.6 mmol, 50% water content) at 0° C. under nitrogen atmosphere. The reaction system was stirred at 0° C. for 15 min and left to stand for liquid separation. The upper organic phase was collected, and dried over anhydrous sodium sulfate. Intermediate 61-3 (600 mg, 2.04 mmol) and palladium acetate (92 mg, 0.41 mmol) were dissolved in diethyl ether (15 mL) at 0° C. under nitrogen atmosphere, and a fresh solution of diazomethane in diethyl ether was added dropwise. After the completion of the dropwise addition, the reaction system was slowly warmed to room temperature and stirred for 16 h. The reaction system was added with absolute methanol (10 mL) to quench the reaction and filtered, and the filtrate was concentrated by rotary evaporation to give a crude product. The crude product was purified by column chromatography to give intermediate 61-4 (520 mg, 82.7% yield) in the form of a colorless oil. MS $[M+Na]^+$=330.8.

Step (3) Preparation of 2-(1-(((2,4-dimethoxybenzyl)oxo)carbonyl)cyclopropyl)acetic acid 61-5

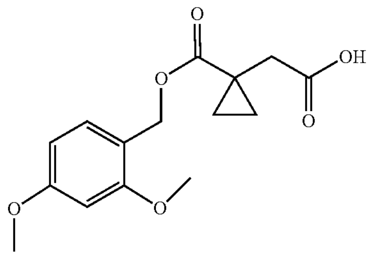

To a mixture of intermediate 61-4 (500 mg, 1.62 mmol) in tetrahydrofuran (40 mL) and water (10 mL) was added lithium hydroxide monohydrate (11.9 mL, 11.9 mmol) at 0° C. The reaction was stirred at 0° C. for 8 h. Then the reaction system was warmed to room temperature, adjusted to pH 4 with diluted hydrochloric acid, and extracted with DCM (20 mL×3). The organic phases were combined, washed with saturated brine (30 mL), dried over anhydrous sodium sulfate, filtered and concentrated by rotary evaporation to give intermediate 61-5 (320 mg, 73.2% yield, crude product) in the form of a yellow oil. MS $[M-H]^+$=292.4.

Step (4) Preparation of methyl (S)-2-((2-(4-(2-(1-(((2,4-dimethoxybenzyl)oxo)carbonyl)cyclopropyl)acetamido)-2,6-difluorophenyl)-7-methylimidazo[1,2-a]pyridin-3-yl)methyl)morpholine-4-carboxylate 61-6

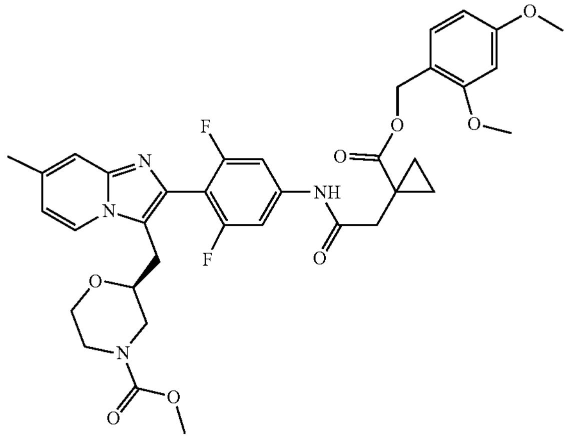

To a solution of intermediate 61-5 (300 mg, 1.02 mmol) in DMF (5 mL) were added DIEA (527 mg, 4.08 mmol) and HATU (466 mg, 1.22 mmol) at room temperature under nitrogen atmosphere. The reaction system was stirred at 45° C. for 0.5 h, added with intermediate 3-1 (213 mg, 0.51 mmol), and stirred at 45° C. for another 18 h. Then the reaction system was cooled to room temperature, added with water (10 mL), and extracted with EA (10 mL×3). The organic phases were combined, washed with saturated brine (20 mL), dried over anhydrous sodium sulfate, filtered and concentrated by rotary evaporation. The crude product was purified by silica gel column chromatography to give intermediate 61-6 (160 mg, 22.6% yield) in the form of a yellow solid. MS $[M+H]^+$=692.7.

Step Preparation of (S)-1-(2-((3,5-difluoro-4-(3-((4-(carbomethoxy<methoxycarbonyl>)morpholin-2-yl)methyl)-7-methylimidazo[1,2-a]pyridin-2-yl)phenyl)amino)-2-carbonylethyl)cyclopropanecarboxylic acid

61

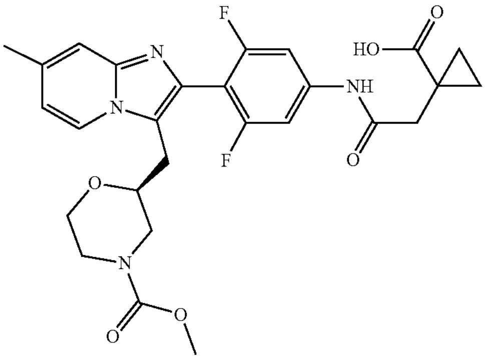

To a solution of intermediate 61-6 (100 mg, 0.14 mmol) in dichloromethane (2 mL) was added trifluoroacetic acid (1 mL) at room temperature. The reaction system was stirred at room temperature for 3 h and concentrated. The residue was separated by preparative high performance liquid chromatography, and lyophilized to give compound 61 (29 mg, 36.9% yield) in the form of a white solid. MS $[M+H]^+$=542.7.

1H NMR (400 MHZ, $CDCl_3$) δ 10.44 (brs, 1H), 8.51 (d, J=7.0 Hz, 1H), 7.96 (s, 1H), 7.43 (d, J=11.1 Hz, 2H), 7.09 (d, J=6.7 Hz, 1H), 4.10-3.75 (m, 3H), 3.69 (s, 3H), 3.65-3.61 (m, 1H), 3.45-3.35 (m, 1H), 3.05-2.85 (m, 3H), 2.76-2.68 (m, 1H), 2.58 (s, 3H), 1.39 (s, 2H), 0.94 (s, 2H).

Example 62

62

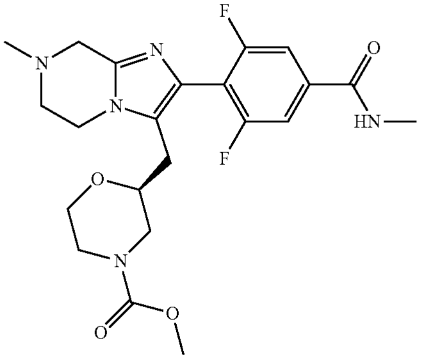

The compound was prepared according to the preparation method as described in Example 44. LC-MS: $[M+H]^+$=464.2.

Example 63

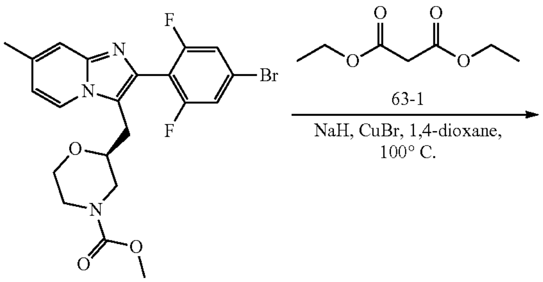

2-7

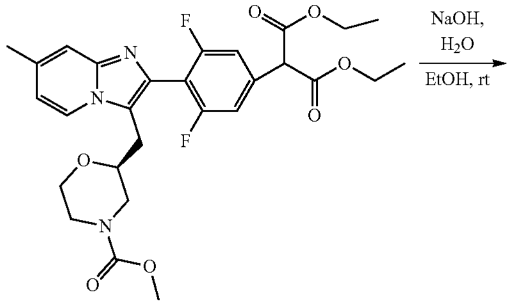

63-2

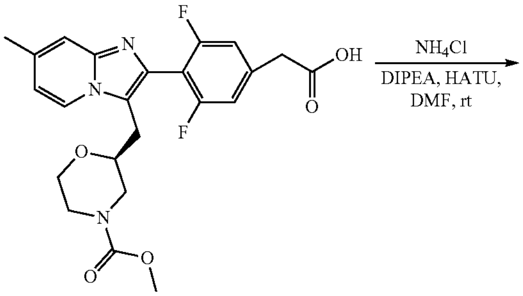

63-3

-continued

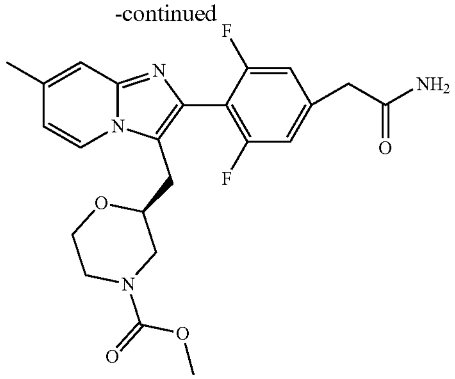

63

Step (1) Preparation of methyl (S)-2-((2-(4-(diethylmalonate)-2,6-difluorophenyl)-7-methylimidazo[1,2-a]pyridin-3-yl)methyl)morpholine-4-carboxylate 63-2

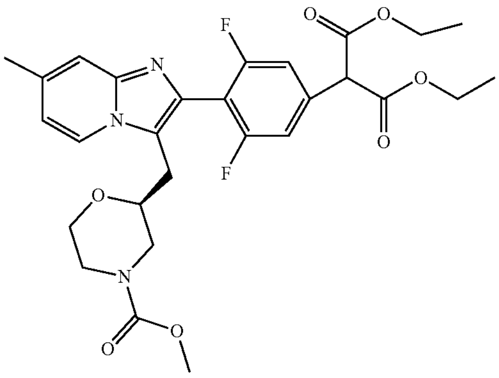

Intermediate 2-7 (300 mg, 0.62 mmol), 1,3-diethyl malonate (200 mg, 1.24 mmol) and bromoidenone (180 mg, 1.24 mmol) were dissolved in 1,4-dioxane (3 mL), and sodium hydride (60%, 55 mg, 1.36 mmol) was added in portions under nitrogen atmosphere. The reaction system was reacted at 100° C. for 10 h. After the reaction was completed, the reaction system was cooled to room temperature, added with water (20 mL) to quench the reaction, and extracted with dichloromethane (20 mL×3). The organic phases were combined, washed with saturated brine (20 mL), dried over magnesium sulfate, filtered and concentrated by rotary evaporation. The crude product was purified by column chromatography to give intermediate 63-2 (230 mg, 66% yield) in the form of a yellow oil. LC-MS: $[M+H]^+$=560.2.

Step (2) (S)-2-(3,5-difluoro-4-(3-((4-(methoxycarbonyl)morpholin-2-yl)methyl)-7-methylimidazo[1,2-a]pyridin-2-yl)phenyl)acetic acid 63-3

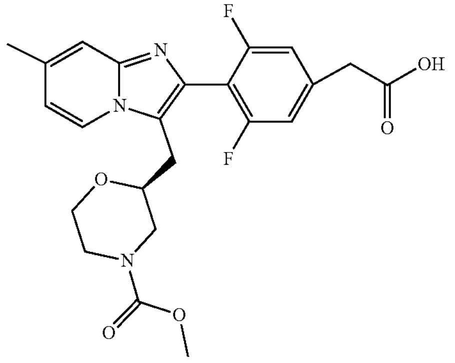

Intermediate 63-2 (210 mg, 0.38 mmol) was dissolved in absolute ethanol (1.5 mL), and sodium hydroxide solution (3 M, 45 mg, 1.14 mmol) was added. The reaction system was reacted at room temperature for 1 h. After the reaction was competed, the reaction system was adjusted to pH 6 with hydrochloric acid solution (1 M), added with water (5 mL), and extracted with dichloromethane (20 mL×3). The organic phases were combined, washed with saturated brine (20 mL), dried over magnesium sulfate, filtered and concentrated by rotary evaporation. The residue was purified by column chromatography to give intermediate 63-3 (140 mg, 77% yield) in the form of a yellow oil. LC-MS: $[M+H]^+$=460.2.

Step (3) Preparation of methyl (S)-2-((2-(4-(2-amino-2-carbonylethyl)-2,6-difluorophenyl)-7-methylimidazo[1,2-a]pyridin-3-yl)methyl)morpholine-4-carboxylate

63

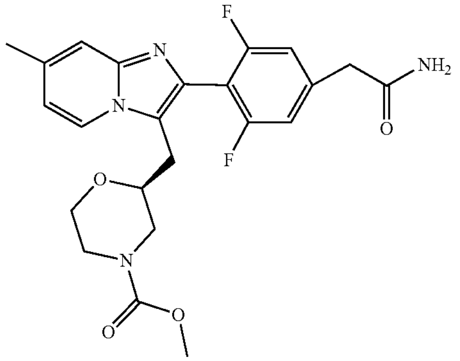

Intermediate 63-3 (70 mg, 0.15 mmol) and 2-(7-azobenzotriazol)-N,N,N',N'-tetramethyluronium hexafluorophosphate (87 mg, 0.23 mmol) were dissolved in N,N-dimethylformamide (2 mL) under nitrogen atmosphere. The reaction system was reacted at room temperature for 10 min, added with N,N-diisopropylethylamine (60 mg, 0.46 mmol) and ammonium chloride (10 mg, 0.19 mmol), and reacted at room temperature for another 2 h. After the reaction was completed, the reaction system was added with water (20 mL), and extracted with ethyl acetate (30 mL×3). The organic phases were combined, washed with saturated brine (30 mL), dried over anhydrous sodium sulfate, filtered and concentrated by rotary evaporation. The crude product was purified by preparative chromatography to give compound 63 (10.5 mg, 15% yield) in the form of a white solid.

LC-MS: $[M+H]^+$=459.2. $^1$H NMR (400 MHZ, CDCl3): δ8.60 (brs, 1H), 7.97 (brs, 1H), 7.67-7.62 (brs, 1H), 7.27-7.08 (m, 3H), 6.50 (brs, 1H), 4.08-3.78 (m, 4H), 3.73 (s, 3H), 3.71-3.58 (m, 2H), 3.45-3.37 (m, 1H), 3.07-3.03 (m, 2H), 3.00-2.92 (m, 1H), 2.77-2.69 (m, 1H), 2.62 (s, 3H).

Example 64

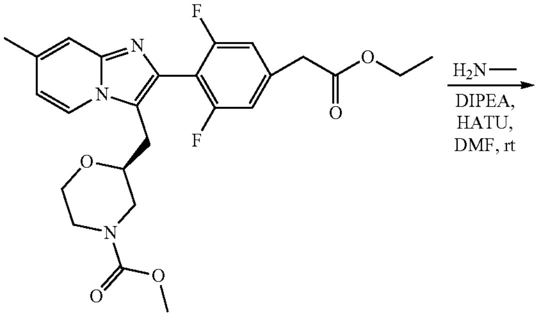

64-1

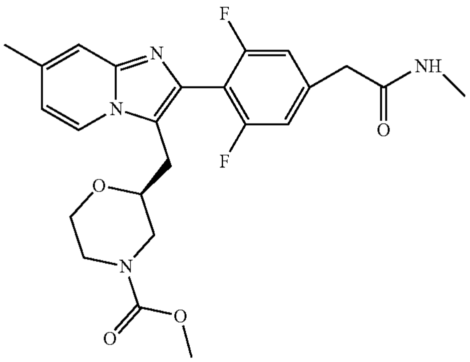

64

Step (1) Preparation of methyl (S)-2-((2-(4-(2-ethoxy-2-oxoethyl)-2,6-difluorophenyl)-7-methylimidazo[1,2-a]pyridin-3-yl)methyl)morpholine-4-carboxylate 64-1

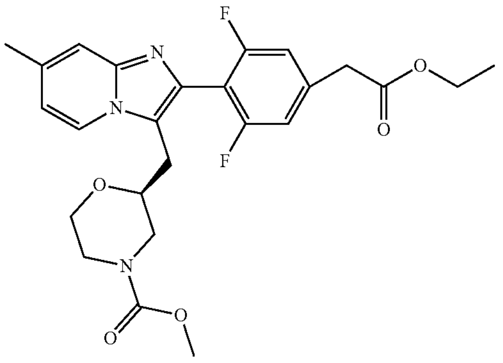

Compound 63-3 (459 mg, 1 mmol) was dissolved in absolute ethanol (10 mL), and $H_2SO_4$ (0.1 mmol) was added. The reaction system was heated to reflux. After the reaction was completed as monitored by TLC, the reaction system was diluted with water with the pH adjusted to be neutral, and concentrated under reduced pressure. The aqueous phase was extracted with EA. The organic phase was dried over anhydrous $MgSO_4$, filtered, and concentrated under reduced pressure to give intermediate 64-1 (0.36 g, 74% yield), LC-MS: $[M+H]^+$=488.2.

Step (2) Preparation of methyl (S)-2-((2-(4-(2~(methylamino)-2-oxoethyl)-2,6-difluorophenyl)-7-methylimidazo[1,2-a]pyridin-3-yl)methyl)morpholine-4-carboxylate

64

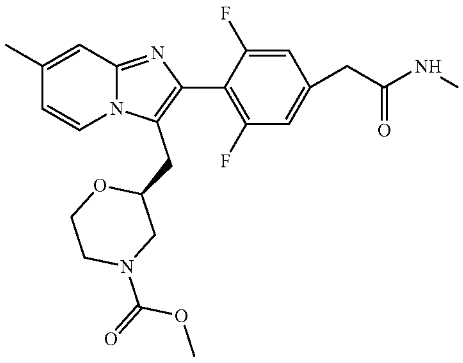

Intermediate 64-1 (70 mg, 0.15 mmol) and 2-(7-azobenzotriazol)-N,N,N,N-tetramethyluronium hexafluorophosphate (87 mg, 0.23 mmol) were dissolved in N,N-dimethylformamide (2 mL) under nitrogen atmosphere. The reaction system was reacted at room temperature for 10 min, added with N,N-diisopropylethylamine (60 mg, 0.46 mmol) and a solution of methylamine in tetrahydrofuran (1 M, 0.1 mL, 0.15 mmol), and reacted at room temperature for another 2 h. After the reaction was completed, the reaction system was added with water (20 mL), and extracted with ethyl acetate (30 mL×3). The organic phases were combined, washed with saturated brine (30 mL×3), dried over anhydrous sodium sulfate, filtered and concentrated by rotary evaporation to give a crude product. The crude product was purified by high performance liquid chromatography to give compound 64 (17.2 mg, 24% yield) in the form of a white solid.

LC-MS: $[M+H]^+$=473.2. $^1H$ NMR (400 MHz, CDCl3): δ8.59 (brs, 1H), 7.92 (s, 1H), 7.55 (brs, 1H), 7.19 (d, J=7.4 Hz 1H), 7.08 (d, J=8.1 Hz, 2H), 4.10-3.90 (m, 3H), 3.86-3.78 (m, 1H), 3.73 (s, 3H), 3.73-3.65 (m, 2H), 3.46-3.35 (m, 1H), 3.08-3.02 (m, 2H), 3.00-2.90 (m, 1H), 2.85 (s, 3H), 2.76-2.70 (m, 1H), 2.62 (s, 3H).

Example 65

65

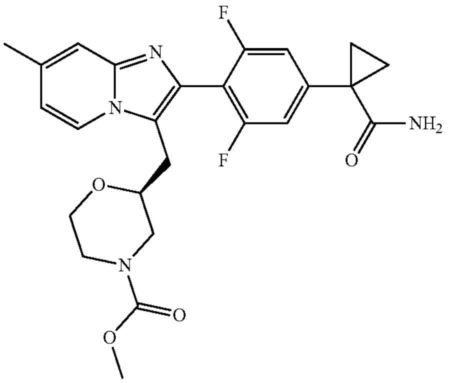

The compound was prepared according to the preparation method as described in Example 63. LC-MS: $[M+H]^+$=485.2.

Example 66

66

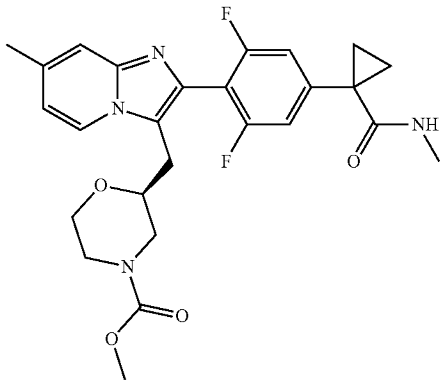

The compound was prepared according to the preparation method as described in Example 63. LC-MS: $[M+H]^+$=499.3.

Example 67

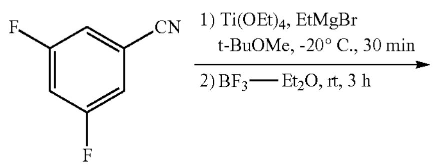

67-1

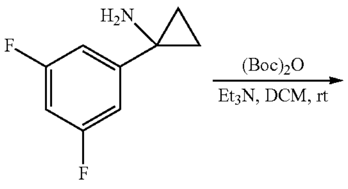

67-2

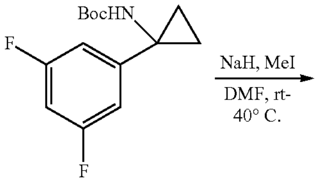

67-3

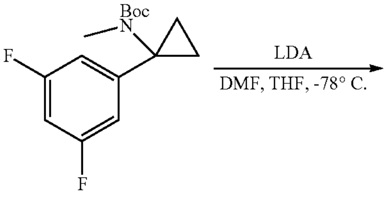

67-4

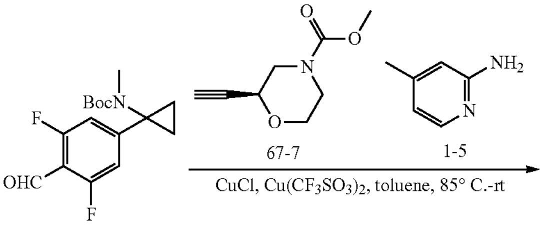

67-5

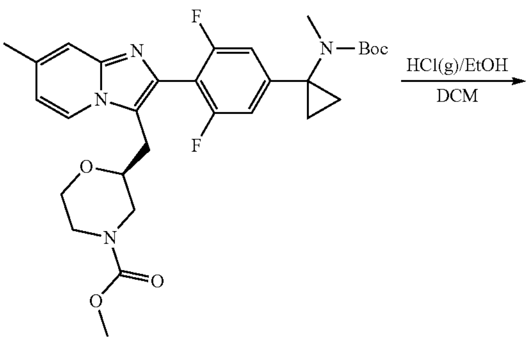

67-8

-continued

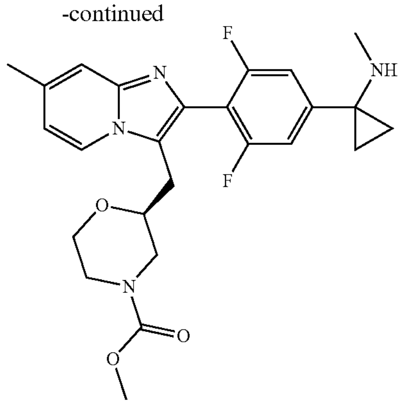

67

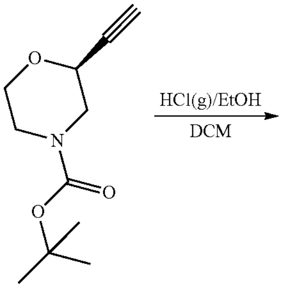

1-4

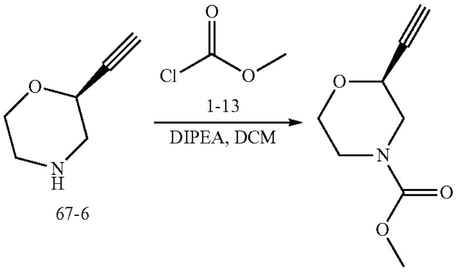

67-6

67-7

Step (1) Preparation of 1-(3,5-difluorophenyl)cyclopropane-1-amine 67-2

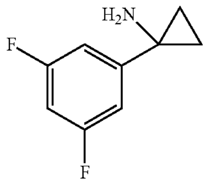

3,5-difluorobenzonitrile (10.0 g, 71.89 mmol) and tetraisopropyl titanate (27.0 g, 95.00 mmol) were dissolved in methyl tert-butyl ether (120 mL), and ethyl magnesium bromide (3 M in diethyl ether, 55 mL, 165.35 mmol) was added at −20° C. under nitrogen atmosphere. The reaction system was reacted at this temperature for 30 min, added with boron trifluoride diethyl ether (46.5%, 44 g, 143.78 mmol), and stirred at room temperature for another 3 h. Then the reaction system was added with sodium hydroxide solution (3 M, 72 mL, 215.67 mmol) and filtered, and the filtrate was added with water (100 mL) and extracted with dichloromethane (150 mL×3). The organic phases were combined, washed with saturated brine (100 mL×2), dried over anhydrous sodium sulfate, filtered and concentrated by rotary evaporation to give a crude product. The crude product was purified by silica gel column chromatography to give intermediate 67-2 (2 g, 16.6% yield) in the form of a yellow oil, MS $[M+H]^+$=170.0.

Step (2) Preparation of tert-butyl (1-(3,5-difluorophenyl)cyclopropyl)carbamate 67-3

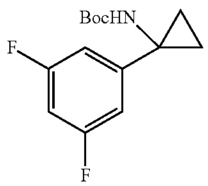

Intermediate 67-2 (2.0 g, 11.83 mmol) was dissolved in anhydrous dichloromethane (20 mL), and di-tert-butyl dicarbonate (3.9 g, 17.75 mmol) and triethylamine (2.4 g, 23.67 mmol) were added under nitrogen atmosphere. The reaction system was reacted at room temperature overnight. Then the reaction system was added with water (50 mL), and extracted with dichloromethane (50 mL). The organic phase was washed with saturated brine (50 mL×2), dried over anhydrous sodium sulfate, filtered and concentrated by rotary evaporation to give a crude product. The crude product was purified by silica gel column chromatography to give intermediate 67-3 (640 mg, 18.08% yield) in the form of a white solid. MS $[M+H]^+$=269.9.

Step (3) Preparation of tert-butyl (1-(3,5-difluorophenyl)cyclopropyl)(methyl)carbamate 67-4

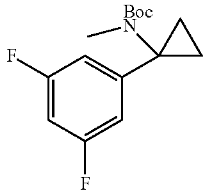

Intermediate 67-3 (620 mg, 2.30 mmol) was dissolved in anhydrous N,N-dimethylformamide (5 mL) under nitrogen atmosphere, and sodium hydride (60%, 138 mg, 3.45 mmol) was added. The reaction system was reacted at room temperature for 30 min, added with methyl iodide (720 mg, 5.07 mmol) and reacted at 40° C. for 1 h. Then the reaction system was added with ice water (20 mL) to quench the reaction, and extracted with ethyl acetate (20 mL×2). The organic phases were combined, washed with saturated brine (20 mL×2), dried over anhydrous sodium sulfate, filtered and concentrated by rotary evaporation to give a crude product. The crude product was purified by silica gel column chromatography to give intermediate 67-4 (260 mg, 40% yield) in the form of a white solid. MS $[M+H]^+$=283.9.

Step (4) Preparation of tert-butyl (1-(3,5-difluoro-4-formylphenyl)cyclopropyl)(methyl)carbamate 67-5

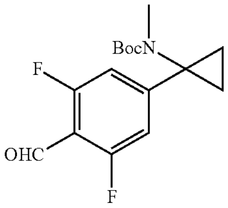

Intermediate 67-4 (260 mg, 0.92 mmol) was dissolved in anhydrous tetrahydrofuran (5 mL) under nitrogen atmosphere, and lithium diisopropylamide (2 M in tetrahydrofuran, 0.6 mL, 1.10 mmol) was added dropwise at −78° C. After the completion of the dropwise addition, the reaction system was reacted at −78° C. for 1 h, added with anhydrous N,N-dimethylformamide (67 mg, 0.92 mmol), and reacted for another 30 min. After the reaction was completed, the reaction system was added with saturated ammonium chloride solution to quench the reaction, diluted with water (20 mL), and extracted with ethyl acetate (20 mL×2). The organic phases were combined, washed with saturated brine (20 mL×2), dried over anhydrous sodium sulfate, filtered and concentrated by rotary evaporation. The crude product was purified by silica gel column chromatography to give intermediate 67-5 (250 mg, 85% yield) in the form of a white solid. MS $[M+H]^+$=311.9.

Step (5) Preparation of (S)-2-ethynylmorpholine 67-6

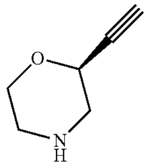

Intermediate 1-4 (200 mg, 0.95 mmol) was dissolved in anhydrous dichloromethane (3 mL), and a solution of HCl in ethanol (33%, 0.5 mL) was added at 0° C. The reaction system was reacted at room temperature for 1 h. After the reaction was completed, the reaction system was concentrated by rotary evaporation to give intermediate 67-6 (230 mg, crude product) in the form of a yellow oil, MS $[M+H]^+$=120.0.

Step (6) Preparation of methyl (S)-2-ethynylmorpholine-4-carboxylate 67-7

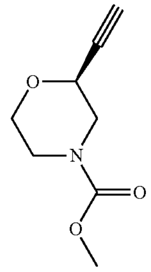

Intermediate 67-6 (230 mg, crude product, 0.95 mmol) and N,N-diisopropylethylamine (1.1 g, 8.51 mmol) were dissolved in anhydrous dichloromethane (3 mL), and methyl chloroformate (180 mg, 1.90 mmol) was added dropwise slowly in an ice water bath. After the completion of the dropwise addition, the reaction system was reacted at 0° C. for 1 h. After the reaction was completed, the reaction system was added with water (15 mL), and extracted with dichloromethane (20 mL×3). The organic phases were combined, washed with saturated brine, dried over anhydrous sodium sulfate, filtered and concentrated by rotary evaporation to give intermediate 67-7 (160 mg, crude product) in the form of a yellow oil. MS $[M+H]^+$=169.7.

Step (7) Preparation of methyl (S)-2-((2-(4-(1-((tert-butoxycarbonyl)(methyl)amino) cyclopropyl)-2,6-difluorophenyl)-7-methylimidazo[1,2-a]pyridin-3-yl)methyl)morpholine-4-carboxylate 67-8

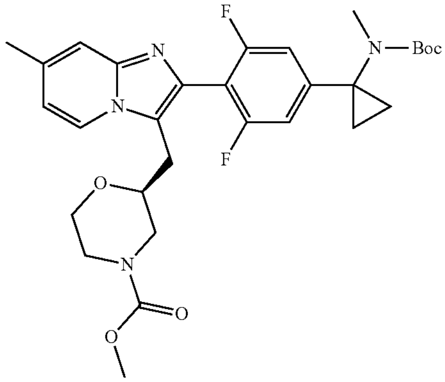

Intermediate 67-5 (250 mg, 0.80 mmol), 4-methylpyridin-2-amine (87 mg, 0.80 mmol), methyl (S)-2-ethynylmorpholine-4-carboxylate (136 mg, 0.80 mmol), copper(I) chloride (24 mg, 0.24 mmol) and copper(II) trifluoromethanesulfonate (87 mg, 0.24 mmol) were dissolved in toluene solution (3 mL) under nitrogen atmosphere. The reaction system was reacted at 85° C. for 10 min, added with N,N-dimethylacetamide (0.1 mL), and stirred at 85° C. for another 5 h. Then the reaction system was reacted at room temperature overnight. The resulting reaction system was filtered, and the filtrate was added with water (20 mL) and extracted with dichloromethane (30 mL×3). The organic phases were combined, washed with saturated brine (30 mL×2), dried over anhydrous sodium sulfate, filtered and concentrated by rotary evaporation to give a crude product. The crude product was purified by silica gel column chromatography to give intermediate 67-8 (150 mg, 32.6% yield) in the form of a yellow oil. MS $[M+H]^+$=570.8.

Step (8) Preparation of methyl (S)-2-((2-(2,6-difluoro-4-(1-(methylamino)cyclopropyl)phenyl)-7-methylimidazo[1,2-a]pyridin-3-yl)methyl)morpholine-4-carboxylate

67

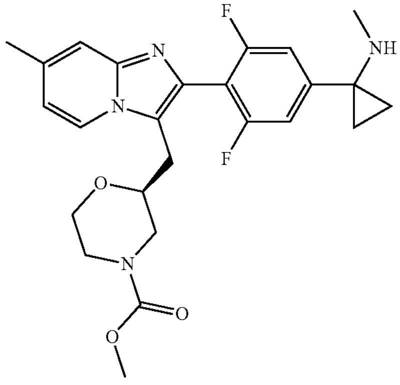

Intermediate 67-8 (150 mg, 0.26 mmol) was dissolved in anhydrous dichloromethane (3 mL), and a solution of HCl in ethanol (33%, 0.5 mL) was added at 0° C. The reaction system was reacted at room temperature for 1 h. After the reaction was completed, the reaction system was concentrated by rotary evaporation, diluted with dichloromethane (30 mL), dissolved with saturated sodium bicarbonate solution (10 mL), and stirred for 5 min. Then the reaction system was extracted. The organic phase was dried over anhydrous sodium sulfate, filtered and concentrated to give a crude product. The crude product was purified by high performance liquid chromatography to give compound 67 (55.4 mg, 43.5% yield) in the form of a white solid. MS $[M+H]^+$=470.8.

1H NMR (400 MHz, MeOD) δ 8.85 (d, J=7.1 Hz, 1H), 7.73 (s, 1H), 7.59 (d, J=8.4 Hz, 2H), 7.41 (d, J=7.0 Hz, 1H), 4.02-3.93 (m, 1H), 3.87-3.73 (m, 2H), 3.70 (s, 3H), 3.69-3.62 (m, 1H), 3.39-3.35 (m, 1H), 3.28-3.23 (m, 2H), 2.99-2.85 (m, 1H), 2.75 (s, 3H), 2.74-2.66 (m, 1H), 2.65 (s, 3H), 1.61-1.54 (m, 2H), 1.52-1.46 (m, 2H).

Example 68

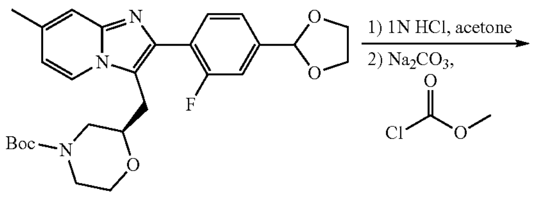

68-0

-continued

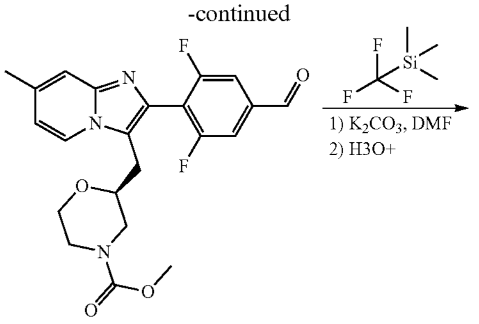

68-1

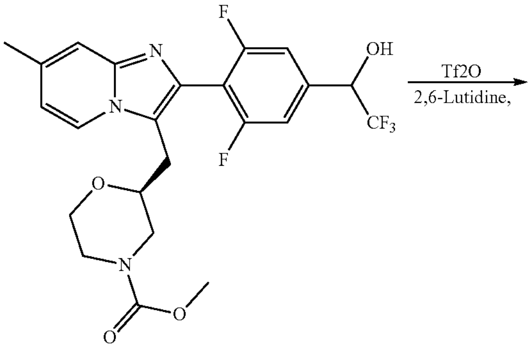

68-2

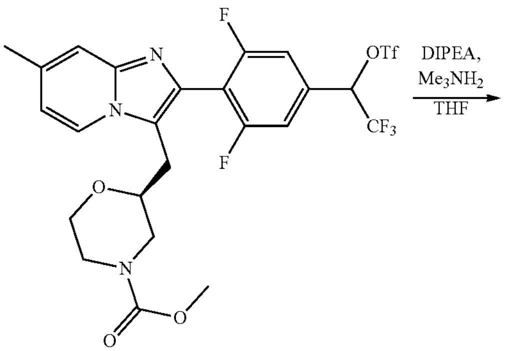

68-3

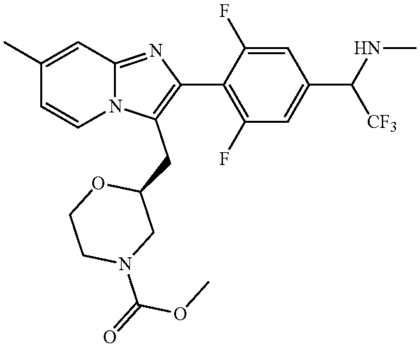

68

Step (1) Preparation of methyl (S)-2-((2-(2,6-difluoro-4-formylphenyl)-7-methylimidazo[1,2-a]pyridin-3-yl)methyl)morpholine-4-carboxylate 68-1

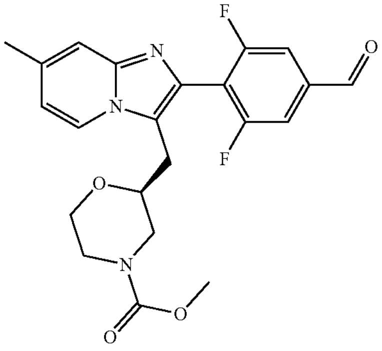

Tert-butyl (R)-2-((2-(4-(1,3-dioxan-2-yl)-2-fluorophenyl)-7-methylimidazo[1,2-a]pyridin-3-yl)methyl)morpholine-4-carboxylate (2.0 g, 4.0 mmol) was dissolved in acetone (15 mL). The reaction system was cooled to 0° C., added dropwise with diluted hydrochloric acid (1 N, 5 mL), and warmed to room temperature and stirred for 4 h. Then the reaction system was adjusted to pH 8 with saturated sodium carbonate solution (8 mL), added dropwise with methyl chloroformate (0.45 g, 4.8 mmol) at 0° C., and stirred at 0° C. for 1 h. The resulting reaction system was added with water (50 mL), and extracted with dichloromethane (60 mL×3). The organic phases were combined, washed with saturated brine (100 mL×2), dried over anhydrous sodium sulfate, filtered and concentrated. The residue was separated by silica gel column chromatography to give intermediate 68-1 (770 mg, 46% yield) in the form of a yellow solid. LC-MS $[M+H]^+$=430.

Step (2) Preparation of methyl (S)-2-((2-(2,6-difluoro-4-(2.2.2-trifluoro-1-hydroxyethyl)phenyl)-7-methylimidazo[1,2-a]pyridin-3-yl)methyl)morpholine-4-carboxylate 68-2

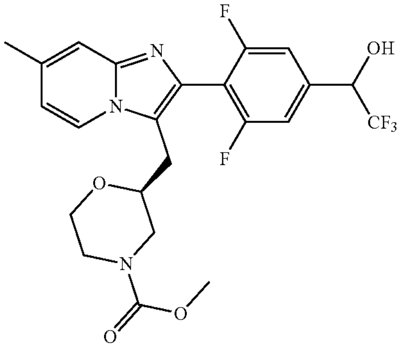

Intermediate 68-1 (100 mg, 0.23 mmol) was dissolved in N,N-dimethylformamide (2 mL) under nitrogen atmosphere, and potassium carbonate (16 mg, 0.11 mmol) was added, followed by the dropwise addition of trifluoromethyl trimethylsilane (50 mg, 0.30 mmol). The reaction system was stirred at room temperature for 4 h, added with HCl (2 mL, 2 N), and stirred at room temperature overnight. Then the reaction system was added with water (20 mL), and extracted with dichloromethane (15 mL×3). The organic phases were combined, washed with saturated brine (20 mL×2), dried over anhydrous sodium sulfate, filtered and concentrated. The residue was separated by silica gel column chromatography to give intermediate 68-2 (80 mg, 69% yield) in the form of a yellow solid. LC-MS: $[M+H]^+$=500.

Step (3) Preparation of methyl (S)-2-((2-(2,6-difluoro-4-(2,2,2-trifluoro-1-((trifluoromethyl)sulfonyl)oxy)ethyl))-7-methylimidazo[1,2-a]pyridin-3-yl)methyl)morpholine-4-carboxylate 68-3

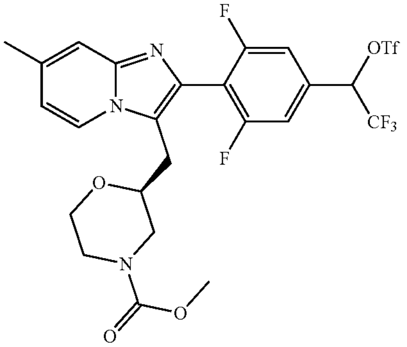

Intermediate 68-2 (80 mg, 0.16 mmol) and 2,6-dimethylpyridine (34 mg, 0.32 mmol) were dissolved in dichloromethane (3 mL) under nitrogen atmosphere. The reaction system was cooled to 0° C., added dropwise with trifluoromethanesulfonic anhydride (81 mg, 0.29 mmol), and stirred for 1 h. Then the reaction system was concentrated to give intermediate 68-3 (100 mg) in the form of a brown solid, which was used directly in the next step. LC-MS: $[M+H]^+$=632.

Step (4) Preparation of methyl (S)-2-((2-(2,6-difluoro-4-(2,2,2-trifluoro-1-(methylamino)ethyl)phenyl)-7-methylimidazo[1,2-a]pyridin-3-yl)methyl)morpholine-4-carboxylate

68

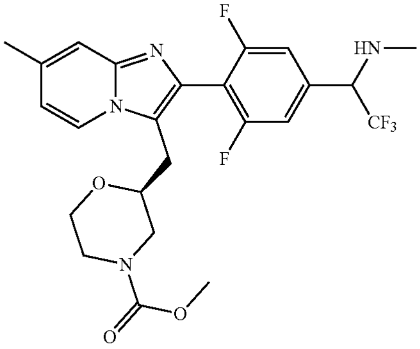

Intermediate 68-3 (100 mg, 0.16 mmol) and N,N-diisopropylethylamine (62 mg, 0.48 mmol) were dissolved in tetrahydrofuran (2 mL), and methylamine in tetrahydrofuran (1 mL, 2 N) was added. The reaction system was stirred at room temperature for 2 h under nitrogen atmosphere. Then the reaction system was added with water (20 mL) to quench the reaction, and extracted with dichloromethane (10 mL×3). The organic phases were combined, washed with saturated brine (10 mL×2), dried over anhydrous sodium sulfate, filtered and concentrated. The residue was purified by preparative chromatography to give compound 68 (trifluoroacetate salt, 18.3 mg, 22% yield) in the form of a white solid. LC-MS: $[M+H]^+$=513.

$^1$H NMR (400 MHZ, CDCl3) δ 8.58 (d, J=6.9 Hz, 1H), 7.95 (s, 1H), 7.37 (d, J=8.1 Hz, 2H), 7.16 (d, J=7.0 Hz, 1H), 6.56 (brs, 2H), 4.62-4.52 (m, 1H), 4.14-3.77 (m, 3H), 3.72 (s, 3H), 3.71-3.65 (m, 1H), 3.46-3.36 (m, 1H), 3.12-3.11 (m, 2H), 2.01-2.88 (m, 1H), 2.78-2.68 (m, 1H), 2.61 (s, 6H).

Example 69

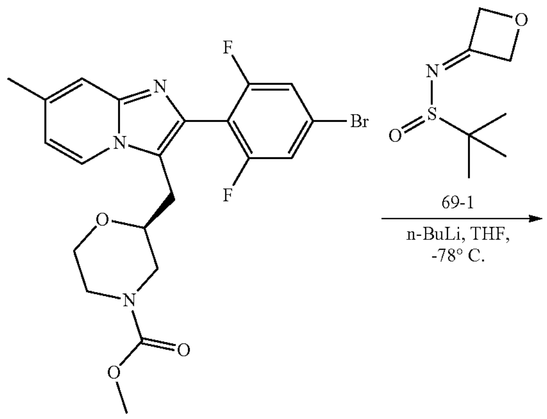

2-7

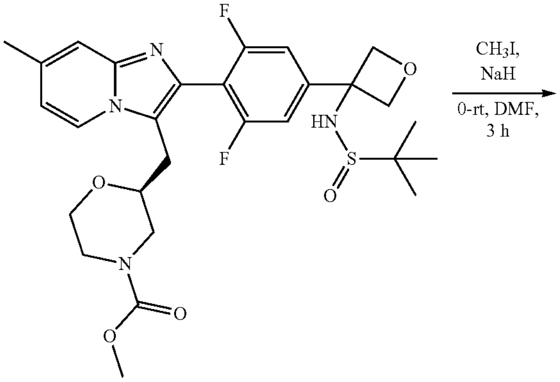

69-2

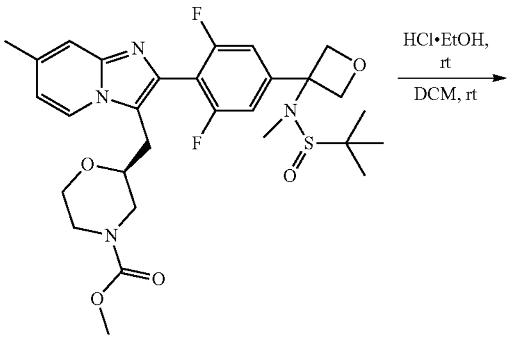

69-3

-continued

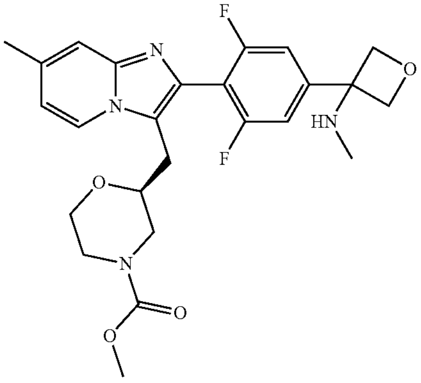

69

Step (1) Preparation of methyl (2S)-2-((2-(4-(3-((tert-butylsulfinyl)amino)oxetan-3-yl)-2,6-difluorophenyl)-7-methylimidazo[1,2-a]pyridin-3-yl)methyl)morpholine-4-carboxylate 69-2

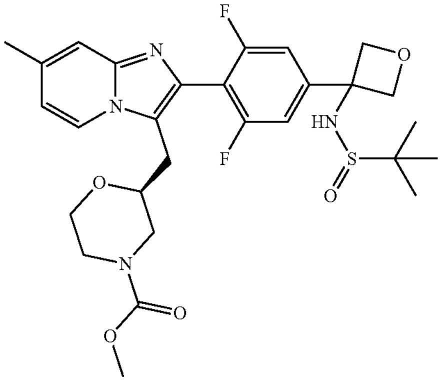

Intermediate 2-7 (300 mg, 0.63 mmol) was dissolved in tetrahydrofuran (5 mL) under nitrogen atmosphere, and n-butyllithium (0.32 mL, 0.76 mmol) was added dropwise at −78° C. in a dry ice-acetone bath. After the completion of the dropwise addition, the reaction system was reacted for 15 min, added dropwise with a solution of 2-methyl-N-(oxetan-3-ylidene) propane-2-sulfinamide (121 mg, 0.69 mmol) in tetrabydrofuran (1 mL), and reacted at −78° C. for 3 h. Then the reaction system was added with saturated aqueous ammonium chloride solution (2 mL) to quench the reaction, diluted with water (20 mL), and extracted with ethyl acetate (20 mL×2). The organic phases were combined, washed with saturated brine (15 mL×2), dried over anhydrous sodium sulfate, filtered and concentrated. The crude product was purified by silica gel column chromatography to give intermediate 69-2 (60 mg, 70% purity, 12% yield) in the form of a brown solid. ESI-MS $[M+H]^+$: 576.7.

Step (2) Preparation of methyl (2S)-2-((2-(4-(3-((tert-butylsulfinyl)(methyl)amino)oxetan-3-yl)-2,6-difluorophenyl)-7-methylimidazo[1,2-a]pyridin-3-yl)methyl)morpholine-4-carboxylate 69-3

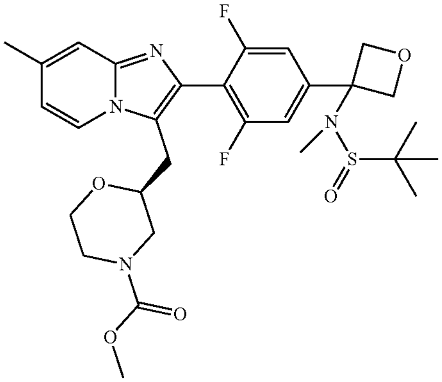

Intermediate 69-2 (60 mg, 0.10 mmol) was dissolved in anhydrous N,N-dimethylformamide (1 mL) under nitrogen atmosphere, and sodium hydride (10 mg, 0.25 mmol) was added in an ice water bath. The reaction system was stirred for 0.5 h, added dropwise with a solution of iodomethane (21 mg, 0.15 mmol) in N,N-dimethylformamide (0.5 mL), and stirred at 0° C. for 3 h. Then the reaction system was poured into ice water (15 mL), and extracted with ethyl acetate (15 mL×2). The organic phases were combined, washed with saturated brine (10 mL×3), dried over sodium sulfate, filtered and concentrated. The residue was purified by silica gel column chromatography to give intermediate 69-3 (50 mg, 70% purity, 57% yield) in the form of a brown solid. ESI-MS $[M+H]^+$: 590.8.

Step (3) Preparation of methyl (S)-2-((2-(2,6-difluoro-4-(3-(methylamino)oxetan-3-yl)phenyl)-7-methylimidazo[1,2-a]pyridin-3-yl)methyl)morpholine-4-carboxylate

69

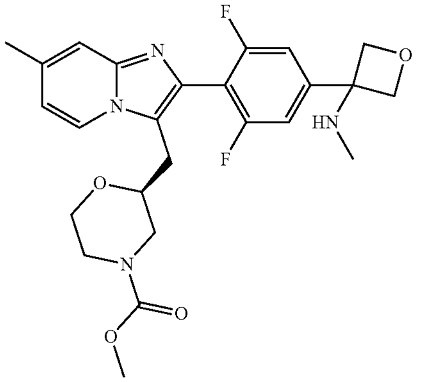

Intermediate 69-3 (50 mg, 0.085 mmol) was dissolved in dichloromethane (1.5 mL), and a solution of HCl in ethanol (0.1 mL, 0.40 mmol) was added dropwise at 0° C. The reaction system was stirred for 15 min, poured into ice water (10 mL), adjusted to pH 8 with saturated sodium bicarbonate solution, and extracted with dichloromethane (10 mL×2). The organic phases were combined, washed with saturated brine (10 mL), dried over anhydrous sodium sulfate, filtered and concentrated. The crude product was purified by preparative high performance liquid chromatography to give compound 69 (6.4 mg, 15.6% yield) in the form of a white solid. ESI-MS $[M+H]^+$: 486.8.

$^1H$ NMR (400 MHZ, $CDCl_3$) δ 8.26 (d, J=7.0 Hz, 1H), 7.50 (s, 1H), δ 7.20 (d, J=8.5 Hz, 2H), 6.74 (d, J=6.2 Hz, 1H), 4.93 (d, J=6.7 Hz, 2H), 4.82 (d, J=6.7 Hz, 2H), 3.98-3.80 (m, 3H), 3.70 (s, 3H), 3.64-3.60 (m, 1H), 3.47-3.36 (m, 1H), 3.10-2.97 (m, 2H), 2.97-2.86 (m, 1H), 2.65 (dd, J=13.1, 10.7 Hz, 1H), 2.47 (s, 3H), 2.35 (s, 3H).

Example 70

70

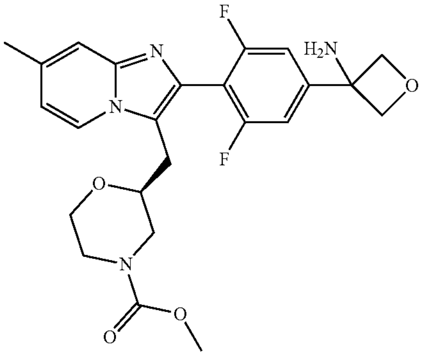

The compound was prepared according to the preparation method as described in Example 63. LC-MS: $[M+H]^+$=473.3.

Example 71

Preparation of methyl (S)-2-((2-(2,6-difluoro-4-(oxetan-3-ylamino)phenyl)-7-methylimidazo[1,2-a]pyridin-3-yl)methyl)morpholine-4-carboxylate

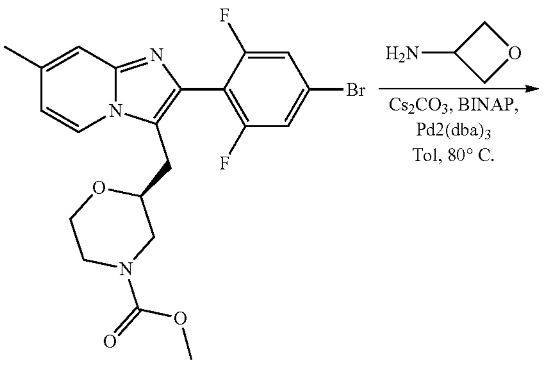

2-7

-continued

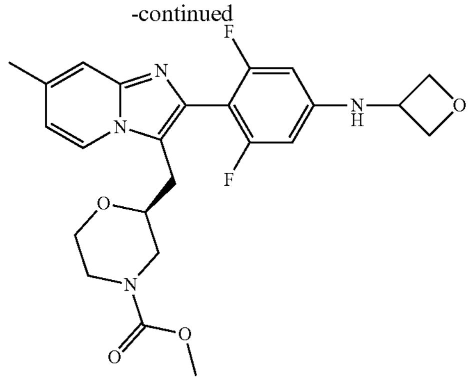

71

Intermediate 2-7 (40 mg, 0.08 mmol), 3-oxetane (7 mg, 0.096 mmol), cesium carbonate (78 mg, 0.24 mmol), tris (dibenzylideneacetone) dipalladium (7 mg, 0.008 mmol) and (±)-2,2'-bis-(diphenylphosphino)-1,1'-binaphthalene (10 mg, 0.016 mmol) were dissolved in anhydrous toluene (5 mL). The reaction system was reacted at 80° C. for 16 h under nitrogen atmosphere, filtered and concentrated by rotary evaporation to give a crude product. The crude product was purified by preparative high performance liquid chromatography to give compound 71 (25 mg, 62.5% yield) in the form of a white solid. MS $[M+H]^+$=473.1.

1H NMR (400 MHZ, d6-DMSO) δ 8.35 (d, J=7.0 Hz, 1H), 7.30 (s, 1H), 7.15 (d, J=6.5 Hz, 1H), 6.78 (dd, J=7.1, 1.6 Hz, 1H), 6.27 (d, J=10.6 Hz, 2H), 4.88 (t, J=6.5 Hz, 2H), 4.61 (dt, J=13.1, 6.7 Hz, 1H), 4.44 (td, J=6.1, 2.1 Hz, 2H), 373-3.64 (m, 3H), 3.56 (s, 3H), 3.51-3.45 (m, 1H), 3.25 (dt, J=11.7, 2.6 Hz, 1H), 3.04-2.92 (m, 2H), 2.90-2.77 (m, 1H), 2.60-2.46 (m, 1H), 2.36 (s, 3H).

Example 72

72

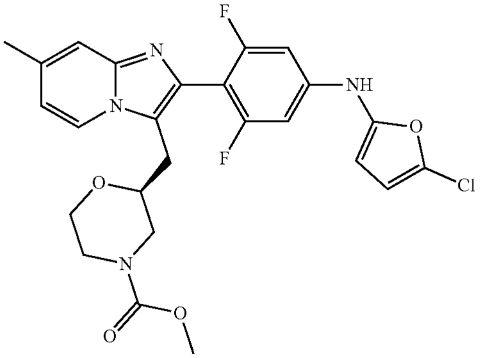

The compound was prepared according to the preparation method as described in Example 25. LC-MS: $[M+H]^+$=517.1.

Example 73

73

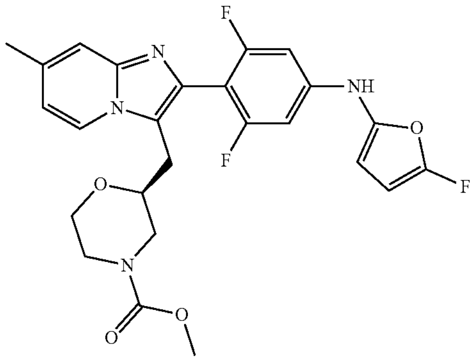

The compound was prepared according to the preparation method as described in Example 25. LC-MS: $[M+H]^+$=501.2.

Example 74

74

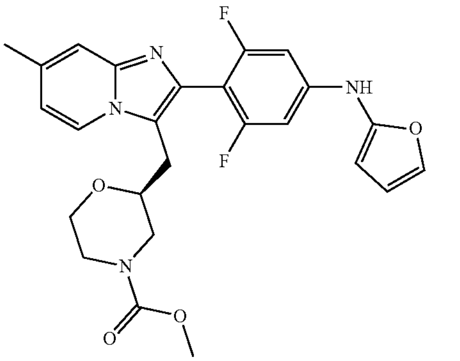

The compound was prepared according to the preparation method as described in Example 25. LC-MS: $[M+H]^+$=483.3.

Example 75

Preparation of methyl 2-((2-(2,6-difluoro-4-((tetrahydrofuran-3-yl)amino)phenyl)-7-methylimidazo[1,2-a]pyridin-3-yl)methyl)morpholine-4-carboxylate

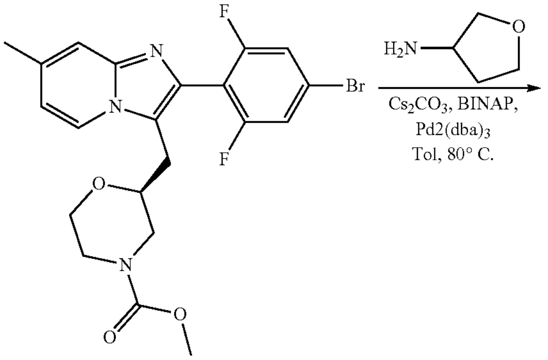

2-7

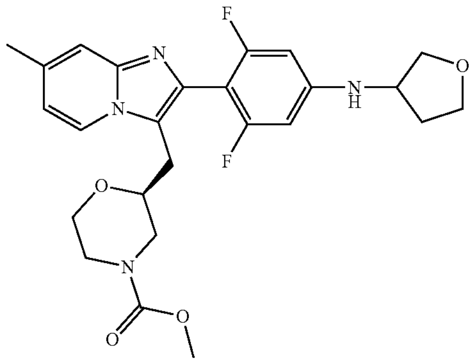

75

Intermediate 2-7 (50 mg, 0.10 mmol) was dissolved in toluene (5 mL) under nitrogen atmosphere, and oxolane-3-amine (11 mg, 0.12 mmol), cesium carbonate (98 mg, 0.30 mmol), tris(dibenzylideneacetone) dipalladium (9 mg, 0.01 mmol), and (+)-2,2'-bis-(diphenylphosphino)-1,1'-binaphthalene (13 mg, 0.02 mmol) were added. The reaction system was stirred at 80° C. overnight. Then the reaction system was filtered and concentrated. The residue was separated by preparative high performance liquid chromatography to give compound 75 (14.7 mg, 30.0% yield) in the form of a white solid. LC-MS: $[M+H]^+$=487.1.

1H NMR (400 MHZ, MeOD) δ 8.47 (d, J=6.8 Hz, 1H), 7.38 (s, 1H), 6.95 (d, J=6.5 Hz, 1H), 6.37 (d, J=10.9 Hz, 2H), 4.19-4.08 (m, 1H), 4.99-3.95 (m, 2H), 3.90-3.78 (m, 4H), 3.77-3.73 (m, 1H), 3.68 (s, 3H), 3.62-3.57 (m, 1H), 3.43-3.36 (m, 1H), 3.14-3.03 (m, 2H), 2.97-2.85 (m, 1H), 2.72-2.62 (m, 1H), 2.49 (s, 3H), 2.38-2.28 (m, 1H), 1.98-1.88 (m, 1H).

Example 76

Preparation of methyl (S)-2-((2-(2,6-difluoro-4-((tetrahydro-2H-pyran-4-yl)amino)phenyl)-7-methylimidazo[1,2-a]pyridin-3-yl)methyl)morpholine-4-carboxylate

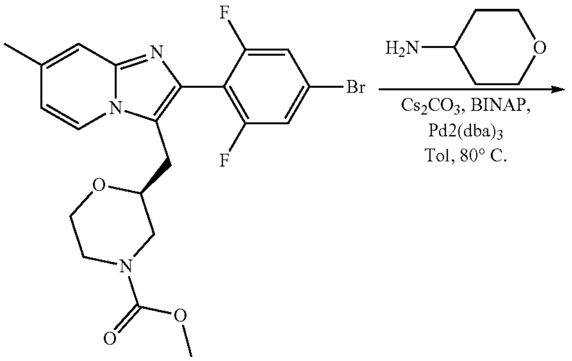

2-7

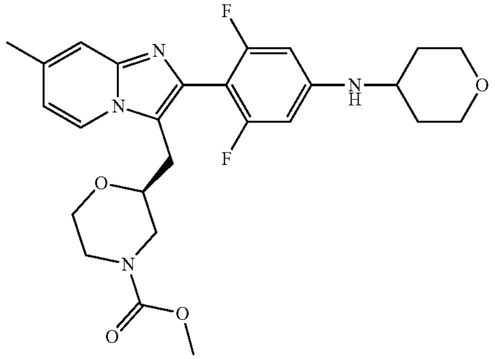

76

Intermediate 2-7 (80 mg, 0.17 mmol) was dissolved in toluene (5 mL) under nitrogen atmosphere, and tetrahydro-2H-pyran-4-amine (21 mg, 0.20 mmol), cesium carbonate (166 mg, 0.51 mmol), tris(dibenzylideneacetone) dipalladium (16 mg, 0.017 mmol), and (+)-2,2'-bis-(diphenylphosphino)-1,1'-binaphthalene (21 mg, 0.034 mmol) were added sequentially. The reaction system was stirred at 80° C. overnight. Then the reaction system was filtered and concentrated. The residue was separated by preparative high performance liquid chromatography to give compound 76 (51.9 mg, 58.8% yield) in the form of a white solid. LC-MS: $[M+H]^+$=501.2.

1H NMR (400 MHz, DMSO) δ 8.36 (d, J=7.0 Hz, 1H), 7.31 (s, 1H), 6.80 (d, J=6.6 Hz, 1H), 6.41-6.34 (m, 1H), 6.38 (d, J=11.0 Hz, 2H), 3.91-3.85 (m, 2H), 3.75-3.63 (m, 3H), 3.56 (s, 3H), 3.55-3.41 (m, 4H), 3.32-3.22 (m, 1H), 3.05-2.92 (m, 2H), 2.90-2.76 (m, 1H), 2.62-2.50 m, 1H), 2.38 (s, 3H), 1.94-1.86 (m, 2H), 1.45-1.34 (m, 2H).

Example 77

77

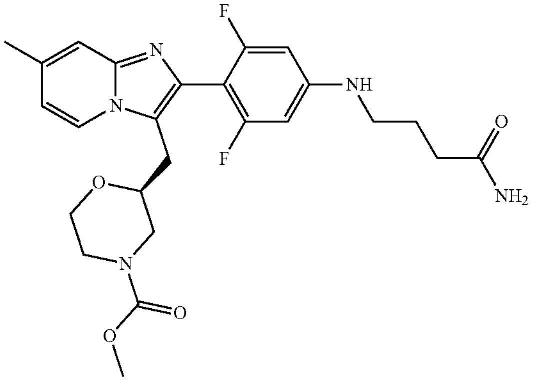

The compound was prepared according to the preparation method as described in Example 25. LC-MS: $[M+H]^+$=502.2.

Example 78

78

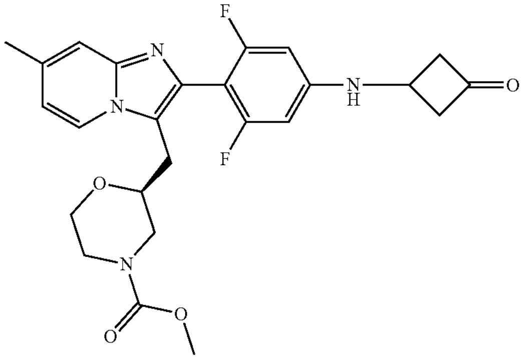

The compound was prepared according to the preparation method as described in Example 25. LC-MS: $[M+H]^+$=485.2.

Example 79

Preparation of methyl (2S)-2-((2-(2,6-difluoro-4-((3-carbonylcyclopentyl)amino)phenyl)-7-methylimidazo[1,2-a]pyridin-3-yl)methyl)morpholine-4-carboxylate

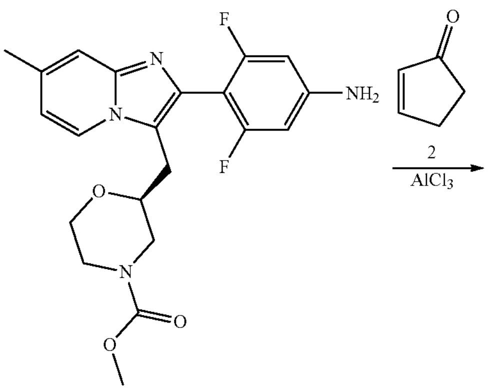

3-1

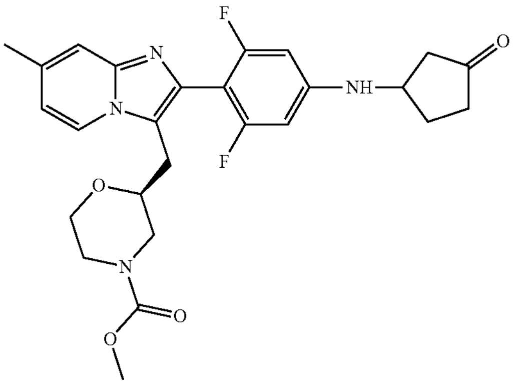

79

Intermediate 3-1 (60.0 mg, 0.14 mmol) was dissolved in cyclopent-2-enone (3 mL) under nitrogen atmosphere, and anhydrous aluminium trichloride (117.5 mg, 1.15 mmol) was added. The reaction system was reacted at room temperature for 18 h. Then the reaction system was filtered and concentrated. The crude product was separated by preparative high performance liquid chromatography, and lyophilized to give compound 79 (29.7 mg, 42% yield) in the form of a white solid. LC-MS: $[M+H]^+$=499.3.

1H NMR (400 MHZ, $CDCl_3$) δ 8.21 (brs, 1H), 7.46 (brs, 1H), 6.70 (brs, 1H), 6.27 (d, J=9.9 Hz, 2H), 4.17-4.08 (m, 1H), 4.00-3.76 (m, 3H), 3.70 (s, 3H), 3.64-3.56 (m, 1H), 3.47-3.36 (m, 1H), 3.02-2.97 (m, 2H), 2.94-2.85 (m, 1H), 2.75 (dd, J=18.2, 6.5 Hz, 1H), 2.64 (dd, J=13.1, 10.7 Hz, 1H), 2.56-2.48 (m, 1H), 2.44 (s, 3H), 2.39-2.32 (m, 1H), 2.30-2.22 (m, 1H), 2.12-2.00 (m, 2H).

Example 80

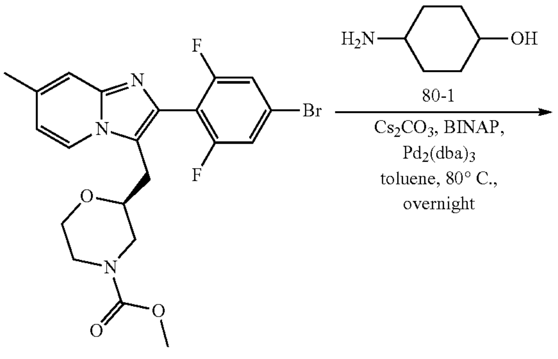

2-7

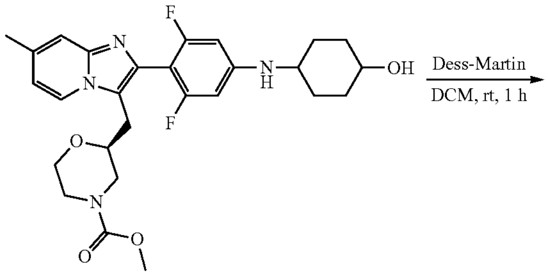

80-2

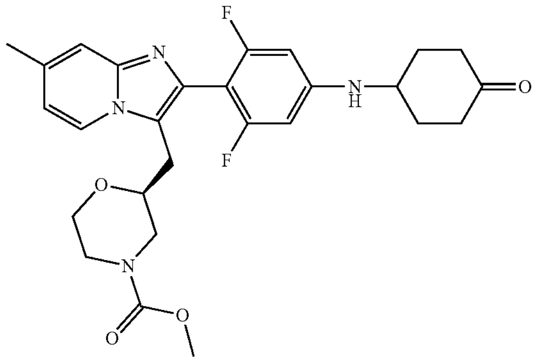

80

Step (1) Preparation of methyl (S)-2-((2-(2,6-difluoro-4-((4-hydroxycyclohexyl)amino)phenyl)-7-methylimidazo[1,2-a]pyridin-3-yl)methyl)morpholine-4-carboxylate 80-2

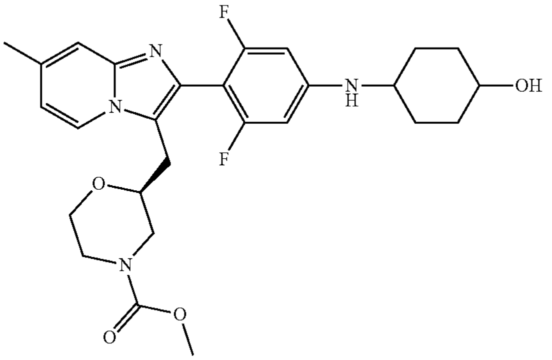

Intermediate 2-7 (200 mg, 0.42 mmol) was dissolved in anhydrous toluene (3 mL) under nitrogen atmosphere, and 4-aminocyclohexanol (58 mg, 0.50 mmol), cesium carbonate (407 mg, 1.25 mmol), (+)-2,2'-bis-(diphenylphosphino)-1,1'-binaphthalene (52 mg, 0.084 mmol) and tris(dibenzylideneacetone) dipalladium (40 mg, 0.043 mmol) were added. The reaction system was reacted at 80° C. overnight. After the reaction was completed, the reaction system was cooled to room temperature and filtered, and the filtrate was added with water (20 mL) and extracted with dichloromethane (30 mL×3). The organic phases were combined, washed with saturated brine (30 mL), dried over anhydrous sodium sulfate, filtered and concentrated by rotary evaporation to give a crude product. The crude product was purified by silica gel column chromatography to give intermediate 80-2 (150 mg, 70% yield) in the form of a yellow oil. LC-MS: $[M+H]^+$=514.8.

Step (2) Preparation of methyl (S)-2-((2-(2,6-difluoro-4-((4-carbonylcyclohexyl)amino)phenyl)-7-methylimidazo[1,2-a]pyridin-3-yl)methyl)morpholine-4-carboxylate

80

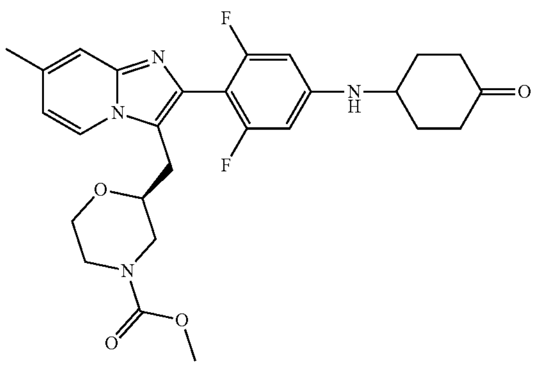

Intermediate 80-2 (150 mg, 0.29 mmol) was dissolved in anhydrous dichloromethane (2 mL) under nitrogen atmosphere, and Dess-Martin periodinane (185 mg, 0.44 mmol) was added. The reaction system was reacted at room temperature for 1 h. Then the reaction system was added with water (20 mL), and extracted with dichloromethane (20 mL×3). The organic phases were combined, washed with saturated brine (20 mL), dried over sodium sulfate, filtered and concentrated by rotary evaporation to give a crude product. The crude product was purified by preparative high performance liquid chromatography to give compound 80 (20.2 mg, 20.3% yield) in the form of a white solid. LC-MS: $[M+H]^+$=512.8.

$^1H$ NMR (400 MHZ, MeOD) δ 8.82-8.78 (m, 1H), 7.65-7.64 (m, 1H), 7.38-7.36 (m, 1H), 6.53 (d, J=11.7 Hz, 1H), 6.46-6.41 (m, 1H), 3.98-3.95 (m, 1H), 3.92-3.75 (m, 3H), 3.70 (s, 3H), 3.39-3.35 (m, 1H), 3.25-3.18 (m, 2H), 2.99-2.90 (m, 1H), 2.80-2.72 (m, 1H), 2.63 (s, 3H), 2.59-2.55 (m, 1H), 2.48-2.44 (m, 1H), 2.34-2.29 (m, 1H), 1.97-1.95 (m, 2H), 1.86-1.49 (m, 4H).

Example 81

Preparation of methyl (2S)-2-((2-(4-((1,1-dihydroxytetrahydrothiophen-3-yl)amino)-2,6-difluorophenyl)-7-methylimidazo[1,2-a]pyridin-3-yl)methyl)morpholine-4-carboxylate

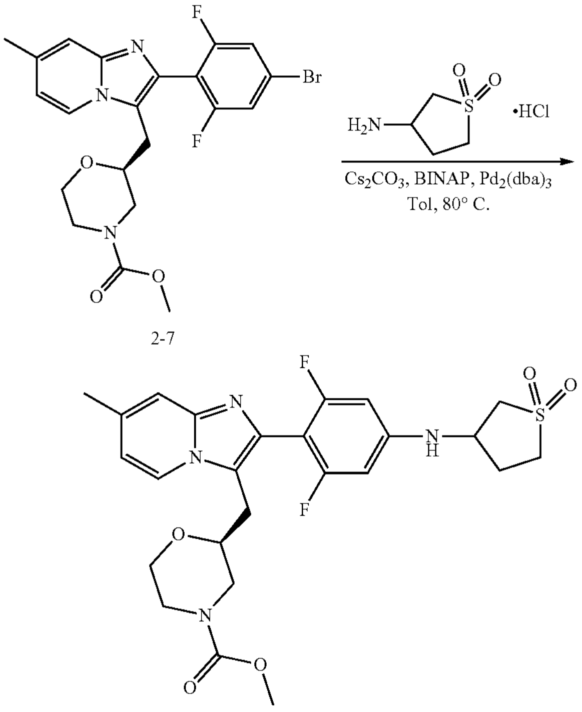

2-7

81

Intermediate 2-7 (80 mg, 0.16 mmol), 3-aminotetrahydrothiophene 1,1-disulfone hydrochloride (43 mg, 0.24 mmol), cesium carbonate (217 mg, 0.64 mmol), (+)-2,2'-bis-(diphenylphosphino)-1,1'-binaphthalene (21 mg, 0.03 mmol), and tris(dibenzylideneacetone) dipalladium (15 mg, 0.02 mmol) were dissolved in toluene (3 mL) under nitrogen atmosphere. The reaction system was heated to 80° C., and reacted overnight. Then the reaction system was cooled to room temperature, added with water (20 mL) to quench the reaction, and extracted with dichloromethane (15 mL×3). The organic phases were combined, washed with saturated brine (15 mL), dried over anhydrous sodium sulfate, filtered and concentrated. The residue was separated by preparative high performance liquid chromatography to give compound 81 (32.4 mg, 36% yield) in the form of a yellow solid, LC-MS: $[M+H]^+$=535.1.

$^{1}$H NMR (400 MHZ, CDCl3) δ 8.26 (s, 1H), 7.55 (d, J=7.4 Hz, 1H), 6.77 (d, J=6.9 Hz, 1H), 6.27 (d, J=9.8 Hz, 2H), 4.37-4.30 (m, 1H), 4.01-3.79 (m, 3H), 3.70 (s, 3H), 3.63-3.56 (m, 1H), 3.55-3.48 (m, 1H), 3.45-3.32 (m, 2H), 3.25-3.16 (m, 1H), 3.13-3.05 (m, 1H), 3.03-2.86 (m, 3H), 2.67-2.62 (m, 2H), 2.46 (s, 3H), 2.45-2.36 (m, 1H).

Example 82

82

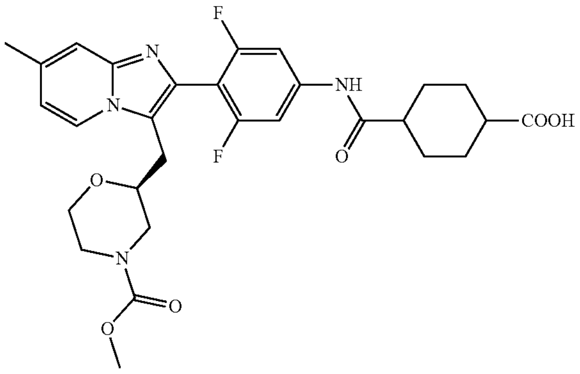

The compound was prepared according to the preparation method as described in Example 25. LC-MS: $[M+H]^+$=571.2.

Example 83

83

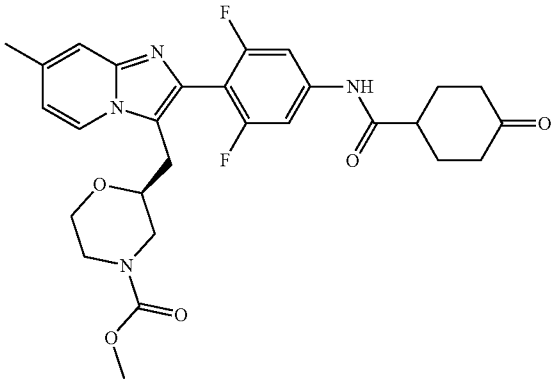

The compound was prepared according to the preparation method as described in Example 25. LC-MS: $[M+H]^+$=541.3.

Example 84

84

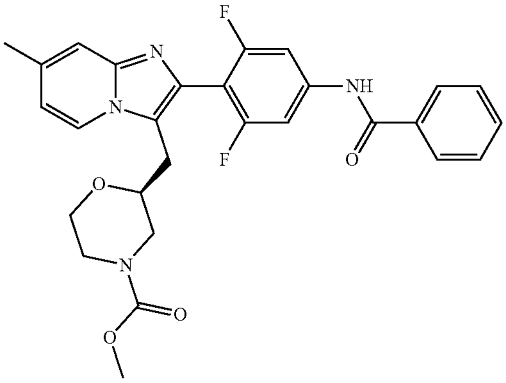

The compound was prepared according to the preparation method as described in Example 25. LC-MS: $[M+H]^+$=521.2.

Example 85

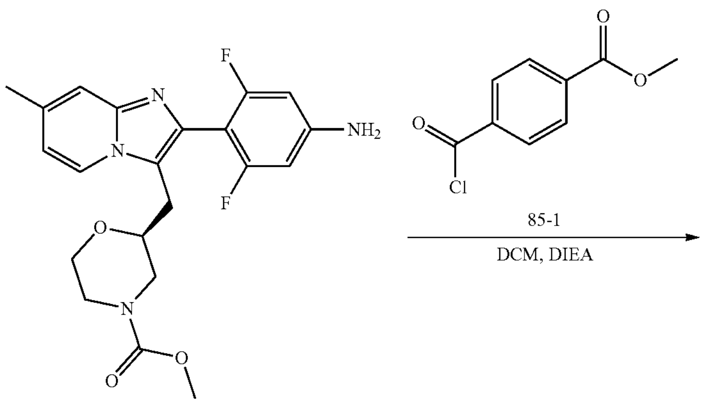

3-1

-continued

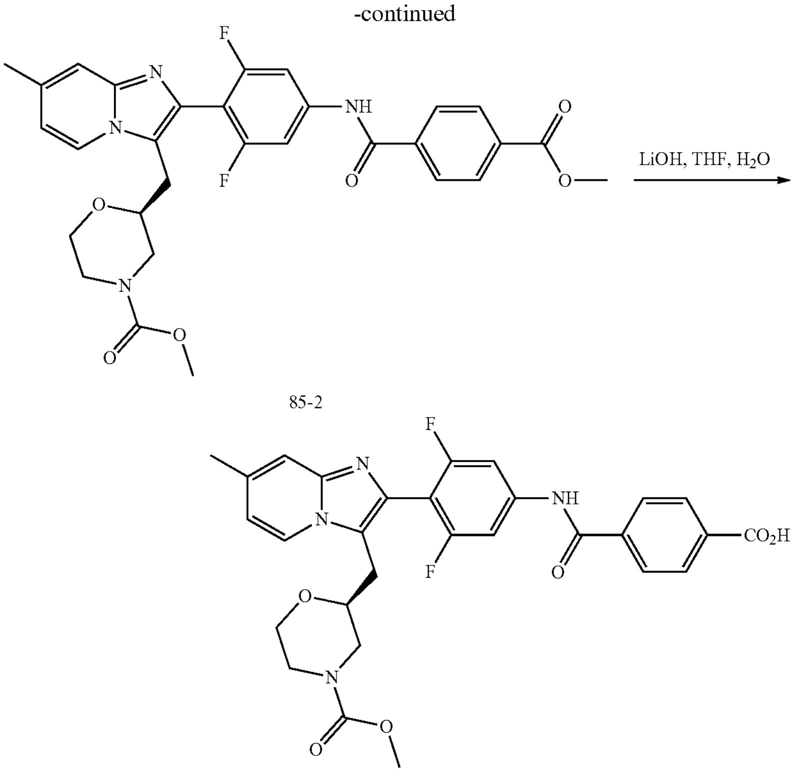

85-2

85

Step (1) Preparation of methyl (S)-2-((2-(4-amino-2,6-difluorophenyl)-7-methylimidazo[1,2-a]pyridin-3-yl)methyl)morpholine-4-carboxylate 85-2

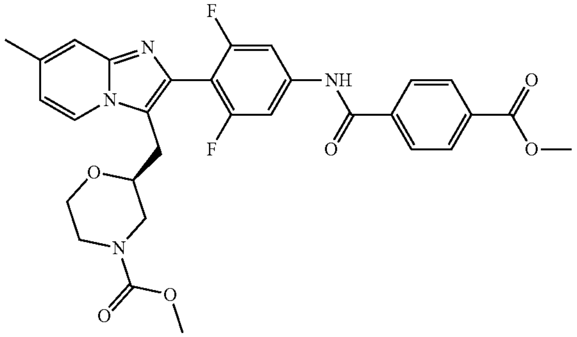

Intermediate 3-1 (80 mg, 0.19 mmol) and diisopropylethylamine (74 mg, 0.57 mmol) were dissolved in dichloromethane (10 mL). The reaction system was cooled to 0° C., added dropwise with a solution of methyl 4-(chloroformyl)benzoate (75 mg, 0.38 mmol) in dichloromethane (0.2 mL), and stirred at room temperature for 12 h. Then the reaction system was diluted with dichloromethane (10 mL) and washed with saturated brine (10 mL). The organic phase was dried over anhydrous sodium sulfate, filtered, and concentrated to give a crude product. The crude product was purified by silica gel column chromatography to give intermediate 85-2 (100 mg, 49% yield) in the form of a white solid. MS $[M+H]^+$=579.2.

Step (2) Preparation of (S)-4-((3,5-difluoro-4-(3-((4-(carbomethoxy<methoxycarbonyl>)morpholin-2-yl)methyl)-7-methylimidazo[1,2-a]pyridin-2-yl) phenyl) carbamoyl)benzoic acid

85

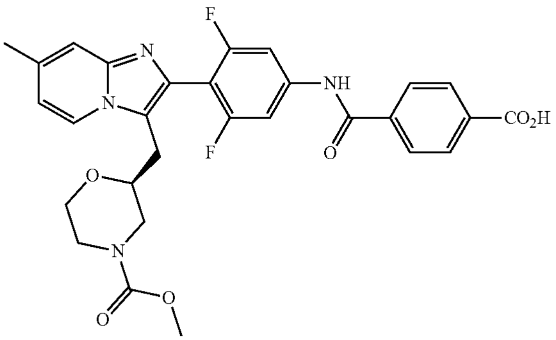

Intermediate 85-2 (50 mg, 0.09 mmol) was dissolved in tetrahydrofuran (5 mL) and water (1 mL), and lithium hydroxide monohydrate (22 mg, 0.55 mmol) was added. The reaction system was stirred at room temperature for 1 h. After the reaction was completed, the reaction system was adjusted to pH 4-5 with diluted hydrochloric acid (1 N), and concentrated by rotary evaporation to give a crude product.

The crude product was purified by preparative high performance liquid chromatography to give compound 85 (35 mg, 59% yield) in the form of a white solid. MS $[M+H]^+$=565.2.

1H NMR (400 MHZ, d6-DMSO) δ 13.24 (s, 1H), 10.84 (s, 1H), 8.42 (d, J=6.9 Hz, 1H), 8.10 (q, J=7.0 Hz, 4H), 7.69 (d, J=9.9 Hz, 2H), 7.35 (s, 1H), 6.83 (d, J=7.1 Hz, 1H), 3.77-3.59 (m, 3H), 3.56 (s, 3H), 3.52-3.46 (m, 1H), 3.30-3.22 (m, 1H), 3.08-3.00 (m, 2H), 2.90-7.74 (m, 1H), 2.60-2.48 (m, 1H), 2.39 (s, 3H).

Example 86

86

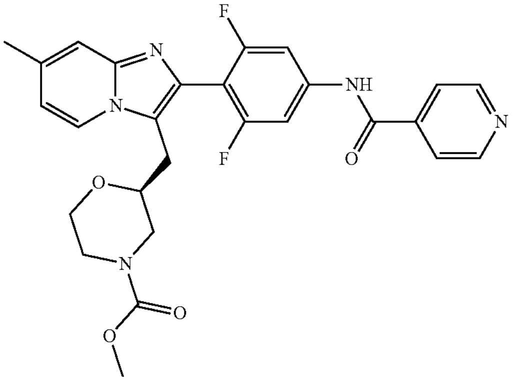

The compound was prepared according to the preparation method as described in Example 25. LC-MS: $[M+H]^+$=522.2.

Example 87

87

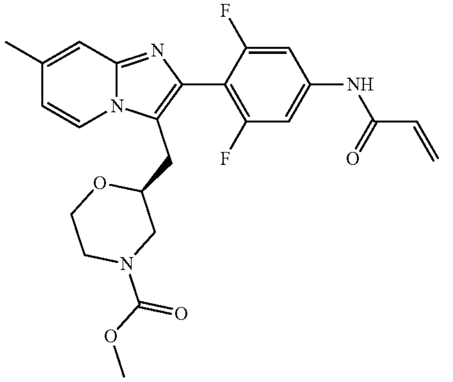

The compound was prepared according to the preparation method as described in Example 25. LC-MS: $[M+H]^+$=471.2.

Example 88

88

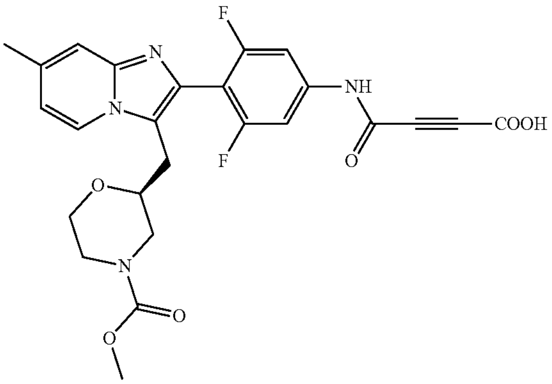

The compound was prepared according to the preparation method as described in Example 25. LC-MS: $[M+H]^+$=513.3.

Example 89

Preparation of methyl (S)-2-((2-(4~ (1-cyanocyclopropane-1-carboxamido)-2,6-difluorophenyl)-7-methylimidazo[1,2-a]pyridin-3-yl)methyl)morpholine-4-carboxylate

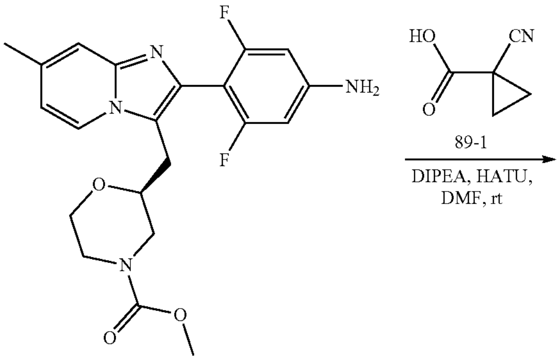

3-1

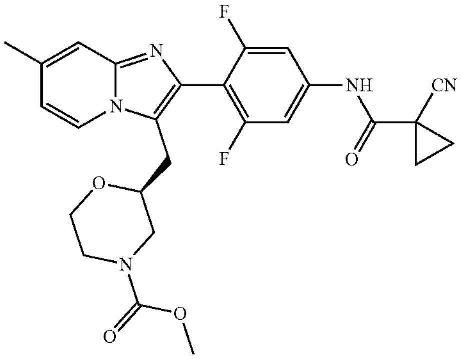

89

1-cyanocyclopropane-1-carboxylic acid (52 mg, 0.47 mmol) and 2-(7-azabenzotriazol-1-yl)-N,N,N',N'-tetramethyluronium hexafluorophosphate (180 mg, 0.47 mmol) were dissolved in anhydrous N,N-dimethylformamide (2 mL) under nitrogen atmosphere. The reaction system was reacted at room temperature for 10 min, added with N,N-diisopropylethylamine (162 mg, 1.25 mmol) and intermediate 3-1 (130 mg, 0.31 mmol), and reacted at room temperature overnight. Then the reaction system was added with water (20 mL), and extracted with ethyl acetate (30 mL×3). The organic phases were combined, washed with saturated brine (30 mL×3), dried over anhydrous sodium sulfate, filtered and concentrated by rotary evaporation to give a crude product. The crude product was purified by high performance liquid chromatography to give compound 89 (35.8 mg, 23% yield) in the form of a white solid.

LC-MS: $[M+H]^+$=510.6. 1H NMR (400 MHZ, MeOD): δ8.83 (d, J=7.1 Hz, 1H), 7.69 (s, 1H), 7.67 (d, J=10.1 Hz, 2H), 7.40 (dd, J=7.1, 1.5 Hz, 1H), 3.98 (d, J=12.8 Hz, 1H), 3.83 (d, J=13.6 Hz, 1H), 3.76 (d, J=9.2 Hz, 1H), 3.70 (s, 3H), 3.70-3.65 (m, 1H), 3.37-3.34 (m, 1H), 3.24 (d, J=5.3 Hz, 2H), 3.00-2.85 (m, 1H), 280-2.67 (m, 1H), 2.64 (s, 3H), 1.81-1.76 (m, 2H), 1.75-1.70 (m, 2H).

Example 90

90

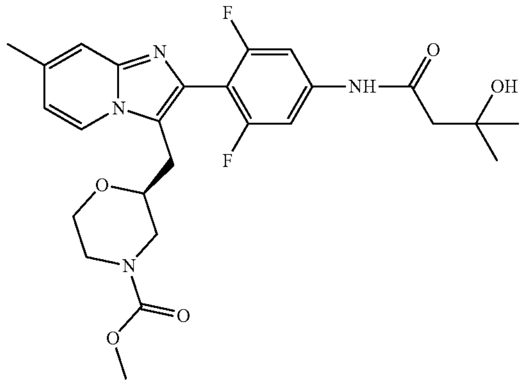

The compound was prepared according to the preparation method as described in Example 25. LC-MS: $[M+H]^+$=517.2.

Example 91

91

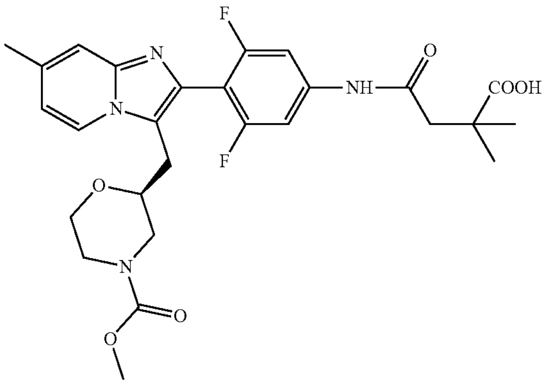

The compound was prepared according to the preparation method as described in Example 25. LC-MS: $[M+H]^+$=545.4.

Example 92

92

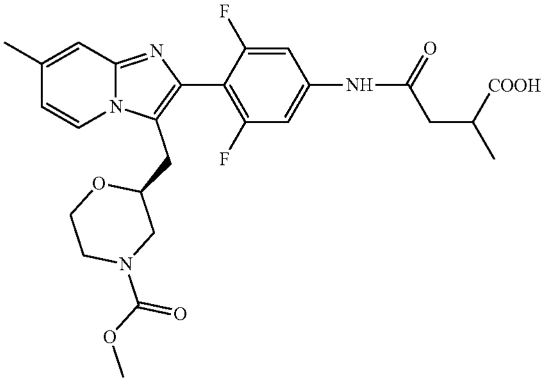

The compound was prepared according to the preparation method as described in Example 25. LC-MS: $[M+H]^+$=531.2.

Example 93

93

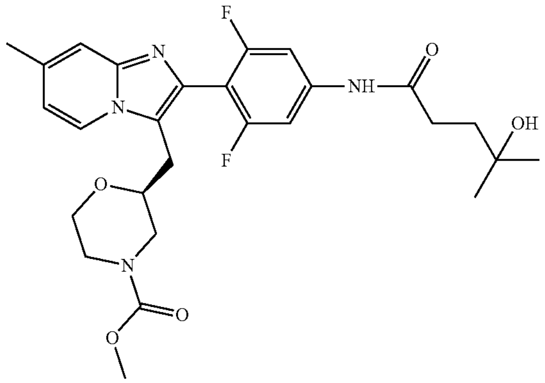

The compound was prepared according to the preparation method as described in Example 25. LC-MS: $[M+H]^+$=531.4.

Example 94

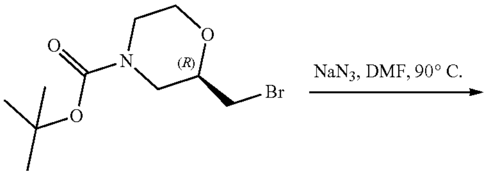

94-1

-continued

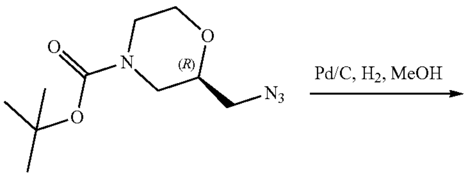

94-2

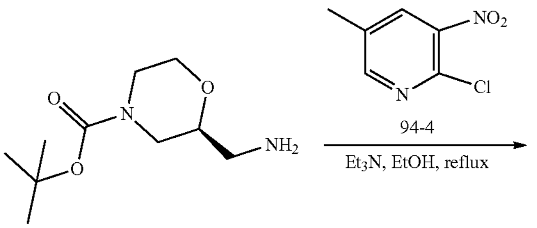

94-3

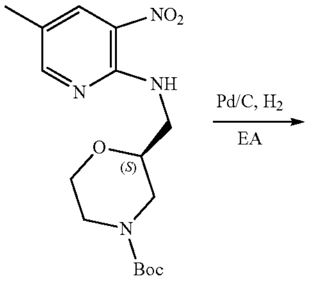

94-5

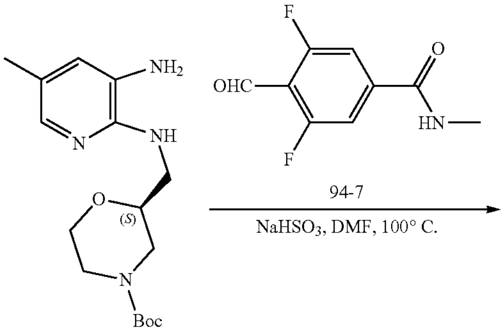

94-6

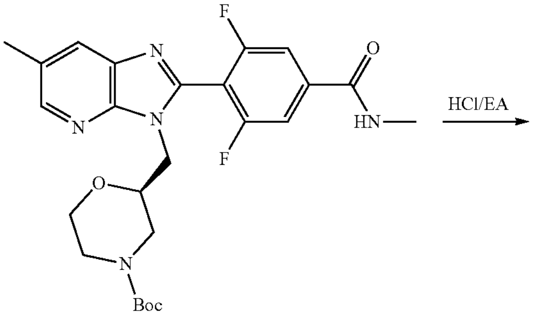

94-8

-continued

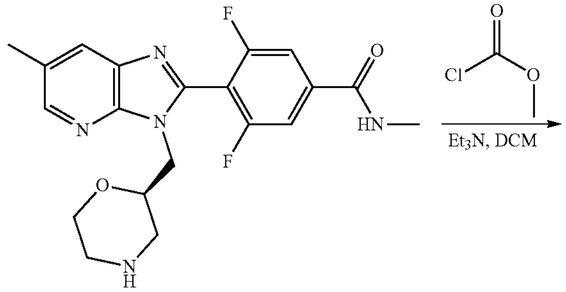

94-9

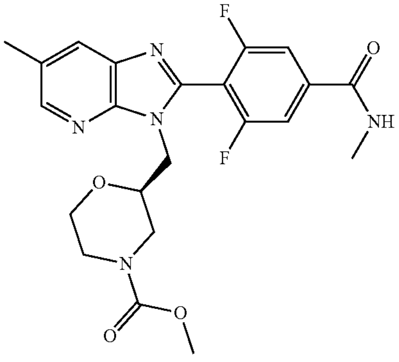

94

Step (1) Preparation of tert-butyl (R)-2-(azidomethyl)morpholine-4-carboxylate 94-2

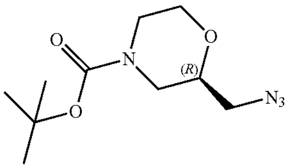

Tert-butyl (R)-2-(bromomethyl)morpholine-4-carboxylate (1.0 g, 3.58 mmol) was dissolved in N,N-dimethylformamide (8 mL), and sodium azide (700 mg, 10.75 mmol) was added. The reaction system was heated to 90° C. for 8 h. Then the reaction system was cooled to room temperature, added with water (40 mL) to quench the reaction, and extracted with ethyl acetate (20 mL×3). The organic phases were combined, washed with saturated brine (15 mL×2), dried over anhydrous sodium sulfate, and concentrated. The residue was separated by column chromatography to give intermediate 94-2 (738 mg, 92% yield) in the form of a white solid. LC-MS: $[M+H]^+$=243.2.

Step (2) Preparation of tert-butyl (S)-2-(aminomethyl)morpholine-4-carboxylate 94-3

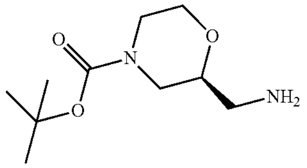

Intermediate 94-2 (738 mg, 3.05 mmol) was dissolved in methanol (10 mL), and wet palladium on carbon catalyst (200 mg, 10% w/w) was added. The reaction system was purged with hydrogen and reacted at room temperature for 2.5 h. Then the reaction system was filtered and concentrated to give intermediate 94-3 (580 mg, 82% yield) in the form of a light yellow oil. LC-MS: $[M+H]^+$=217.2.

Step (3) Preparation of tert-butyl (S)-2-(((5-methyl-3-nitropyridin-2-yl)amino)methyl)morpholine-4-carboxylate 94-5

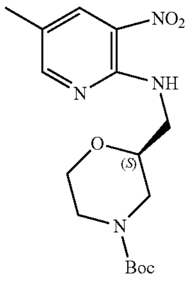

Intermediate 94-3 (580 mg, 2.68 mmol) was dissolved in ethanol (10 mL), and 2-chloro-5-methyl-3-nitropyridine (509 mg, 2.95 mmol) and triethylamine (895 mg, 8.84 mmol) were added. The reaction system was heated to reflux for 24 h. Then the reaction system was concentrated by rotary evaporation. The residue was separated by column chromatography (PE/EA=4/1) to give intermediate 94-5 (710 mg, 75% yield) in the form of a yellow solid. LC-MS: $[M+H]^+$=353.1.

Step (4) Preparation of tert-butyl (S)-2-(((3-amino-5-methylpyridin-2-yl)amino)methyl)morpholine-4-carboxylate 94-6

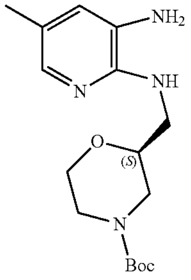

Intermediate 94-5 (326 mg, 0.96 mmol) was dissolved in ethyl acetate (20 mL), and wet palladium on carbon catalyst (50 mg, 10% w/w) was added. The reaction system was purged with hydrogen and stirred at room temperature for 2.5 h. Then the reaction system was filtered and concentrated to give intermediate 94-6 (266 mg, 81% yield) in the form of a yellow solid. LC-MS: $[M+H]^+$=323.2.

Step (5) Preparation of tert-butyl (S)-2-((2-(2,6-difluoro-4-(methylcarbamoyl)phenyl)-6-methyl-3H-imidazo[4,5-b]pyridin-3-yl)methyl)morpholine-4-carboxylate 94-8

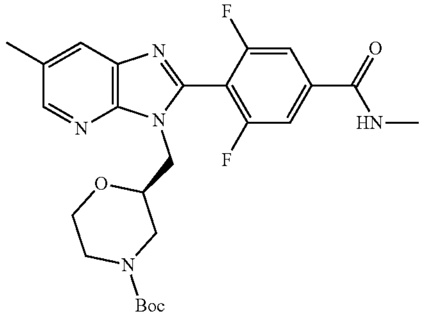

Intermediate 94-6 (266 mg, 0.82 mmol), sodium bisulfite (512 mg, 4.92 mmol), and 3,5-difluoro-4-formyl-N-methylbenzamide (213 mg, 1.07 mmol) were dissolved in N,N-dimethylformamide (8 mL). The reaction system was heated to 100° C. and reacted for 15 h. After the reaction was completed, the reaction system was added with water (30 mL) to quench the reaction, and extracted with dichloromethane (20 mL×3). The organic phases were combined, washed with saturated brine (30 mL), dried over anhydrous sodium sulfate, filtered and concentrated. The reaction system was separated by column chromatography (EA) to give intermediate 94-8 (210 mg, 46% yield) in the form of a yellow solid. LC-MS: [M+H]=502.1.

Step (6) Preparation of (R)-3,5-difluoro-N-methyl-4-(6-methyl-3-(morpholin-2-yl-methyl)-3H-imidazo[4,5-b]pyridin-2-yl)benzamide 94-9

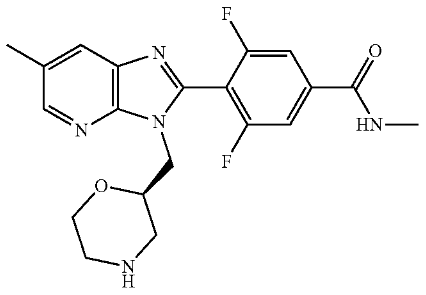

Intermediate 94-8 (210 mg, 0.52 mmol) was dissolved in ethyl acetate (4 mL), and a solution of HCl in ethyl acetate (1 mL, 4 N) was added dropwise. The reaction system was stirred at room temperature for 2.5 h. Then the reaction system was concentrated to give intermediate 94-9 (hydrochloride, 222 mg, crude product) in the form of a yellow solid, which was used directly in the next step. LC-MS: $[M+H]^+$=402.1.

Step (7) Preparation of methyl (S)-2-((2-(2,6-difluoro-4-(methylcarbamoyl)phenyl)-6-methyl-3H-imidazo[4,5-b]pyridin-3-yl)methyl)morpholine-4-carboxylate

94

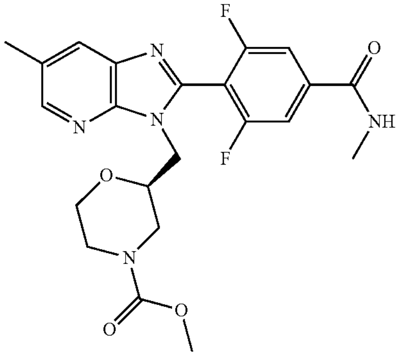

Intermediate 94-9 (222 mg, 0.52 mmol) was dissolved in anhydrous dichloromethane (10 mL), and triethylamine (157 mg, 1.56 mmol) was added. Under nitrogen atmosphere, the reaction system was cooled to 0° C., added dropwise with methyl chloroformate (59 mg, 0.62 mmol), and reacted for 3 h. Then the reaction system was diluted with dichloromethane (20 mL) and washed with water (20 mL). The aqueous phase was extracted with dichloromethane (15 mL×2). The organic phases were combined, dried over anhydrous sodium sulfate, and concentrated. The residue was purified by preparative high performance liquid chromatography to give compound 94 (64 mg, 27% yield) in the form of a white solid. LC-MS: $[M+H]^+$=460.8.

$^1$H NMR (400 MHZ, $CDCl_3$): δ 8.39 (s, 1H), 8.03 (s, 1H), 7.56 (brs, 2H), 7.02 (brs, 1H), 4.50-4.41 (m, 1H), 4.25-4.15 (m, 1H), 4.12-3.96 (m, 1H), 3.85-3.65 (m, 5H), 3.65-3.55 (m, 1H), 3.30-3.20 (m, 1H), 3.07 (s, 3H), 2.85-2.70 (m, 1H), 2.57 (s, 3H), 2.56-2.46 (m, 1H).

Example 95

95

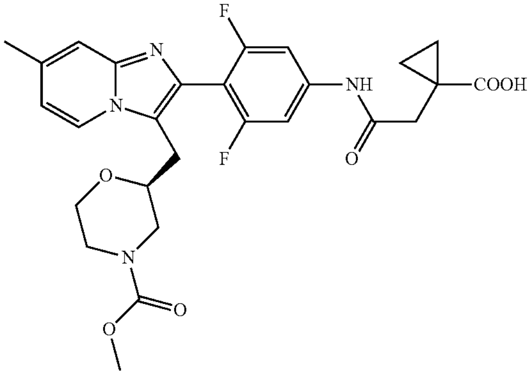

The compound was prepared according to the preparation method as described in Example 25. LC-MS: $[M+H]^+$=543.3.

Example 96

96

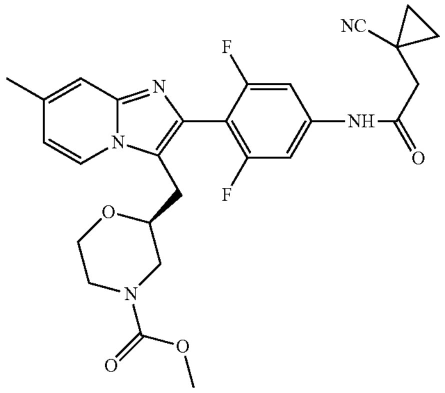

The compound was prepared according to the preparation method as described in Example 25. LC-MS: $[M+H]^+$=524.3.

Example 97

Preparation of methyl (S)-2-((2-(2,6-difluoro-4-(methoxycarbonyl)cyclopropane-1-carboxamido) phenyl)-7-methylimidazo[1,2-a]pyridin-3-yl)methyl) morpholine-4-carboxylate

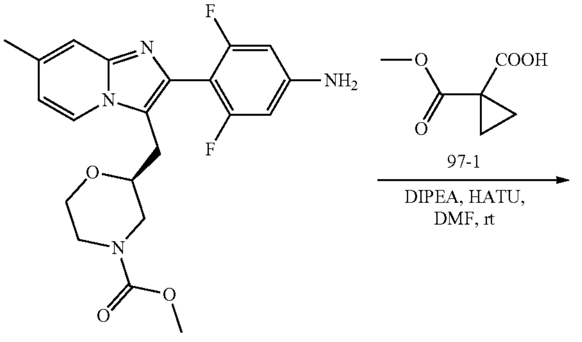

3-1

97-1

97

Intermediate 97-1 (31 mg, 0.22 mmol) and 2-(7-azabenzotriazol-1-yl)-N,N,N',N'-tetramethyluronium hexafluorophosphate (82 mg, 0.22 mmol) were dissolved in anhydrous N,N-dimethylformamide (1.0 mL) under nitrogen atmosphere. The reaction system was reacted at room temperature for 10 min, added with N,N-diisopropylethylamine (75 mg, 0.58 mmol) and intermediate 3-1 (60 mg, 0.14 mmol), and reacted at room temperature overnight. Then the reaction system was added with water (20 mL) to quench the reaction, and extracted with ethyl acetate (20 mL×3). The organic phases were combined, washed with saturated brine (30 mL×2), dried over anhydrous sodium sulfate, filtered and concentrated by rotary evaporation to give a crude product. The crude product was purified by high performance liquid chromatography to give compound 97 (11.7 mg, 15% yield) in the form of a yellow solid. LC-MS: $[M+H]^+$=543.7.

$^1$H NMR (400 MHZ, MeOD) δ 8.84 (d, J=7.1 Hz, 1H), 7.70 (s, 1H), 7.64 (d, J=10.1 Hz, 2H), 7.41 (dd, J=7.1, 1.4 Hz, 1H), 4.01-3.97 (m, 1H), 3.85-3.82 (m, 1H), 3.80 (s, 3H), 3.78-3.71 (m, 2H), 3.70 (s, 3H), 3.39-3.35 (m, 1H), 3.28-3.21 (m, 2H), 2.98-2.90 (m, 1H), 2.80-2.70 (m, 1H), 2.65 (s, 3H), 1.71-1.64 (m, 4H).

Example 98

98

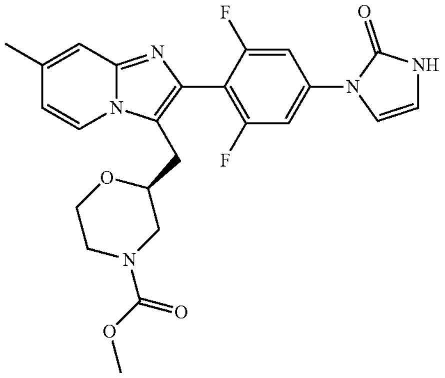

The compound was prepared according to the preparation method as described in Example 5. LC-MS: $[M+H]^+$=484.2.

Example 99

99

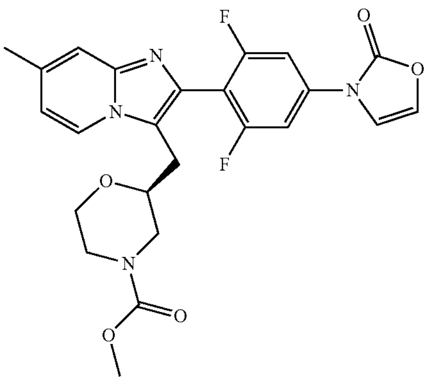

The compound was prepared according to the preparation method as described in Example 5. LC-MS: $[M+H]^+$=485.3.

Example 100

100

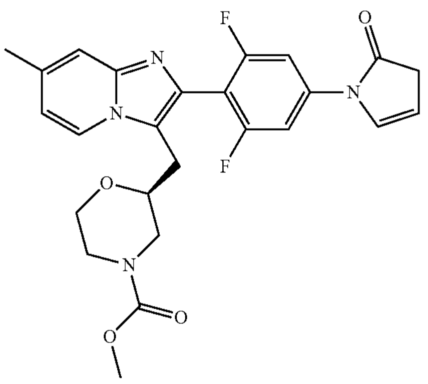

The compound was prepared according to the preparation method as described in Example 5. LC-MS: $[M+H]^+$=483.4.

Example 101

101

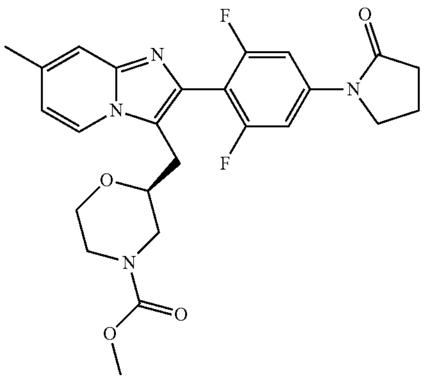

The compound was prepared according to the preparation method as described in Example 5. LC-MS: $[M+H]^+$=485.2.

Example 102

102

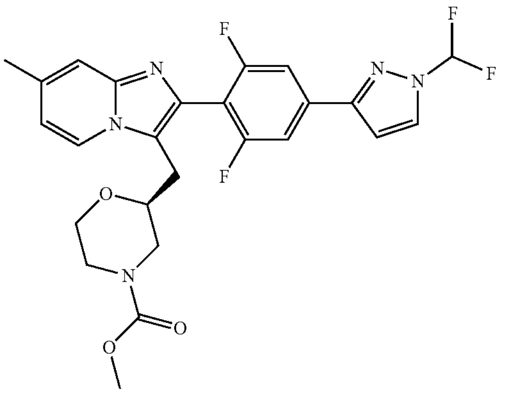

The compound was prepared according to the preparation method as described in Example 4. LC-MS: $[M+H]^+$=518.2.

Example 103

103

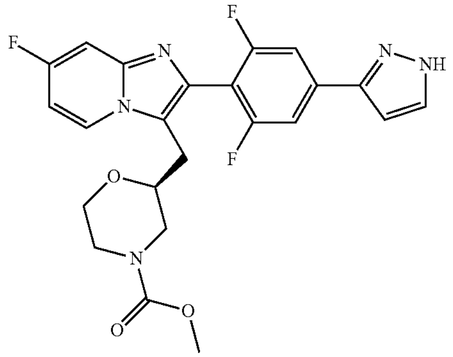

The compound was prepared according to the preparation method as described in Example 15. LC-MS: $[M+H]^+$=472.5.

Example 104

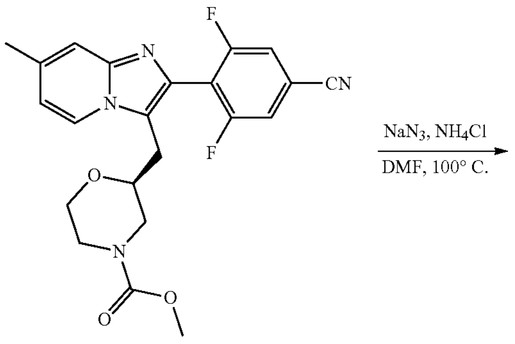

6

-continued

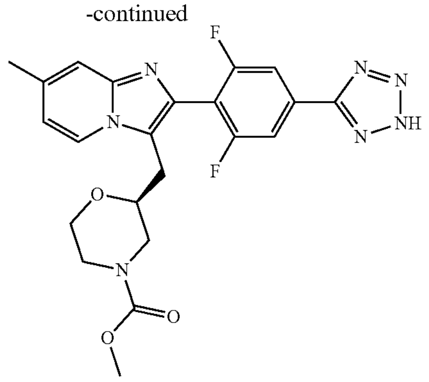

104

Compound 6 (540 mg, 1.27 mmol) was dissolved in DMF (15 mL), and a magnetic stirrer was added, followed by the addition of $NaN_3$ (247.7 mg, 3.81 mmol) and $NH_4Cl$ (271 mg, 5.08 mmol). The reaction system was slowly heated to 100° C. and reacted overnight. After the reaction was completed as detected by LCMS, the reaction system was dissolved with water, and extracted with EA, followed by liquid separation. The organic phase was dried over anhydrous sodium sulfate, and concentrated by rotary evaporation to give a crude product (200 mg). The crude product was separated by prep-HPLC, and lyophilized to give compound 104 (54.1 mg, 95.03% purity) in the form of an off-white solid.

LCMS [M+H]+=470.10. $^1$H NMR (400 MHZ, CD3OD) δ 8.81 (d, J=7.2 Hz, 1H), 7.96 (m, 2H), 7.69 (s, 1H), 7.36 (dd, J=1.2 Hz, 7.2 Hz, 1H), 4.01 (m, 1H), 3.85 (m, 1H), 3.73 (m, 2H), 3.68 (s, 3H), 3.37 (m, 1H), 3.26 (m, 2H), 2.92 (br, 1H), 2.75 (m, 1H), 2.64 (s, 3H).

Example 105

105

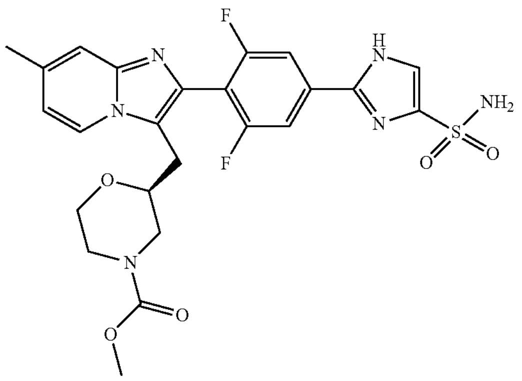

The compound was prepared according to the preparation method as described in Example 7. LC-MS: $[M+H]^+$=547.2.

Example 106

106

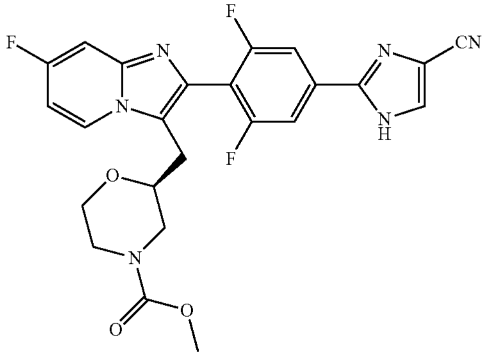

The compound was prepared according to the preparation method as described in Example 38. LC-MS: [M+H]$^+$=497.4.

Example 107

Preparation of (S)-1-(3,5-difluoro-4-(3-((4-(carbomethoxy<methoxycarbonyl>)morpholin-2-yl)methyl)-7-methylimidazo[1,2-a]pyridin-2-yl)phenyl)-1H-imidazole-4-carboxylic acid

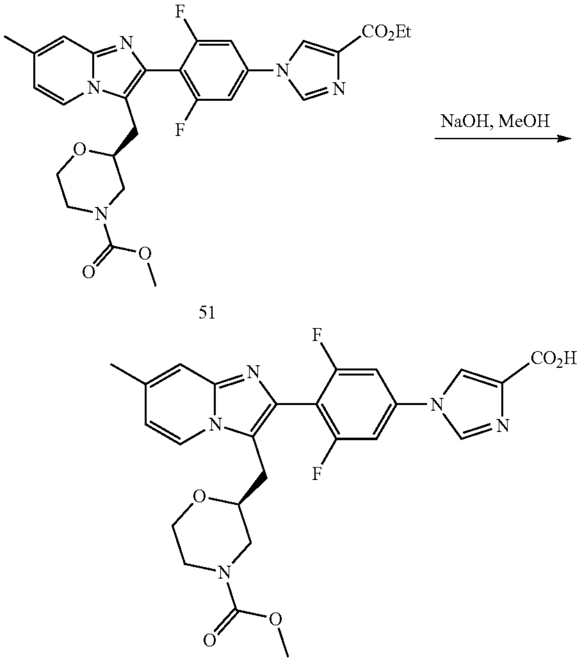

51

107

Compound 51 (30 mg, 0.06 mmol) and sodium hydroxide (7 mg, 0.30 mmol) were dissolved in methanol (2 mL) and water (1 mL). The reaction system was stirred at room temperature for 1 h. Then the reaction system was adjusted to pH 4-5 with diluted hydrochloric acid (1 N), and concentrated by rotary evaporation to give a crude product. The crude product was purified by preparative high performance liquid chromatography to give compound 107 (10 mg, 33% yield) in the form of a white solid. MS [M+H]$^+$=512.1.

1H NMR (400 MHZ, d6-DMSO) δ 8.56 (brs, 1H), 8.44 (d, J=5.0 Hz, 1H), 7.89 (brs, 1H), 7.37 (brs, 1H), 6.84 (d, J=6.3 Hz, 1H), 3.74-3.60 (m, 3H), 3.56 (s, 3H), 3.51-3.45 (m, 1H), 3.26-3.21 (m, 1H), 3.10-2.98 (m, 2H), 2.88-2.75 (m, 1H), 2.60-2.48 (m, 1H), 2.38 (s, 3H).

Example 108

108

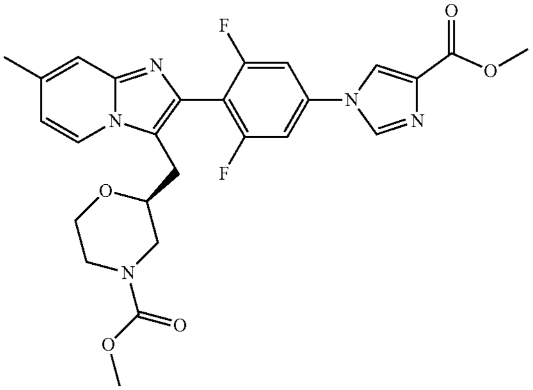

The compound was prepared according to the preparation method as described in Example 50. LC-MS: [M+H]$^+$=526.2.

Example 109

Preparation of methyl (S)-2-((2-(2,6-difluoro-4-(4-trifluoromethyl-1H-imidazol-1-yl)phenyl)-7-methylimidazo[1,2-a]pyridin-3-yl)methyl)morpholine-4-carboxylate

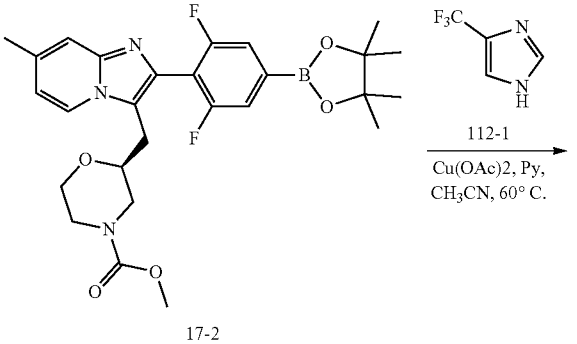

17-2

-continued

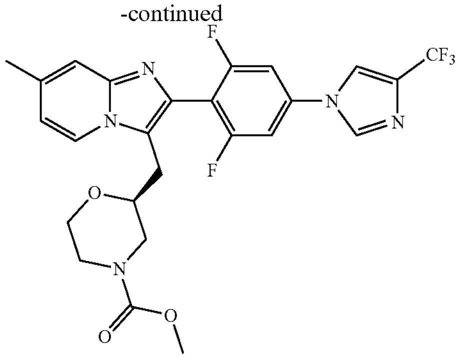

109

Intermediate 17-2 (130 mg, 0.25 mmol), 4-(trifluoromethyl)-1H-imidazole (40 mg, 0.3 mmol), copper(II) acetate (67 mg, 0.37 mmol), and pyridine (39 mg, 0.5 mmol) were dissolved in acetonitrile (2 mL). The reaction system was heated to 60° C. and reacted overnight. Then the reaction system was cooled to room temperature, diluted with water (10 mL), and extracted with dichloromethane (10 mL×3). The organic phases were combined, washed with saturated brine (10 mL×2), dried over anhydrous sodium sulfate, filtered and concentrated. The crude product was purified by preparative high performance liquid chromatography to give compound 109 (13 mg, 9% yield) in the form of a white solid.

LC-MS: $[M+H]^+$=536.4. $^1$H NMR (400 MHZ, $CDCl_3$): δ 8.29 (d, J=7.3 Hz, 1H), 7.99 (s, 1H), 7.70 (s, 1H), 7.61 (s, 1H), 7.19 (d, J=7.2 Hz, 1H), 6.83 (d, J=7.0 Hz, 1H), 4.10-3.80 (m, 3H), 3.71 (s, 3H), 3.65-3.57 (m, 1H), 3.46-3.35 (m, 1H), 3.09-2.95 (m, 3H), 2.70-2.62 (m, 1H), 2.49 (s, 3H).

Example 110

Preparation of methyl (S)-2-((2-(4~ (4-carbamoyl-1H-imidazol-1-yl)-2,6-difluorophenyl)-7-methylimidazo[1,2-a]pyridin-3-yl)methyl)morpholine-4-carboxylate

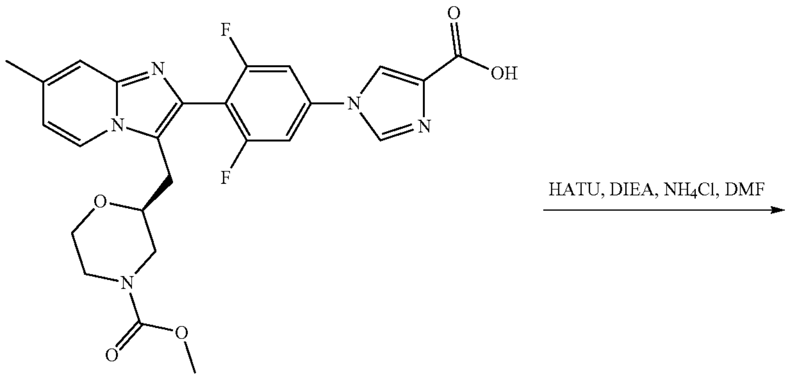

107

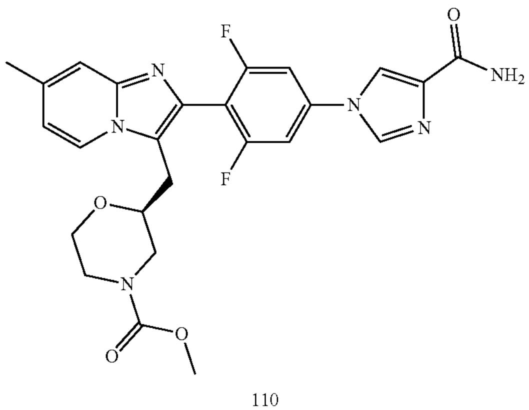

110

Compound 107 (30 mg, 0.06 mmol), HATU (34 mg, 0.09 mmol) and N,N-diisopropylethylamine (23 mg, 0.18 mmol) were dissolved in N,N-dimethylformamide (2 mL). The reaction system was stirred at room temperature for 5 min, added with anhydrous ammonium chloride (10 mg, 0.18 mmol), and stirred at room temperature for another 1 h. Then the reaction system was added with saturated brine (15 mL) to quench the reaction, and extracted with ethyl acetate (10 mL×2). The organic phases were combined, dried over anhydrous sodium sulfate, filtered and concentrated to give a crude product. The crude product was purified by silica gel column chromatography to give compound 110 (28 mg, 83% yield) in the form of a white solid. LC-MS: $[M+H]^+$=511.1.

1H NMR (400 MHZ, MEOD) δ 8.43 (d, J=7.2 Hz, 1H), 8.36 (d, J=1.3 Hz, 1H), 8.27 (d, J=1.3 Hz, 1H), 7.62 (d, J=8.1 Hz, 2H), 7.37 (s, 1H), 6.90 (dd, J=7.1, 1.6 Hz, 1H), 3.89-3.76 (m, 3H), 3.67 (s, 3H), 3.63-3.58 (m, 1H), 3.41-3.35 (m, 1H), 3.16-3.10 (m, 2H), 2.98-2.82 (m, 1H), 2.72-2.58 (m, 1H), 2.48 (s, 3H).

Example 111

111

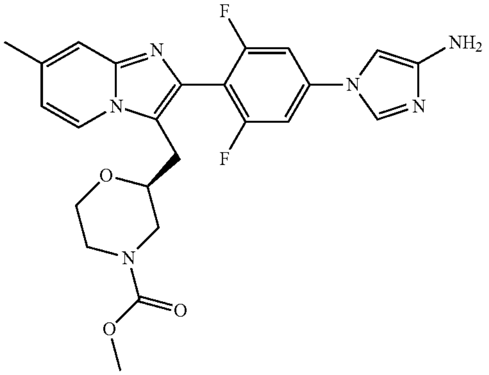

The compound was prepared according to the preparation method for compound 5. MS $[M+H]^+$=483.3.

Example 112

112

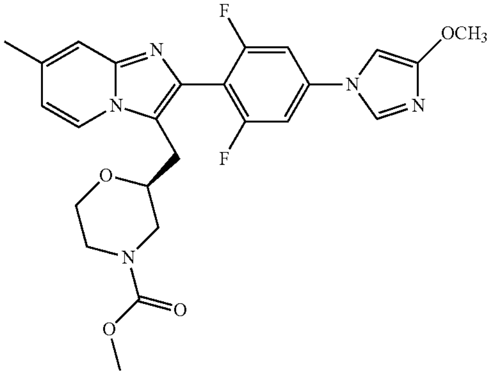

The compound was prepared according to the preparation method for compound 5. MS $[M+H]^+$=498.2.

Example 113

113

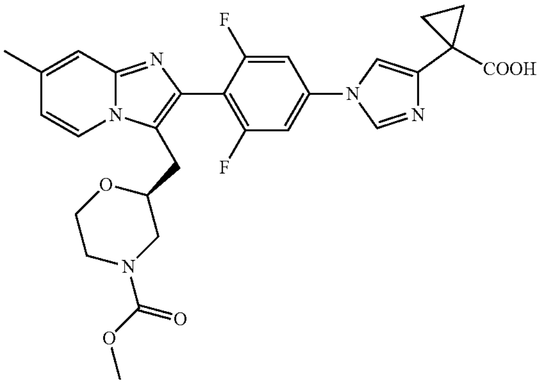

The compound was prepared according to the preparation method for compound 5. MS $[M+H]^+$=552.2.

Example 114

Preparation of (S)-2-(3,5-difluoro-4-(3-((4-(methoxycarbonyl)morpholin-2-yl)methyl)-7-methylimidazo[1,2-a]pyridin-2-yl)phenyl)oxazole-4-carboxylic acid

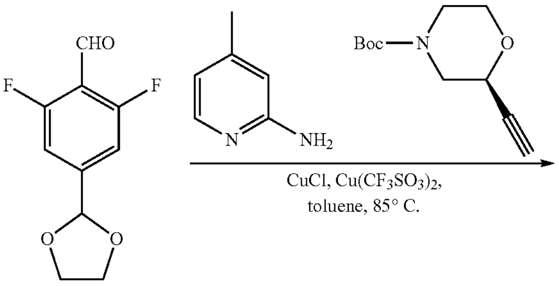

114-1

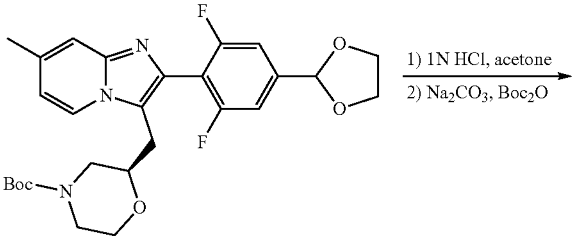

114-2

-continued

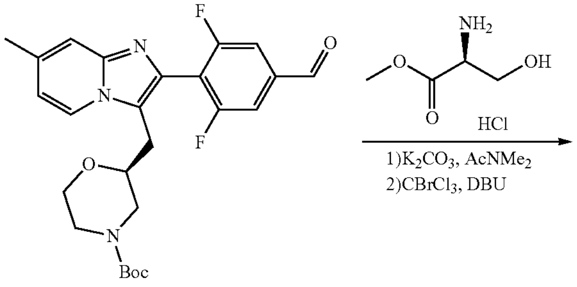

114-3

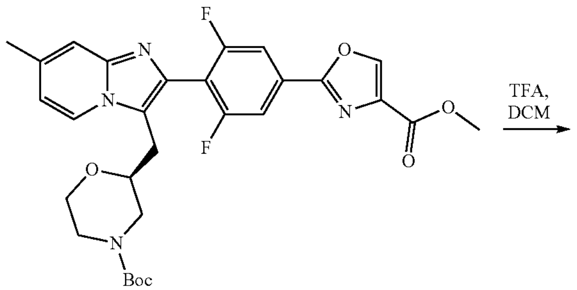

114-4

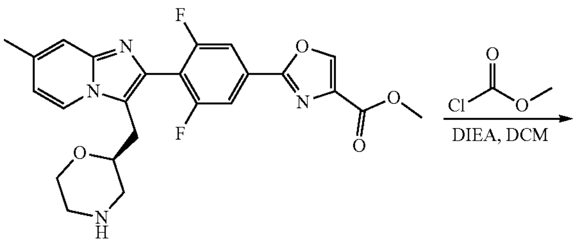

114-5

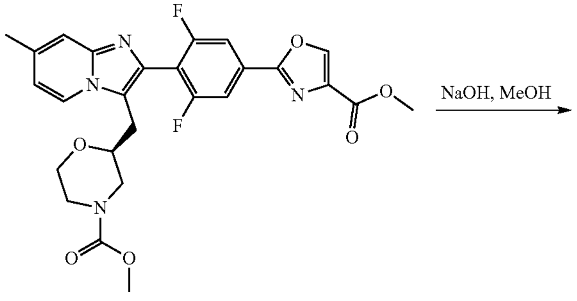

114-6

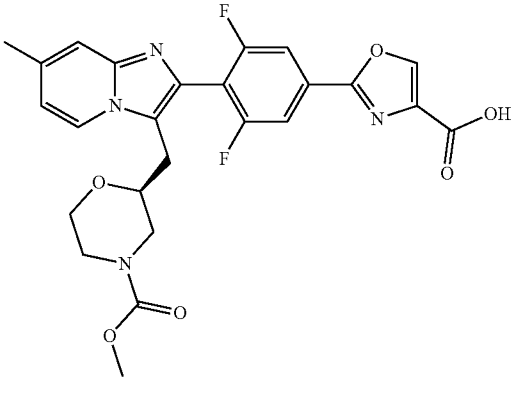

114

Step (1) Preparation of methyl (R)-2-((2-(4-(1,3-dioxolan~2-yl)-2,6-difluorophenyl)-7-methylimidazo[1,2-a]pyridin-3-yl)methyl)morpholine-4-carboxylate 114-2

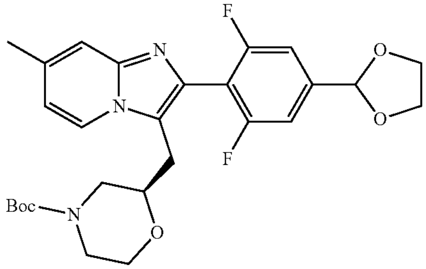

4-(1,3-dioxolan-2-yl)-2,6-difluorobenzaldehyde (600 mg, 2.8 mmol), 4-methylpyridin-2-amine (302.8 mg, 2.8 mmol), tert-butyl (S)-2-ethynylmorpholine-4-carboxylate (595 mg, 2.8 mmol), copper(I) chloride (84 mg, 0.84 mmol), and copper(II) trifluoromethanesulfonate (304 mg, 0.84 mmol) were dissolved in toluene (10 mL). The reaction system was stirred at 85° C. for 30 min, added dropwise with N,N-dimethylacetamide (0.1 mL), and stirred at 85° C. overnight. Then the reaction system was concentrated under reduced pressure. The crude product was purified by silica gel column chromatography to give intermediate 114-2 (1.2 g, 55.36% yield) in the form of a yellow solid. MS $[M+H]^+$=516.2.

Step (2) Preparation of tert-butyl (S)-2-((2-(2,6-difluoro-4-formylphenyl)-7-methylimidazo[1,2-a]pyridin-3-yl)methyl)morpholine-4-carboxylate 114-3

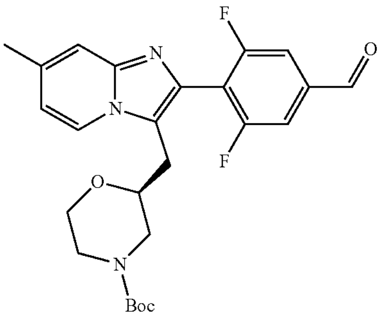

Intermediate 114-2 (1.2 g, 2.33 mmol) was dissolved in acetone (10 mL) at room temperature, and diluted hydrochloric acid (10 mL, 1 N) was added. The reaction system was stirred overnight. After the reaction was completed, the reaction system was adjusted to pH 8-9 with saturated sodium carbonate solution, added with BOC-anhydride (766 mg, 3.5 mmol), and stirred at room temperature for 5 h. Then the reaction system was extracted with ethyl acetate (20 mL×3). The organic phases were combined, washed with saturated brine (20 mL), dried over anhydrous sodium sulfate, filtered and concentrated. The crude product was purified by silica gel column chromatography to give intermediate 114-3 (563 mg, 51.3% yield) in the form of a yellow solid. MS $[M+H]^+$=471.2.

Step (3) Preparation of tert-butyl (S)-2-((2-(2,6-difluoro-4-(4-(carbomethoxy<methoxycarbonyl>) oxazol-2-yl)phenyl)-7-methylimidazo[1,2-a]yridin-3-yl)methyl)morpholine-4-carboxylate 114-4

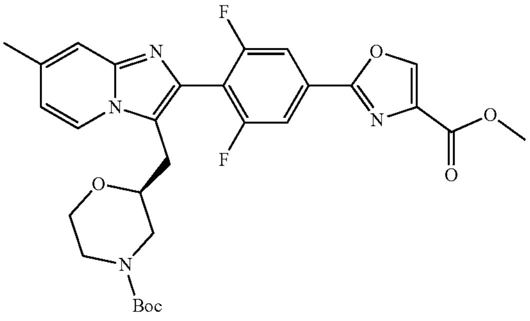

Intermediate 114-3 (495 mg, 1.05 mmol) was dissolved in N,N-dimethylacetamide (4 mL) under nitrogen atmosphere, and methyl (2S)-2-amino-3-hydroxypropionate acid (163 mg, 1.05 mmol) and potassium carbonate (290 mg, 2.10 mmol) were added. The reaction system was stirred at room temperature for 18 h. Then the reaction system was cooled to 0° C., added with bromotrichloromethane (625 mg, 3.15 mmol) and 1,8-diaza-cyclo[5.4.0]undec-7-ene (480 mg, 3.15 mmol), stirred at 0° C. for 2 h, and stirred at room temperature for 24 h. The resulting reaction system was added with water (20 mL) to quench the reaction and extracted with diethyl ether (20 mL×3). The organic phases were combined, dried over anhydrous sodium sulfate, filtered and concentrated by rotary evaporation. The crude product was purified by silica gel column chromatography to give intermediate 114-4 (231 mg, 37.2% yield) in the form of a yellow solid. MS $[M+H]^+$=569.2.

Step (4) Preparation of methyl (S)-2-(3,5-difluoro-4-(7-methyl-3-(morpholin-2-ylmethyl)imidazo[1,2-a]pyridin-2-yl)phenyl)oxazole-4-carboxylate 114-5

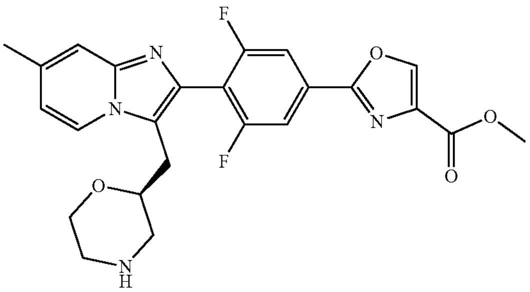

Intermediate 114-4 (231, 0.41 mmol) was dissolved in dichloromethane (4 mL), and trifluoroacetic acid (1 mL) was added. The reaction system was stirred at room temperature for 2 h. Then the reaction system was concentrated by rotary evaporation under reduced pressure, diluted with dichloromethane (30 mL), and slowly added with saturated sodium bicarbonate solution (20 mL) while stirring, followed by liquid separation. The aqueous phase was extracted with dichloromethane (20 mL). The organic phases were combined, washed with saturated brine (20 mL), dried over anhydrous sodium sulfate, filtered and concentrated by rotary evaporation to give intermediate 114-5 (195 mg, 97.6% yield) in the form of a brown solid. MS $[M+H]^+$=469.1.

Step (5) Preparation of methyl (S)-2-((2-(2,6-difluoro-4-(4-(carbomethoxy<methoxycarbonyl>)oxazol-2-yl)phenyl)-7-methylimidazo[1,2-a]pyridin-3-yl)methyl)morpholine-4-carboxylate 114-6

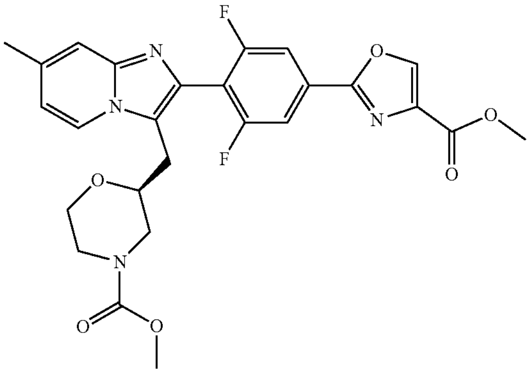

Intermediate 114-5 (150 mg, 0.30 mmol) and diisopropylethylamine (160 mg, 1.20 mmol) were dissolved in DCM (10 mL) at 0° C. under nitrogen atmosphere. The reaction system was stirred for 10 min, and added dropwise with methyl chloroformate (34 mg, 0.36 mmol). After the completion of the dropwise addition, the reaction was reacted for 2 h. Then the reaction system was concentrated by rotary evaporation. The crude product was purified by silica gel column chromatography to give intermediate 114-6 (110 mg, 66.7% yield) in the form of a white solid. MS $[M+H]^+$=527.1.

Step (6) Preparation of 2-[3,5-difluoro-4-(3-{[(2S)-4-(carbomethoxy<methoxycarbonyl>)morpholin-2-yl]methyl}-7-methylimidazo[1,2-a]pyridin-2-yl) phenyl]-1,3-oxazole-4-carboxylic acid

114

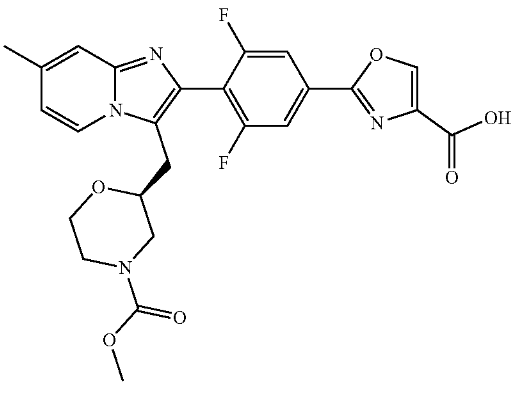

Intermediate 114-6 (80 mg, 0.15 mmol) was dissolved in methanol (2 mL), and sodium hydroxide solution (1.5 mL, 1 N) was added. The reaction system was reacted at room temperature for 2 h. Then the reaction system was adjusted to pH 5 with diluted hydrochloric acid and concentrated. The residue was separated by preparative high performance liquid chromatography to give compound 114 (33 mg, 40% yield) in the form of a white solid. LC-MS $[M+H]^+$=513.1.

1H NMR (400 MHZ, DMSO) δ13.24 (brs, 1H), 8.99 (s, 1H), 8.47 (d, J=7.1 Hz, 1H), 7.81 (d, J=7.5 Hz, 2H), 7.39 (s, 1H), 6.88 (d, J=7.0 Hz, 1H), 3.82-3.73 (m, 1H), 3.69-3.60 (m, 2H), 3.56 (s, 3H), 3.49 (s, 1H), 3.27-3.18 (m, 1H), 3.14-3.00 (m, 2H), 2.87-2.75 (m, 1H), 2.55-2.45 (m, 1H), 2.40 (s, 3H).

Example 115

115

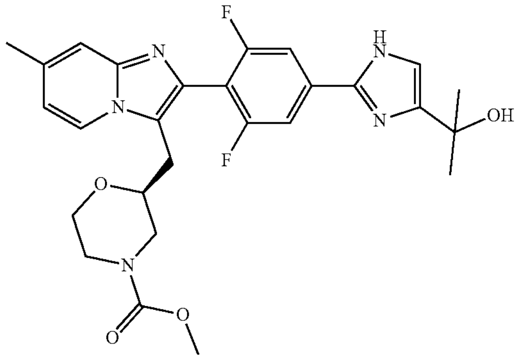

The compound was prepared according to the preparation method as described in Example 114. LC-MS: $[M+H]^+$=493.2.

Example 116

116

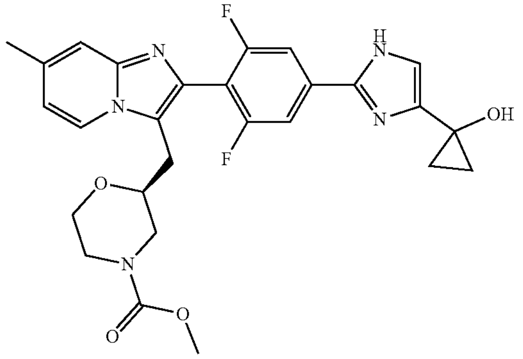

The compound was prepared according to the preparation method as described in Example 114. LC-MS: $[M+H]^+$=493.2.

Example 117

Preparation of methyl (S)-2-((2-(2,6-difluoro-4-(4-(2-hydroxypropan-2-yl)-1H-imidazol-1-yl)phenyl)-7-methylimidazo[1,2-a]pyridin-3-yl)methyl)morpholine-4-carboxylate

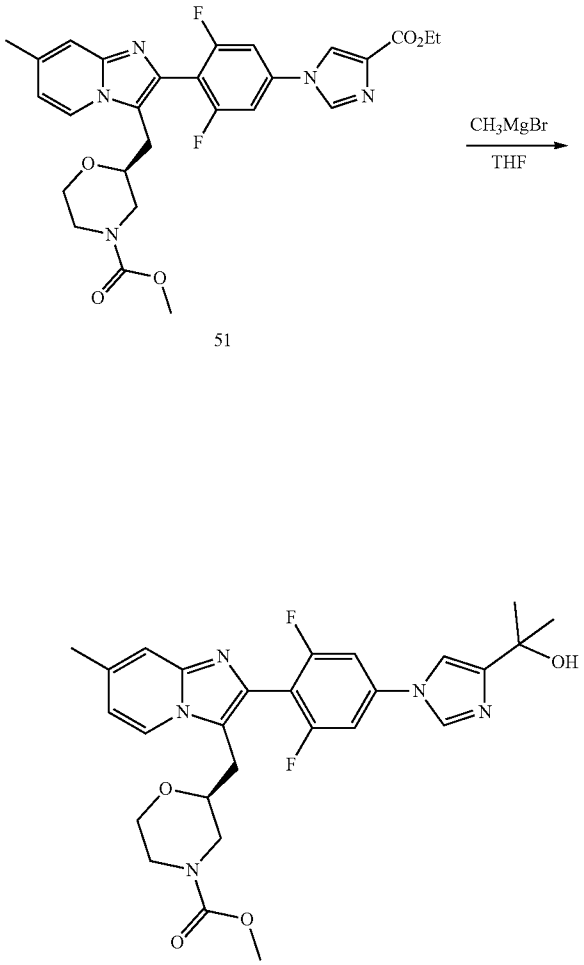

51

117

Compound 51 (30 mg, 0.06 mmol) was dissolved in tetrahydrofuran (2 mL), and a solution of methyl magnesium bromide in n-hexane (3 M, 0.06 mL, 0.18 mmol) was added dropwise under nitrogen atmosphere in an ice water bath. After the completion of the dropwise addition, the reaction system was stirred at room temperature for 1 h. Then the reaction system was added with saturated ammonium chloride solution to quench the reaction, and concentrated by rotary evaporation to give a crude product. The crude product was purified by preparative high performance liquid chromatography to give compound 117 (5 mg, 17% yield) in the form of a white solid. MS $[M+H]^+$=526.1.

1H NMR (400 MHZ, d6-DMSO) δ 8.43 (d, J=7.0 Hz, 1H), 8.38 (d, J=1.2 Hz, 1H), 7.73 (d, J=8.8 Hz, 2H), 7.71 (d, J=1.4 Hz, 1H), 7.36 (s, 1H), 6.85 (dd, J=7.1, 1.5 Hz, 1H), 4.84 (s, 1H), 3.78-3.60 (m, 3H), 3.56 (s, 3H), 3.52-3.46 (m, 1H), 3.29-3.21 (m, 1H), 3.08-3.02 (m, 2H), 2.90-2.75 (m, 1H), 2.60-2.46 (m, 1H), 2.39 (s, 3H), 1.45 (s, 6H).

Example 118

118

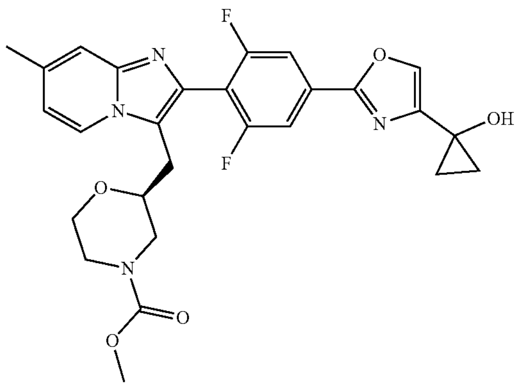

The compound was prepared according to the preparation method as described in Example 114. MS $[M+H]^+$=525.2.

Example 119

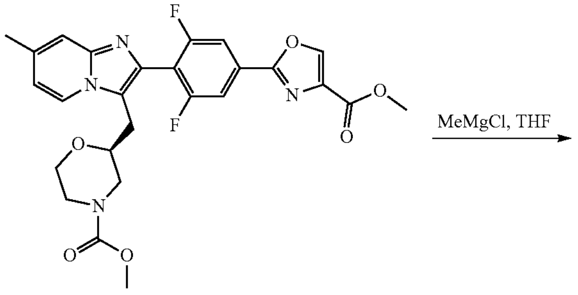

114-6

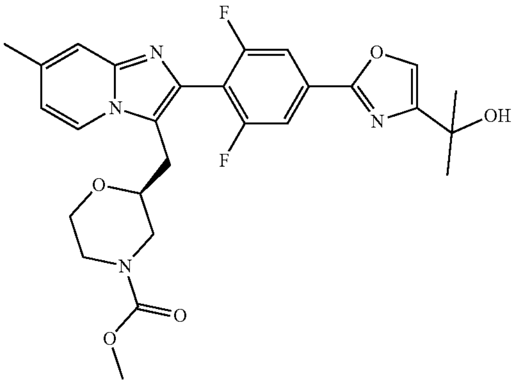

119

Preparation of methyl (S)-2-((2-(2,6-difluoro-4-(4-(2-hydroxypropyl-2-yl)oxazol-2-yl)phenyl)-7-methylimidazo[1,2-a]pyridin-3-yl)methyl)morpholine-4-carboxylate Intermediate 114-6 (150 mg, 0.29 mmol) was dissolved in tetrahydrofuran (8 mL), and methylmagnesium chloride (0.3 mL, 3.0 M) was added dropwise with the temperature maintained at −20° C. The reaction system was stirred at this temperature for 4 h. Then the reaction system was added with a small amount of water to quench the reaction, and concentrated. The residue was separated by preparative chromatography to give compound 119 (10.8 mg, 7.1% yield) in the form of a white solid. LC-MS $[M+H]^+$: 527.0.

1H NMR (400 MHZ, $CDCl_3$) δ 8.43 (d, J=7.2 Hz, 1H), 7.89 (s, 1H), 7.80 (d, J=7.9 Hz, 1H), 7.36 (s, 1H), 6.89 (dd, J=7.1, 1.5 Hz, 1H), 3.89-3.74 (m, 3H), 3.70 (s, 3H), 3.64-3.57 (m, 1H), 3.41-3.33 (m, 1H), 3.16-3.09 (m, 2H), 2.96-2.80 (m, 1H), 2.70-2.55 (m, 1H), 2.49 (s, 3H), 1.61 (s, 6H).

Example 120

120

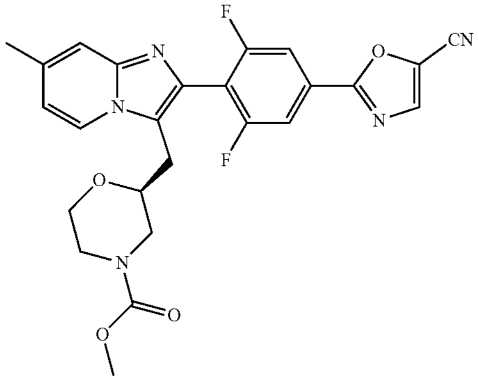

The compound was prepared according to the preparation method as described in Example 10. LC-MS: $[M+H]^+$=494.3.

Example 121

121

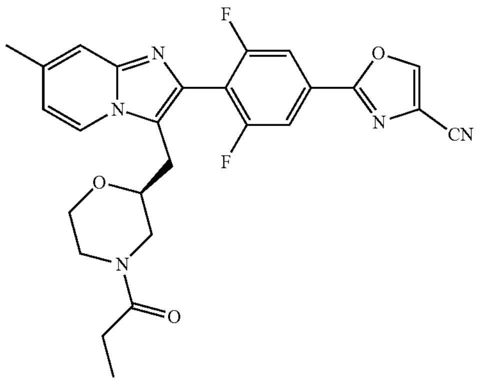

The compound was prepared according to the preparation method as described in Example 10. LC-MS: $[M+H]^+$=492.4.

Example 122

122

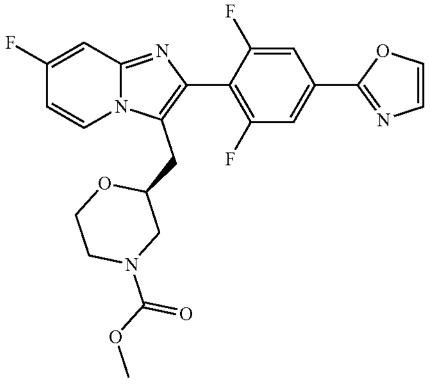

The compound was prepared according to the preparation method as described in Example 10. LC-MS: [M+H]$^+$=473.5.

Example 123

123

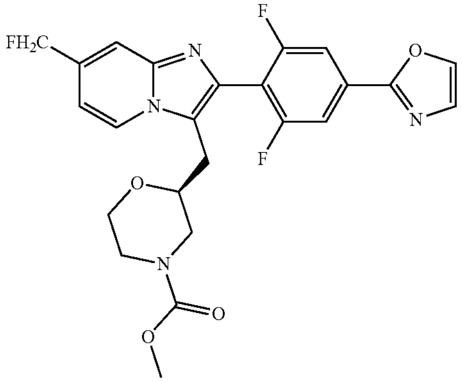

The compound was prepared according to the preparation method as described in Example 10. LC-MS: [M+H]$^+$=487.1.

Example 124

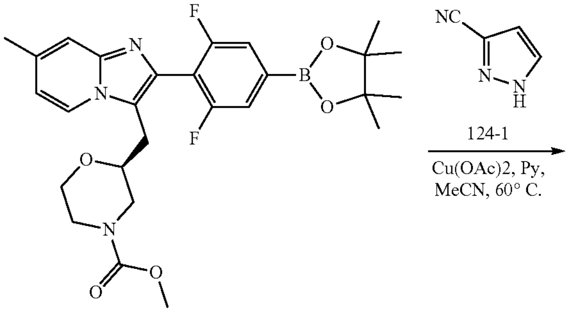

124-1

17-2

-continued

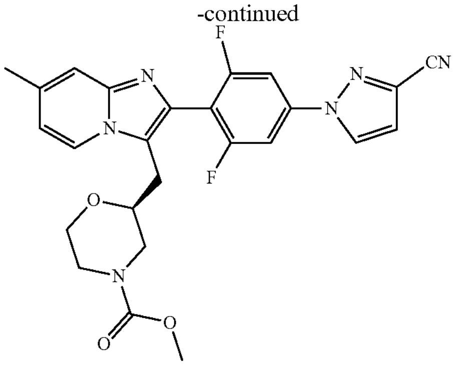

124

+

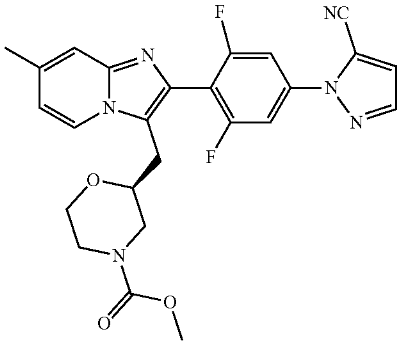

124-2

Intermediate 17-2 (190 mg, 0.36 mmol), 1H-pyrazole-3-carbonitrile (40 mg, 0.43 mmol), anhydrous copper(II) acetate (98 mg, 0.54 mmol) and pyridine (57 mg, 0.72 mmol) were dissolved in acetonitrile (3 mL). The reaction system was heated to 60° C. and reacted overnight. Then the reaction system was cooled to room temperature, diluted with water (20 mL), and extracted with dichloromethane (20 mL×3). The organic phases were combined, washed with saturated brine (20 mL×2), dried over anhydrous sodium sulfate, filtered and concentrated. The crude product was purified by preparative high performance liquid chromatography to give compound 124 (70 mg, white solid) and compound 124-2 (5 mg, 42% yield) in the form of a white solid. LC-MS: [M+H]$^+$=493.3.

Compound 124: $^1$H NMR (400 MHZ, $CDCl_3$) δ8.33 (d, J=6.0 Hz, 1H), 8.08 (d, J=2.4 Hz, 1H), 7.70 (brs, 1H), 7.52 (d, J=8.0 Hz, 2H), 6.95 (d, J=2.5 Hz, 1H), 6.88 (d, J=6.0 Hz, 1H), 4.05-3.76 (m, 3H), 3.71 (s, 3H), 3.66-3.58 (m, 1H), 3.46-3.36 (m, 1H), 3.10-2.83 (m, 3H), 2.70-2.62 (m, 1H), 2.51 (s, 3H).

Compound 124-2: $^1$H NMR (400 MHZ, $CDCl_3$) δ 8.29 (brs, 1H), 7.88 (s, 1H), 7.70-7.50 (m, 3H), 7.14 (s, 1H), 6.83 (brs, 1H), 4.08-3.75 (m, 3H), 3.70 (s, 3H), 3.66-3.58 (m, 1H), 3.46-3.36 (m, 1H), 3.10-2.85 (m, 3H), 2.72-2.62 (m, 1H), 2.49 (s, 3H).

Example 125

Step (1) Preparation of (S)-3,5-difluoro-4-(7-methyl-3-(morpholinyl-2-methyl)imidazo[1,2-a]pyridin-2-yl)-1H-pyrazole-3-carboxylic acid

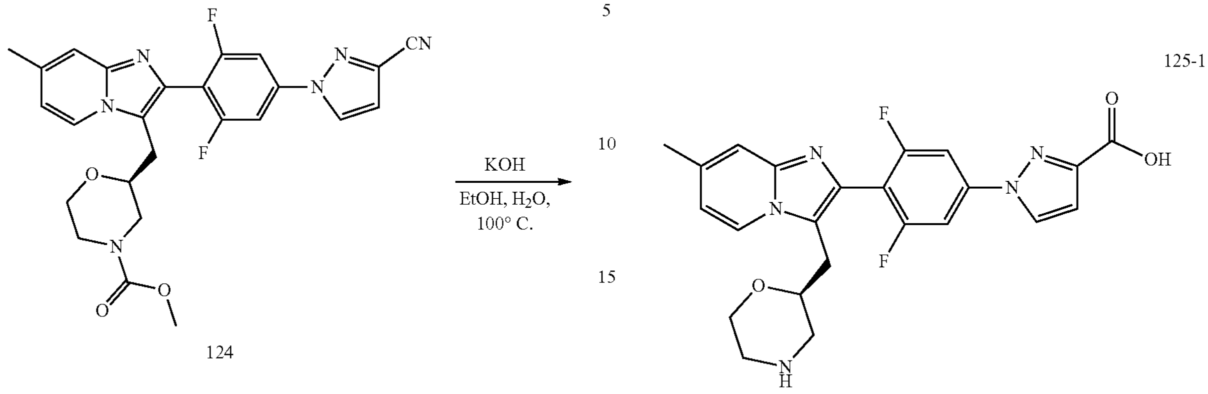

124

125-1

Compound 124 (40 mg, 0.08 mmol) was dissolved in ethanol (2 mL) and water (1 mL), and potassium hydroxide (13 mg, 0.24 mmol) was added. The reaction system was reacted at 100° C. for 12 h under nitrogen atmosphere. The the reaction system was cooled to room temperature, and concentrated to give intermediate 125-1 (40 mg, crude product), which was used directly in the next step. LC-MS: $[M+H]^+$=454.2.

Step (2) Preparation of (S)-1-(3,5-difluoro-4-(3-((4-(methoxycarbonyl)morpholin-2-yl)methyl)-7-methylimidazo[1,2-a]pyridin-2-yl)phenyl)-1H-pyrazole-3-carboxylic acid

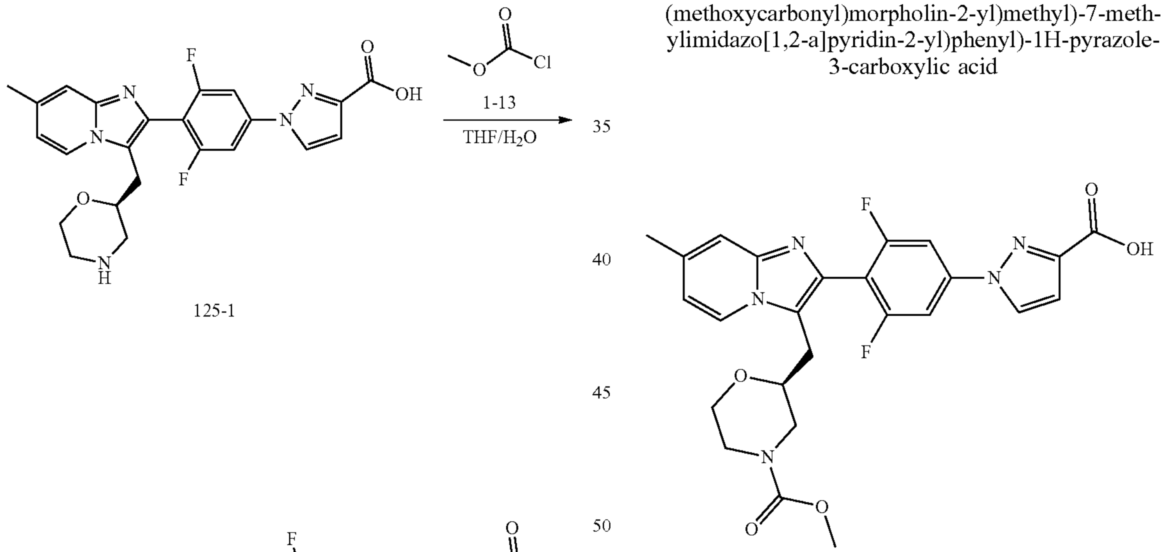

125-1

125

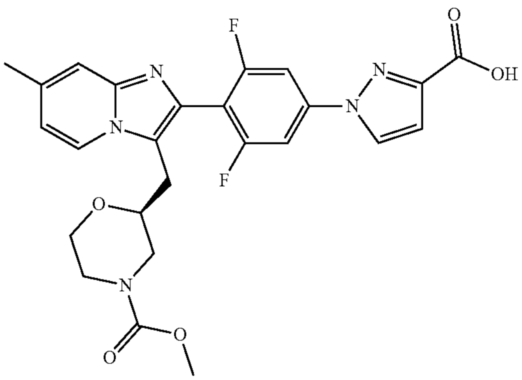

125

The intermediate 125-1 (40 mg, 0.08 mmol, crude product) was dissolved in tetrahydrofuran/water (2 mL, 1/1), and methyl chloroformate (10 mg, 0.108 mmol) was added dropwise in an ice water bath. The reaction system was reacted at this temperature for 1 h. Then the reaction system was adjusted to pH 4 with diluted hydrochloric acid, and concentrated. The residual aqueous phase was lyophilized. The crude product was purified by preparative high performance liquid chromatography to give compound 125 (7.6 mg, 18% yield), LC-MS: $[M+H]^+$=512.3.

$^1H$ NMR (400 MHz, CDCl3) δ 8.28 (d, J=7.0 Hz, 1H), 7.98 (d, J=2.1 Hz, 1H), 7.70 (s, 1H), 7.49 (d, J=8.2 Hz, 2H), 7.07 (d, J=2.4 Hz, 1H), 6.81 (d, J=7.0 Hz, 1H), 4.06-3.78 (m, 3H), 3.70 (s, 3H), 3.66-3.58 (m, 1H), 3.46-3.35 (m, 1H), 3.05-2.85 (m, 3H), 2.70-2.62 (m, 1H), 2.49 (s, 3H).

Example 126

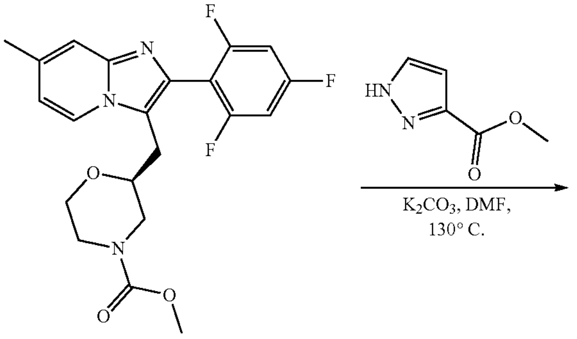

126-1

Step (1) Preparation of methyl (S)-2-((2-(2,6-difluoro-4-(3-(carbomethoxy<methoxycarbonyl>)1H-pyrazol-1-yl)phenyl)-7-methylimidazo[1,2-a]pyridin-3-yl)methyl)morpholine-4-carboxylate 126-2

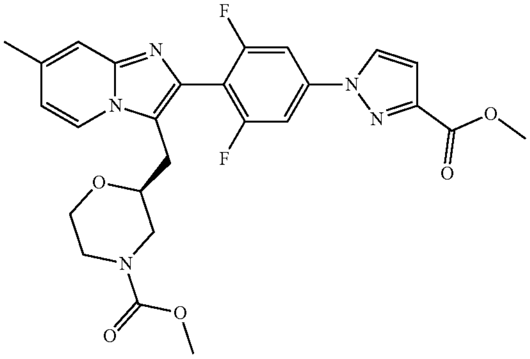

Methyl (S)-2-((7-methyl-2-(2,4,6-trifluorophenyl)imidazo[1,2-a]pyridin-3-yl)methyl)morpholine-4-carboxylate (700 mg, 1.67 mmol), methyl 3-pyrazolecarboxylate (210 mg, 1.67 mmol) and anhydrous potassium carbonate (692 mg, 5.00 mmol) were dissolved in N,N-dimethylformamide (15 mL) under nitrogen atmosphere. The reaction system was stirred at 130° C. for 4 h. Then the reaction system was cooled, added with ice water (15 mL) to quench the reaction, and extracted with ethyl acetate (10 mL×3). The organic phases were combined, washed with saturated brine (10 mL), dried over anhydrous sodium sulfate, filtered and concentrated. The crude product was purified by silica gel column chromatography to give intermediate 126-2 (300 mg, 80% purity, 27% yield) in the form of a yellow solid. MS $[M+H]^+$=526.2.

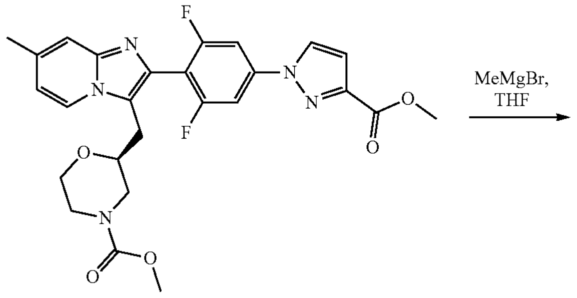

126-2

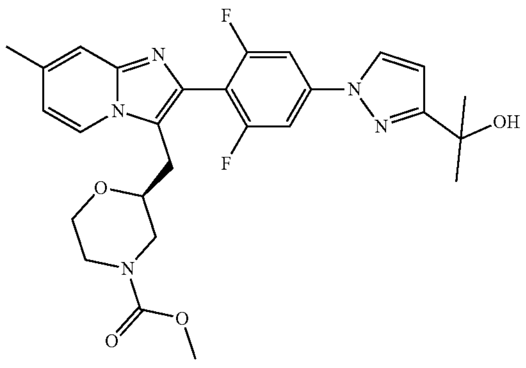

126

Step (2) Preparation of methyl (S)-2-((2-(2,6-difluoro-4-(3-(2-hydroxypropan-2-yl)-1H-pyrazol-1-yl)phenyl)-7-methylimidazo[1,2-a]pyridin-3-yl)methyl)morpholine-4-carboxylate

126

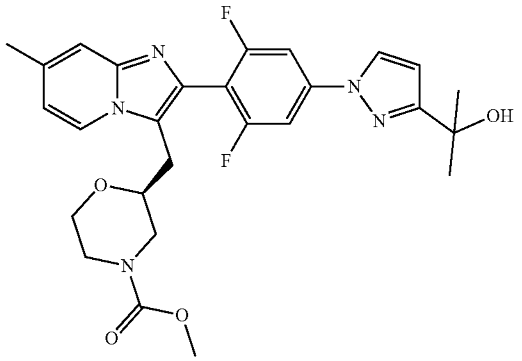

Intermediate 126-2 (150 mg, 0.28 mmol) was dissolved in tetrahydrofuran (5 mL) under nitrogen atmosphere. The reaction system was cooled to 0° C. in an ice water bath, added dropwise with methyl magnesium bromide solution (3 M, 0.3 mL, 0.9 mmol) with the temperature maintained at 0° C., and stirred for 1 h. Then the reaction system was added with saturated ammonium chloride solution (10 mL) at 0° C. to quench the reaction, and extracted with ethyl acetate (10 mL×3). The organic phases were combined, washed with saturated brine (15 mL), dried over anhydrous sodium sulfate, filtered and concentrated. The crude product was purified by preparative high performance liquid chromatography to give compound 126 (30 mg, 17% yield) in the form of a white solid. MS $[M+H]^+$=525.8.

$^1$H NMR (400 MHZ, MEOD): δ 8.45 (d, J=7.0 Hz, 1H), 8.31 (d, J=2.6 Hz, 1H), 7.67 (d, J=8.9 Hz, 2H), 7.39 (s, 1H), 6.93 (d, J=7.1 Hz, 1H), 6.60 (d, J=2.6 Hz, 1H), 3.89-3.76 (m, 3H), 3.66 (s, 3H), 3.64-3.60 (m, 1H), 3.42-3.35 (m, 1H), 3.16-3.11 (m, 2H), 3.00-2.85 (m, 1H), 2.71-2.60 (m, 1H), 2.49 (s, 3H), 1.64 (s, 6H).

Example 127

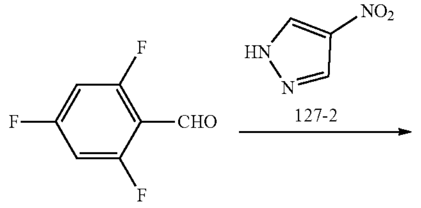

127-1

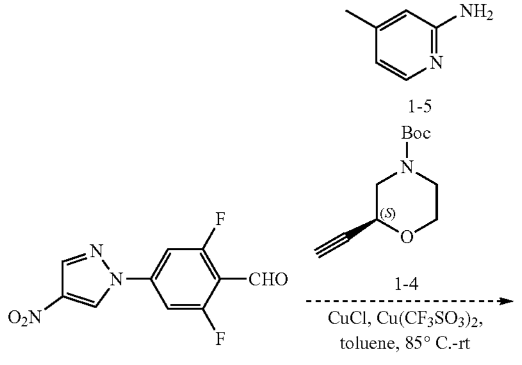

127-3

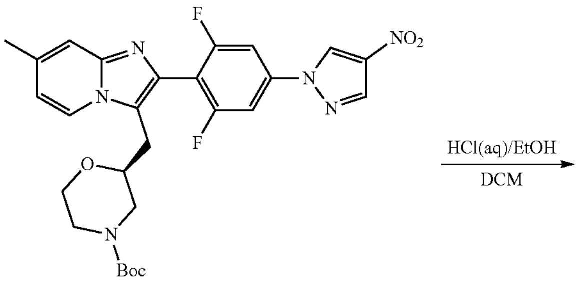

127-4

-continued

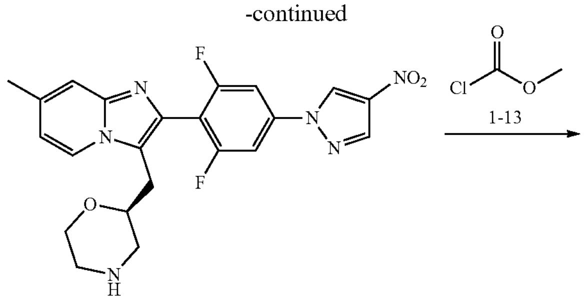

127-5

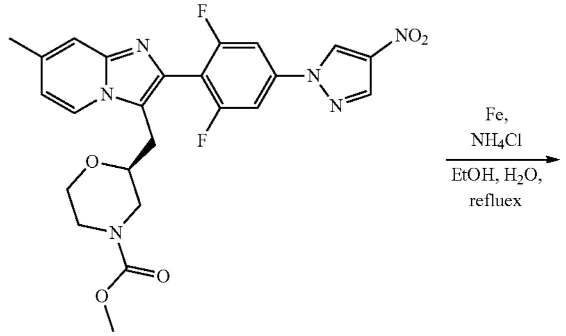

127-6

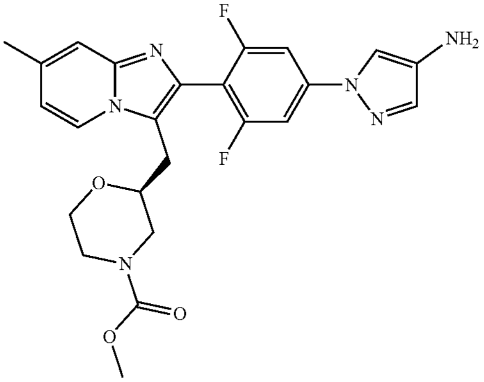

127

Step (1) Preparation of 2,6-difluoro-4-(4-nitro-1H-pyrazol-1-yl)benzaldehyde 127-3

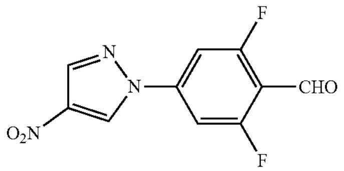

2,4,6-trifluorobenzaldehyde (2.0 g, 12.5 mmol), 4-nitro-1H-pyrazole (1.4 g, 12.5 mmol) and triethylamine (3.8 g, 37.5 mmol) were dissolved in acetonitrile (20 mL) under nitrogen atmosphere. The reaction system was heated to reflux for 3 h. Then the reaction system was cooled to room temperature, added with water (50 mL) to quench the reaction, and extracted with ethyl acetate (30 mL×2). The organic phases were combined, washed with saturated brine (30 mL×2), dried over anhydrous sodium sulfate, filtered and concentrated. The crude product was purified by silica gel column chromatography to give intermediate 127-3 (450 mg, 14% yield) in the form of a yellow solid. LC-MS $[M+H]^+$=254.

Step (2) Preparation of tert-butyl (S)-2-((2~ (2,6-difluoro-4~ (4-nitro-1H-pyrazol-1-yl)phenyl)-7-methylimidazo[1,2-a]pyridin-3-yl)methyl)morpholine-4-carboxylate 127-4

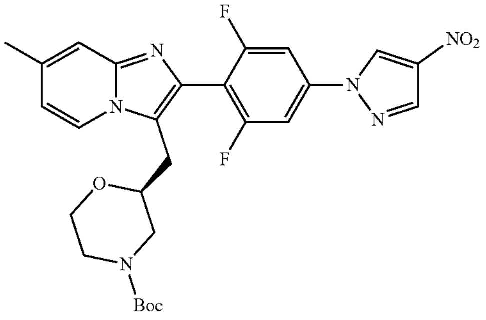

Intermediate 127-3 (450 mg, 1.78 mmol), 4-methylpyridin-2-amine (192 mg, 1.78 mmol), tert-butyl (S)-2-ethynylmorpholine-4-carboxylate (375 mg, 1.78 mmol), copper (I) chloride (53 mg, 0.53 mmol) and copper(II) trifluoromethanesulfonate (193 mg, 0.53 mmol) were dissolved in toluene (5 mL) under nitrogen atmosphere The reaction system was heated to 85° C. and stirred for 20 min, added with N,N-dimethylacetamide (0.15 mL), and reacted at 85° C. for 5 h. Then the reaction system was cooled to room temperature and reacted overnight. Then the reaction system was added with water (30 mL) to quench the reaction, and extracted with dichloromethane (15 mL×3). The organic phases were combined, washed with saturated brine (15 mL), dried over anhydrous sodium sulfate, filtered and concentrated. The residue was purified by silica gel column chromatography to give intermediate 127-4 (260 mg, 26% yield) in the form of a brown oily liquid. LC-MS $[M+H]^+$=555.2.

Step (3) Preparation of (S)-2-((2-(2,6-difluoro-4-(4-nitro-1H-pyrazol-1-yl)phenyl)-7-methylimidazo[1,2-a]pyridin~3-yl)methyl)morpholine 127-5

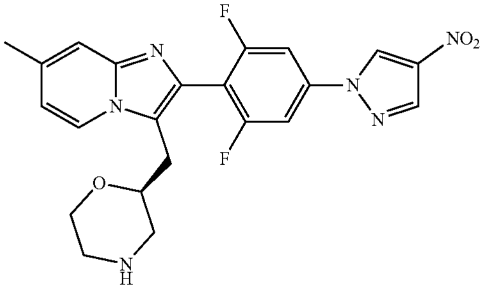

Intermediate 127-4 (260 mg, 0.5 mmol) was dissolved in dichloromethane (3 mL). The reaction system was cooled to 0° C. in an ice water bath, added dropwise with a solution of HCl in ethanol (33%, 1 mL), and stirred at room temperature for 1 h. Then the reaction system was concentrated by rotary evaporation to give intermediate 127-5 (280 mg, crude product), which was used directly in the next step. LC-MS $[M+H]^+$=455.2.

Step (4) Preparation of methyl (S)-2-((2-(2,6-difluoro-4-(4-nitro-1H-pyrazol-1-yl)phenyl)-7-methylimidazo[1,2-a]pyridin-3-yl)methyl)morpholine-4-carboxylate 127-6

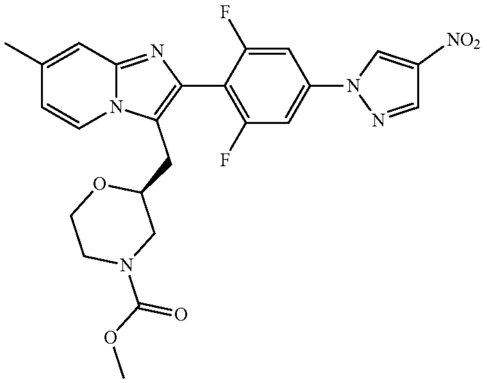

Intermediate 127-5 (200 mg, 0.44 mmol) and N,N-diisopropylethylamine (284 mg, 2.20 mmol) were dissolved in dichloromethane (3 mL) under nitrogen atmosphere. The reaction system was added dropwise with methyl chloroformate (50 mg, 0.52 mmol) at 0° C. in an ice water bath. After the completion of the dropwise addition, the reaction system was reacted for 1 h. Then the reaction system was added with water (20 mL) to quench the reaction, and extracted with dichloromethane (15 mL×3). The organic phases were combined, washed with saturated brine (15 mL), dried over anhydrous sodium sulfate, filtered and concentrated. The residue was separated by silica gel column chromatography to give intermediate 127-6 (110 mg, 48% yield) in the form of a brown solid. LC-MS $[M+H]^+$=513.3.

$^1$H NMR (400 MHZ, CDCl3) δ 8.71 (s, 1H), 8.34 (s, 1H), 8.25 (d, J=7.1 Hz, 1H), 7.52-7.48 (m, 3H), 6.78 (s, 1H), 4.00-3.75 (m, 3H), 3.70 (s, 3H), 3.67-3.56 (m, 1H), 3.45-3.35 (m, 1H), 3.10-2.85 (m, 3H), 2.68-2.60 (m, 1H), 2.47 (s, 3H).

Step (5) Preparation of methyl (S)-2-((2-(4-(4-amino-1H-pyrazol-1-yl)-2,6-difluorophenyl)-7-methylimidazo[1,2-a]pyridin-3-yl)methyl)morpholine-4-carboxylate

127

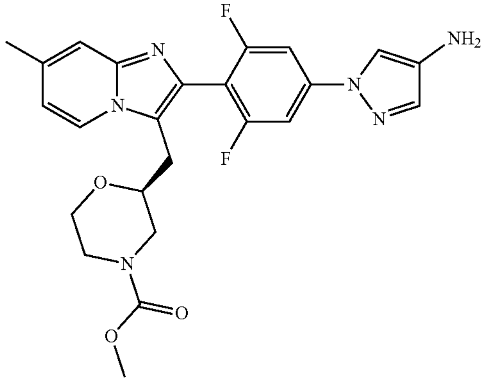

Intermediate 127-6 (80 mg, 0.15 mmol) and saturated ammonium chloride (0.5 mL) were dissolved in ethanol (2 mL) under nitrogen atmosphere. The reaction system was heated to 80° C., added with iron powder (44 mg, 0.75 mmol), and stirred for 15 min. Then the reaction system was cooled to room temperature, filtered and concentrated. The crude product was purified by preparative high performance liquid chromatography to give compound 127 (9 mg, 12% yield) in the form of a white solid. LC-MS $[M+H]^+$=483.2.

1H NMR (400 MHZ, CDCl3) δ 8.25 (d, J=7.1 Hz, 1H), 7.53 (s, 1H), 7.52 (s, 1H), 7.46 (s, 1H), 7.34 (d, J=8.7 Hz, 2H), 6.76 (d, J=7.0 Hz, 1H), 4.00-3.75 (m, 3H), 3.69 (s, 3H), 3.66-3.56 (m, 1H), 3.45-3.35 (m, 1H), 3.08-2.85 (m, 3H), 2.67-2.61 (m, 1H), 2.46 (s, 3H).

Example 128

Preparation of methyl (S)-2-((2-(2,6-difluoro-4-(4-hydroxy-1H-pyrazol-1-yl)phenyl)-7-methylimidazo[1,2-a]pyridin-3-yl)methyl)morpholine-4-carboxylate

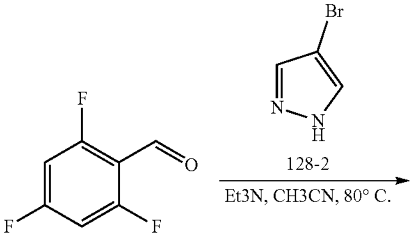

128-1

-continued

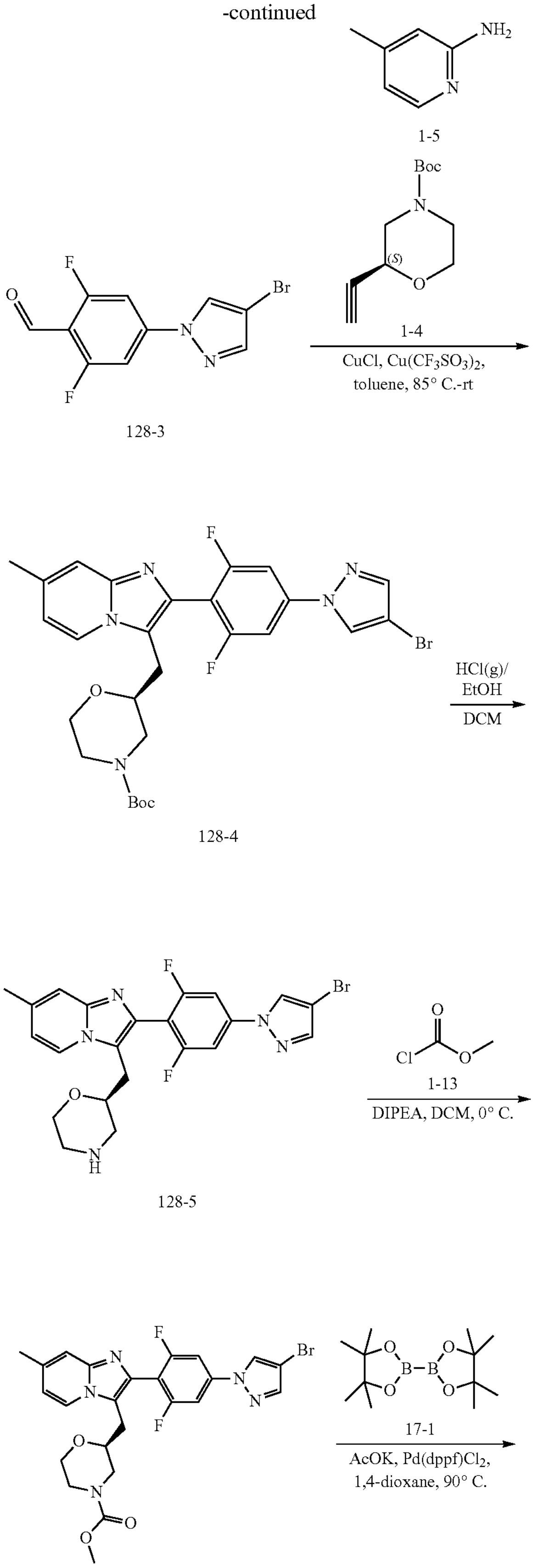

128-3

128-4

128-5

128-6

-continued

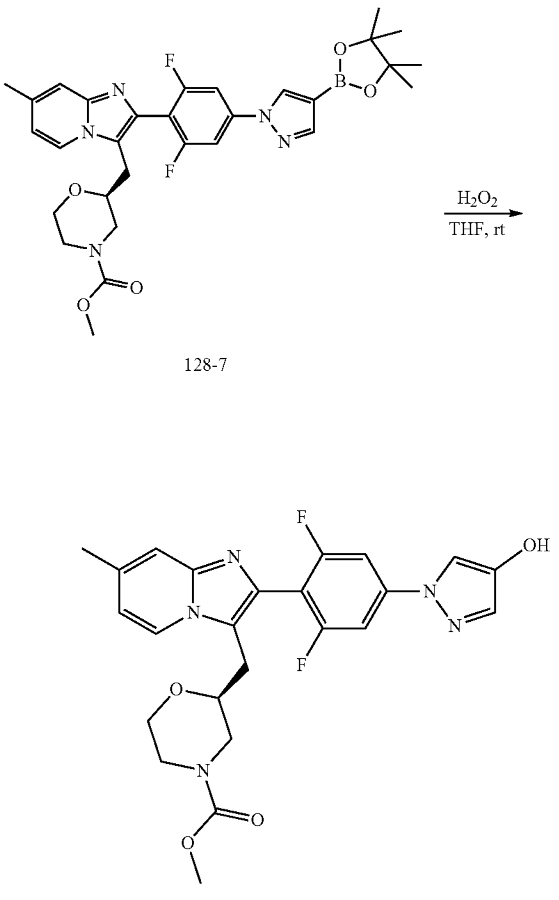

128-7

128

Step (1) Preparation of 4-(4-bromo-1H-pyrazol-1-yl)-2,6-difluorobenzaldehyde 128-3

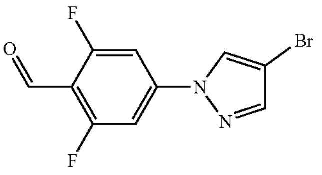

2,4,6-trifluorobenzaldehyde (2.0 g, 12.49 mmol) was dissolved in anhydrous acetonitrile (20 mL), and 4-bromopyrazole (1.8 g, 12.49 mmol) and triethylamine (3.8 g, 37.47 mmol) were added under nitrogen atmosphere. The reaction system was reacted at 80° C. for 1 h. Then the reaction system was cooled to room temperature, added with water (60 mL), and extracted with ethyl acetate (80 mL×3). The organic phases were combined, washed with saturated brine (50 mL×2), dried over anhydrous sodium sulfate, filtered and concentrated. The crude product was purified by silica gel column chromatography to give intermediate 128-3 (800 mg, 22.2% yield) in the form of a white solid. MS $[M+H]^+$=287.7.

Step (2) Preparation of tert-butyl (S)-2-((2-(4-(4-bromo-1H-pyrazol-1-yl)-2,6-difluorophenyl)-7-methylimidazo[1,2-a]pyridin-3-yl)methyl)morpholine-4-carboxylate 128-4

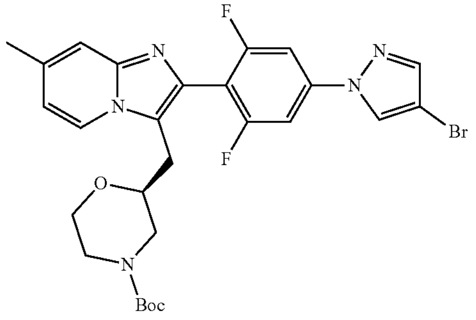

Intermediate 128-3 (600 mg, 2.09 mmol), 4-methylpyridin-2-amine (226 mg, 2.09 mmol), tert-butyl (S)-2-ethynylmorpholine-4-carboxylate (442 mg, 2.09 mmol), copper (I) chloride (62 mg, 0.63 mmol) and copper(II) trifluoromethanesulfonate (227 mg, 0.63 mmol) were dissolved in toluene solution (6 mL) under nitrogen atmosphere. The reaction system was reacted at 85° C. for 10 min, added with N,N-dimethylacetamide (0.2 mL), and reacted at 85° C. for another 5 h. Then the reaction system was reacted at room temperature overnight. After the reaction was completed, the reaction system was filtered, and the filtrate was added with water (30 mL), and extracted with dichloromethane (30 mL×3). The organic phases were combined, washed with saturated brine (40 mL), dried over anhydrous sodium sulfate, filtered and concentrated. The crude product was purified by silica gel column chromatography to give intermediate 128-4 (200 mg, 17% yield) in the form of a yellow oil. MS $[M+H]^+$=588.8.

Step (3) Preparation of (S)-2-((2-(4-(4-bromo-1H-pyrazol-1-yl)-2,6-difluorophenyl)-7-methylimidazo[1,2-a]pyridin-3-yl)methyl)morpholine 128-5

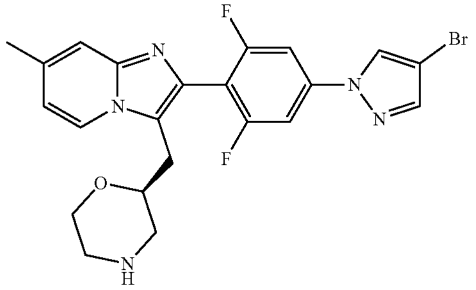

Intermediate 128-4 (200 mg, 0.34 mmol) was dissolved in dichloromethane (2 mL), and a solution of HCl in ethanol (33%, 0.5 mL) was added dropwise with the temperature maintained at 0° C. After the completion of the dropwise addition, the reaction system was reacted at room temperature for 2 h. Then the reaction system was added dropwise with saturated sodium bicarbonate solution to adjust the pH to 8 with the temperature maintained at 0° C., added with water (10 mL), and extracted with dichloromethane (20 mL×3). The organic phases were combined, washed with saturated brine (20 mL), dried over anhydrous sodium sulfate, filtered and concentrated to give intermediate 128-5 (180 mg, crude product) in the form of a yellow oil. MS $[M+H]^+$=488.7.

Step (4) Preparation of methyl (S)-2-((2-(4-(4-bromo-1H-pyrazol-1-yl)-2,6-difluorophenyl)-7-methylimidazo[1,2-a]pyridin-3-yl)methyl)morpholine-4-carboxylate 128-6

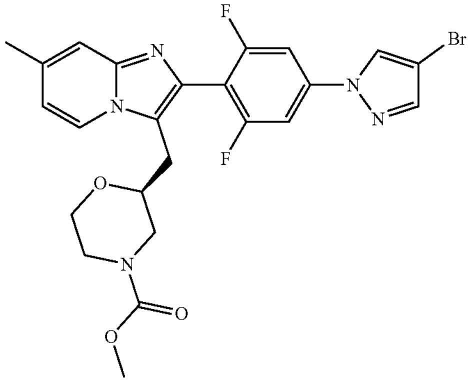

Intermediate 128-5 (180 mg, 0.34 mmol) and N,N-diisopropylethylamine (143 mg, 1.11 mmol) were dissolved in dichloromethane (2 mL), and methyl chloroformate (42 mg, 0.44 mmol) was added dropwise under nitrogen atmosphere with the temperature maintained at 0° C. After the completion of the dropwise addition, the reaction system was reacted at 0° C. for 1 h. Then the reaction system was added with water (10 mL), and extracted with dichloromethane (15 mL×3). The organic phases were combined, washed with saturated brine (20 mL), dried over anhydrous sodium sulfate, filtered and concentrated. The crude product was purified by silica gel column chromatography to give intermediate 128-6 (150 mg, 81% yield) in the form of a yellow solid. MS $[M+H]^+$=546.7.

Step (5) Preparation of methyl (S)-2-((2-(2,6-difluoro-4-(4-(4,4,5,5-tetramethyl-1,3,2-dioxaborolan-2-yl)-1H-pyrazol-1-yl)phenyl)-7-methylimidazo[1,2-a]pyridin-3-yl)methyl)morpholine-4-carboxylate 128-7

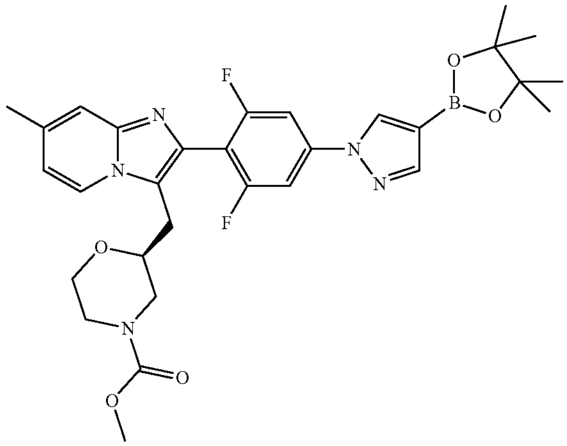

Intermediate 128-6 (150 mg, 0.27 mmol) was dissolved in anhydrous 1,4-dioxane (2 mL) under nitrogen atmosphere, and 4,4,4',4',5,5,5',5'-octamethyl-2,2'-bis(1,3,2-dioxaborolan) (87 mg, 0.34 mmol), potassium acetate (54 mg, 0.55 mmol) and [1,1'-bis(diphenylphosphino) ferrocene]dichloropalladium (10 mg, 0.014 mmol) were added. The reaction system was reacted at 90° C. for 2 h. After the reaction was completed, the reaction system was cooled to room temperature, filtered and concentrated by rotary evaporation to give intermediate 128-7 (180 mg, crude product) in a yellow oil, MS $[M+H]^+$=593.7.

Step (6) Preparation of methyl (S)-2-((2-(2,6-difluoro-4-(4-hydroxy-1H-pyrazol-1-yl)phenyl)-7-methylimidazo[1,2-a]pyridin-3-yl)methyl)morpholine-4-carboxylate

128

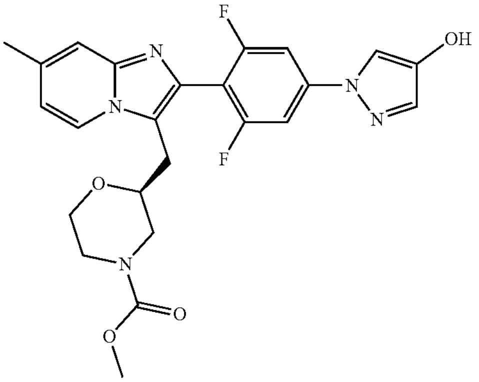

Intermediate 128-7 (180 mg, 0.27 mmol) was dissolved in tetrahydrofuran (2 mL), and hydrogen peroxide (0.5 mL) was added dropwise. The reaction system was reacted at room temperature for 1 h. After the reaction was completed, the reaction system was added dropwise with saturated sodium thiosulfate solution (2 mL) to quench the reaction, added with water (10 mL), and extracted with dichloromethane (15 mL×3). The organic phases were combined, washed with saturated brine (20 mL), dried over anhydrous sodium sulfate, filtered and concentrated. The crude product was purified by high performance liquid chromatography to give compound 128 (22.9 mg, 17.3% yield) in the form of a white solid. MS $[M+H]^+$=483.8.

$^1$H NMR (400 MHZ, MeOD) δ 8.86 (d, J=7.1 Hz, 1H), 7.93 (s, 1H), 7.72 (s, 1H), 7.70 (d, J=9.6 Hz, 2H), 7.50 (s, 1H), 7.42 (dd, J=7.1, 1.5 Hz, 1H), 4.03-4.00 (m, 1H), 3.85-3.76 (m, 3H), 3.69 (s, 3H), 3.40-3.36 (m, 1H), 3.28-3.26 (m, 2H), 2.99-2.90 (m, 1H), 2.80-2.72 (m, 1H), 2.66 (s, 3H).

Example 129

Preparation of methyl (S)-2-((2-(2,6-difluoro-4-(4-methoxy-1H-pyrazol-1-yl)phenyl)-7-methylimidazo[1,2-a]pyridin-3-yl)methyl)morpholine-4-carboxylate

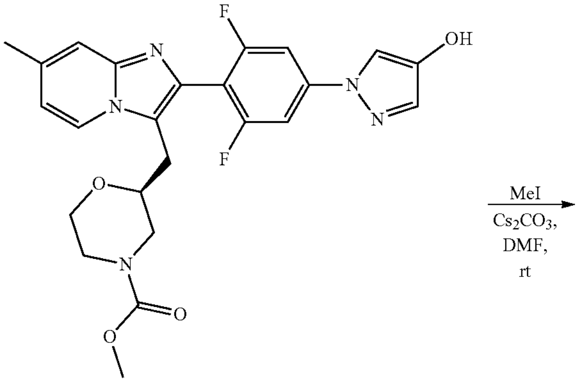

128

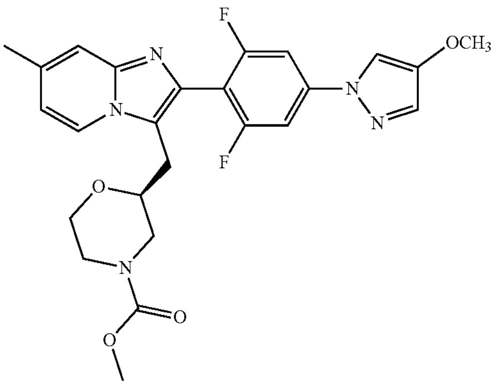

129

Compound 128 (45 mg, 0.09 mmol) was dissolved in N,N-dimethylformamide (1 mL) under nitrogen atmosphere, and cesium carbonate (36 mg, 0.11 mmol) and iodomethane (20 mg, 0.14 mmol) were added sequentially. The reaction system was reacted at room temperature for 1 h. After the reaction was completed, the reaction system was added with water (10 mL) to quench the reaction, and extracted with ethyl acetate (15 mL×3). The organic phases were combined, washed with saturated brine (20 mL×2), dried over anhydrous sodium sulfate, filtered and concentrated by rotary evaporation. The crude product was purified by high performance liquid chromatography to give compound 129 (5.3 mg, 11.4% yield) in the form of a white solid. MS $[M+H]^+$=497.8.

$^1$H NMR (400 MHZ, MeOD) δ 8.42 (d, J=7.0 Hz, 1H), 8.15 (s, 1H), 7.59 (d, J=9.0 Hz, 2H), 7.56 (s, 1H), 7.35 (s, 1H), 6.88 (dd, J=7.2 Hz, 1.2 Hz, 1H), 3.86 (s, 3H), 3.86-3.76 (m, 3H), 3.66 (s, 3H), 3.63-3.58 (m, 1H), 3.42-3.36 (m, 1H), 3.12-3.11 (m, 2H), 2.93-2.88 (m, 1H), 2.68-2.61 (m, 1H), 2.47 (s, 3H).

Example 130

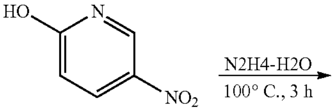

130-1

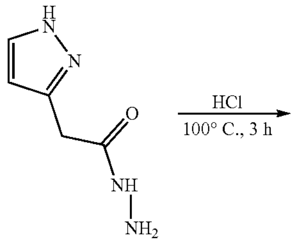

130-2

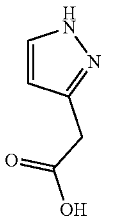

130-3

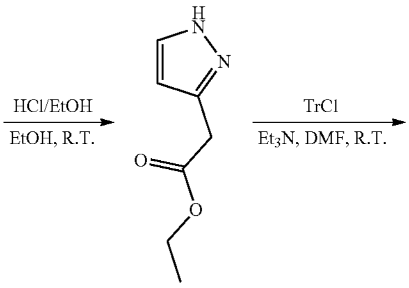

130-4

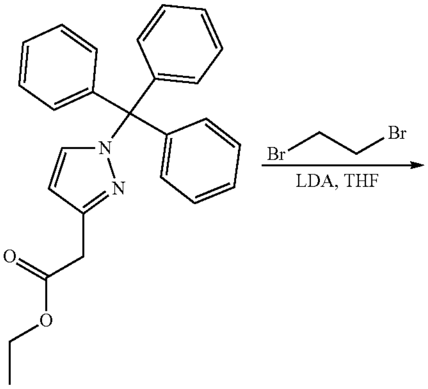

130-5

-continued

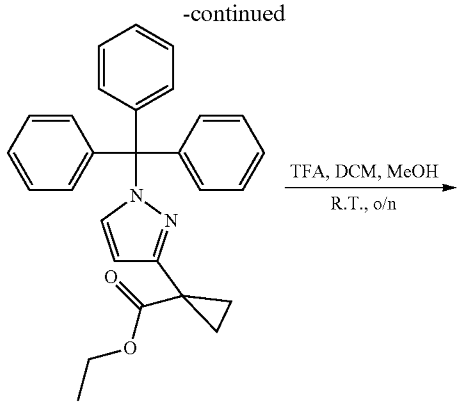

130-6

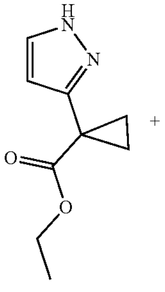

130-7

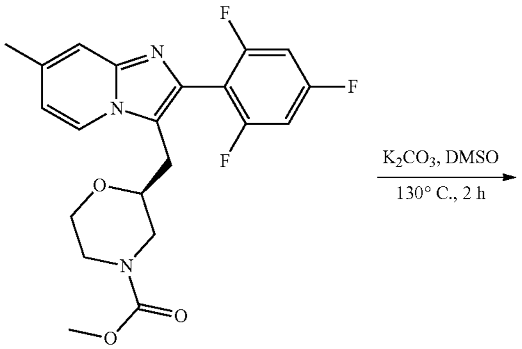

126-1

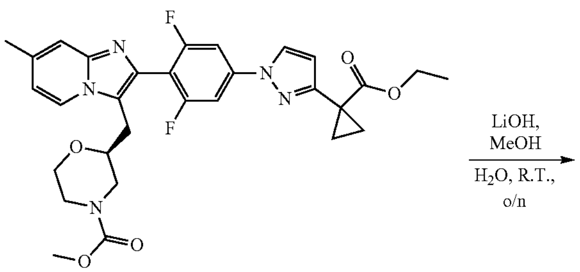

130-8

-continued

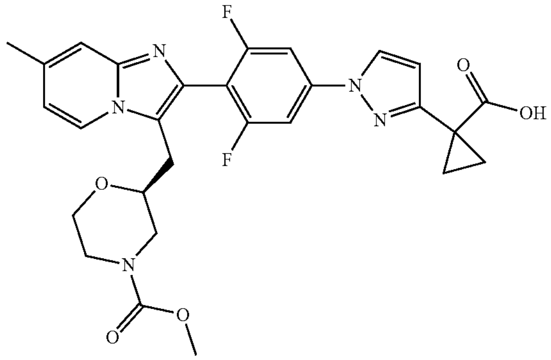

130

Step (1) Preparation of 2-(1H-pyrazol-3-yl)acethydrazide 130-2

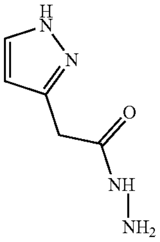

5-nitropyridin-2-ol (10.0 g, 71.38 mmol) was dissolved in hydrazine hydrate (50 mL). The reaction system was stirred at 100° C. for 3 h. After the reaction was completed, the reaction system was concentrated by rotary evaporation to give intermediate 130-2 (10.0 g, crude product) in the form of a red oil. LC-MS [M+H]=140.7.

Step (2) Preparation of 2-(1H-pyrazol-3-yl)acetic acid 130-3

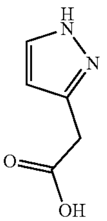

Intermediate 130-2 (10 g) was added to concentrated hydrochloric acid (100 mL) under nitrogen atmosphere. The reaction system was heated to 100° C. and stirred for 3 h. After the reaction was completed, the reaction system was concentrated by rotary evaporation to give intermediate 130-3 (10 g, crude product) in the form of a colorless transparent oil, MS [M+H]+=127.0.

Step (3) Preparation of ethyl 2-(1H-pyrazol-3-yl)acetate 130-4

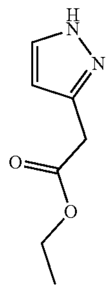

Intermediate 130-3 (10.0 g, crude product) was dissolved in ethanol (15 mL), and a solution of HCl in ethanol (33%, 12.5 mL) was added. The reaction system was stirred at room temperature for 3 h. After the reaction was completed, the reaction system was concentrated by rotary evaporation to give intermediate 130-4 (12 g, crude product) in the form of a brown oil, MS $[M+H]^+$=155.0.

Step (4) Preparation of ethyl 2-(1-trityl-1H-pyrazol-3-yl)acetate 130-5

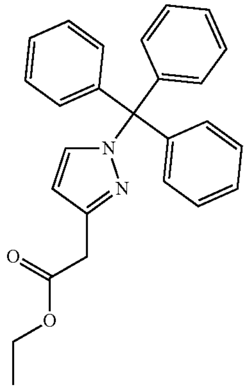

Intermediate 130-4 (12.0 g, crude product) was dissolved in anhydrous DMF (100 mL), and triphenylmethyl chloride (20.0 g, 77.42 mmol) and triethylamine (28.8 g, 285.5 mmol) were added. The reaction system was stirred at room temperature overnight. After the reaction was completed, the reaction system was added with water (300 mL), and extracted with ethyl acetate (100 mL×3). The organic phases were combined, washed with saturated brine (150 mL×3), dried over anhydrous sodium sulfate, filtered and concentrated by rotary evaporation. The crude product was purified by silica gel column chromatography to give intermediate 130-5 (2.3 g, 7.5% yield) in the form of a white solid. MS $[M+H]^+$=418.8.

Step (5) Preparation of ethyl 1-(1-trityl-1H-pyrazol-3-yl)cyclopropane-1-carboxylate 130-6

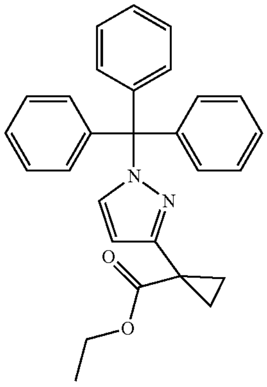

Intermediate 130-5 (1.0 g, 2.52 mmol) was dissolved in anhydrous tetrahydrofuran (20 mL). The reaction system was cooled to −78° C., added dropwise with lithium diisopropylamide (2.4 mL, 2 N, 4.80 mmol), and stirred at −78° C. for 20 min. Then the reaction system was added with dibromoethane (2.8 g, 15.13 mmol), slowly warmed to room temperature, and stirred overnight. After the reaction was completed, the reaction system was added with saturated ammonium chloride (10 mL), diluted with water (20 mL), and extracted with ethyl acetate (30 mL×2). The organic phases were combined, washed with saturated brine (30 mL), dried over anhydrous sodium sulfate, filtered, and concentrated by rotary evaporation. The crude product was purified by silica gel column chromatography to give intermediate 130-6 (550 mg, 51.6% yield) in the form of a yellow oil. MS $[M+H]^+$=444.8.

Step (6) Preparation of ethyl 1-(1H-pyrazol-3-yl)cyclopropane-1-carboxylate 130-7

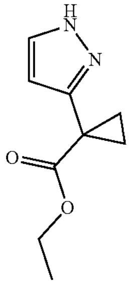

Intermediate 130-6 (400 mg, 1.01 mmol) was dissolved in dichloromethane (2 mL) and methanol (2 mL), and trifluoroacetic acid (1.2 mL) was added. The reaction system was stirred at room temperature overnight. After the reaction was completed, the reaction system was adjusted to pH 10 with saturated sodium carbonate solution, and extracted with dichloromethane (15 mL×3). The organic phases were combined, dried over sodium sulfate, filtered and concentrated by rotary evaporation. The crude product was purified by silica gel column chromatography to give intermediate 130-7 (65 mg, 35.6% yield) in the form of a white solid, MS $[M+H]^+$=181.0.

Step (7) Preparation of methyl (S)-2-(2-(4-(3-(1-(carbethoxy<ethoxycarbonyl>)cyclopropyl)-1H-pyrazol-1-yl)-2,6-difluorophenyl)-7-methylimidazo[1,2-a]pyridin-3-yl)methyl)morpholine-4-carboxylate 130-8

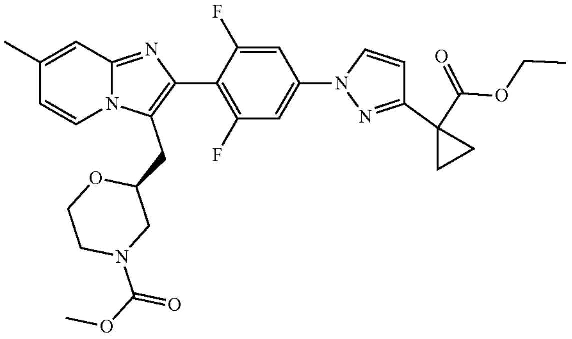

Intermediate 130-7 (35 mg, 0.19 mmol) was dissolved in anhydrous DMSO (1.5 mL), and intermediate 126-1 (87 mg, 0.21 mmol) and potassium carbonate (66 mg, 0.48 mmol) were added. The reaction system was stirred at 130° C. overnight. After the reaction was completed, the reaction system was added with water (15 mL), and extracted with ethyl acetate (10 mL×3). The organic phases were combined, washed with saturated brine (10 mL), dried over sodium sulfate, filtered and concentrated by rotary evaporation. The crude product was purified by silica gel column chromatography to give intermediate 130-8 (25 mg, 22.7% yield) in the form of a white solid. MS $[M+H]^+$=579.8.

Step (8) Preparation of (S)-1-(1-(3,5-difluoro-4-(3-((4-(carbomethoxy<methoxycarbonyl>)morpholin-2-yl)methyl)-7-methylimidazo[1,2-a]pyridin-2-yl)phenyl)-1H-pyrazol-3-yl)cyclopropane-1-carboxylic acid

130

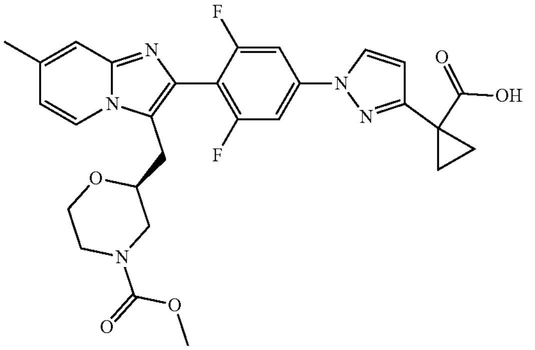

Intermediate 130-8 (25 mg, 0.044 mmol) was dissolved in tetrahydrofuran (1 mL)/methanol (1 mL), and lithium hydroxide solution (0.5 mL, 1 N) was added. The reaction system was stirred at room temperature overnight. After the reaction was completed, the reaction system was adjusted to pH 4 with diluted hydrochloric acid, and extracted with ethyl acetate (5 mL×3). The organic phases were combined, dried over anhydrous sodium sulfate, filtered and concentrated. The crude product was separated by high performance liquid chromatography, and lyophilized to give compound 130 (5.0 mg, 20.6% yield) in the form of a white solid. MS $[M+H]^+$ =551.7.

$^1$H NMR (400 MHz, CDCl3) δ 8.31 (d, J=6.6 Hz, 1H), 7.93 (d, J=2.6 Hz, 1H), 7.63 (s, 1H), 7.38 (d, J=8.2 Hz, 2H), 6.84 ((d, J=6.8 Hz, 1H), 6.33 (s, 1H), 3.05-3.77 (m, 3H), 3.70 (s, 3H), 3.66-2.59 (m, 1H), 3.46-3.37 (m, 1H), 3.10-2.99 (m, 2H), 2.99-2.87 (m, 1H), 2.70-2.63 (m, 1H), 2.50 (s, 3H), 1.94 (dd, J=7.6, 4.0 Hz, 2H), 1.47 (dd, J=7.6, 4.1 Hz, 2H)

Example 131

131

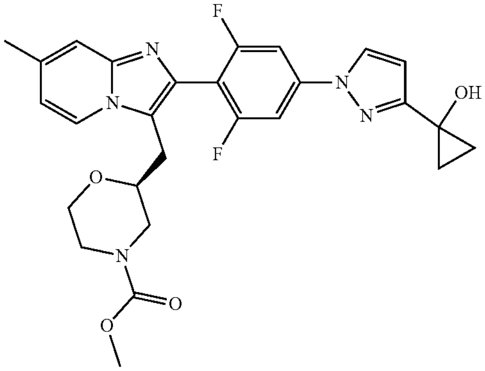

The compound was prepared according to the preparation method as described in Example 126. LC-MS: $[M+H]^+$=524.2.

Example 132

132

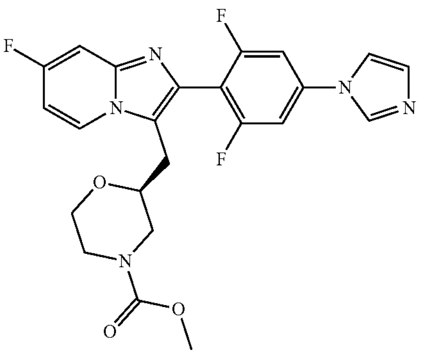

The compound was prepared according to the preparation method as described in Example 5. LC-MS: $[M+H]^+$=472.2.

Example 133

Preparation of methyl (S)-2-((2-(4-(4-(1-carbamylcyclopropyl)-1H-imidazol-2-yl)-2,6-difluorophenyl)-7-methylimidazo[1,2-a]pyridin-3-yl)methyl)morpholine-4-carboxylate

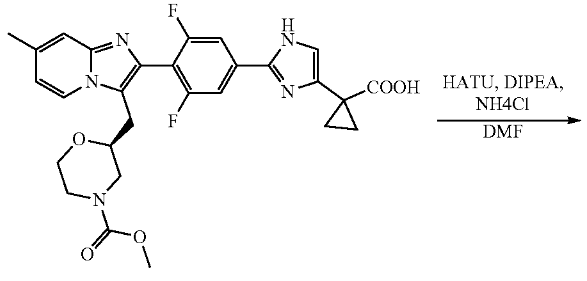

59

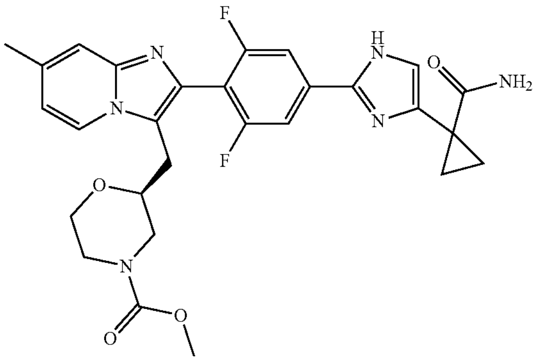

133

Compound 59 (400 mg, 0.72 mmol) and 2-(7-azabenzotriazol-1-yl)-N,N,N',N'-tetramethyluronium hexafluorophosphate (410 mg, 1.08 mmol) were dissolved in N,N-dimethylformamide (5 mL). The reaction system was stirred at room temperature for 10 min under nitrogen atmosphere, added with N,N-diisopropylethylamine (279 mL, 2.16 mmol) and ammonium chloride (58 mg, 1.1 mmol), and stirred at room temperature for another 2 h. Then the reaction system was added with water (30 mL) to quench the reaction, and extracted with ethyl acetate (15 mL×3). The organic phases were combined, washed with saturated brine (10 mL×3), dried over anhydrous sodium sulfate, filtered and concentrated. The residue was separated by silica gel column chromatography to give a crude product (200 mg) in the form of a brown solid. The crude product (50 mg) was purified by preparative chromatography to give compound 133 (11.1 mg) in the form of a white solid. LC-MS $[M+H]^+$: 551.

1H NMR (400 MHZ, CDCl3) δ 8.27 (d, J=6.9 Hz, 1H), 7.47 (s, 1H), 7.39 (d, J=8.3 Hz, 2H), 6.96 (s, 1H), 6.80 (d, J=6.9 Hz, 1H), 5.56 (brs, 1H), 3.90-3.80 (m, 3H), 3.66 (s, 3H), 3.62-3.54 (m, 1H), 3.43-3.34 (m, 1H), 3.04-2.82 (m, 3H), 2.67-2.56 (m, 1H), 2.51 (s, 3H), 1.65-1.59 (m, 2H), 1.15-1.09 (m, 2H).

Example 134

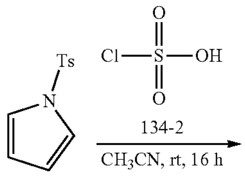

134-1

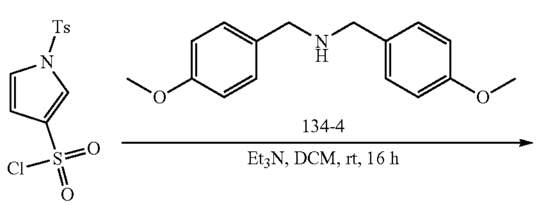

134-3

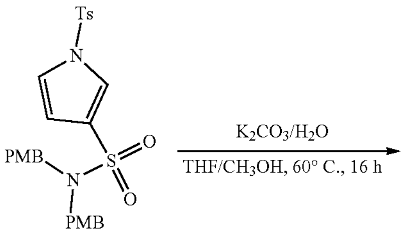

134-5

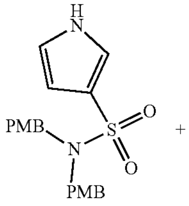

134-6

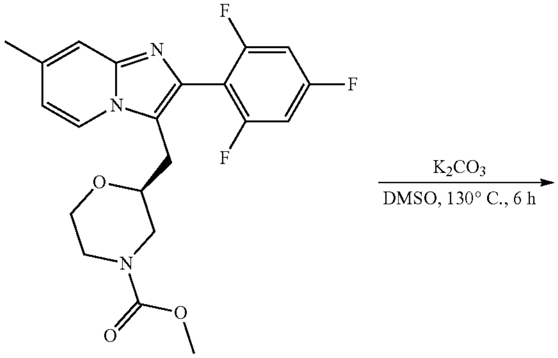

134-7

-continued

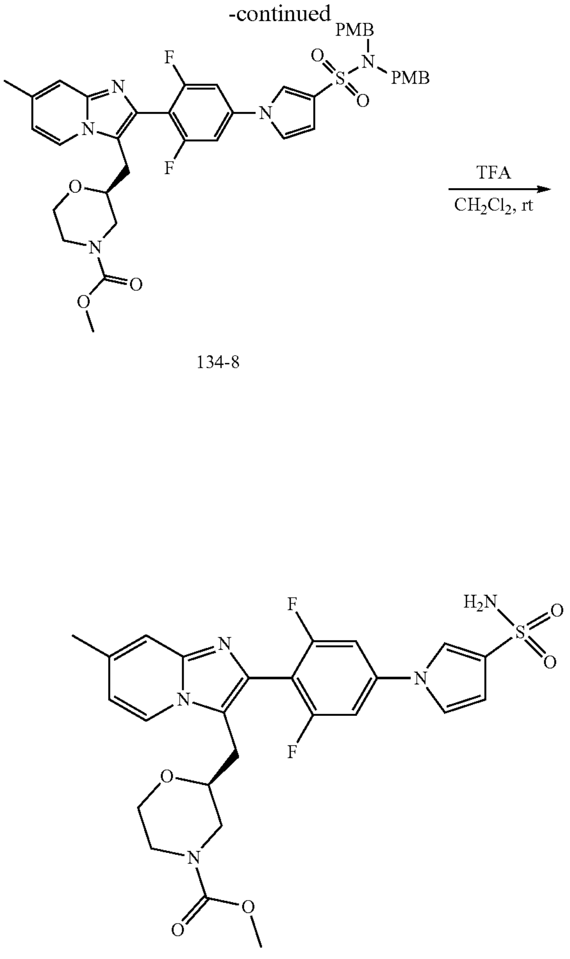

134-8

134

Step (1) Preparation of 1-tosyl-1H-pyrrol-3-sulfonyl chloride 134-3

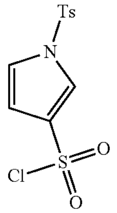

N-p-toluenesulfonylpyrrole (2.00 g, 9.01 mmol) was dissolved in acetonitrile (20 mL), and chlorosulfonic acid (5 mL) was added dropwise slowly at 0° C. in an ice water bath. The reaction system was reacted at room temperature overnight. Then the reaction system was added dropwise slowly to an ice (100 g), and extracted with dichloromethane (80 mL×2). The organic phases were combined, washed with saturated sodium bicarbonate (30 mL×2), dried over anhydrous sodium sulfate, filtered and concentrated. The residue was purified by silica gel column chromatography to give intermediate 134-3 (600 mg, 21% yield) in the form of a white solid.

Step (2) Preparation of N,N-bis(4-methoxybenzyl)-1-tosyl-1H-pyrrol-3-sulfonamide 134-5

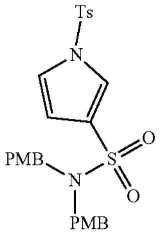

Bis-(4-methoxybenzyl)-amine (195 mg, 0.76 mmol) and triethylamine (191 mg, 1.89 mmol) were dissolved in dichloromethane (5 mL) under nitrogen atmosphere, and a solution of intermediate 134-3 (200 mg, 0.63 mmol) in dichloromethane (1 mL) was added dropwise at 0° C. in an ice water bath. The reaction system was stirred at room temperature overnight. Then the reaction system was poured into water (20 mL), and extracted with dichloromethane (30 mL×2). The organic phases were combined, washed with saturated brine (30 mL), filtered and concentrated. The crude product was purified by silica gel column chromatography to give intermediate 134-5 (300 mg, 88% yield) in the form of a white solid. MS $[M+Na]^+$=562.

Step (3) Preparation of N,N-bis(4-methoxybenzyl)-1H-pyrrol-3-sulfonamide 134-6

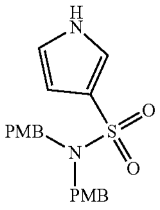

Intermediate 134-5 (800 mg, 1.48 mmol) was dissolved in methanol (10 mL) and tetrahydrofuran (10 mL), and aqueous potassium carbonate solution (3 mL, 7.40 mmol) was added. The reaction system was stirred at 60° C. overnight. Then the reaction system was concentrated under reduced pressure. The residue was adjusted to pH 4 with acetic acid, diluted with ethyl acetate (50 mL), washed with saturated brine (30 mL), dried over anhydrous sodium sulfate, filtered and concentrated. The crude product was purified by silica gel column chromatography to give intermediate 134-6 (500 mg, 88% yield) in the form of a white solid. MS $[M+Na]^+$=408.8.

Step (4) Preparation of methyl (S)-2-((2-(4-(3-(N,N-bis(4-methoxybenzyl)sulfamoyl)-1H-pyrrol-1-yl)-2,6-difluorophenyl)-7-methylimidazo[1,2-a]pyridin-3-yl)methyl)morpholine-4-carboxylate 134-8

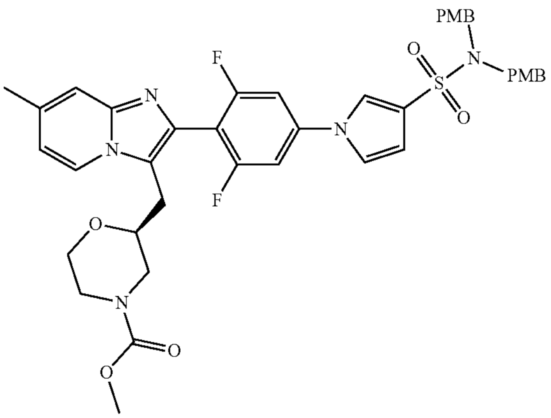

Methyl (S)-2-((7-methyl-2-(2,4,6-trifluorophenyl)imidazo[1,2-a]pyridin-3-yl)methyl)morpholine-4-carboxylate (271 mg, 0.65 mmol, intermediate 134-7, prepared according to the preparation method for intermediate 2-7, LC-MS: $[M+H]^+$=420.2) was dissolved in dimethyl sulfoxide (5 mL), and potassium carbonate (269 mg, 1.95 mmol) and N,N-bis(4-methoxybenzyl)-1H-pyrrol-3-sulfonamide (251 mg, 0.65 mmol) were added. The reaction system was reacted at 130° C. for 6 h under nitrogen atmosphere. Then the reaction system was added with water (30 mL), and extracted with ethyl acetate (30 mL×2). The organic phases were combined, washed with saturated brine (20 mL×2), filtered and concentrated. The crude product was purified by silica gel column chromatography to give intermediate 134-8 (320 mg, 44% yield) in the form of a brown solid. MS $[M+H]^+$=786.2.

Step (5) Preparation of methyl (S) 2-((2-(2,6-difluoro-4-(3-sulfamoyl-1H-pyrrol-1-yl)phenyl)-7-methylimidazo[1,2-a]pyridin-3-yl)methyl)morpholine-4-carboxylate

134

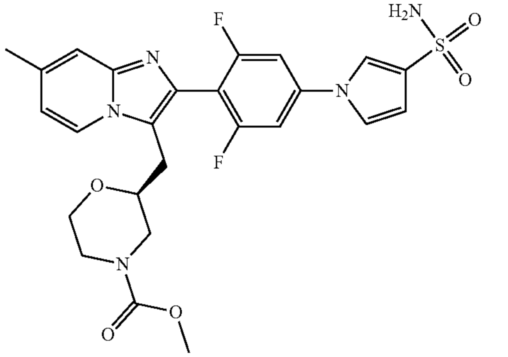

Intermediate 134-8 (280 mg, 0.36 mmol) was dissolved in dichloromethane (3 mL), and trifluoroacetic acid (3 mL) was added. The reaction system was reacted at room temperature for 16 h. Then the reaction system was concentrated under reduced pressure. The crude product was dissolved in dichloromethane (40 mL), washed with aqueous sodium bicarbonate solution (10%, 10 mL×2), dried over anhydrous sodium sulfate, filtered and concentrated. The crude product was purified by preparative chromatography to give compound 134 (22.6 mg, 12% yield) in the form of a white solid. MS $[M+H]^+$=545.7.

1H NMR (400 MHZ, CDCl3) δ 8.23 (d, J=7.0 Hz, 1H), 7.73-7.63 (m, 1H), 7.45 (s, 1H), 7.16-7.13 (m, 1H), 7.11 (d, J=7.7 Hz, 2H), 6.80-6.69 (m, 2H), 4.96 (s, 2H), 4.00-3.82 (m, 3H), 3.70 (s, 3H), 3.64-3.58 (m, 1H), 3.45-3.38 (m, 1H), 3.12-2.99 (m, 2H), 2.98-2.88 (m, 1H), 2.69-2.59 (m, 1H), 2.46 (s, 3H).

Example 135

135

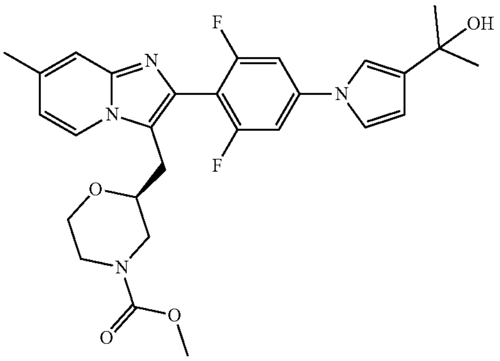

The compound was prepared according to the preparation method as described in Example 126. LC-MS: $[M+H]^+$=525.2.

Example 136

136

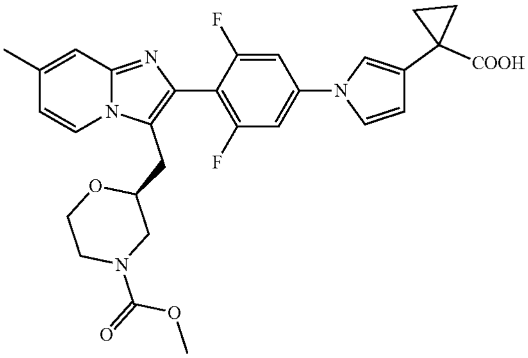

The compound was prepared according to the preparation method for compound 5. LC-MS: $[M+H]^+$=551.2.

Example 137

137

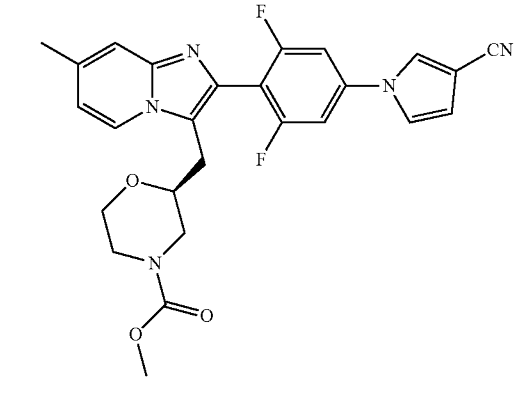

The compound was prepared according to the preparation method for compound 5. LC-MS: $[M+H]^+$=492.7.

Example 138

-continued

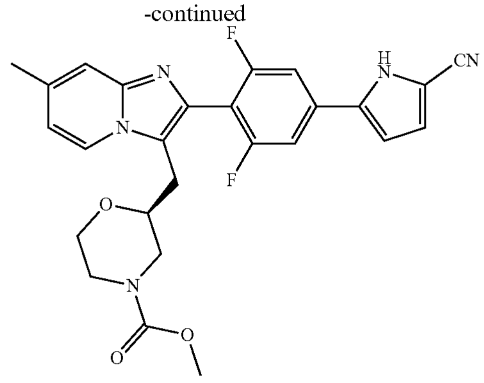

138

Step (1) Preparation of methyl (S)-2-((2-(4-(1-(tert-butoxycarbonyl)-5-cyano-pyrrol-2-yl)-2,6-difluoro-phenyl)-7-methylimidazo[1,2-a]pyridin-3-yl)-methyl)morpholine-4-carboxylate

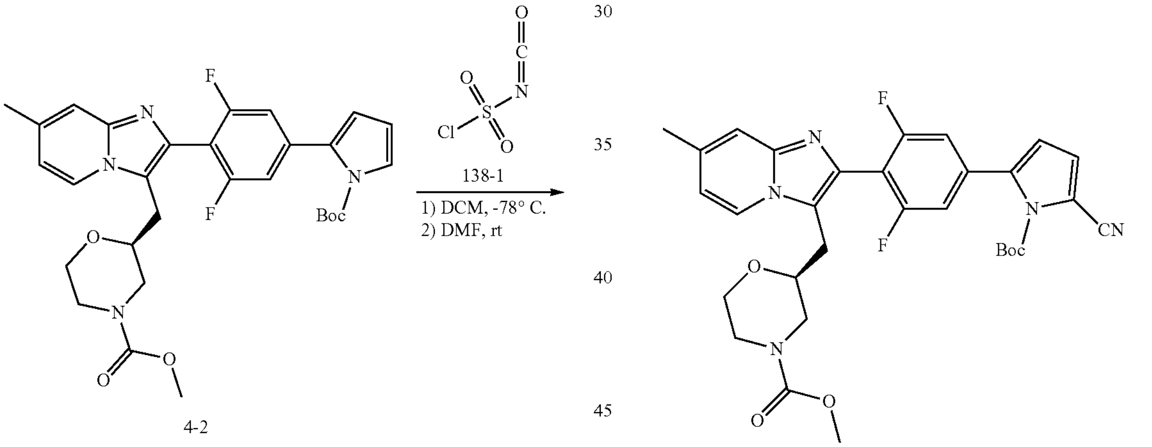

4-2

138-2

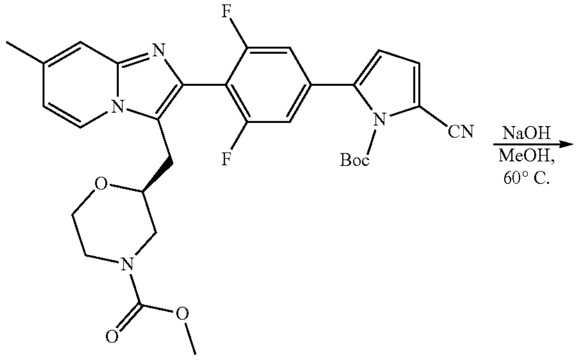

138-2

Intermediate 4-2 (290 mg, 0.51 mmol) was dissolved in anhydrous dichloromethane (5 mL) under nitrogen atmosphere, and chlorosulfonyl isocyanate (58 mg, 0.41 mmol) was added dropwise slowly at −78° C. After the completion of the dropwise addition over 2 min, the reaction system was reacted at −78° C. for 1 h, added dropwise with N,N-dimethylformamide (0.44 mL) over 1 min, and reacted at room temperature for 1 h. Then the reaction system was added with water (20 mL), and extracted with dichloromethane (50 mL×3). The organic phases were combined, washed with saturated brine (20 mL), dried over magnesium sulfate, filtered and concentrated by rotary evaporation to give a crude product. The crude product was purified by silica gel column chromatography to give intermediate 138-2 (200 mg, 66% yield) in the form of a yellow solid. LC-MS: $[M+H]^+$=592.8.

Step (2) Preparation of methyl (S)-2-((2-(2,6-difluoro-4-(5-cyano-1H-pyrrol-2-yl)phenyl)-7-methylimidazo[1,2-a]pyridin-3-yl)methyl)morpholine-4-carboxylate

138

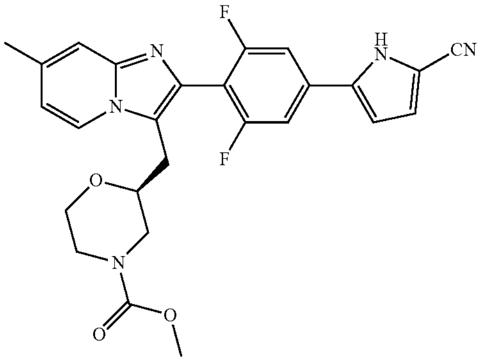

Intermediate 138-2 (200 mg, 0.41 mmol) was dissolved in absolute methanol (3 mL), and sodium hydroxide solution (3 M, 0.4 mL) was added. The reaction system was reacted at 60° C. for 1 h. After the reaction was completed, the reaction system was added dropwise with diluted hydrochloric acid (1 M) to adjust the pH to 6, added with water (10 mL), and extracted with dichloromethane (20 mL×3). The organic phases were combined, washed with saturated brine (20 mL), dried over magnesium sulfate, filtered and concentrated by rotary evaporation to give a crude product. The crude product was purified by high performance liquid chromatography to give compound 138 (41.2 mg, 25% yield) in the form of a yellow solid. LC-MS: $[M+H]^+=492.7$.

$^1H$ NMR (400 MHZ, MeOD) δ 8.85 (d, J=7.3 Hz, 1H), 7.72 (s, 1H), 7.64 (d, J=9.3 Hz, 2H), 7.42-7.41 (m, 1H), 6.99 (d, J=4.0 Hz, 1H), 6.91 (d, J=4.0 Hz, 1H), 4.02-3.99 (m, 1H), 3.85-3.75 (m, 3H), 3.69 (s, 3H), 3.39-3.34 (m, 1H), 3.28-3.26 (m, 2H), 3.00-2.88 (m, 1H), 2.81-2.71 (m, 1H), 2.65 (s, 3H).

Example 139

Preparation of methyl (S)-2-((2-(4-(5-cyanothiophen-2-yl)-2,6-difluorophenyl)-7-methylimidazo[1,2-a]pyridin-3-yl)methyl)morpholine-4-carboxylate

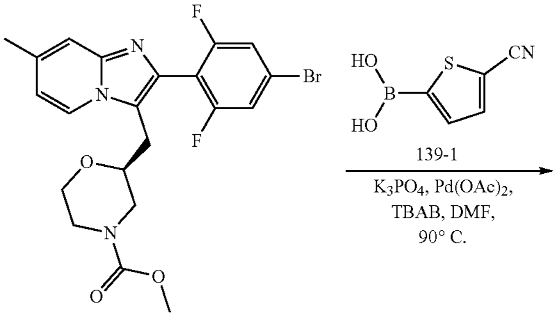

2-7

-continued

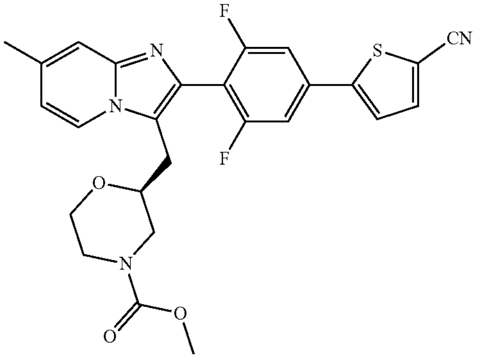

139

Intermediate 2-7 (100 mg, 0.21 mmol) was dissolved in anhydrous N,N-dimethylformamide (2 mL), and (5-cyano-thiophen-2-yl) boronic acid (32 mg, 0.21 mmol), potassium phosphate (132 mg, 0.62 mmol), palladium acetate (9.4 mg, 0.042 mmol) and tetrabutylammonium bromide (20 mg, 0.062 mmol) were added under nitrogen atmosphere. The reaction system was reacted at 90° C. for 12 h. After the reaction was completed, the reaction system was cooled to room temperature and filtered, and the filtrate was added with water (20 mL), and extracted with ethyl acetate (20 mL×3). The organic phases were combined, washed with saturated brine (20 mL×2), dried over anhydrous sodium sulfate, filtered and concentrated by rotary evaporation to give a crude product. The crude product was purified by high performance liquid chromatography to give compound 139 (3.8% yield) in the form of a yellow solid.

LC-MS: $[M+H]^+=509.7$. $^1H$ NMR (400 MHz, MeOD): δ 8.47 (d, J=6.8 Hz, 1H), 7.83 (d, J=4.0 Hz, 1H), 7.71 (d, J=4.0 Hz, 1H), 7.59 (d, J=8.3 Hz, 2H), 7.40 (s, 1H), 6.95 (d, J=7.0 Hz, 1H), 3.79-3.89 (m, 3H), 3.67 (s, 3H), 3.63-3.59 (m, 1H), 3.40-3.37 (m, 1H), 3.14-3.13 (m, 2H), 2.93-2.88 (m, 1H), 2.70-2.61 (m, 1H), 2.49 (s, 3H).

Example 140

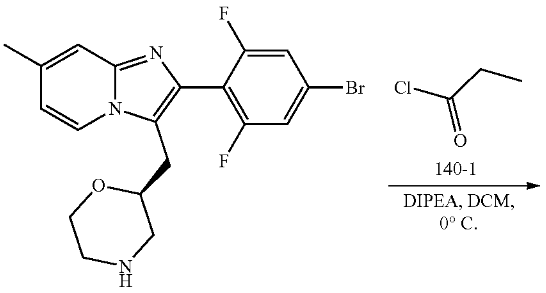

2-5

-continued

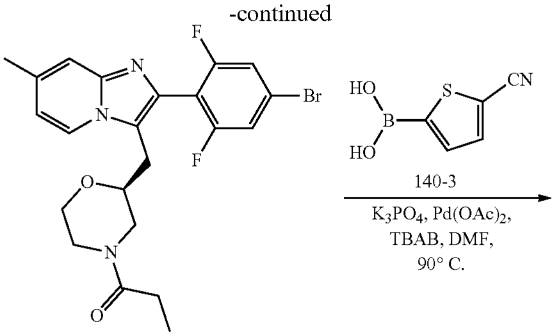

140-2

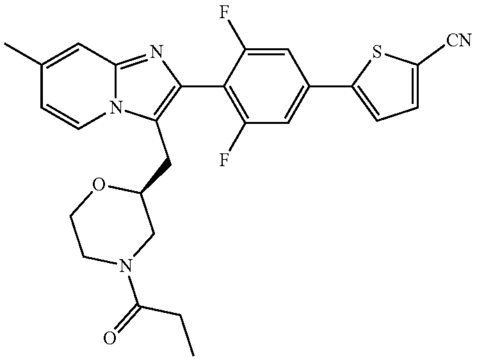

140

Step (1) Preparation of (S)-1-(2-((2-(4-bromo-2,6-difluorophenyl)-7-methylimidazo[1,2-a]pyridin-3-yl)methyl)morpholino)propan-1-one 140-2

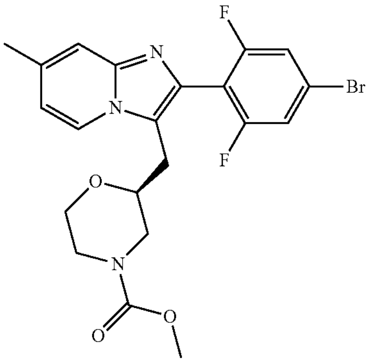

Intermediate 2-5 (500 mg, 1.18 mmol) was dissolved in anhydrous dichloromethane (5 mL), and under nitrogen atmosphere, N,N'-diisopropylethylamine (304 mg, 2.36 mmol) was added, followed by the dropwise addition of propionyl chloride (131 mg, 1.42 mmol) with the temperature maintained at 0° C. After the completion of the dropwise addition, the reaction system was reacted at 0° C. for 2 h. After the reaction was completed, the reaction system was added with water (40 mL), and extracted with dichloromethane (30 mL×3). The organic phases were combined, washed with saturated brine (40 mL), dried over magnesium sulfate, filtered and concentrated by rotary evaporation to give a crude product. The crude product was purified by silica gel column chromatography to give intermediate 140-2 (450 mg, 79% yield) in the form of a brown solid, LC-MS: [M+H]+=478.7.

Step (2) Preparation of (S)-5-(3,5-difluoro-4-(7-methyl-3-((4-propionylmorpholin-2-yl)methyl)imidazo[1,2-a]pyridin-2-yl)phenyl)thiopbene-2-carbonitrile

140

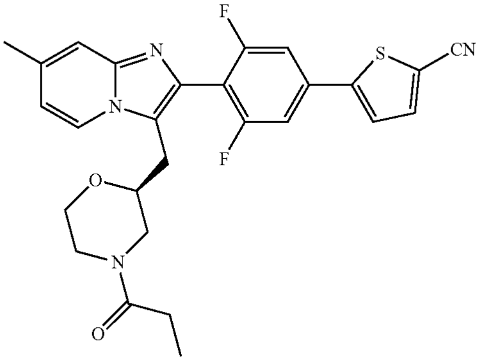

Intermediate 140-2 (100 mg, 0.21 mmol) was dissolved in anhydrous N,N-dimethylformamide (2 mL), and (5-cyanothiophen-2-yl) boronic acid (32 mg, 0.21 mmol), potassium phosphate (134 mg, 0.63 mmol), palladium acetate (9.6 mg, 0.043 mmol) and tetrabutylammonium bromide (22 mg, 0.068 mmol) were added under nitrogen atmosphere. The reaction system was reacted at 90° C. for 12 h. After the reaction was completed, the reaction system was cooled to room temperature and filtered, and the filtrate was added with water (20 mL), and extracted with ethyl acetate (20 mL×3). The organic phases were combined, washed with saturated brine (20 mL×2), dried over anhydrous sodium sulfate, filtered and concentrated by rotary evaporation to give a crude product. The crude product was purified by high performance liquid chromatography to give compound 140 (14.7 mg, 13.9% yield) in the form of a yellow solid.

LC-MS: $[M+H]^+$=507.6. $^1$H NMR (400 MHZ, MeOD): δ8.45 (brs, 1H), 7.83 (d, J=4.0 Hz, 1H), 7.70 (d, J=3.8 Hz, 1H), 7.58 (t, 2H), 7.37 (brs, 1H), 6.95-6.87 (m, 1H), 4.32-4.23 (m, 1H), 3.84-3.81 (m, 1H), 3.77-3.68 (m, 1H), 3.65-3.56 (m, 1H), 3.44-3.36 (m, 1H), 3.16-3.15 (m, 2H), 2.96-2.85 (m, 1H), 2.76-2.63 (m, 1H), 2.48 (s, 3H), 2.40-2.27 (m, 2H), 1.09-1.03 (m, 3H).

Example 141

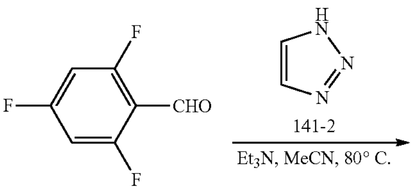

141-1

-continued

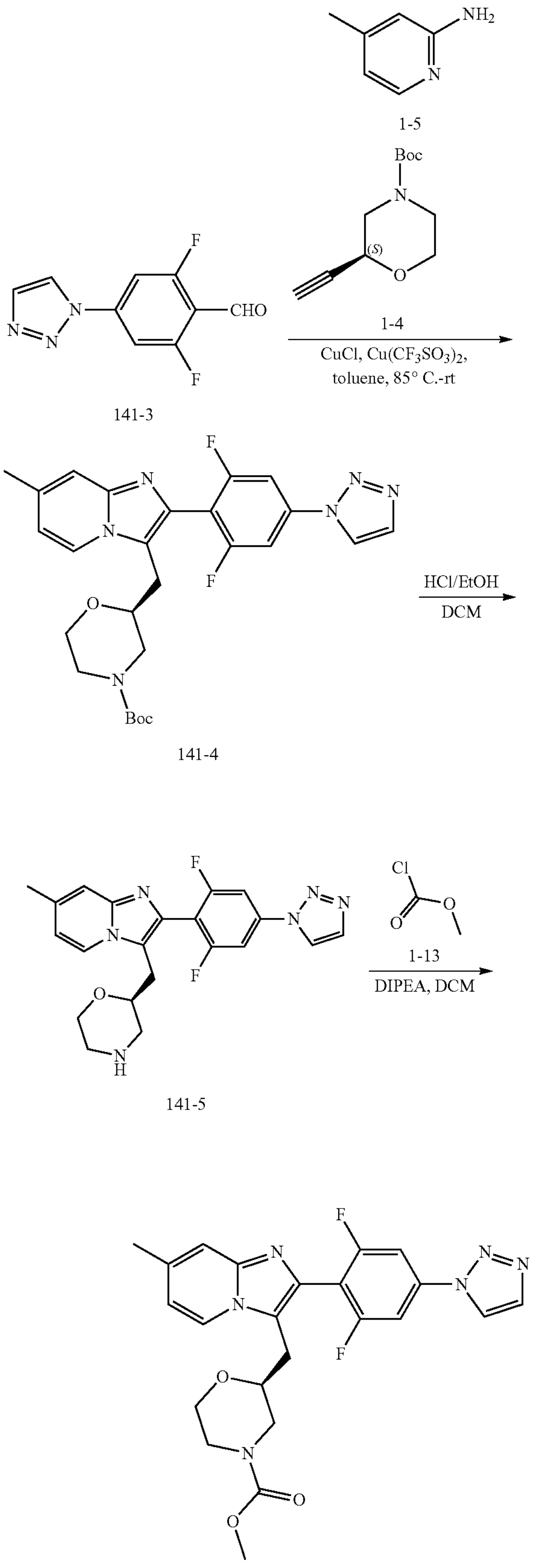

141

Step (1) Preparation of 2,6-difluoro-4-(1H-1,2,3-triazol-1-yl)benzaldehyde 141-3

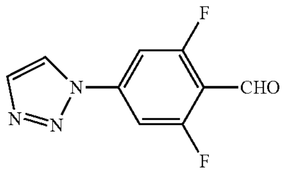

2,4,6-trifluorobenzaldehyde (4.0 g, 24.98 mmol) was dissolved in acetonitrile (40 mL), and 1H-1,2,3-triazole (1.7 g, 24.98 mmol) and triethylamine (7.6 g, 74.95 mmol) were added. The reaction system was stirred at 80° C. overnight. After the reaction was completed, the reaction system was concentrated by rotary evaporation. The residue was purified by silica gel column chromatography to give intermediate 141-3 in the form of a light yellow oil (530 mg, 10.2% yield). LC-MS: $[M+H]^+=209.9$.

Step (2) Preparation of tert-butyl (S)-2-((2-(2,6-difluoro-4-(1H-1,2,3-triazol-1-yl)phenyl)-7-methyl-imidazo[1,2-a]pyridin-3-yl)methyl)morpholine-4-carboxylate 141-4

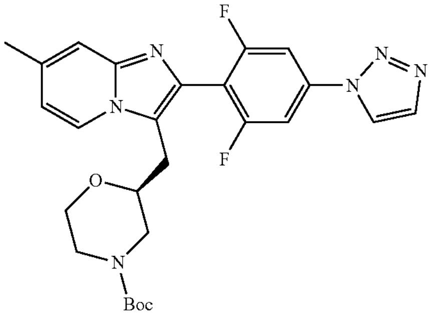

Intermediate 141-3 (520 mg, 2.49 mmol), intermediate 1-5 (268 mg, 2.49 mmol), intermediate 1-4 (525 mg, 2.49 mmol), copper(I) chloride (74 mg, 0.75 mmol) and copper (II) trifluoromethanesulfonate (271 mg, 0.75 mmol) were dissolved in anhydrous toluene (5 mL) under nitrogen atmosphere. The reaction system was heated to 85° C., added with N,N'-dimethylacetamide (0.2 mL), and stirred at 85° C. overnight. After the reaction was completed, the reaction system was filtered, and the filtrate was added with water (20 mL), and extracted with dichloromethane (15 mL×2). The organic phases were combined, dried over anhydrous sodium sulfate, filtered and concentrated to give a crude product. The crude product was purified by silica gel column chromatography to give intermediate 141-4 (80 mg, 6.7% yield) in the form of a colorless oil, LC-MS: $[M+H]^+=510.8$.

Step (3) Preparation of (S)-2-((2-(2,6-difluoro-4-(1H-1,2,3-triazol-1-yl)phenyl)-7-methylimidazo[1,2-a]pyridin-3-yl)methyl)morpholine 141-5

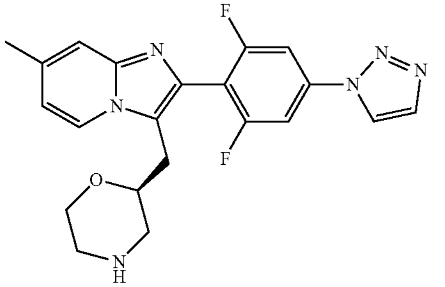

Intermediate 141-4 (80 g, 0.16 mmol) was dissolved in anhydrous dichloromethane (1 mL), and a solution of HCl in ethanol (0.3 mL) was added. The reaction system was stirred at room temperature for 3 h. After the reaction was completed, the reaction system was concentrated by rotary evaporation to give intermediate 141-5 (128 mg, crude product) in the form of a white solid, LC-MS $[M+H]^+$=410.8.

Step (4) Preparation n of methyl (S)-2-((2-(2,6-difluoro-4-(1H-1,2,3-triazol-1-yl)phenyl)-7-methyl-imidazo[1,2-a]pyridin-3-yl)methyl)morpholine-4-carboxylate

141

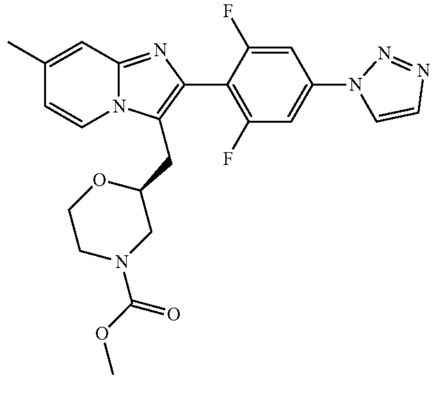

Intermediate 141-5 (128 mg, 0.16 mmol, crude product) was dissolved in anhydrous dichloromethane (5 mL), and under nitrogen atmosphere, N,N'-diisopropylethylamine (200 mg, 1.56 mmol) was added, followed by the dropwise addition of a solution of methyl chloroformate in dichloromethane (10 mg/mL, 1.8 mL, 0.19 mmol) with the temperature maintained at 0° C. After the completion of the dropwise addition, the reaction system was reacted at 0° C. for 2 h. After the reaction was completed, the reaction system was added with water (20 mL), and extracted with dichloromethane (10 mL×3). The organic phases were combined, washed with saturated brine (10 mL), dried over sodium sulfate, filtered and concentrated to give a crude product. The crude product was purified by silica gel column chromatography to give a product. The product was separated by preparative by high performance liquid chromatography to give compound 141 (14 mg, 19.35% yield) in the form of a white solid, LC-MS: [M+H]+=468.8.

1H NMR (400 MHZ, CDCl3) δ 8.23 (d, J=7.1 Hz, 1H), 8.08 (d, J=1.0 Hz, 1H), 7.93 (d, J=1.0 Hz, 1H), 7.55 (d, J=7.6 Hz, 2H), 7.47 (s, 1H), 6.75 (d, J=6.7 Hz, 1H), 4.05-3.80 (m, 3H), 3.70 (s, 3H), 3.65-3.57 (m, 1H), 3.46-3.36 (m, 1H), 3.10-2.85 (m, 3H), 2.70-2.60 (m, 1H), 2.46 (s, 3H).

Example 142

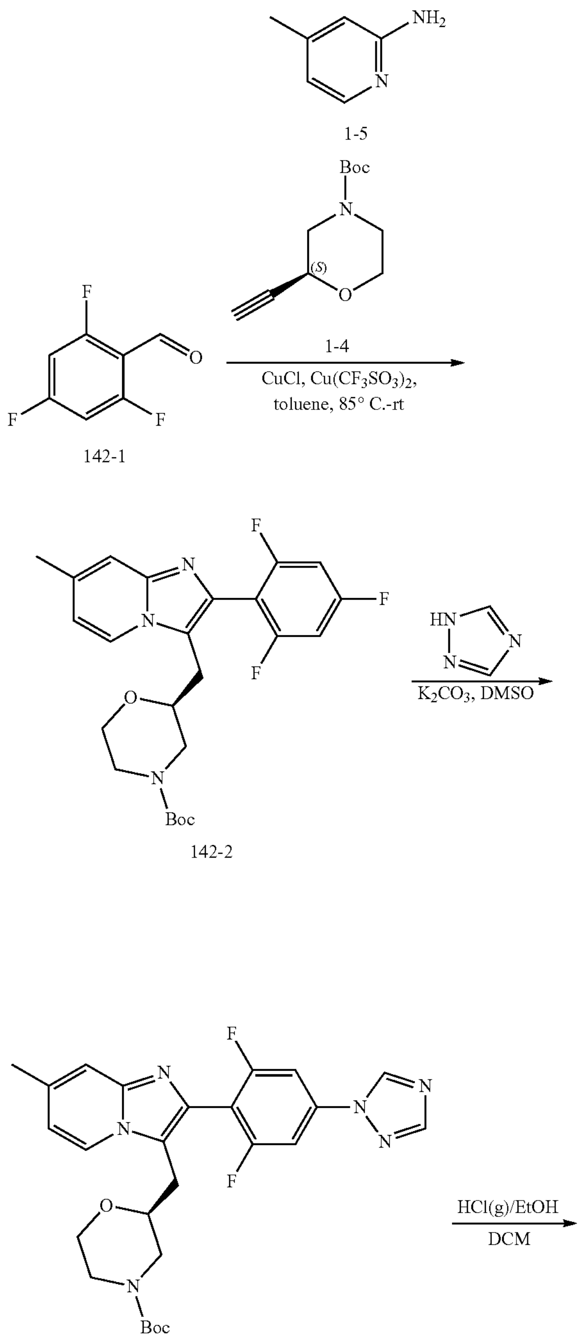

1-5

1-4

142-1

142-2

142-3

-continued

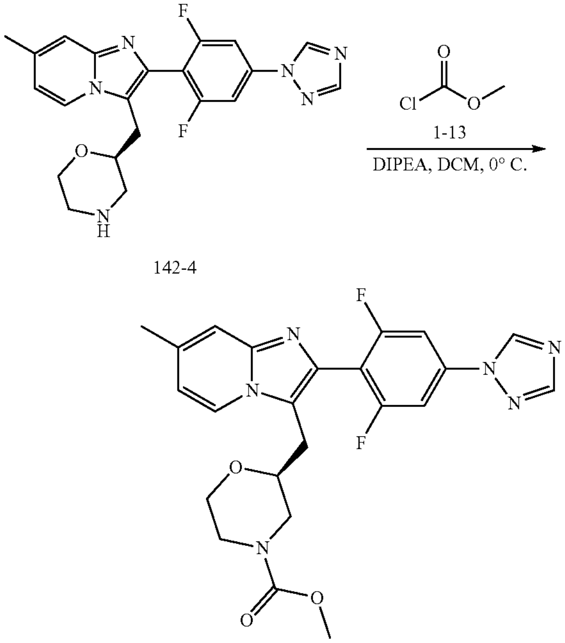

142-4

142

Step (1) Preparation of tert-butyl (S)-2-((7-methyl-2-(2,4,6-trifluorophenyl)imidazo[1,2-a]pyridin-3-yl) methyl)morpholine-4-carboxylate 142-2

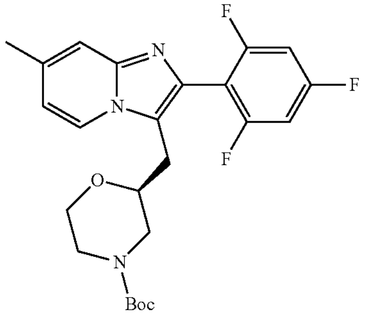

2,4,6-trifluorobenzaldehyde (3.0 g, 18.74 mmol), 4-methylpyridin-2-amine (2.0 g, 18.74 mmol), tert-butyl (S)-2-ethynylmorpholine-4-carboxylate (4 g, 18.74 mmol), copper (I) chloride (562 mg, 5.68 mmol) and copper(II) trifluoromethanesulfonate (2.1 g, 5.68 mmol) were dissolved in toluene solution (30 mL) under nitrogen atmosphere. The reaction system was reacted at 85° C. for 10 min, added with N,N-dimethylacetamide (0.5 mL), and reacted at 85° C. for another 5 h. Then the reaction system was reacted at room temperature overnight. After the reaction was completed, the reaction system was filtered, and the filtrate was added with water (50 mL), and extracted with dichloromethane (100 mL×3). The organic phases were combined, washed with saturated brine (50 mL×2), dried over anhydrous sodium sulfate, filtered and concentrated by rotary evaporation to give a crude product. The crude product was purified by silica gel column chromatography to give intermediate 142-2 (3.0 g, 34.8% yield) in the form of a yellow oil, MS $[M+H]^+$=461.8.

Step (2) Preparation of tert-butyl (S)-2-((2-(2,6-difluoro-4-(1H-1,2,4-triazol-1-yl)phenyl)-7-methylimidazo[1,2-a]pyridin-3-yl)methyl)morpholine-4-carboxylate 142-3

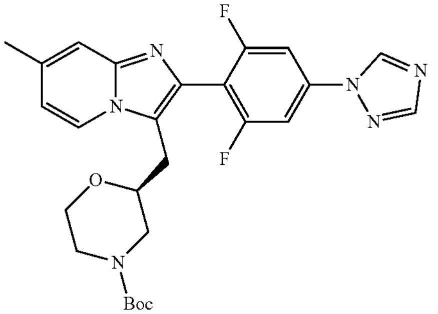

Intermediate 142-2 (300 mg, 0.65 mmol) was dissolved in anhydrous dimethyl sulfoxide (3 mL), and 1,2,4-triazole (40 mg, 0.58 mmol) and potassium carbonate (180 mg, 1.30 mmol) were added under nitrogen atmosphere. The reaction system was reacted at 85° C. for 1 h. Then the reaction system was cooled to room temperature, added with water (20 mL), and extracted with ethyl acetate (20 mL×3). The organic phases were combined, washed with saturated brine (20 mL×2), dried over anhydrous sodium sulfate, filtered and concentrated. The crude product was purified by silica gel column chromatography to give intermediate 142-3 (150 mg, 45.2% yield) in the form of a yellow oil. MS $[M+H]^+$=510.8.

Step (3) Preparation of (S)-2-((2-(2,6-difluoro-4-(1H-1,2,4-triazol-1-yl)phenyl)-7-methylimidazo[1,2-a]pyridin-3-yl)methyl)morpholine 142-4

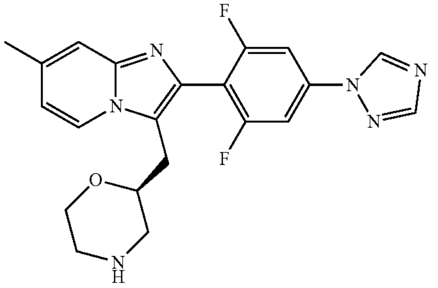

Intermediate 142-3 (150 mg, 0.29 mmol) was dissolved in dichloromethane (2 mL), and a solution of HCl in ethanol (33%, 0.5 mL) was added dropwise with the temperature maintained at 0° C. After the completion of the dropwise addition, the reaction system was reacted at room temperature for 2 h. Then the reaction system was adjusted to pH 8 with saturated sodium bicarbonate solution, diluted with water (10 mL), and extracted with dichloromethane (20 mL×3). The organic phases were combined, washed with saturated brine (20 mL), dried over anhydrous sodium sulfate, filtered and concentrated to give intermediate 142-4 (130 mg, crude product) in the form of a yellow solid, MS $[M+H]^+$=410.8.

Step (4) Preparation of methyl (S)-2-((2-(2,6-difluoro-4-(1H-1,2,4-triazol-1-yl)phenyl)-7-methylimidazo[1,2-a]pyridin-3-yl)methyl)morpholine-4-carboxylate

142

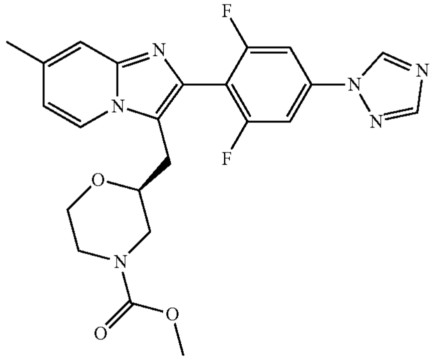

Intermediate 142-4 (130 mg, 0.29 mmol) and N,N-diisopropylethylamine (123 mg, 0.95 mmol) were dissolved in dichloromethane (2 mL), and methyl chloroformate (36 mg, 0.38 mmol) was added dropwise under nitrogen atmosphere with the temperature maintained at 0° C. After the completion of the dropwise addition, the reaction system was reacted at 0° C. for 1 h. Then the reaction system was added with water (20 mL), and extracted with dichloromethane (30 mL×3). The organic phases were combined, washed with saturated brine (20 mL), dried over anhydrous sodium sulfate, filtered and concentrated to give a crude product. The crude product was purified by high performance liquid chromatography to give compound 142 (30.4 mg, 20.5% yield) in the form of a yellow solid. MS $[M+H]^+$=468.7.

1H NMR (400 MHz, MeOD) δ 9.35 (s, 1H), 8.88 (d, J=7.1 Hz, 1H), 8.29 (s, 1H), 7.97 (d, J=8.7 Hz, 2H), 7.75 (s, 1H), 7.44 (dd, J=7.1, 1.4 Hz, 1H), 4.05-4.02 (m, 1H), 3.85-3.74 (m, 3H), 3.69 (s, 3H), 3.39-3.35 (m, 1H), 3.31-3.22 (m, 2H), 2.98-2.88 (m, 1H), 2.81-2.71 (m, 1H), 2.67 (s, 3H).

Example 143

Preparation of methyl (S)-2-((2-(2,6-difluoro-4-(4H-1,2,4-triazol-4-yl)phenyl)-7-methylimidazo[1,2-a]pyridin-3-yl)methyl)morpholine-4-carboxylate -continued

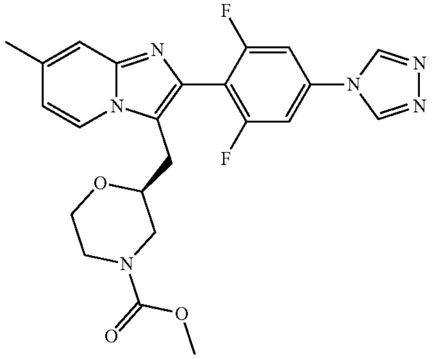

143

Intermediate 3-1 (75 mg, 0.18 mmol) and diformylhydrazide (486 mg, 0.54 mmol) were dissolved in anhydrous pyridine (10 mL). The reaction system was cooled to 0° C., added dropwise with triethylamine (128 mg, 1.26 mmol) and trimethylchlorosilane (294 mg, 2.7 mmol) sequentially under nitrogen atmosphere, an stirred under reflux for 24 h. Then the reaction system was concentrated under reduced pressure, added with saturated brine (10 mL), adjusted to pH 7-8 with saturated sodium bicarbonate solution, and extracted with DCM (10 mL×3). The organic phases were combined, dried over anhydrous sodium sulfate, filtered and concentrated. The crude product was purified by preparative thin-layer chromatography to give compound 143 (30 mg, 36% yield) in the form of a white solid. MS $[M+H]^+$=469.2.

1H NMR (400 MHz, d6-DMSO) δ 9.31 (s, 2H), 8.44 (d, J=7.1 Hz, 1H), 7.85 (d, J=8.2 Hz, 2H), 7.37 (s, 1H), 6.85 (d, J=7.1 Hz, 1H), 3.82-3.84 (m, 1H), 3.70-3.61 (m, 2H), 3.56 (s, 3H), 3.52-3.45 (m, 1H), 3.29-3.21 (m, 1H), 3.12-3.00 (m, 2H), 2.90-2.71 (m, 1H), 2.59-2.45 (m, 1H), 2.39 (s, 3H).

Example 144

Preparation of methyl (S)-2-((2-(4-(4-(1-cyanochloropropyl)-1H-imidazol-2-yl)-2,6-difluorophenyl)-7-methylimidazo[1,2-a]pyridin-3-yl)methyl)morpholine-4-carboxylate

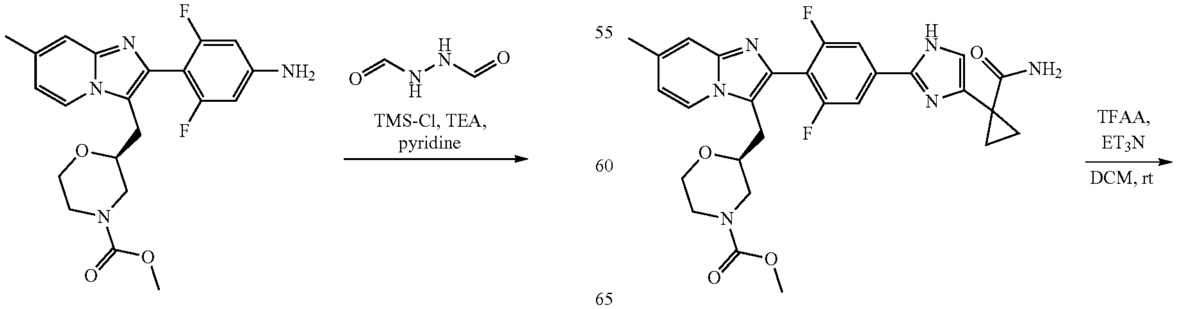

3-1

133

-continued

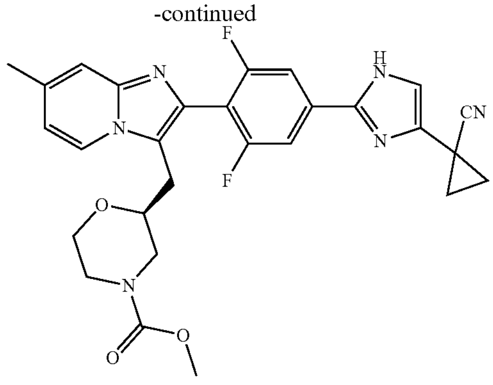

144

Compound 133 (150 mg, 0.27 mmol) and triethylamine (121 mg, 1.20 mmol) were dissolved in dichloromethane (3 mL). Under nitrogen atmosphere, the reaction system was cooled to 0° C., added dropwise with trifluoroacetic anhydride (125 mg, 0.60 mmol), and stirred at room temperature overnight. Then the reaction system was added with water (10 mL) to quench the reaction, and extracted with dichloromethane (10 mL×3). The organic phases were combined, washed with saturated brine (10 mL), dried over anhydrous sodium sulfate, filtered and concentrated. The residue was purified by preparative chromatography to give compound 144 (23.7 mg, 16% yield) in the form of a white solid. LC-MS $[M+H]^+$: 533.

1H NMR (400 MHZ, CDCl3) δ 8.35 (s, 1H), 7.62 (s, 1H), 7.44 (d, J=8.2 Hz, 2H), 7.23 (s, 1H), 6.91 (d, J=7.1 Hz, 1H), 4.00-3.75 (m, 3H), 3.68 (s, 3H), 3.62-3.53 (m, 1H), 3.44-3.33 (m, 1H), 3.03-2.82 (m, 3H), 2.66-2.56 (m, 1H), 2.55 (s, 3H), 1.68-1.58 (m, 4H).

Example 145

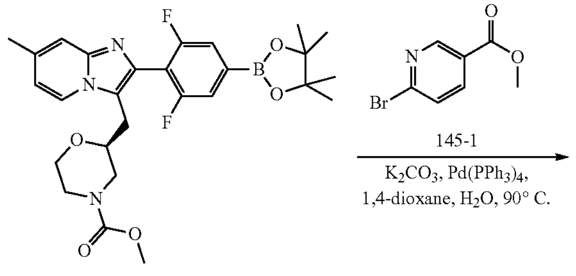

17-2

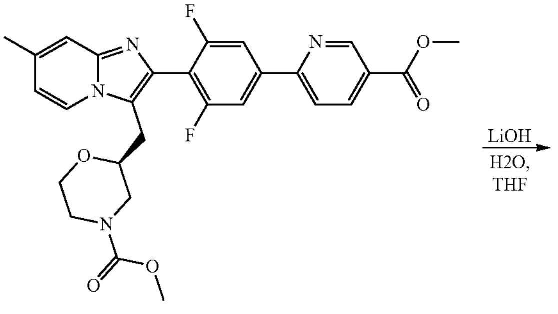

145-2

-continued

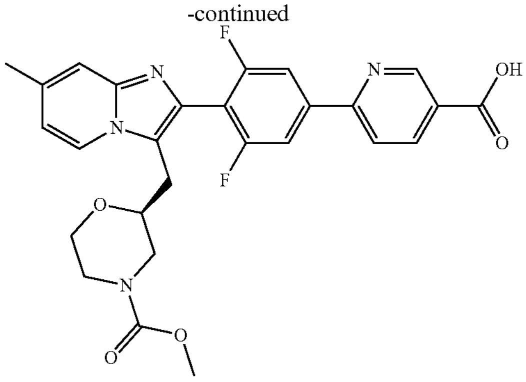

145

Step (1) Preparation of methyl (S)-2-((2-(2,6-difluoro-4-(methoxycarbonyl)pyridin-2-yl)phenyl)-7-methylimidazo[1,2-a]pyridin-3-yl)methyl)morpholine-4-carboxylate 145-2

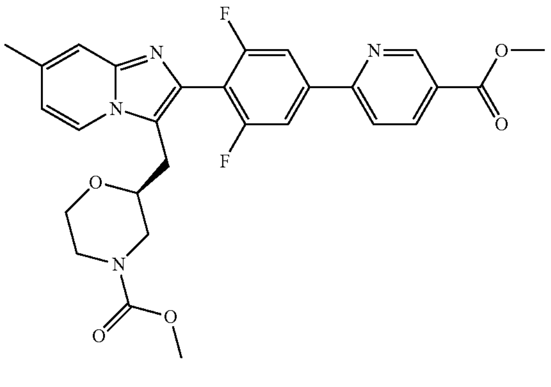

Intermediate 17-2 (130 mg, 0.25 mmol) was dissolved in anhydrous 1,4-dioxane (5 mL) under nitrogen atmosphere, and methyl 6-bromonicotinate (64 mg, 0.30 mmol), potassium carbonate (103 mg, 0.74 mmol), and tetrakis(triphenylphosphine)palladium (30 mg, 0.025 mmol) were added, followed by the addition of water (0.5 mL). The reaction system was reacted at 90° C. for 2 h. Then the reaction system was cooled to room temperature, added with water (20 mL), and extracted with dichloromethane (30 mL×3). The organic phases were combined, washed with saturated brine (30 mL×2), dried over anhydrous magnesium sulfate, filtered and concentrated by rotary evaporation. The crude product was purified by silica gel column chromatography to give intermediate 145-2 (70 mg, 53% yield) in the form of a yellow solid. LC-MS $[M+H]^+$=553.2.

Step (2) Preparation of methyl (S)-2-((2-(2,6-difluoro-4-nicotinic acid)phenyl)-7-methylimidazo[1,2-a]pyridin-3-yl)-methyl)morpholine-4-carboxylate

145

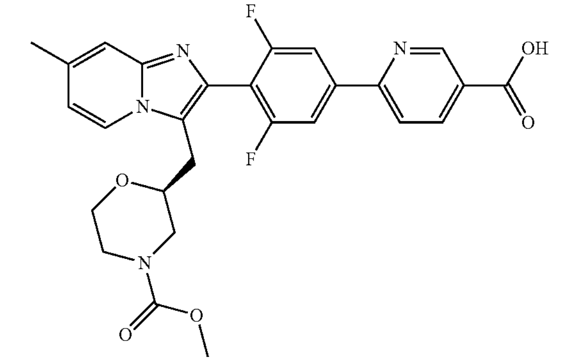

Intermediate 145-2 (70 mg, 0.13 mmol) was dissolved in tetrahydrofuran (1.5 mL), and lithium hydroxide solution (3 M, 0.13 mL) was added dropwise. The reaction system was reacted at room temperature for 1 h. After the reaction was completed, the reaction system was added dropwise with diluted hydrochloric acid (1 M) to adjust the pH to 6, added with water (10 mL), and extracted with dichloromethane (20 mL×3). The organic phases were combined, washed with saturated brine (20 mL), dried over magnesium sulfate, filtered and concentrated by rotary evaporation to give a crude product. The crude product was purified by high performance liquid chromatography to give compound 145 (30.1 mg, 44% yield) in the form of a white solid. LC-MS: $[M+H]^+$=523.6.

$^1$H NMR (400 MHZ, MeOD) δ 9.30 (d, J=2.1 Hz, 1H), 8.88 (d, J=7.1 Hz, 1H), 8.53 (dd, J=8.3, 2.1 Hz, 1H), 8.21 (d, J=8.3 Hz, 1H), 8.13 (d, J=9.3 Hz, 2H), 7.75 (s, 1H), 7.44 (dd, J=7.1, 1.5 Hz, 1H), 4.03-4.01 (m, 1H), 3.87-3.70 (m, 3H), 3.69 (s, 3H), 3.40-3.36 (m, 1H), 3.31-3.23 (m, 2H), 2.98-2.89 (m, 1H), 2.82-2.71 (m, 1H), 2.67 (s, 3H).

Example 146

Preparation of methyl (S)-2-((2-(2,6-difluoro-4-(formamido)pyridinyl)phenyl)-7-methylimidazo[1,2-a]pyridin-3-yl)methyl)morpholine-4-carboxylate

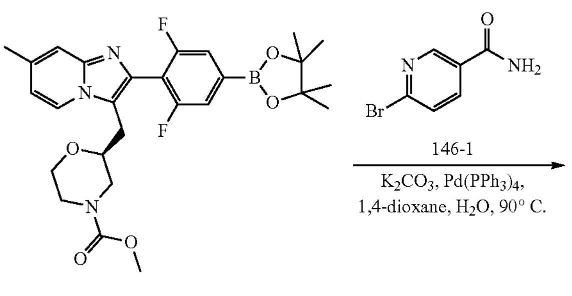

17-2

-continued

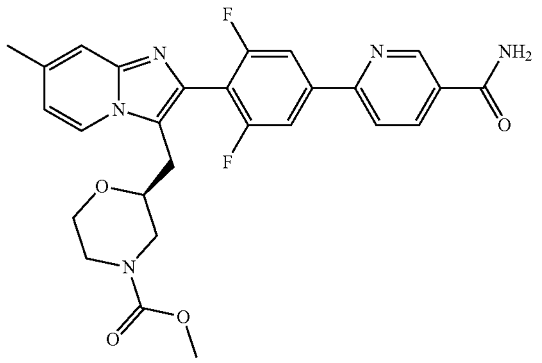

146

Intermediate 17-2 (120 mg, 0.23 mmol) was dissolved in 1,4-dioxane (3 mL) under nitrogen atmosphere, and 6-bromonicotinamide (55 mg, 0.27 mmol), potassium carbonate (95 mg, 0.69 mmol) and tetrakis (triphenylphosphine)palladium (27 mg, 0.023 mmol) were added, followed by the addition of water (0.5 mL). The reaction system was reacted at 90° C. for 2 h. Then the reaction system was cooled to room temperature, added with water (20 mL), and extracted with dichloromethane (30 mL×3). The organic phases were combined, washed with saturated brine (30 mL×2), dried over anhydrous magnesium sulfate, filtered and concentrated by rotary evaporation to give a crude product. The crude product was purified by high performance liquid chromatography to give compound 146 (16.9 mg, 14% yield) in the form of a yellow solid.

LC-MS: $[M+H]^+$=522.6. $^1$H NMR (400 MHZ, MeOD): δ 9.21 (d, J=2.1 Hz, 1H), 8.88 (d, J=7.2 Hz, 1H), 8.42 (dd, J=8.3, 2.3 Hz, 1H), 8.20 (d, J=8.3 Hz, 1H), 8.12 (d, J=9.4 Hz, 2H), 7.75 (s, 1H), 7.44 (dd, J=7.1, 1.4 Hz, 1H), 4.04-4.01 (m, 1H), 3.86-3.71 (m, 3H), 3.70 (s, 3H), 3.40-3.36 (m, 1H), 3.31-3.25 (m, 2H), 2.99-2.90 (m, 1H), 2.83-2.73 (m, 1H), 2.67 (s, 3H).

Example 147

Preparation of methyl (S)-2-((2-(2,6-difluoro-4-hydroxypyridinyl)phenyl)-7-methylimidazo[1,2-a]pyridin-3-yl)methyl)morpholine-4-carboxylate

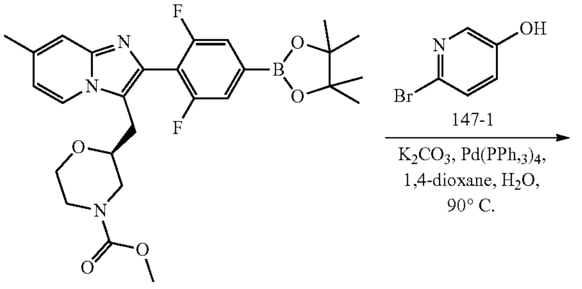

17-2

-continued

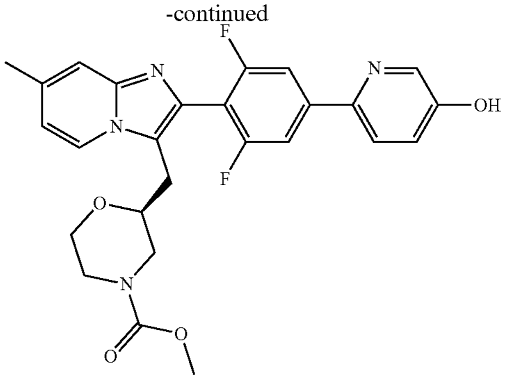

147

Intermediate 17-2 (130 mg, 0.25 mmol) was dissolved in 1,4-dioxane (5 mL) under nitrogen atmosphere, and 2-bromo-5-hydroxypyridine (51 mg, 0.30 mmol), potassium carbonate (102 mg, 0.74 mmol) and tetrakis(triphenylphosphine)palladium (28 mg, 0.025 mmol) were added, followed by the addition of water (0.5 mL). The reaction system was reacted at 90° C. for 2 h. After the reaction was completed, the reaction system was cooled to room temperature, added with water (20 mL), and extracted with dichloromethane (30 mL×3). The organic phases were combined, washed with saturated brine (30 mL×2), dried over anhydrous sodium sulfate, filtered and concentrated by rotary evaporation to give a crude product. The crude product was purified by high performance liquid chromatography to give compound 147 (62.7 mg, 51.4% yield) in the form of a yellow solid.

LC-MS: $[M+H]^+$=495.2. $^1H$ NMR (400 MHZ, DMSO): δ 10.49 (s, 1H), 8.91 (d, J=7.1 Hz, 1H), 8.30 (d, J=2.8 Hz, 1H), 8.08 (d, J=8.7 Hz, 1H), 8.01 (d, J=9.7 Hz, 2H), 7.80 (s, 1H), 7.44 (dd, J=7.1, 1.2 Hz, 1H), 7.34 (dd, J=8.7, 2.9 Hz, 1H), 3.94 (d, J=12.8 Hz, 1H), 3.64-3.62 (m, 3H), 3.58 (s, 3H), 3.34-3.12 (m, 3H), 2.88-2.76 (m, 1H), 2.68-2.62 (m, 1H), 2.58 (s, 3H).

Examples 148-170

Examples 148, 151, 152, 154, 155, 156 and 157 were prepared using the corresponding starting materials according to the method as described in Example 2. Examples 165-166 were prepared according to the synthesis method as described in Example 10; and Example 170 was prepared according to the synthesis method as described in Example 25.

| Number | Compound structure | ESI-MS $[M + H]^+$ |
| --- | --- | --- |
| Example 148 | 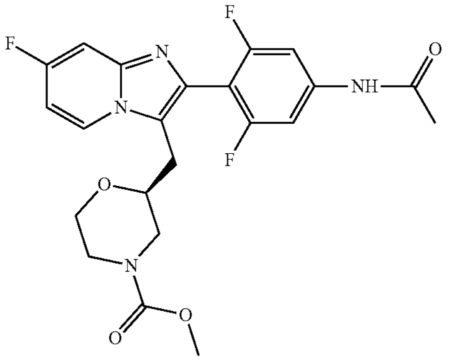 [SMILES: COC(=O)N1CCO[C@@H](Cc2c(-c3c(F)cc(NC(C)=O)cc3F)nc3cc(F)ccn23)C1] | 463.2 |
| Example 151 | 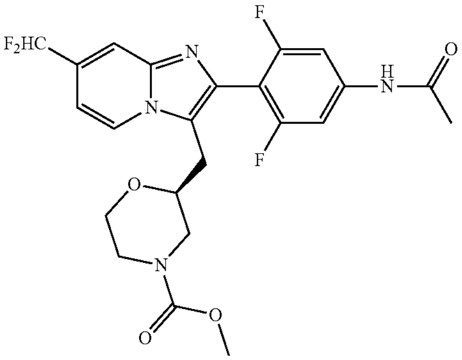 [SMILES: COC(=O)N1CCO[C@@H](Cc2c(-c3c(F)cc(NC(C)=O)cc3F)nc3cc(C(F)F)ccn23)C1] | 495.1 |

-continued
| Number | Compound structure | ESI-MS [M + H]+ |
|---|---|---|
| Example 152 | 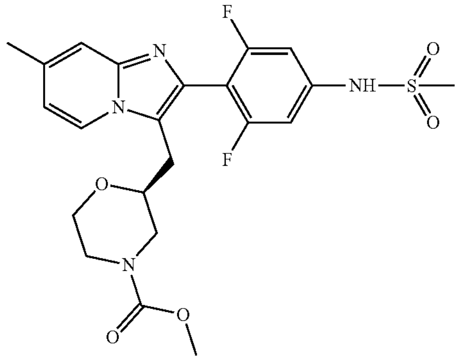 | 495.4 |
| Example 154 | 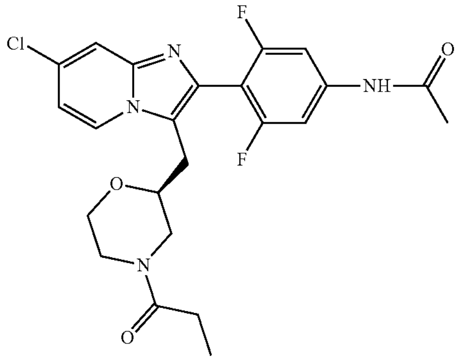 [SMILES: CCC(=O)N1CCO[C@@H](Cc2c(-c3c(F)cc(NC(C)=O)cc3F)nc3cc(Cl)ccn23)C1] | 477.2 |
| Example 155 | 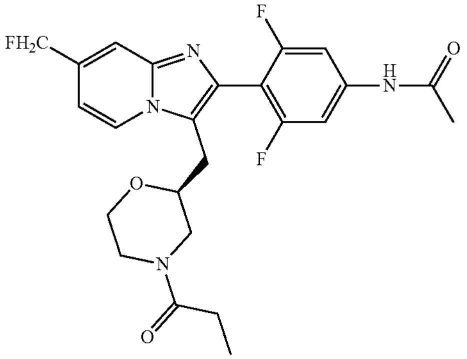 | 475.6 |
| Example 156 | 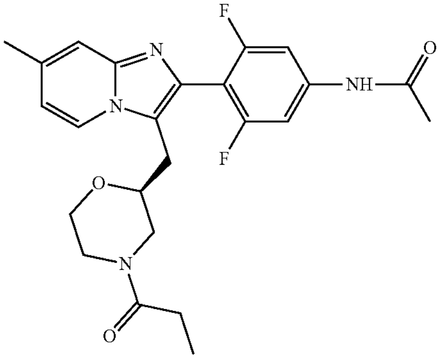 [SMILES: CCC(=O)N1CCO[C@@H](Cc2c(-c3c(F)cc(NC(C)=O)cc3F)nc3cc(C)ccn23)C1] | 457.2 |

-continued
| Number | Compound structure | ESI-MS [M + H]+ |
|---|---|---|
| Example 157 | 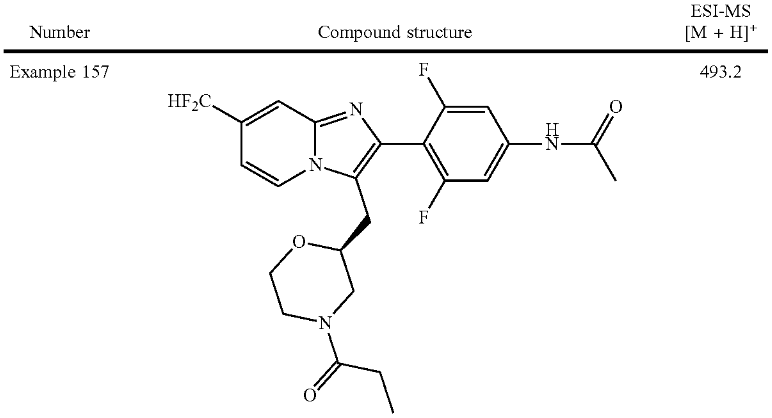 | 493.2 |
| Example 165 | 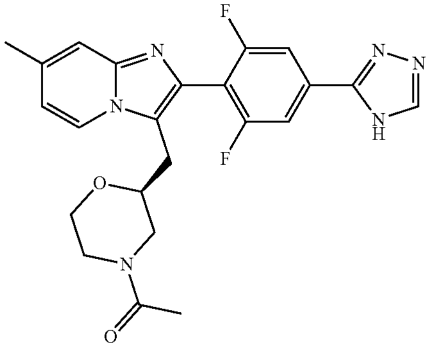 165 | 453.4 |
| Example 166 | 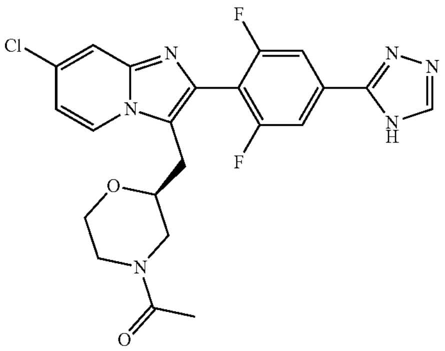 166 | 473.5 |
| Example 170 | 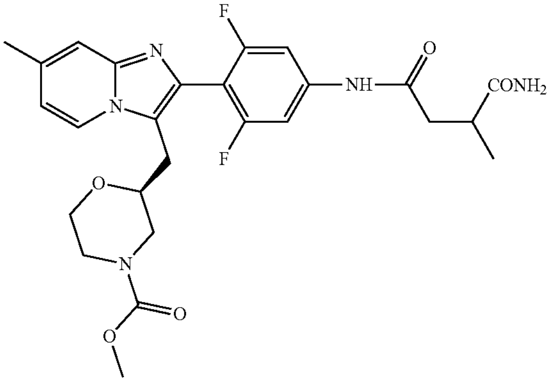 170 | 530.3 |

Example 150

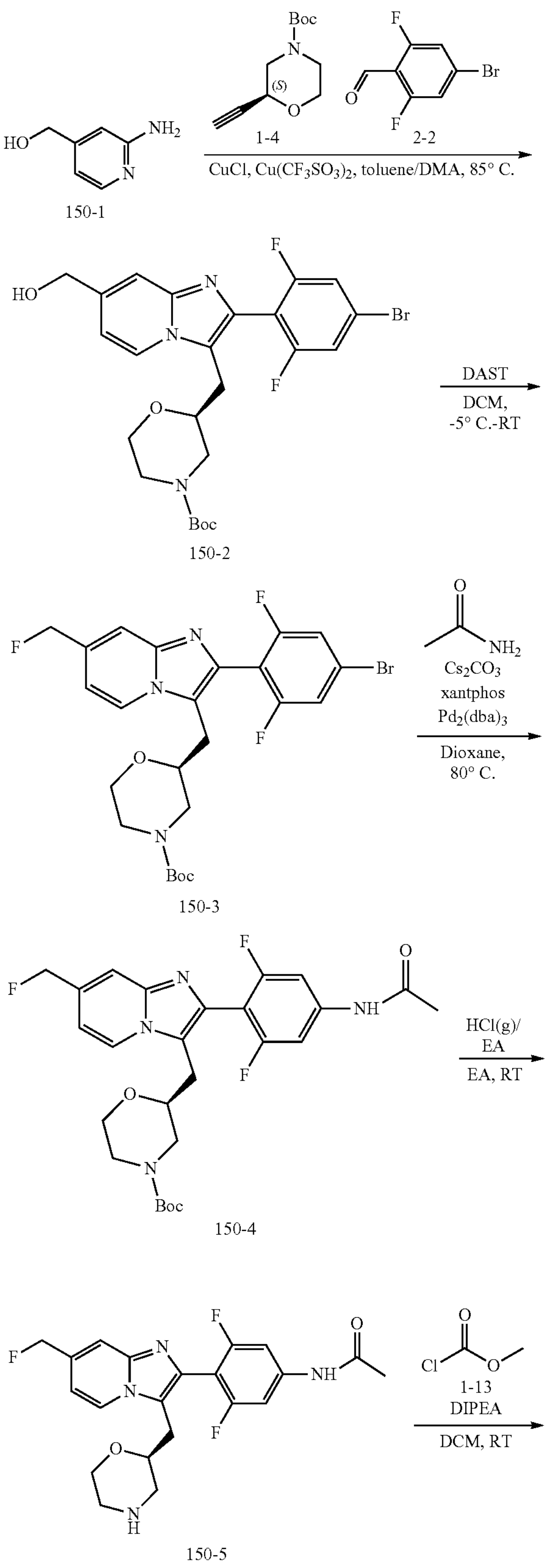

-continued

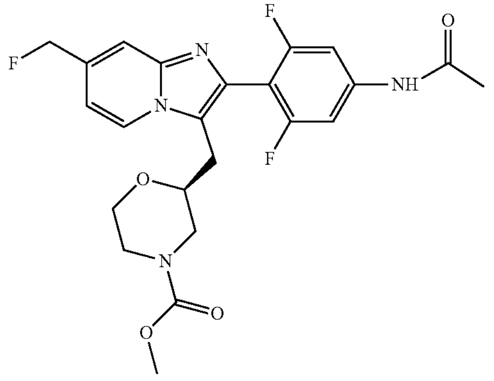

150

Step (1) Preparation of tert-butyl (S)-2-((2-(4-bromo-2,6-difluorophenyl)-7-(hydroxymethyl)imidazo[1,2-a]pyridin-3-yl)methyl)morpholine-4-carboxylate 150-2

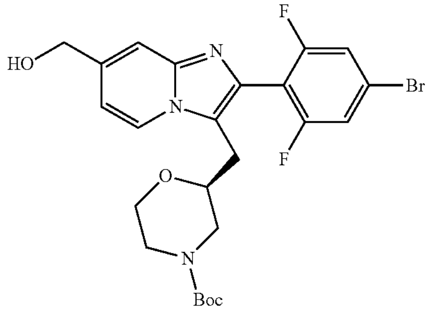

Intermediate 150-1 (2 g, 16 mmol), intermediate 1-4 (3.4 g, 16 mmol), intermediate 2-2 (3.6 g, 16 mmol), CuCl (0.5 g, 6 mmol) and $Cu(CF_3SO_3)_2$ (1.75 g, 6 mmol) were added to toluene (60 mL) sequentially. The reaction system was purged with $N_2$ four times, and stirred at room temperature for 15 min. Then the reaction system was heated to 85° C., added with DMA (1 mL), heated and reacted for 5 h, and cooled and stirred overnight (16.5 h) after the heating was stopped. After the reaction was completed as detected by LCMS, the reaction system was diluted with DCM (100 mL), added with water (80 mL) and 25% aqueous ammonia (15 mL), stirred for 30 min, and left to stand to separate the DCM phase. The aqueous phase was extracted with DCM (100 mL×2). The DCM phases were combined, washed with saturated aqueous ammonium chloride solution and saturated brine sequentially, dried over anhydrous sodium sulfate, and filtered, and the filtrate was concentrated under reduced pressure to give a crude product. The crude product was purified by column chromatography to give intermediate 150-2 (3.4 g) in the form of a light yellow oil.

Step (2)

150-3

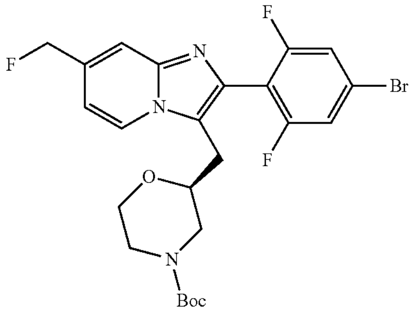

Intermediate 150-2 (1.3 g, 2.42 mmol) was dissolved in DCM (30 mL). The reaction system was purged with $N_2$ three times, and cooled to −5° C. below. Then DAST (0.40 mL, 3.03 mmol) was diluted with DCM (5 mL), and added dropwise to the reaction system. The resulting reaction system was warmed to room temperature and reacted for 16 h. After the reaction was completed as detected by TLC, the reaction system was cooled to 5° C. below, diluted with DCM, slowly poured into saturated $NaHCO_3$ solution at 5° C. below, stirred, and left to stand to separate the DCM phase. The aqueous phase was extracted with DCM (30 mL×2). The DCM phases were combined, washed with saturated brine, dried over anhydrous sodium sulfate, and filtered, and the filtrate was concentrated under reduced pressure to give a crude product. The crude product was purified by silica gel column chromatography to give intermediate 150-3 (0.32 g) in the form of a yellow oil.

Step (3) Preparation of tert-butyl (S)-2-((2-(4-acetamido-2,6-difluorophenyl)-7-(fluoromethyl)imidazo [1,2-a]pyridin-3-yl)methyl)morpholine-4-carboxylate 150-4

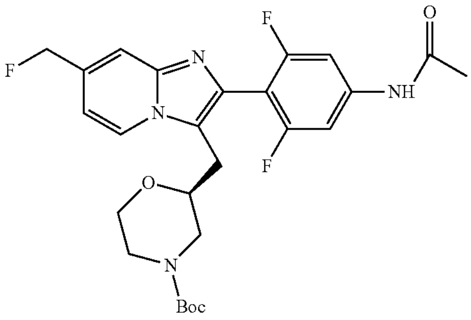

Intermediate 150-3 (0.32 g, 0.59 mmol), acetamide (0.05 g, 0.71 mmol), $Cs_2CO_3$ (0.29 g, 0.71 mmol), and Xantphos (0.07 g, 0.12 mmol) were added to dioxane (8 mL) sequentially. The reaction system was purged with $N_2$ three times, added with $Pd_2(dba)_3$ (0.05 g, 0.06 mmol), purged with $N_2$ three times, and reacted at 80° C. for 19 h. After the reaction was completed as detected by TLC, the reaction system was diluted with DCM (15 mL) and water (30 mL), stirred, and left to stand to separate the DCM phase. The aqueous phase was extracted with DCM (15 mL×2). The DCM phases were combined, washed with saturated brine, dried over anhydrous sodium sulfate, and filtered, and the filtrate was concentrated under reduced pressure to give intermediate 150-4 (0.47 g, crude product) in the form of a red oil, which was used directly in the next step.

Step (4) Preparation of (S)—N-(3,5-difluoro-4-(7-(fluoromethyl)-3-(morpholin-2-ylmethyl)imidazo[1,2-a]pyridin-2-yl)phenyl)acetamide 150-5

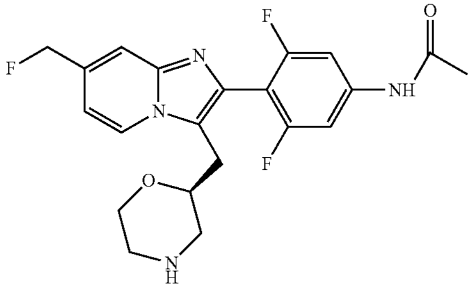

Intermediate 150-4 (0.47 g, crude product) was dissolved in EA (5 mL), and a solution of HCl in EA (15 mL) was added. The reaction system was reacted at room temperature for 5.5 h. After the reaction was completed as detected by TLC, the reaction system was diluted with EA (10 mL) and water (10 mL), back-extracted with stirring to give an aqueous phase, and the EA phase was back-extracted with water (10 mL×1). The aqueous phases were combined, added with DCM (15 mL), adjusted to pH 9-10 with $Na_2CO_3$ solid, stirred, and left to stand to separate the DCM phase. The aqueous phase was extracted with DCM (15 mL×2). The DCM phases were combined, dried over anhydrous sodium sulfate, and filtered, and the filtrate was concentrated under reduced pressure to give intermediate 150-5 (0.2 g) in the form of a red oil.

Step (5) Preparation of methyl (S)-2-((2-(4-acetamido-2,6-difluorophenyl)-7-(fluoromethyl)imidazo [1,2-a]pyridin-3-yl)methyl)morpholine-4-carboxylate

150

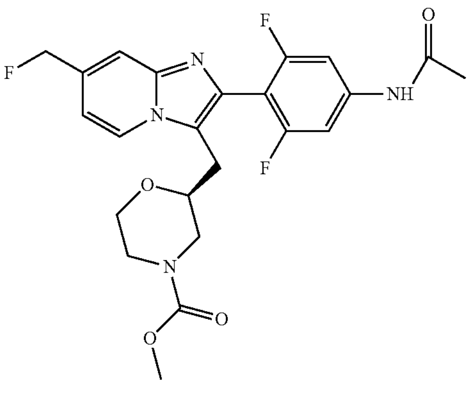

Intermediate 150-5 (100 mg, 0.227 mmol) was dissolved in DCM (4 mL), and DIPEA (0.4 mL) was added. The reaction system was purged with $N_2$ once, and cooled to 5° C. below. Then the reaction system was added dropwise with methyl chloroformate (43 mg, 0.504 mmol), warmed to room temperature and reacted for 1 h. After the reaction was completed as detected by TLC, the reaction system was diluted with DCM (15 mL) and water (20 mL), stirred, and left to stand to separate the DCM phase. The aqueous phase was extracted with DCM (15 mL×2). The DCM phases were combined, washed with saturated brine, dried over anhydrous sodium sulfate, and filtered, and the filtrate was concentrated under reduced pressure to give a crude product. The crude product was separated by prep-HPLC, and lyophilized to give compound 150 (20.2 mg, 98.34% purity) in the form of a white solid.

LC-MS: $[M+H]^+$=477.25. 1H NMR (400 MHZ, CD3OD) δ 8.52 (d, J=7.1 Hz, 1H), 8.52 (d, J=7.1 Hz, 8H), 8.52 (d, J=7.1 Hz, 1H), 7.54 (s, 7H), 7.46-7.37 (m, 13H), 6.99 (d, J=7.1 Hz, 8H), 5.54 (s, 7H), 5.42 (s, 7H), 4.98-4.83 (m, 169H), 4.79 (d, J=15.2 Hz, 2H), 4.58 (s, 9H), 3.80 (t, J=13.0 Hz, 25H), 3.66 (d, J=11.2 Hz, 19H), 3.58 (s, 8H), 3.33 (tt, J=6.6, 3.2 Hz, 27H), 3.21-3.04 (m, 15H), 2.89 (s, 10H), 2.63 (s, 15H), 2.17 (s, 18H).

Example 153

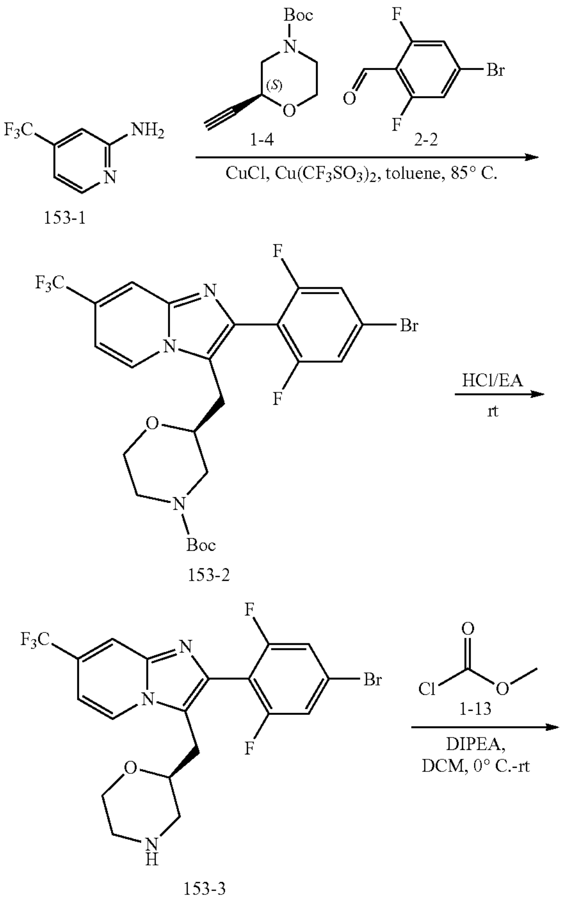

153-1
153-2
153-3

-continued

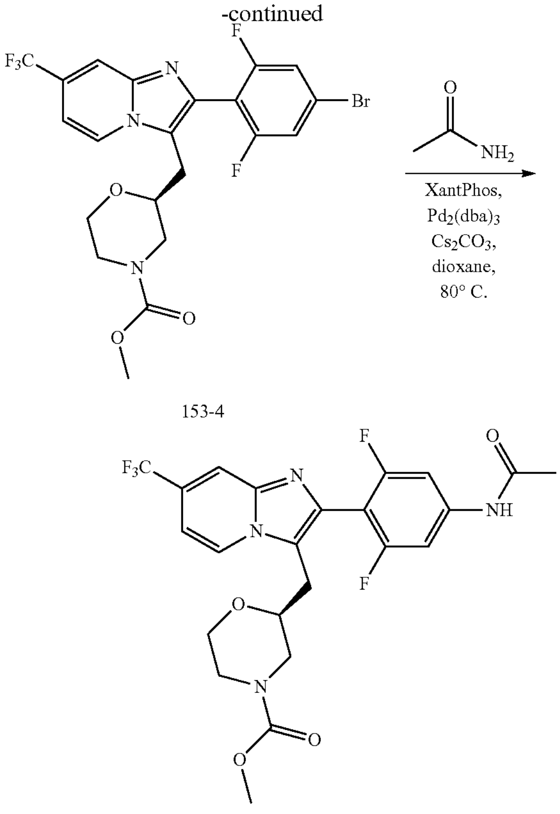

153-4
153

Step (1) Preparation of tert-butyl (S)-2-((2-(4-bromo-2,6-difluorophenyl)-7-(trifluoromethyl)imidazo[1,2-a]pyridin-3-yl)methyl)morpholine-4-carboxylate 153-2

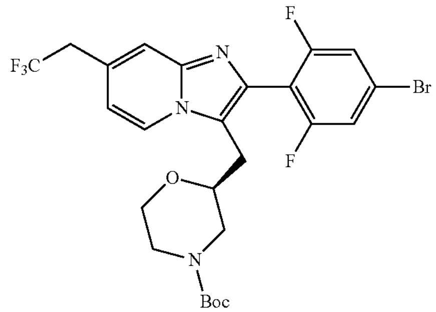

Compound 153-1 (0.77 g, 4.74 mmol), intermediate 1-4 (1.0 g, 4.74 mmol), intermediate 2-2 (1.04 g, 4.74 mmol), CuCl (0.14 g, 1.42 mmol) and $Cu(CF_3SO_3)_2$ (0.51 g, 1.42 mmol) were dissolved in toluene (10 mL) sequentially. The reaction system was purged with $N_2$ four times, and stirred at room temperature for 15 min. Then the reaction system was heated to 85° C., added with DMA (0.3 mL), heated and reacted for 6 h, and cooled and stirred overnight (16 h) after the heating was stopped. After the reaction was completed as detected by LCMS, the reaction system was diluted with DCM (100 mL), added with water (100 mL) and 25% aqueous ammonia (10 mL), stirred for 10 min, and left to stand to separate the DCM phase. The aqueous phase was extracted with DCM (50 mL×3). The DCM phases were combined, washed with saturated aqueous ammonium chloride solution and saturated brine sequentially, dried over anhydrous sodium sulfate, and filtered, and the filtrate was concentrated under reduced pressure to give a crude product. The crude product was purified by silica gel column chromatography (a small amount of methanol) to give intermediate 153-2 (0.8 g, 86.37% purity) in the form of a yellow foamy solid. LC-MS: $[M+H]^+$=578.03.

Step (2) Preparation of (S)-2-((2-(4-bromo-2,6-difluorophenyl)-7-(trifluoromethyl)imidazo[1,2-a]pyridin-3-yl)methyl)morpholine 153-3

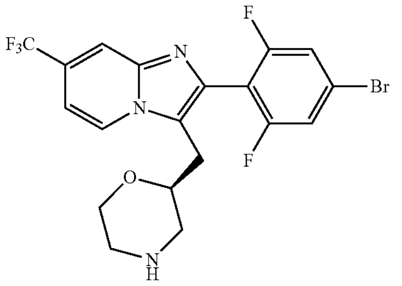

Intermediate 153-2 (0.8 mg, 1.4 mmol) was dissolved in EA (10 mL). The reaction system was cooled to ° C. below. Then the reaction system was added with a solution of HCl in EA (3 M, 15 mL), and reacted at room temperature for 1 h and 50 min. After the reaction was completed as detected by LCMS, the reaction system was diluted with EA (10 mL) and back-extracted with water (20 mL×2). The aqueous phases were combined, added with DCM (20 mL), adjusted to pH 8-9 with $Na_2CO_3$ solid, stirred, and left to stand to separate the DCM phase. The aqueous phase was extracted with DCM (20 mL×2). The DCM phases were combined, dried over anhydrous sodium sulfate, and filtered, and the filtrate was concentrated under reduced pressure to give intermediate 153-3 (0.65 g, 94.48% purity) in the form of a yellow oil. LC-MS: $[M+H]^+$=476.0.

Step (3) Preparation of methyl (S)-2-((2-(4-bromo-2,6-difluorophenyl)-7-(trifluoromethyl)imidazo[1,2-a]pyridin-3-yl)methyl)morpholine-4-carboxylate 153-4

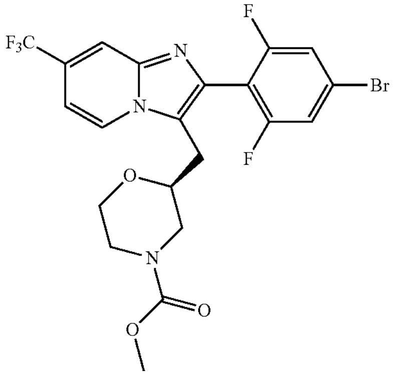

Intermediate 153-3 (650 mg, 1.4 mmol) was dissolved in DCM (10 mL), and DIPEA (0.21 mL) was added. The reaction system was purged with $N_2$ once, and cooled to 5° C. below. Then the reaction system was added dropwise with methyl chloroformate (150 mg, 1.6 mmol), and reacted at room temperature for 2 h. After the reaction was completed as detected by LCMS, the reaction system was diluted with DCM (10 mL) and water (30 mL), stirred, and left to stand to separate the DCM phase. The aqueous phase was extracted with DCM (15 mL×2). The DCM phases were combined, dried over anhydrous sodium sulfate, and concentrated at 40° C. to give intermediate 153-4 (650 mg, 93.67% purity, crude product) in the form of a yellow foamy solid. LC-MS: $[M+H]^+$=534.05.

Step (4) Preparation of methyl (S)-2-((2-(4-acetamido-2,6-difluorophenyl)-7-(trifluoromethyl)imidazo[1,2-a]pyridin-3-yl)methyl)morpholine-4-carboxylate

153

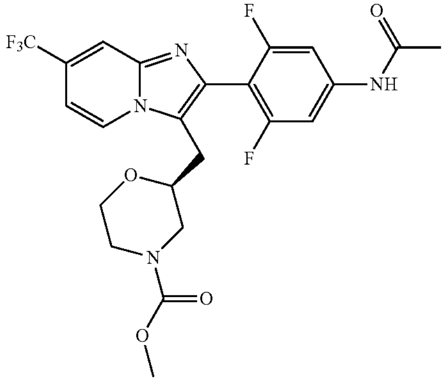

Intermediate 153-4 (300 mg, 0.56 mmol), acetamide (70 mg, 0.84 mmol), $Cs_2CO_3$ (350 mg, 0.84 mmol), Xantphos (40 mg, 0.056 mmol), and $Pd_2(dba)_3$ (60 mg, 0.056 mmol) were dissolved in dioxane (10 mL) sequentially. The reaction system was purged with $N_2$ four times and reacted at 80° C. for 20 h. After the reaction was completed as detected by LCMS, the reaction system was diluted with DCM (15 mL) and water (30 mL), stirred, and left to stand to separate the DCM phase. The aqueous phase was extracted with DCM (15 mL×2). The DCM phases were combined, washed with saturated brine, dried over anhydrous sodium sulfate, and filtered, and the filtrate was concentrated under reduced pressure to give a crude product. The crude product was separated by prep-HPLC ($H_2O/CH_3CN$), and lyophilized to give compound 153 (60 mg, 99.01% purity) in the form of a white solid. LC-MS: $[M+H]^+$=513.15.

$^1H$ NMR (400 MHZ, d-DMSO) δ 10.45 (s, 1H), 8.74 (d, J=7.3 Hz, 1H), 8.08 (s, 1H), 7.45 (d, J=9.9 Hz, 2H), 7.24 (dd, J=7.3, 1.8 Hz, 1H), 3.78 (d, J=12.9 Hz, 1H), 3.65 (t, J=10.7 Hz, 2H), 3.56 (s, 3H), 3.51 (s, 1H), 3.23 (td, J=11.8, 2.8 Hz, 1H), 3.10 (dd, J=15.4, 7.2 Hz, 2H), 2.81 (s, 1H), 2.54 (s, 1H), 2.11 (s, 3H).

Example 158

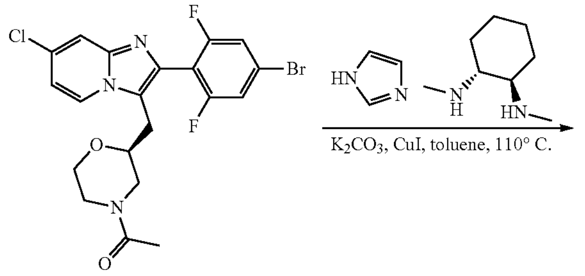

158-1

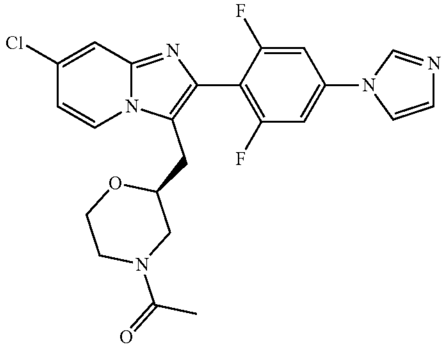

158

Step (1) Preparation of (S)-1-(2-((2-(4-bromo-2,6-difluorophenyl)-7-chloroimidazo[1,2-a]pyridin-3-yl)methyl)morpholino)ethan-1-one 158-1

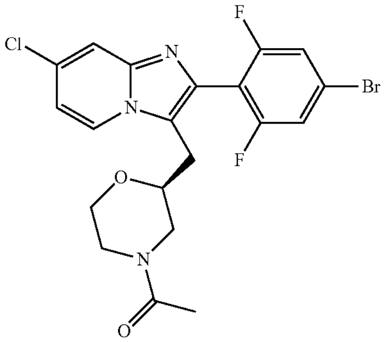

The compound was prepared according to the preparation method for intermediate 2-7. LC-MS: $[M+H]^+$=484.0.

Step (2) Preparation of (S)-1-(2-((7-chloro-2-(2,6-difluoro-4-(1H-imidazol-1-yl)phenyl)imidazo[1,2-a]pyridin-3-yl)methyl)morpholino)ethan-1-one

158

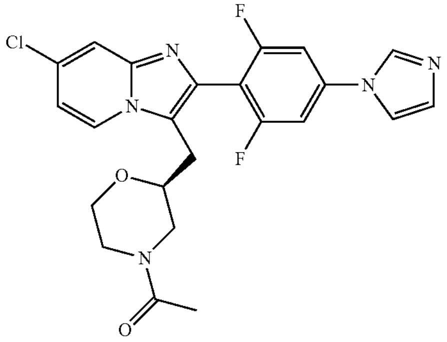

Intermediate 158-1 (120 mg, 0.25 mmol) was dissolved in toluene (2 mL), and imidazole (25 mg, 0.37 mmol), potassium carbonate (103 mg, 0.75 mmol), copper(I) iodide (4.7 mg, 0.025 mmol) and trans-(1R,2R)—N,N'-dimethyl-1,2-cyclohexanediamine (3.5 mg, 0.025 mmol) were added under nitrogen atmosphere. The reaction system was reacted at 110° C. overnight. After the reaction was completed, the reaction system was cooled to room temperature and filtered, and the filtrate was added with water (20 mL) and extracted with dichloromethane (50 mL×3). The organic phases were combined, washed with saturated brine (50 mL), dried over anhydrous sodium sulfate, filtered and concentrated by rotary evaporation to give a crude product. The crude product was purified by preparative chromatography to give compound 158 (13.6 mg, 12% yield) in the form of a white solid. MS $[M+H]^+$=471.7.

$^1H$ NMR (400 MHZ, MeOD) δ 8.59 (t, 1H), 8.39 (s, 1H), 7.79 (s, 1H), 7.65-7.63 (m, 1H), 7.61-7.57 (m, 2H), 7.23 (s, 1H), 7.09-7.00 (m, 1H), 4.33-4.24 (m, 1H), 3.92-3.54 (m, 3H), 3.47-3.36 (m, 1H), 3.23-3.12 (m, 2H), 3.01-2.63 (m, 1H), 2.53-2.45 (m, 1H), 2.06 (d, 3H).

Example 159

Preparation of (S)-1-(2-((7-chloro-2-(2,6-difluoro-4-(oxazol-2-yl)phenyl)imidazo[1,2-a]pyridin-3-yl)methyl)morpholino)ethan-1-one

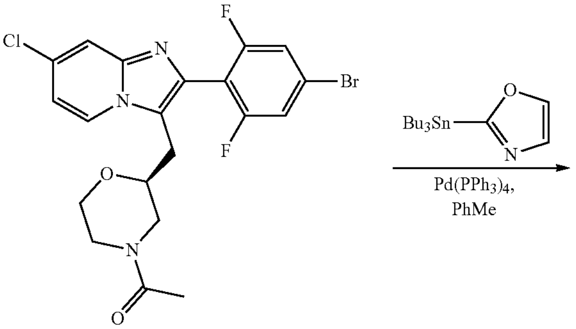

158-1

-continued

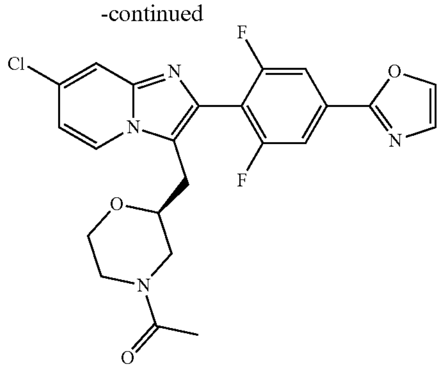

159

Intermediate 158-1 (4.2 g, 8.66 mmol) and tetrakis(triphenylphosphine)palladium (2.0 g, 1.73 mmol) were added to toluene (125 mL) sequentially. The reaction system was stirred under nitrogen atmosphere. Then the reaction system was injected with 2-(tributylstannyl)oxazole (4.9 g, 13.00 mmol) via a syringe, and heated to 80° C. and reacted overnight. Little intermediate 158-1 was remained as detected by TLC, and the work-up was directly performed. The reaction system was cooled, added with saturated aqueous potassium fluoride solution (100 mL), and stirred for 30 min. Then the reaction was extracted with DCM (100 mL), followed by liquid separation. The aqueous phase was back-extracted with DCM (50 mL×2). The organic phases were combined, washed with saturated brine (200 mL), dried over anhydrous sodium sulfate, and concentrated by rotary evaporation. The crude product was purified by preparative chromatography to give compound 159 (0.49 g, 99% purity) in the form of a white solid. LC-MS: $[M+H]^+$=473.05.

$^1$H NMR (400 MHz, dmso) δ 8.66-8.55 (m, 18H), 8.64-8.56 (m, 17H), 8.34 (s, 16H), 8.34 (s, 14H), 7.77 (dd, J=7.6, 2.5 Hz, 45H), 7.77 (dd, J=7.6, 2.5 Hz, 47H), 7.50 (s, 15H), 7.50 (s, 14H), 7.08 (td, J=7.1, 1.9 Hz, 17H), 7.08 (td, J=7.1, 1.9 Hz, 17H), 4.20 (d, J=12.8 Hz, 13H), 4.20 (d, J=12.8 Hz, 11H), 4.05 (d, J=12.0 Hz, 9H), 4.05 (d, J=12.0 Hz, 13H), 3.74 (d, J=12.8 Hz, 9H), 3.70 (dd, J=30.3, 12.1 Hz, 29H), 3.67 (d, J=11.5 Hz, 17H), 3.55 (d, J=13.5 Hz, 19H), 3.45 (dd, J=7.2, 3.2 Hz, 11H), 3.58-3.20 (m, 61H), 3.26 (dd, J=11.6, 9.5 Hz, 11H), 3.26 (dd, J=11.6, 9.5 Hz, 31H), 3.26 (dd, J=11.6, 9.5 Hz, 29H), 3.20-2.94 (m, 51H), 3.23-3.09 (m, 38H), 2.80 (dd, J=12.7, 10.7 Hz, 9H), 2.80 (dd, J=12.7, 10.7 Hz, 10H), 2.55 (d, J=3.1 Hz, 6H), 2.64-2.45 (m, 22H), 2.39-2.22 (m, 12H), 2.36-2.24 (m, 11H), 1.92 (s, 47H), 1.92 (s, 48H).

Example 160

Preparation of (S)-1-(2-((7-chloro-2-(2,6-difluoro-4-(1H-pyrazol-1-yl)phenyl)imidazo[1,2-a]pyridin-3-yl)methyl)morpholino)ethan-1-one

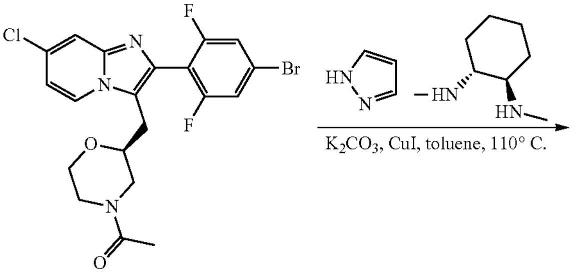

158-1

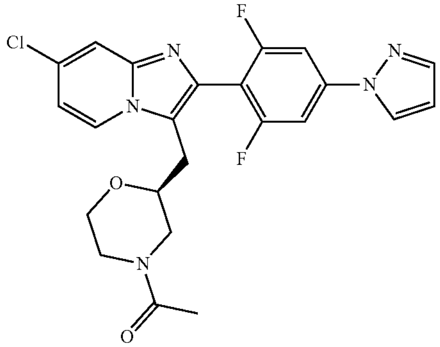

160

Intermediate 158-1 (170 mg, 0.35 mmol) was dissolved in toluene (2 mL), and parazole (36 mg, 0.53 mmol), potassium carbonate (145 mg, 1.05 mmol), copper(I) iodide (7 mg, 0.037 mmol) and trans-(1R,2R)—N,N-dimethyl-1,2-cyclohexanediamine (5 mg, 0.035 mmol) were added under nitrogen atmosphere. The reaction system was reacted at 110° C. overnight. After the reaction was completed, the reaction system was cooled to room temperature and filtered, and the filter cake was washed with dichloromethane. The filtrate was added with water (30 mL) and extracted with dichloromethane (50 mL×3). The organic phases were combined, washed with saturated brine (50 mL), dried over anhydrous sodium sulfate, filtered and concentrated by rotary evaporation to give a crude product. The crude product was purified by preparative chromatography to give compound 160 (5.8 mg, 3.5% yield) in the form of a white solid. MS $[M+H]^+$=471.7.

1H NMR (400 MHZ, MeOD) δ 8.93 (dd, J=7.4, 3.2 Hz, 1H), 8.47 (d, J=2.6 Hz, 1H), 8.02-7.98 (m, 1H), 7.85-7.82 (m, 3H), 7.51 (dd, J=7.4, 2.0 Hz, 1H), 6.65-6.64 (m, 1H), 4.43-4.40 (m, 0.5H), 4.29-4.26 (m, 0.5H), 3.92-3.89 (m, 1H), 3.86-3.80 (m, 1H), 3.72-3.69 (m, 1H), 3.46-3.36 (m, 1H), 3.31-3.21 (m, 2H), 3.08-3.02 (m, 1H), 2.75-2.70 (m, 0.5H), 2.58-2.52 (m, 0.5H), 2.08 (s, 3H).

Example 161

Preparation of methyl (S)-2-((2-(4-amino-2,6-difluorophenyl)-7-chloroimidazo[1,2-a]pyridin-3-yl)methyl)morpholine-4-carboxylate

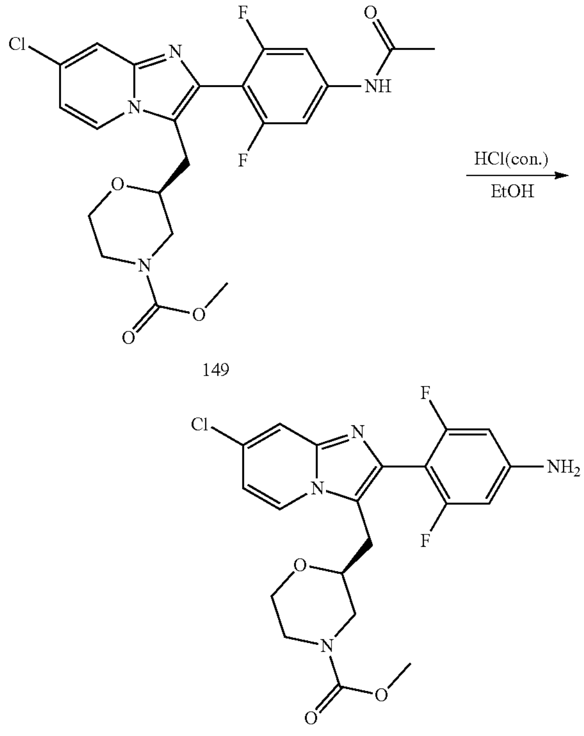

149

161

Compound 149 (0.3 g) was dissolved in EtOH (4 mL), and concentrated HCl (6 mL) was added. The reaction system was stirred at 100° C. for 2 h. The starting material was consumed, and a new spot was generated as detected by TLC. Then the reaction system was concentrated. The crude product was separated by preparative reverse phase chromatography to give compound 161 (0.14 g) in the form of a white solid, MS $[M+H]^+$=437.2.

$^1$H-NMR (1H NMR (400 MHZ, DMSO) δ 8.44, 7.56, 6.88, 6.68, 6.68, 4.07, 4.05, 3.96, 3.93, 3.82, 3.78, 3.69, 3.51, 3.46, 2.73, 2.48.) (NB190027 March 2).

Example 162

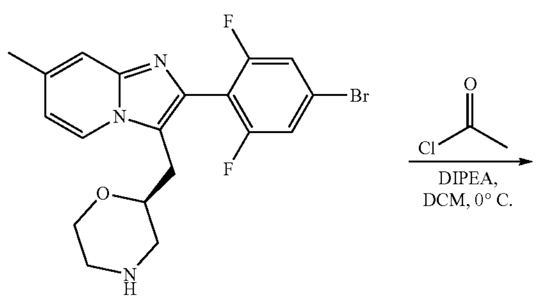

2-5

-continued

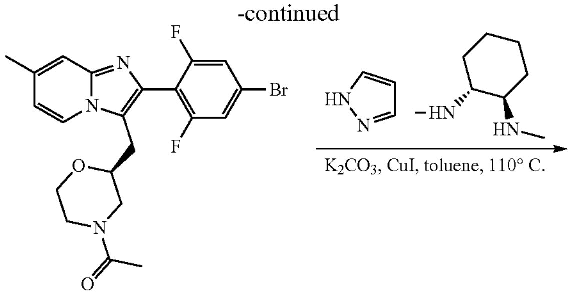

162-1

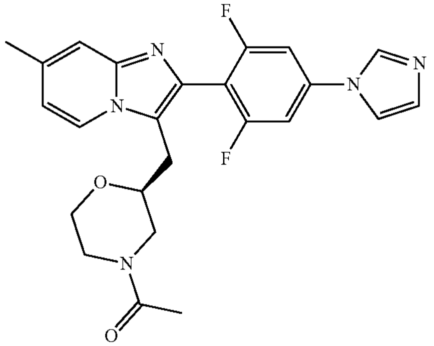

162

Step (1) Preparation of (S)-1-(2-((2-(4-bromo-2,6-difluorophenyl)-7-methylimidazo[1,2-a]pyridin-3-yl)methyl)morpholino)ethan-1-one 162-1

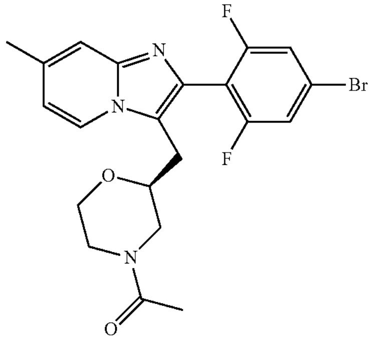

Intermediate 2-5 (1.20 g, 2.84 mmol) and N,N-diisopropylethylamine (1.10 g, 8.51 mmol) were dissolved in dichloromethane (6 mL), and acetyl chloride (268 mg, 3.41 mmol) was added dropwise in an ice water bath with the temperature maintained at 0° C. After the completion of the dropwise addition was completed, the reaction system was reacted at 0° C. for 2 h. After the reaction was completed, the reaction system was added with water (30 mL) and extracted with dichloromethane (50 mL×3). The organic phases were combined, washed with saturated brine (50 mL), dried over anhydrous sodium sulfate, filtered and concentrated by rotary evaporation to give a crude product. The crude product was purified by silica gel column chromatography (petroleum ether:ethyl acetate=5:1) to give intermediate 162-1 (700 mg, 53.8% yield) in the form of a yellow oil. MS $[M+H]^+$=464.9.

Step (2) Preparation of (S)-1-(2-((2-(2,6-difluoro-4-(1H-imidazol-1-yl)phenyl)-7-methylimidazo[1,2-a]pyridin-3-yl)methyl)morpholino)ethan-1-one

162

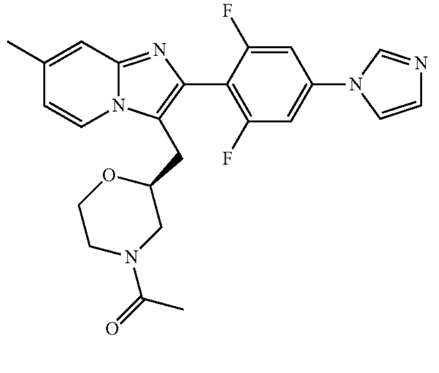

Intermediate 162-1 (150 mg, 0.32 mmol) was dissolved in toluene (2 mL), and imidazole (33 mg, 0.48 mmol), potassium carbonate (135 mg, 0.98 mmol), copper(I) iodide (6 mg, 0.032 mmol) and trans-(1R,2R)—N,N'-dimethyl-1,2-cyclohexanediamine (4.6 mg, 0.032 mmol) were added under nitrogen atmosphere. The reaction system was reacted at 110° C. overnight. After the reaction was completed, the reaction system was cooled to room temperature and filtered, and the filtrate was added with water (20 mL) and extracted with dichloromethane (30 mL×3). The organic phases were combined, washed with saturated brine (50 mL), dried over anhydrous sodium sulfate, filtered and concentrated by rotary evaporation to give a crude product. The crude product was purified by preparative chromatography to give compound 162 (21.3 mg, 14.6% yield) in the form of a white solid. MS $[M+H]^+$=451.8.

1H NMR (400 MHZ, MeOD) δ 8.48 (t, 1H), 8.42 (s, 1H), 7.80 (s, 1H), 7.59 (t, 2H), 7.39 (s, 1H), 7.24 (s, 1H), 6.97-6.91 (m, 1H), 4.33-4.23 (m, 1H), 3.84-3.81 (m, 1H), 3.79-3.68 (m, 1H), 3.67-3.56 (m, 1H), 3.45-3.34 (m, 1H), 3.22-3.21 (m, 0.5H), 3.17-3.15 (m, 2H), 2.98-2.92 (m, 0.5H), 2.73-2.67 (m, 0.5H), 2.49 (s, 3H), 2.47-2.44 (m, 0.5H), 2.05 (d, 3H).

Example 163

Preparation of (S)-1-(2-((2-(2,6-difluoro-4-(oxazol-2-yl)phenyl)-7-methylimidazo[1,2-a]pyridin-3-yl)methyl)morpholino)ethan-1-one

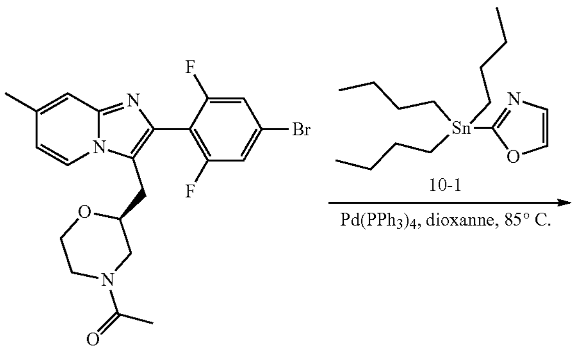

162-1

-continued

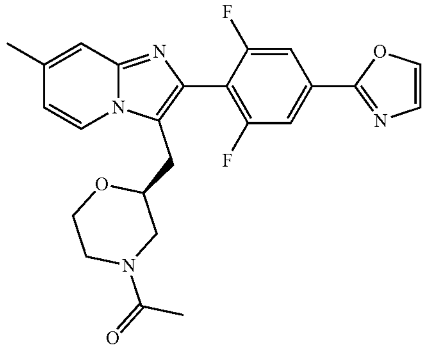

163

Intermediate 162-1 (150 mg, 0.32 mmol) was dissolved in 1,4-dioxane (2 mL), and 2-(tributylstannyl)oxazole (174 mg, 0.48 mmol) and tetrakis(triphenylphosphine)palladium (37 mg, 0.032 mmol) were added under nitrogen atmosphere. The reaction system was reacted at 85° C. overnight. After the reaction was completed, the reaction system was cooled to room temperature and filtered, and the filtrate was added with water (30 mL) and extracted with dichloromethane (50 mL×3). The organic phases were combined, washed with saturated brine (50 mL), dried over anhydrous sodium sulfate, filtered and concentrated by rotary evaporation to give a crude product. The crude product was purified by preparative chromatography to give compound 163 (78.8 mg, 54% yield) in the form of a white solid. MS [M+H]=452.8.

$^1$H NMR (400 MHZ, MeOD) δ 8.47 (t, 1H), 8.11 (s, 1H), 7.85-7.75 (m, 2H), 7.42 (s, 1H), 7.39 (s, 1H), 6.93 (d, J=6.1 Hz, 1H), 4.32-4.22 (m, 1H), 3.84-3.76 (m, 1H), 3.69-3.65 (m, 1H), 3.61-3.54 (m, 1H), 3.45-3.35 (m, 1H), 3.17-3.16 (m, 2H), 2.99-2.88 (m, 1H), 2.74-2.63 (m, 1H), 2.49 (s, 3H), 2.04 (d, 3H).

Example 164

Preparation of methyl (S)-2-(2-(2,6-difluoro-4-(3-propionyl-1H-pyrazol-1-yl)phenyl)-7-methylimidazo[1,2-a]pyridin-3-yl)methyl)morpholine-4-carboxylate

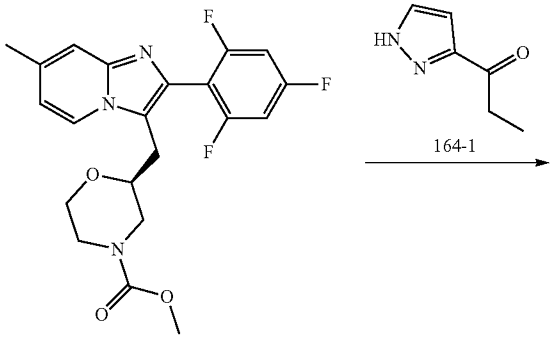

134-7

-continued

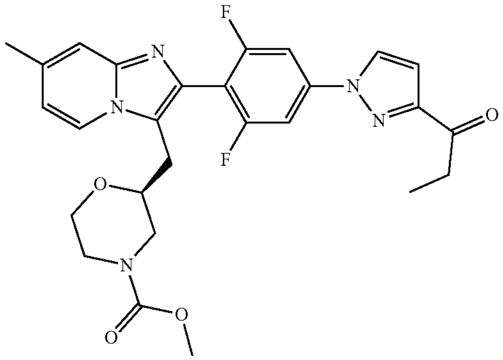

164

-continued

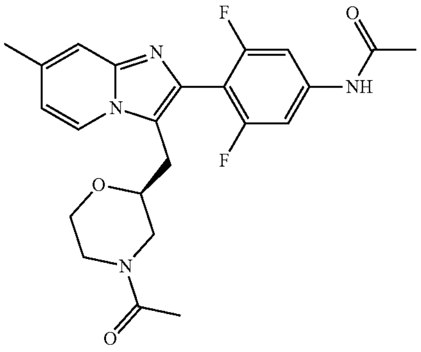

167

Intermediate 134-7 (50 mg, 0.12 mmol), 1-(1H-pyrazol-3-yl) propan-1-one (30 mg, 0.12 mmol) and potassium carbonate (30 mg, 0.36 mmol) were added to dimethyl sulfoxide (5 mL). The reaction system was stirred at 130° C. for 4 h under nitrogen atmosphere. The the reaction system was cooled to room temperature and filtered, and the filtrate was dispersed in ethyl acetate (15 mL), washed with saturated brine (20 mL), dried over anhydrous sodium sulfate, filtered and concentrated. The crude product was purified by preparative chromatography to give compound 164 (5 mg, 7.5% yield) in the form of a yellow solid.

MS $[M+H]^+$=523.8. $^1$H NMR (400 MHZ, d4-MeOD) δ 8.51 (d, J=2.7 Hz, 1H), 8.43 (d, J=6.9 Hz, 1H), 7.80 (d, J=8.5 Hz, 2H), 7.37 (s, 1H), 7.03 (d, J=2.6 Hz, 1H), 6.89 (dd, J=7.0, 1.5 Hz, 1H), 3.89-3.78 (m, 3H), 3.66 (s, 3H), 3.68-3.58 (m, 1H), 3.42-3.37 (m, 1H), 3.21-3.12 (m, 4H), 2.94-2.85 (m, 1H), 2.66-2.62 (m, 1H), 2.48 (s, 3H), 1.25 (t, J=7.3 Hz, 3H).

Example 167

Preparation of (S)—N-(4-(3-((4-acetylmorpholin-2-yl)methyl)-7-methylimidazo[1,2-a]pyridin-2-yl)-3,5-difluorophenyl)acetamide

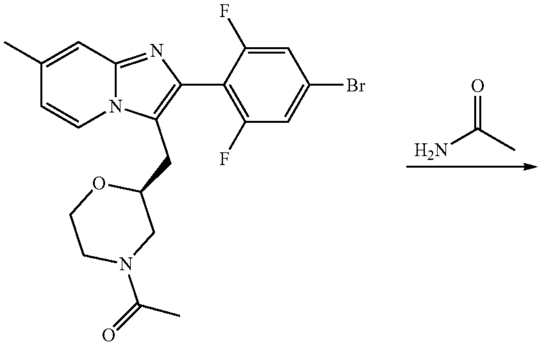

162-1

Intermediate 162-1 (240 mg, 0.518 mmol) and acetamide (45.9 mg, 0.778 mmol), cesium carbonate (150 mg, 0.778 mmol) and 4,5-bis(diphenylphosphino)-9,9-dimethylxanthene (6.00 mg, 0.010 mmol) were added to a reaction flask, and 1,4-dioxane was added. The reaction system was purged with $N_2$, added with tris(dibenzylideneacetone) dipalladium (9.50 mg, 0.010 mmol), purged with $N_2$ again, and heated to 80° C. and reacted for 4 h. After the reaction was completed as monitored by LCMS, the reaction system was added with water, and extracted with dichloromethane (30 mL×2). The ester phase was dried over anhydrous sodium sulfate, and concentrated to remove dichloromethane. The residue was purified by preparative high performance liquid chromatography to give compound 167 (102 mg, 52.4% yield) in the form of a white solid. LC-MS $[M+H]^+$=443.1. $^1$H NMR (400 MHZ, DMSO-$d_6$) δ 10.40 (s, 1H), 8.42-8.35 (m, 1H), 7.41 (dd, J=9.8, 1.7 Hz, 2H), 7.32 (s, 1H), 6.80 (dd, J=9.6, 4.1 Hz, 1H), 4.07 (dd, J=23.0, 13.0 Hz, 1H), 3.73-3.56 (m, 2H), 3.51-3.36 (m, 1H), 3.32-3.22 (m, 1H), 3.15 (td, J=11.7, 2.6 Hz, 1H), 3.01 (dd, J=5.8, 2.7 Hz, 2H), 2.77 (dd, J=12.9, 10.5 Hz, 1H), 2.59-2.52 (m, 1H), 2.37 (s, 3H), 2.26 (dd, J=12.6, 11.1 Hz, 1H), 2.10 (s, 3H), 1.91 (d, J=12.7 Hz, 3H).

Example 168

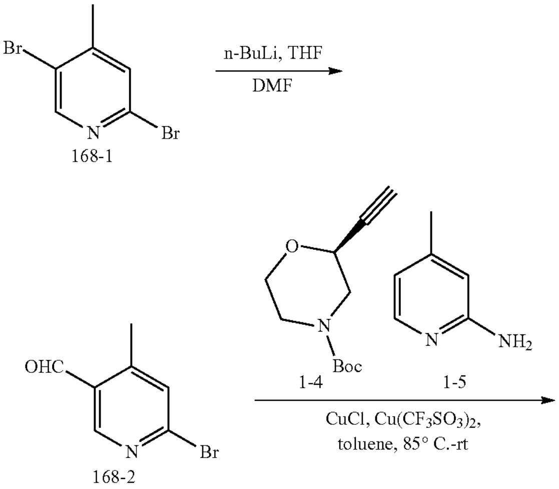

-continued

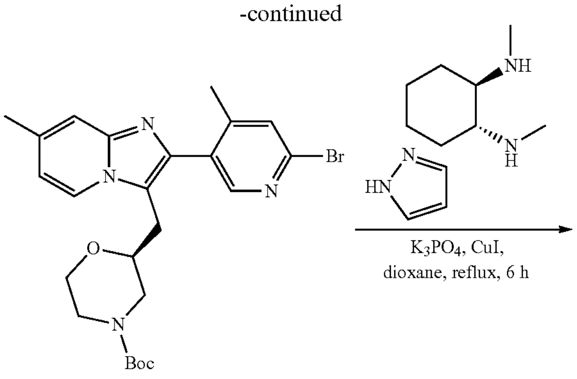

168-3

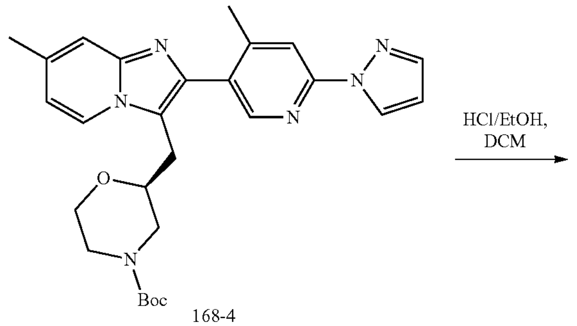

168-4

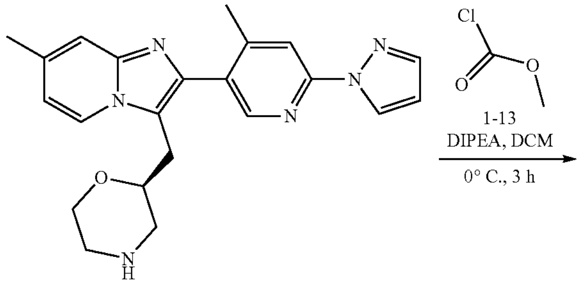

168-5

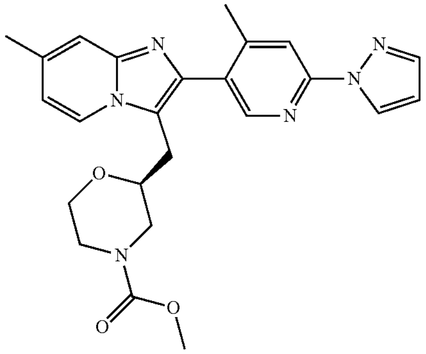

168

Step (1) Preparation of 6-bromo-4-methyl nicotinaldehyde 168-2

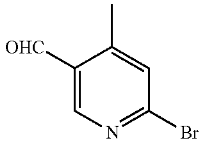

2,5-dibromo-4-methylpyridine (5.0 g, 17.19 mmol) was dissolved in tetrahydrofuran (60 mL) under nitrogen atmosphere. The reaction system was cooled to ~78° C., added with n-butyllithium (7.5 mL, 2.4 N), and stirred at this temperature for 30 min. Then the reaction system was added with N,N-dimethylformamide (2.5 g, 34.38 mmol), and reacted at −78° C. for 3 h. The resulting reaction system was added with diluted hydrochloric acid (1 N, 20 mL) to quench the reaction, diluted with ethyl acetate (100 mL), washed with saturated sodium bicarbonate solution (80 mL) and saturated brine (80 mL) sequentially, dried over anhydrous sodium sulfate, filtered and concentrated. The residue was purified by silica gel column chromatography to give intermediate 168-2 (2.3 g, 54% yield) in the form of a white solid. LC-MS $[M+H]^+$: 199.8.

Step (2) Preparation of tert-butyl (S)-2-((2-(6-bromo-4-methylpyridin-3-yl)-7-methylimidazo[1,2-a]pyridin-3-yl)methyl)morpholine-4-carboxylate 168-3

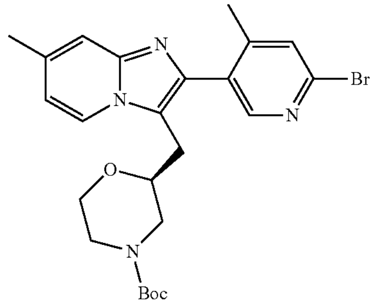

Intermediate 168-2 (320 mg, 1.50 mmol), tert-butyl (2S)-2-etbyny lmorpholin-4-ylcarboxylate (317 mg, 1.50 mmol), 4-methylpyridin-2-amine (162 mg, 1.50 mmol), copper(I) chloride (45 mg, 0.45 mmol) and copper(II) trifluoromethanesulfonate (163 mg, 0.45 mmol) were added to anhydrous toluene (6 mL) under nitrogen atmosphere. The reaction system was heated to 85° C., added dropwise with N,N-dimethylacetamide (0.1 mL), and stirred at 85° C. overnight. After the reaction was completed, the reaction system was cooled to room temperature, filtered and concentrated by rotary evaporation. The crude product was purified by silica gel column chromatography to give intermediate 168-3 (324 mg, 41% yield) in the form of a brown powdery solid. MS $[M+H]^+$=500.7.

Step (3) Preparation of tert-butyl (S)-2-((7-methyl-2-(4-methyl-6-(1H-pyrazol-1-yl)pyridin-3-yl)imidazo[1,2-a]pyridin-3-yl)methyl)morpholine-4-carboxylate

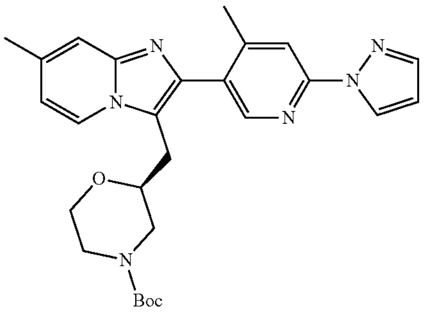

168-4

Intermediate 168-3 (320 mg, 0.64 mmol), 1H-pyrazole (130 mg, 1.92 mmol), copper(I) iodide (12 mg, 0.06 mmol), (1R,2R)—$N_1$,$N_2$-dimethylcyclohexane-1,2-diamine (18 mg, 0.13 mmol) and potassium phosphate (408 mg, 1.92 mmol) were added to dioxane (5 mL) under nitrogen atmosphere. The reaction system was reacted at 100° C. for 6 h. Then the reaction system was cooled to room temperature, added with water (15 mL) to quench the reaction, filtered, and extracted with ethyl acetate (20 mL×3). The organic phases were combined, washed with saturated brine (20 mL), dried over anhydrous sodium sulfate, filtered and concentrated by rotary evaporation. The crude product was purified by silica gel column chromatography to give intermediate 168-4 (170 mg, 55% yield) in the form of a brownish-yellow oil. MS $[M+H]^+$=488.9.

Step (4) Preparation of (S)-2-((7-methyl-2-(4-methyl-6-(1H-pyrazol-1-yl)pyridin-3-yl)imidazo[1,2-a]pyridin-3-yl)methyl)morpholine

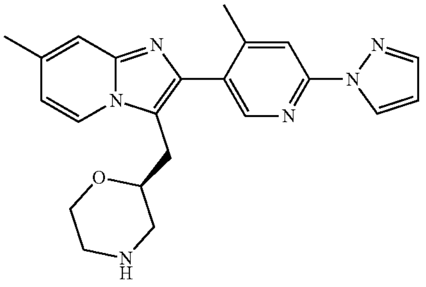

168-5

Intermediate 168-4 (170 g, 0.35 mmol) was dissolved in dichloromethane (5 mL), and a solution of HCl in ethanol (33%, 1.0 mL) was added. The reaction system was stirred at room temperature for 3 h. After the reaction was completed, the reaction system was concentrated by rotary evaporation to give intermediate 168-5 (145 mg) in the form of a brown solid, MS $[M+H]^+$=388.9.

Step (5) Preparation of methyl (S)-2-((7-methyl-2-(4-methyl-6-(1H-pyrazol-1-yl)pyridin-3-yl)imidazo[1,2-a]pyridin-3-yl)methyl)morpholine-4-carboxylate

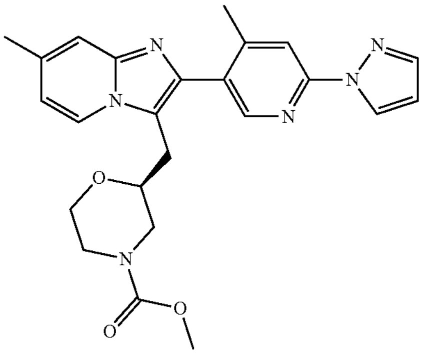

168

Intermediate 168-5 (135 mg, 0.35 mmol) was dissolved in anhydrous dichloromethane (5 mL) under nitrogen atmosphere, and diisopropylethylamine (225 mg, 1.75 mmol) was added at 0° C., followed by the dropwise addition of a solution of methyl chloroformate in dichloromethane (10 mg/mL, 3.5 mL). The reaction system was stirred at 0° C. for 2 h. After the reaction was completed, the reaction system was added with water (20 mL), and extracted with dichloromethane (20 mL×3). The organic phases were combined, washed with saturated brine (20 mL), dried over sodium sulfate, filtered and concentrated by rotary evaporation. The crude product was purified by silica gel column chromatography (dichloromethane:ethyl acetate=2:1) to give a product. The product was purified by preparative by high performance liquid chromatography to give compound 168 (45 mg, 21% yield) in the form of a white solid.

MS $[M+H]^+$=446.8. $^1$H NMR (400 MHZ, $CDCl_3$) δ 8.60 (d, J=2.2 Hz, 1H), 8.33 (s, 1H), 8.09 (d, J=7.1 Hz, 1H), 7.96 (s, 1H), 7.77 (s, 1H), 7.39 (s, 1H), 6.71 (d, J=7.1 Hz, 1H), 6.51-6.47 (m, 1H), 4.00-3.75 (m, 3H), 3.67 (s, 3H), 3.62-3.52 (m, 1H), 3.45-3.34 (m, 1H), 3.08-2.98 (m, 2H), 2.96-2.86 (m, 1H), 2.63-2.52 (m, 1H), 2.44 (s, 3H), 2.41 (s, 3H).

Example 169

Preparation of methyl (S)-2-((2-(2,6-difluoro-4-(2-oxo-2,5-dihydro-1H-pyrrol-1-yl)phenyl)-7-methyl-imidazo[1,2-a]pyridin-3-yl)methyl)morpholine-4-carboxylate

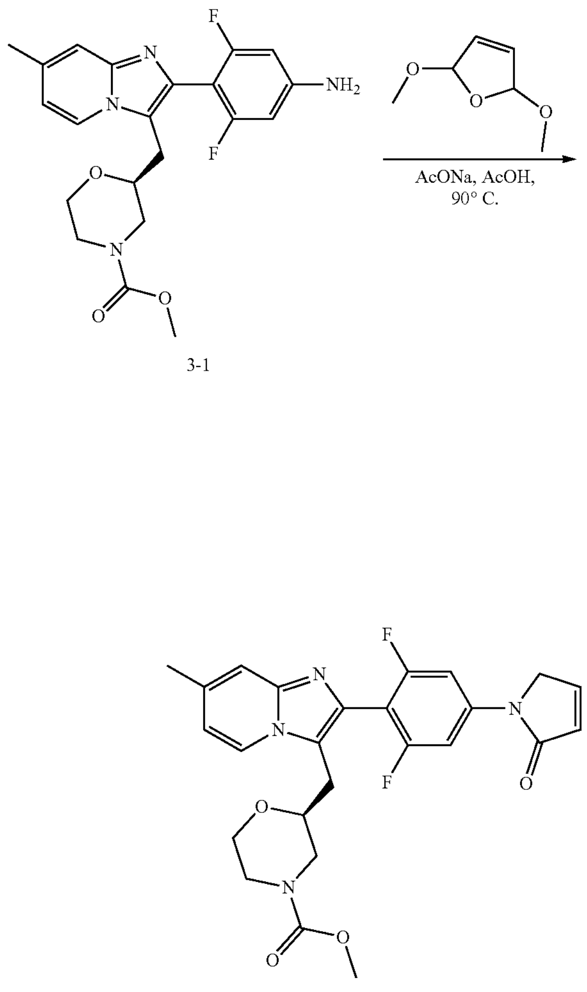

3-1

169

Intermediate 3-1 (100 mg, 0.24 mmol) was dissolved in acetic acid (1 mL) under nitrogen atmosphere, and 2,5-dimethoxy-2,5-dihydrofuran (35 mg, 0.26 mmol) and sodium acetate (50 mg, 0.48 mmol) were added. The reaction system was reacted at 90° C. for 2 h. After the reaction was completed, the reaction system was cooled to room temperature, filtered and concentrated by rotary evaporation. The crude product was separated by preparative by high performance liquid chromatography to give compound 169 (20.2 mg, 17.4% yield) in the form of a white solid. MS $[M+H]^+$=482.8.

$^1$H NMR (400 MHZ, MeOD) δ 8.42 (d, J=7.0 Hz, 1H), 7.70 (d, J=10.1 Hz, 2H), 7.50 (dt, J=6.1, 1.9 Hz, 1H), 7.35 (s, 1H), 6.89 (dd, J=7.1, 1.4 Hz, 1H), 6.29 (dt, J=4.3, 1.9 Hz, 1H), 4.66 (t, J=1.8 Hz, 2H), 3.82-3.79 (m, 3H), 3.67 (s, 3H), 3.63-3.57 (m, 1H), 3.41-3.38 (m, 1H), 3.15-3.08 (m, 2H), 2.95-2.86 (m, 1H), 2.70-2.59 (m, 1H), 2.47 (s, 3H).

Example 171

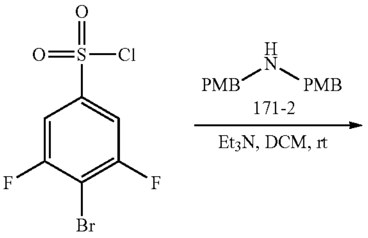

171-1

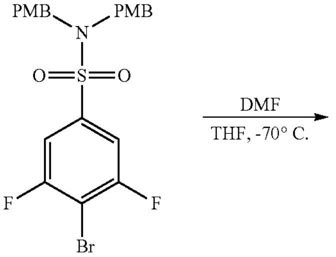

171-3

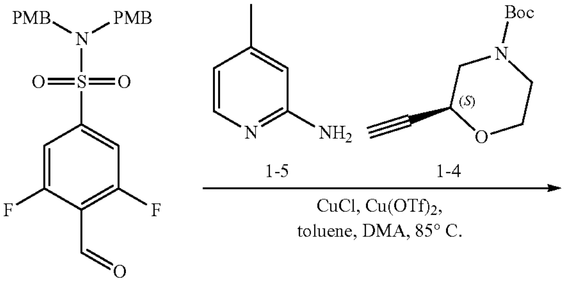

171-4

1-5

1-4

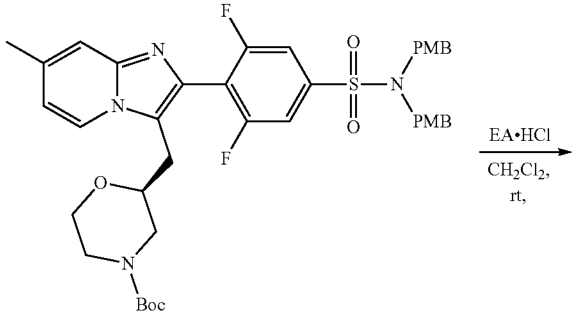

171-5

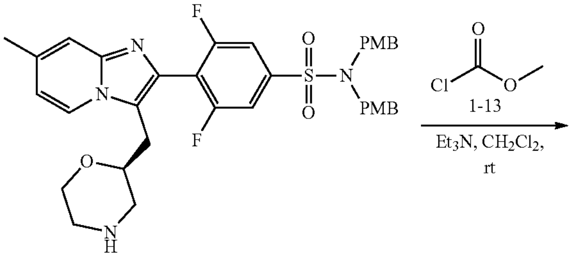

171-6

-continued

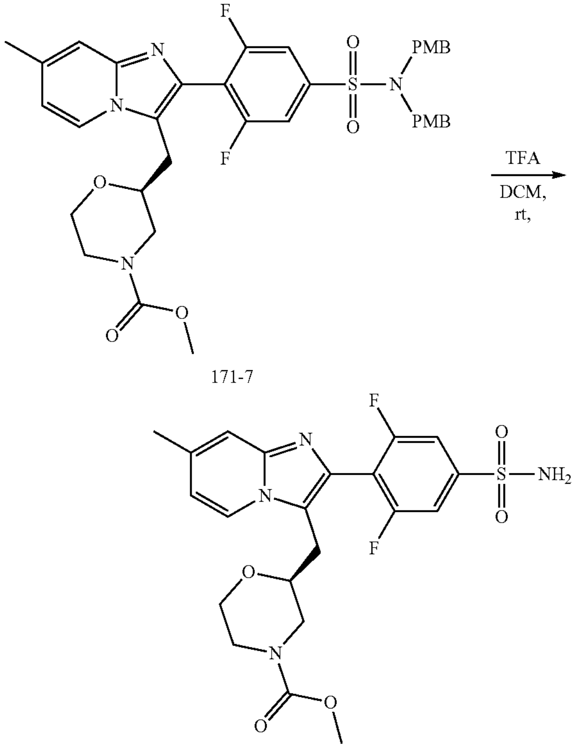

171-7

171

Step (1) Preparation of 4-bromo-3,5-difluoro-N,N-bis(4-methoxybenzyl)benzenesulfonamide 171-3

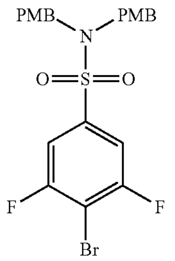

Bis (4-methoxybenzyl)amine (36.0 g, 140 mmol, compound 171-2) and $Et_3N$ (21.2 g, 210 mmol) were dissolved in dichloromethane (1000 mL) sequentially. The reaction system was stirred in an ice bath, and added with 4-bromo-3,5-difluorobenzenesulfonyl chloride (40.5 g, 139 mmol, compound 171-1) in portions (an exothermic reaction) with the internal temperature maintained at less than 10° C. After the addition of compound 171-1, the ice bath was removed and the reaction system was reacted at room temperature for 1.0 h. After compound 171-1 was consumed as detected by TLC (PE/EA=10/1), the DCM phase was washed with aqueous citric acid solution (400 mL×2, 10% in wt.) and saturated brine (400 mL) sequentially, dried over anhydrous sodium sulfate, and concentrated by rotary evaporation to give intermediate 171-3 (68.3 g, 96% yield) in the form of a white solid. LC-MS: $[M+H]^+$=511.1.

Step (2) Preparation of 3,5-difluoro-4-formyl-N,N-bis(4-methoxybenzyl)benzenesulfonamide 171-4

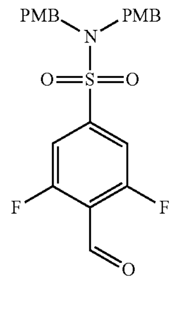

Intermediate 171-3 (68.3 g, 133.3 mmol) was dissolved in THF (800 mL). The reaction system was heated to 40° C. to dissolve the undissolved solid, purged with $N_2$ three times, and cooled to −70° C. below. Then the reaction system was added dropwise with n-butyllithium (2.5 M, 64 mL, 1.2 eq) slowly with the internal temperature maintained at less than −70° C. After the completion of the dropwise addition of n-butyllithium, the reaction was reacted for 45 min, added with DMF (12.7 g, 1.3 eq), and reacted for another 2.0 h. The reaction system was added with hydrochloric acid (0.5 M) to quench the reaction and adjust the pH to 4, followed by liquid separation. The organic phase was concentrated by rotary evaporation. The aqueous phase was extracted with DCM (300 mL×2). The residue after the rotary evaporation of THE was dissolved in the combined DCM phases, which was then washed with saturated brine, dried and concentrated by rotary evaporation to give a crude product (74 mg). The crude product was purified by column chromatography to give intermediate 171-4 (55 g, 90% yield, pure product) in the form of a white solid. LC-MS: $[M+H]^+$=461.2.

Step (3) Preparation of tert-butyl (S)-2-((2-(4-(N,N-bis(4-methoxybenzyl)sulfamoyl)-2,6-difluorophenyl)-7-methylimidazo[1,2-a]pyridin-3-yl)methyl) morpholine-4-carboxylate 171-5

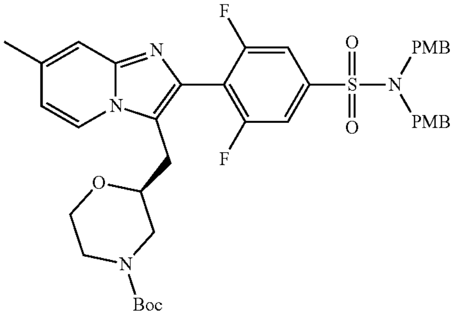

To a 100 mL round-bottom flask were added intermediate 171-4 (18.2 g, 39.4 mmol, 1.0 eq), 4-methylpyridin-2-amine (4.26 g, 39.4 mmol, 1.0 eq, compound 1-5), tert-butyl (S)-2-ethynylmorpholine-4-carboxylate (8.33 g, 39.4 mmol, 1.0 eq, compound 1-4), CuCl (1.17 g, 11.8 mmol, 0.3 eq), $Cu(OTf)_2$ (4.34 g, 11.8 mmol, 0.3 eq), toluene (200 mL) and DMA (12 mL) sequentially. The reaction system was purged with nitrogen 3 times, and heated in an oil bath at 85° C. overnight (12 h). The starting material (compound 1-5) was consumed, and intermediate 171-4 was remained as detected by TLC. Then the reaction system was cooled to room temperature, added with aqueous ammonia (100 mL) and water (150 mL), and stirred for 5 min, followed by liquid separation to give a toluene phase. The aqueous phase was extracted with DCM (150 mL×2). The organic phase was washed with saturated brine, dried over anhydrous sodium sulfate, and concentrated by rotary evaporation. The residue was purified by column chromatography to give intermediate 171-5 (11.2 g, 96% purity, 37% yield) in the form of a yellow solid. LC-MS: $[M+H]^+$=761.9.

Step (4) Preparation of (S)-3,5-difluoro-N,N-bis(4-methoxybenzyl)-4-(7-methyl-3-(morpholin-2-ylmethyl)imidazo[1,2-a]pyridin-2-yl)benzenesulfonamide 171-6

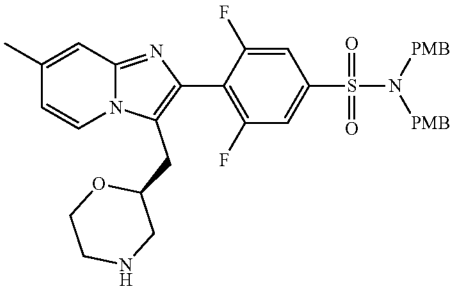

Intermediate 171-5 (11.2 g, 14.7 mol) was dissolved in DCM (33 mL), and a solution of HCl in dioxane (4 M, 33 mL) was added. The reaction system was stirred at room temperature for 1.0 h. After the reaction was completed as detected by TLC, the reaction system was added with water (100 mL) and dichloromethane (200 mL). The aqueous phase was adjusted to pH 9-10 (weak alkalinity) with sodium carbonate, followed by liquid separation to give a DCM phase. The aqueous phase was extracted with DCM (100 mL×2). The DCM phases were combined, washed with saturated brine, dried and concentrated by rotary evaporation to give intermediate 171-6 (9.7 g) in the form of a white solid, which was used directly in the next step. LC-MS: $[M+H]^+$=622.2.

Step (5) Preparation of methyl (S)-2-((2-(4-(N,N-bis(4-methoxybenzyl)sulfamoyl)-2,6-difluorophenyl)-7-methylimidazo[1,2-a]pyridin-3-yl)methyl)morpholine-4-carboxylate 171-7

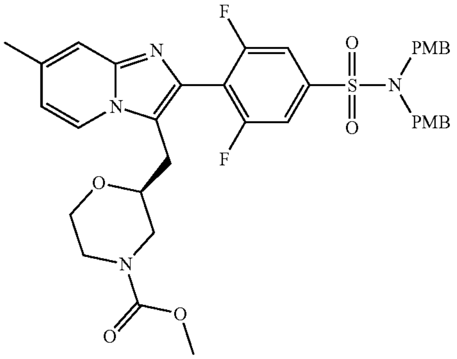

Intermediate 171-6 (9.7 g, 14.7 mmol, 1.0 eq) was dissolved in DCM (40 mL), and $Et_3N$ (2.96 g, 29.3 mmol, 2.0 eq) was added, followed by the dropwise addition of methyl chloroformate (2.08 g, 22 mmol, 1.5 eq). The reaction system was reacted for 1.0 h. After the reaction was completed as detected by TLC, the reaction system was added with water (150 mL) and DCM (200 mL), and stirred for 10 min, followed by liquid separation to give a DCM phase. The aqueous phase was extracted with DCM (50 mL×2). The DCM phases were combined, washed with saturated sodium chloride solution, dried over anhydrous sodium sulfate, and concentrated by rotary evaporation. The residue was purified by column chromatography to give intermediate 171-7 (9.4 g, 89% yield) in the form of a white solid. LC-MS: $[M+H]^+$=720.9.

Step (6) Preparation of methyl (S)-2-((2-(2,6-difluoro-4-sulfamoylphenyl)-7-methylimidazo[1,2-a]pyridin-3-yl)methyl)morpholine-4-carboxylate

171

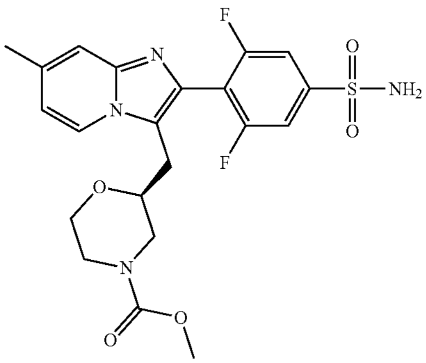

Intermediate 171-7 (9.4 g) was dissolved in DCM (30 mL), and TFA (30 mL) was added. The reaction system was stirred at 35° C. overnight. A product (80% yield) was generated as detected by LCMS. Then the reaction system was supplemented with TFA (10 mL), and reacted at 40° C. for 4.0 h. The resulting reaction system was concentrated by rotary evaporation. The crude product was dissolved with acetonitrile and separated by preparative chromatography to give compound 171 (3.165 g, 50.6% yield) in the form of a white solid. LC-MS: $[M+H]^+$=481.1.
$^1H$ NMR (400 MHZ, DMSO-$d_6$) δ 8.41 (d, J=7.11 Hz, 1H), 7.69 (s, 2H), 7.59 (d, J=6.6, 2H), 7.33 (s, 1H), 6.84-6.78 (m, 1H), 3.76 (d, J=12.5 Hz, 1H), 3.60 (d, J=11.6 Hz, 2H), 3.53 (s, 3H), 3.44 (d, J=3.6 Hz, 1H), 3.31 (s, 1H), 3.24-3.14 (m, 1H), 3.02 (qd, J=15.7, 6.1 Hz, 2H), 2.77 (s, 1H), 2.34 (s, 3H).
Example 172
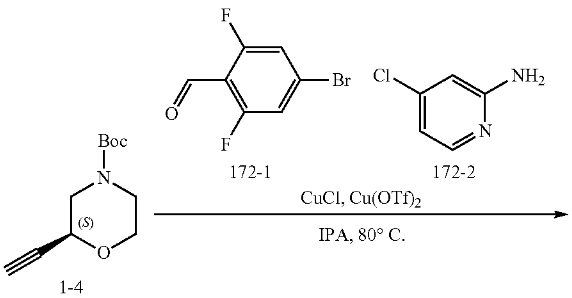
172-1 172-2
1-4
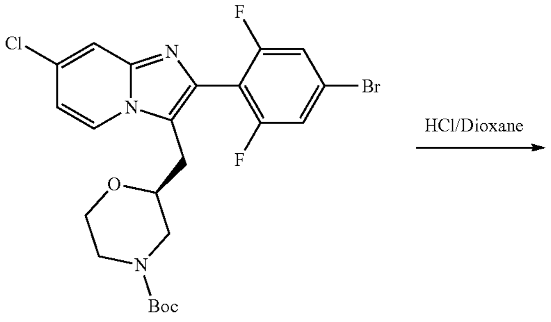
172-3
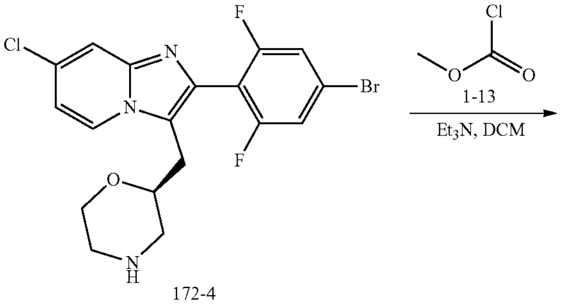
172-4
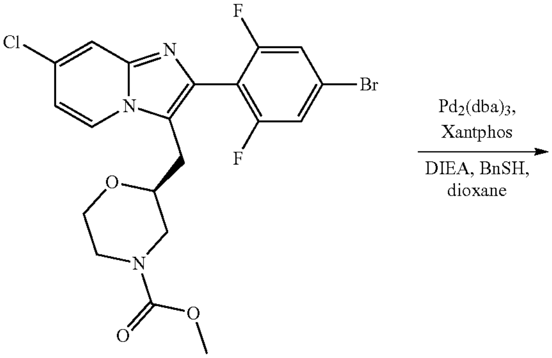
172-5
-continued
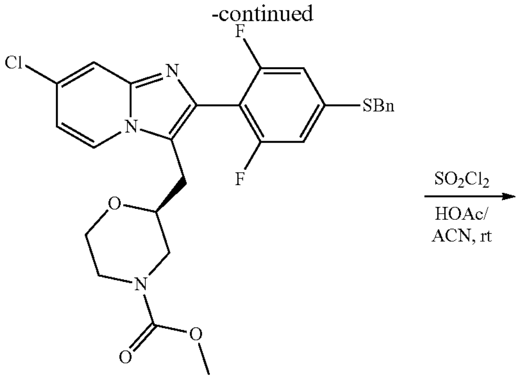
172-6
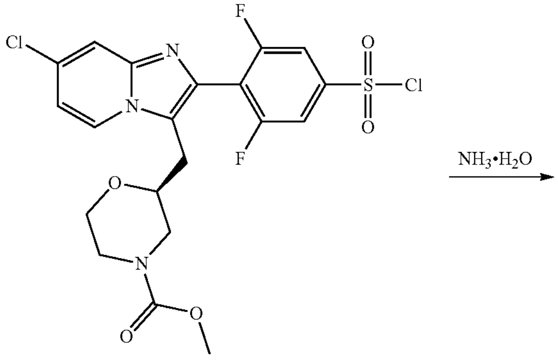
172-7
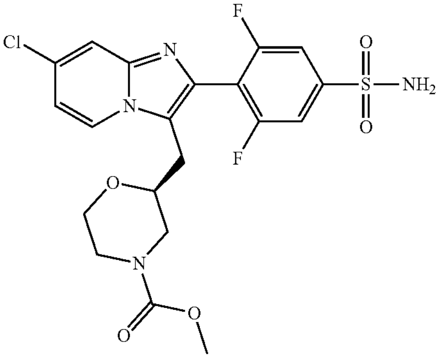
172

Step (1) Preparation of tert-butyl (S)-2-((2-(4-bromo-2,6-difluorophenyl)-7-chloroimidazo[1,2-a]pyridin-3-yl)methyl)morpholine-4-carboxylate 172-3

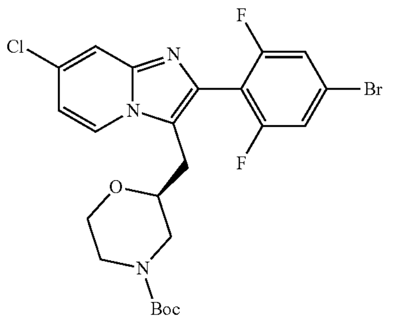

To a 100 mL round-bottom flask were added tert-butyl (S)-2-ethynylmorpholine-4-carboxylate (3.1 g, 1.0 eq, intermediate 1-4), 4-bromo-2,6-difluorobenzaldehyde (2.76 g, 1.0 eq, compound 172-1), 4-chloropyridin-2-amine (1.61 g, 1.0 eg, compound 172-2), CuCl (0.37 g, 0.3 eq), $Cu(OTf)_2$ (1.36 g, 0.3 eq) and isopropanol (50 mL) sequentially. The reaction system was purged with nitrogen 3 times, and reacted in an oil bath at 80° C. overnight. The starting material (compound 172-2) was consumed as detected by TLC. The reaction system was concentrated by rotary evaporation to remove isopropanol, and extracted with EA and aqueous ammonia sequentially. The EA phase was washed with saturated brine and citric acid sequentially, dried over anhydrous sodium sulfate, and concentrated by rotary evaporation. The residue was purified by column chromatography to give intermediate 172-3 (3.0 g, 78% purity) in the form of a white solid. LC-MS: $[M+H]^+$=542.2.

Step (4) Preparation of (S)-2-((2-(4-bromo-2,6-difluorophenyl)-7-chloroimidazo[1,2-a]pyridin-3-yl)methyl)morpholine 172-4

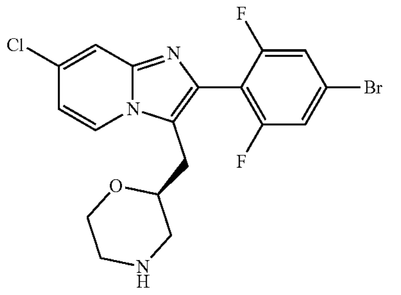

Intermediate 172-3 (2.67 g) was dissolved in dichloromethane (24 mL), and a solution of HCl in dioxane (24 mL) was added. The reaction system was stirred at room temperature for 1.0 h. After the reaction was completed as detected by TLC, the reaction system was concentrated by rotary evaporation, added with water (15 mL) and dichloromethane (15 mL), and extracted to give an aqueous phase. The aqueous phase was adjusted to pH 8-9 (weak alkalinity) with aqueous sodium carbonate solution, followed by liquid separation to give a dichloromethane phase. The aqueous phase was extracted with dichloromethane (10 ml×2). The dichloromethane phases were combined, washed with saturated brine, and concentrated by rotary evaporation to give intermediate 172-4 (1.70 g, 88.6% purity) in the form of a white solid. LC-MS: $[M+H]^+$=442.1.

Step (5) Preparation of methyl (S)-2-((2-(4-bromo-2,6-difluorophenyl)-7-chloroimidazo[1,2-a]pyridin-3-yl)methyl)morpholine-4-carboxylate 172-5

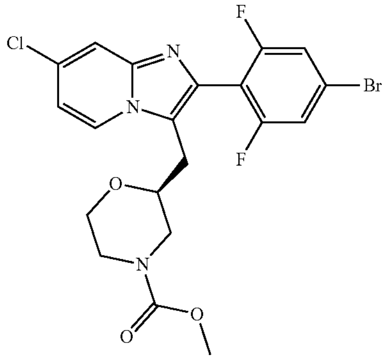

Intermediate 172-4 (1.4 g, 1.0 eq) was dissolved in dichloromethane (10 mL), and triethylamine (480 mg, 1.5 eq) was added, followed by the dropwise addition of methyl chloroformate (388 mg, 1.3 eq). The reaction system was reacted for 1.0 h, and a product was generated as detected by LC-MS. After the reaction was completed, the reaction system was added with water (10 mL), and stirred for 30 min, followed by liquid separation to give a dichloromethane phase. The aqueous phase was extracted with dichloromethane (10 mL×2). The dichloromethane phases were combined, washed with saturated sodium chloride solution, dried over anhydrous sodium sulfate, and concentrated by rotary evaporation. The residue was purified by column chromatography to give intermediate 172-5 (1.01 g, 93.02% purity) in the form of a white solid.

LC-MS: $[M+H]^+$=499.8.

Step (6) Preparation of methyl (S)-2-((2-(4-(benzylthio)-2,6-difluorophenyl)-7-chloroimidazo[1,2-a]pyridin-3-yl)methyl)morpholine-4-carboxylate 172-6

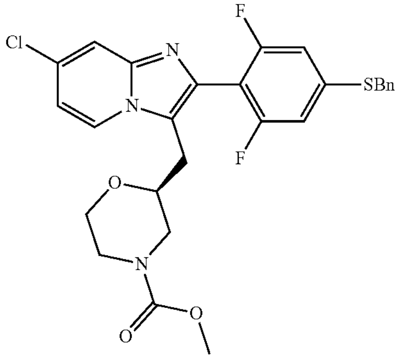

Intermediate 172-5 (0.73 g, 1.0 eq) was dissolved in dioxane (4 mL), and BnSH (0.24 g, 1.3 eq), $Pd_2(dba)_3$ (0.04 g, 0.03 eq), Xantphos (0.04 g, 0.05 eq) and DIEA (0.60 g, 3.0 eq) were added. The reaction system was purged with $N_2$ three times and reacted at 80° C. overnight. The starting material was consumed completely as monitored by LCMS. The reaction system was added with dichloromethane (10 mL) and water (10 mL), followed by liquid separation to give a dichloromethane phase. The aqueous phase was extracted with dichloromethane (10 ml×2). The dichloromethane phases were combined, washed with saturated sodium chloride solution, dried over anhydrous sodium sulfate, and concentrated by rotary evaporation. The residue was purified by column chromatography to give intermediate 172-6 (0.82 g, 91.53% purity) in the form of a white solid. LC-MS: $[M+H]^+$=544.2.

Step (7) Preparation of methyl (S)-2-((7-chloro-2-(4-(chlorosulfonyl)-2,6-difluorophenyl)imidazo[1,2-a]pyridin-3-yl)methyl)morpholine-4-carboxylate 172-7

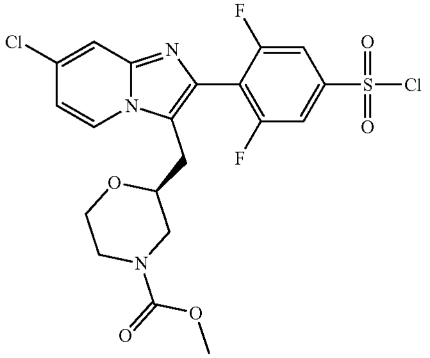

Intermediate 172-6 (510 mg) was added to a reaction flask, and dissolved with acetonitrile (3 mL), followed by the addition of glacial acetic acid (281 mg, 5.0 eq). The reaction system was added dropwise with $SO_2Cl_2$ (506 mg, 4.0 eq) in an ice bath, and reacted at 0° C. for 1 h. The starting material was consumed, and intermediate 172-7 was generated as detected by LCMS. The reaction system was used directly in the next step without treatment.

Step (8) Preparation of methyl (S)-2-((7-chloro-2-(2,6-difluoro-4-sulfamoylphenyl)imidazo[1,2-a]pyridin-3-yl)methyl)morpholine-4-carboxylate

172

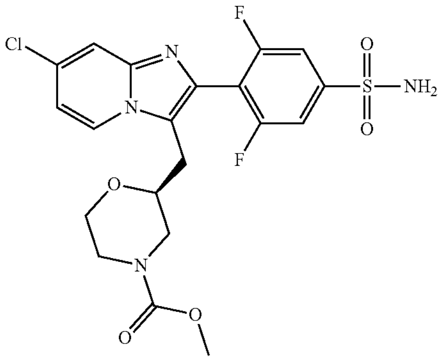

Aqueous ammonia (2 mL) was diluted with acetonitrile (1 mL) and added dropwise to the above reaction system at 0° C. The reaction system was reacted at room temperature for 0.5 h. The starting material was consumed completely, and a target product was generated as detected by LCMS. The reaction system was extracted with water and ethyl acetate twice, washed with saturated brine, dried over anhydrous sodium sulfate, and concentrated. The residue was purified by preparative chromatography to give compound 172 (185 mg, 99.74% purity) in the form of a white solid. LC-MS: $[M+H]^+$=501.1.

$^1H$ NMR (400 MHZ, DMSO-$d_6$) δ=8.11 (d, J=7.4, 1H), 7.29 (d, J=1.6, 1H), 7.22 (s, 2H), 7.14 (d, J=6.6, 2H), 6.60 (dd, J=7.4, 2.1, 1H), 3.33 (d, J=12.8, 1H), 3.13 (d, J=11.3, 2H), 3.07 (s, 3H), 2.97 (d, J=7.8, 1H), 2.77-2.69 (m, 1H), 2.69-2.61 (m, 1H), 2.53 (dd, J=15.5, 8.3, 1H).

Example 173

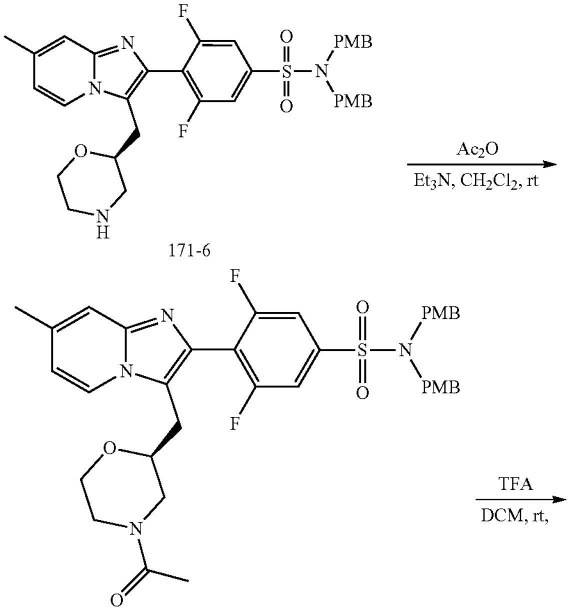

171-6

173-1

-continued

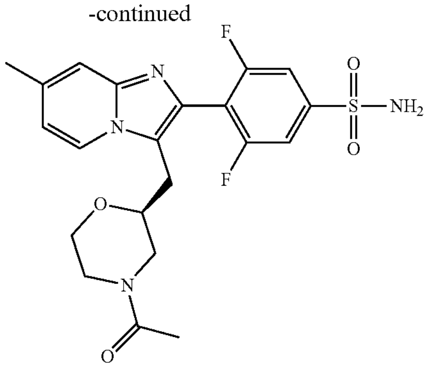

173

Step (1) Preparation of (S)-3,5-difluoro-N,N-bis(4-methoxybenzyl)-4-(7-methyl-3-(morpholin-2-ylmethyl)imidazo[1,2-a]pyridin-2-yl)benzenesulfonamide 173-1

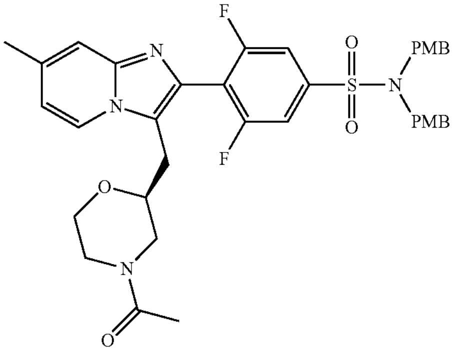

Intermediate 171-6 was prepared according to the steps in Example 1. Intermediate 171-6 (620 mg, 0.94 mmol, 1.0 eq) was dissolved in DCM (5 mL), and $Et_3N$ (236 mg, 2.34 mmol, 2.5 eq) was added, followed by the dropwise addition of acetic anhydride (191 mg, 1.88 mmol, 2 eq). The reaction system was reacted for 1.0 h. After the reaction was completed as detected by TLC, the reaction system was added with water (30 mL) and DCM (50 mL), and stirred for 10 min, followed by liquid separation to give a DCM phase. The aqueous phase was extracted with DCM (20 mL×2). The DCM phases were combined, washed with saturated sodium chloride solution, dried over anhydrous sodium sulfate, and concentrated by rotary evaporation. The residue was purified by column chromatography to give intermediate 173-1 (450 mg, 68.3% yield) in the form of a white solid. LC-MS: $[M+H]^+$=705.2.

Step (2) Preparation of (S)-4-(3-((4-acetylmorpholin-2-yl)methyl)-7-methylimidazo[1,2-a]pyridin-2-yl)-3,5-difluorobenzenesulfonamide

173

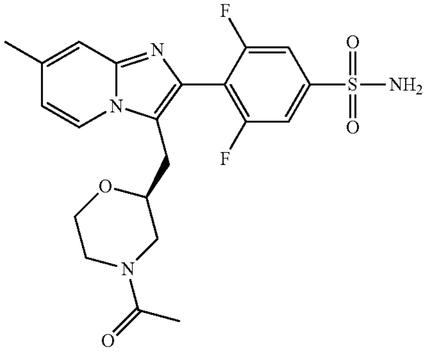

Intermediate 173-1 (420 mg) was dissolved in DCM (2 mL), and TFA (2 mL) was added. The reaction system was stirred at room temperature overnight. Then the reaction system was heated to 35° C. and reacted for 4.0 h, and the work-up was performed. The reaction system was added with water (20 mL) and DCM (20 mL). The aqueous phase was adjusted to pH 9 with sodium carbonate solution, followed by liquid separation to give a DCM phase. The aqueous phase was extracted with DCM (20 mL×2). The DCM phases were combined, washed with saturated brine, dried over anhydrous sodium sulfate, and concentrated by rotary evaporation. The residue was purified by column chromatography to give a product, which was then slurried with DCM/PE (1:10) to give compound 173 (104 mg, 37.5% yield) in the form of a white solid.

$^1$H NMR (400 MHZ, $CDCl_3$) δ 8.23 (1H, dd, J 36.9, 6.8), 7.60 (1H, s), 7.53 (2H, t, J 6.0), 6.80 (2H, t, J 12.6), 6.57 (1H, s), 4.37 (1H, t, J 11.4), 3.91-3.72 (1H, m), 3.51 (2H, d, J 12.1), 3.35 (1H, dd, J 21.8, 11.9), 3.16 (0.5H, t, J 11.6), 3.09-2.78 (2H, m), 2.66 (0.5H, t, J 11.1), 2.47 (3H, d, J 3.8), 2.44-2.32 (0.5H, m), 2.04 (2H, s), 1.98 (1H, s), 1.82 (2H, s).

Example 174

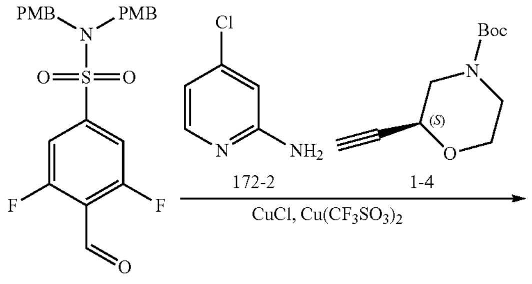

171-4 172-2 1-4

-continued

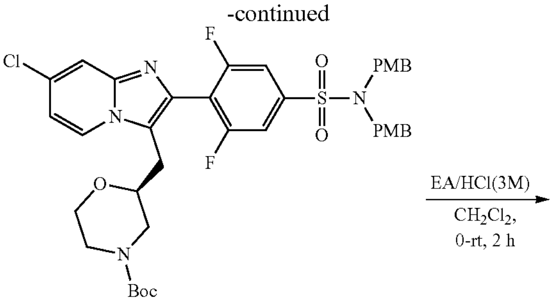

174-1

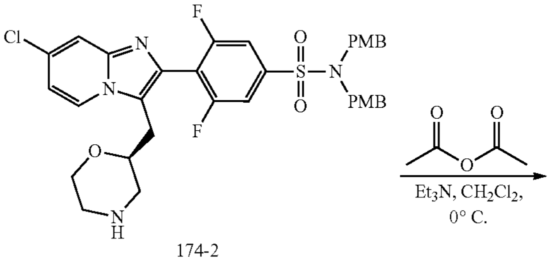

174-2

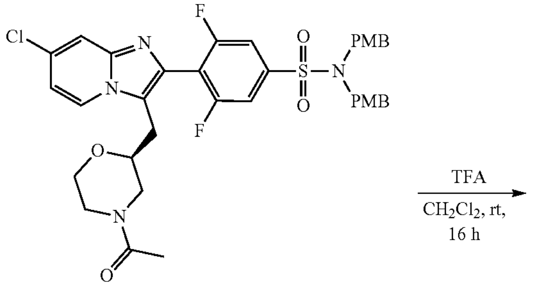

174-3

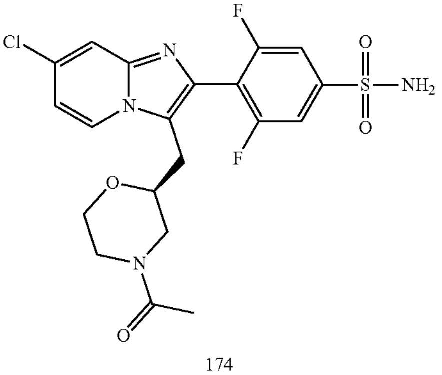

174

Step (1) 1) Preparation of tert-butyl (S)-2-((2-(4-(N,N-bis(4-methoxybenzyl)sulfamoyl)-2,6-difluorophenyl)-7-chloroimidazo[1,2-a]pyridin-3-yl)methyl) morpholine-4-carboxylate 174-1

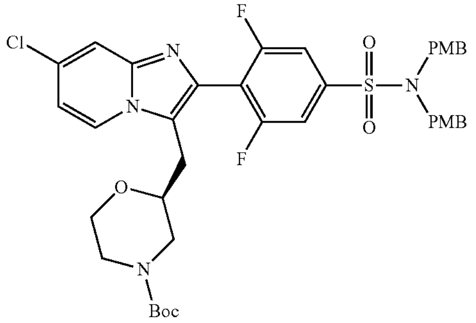

3,5-difluoro-4-formyl-N,N-bis(4-methoxybenzyl)benzenesulfonamide (29 g, 62.84 mmol), 4-chloropyridin-2-amine (8.08 g, 62.84 mmol) and tert-butyl (S)-2-ethynylmorpholine-4-carboxylate (13.28 g, 62.84 mmol) were dissolved in toluene (150 mL) and dimethylacetamide (150 mL). The reaction system was stirred well, and into which copper (1) chloride (1.87 g, 18.85 mmol) and copper(II) trifluoromethanesulfonate (6.82 g, 18.85 mmol) were added, and reacted at 85° C. for 16 h under nitrogen atmosphere. Then the reaction system was added with water (750 mL), and extracted with ethyl acetate (150 mL×2). The organic phase was washed with aqueous ammonia (100 mL×1) and saturated brine (100 mL×2) sequentially, dried over anhydrous sodium sulfate, filtered and concentrated. The crude product was purified by silica gel column chromatography (petroleum ether:ethyl acetate=10:1-3:1) to give intermediate 174-1 (18 g, 85% purity, 39% yield) in the form of a brownish-yellow foamy solid. LC-MS: $[M+H]^+$=783.0.

Step (2) Preparation of (S)-4-(7-chloro-3-(morpholin-2-ylmethyl)imidazo[1,2-a]pyridin-2-yl)-3,5-difluoro-N,N-bis(4-methoxy benzyl)benzenesulfonamide 174-2

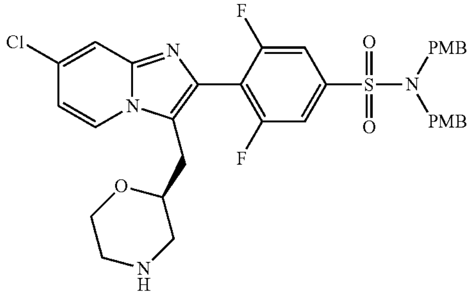

Intermediate 174-1 (17 g, 21.7 mmol) was dissolved in dichloromethane (60 mL), and a solution of HCl in ethyl acetate (60 mL, 3 M) was added dropwise with the temperature maintained at 0° C. After the completion of the dropwise addition, the reaction system was reacted at room temperature for 2 h. The starting material was consumed completely as detected by TLC (PE/EA=3/1, Rf=0.1). The reaction system was concentrated under reduced pressure. The crude product was adjusted to pH 8 with aqueous sodium bicarbonate solution, extracted with ethyl acetate (150 mL×2), dried over anhydrous sodium sulfate with stirring for 20 min, filtered and concentrated to give intermediate 174-2 (13 g, 90% purity, 87% yield) in the form of a brown foamy solid, LC-MS (M+H)+=683.0.

Step (3) Preparation of (S)-4-(3-((4-acetylmorpholin-2-yl)methyl)-7-chloroimidazo[1,2-a]pyridin-2-yl)-3,5-difluoro-N,N-bis(4-methoxybenzyl)benzenesulfonamide 174-3

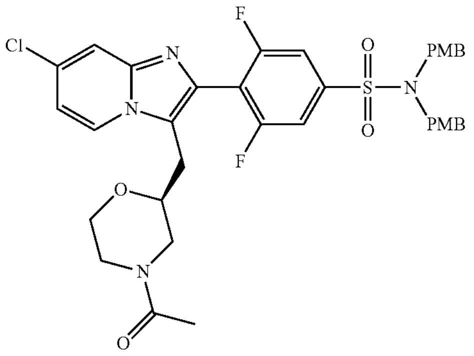

Intermediate 174-2 (1.5 g, 2.2 mmol) was dissolved in dichloromethane (15 mL), and triethylamine (444 mg, 4.39 mmol) was added at 0° C., followed by the dropwise addition of acetic anhydride (336 g, 3.29 mmol). The reaction system was reacted at 0° C. for 1 h. Then the reaction system was added with saturated aqueous sodium chloride solution (40 mL), extracted with dichloromethane (50 mL×2), dried over anhydrous sodium sulfate, filtered and concentrated. The crude product was purified by silica gel column chromatography (PE/EA=1/4-1/2) to give intermediate 174-3 (1.1 g, 69% yield) in the form of a yellowish-white solid, LC-MS: $[M+H]^+$=725.1.

Step (4) Preparation of (S)-4-(3-((4-acetylmorpholin-2-yl)methyl)-7-chloroimidazo[1,2-a]pyridin-2-yl)-3,5-difluorobenzenesulfonamide

174

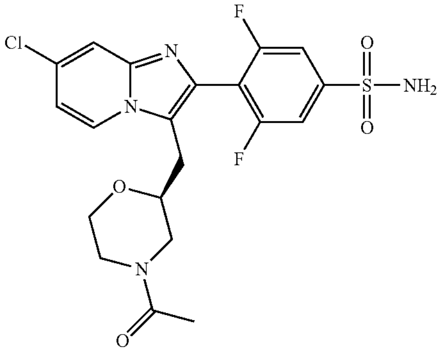

Intermediate 174-3 (1.1 g, 1.52 mmol) was dissolved in dichloromethane (15 mL), and trifluoroacetic acid (3 mL) was added at 0° C. The reaction system was reacted at room temperature for 16 h. The reaction system was added dropwise to an aqueous sodium bicarbonate solution to adjust the pH to 8, and extracted with dichloromethane (50 mL×3). The organic phase was washed twice with saturated brine, dried over anhydrous sodium sulfate, filtered and concentrated. The residue was purified by preparative chromatography. The resulting acetonitrile, water, and trifluoroacetic acid phases were concentrated, adjusted to pH 8 with sodium bicarbonate solution, extracted with ethyl acetate (300 mL×3), washed with saturated brine (100 mL×2), dried over anhydrous sodium sulfate with stirring for 20 min, filtered and concentrated. The solid after concentration was washed three times with acetonitrile, added with acetonitrile (10 mL) and pure water (30 mL), and lyophilized to give compound 174 (358 mg, 97% purity) in the form of a white solid. LC-MS: $[M+H]^+$=484.2.

$^1$H NMR (400 MHZ, DMSO-$d_6$) δ 8.62 (t, J=7.3 Hz, 1H), 7.82-7.77 (m, 1H), 7.73 (d, J=2.3 Hz, 2H), 7.64 (d, J=6.6 Hz, 2H), 7.10 (td, J=7.3, 2.3 Hz, 1H), 4.26-4.19 (m, 1H), 4.05 (d, J=13.3 Hz, 1H), 3.78 (d, J=12.7 Hz, 1H), 3.69-3.60 (m, 1H), 3.56 (d, J=13.3 Hz, 1H), 3.52-3.37 (m, 1H), 3.25 (td, J=11.5, 2.3 Hz, 1H), 3.20-2.97 (m, 3H), 2.80 (dd, J=12.9, 10.5 Hz, 1H), 2.54 (dd, J=12.7, 2.9 Hz, 1H), 2.29 (dd, J=12.8, 10.9 Hz, 1H), 1.94 (d, J=4.2 Hz, 3H).

Example 175

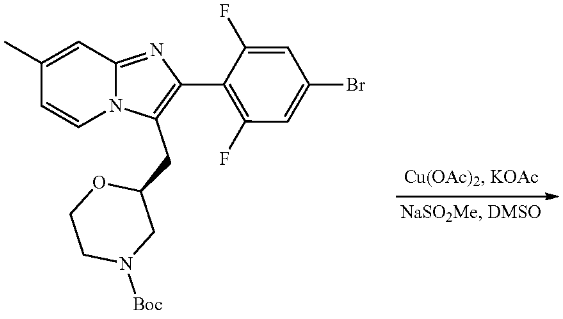

2-4

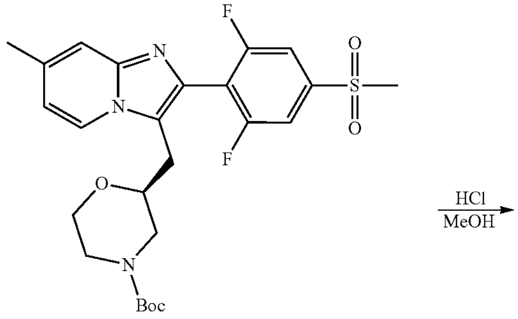

175-1

-continued

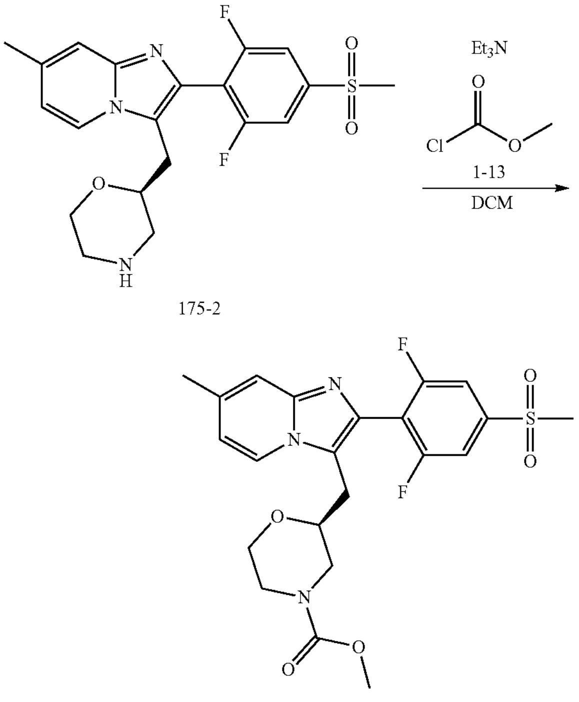

175-2

175

Step (1) Preparation of tert-butyl (S)-2-((2-(2,6-difluoro-4-(methylsulfonyl)phenyl)-7-methylimidazo[1,2-a]pyridin-3-yl)methyl)morpholine-4-carboxylate 175-1

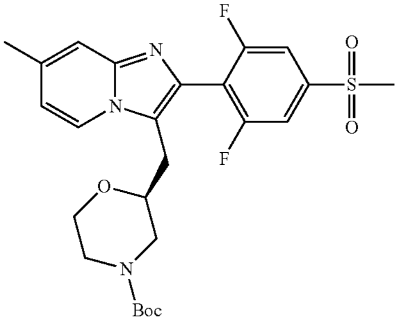

Intermediate 2-4 was prepared according to the steps in Example 2. Intermediate 2-4 (90 mg), $NaSO_2Me$ (22 mg), $Cu(OAc)_2$ (32 mg) and KOAc (34 mg) were added to a reaction flask containing DMSO (5 mL) sequentially. The reaction system was reacted at 100° C. overnight. The starting material was consumed, and a new spot was generated as detected by TLC (PE/EtOAc=1/1). The reaction system was added with EtOAc (10 mL), washed with $NH_4Cl$ (10 mL×3) and saturated brine (10 mL×3) sequentially, dried over $Na_2SO_4$, and concentrated to give crude product. The crude product was purified by prep-TLC to give intermediate 175-1 (28 mg) in the form of a white solid. LC-MS: $[M+H]^+$=522.1.

Step (2) Preparation of (S)-2-((2-(2,6-difluoro-4-(methylsulfonyl)phenyl)-7-methylimidazo[1,2-a]pyridin-3-yl)methyl)morpholine 175-2

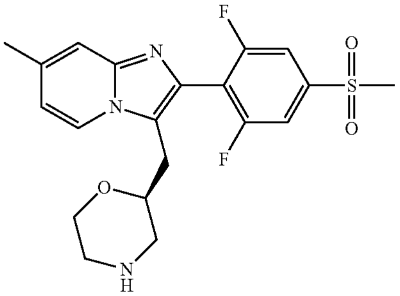

To intermediate 175-1 (0.1 g) was added a solution of HCl in methanol (3 mL, 4 M) at room temperature. The reaction system was reacted at room temperature for 1 h. Then the reaction mixture was concentrated by rotary evaporation to give intermediate 175-2 (80 mg) in the form of a yellow solid, which was used directly in the next step without purification.

Step (3) Preparation of methyl (S)-2-((2-(2,6-difluoro-4-(methylsulfonyl)phenyl)-7-methylimidazo[1,2-a]pyridin-3-yl)methyl)morpholine-4-carboxylate

175

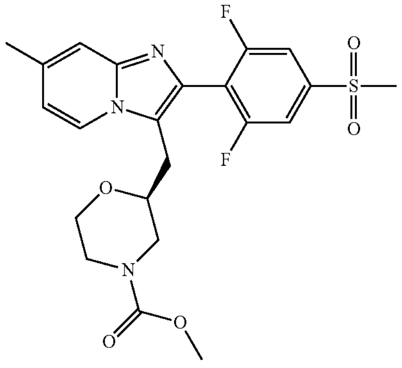

Intermediate 175-2 (80 mg) was added into a reaction flask containing DCM (5 mL), and triethylamine (30 mg) was added. The reaction system was added with methyl chloroformate (27 mg) at 0° C. and reacted at this temperature for 1 b. The starting material was consumed, and a target product was generated as detected by TLC. The product was purified by preparative chromatography to give compound 175 (20 mg, 99.1% purity) in the form of a white solid. LC-MS: $[M+H]^+$=480.1.

$^1H$ NMR (400 MHZ, DMSO-$d_6$) δ 8.44 (d, J=7.2 Hz, 1H), 7.81 (d, J=6.1 Hz, 1H), 7.37 (s, 1H), 6.85 (d, J=6.9 Hz, 1H), 3.77 (d, J=11.6 Hz, 1H), 3.63 (d, J=11.9 Hz, 2H), 3.55 (s, 2H), 3.46 (s, 1H), 3.39 (s, 2H), 3.28-3.16 (m, 1H), 3.13-2.97 (m, 1H), 2.38 (s, 2H).

Example 176
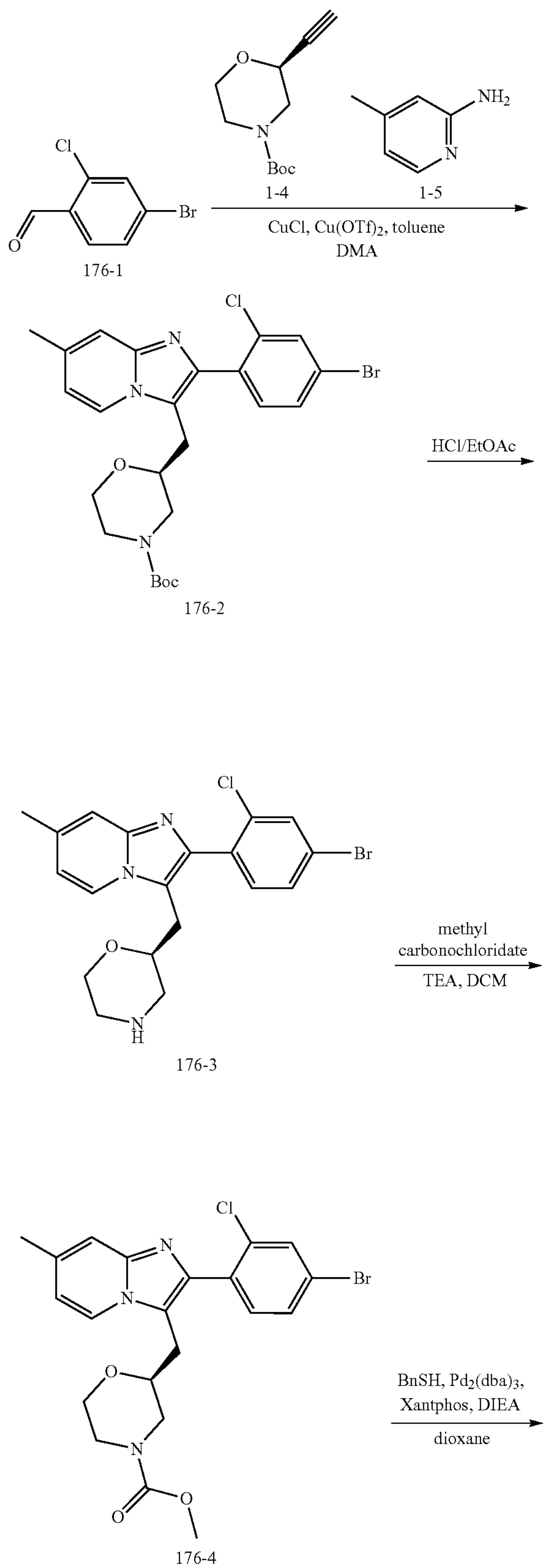
176-1
176-2
176-3
176-4
-continued
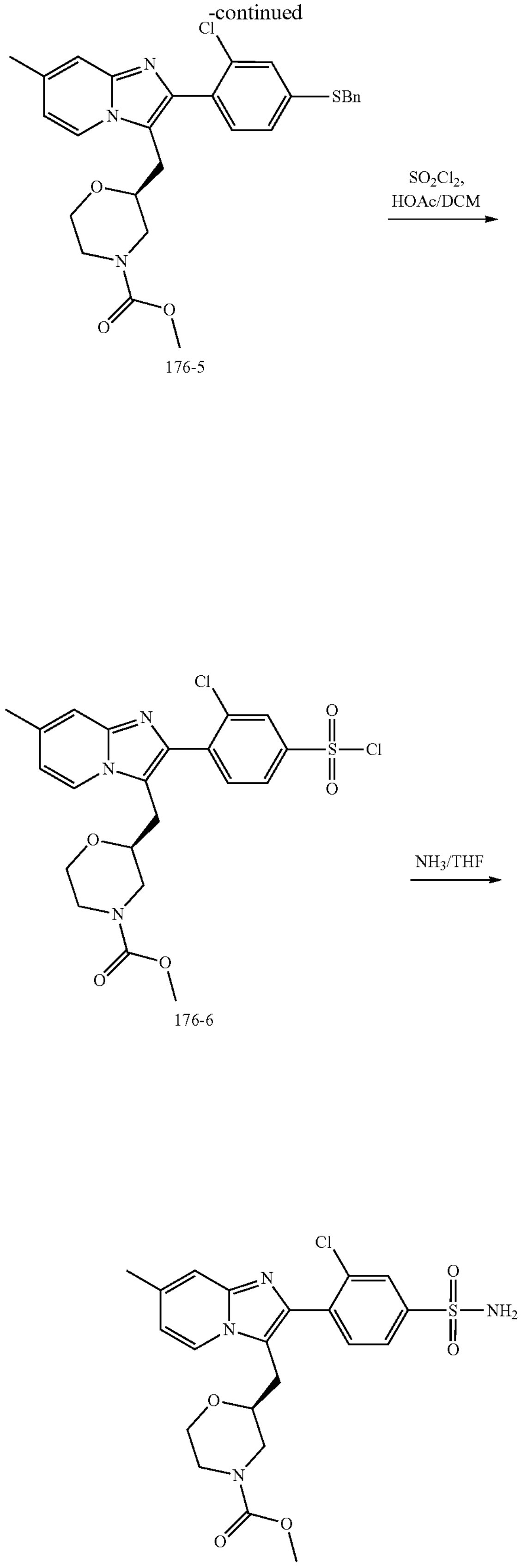
176-5
176-6
176

Step (1) Preparation of tert-butyl (S)-2-((2-(4-bromo-2-chlorophenyl)-7-methylimidazo[1,2-a]pyridin-3-yl)methyl)morpholine-4-carboxylate 176-2

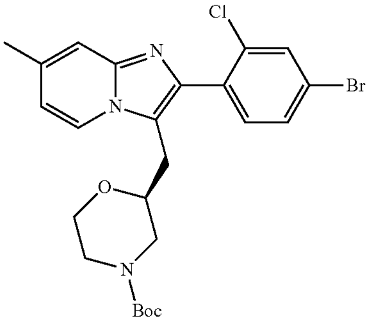

To a 100 mL round-bottom flask were added 4-bromo-2-chlorobenzaldehyde (2.0 g, 1 eq, compound 176-1), compound 1-4 (1.9 g, 1 eq), compound 1-5 (1.0 g, 1 eq), CuCl (0.27 g, 0.3 eq), Cu(OTf): (0.99 g, 0.3 eq), toluene (20 mL) and DMA (2 mL) sequentially. The reaction system was purged with nitrogen 3 times, heated in an oil bath at 85° C. and reacted overnight (12 h). The starting material (compound 176-1) was consumed as detected by TLC. Then the reaction system was cooled to room temperature, added with aqueous ammonia (10 mL) and water (15 mL), and stirred for 5 min, followed by liquid separation to give a toluene phase. The aqueous phase was extracted with DCM (15 mL×2). The organic phase was washed with saturated brine, dried over anhydrous sodium sulfate, and concentrated by rotary evaporation to give intermediate 176-2 (1.46 g, 95% purity) in the form of a yellow oil. LC-MS: $[M+H]^+$=520.2.

Step (2) Preparation of (S)-2-((2-(4-bromo-2-chlorophenyl)-7-methylimidazo[1,2-a]pyridin-3-yl)methyl)morpholine 176-3

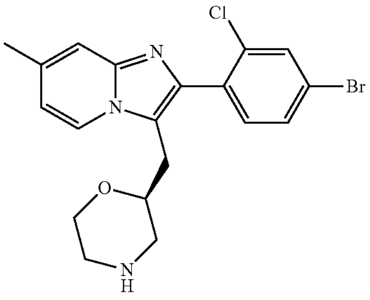

Intermediate 176-2 (1.46 g) was dissolved in methanol (5 mL), and a solution of HCl in EtOAc (4 M, 10 mL) was added. The reaction system was stirred at room temperature for 1 h. After the reaction was completed as detected by TLC, the reaction system was added with water (10 mL) and dichloromethane (20 mL). The aqueous phase was adjusted to pH 9-10 (weak alkalinity) with sodium carbonate, followed by liquid separation to give a DCM phase. The aqueous phase was extracted with DCM (10 mL×2). The DCM phases were combined, washed with saturated brine, dried and concentrated by rotary evaporation to give intermediate 176-3 (1.05 g, 90% purity) in the form of a yellow oil. LC-MS: $[M+H]^+$=420.1.

Step (3) Preparation of methyl (S)-2-((2-(4-bromo-2-chlorophenyl)-7-methylimidazo[1,2-a]pyridin-3-yl)methyl)morpholine-4-carboxylate 176-4

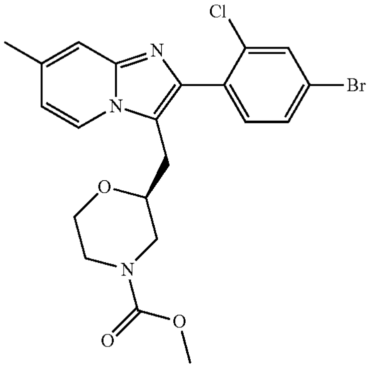

Intermediate 176-3 (1.05 g, 1.0 eq) was dissolved in DCM (10 mL), and DIPEA (0.65 g, 2.0 eq) was added, followed by the dropwise addition of methyl chloroacetate (0.27 g, 1.5 eq). The reaction system was reacted for 1 h. After the reaction was completed as detected by TLC, the reaction system was added with water (10 mL) and DCM (20 mL), and stirred for 10 min, followed by liquid separation to give a DCM phase. The aqueous phase was extracted with DCM (10 mL×2). The DCM phases were combined, washed with saturated sodium chloride, dried over anhydrous sodium sulfate, and concentrated by rotary evaporation. The residue was purified by column chromatography to give intermediate 176-4 (0.88 g, 96% purity). LC-MS: $[M+H]^+$=478.2.

Step (4) Preparation of methyl (S)-2-((2-(4~ (benzylthio)-2-chlorophenyl)-7-methylimidazo[1,2-a]pyridin-3-yl)methyl)morpholine-4-carboxylate 176-5

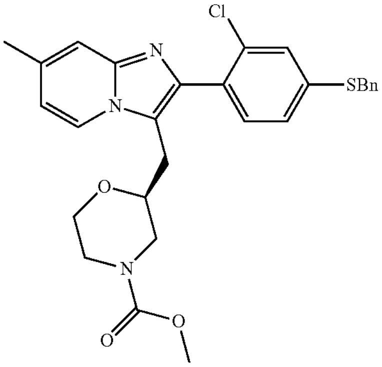

Intermediate 176-4 (0.78 g, 1.0 eq) was dissolved in dioxane (10 mL), and BnSH (0.23 g, 1.1 eq), $Pd_2(dba)_3$ (0.15 g, 0.1 eq), Xantphos (0.1 g, 0.1 eq) and DIPEA (0.42 g, 2.0 eq) were added. The reaction system was purged with $N_2$ three times, and reacted at 85° C. overnight. The starting material was consumed completely as monitored by TLC. After the reaction was completed, the reaction system was added with water (10 mL) and EA (20 mL), and stirred for 10 min, followed by liquid separation to give an EtOAc phase. The aqueous phase was extracted with EtOAc (10 mL×2). The EtOAc phases were combined, washed with saturated sodium chloride, dried over anhydrous sodium sulfate, and concentrated by rotary evaporation. The residue was purified by column chromatography to give intermediate 176-5 (0.85 g, 92% purity) in the form of a yellow oil. LC-MS: $[M+H]^+$=522.0.

Step (5) Preparation of methyl (S)-2-((2-(2-chloro-4-(chlorosulfonyl)phenyl)-7-methylimidazo[1,2-a]pyridin-3-yl)methyl)morpholine-4-carboxylate 176-6

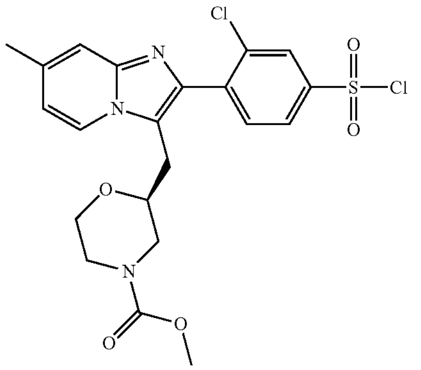

Intermediate 176-5 (150 mg) was added to a reaction flask containing DCM (1 mL), glacial acetic acid (86.3 mg, 5.0 eq) was added, and $SO_2Cl$, (154.9 mg, 4.0 eq) was added dropwise in an ice bath. The reaction system was reacted at room temperature for 2 h. The starting material was consumed, and intermediate 176-6 was generated as detected by LCMS. The reaction system was used directly in the next step without treatment.

Step (6) Preparation of methyl (S)-2-((2-(2-chloro-4-sulfamoylphenyl)-7-methylimidazo[1,2-a]pyridin-3-yl)methyl)morpholine-4-carboxylate

176

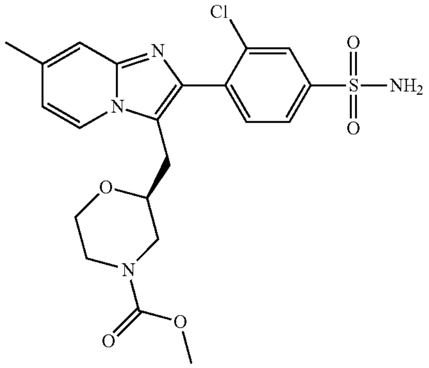

A solution of $NH_3$ in THF (0.4 M, 5 mL) was added dropwise slowly to the above reaction system at 0° C. The reaction system was reacted at room temperature for 2 h. The starting material was consumed completely, and a target product was generated as detected by LCMS. The reaction system was concentrated to dryness, and purified by preparative chromatography to give compound 176 (18 mg) in the form of a white solid. LC-MS: $[M+H]^+$=479.0.

1H NMR (400 MHZ, DMSO-d6) δ 8.43 (d, J=7.1 Hz, 1H), 7.96 (d, J=1.7 Hz, 1H), 7.83 (dd, J=8.0, 1.8 Hz, 1H), 7.71 (d, J=8.0 Hz, 1H), 7.59 (s, 2H), 7.36 (s, 1H), 6.83 (dd, J=7.1, 1.6 Hz, 1H), 3.79-3.59 (m, 3H), 3.56 (s, 3H), 3.51 (s, 1H), 3.23 (dd, J=11.8, 9.1 Hz, 1H), 3.05 (qd, J=15.6, 6.3 Hz, 2H), 2.82 (s, 1H), 2.51 (s, 1H), 2.38 (s, 3H).

Example 177

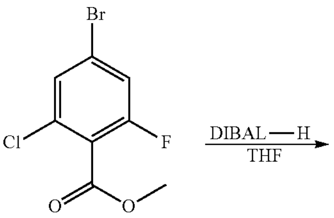

177-1

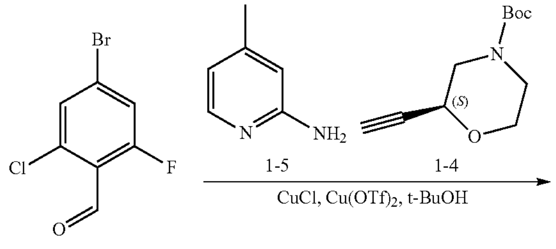

177-2

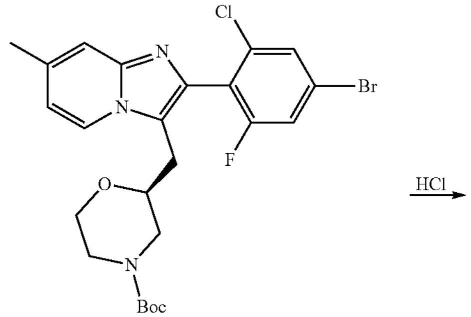

177-3

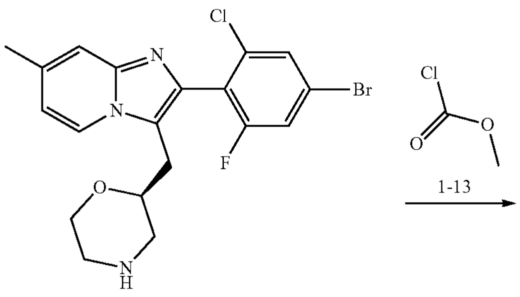

177-4

-continued

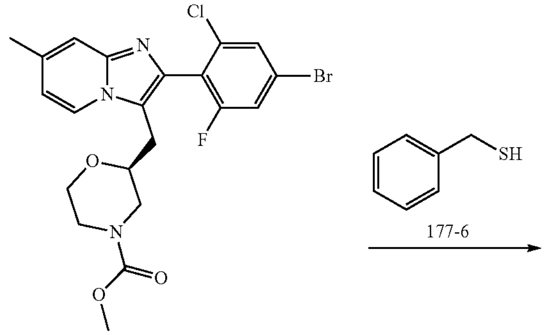

177-5

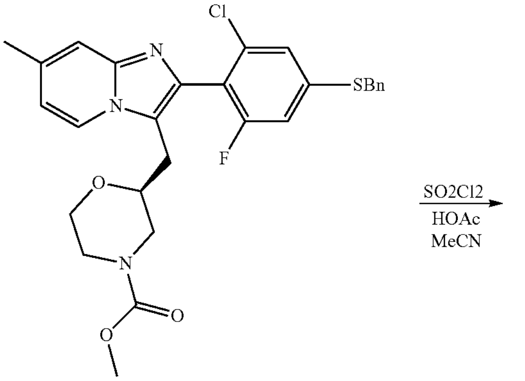

177-7

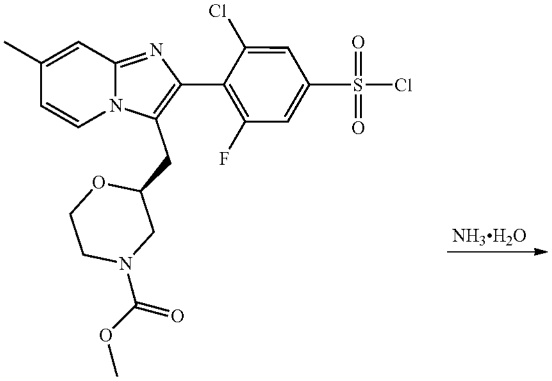

177-8

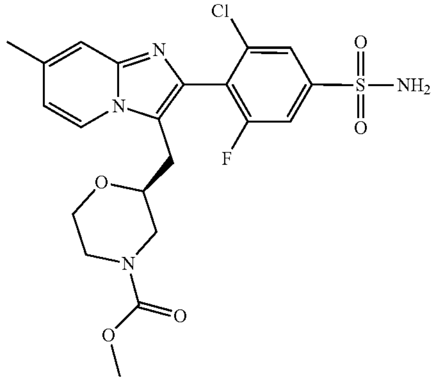

177

Step (1) Preparation of 4-bromo-2-chloro-6-fluorobenzaldehyde 177-2

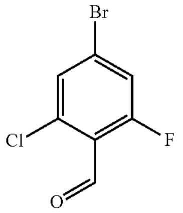

To a 100 mL round-bottom flask were added methyl 4-bromo-2-chloro-6-fluorobenzoate (1.0 g, 1.0 eq, compound 177-1) and anhydrous tetrahydrofuran sequentially. The reaction system was cooled to −70° C., then slowly added with DIBAL-H (3.8 mL, 1.2 eq) and reacted at this temperature for 2 h. The starting material was consumed completely and a new spot was generated as detected by TLC. The reaction system was added with aqueous HCl solution (1 M) to quench the reaction, then stirred at room temperature for 20 min, and extracted with dichloromethane (30 mL×3). The organic phase was washed with saturated brine, dried over anhydrous sodium sulfate, and concentrated by rotary evaporation. The residue was purified by column chromatography to give intermediate 177-2 (0.9 g, 80% purity) in the form of a colorless oil. LC-MS: $[M+H]^+$=237.1.

Step (2) Preparation of tert-butyl (S)-2-((2-(4-bromo-2-chloro-6-fluorophenyl)-7-methylimidazo[1,2-a]pyridin-3-yl)methyl)morpholine-4-carboxylate 177-3

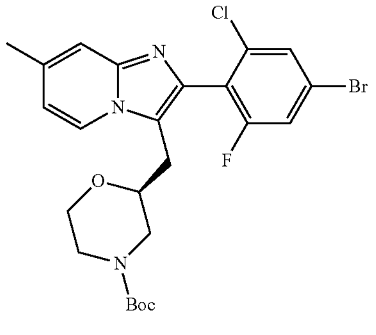

Intermediate 177-2 (0.75 g, 1.0 eq), compound 1-5 (0.67 g, 1.0 eq), compound 1-4 (0.34 g, 1.0 eq), CuCl (0.19 g, 0.3 eq) and $Cu(OTf)_2$ (0.69 g, 0.3 eq) were added to toluene (20 mL) and DMA (2 mL). The reaction system was purged with nitrogen 3 times, heated in an oil bath at 85° C. and reacted overnight (12 h). The starting material compound 1-4 was consumed as detected by TLC. Then the reaction system was cooled to room temperature, added with aqueous ammonia (10 mL) and water (15 mL), and stirred for 5 min, followed by liquid separation to give a toluene phase. The aqueous phase was extracted with dichloromethane (15 mL×2). The organic phase was washed with saturated brine, dried over anhydrous sodium sulfate, and concentrated by rotary evaporation. The residue was purified by column chromatography to give intermediate 177-3 (0.2 g, 99% purity) in the form of a brown foamy solid. LC-MS: $[M+H]^+$=538.1.

Step (3) Preparation of (S)-2-((2-(4-bromo-2-chloro-6-fluorophenyl)-7-methylimidazo[1,2-a]pyridin-3-yl)methyl)morpholine 177-4

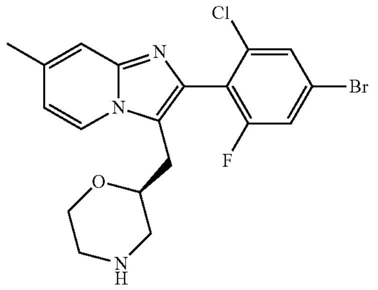

Intermediate 177-3 (0.2 g) was dissolved in methanol (5 mL), and a solution of HCl in EA (10 mL) was added. The reaction system was stirred at room temperature for 1.0 h. After the reaction was completed as detected by TLC, the reaction system was added with water (10 mL) and dichloromethane (20 mL). The aqueous phase was adjusted to pH 9-10 (weak alkalinity) with sodium carbonate, followed by liquid separation to give a dichloromethane phase. The aqueous phase was extracted with dichloromethane (10 mL×2). The dichloromethane phases were combined, washed with saturated brine, dried, filtered and concentrated by rotary evaporation to give intermediate 177-4 (170 mg) in the form of a yellow solid. The crude product was used directly in the next step. LC-MS: $[M+H]^+$=438.1.

Step (4) Preparation of methyl (S)-2-((2-(4-bromo-2-chloro-6-fluorophenyl)-7-methylimidazo[1,2-a]pyridin-3-yl)methyl)morpholine-4-carboxylate 177-5

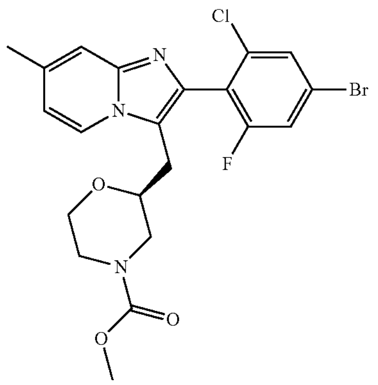

Intermediate 177-4 (170 mg, 1.0 eq) was dissolved in dichloromethane (2 mL), and triethylamine (120 mg, 2.0 eq) was added, followed by the dropwise addition of methyl chloroacetate (55 mg, 1.5 eq). The reaction system was reacted for 1.0 h. After the reaction was completed as detected by TLC, the reaction system was added with water (10 mL) and dichloromethane (20 mL), and stirred for 10 min, followed by liquid separation to give a dichloromethane phase. The aqueous phase was extracted with dichloromethane (10 mL×2). The dichloromethane phases were combined, washed with saturated sodium chloride, dried over anhydrous sodium sulfate, and concentrated by rotary evaporation. The residue was purified by column chromatography to give intermediate 177-5 (175 mg, 96% purity) in the form of a white solid. LC-MS: $[M+H]^+$=496.1.

Step (5) Preparation of methyl (S)-2-((2-(4-(benzylthio)-2-chloro-6-fluorophenyl)-7-methylimidazo[1,2-a]pyridin-3-yl)methyl)morpholine-4-carboxylate 177-7

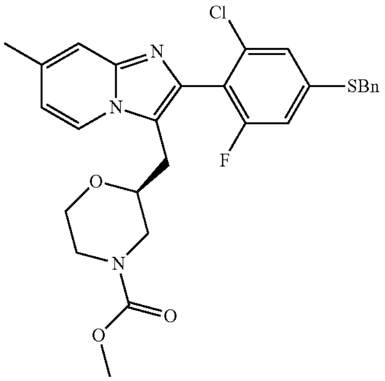

Intermediate 177-5 (175 mg, 1.0 eq) was dissolved in dioxane (10 mL), and BnSH (53 mg, 1.1 eq), $Pd_2(dba)_3$ (36 mg, 0.1 eq), Xantphos (25 mg, 0.1 eq) and DIPEA (95 mg, 2.0 eq) were added. The reaction system was purged with $N_2$ three times and reacted at 85° C. overnight. The starting material was consumed completely as monitored by TLC. After the reaction was completed, the reaction system was added with water (10 mL) and ethyl acetate (20 mL), and stirred for 10 min, followed by liquid separation to give an ethyl acetate phase. The aqueous phase was extracted with ethyl acetate (10 mL×2). The ethyl acetate phases were combined, washed with saturated sodium chloride, dried over anhydrous sodium sulfate, and concentrated by rotary evaporation. The residue was purified by column chromatography to give intermediate 177-7 (165 mg, 95% purity) in the form of a white solid. LC-MS: $[M+H]^+$=540.0.

Step (6) Preparation of methyl (S)-2-((2-(2-chloro-4-(chlorosulfonyl)-6-fluorophenyl)-7-methylimidazo[1,2-a]pyridin-3-yl)methyl)morpholine-4-carboxylate 177-8

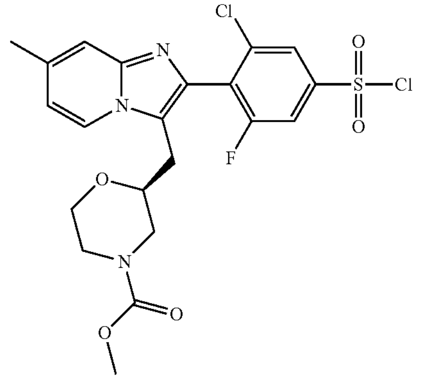

Intermediate 177-7 (160 mg) was added to a reaction flask containing dichloromethane (5 mL), glacial acetic acid (90 mg, 5.0 eq) was added, and $SO_2Cl_2$ (160 mg, 4.0 eq) was added dropwise in an ice bath. The reaction system was reacted at 0° C. for 1 h. The starting material was consumed, and intermediate 177-8 was generated as detected by LCMS. The reaction system was used directly in the next step without treatment.

Step (7) Preparation of methyl (S)-2-((2-(2-chloro-6-fluoro-4-sulfamoylphenyl)-7-methylimidazo[1,2-a]pyridin-3-yl)methyl)morpholine-4-carboxylate

177

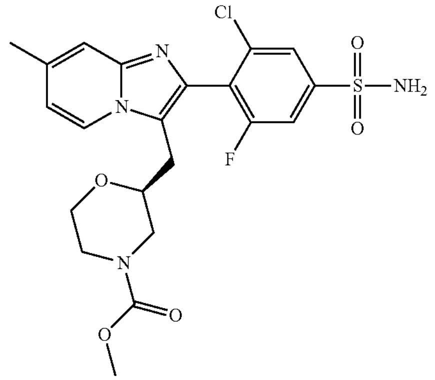

Aqueous ammonia (10 mL) was added dropwise slowly to the above reaction system at 0° C. The reaction system was reacted at 0° C. for 0.2 h. The starting material was consumed completely, and a target product was generated as detected by LCMS. The reaction system was concentrated to dryness, and purified by preparative chromatography, to give compound 177 (80 mg, 98.982% purity) in the form of a white solid. LC-MS: $[M+H]^+$=497.2.

1H NMR (400 MHZ, DMSO-d6) δ 8.44 (d, J=7.1 Hz, 1H), 7.85 (s, 1H), 7.72 (s, 2H), 7.70 (s, 1H), 7.37 (s, 1H), 6.86 (d, J=7.1 Hz, 1H), 3.77 (d, J=11.6 Hz, 1H), 3.63 (d, J=11.9 Hz, 2H), 3.55 (s, 3H), 3.43 (s, 1H), 3.19 (dt, J=11.8, 5.8 Hz, 1H), 3.01 (qd, J=15.5, 6.0 Hz, 2H), 2.78 (s, 1H), 2.52 (s, 1H), 2.38 (s, 3H).

Example 178

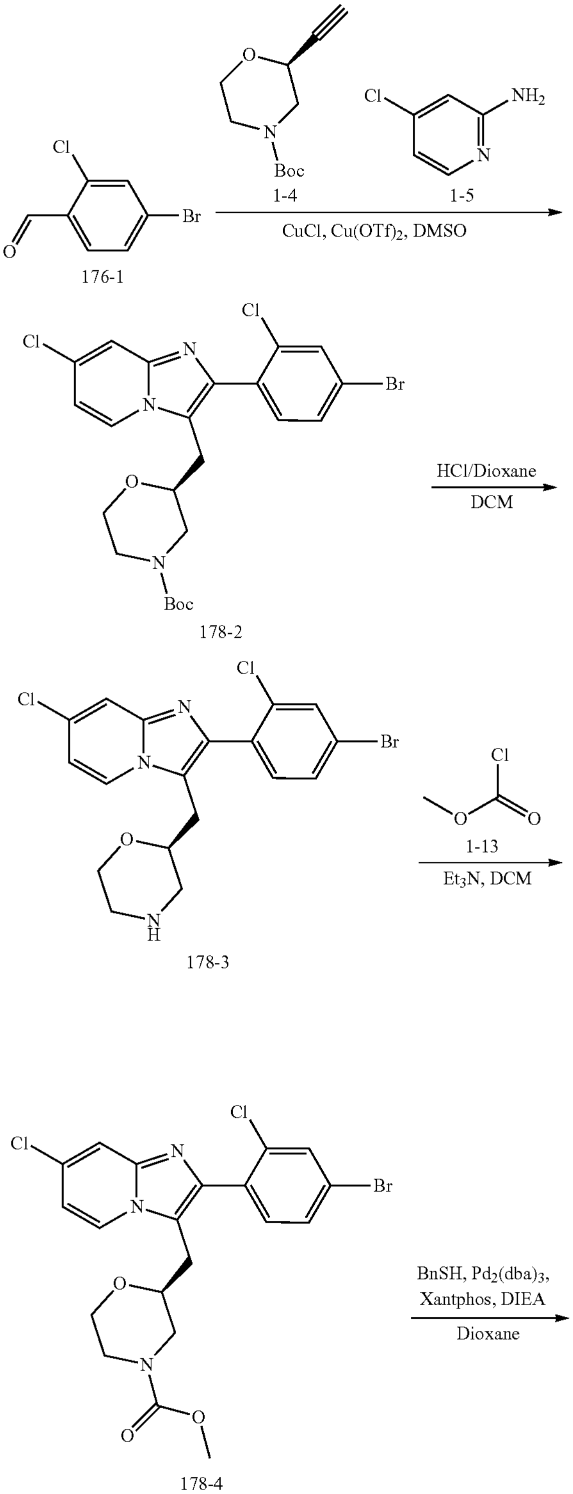

1-4 1-5 176-1 178-2 1-13 178-3 178-4

-continued

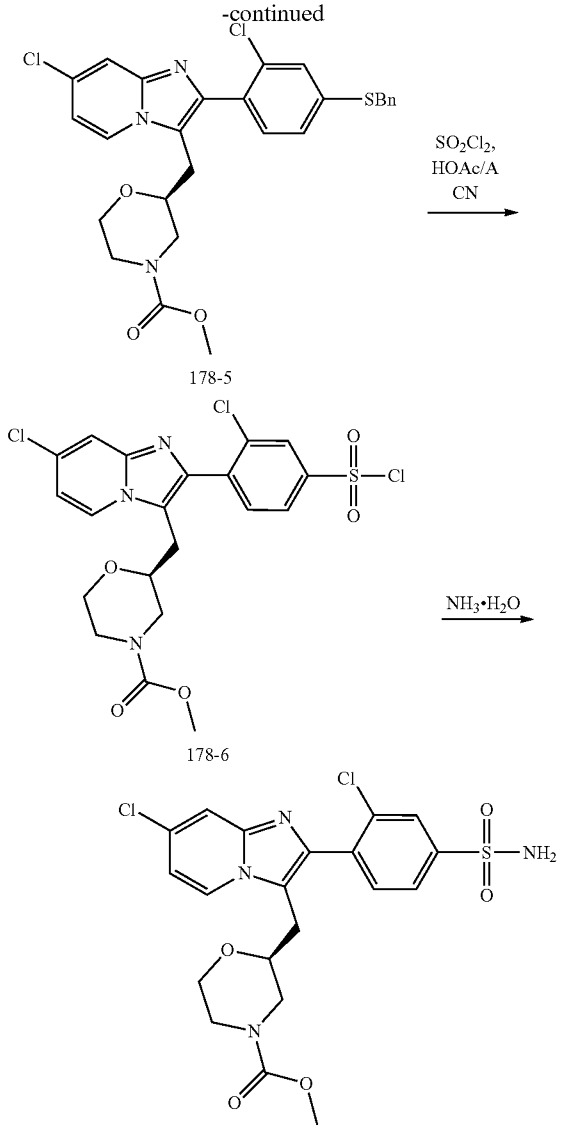

178-5

178-6

178

Step (1) Preparation of tert-butyl (S)-2-((2-(4-bromo-2-chlorophenyl)-7-chloroimidazo[1,2-a]pyridin-3-yl)methyl)morpholine-4-carboxylate

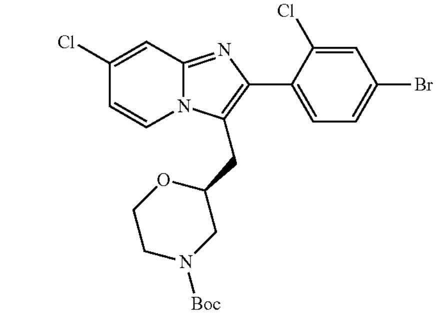

178-2

To a 100 mL round-bottom flask were added compound 1-4 (680 mg, 1.0 eq), compound 176-1 (706 mg, 1.0 eq), 4-chloropyridin-2-amine (413 mg, 1.0 eq, compound 178-1), CuI (61 mg, 0.1 eq), $Cu(OTf)_2$ (116 mg, 0.1 eq) and DMSO (7 mL) sequentially. The reaction system was purged with nitrogen 3 times, heated in an oil bath at 85° C. and reacted overnight (12 h). The starting material compound 1-4 was consumed as detected by TLC. After the reaction system was cooled to room temperature, aqueous ammonium chloride solution (10 mL) and ethyl acetate (15 mL) were added. The reaction system was shaken for 5 min, followed by liquid separation to give an organic phase. The aqueous phase was extracted with ethyl acetate (15 mL×2). The organic phase was washed with saturated brine, dried over anhydrous sodium sulfate, and concentrated by rotary evaporation. The residue was purified by column chromatography to give intermediate 178-2 (0.65 g) in the form of a yellow oil. LC-MS: $[M+H]^+$=540.2.

Step (2) Preparation of (S)-2-((2-(4-bromo-2-chlorophenyl)-7-chloroimidazo[1,2-a]pyridin-3-yl)methyl)morpholine 178-3

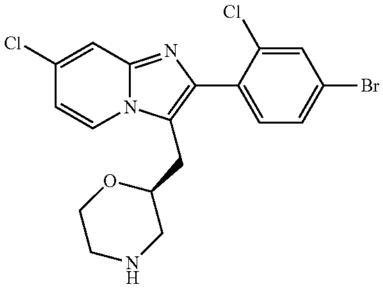

Intermediate 178-2 (0.65 g) was dissolved in dichloromethane (2 mL), and a solution of HCl in dioxane (6 mL) was added. The reaction system was stirred at room temperature for 1.0 h. After the reaction was completed as detected by TLC, The reaction system was concentrated by rotary evaporation, added with water (10 mL) and dichloromethane (20 mL), and extracted to give an aqueous phase. The aqueous phase was adjusted to pH 8-9 (weak alkalinity) with aqueous sodium carbonate solution, followed by liquid separation to give a dichloromethane phase. The aqueous phase was extracted with dichloromethane (10 mL×2). The dichloromethane phases were combined, washed with saturated brine, dried, filtered and concentrated by rotary evaporation to give intermediate 178-3 (512 mg, 95% purity) in the form of a yellow oil. LC-MS: $[M+H]^+$=440.1.

Step (3) Preparation of methyl (S)-2-((2-(4-bromo-2-chlorophenyl)-7-chloroimidazo[1,2-a]pyridin-3-yl) methyl)morpholine-4-carboxylate 178-4

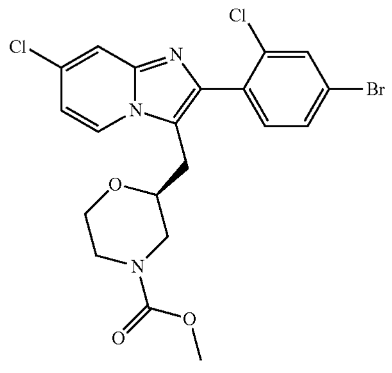

Intermediate 178-3 (500 mg, 1.0 eq) was dissolved in dichloromethane (5 mL), and triethylamine (206 mg, 2.0 eq) was added, followed by the dropwise addition of methyl chloroacetate (115 mg, 1.2 eq). The reaction system was reacted for 1.0 h and a product was generated as detected by LC-MS. After the reaction was completed, the reaction system was added with water (15 mL), and stirred for 30 min, followed by liquid separation to give a dichloromethane phase. The aqueous phase was extracted with dichloromethane (10 mL×2). The dichloromethane phases were combined, washed with saturated sodium chloride, dried over anhydrous sodium sulfate, and concentrated by rotary evaporation to give intermediate 178-4 (0.52 g) in the form of a yellow oil. LC-MS: $[M+H]^+$=498.2.

Step (4) Preparation of methyl (S)-2-((2-(4-benzylthio-2-chlorophenyl)-7-chloroimidazo[1,2-a]pyridin-3-yl)methyl)morpholine-4-carboxylate 178-5

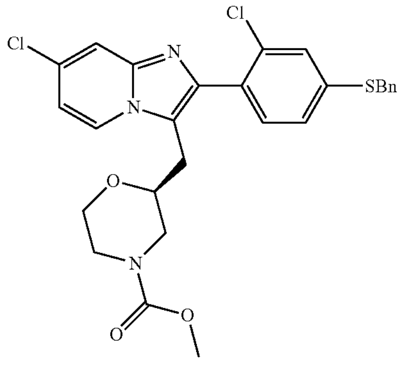

Intermediate 178-4 (0.52 g, 1.0 eq) was dissolved in dioxane (6 mL), and BnSH (0.16 g, 1.2 eq), Pd> (dba); (0.05 g, 0.05 eq), Xantphos (0.06 g, 0.1 eq) and DIEA (0.41 g, 3.0 eq) were added. The reaction system was purged with $N_2$ three times and reacted at 80° C. overnight. The starting material was consumed completely as monitored by LCMS. After the reaction was completed, the reaction system was added with water (10 mL) and ethyl acetate (20 mL), followed by liquid separation to give an ethyl acetate phase. The aqueous phase was extracted with ethyl acetate (10 mL×2). The ethyl acetate phases were combined, washed with saturated sodium chloride, dried over anhydrous sodium sulfate, and concentrated by rotary evaporation. The residue was purified by column chromatography to give intermediate 178-5 (0.48 g, 86% purity) in the form of a yellow oil. LC-MS: $[M+H]^+$=542.2.

Step (5) Preparation of methyl (S)-2-((7-chloro-2-(2-chloro-4-(chlorosulfonyl)phenyl)imidazo[1,2-a] pyridin-3-yl)methyl)morpholine-4-carboxylate 178-6

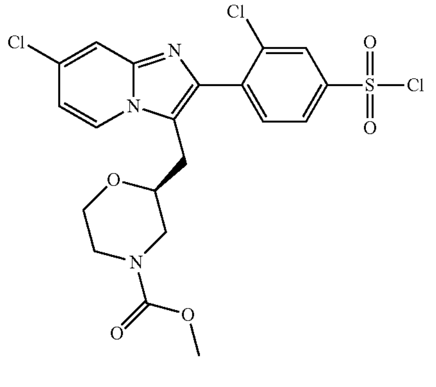

Intermediate 178-5 (220 mg) was added to a reaction flask of acetonitrile (3 mL), glacial acetic acid (121 mg, 5.0 eq) was added, and $SO_2Cl_2$ (218 mg, 4.0 eq) was added dropwise in an ice bath. The reaction system was reacted at 0° C. for 1 h. The starting material was consumed, and intermediate 178-6 was generated as detected by LCMS. The reaction system was used directly in the next step without treatment.

Step (6) Preparation of methyl (S)-2-((7-chloro-2-(2-chloro-4-sulfamoylphenyl)imidazo[1,2-a]pyridin-3-yl)methyl)morpholine-4-carboxylate

178

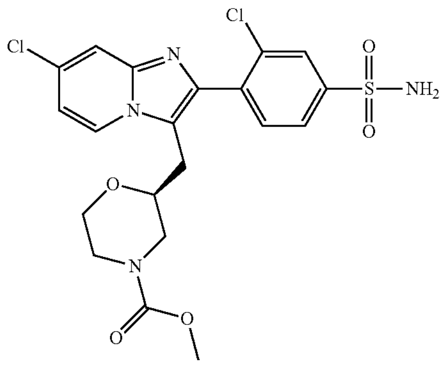

Aqueous ammonia (1.5 mL) was diluted with acetonitrile (1 mL) and added dropwise to the above reaction system at 0° C. The reaction system was reacted at room temperature for 0.5 h. The starting material was consumed completely and a target product was generated as detected by LC-MS.

The reaction system was extracted with water and ethyl acetate twice, washed with saturated brine, dried over anhydrous sodium sulfate, and concentrated. The residue was purified by preparative chromatography to give compound 178 (30 mg, 99.6% purity) in the form of a white solid. LC-MS: $[M+H]^+$=499.1.

$^1$H NMR (400 MHZ, DMSO-$d_6$) δ 8.61 (d, J=7.4 Hz, 1H), 7.98 (s, 1H), 7.85 (d, J=9.6 Hz, 1H), 7.79 (d, J=2.1 Hz, 1H), 7.73 (d, J=8.0 Hz, 1H), 7.61 (s, 2H), 7.09 (dd, J=7.4, 2.1 Hz, 1H), 3.79 (d, J=12.5 Hz, 1H), 3.63 (d, J=11.5 Hz, 3H), 3.56 (s, 4H), 3.51 (s, 1H), 3.26-3.21 (m, 2H), 3.20-3.14 (m, 1H), 3.12 (s, 1H), 3.03 (dd, J=15.6, 8.4 Hz, 1H), 2.81 (s, 1H).

Example 179

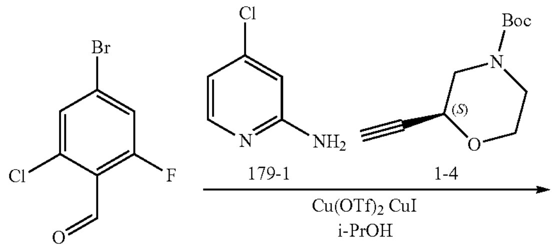

177-2 179-1 1-4

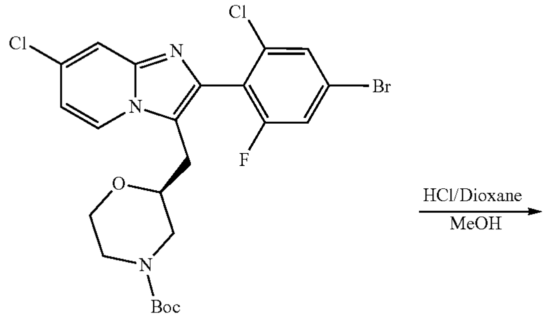

179-2

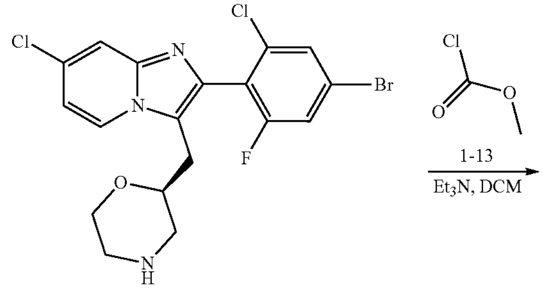

179-3

-continued

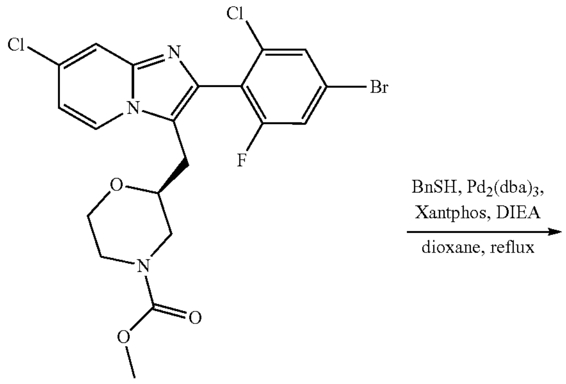

179-4

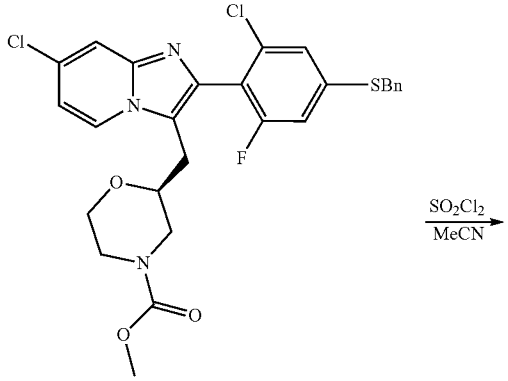

179-5

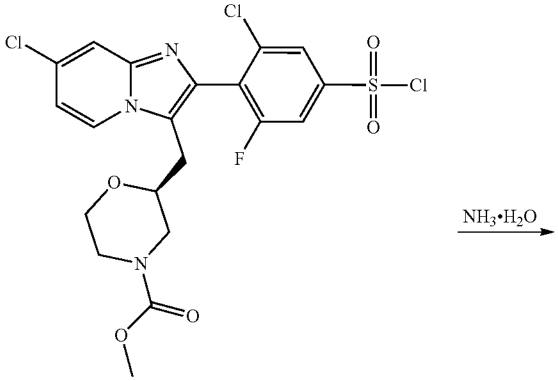

179-6

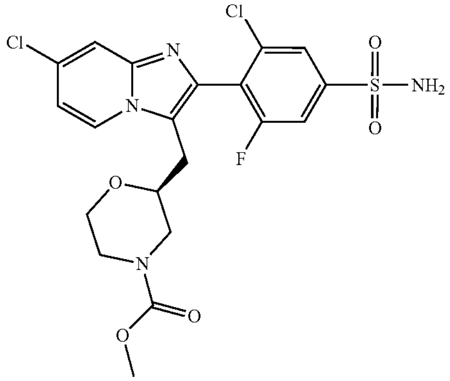

179

Step (1) Preparation of tert-butyl (S)-2-((2-(4-bromo-2-chloro-6-fluorophenyl)-7-chloroimidazo[1,2-a]pyridin-3-yl)methyl)morpholine-4-carboxylate 179-2

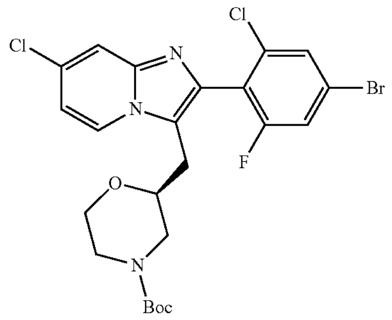

Intermediate 177-2 (2.16 g, 1.0 eq), 4-chloropyridin-2-amine (1.17 g, 1.0 eq, compound 179-1), compound 1-4 (1.92 g, 1.0 eq), CuI (0.19 g, 0.1 eq) and Cu(OTf), (0.33 g, 0.1 eq) were added to isopropanol (25 mL). The reaction system was purged with nitrogen 3 times, heated in an oil bath at 85° C. and reacted overnight (12 h). The starting material compound 1-4 was consumed as detected by TLC, work-up: the reaction system was cooled to room temperature, added with aqueous ammonia (10 mL) and water (15 mL), and stirred for 5 min, followed by liquid separation to give a toluene phase. The aqueous phase was extracted with dichloromethane (15 mL×2). The organic phase was washed with saturated brine, dried over anhydrous sodium sulfate, and concentrated by rotary evaporation. The residue was purified by column chromatography to give intermediate 179-2 (0.93 g, 92% purity) in the form of a light yellow foamy solid.

LC-MS: $[M+H]^+$=558.0.

Step (2) Preparation of (S)-2-((2-(4-bromo-2-chloro-6-fluorophenyl)-7-chloroimidazo[1,2-a]pyridin-3-yl)methyl)morpholine 179-3

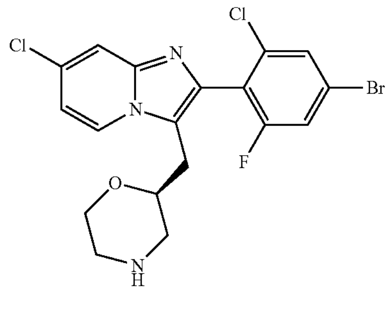

Intermediate 179-2 (0.93 g) was dissolved in methanol (10 mL), and a solution of HCl in dioxane (10 mL) was added. The reaction system was stirred at room temperature for 1.0 h. After the reaction was completed as detected by TLC, the reaction system was added with water (10 mL) and dichloromethane (20 mL). The aqueous phase was adjusted to pH 9-10 (weak alkalinity) with sodium carbonate, followed by liquid separation to give a dichloromethane phase. The aqueous phase was extracted with dichloromethane (10 mL×2). The dichloromethane phases were combined, washed with saturated brine, dried, and concentrated by rotary evaporation to give intermediate 179-3 (0.78 g) in the form of a white solid, LC-MS: $[M+H]^+$=458.1. The crude product was used directly in the next step.

Step (3) Preparation of methyl (S)-2-((2-(4-bromo-2-chloro-6-fluorophenyl)-7-chloroimidazo[1,2-a]pyridin-3-yl)methyl)morpholine-4-carboxylate 179-4

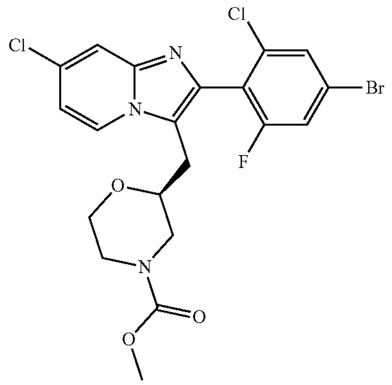

Intermediate 179-3 (690 mg, 1.0 eq) was dissolved in dichloromethane (10 mL), and triethylamine (380 mg, 2.0 eq) was added, followed by the dropwise addition of methyl chloroacetate (213 mg, 1.5 eq). The reaction system was reacted for 1.0 h. After the reaction was completed as detected by TLC, the reaction system was added with water (10 mL) and dichloromethane (20 mL), and stirred for 10 min, followed by liquid separation to give a dichloromethane phase. The aqueous phase was extracted with dichloromethane (10 mL×2). The dichloromethane phases were combined, washed with saturated sodium chloride, dried over anhydrous sodium sulfate, and concentrated by rotary evaporation. The residue was purified by column chromatography to give intermediate 179-4 (472 mg, 96% purity) in the form of a white solid. LC-MS: $[M+H]^+$=515.9.

Step (4) Preparation of methyl (S)-2-((2-(4-(benzylthio)-2-chloro-6-fluorophenyl)-7-chloroimidazo[1,2-a]pyridin-3-yl)methyl)morpholine-4-carboxylate 179-5

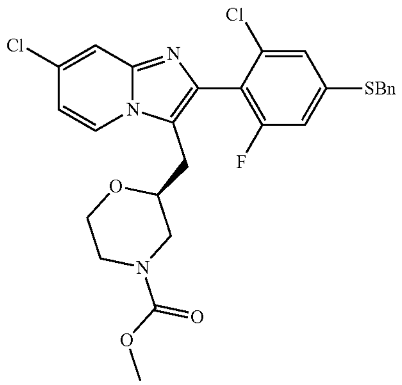

Intermediate 179-4 (420 mg, 1.0 eq) was dissolved in dioxane (10 mL), and BnSH (130 mg, 1.2 eq), $Pd_2(dba)_3$ (84 mg, 0.1 eq), Xantphos (50 mg, 0.1 eq) and DIPEA (210 mg, 2.0 eq) were added. The reaction system was purged with $N_2$ three times and reacted at 85° C. overnight. The starting material was consumed completely as monitored by TLC. After the reaction was completed, the reaction system was added with water (10 mL) and ethyl acetate (20 mL), and stirred for 10 min, followed by liquid separation to give an ethyl acetate phase. The aqueous phase was extracted with ethyl acetate (10 mL×2). The ethyl acetate phases were combined, washed with saturated sodium chloride, dried over anhydrous sodium sulfate, and concentrated by rotary evaporation. The residue was purified by column chromatography to give intermediate 179-5 (465 mg, 94% purity) in the form of a white solid. LC-MS: $[M+H]^+$=560.1.

Step (5) Preparation of methyl (S)-2-((7-chloro-2-(2-chloro-4-(chlorosulfonyl)-6-fluorophenyl)imidazo[1,2-a]pyridin-3-yl)methyl)morpholine-4-carboxylate 179-6

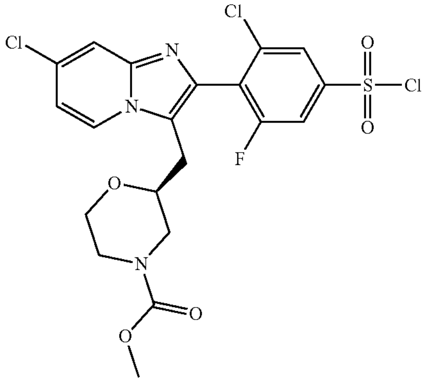

Intermediate 179-5 (415 mg) was added to a reaction flask of dichloromethane (5 mL), glacial acetic acid (224 mg, 5.0 eq) was added, and $SO_2Cl_2$ (415 mg, 4.0 eq) was added dropwise in an ice bath. The reaction system was reacted at 0° C. for 1 h. The starting material was consumed, and intermediate 179-6 was generated as detected by LCMS. The reaction system was used directly in the next step without treatment.

Step (6) Preparation of methyl (S)-2-((7-chloro-2-(2-chloro-6-fluoro-4-sulfamoylphenyl)imidazo[1,2-a]pyridin-3-yl)methyl)morpholine-4-carboxylate

179

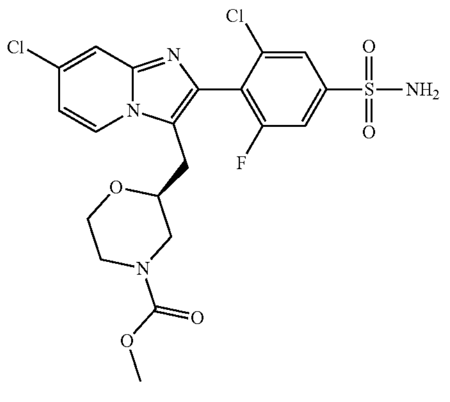

Aqueous ammonia (10 mL) was added dropwise slowly to the above reaction system at 0° C. The reaction system was reacted at 0° C. for 0.2 h. The starting material was consumed completely, and a target product was generated as detected by LCMS. The reaction system was concentrated to dryness. The residue was purified by preparative chromatography to give compound 179 (170 mg, 99.778% purity) in the form of a white solid. LC-MS: $[M+H]^+$=517.2.

$^1H$ NMR (400 MHz, DMSO-$d_6$) δ 8.61 (d, J=7.4 Hz, 1H), 7.79 (dd, J=6.5, 4.4 Hz, 2H), 7.64 (dt, J=8.0, 4.0 Hz, 1H), 7.14-7.05 (m, 1H), 6.94 (s, 1H), 3.81 (d, J=11.7 Hz, 1H), 3.63 (d, J=11.6 Hz, 2H), 3.56 (s, 3H), 3.45 (d, J=3.5 Hz, 1H), 3.20 (td, J=11.4, 2.2 Hz, 1H), 3.04 (ddd, J=23.5, 15.5, 5.9 Hz, 2H), 2.79 (s, 1H), 2.51 (s, 1H).

Example 180

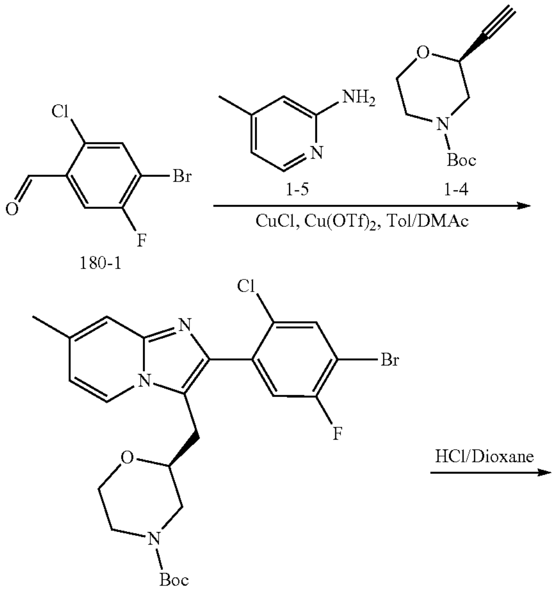

180-1

180-2

-continued

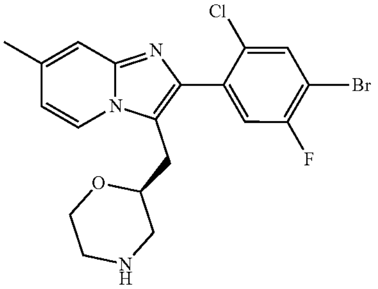

180-3

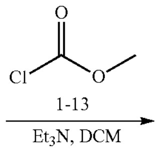

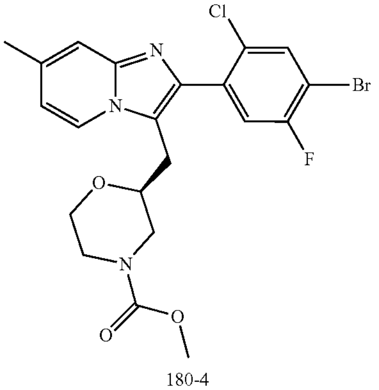

180-4

BnSH, $Pd_2(dba)_3$, Xantphos, DIEA
dioxane, reflux

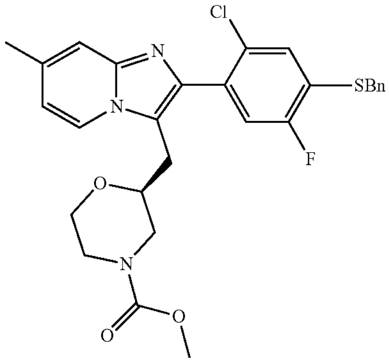

180-5

$SO_2Cl_2$
AcOH/MeCN

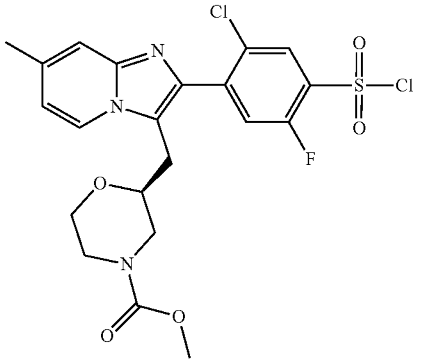

180-6

$NH_3{\bullet}H_2O$

-continued

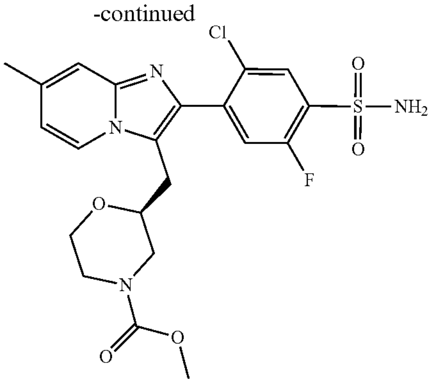

180

Step (1) Preparation of tert-butyl (S)-2-((2-(4-bromo-2-chloro-5-fluorophenyl)-7-methylimidazo[1,2-a]pyridin-3-yl)methyl)morpholine-4-carboxylate 180-2

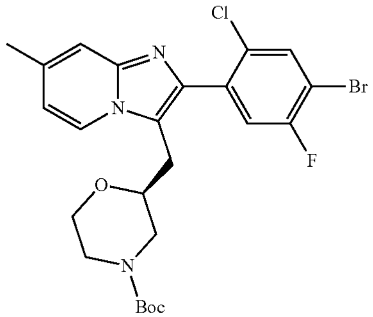

To a 100 mL round-bottom flask were added 4-bromo-2-chloro-5-fluorobenzaldehyde (1.5 g, 6.4 mmol, compound 180-1), compound 1-4 (2.67 g, 12.6 mmol) and compound 1-5 (0.68 g, 6.4 mmol) sequentially, and then toluene (15 mL) and N,N-dimethylacetamide (1 mL) were added, followed by the addition of catalysts copper(I) chloride (187.6 mg, 1.9 mmol) and copper(II) trifluoromethanesulfonate (685.4 mg, 1.9 mmol). The reaction system was purged with nitrogen three times, and reacted at 85° C. for 4 h. After the reaction was completed, a target product was generated as detected by LC-MS. The reaction system was concentrated by rotary evaporation to remove the solvent, dissolved with dichloromethane (50 mL), added with aqueous ammonia (50 mL), and stirred, followed by liquid separation to give an organic phase. The aqueous phase was extracted with DCM (150 mL×3). The organic phase was washed with saturated citric acid solution and saturated brine 3 times, respectively, dried over anhydrous sodium sulfate, and concentrated by rotary evaporation. The residue was purified by column chromatography to give intermediate 180-2 (1.9 g, 59.9% yield) in the form of a light yellow foamy solid powder. LC-MS: $[M+H]^+$=538.1.

Step (2) Preparation of (S)-2-((2-(4-bromo-2-chloro-5-fluorophenyl)-7-methylimidazo[1,2-a]pyridin-3-yl)methyl)morpholine 180-3

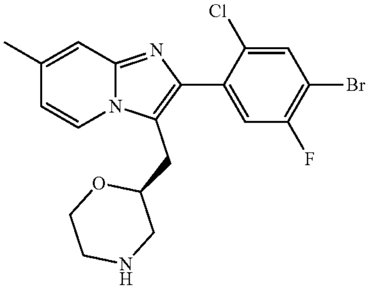

Intermediate 180-2 (0.7 g, 1.4 mmol) was dissolved in dichloromethane (5 mL). The reaction system was added with a solution of HCl in 1,4-dioxane solution (4 mL, 4.0 mol/L) in an ice bath, and then reacted at room temperature for 1.0 h. After the reaction was completed as detected by TLC, the reaction system was concentrated by rotary evaporation to remove the solvent, added with water (5 mL) and ethyl acetate (5 mL), and left to stand for liquid separation to give an aqueous phase. The aqueous phase was adjusted to pH 9-10 (weak alkalinity) with saturated aqueous sodium bicarbonate solution, and then extracted with ethyl acetate (5 mL×3). The organic phases were combined, washed with saturated saline 3 times, and concentrated to give intermediate 180-3 (560 mg, 91.5% yield) in the form of a light yellow oily liquid, which was used directly in the next step. LC-MS: $[M+H]^+$=438.1.

Step (3) Preparation of methyl (S)-2-((2-(4-bromo-2-chloro-5-fluorophenyl)-7-methylimidazo[1,2-a]pyridin-3-yl)methyl)morpholine-4-carboxylate 180-4

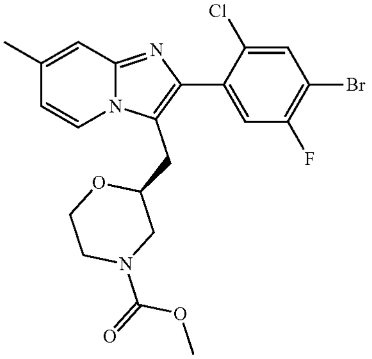

Intermediate 180-3 (560 mg, 1.28 mmol) was dissolved in dichloromethane (5 mL), and triethylamine (260 mg, 2.56 mmol) was added. The reaction system was added with methyl chloroformate (145.5 mg, 1.54 mmol) in an ice bath, reacted at room temperature for 0.5 h, and a product was generated as detected by LC-MS. After the reaction was completed, the reaction system was added with water (5 mL) to quench the reaction and left to stand for liquid separation to give a dichloromethane phase. The aqueous phase was extracted with dichloromethane (5 mL×2). The dichloromethane phases were combined, washed with saturated brine 3 times, dried over anhydrous sodium sulfate, and concentrated to give intermediate 180-4 (520 mg, 81.9% yield) in the form of a white solid. LC-MS: $[M+H]^+$=496.1.

Step (4) Preparation of methyl (S)-2-((2-(4-(benzylthio)-2-chloro-5-fluorophenyl)-7-methylimidazo[1,2-a]pyridin-3-yl)methyl)morpholine-4-carboxylate 180-5

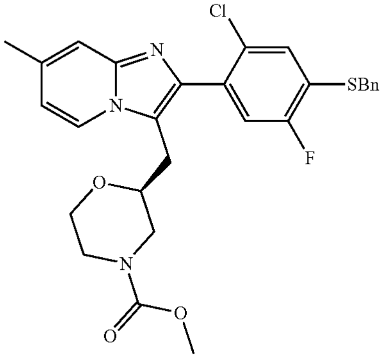

Intermediate 180-4 (520 mg, 1.05 mmol) was dissolved in 1,4-dioxane (10 mL), and Pd> (dba): (28.8 mg, 0.0315 mmol), Xantphos (30.3 mg, 0.0525 mmol), DIEA (401.7 mg, 3.15 mmol) and BnSH (169.6 mg, 1.36 mmol) were added. The reaction system was purged with nitrogen 3 times and reacted at 80° C. overnight. The starting material was consumed completely as detected by LC-MS. After the reaction was completed, water (10 mL) and ethyl acetate (20 mL) were added. The reaction system was stirred and left to stand for liquid separation to give an ethyl acetate phase. The aqueous phase was extracted with ethyl acetate (10 mL×2). The ethyl acetate phases were combined, washed with saturated sodium chloride, dried over anhydrous sodium sulfate, and concentrated. The residue was purified by column chromatography to give intermediate 180-5 (500 mg, 88.5% yield) in the form of a light yellow solid. LC-MS: $[M+H]^+$=440.2.

Step (5) Preparation of methyl (S)-2-((2-(2-chloro-4-(chlorosulfonyl)-5-fluorophenyl)-7-methylimidazo[1,2-a]pyridin-3-yl)methyl)morpholine-4-carboxylate 180-6

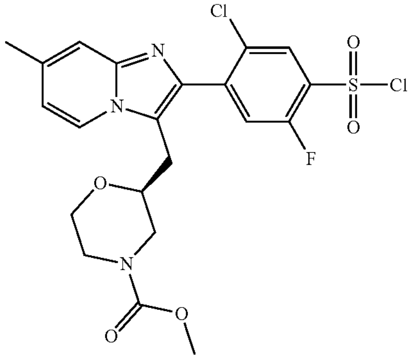

Substrate intermediate 180-5 (500 mg, 0.92 mmol) was added to a reaction flask of acetonitrile (15 mL), glacial acetic acid (276 mg, 4.6 mmol) was added, and sulfonyl chloride (500 mg, 3.7 mmol) was added dropwise slowly in an ice bath. The reaction system was reacted at 0° C. for 1 h. The starting material was consumed and intermediate 180-6 was generated as detected by LC-MS, LC-MS: $[M+H]^+$=515.9. The reaction system was used directly in the next step without treatment.

Step (6) Preparation of methyl (S)-2-((2-(2-chloro-5-fluoro-4-sulfamoylphenyl)-7-methylimidazo[1,2-a]pyridin-3-yl)methyl)morpholine-4-carboxylate

180

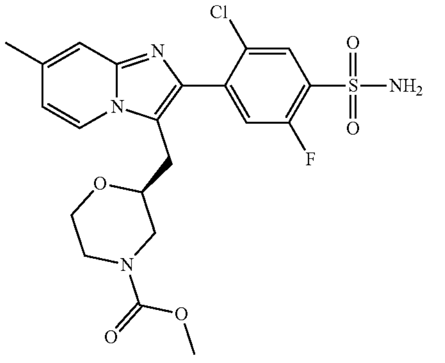

Aqueous ammonia (15 mL) was diluted with acetonitrile (10 mL) and added dropwise to the reaction system of the previous step at 0° C. The reaction system was reacted at room temperature for 0.5 h. The starting material was consumed completely and a target product was generated as detected by LC-MS. The reaction system was left to stand for liquid separation to give an organic phase. The aqueous phase was extracted with ethyl acetate 2 times. The organic phase was washed with saline solution, dried over anhydrous sodium sulfate, and concentrated. The residue was purified by preparative chromatography, and separated by preparative TLC to give compound 180 (140 mg, 99.5% purity) in the form of a white solid, LC-MS: $[M+H]^+$=497.1. $^1$H NMR (400 MHZ, DMSO-$d_6$) δ: 8.42 (d, J=7.1 Hz, 1H), 7.89 (s, 2H), 7.87 (d, J=6.6 Hz, 1H), 7.62 (d, J=10.2 Hz, 1H), 7.35 (s, 1H), 6.83 (dd, J=7.1, 1.6 Hz, 1H), 3.84-3.73 (m, 1H), 3.64 (t, J=11.0 Hz, 2H), 3.58-3.52 (m, 3H), 3.53-3.45 (m, 1H), 3.22 (td, J=11.7, 2.7 Hz, 1H), 3.12 (dd, J=15.6, 4.1 Hz, 1H), 3.00 (dd, J=15.6, 8.2 Hz, 1H), 2.81 (s, 1H), 2.53 (d, J=7.6 Hz, 1H), 2.42-2.29 (m, 3H).

Example 181

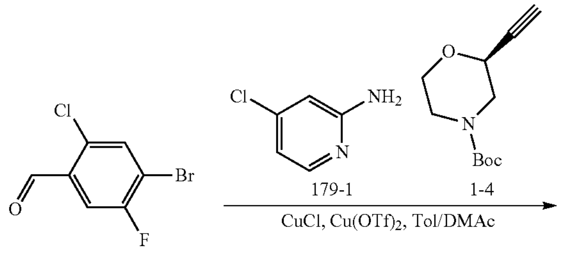

180-1 179-1 1-4

-continued

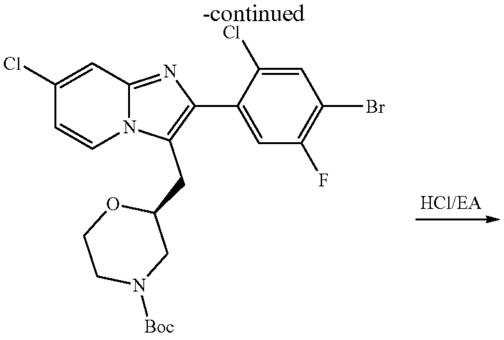

181-1

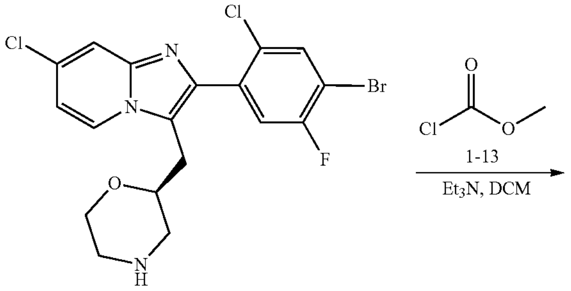

181-2

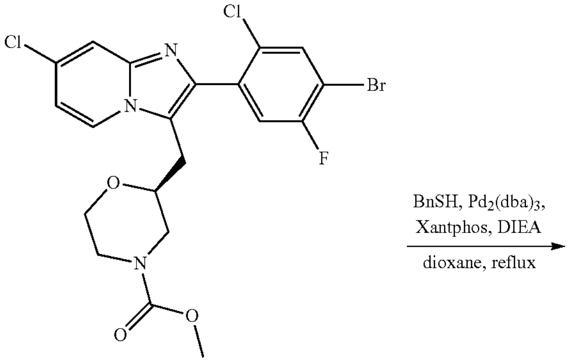

181-3

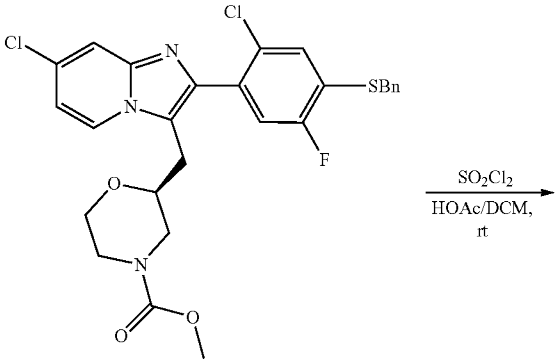

181-4

-continued

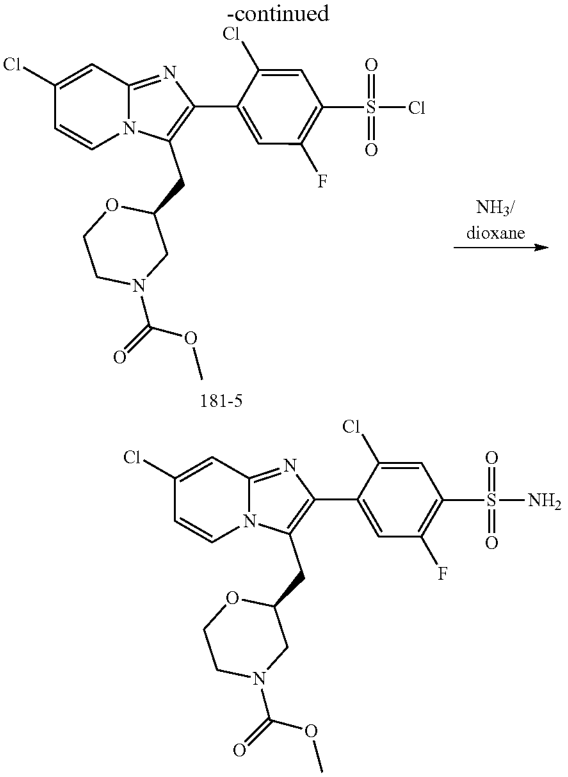

181-5

181

Step (1) Preparation of tert-butyl (S)-2-((2-(4-bromo-2-chloro-5-fluorophenyl)-7-chloroimidazo[1,2-a]pyridin-3-yl)methyl)morpholine-4-carboxylate 181-1

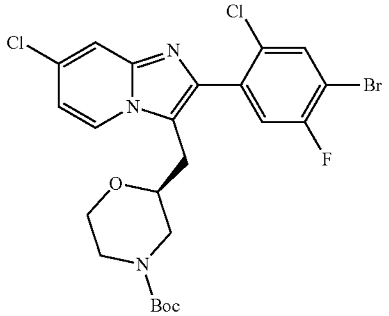

To a 100 mL round-bottom flask were added intermediate 180-1 (1.5 g, 1.0 eq), compound 179-1 (0.81 g, 1.0 eq), compound 1-4 (1.3 g, 1.0 eq), CuCl (0.19 g, 0.3 eq), $Cu(OTf)_2$ (0.69 g, 0.3 eq), toluene (20 mL) and DMA (2 mL) sequentially. The reaction system was purged with nitrogen 3 times, heated in an oil bath at 85° C. and reacted overnight (12 h). The starting material compound 1-4 was consumed as detected by TLC. Then the reaction system was cooled to room temperature, added with aqueous ammonia (10 mL) and water (15 mL), and stirred for 5 min, followed by liquid separation to give a toluene phase. The aqueous phase was extracted with dichloromethane (15 mL×2). The organic phase was washed with saturated brine, dried over anhydrous sodium sulfate, and concentrated by rotary evaporation. The residue was purified by column chromatography to give intermediate 181-1 (0.35 g, 99% purity) in the form of a light yellow foamy solid. LC-MS: $[M+H]^+$=558.1.

Step (2) Preparation of (S)-2-((2-(4-bromo-2-chloro-5-fluorophenyl)-7-chloroimidazo[1,2-a]pyridin-3-yl)methyl)morpholine 181-2

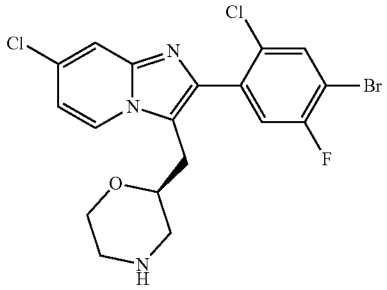

Intermediate 181-1 (0.1 g) was dissolved in methanol (5 mL), and HCV/EtOAc (10 mL, 3 M) was added. The reaction system was stirred at room temperature for 1.0 h. After the reaction was completed as detected by TLC, the reaction system was added with water (10 mL) and dichloromethane (20 mL). The aqueous phase was adjusted to pH 9-10 (weak alkalinity) with sodium carbonate, followed by liquid separation to give a dichloromethane phase. The aqueous phase was extracted with dichloromethane (10 mL×2). The dichloromethane phases were combined, washed with saturated brine, dried, and concentrated by rotary evaporation to give intermediate 181-2 (80 mg) in the form of a white solid. The crude product was used directly in the next step. LC-MS: $[M+H]^+$=458.1.

Step (3) Preparation of methyl (S)-2-((2-(4-bromo-2-chloro-5-fluorophenyl)-7-chloroimidazo[1,2-a]pyridin-3-yl)methyl)morpholine-4-carboxylate 181-3

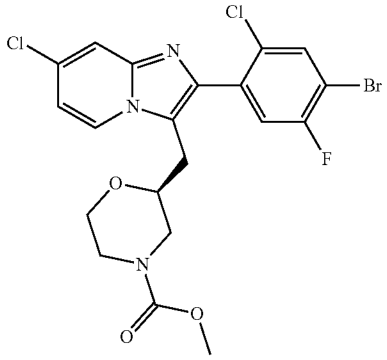

Intermediate 181-2 (80 mg, 1.0 eq) was dissolved in dichloromethane (2 mL), and triethylamine (36 mg, 2.0 eq) was added, followed by the dropwise addition of methyl chloroacetate (25 mg, 1.5 eq). The reaction system was reacted for 1.0 h. After the reaction was completed as detected by TLC, the reaction system was added with water (10 mL) and dichloromethane (20 mL), and stirred for 10 min, followed by liquid separation to give a dichloromethane phase. The aqueous phase was extracted with dichloromethane (10 mL×2). The dichloromethane phases were combined, washed with saturated sodium chloride, dried over anhydrous sodium sulfate, and concentrated by rotary evaporation. The residue was purified by column chromatography to give intermediate 181-3 (0.1 g, 96% purity) in the form of a white solid. LC-MS: $[M+H]^+$=515.9.

Step (4) Preparation of methyl (S)-2-((2-(4-(benzylthio)-2-chloro-5-fluorophenyl)-7-chloroimidazo[1,2-a]pyridin-3-yl)methyl)morpholine-4-carboxylate 181-4

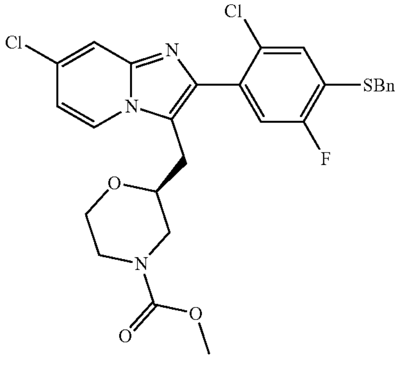

Intermediate 181-3 (0.45 g, 1.0 eq) was dissolved in dioxane (10 mL), and BnSH (0.13 g, 1.1 eq), Pd> (dba): (0.08 g, 0.1 eg), Xantphos (0.05 g, 0.1 eq) and DIPEA (0.23 g, 2.0 eq) were added. The reaction system was purged with $N_2$ three times and reacted at 85° C. overnight. The starting material was consumed completely as monitored by TLC. After the reaction was completed, the reaction system was added with water (10 mL) and ethyl acetate (20 mL), and stirred for 10 min, followed by liquid separation to give an ethyl acetate phase. The aqueous phase was extracted with ethyl acetate (10 mL×2). The ethyl acetate phases were combined, washed with saturated sodium chloride, dried over anhydrous sodium sulfate, and concentrated by rotary evaporation. The residue was purified by column chromatography to give intermediate 181-4 (0.3 g, 95% purity) in the form of a white solid. LC-MS: $[M+H]^+$=560.2.

Step (5) Preparation of methyl (S)-2-((7-chloro-2-(2-chloro-4-(chlorosulfonyl)-5-fluorophenyl)imidazo[1,2-a]pyridin-3-yl)methyl)morpholine-4-carboxylate 181-5

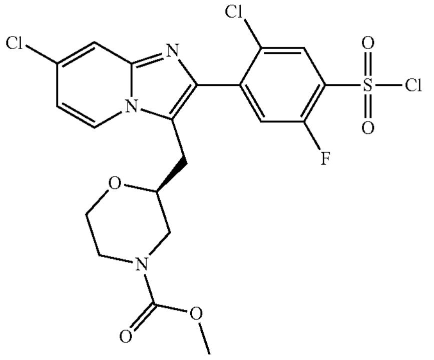

Intermediate 181-4 (280 mg) was added to a reaction flask of dichloromethane (5 mL), glacial acetic acid (150 mg, 5.0 eq) was added, and $SO_2Cl_2$ (270 mg, 4.0 eq) was added dropwise in an ice bath. The reaction system was reacted at room temperature for 1 h. The starting material was consumed, and intermediate 181-5 was generated as detected by LCMS. The reaction system was used directly in the next step without treatment.

Step (6) Preparation of methyl (S)-2-((7-chloro-2-(2-chloro-5-fluoro-4-sulfamoylphenyl)imidazo[1,2-a]pyridin-3-yl)methyl)morpholine-4-carboxylate

181

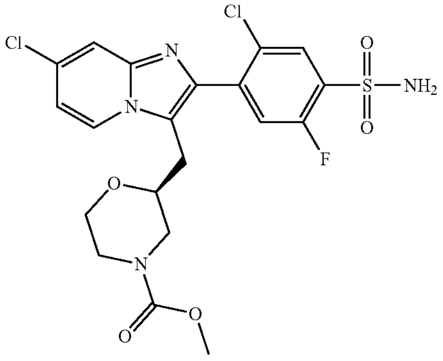

A solution of $NH_3$ in tetrahydrofuran (0.4 M, 5 mL) was added dropwise slowly to the above reaction system at 0° C. The reaction system was reacted at room temperature for 2 h. The starting material was consumed completely, and a target product was generated as detected by LCMS. The reaction system was concentrated to dryness. The residue was purified by preparative chromatography to give compound 181 (30 mg, 99% purity) in the form of a white solid. LC-MS: $[M+H]^+$=517.1.

$^1H$ NMR (400 MHZ, DMSO-$d_6$) δ 8.62 (d, J=7.4 Hz, 1H), 7.94 (s, 2H), 7.90 (d, J=6.6 Hz, 1H), 7.81-7.79 (m, 1H), 7.67 (d, J=10.1 Hz, 1H), 7.10 (dd, J=7.4, 2.2 Hz, 1H), 3.84 (s,

1H), 3.65 (s, 2H), 3.57 (s, 3H), 3.52 (t, J=9.4 Hz, 1H), 3.27-3.16 (m, 2H), 3.04 (dd, J=15, 6, 8.5 Hz, 1H), 2.82 (s, 1H), 2.52 (d, J=1.9 Hz, 1H).

Example 182

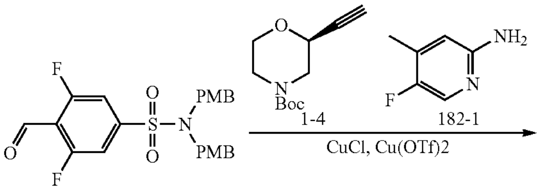

171-4

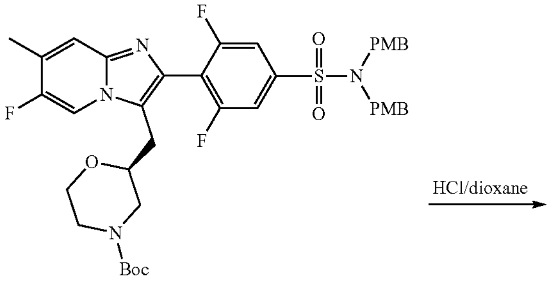

182-2

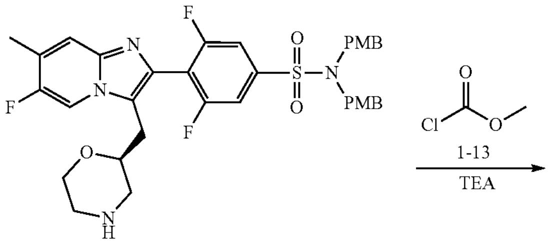

182-3

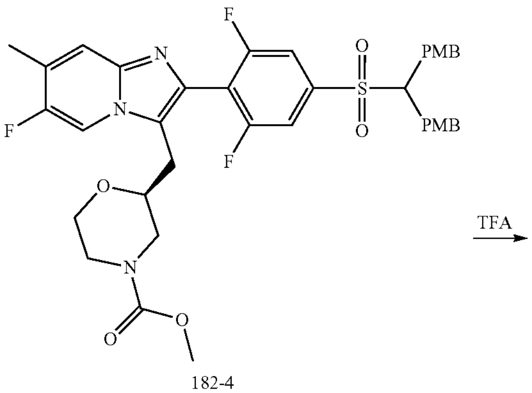

182-4

-continued

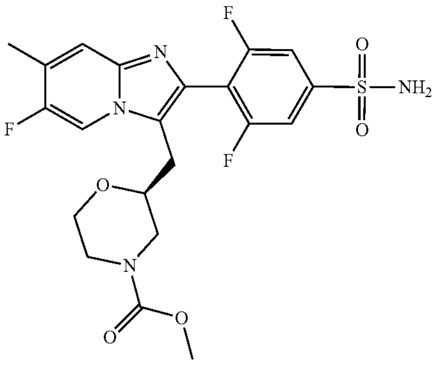
182

Step (1) Preparation of tert-butyl (S)-2-((2-(4-(N,N-bis(4-methoxybenzyl)sulfamoyl)-2,6-difluorophenyl)-6-fluoro-7-methylimidazo[1,2-a]pyridin-3-yl)methyl)morpholine-4-carboxylate 182-2

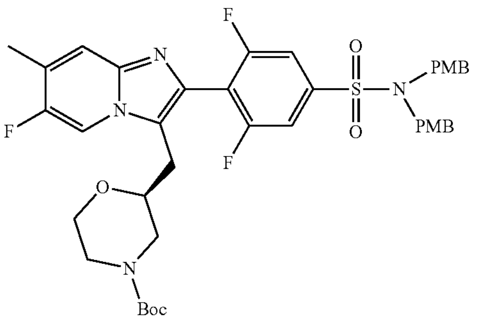

To a 100 mL round-bottom flask were added intermediate 171-4 (1.5 g, 3.25 mmol), 5-fluoro-4-methylpyridin-2-amine (410 mg, 3.25 mmol) and intermediate 1-4 (686.7 mg, 3.25 mmol), and then toluene (15 mL) and dimethyl acetamide (5 mL) were added, followed by the addition of catalysts copper (1) chloride (96.5 mg, 0.98 mmol) and copper(II) trifluoromethanesulfonate (353 mg, 0.98 mmol). The reaction system was purged with nitrogen three times and reacted at 80° C. overnight. After the reaction was completed, a target product was generated as detected by LC-MS. The reaction system was concentrated by rotary evaporation to remove the solvent, dissolved with dichloromethane (50 mL), added with aqueous ammonia (50 mL), and stirred, followed by liquid separation to give an organic phase. The aqueous phase was extracted with dichloromethane (150 mL×3). The organic phase was washed with saturated citric acid solution and saturated brine 3 times, respectively, dried over anhydrous sodium sulfate, and concentrated by rotary evaporation. The residue was purified by column chromatography to give intermediate 182-2 (920 mg, 36.3% yield) in the form of a light yellow oily liquid.

Step (2) Preparation of (S)-3,5-difluoro-4-(6-fluoro-7-methyl-3-(morpholin-2-ylmethyl)imidazo[1,2-a]pyridin-2-yl)-N,N-bis(4-methoxybenzyl)benzene-sulfonamide 182-3

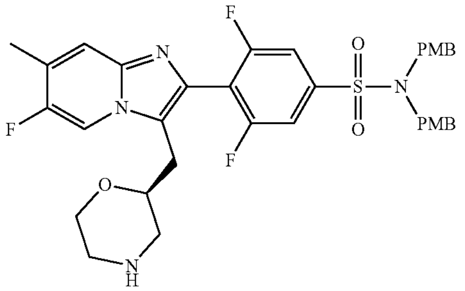

Intermediate 182-2 (410 mg, 0.53 mmol) was dissolved in ethyl acetate (2 mL). The reaction system was added with a solution of HCl in 1,4-dioxane solution (2 mL, 4.0 mol/L) in an ice bath, and then reacted at room temperature for 1.0 h. The reaction was completed as detected by TLC, work-up: the reaction system was concentrated by rotary evaporation to remove the solvent, added with water (2 mL) and ethyl acetate (2 mL), and left to stand for liquid separation to give an aqueous phase. The aqueous phase was adjusted to pH 8-9 (weak alkalinity) with saturated aqueous sodium bicarbonate solution, and then extracted with ethyl acetate (3 mL×3). The organic phases were combined, washed with saturated saline 3 times, and concentrated to give intermediate 182-3 (330 mg, 92.5% yield) in the form of a light yellow oily liquid, which was used directly in the next step. LC-MS: $[M+H]^+$=681.2.

Step (3) Preparation of methyl (S)-2-((2~ (4-(N,N-bis(4-methoxybenzyl)sulfamoyl)-2,6-difluorophenyl)-6-fluoro-7-methylimidazo[1,2-a]pyridin-3-yl)methyl)morpholine-4-carboxylate 182-4

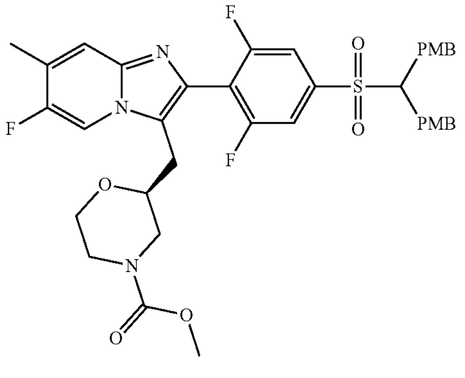

Intermediate 182-3 (330 mg, 0.49 mmol) was dissolved in dichloromethane (2 mL), and triethylamine (100 mg, 0.98 mmol) was added, followed by the dropwise addition of methyl chloroformate (70 mg, 0.73 mmol) in an ice bath. After the addition was completed, the reaction system was reacted at room temperature for 1 h. After the reaction was completed as detected by TLC, the reaction system was added with water (5 mL) to quench the reaction and left to stand for liquid separation to give a dichloromethane phase. The aqueous phase was extracted with dichloromethane (5 mL×2). The dichloromethane phases were combined, washed with saturated brine 3 times, dried over anhydrous sodium sulfate, and concentrated to give intermediate 182-4 (200 mg, 55.1% yield) in the form of a yellow oily liquid. LC-MS: $[M+H]^+$=739.1.

Step (4) Preparation of methyl (S)-2-((2-(2,6-difluoro-4-sulfamoylphenyl)-6-fluoro-7-methylimidazo[1,2-a]pyridin-3-yl)methyl)morpholine-4-carboxylate

182

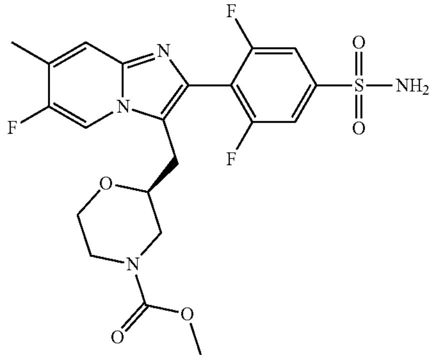

Intermediate 182-4 (200 mg, 0.27 mmol) was dissolved in dichloromethane (2 mL), and trifluoroacetic acid (2 mL) was added. The reaction system was reacted at room temperature overnight. The starting material was consumed completely as detected by TLC, and then the work-up was performed. The reaction system was added with water (5 mL) to quench the reaction, then added with dichloromethane (3 mL), and left to stand for liquid separation to give an aqueous phase. The aqueous phase was adjusted to pH 8-9 (weak alkalinity) with saturated aqueous sodium bicarbonate solution, and then extracted with dichloromethane (5 mL×3). The dichloromethane phases were combined, washed with saturated brine, dried over anhydrous sodium sulfate, and concentrated by rotary evaporation to remove the solvent, and purified by preparative chromatography to give compound 182 (82 mg, 97.8% purity, 60.98% yield) in the form of a white powdery solid. LC-MS: $[M+H]^+$=499.1.

$^1$H NMR (400 MHZ, DMSO-$d_6$) δ 8.71 (d, J=5.5 Hz, 1H), 7.68 (s, 2H), 7.59 (d, J=6.6 Hz, 2H), 7.50 (d, J=7.2 Hz, 1H), 3.80 (d, J=12.3 Hz, 1H), 3.59 (d, J=11.4 Hz, 2H), 3.53 (s, 3H), 3.44 (s, 1H), 3.26 (s, 1H), 3.18 (dd, J=11.8, 9.1 Hz, 1H), 3.06 (dd, J=15.4, 3.8 Hz, 1H), 2.98 (d, J=8.4 Hz, 1H), 2.76 (s, 1H), 2.32 (s, 3H).

Example 183

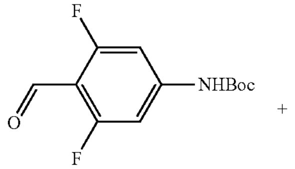

183-1

-continued

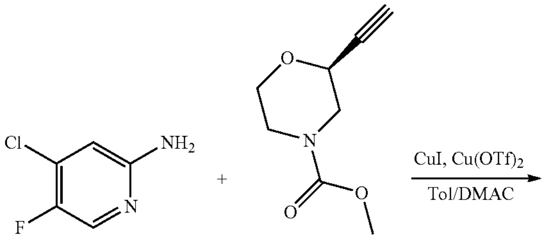

183-2 1-4

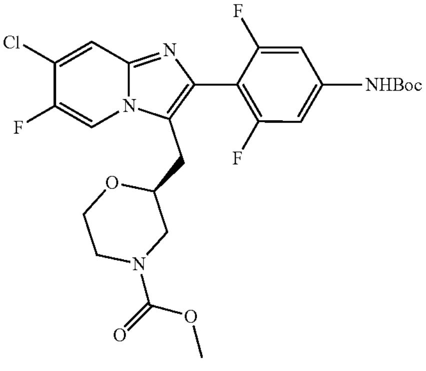

183-3

HCl/EtOAc

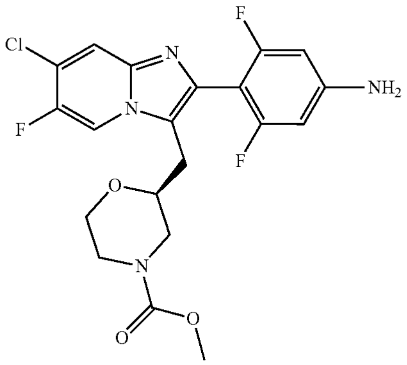

183-4 t-BuONO,
BnSSBn

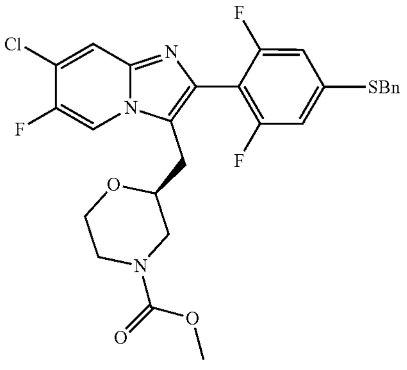

183-5

$SO_2Cl_2$
HOAc/DCM

-continued

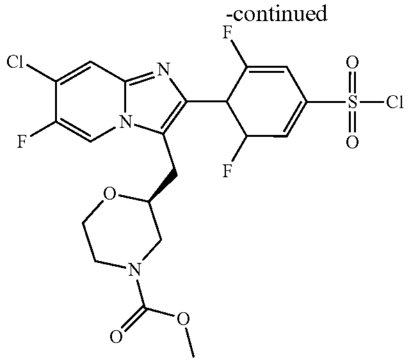

183-6

$NH_3$/MeOH

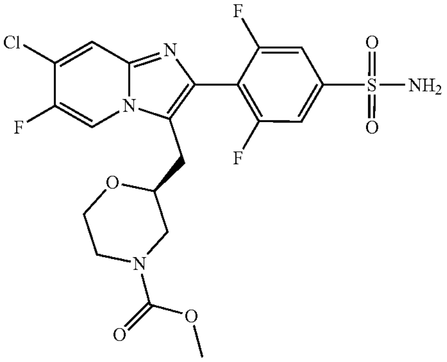

183

Step (1) Preparation of methyl (S)-2-((2-(4-((tert-butoxycarbonyl)amino)-2,6-difluorophenyl)-7-chloro-6-fluoroimidazo[1,2-a]pyridin-3-yl)methyl) morpholine-4-carboxylate 183-3

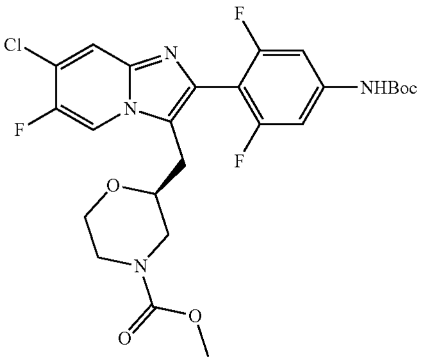

To a 10 mL round-bottom flask were added tert-butyl (3,5-difluoro-4-formylphenyl) carboxylate (0.75 g, 1.0 eq, compound 183-1), 4-chloro-5-fluoropyridin-2-amine (0.43 g, 1.0 cq, compound 183-2), compound 1-4 (0.5 g, 1.0 eq), CuI (0.17 g, 0.3 eq), $Cu(OTf)_2$ (0.32 g, 0.3 eq), toluene (10 mL) and DMA (1 mL) sequentially. The reaction system was purged with nitrogen 3 times, heated in an oil bath at 85° C. and reacted overnight (12 h). The starting material compound 1-4 was consumed as detected by TLC. The reaction system was cooled to room temperature, added with aqueous ammonia (5 mL) and water (15 mL), and stirred for 5 min, followed by liquid separation to give a toluene phase. The aqueous phase was extracted with DCM (15 mL×2). The organic phase was washed with saturated brine, dried over anhydrous sodium sulfate, and concentrated by rotary evaporation. The residue was purified by column chromatography to give intermediate 183-3 (0.18 g) in the form of a white solid. LC-MS: $[M+H]^+$=555.0.

Step (2) Preparation of methyl (S)-2-((2-(4-amino-2,6-difluorophenyl)-7-chloro-6-fluoroimidazo[1,2-a]pyridin-3-yl)methyl)morpholine-4-carboxylate 183-4

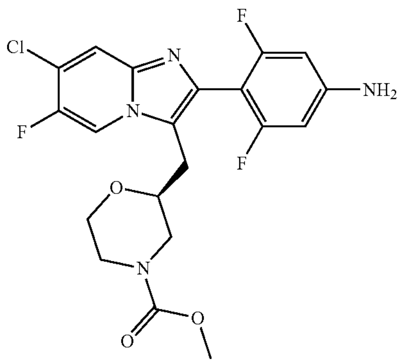

Intermediate 183-3 (0.18 g) was dissolved in methanol (2 mL), and HCl/EtOAc (3 M, 5 mL) was added. The reaction system was stirred at room temperature overnight. After the reaction was completed as detected by TLC, the reaction system was added with water (10 mL) and dichloromethane (20 mL). The aqueous phase was adjusted to pH 9-10 (weak alkalinity) with sodium carbonate, followed by liquid separation to give a DCM phase. The aqueous phase was extracted with DCM (10 mL×2). The DCM phases were combined, washed with saturated brine, dried, and concentrated by rotary evaporation to give intermediate 183-4 (0.12 g) in the form of a white solid. LC-MS: $[M+H]^+$=455.0.

Step (3) Preparation of methyl (S)-2-((2-(4-(benzylthio)-2,6-difluorophenyl)-7-chloro-6-fluoroimidazo[1,2-a]pyridin-3-yl)methyl)morpholine-4-carboxylate 183-5

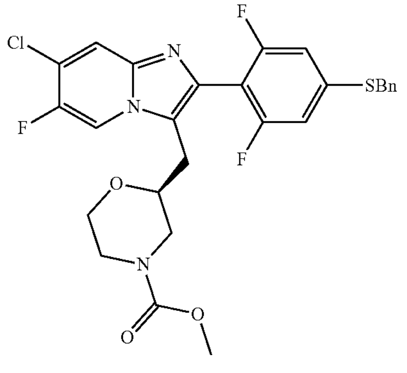

Intermediate 183-4 (0.2 g, 1.0 eq) and BnSSBn (0.11 g, 1.0 eq) were dissolved in MeCN (3 mL). The reaction system was purged with nitrogen three times. Ascorbic acid (40 mg, 0.5 eq) was dissolved with DMSO (0.5 mL) and added to the reaction system, which was then stirred and reacted for 10 min, and then added with t-BuONO (70 mg, 1.5 eq). The starting material was consumed completely as detected by TLC. The reaction system was added with water (2 mL), and then extracted with EtOAc (10 mL×3). The EtOAc phase was washed with saturated brine, dried over $Na_2SO_4$, and concentrated. The residue was purified by column chromatography to give intermediate 183-5 (0.11 g) in the form of a yellow solid. LC-MS: $[M+H]^+$=562.1.

Step (4) Preparation of methyl (S)-2-((7-chloro-2-(4-(chlorosulfonyl)-2,6-difluorophenyl)-6-fluoroimidazo[1,2-a]pyridin-3-yl)methyl)morpholine-4-carboxylate 183-6

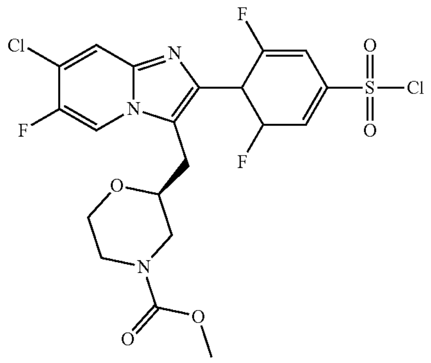

Intermediate 183-5 (100 mg) was added to a reaction flask of DCM (1 mL), glacial acetic acid (53.4 mg, 5.0 eq) was added, and $SO_2Cl$ (96.1 mg, 4.0 eq) was added dropwise in an ice bath. The reaction system was reacted at room temperature for 2 h. The starting material was consumed, and intermediate 183-6 was generated as detected by LCMS. The reaction system was used directly in the next step without treatment. LC-MS: $[M+H]^+$=540.2.

Step (5) Preparation of methyl (S)-2-((7-chloro-2-(2,6-difluoro-4-sulfamoylphenyl)-6-fluoroimidazo[1,2-a]pyridin-3-yl)methyl)morpholine-4-carboxylate

183

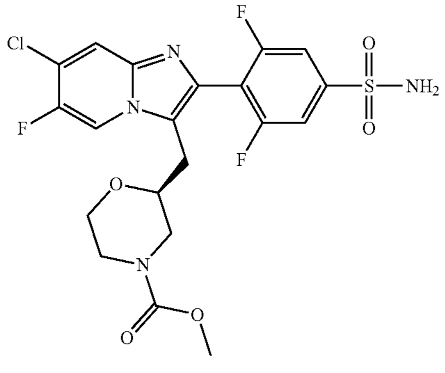

$NH_3$/MeOH (2 mL, 7 M) was added dropwise slowly to the above reaction system at 0° C. and reacted at room temperature for 2 h. The starting material was consumed completely and a target product was generated as detected by LC-MS. The reaction system was concentrated to dryness. The residue was purified by preparative chromatography to give compound 183 (3.0 mg) in the form of a white solid. LC-MS: $[M+H]^+$=519.1.

$^1$H NMR (400 MHZ, DMSO-$d_6$) δ 9.05 (d, J=5.3 Hz, 1H), 8.04 (d, J=7.1 Hz, 1H), 7.73 (s, 2H), 7.64 (d, J=6.7 Hz, 2H), 3.87 (d, J=12.7 Hz, 1H), 3.61 (d, J=8.1 Hz, 3H), 3.57 (s, 4H), 3.50 (d, J=9.9 Hz, 2H), 3.23-3.13 (m, 3H), 3.05-2.80 (m, 1H).

Example 184

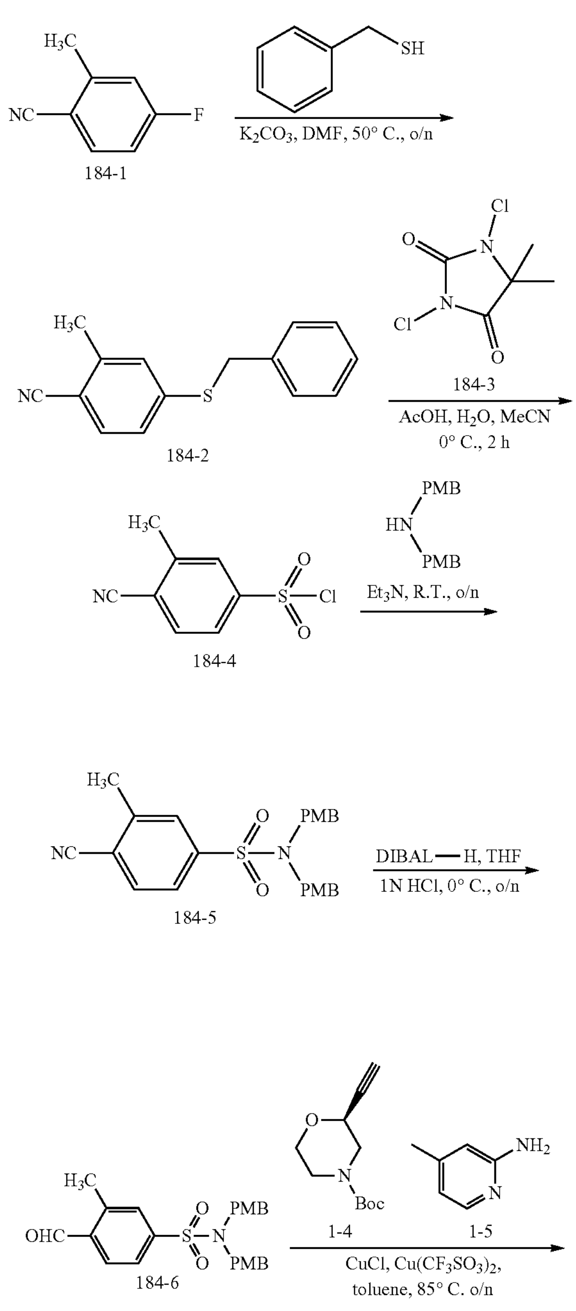

-continued

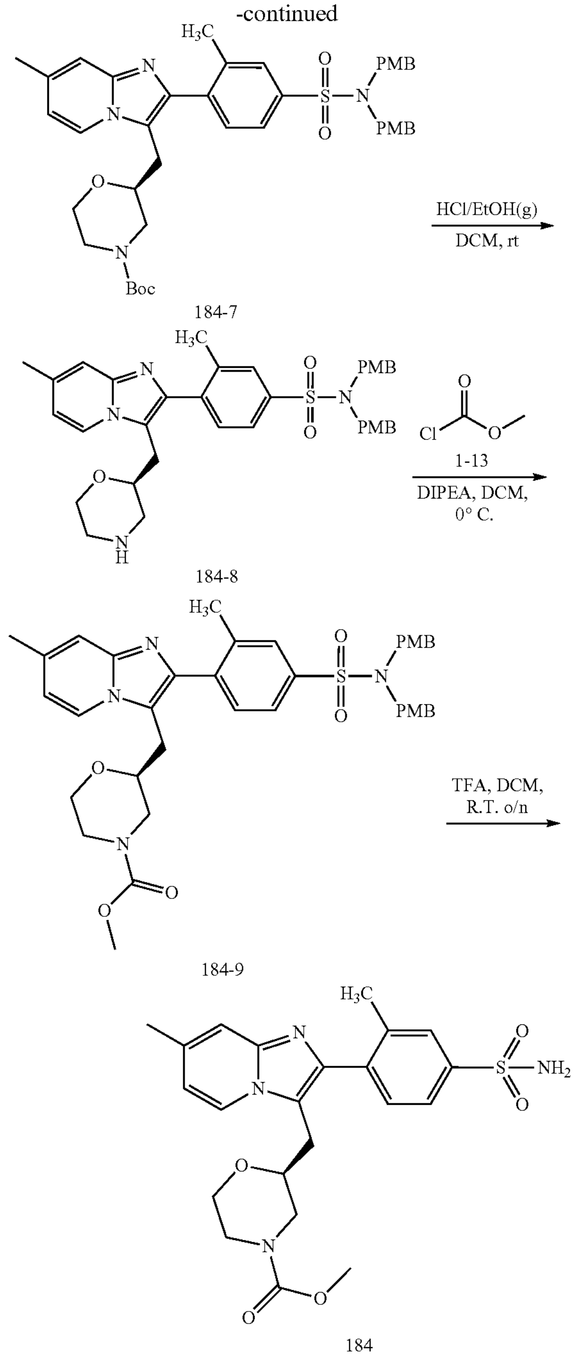

Step (1) Preparation of 4-(benzylthio)-2-methylbenzonitrile

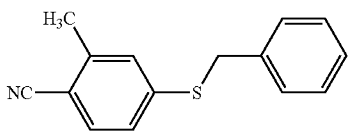

184-2

4-fluoro-2-methylbenzonitrile (5.00 g, 37.00 mmol) was dissolved in N,N-dimethylformamide (30 mL), and potassium carbonate (7.50 g, 54.35 mmol) and benzylthiol (3.5 mL) were added. The reaction system was stirred at 50° C. overnight. Then the reaction system was cooled to room temperature, added with water (80 mL) to quench the reaction and extracted with ethyl acetate (30 mL×3). The organic phases were combined, dried over anhydrous sodium sulfate, filtered and concentrated to give a crude product. The crude product was purified by silica gel column chromatography to give intermediate 184-2 (4.88 g, 52.4% yield) in the form of a yellow solid, LC-MS: $[M+H]^+$=239.8.

Step (2) Preparation of 4-cyano-3-methylbenzenesulfonyl chloride 184-4

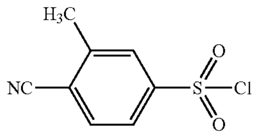

Under nitrogen atmosphere, intermediate 184-2 (4.88 g, 20.39 mmol) was dissolved in a prepared solvent (75 mL of acetonitrile, 3.5 mL of acetic acid, 1.5 mL of water). The reaction system was cooled to 0° C., added with 1,3-dichloro-5,5-dimethylimidazolidine-2,4-dione (8.04 g, 40.78 mmol) in portions, and reacted for 2 h. Then the reaction system was added with water (100 mL) to quench the reaction and extracted with ethyl acetate (50 mL×3). The organic phases were combined, dried over anhydrous sodium sulfate, filtered and concentrated. The crude product was purified by silica gel column chromatography to give intermediate 184-4 (2.8 g, 60.3% yield) in the form of a white solid. $^1$H NMR (301 MHz, CDCl3) δ 8.02 (s, 1H), 7.96 (d, J=8.2, 1H), 7.87 (d, J=8.2 Hz, 1H), 2.71 (s, 3H).

Step (3) Preparation of 4-cyano-N,N-bis(4-methoxybenzyl)-3-methylbenzenesulfonamide 184-5

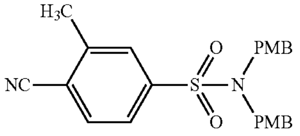

Bis (4-methoxybenzyl)amine (2.80 g, 11.13 mmol) and triethylamine (3.40 g, 33.39 mmol) were dissolved in dichloromethane (50 mL). The reaction system was added with intermediate 184-4 (2.40 g, 11.13 mmol) in an ice water bath, and stirred at room temperature overnight. Then the reaction system was added with water (50 mL) to quench the reaction and extracted with dichloromethane (50 mL×3). The organic phases were combined, dried over anhydrous sodium sulfate, filtered and concentrated. The crude product was purified by silica gel column chromatography to give intermediate 184-5 (3.30 g, 64.9% yield) in the form of a light yellow solid. LC-MS $[M+H]^+$=458.6.

Step (4) Preparation of 4-formyl-N,N-bis(4-methoxybenzyl)-3-methylbenzenesulfonamide 184-6

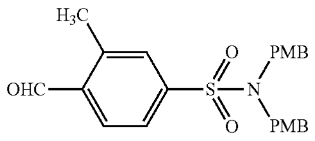

Intermediate 184-5 (3.00 g, 6.87 mmol) was dissolved in anhydrous tetrahydrofuran (60 mL). The reaction system was cooled to 0° C., then added dropwise with a solution of diisobutylaluminum hydride in n-hexane (1 N, 17.2 mL), and stirred at 0° C. overnight. Then the reaction system was added with diluted hydrochloric acid (60 mL, 1 N) to quench the reaction and filtered. The filtrate was extracted with ethyl acetate (50 mL×3). The organic phases were combined, washed with saturated brine (50 mL), dried over anhydrous sodium sulfate, filtered and concentrated by rotary evaporation to give a crude product. The crude product was purified by silica gel column chromatography to give intermediate 184-6 (1.68 g, 55.7% yield) in the form of a white solid. LC-MS $[M+H]^+$=461.6.

Step (5) Preparation of tert-butyl (S)-2-((2-(4-(N,N-bis(4-methoxybenzyl)sulfamoyl)-2-methylphenyl)-7-methylimidazo[1,2-a]pyridin-3-yl)methyl)morpholine-4-carboxylate 184-7

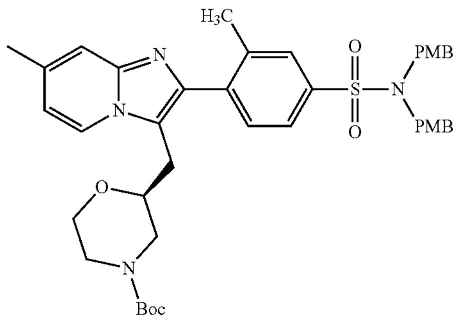

Under nitrogen atmosphere, intermediate 184-6 (500 mg, 1.14 mmol), 4-methylpyridin-2-amine (123 mg, 1.14 mmol), tert-butyl (S)-2-ethynylmorpholin-4-carboxylate (242 mg, 1.14 mmol), copper(I) chloride (35 mg, 0.34 mmol) and copper(II) trifluoromethanesulfonate (124 mg, 0.34 mmol) were dissolved in anhydrous toluene (5 mL). The reaction system was heated to 85° C., then added with N,N'-dimethylacetamide (0.1 mL), and stirred at 85° C. overnight. After the reaction was completed, the reaction system was filtered and concentrated by rotary evaporation to give a crude product. The crude product was purified by silica gel column chromatography to give intermediate 184-7 (380 mg, 42.7% yield) in the form of a white solid. LC-MS $[M+H]^+$=740.5.

Step (6) Preparation of (S)—N,N-(4-methoxybenzyl)-3-methyl-4-(7-methyl-3-(morpholin-2-ylmethyl) imidazo[1,2-a]pyridin-2-yl)benzenesulfonamide 184-8

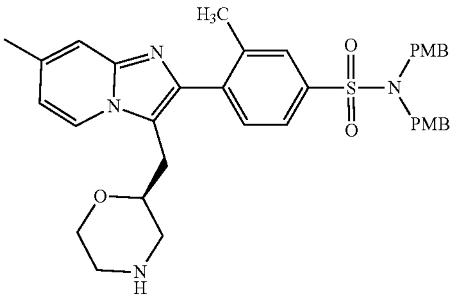

Intermediate 184-7 (380 mg, 0.51 mmol) was dissolved in anhydrous dichloromethane (5 mL), and a solution of HCl in ethanol (1.5 mL, 4 N) was added. The reaction system was stirred at room temperature for 3 h. After the reaction was completed, the reaction system was concentrated by rotary evaporation to give intermediate 184-8 (450 mg, crude product) in the form of a white solid, LC-MS $[M+H]^+$=640.5.

Step (7) Preparation of methyl (S)-2-((2-(4-(N,N-bis(4-methoxybenzyl)sulfamoyl)-2-methylphenyl)-7-methylimidazo[1,2-a]pyridin-3-yl)methyl)morpholine-4-carboxylate 184-9

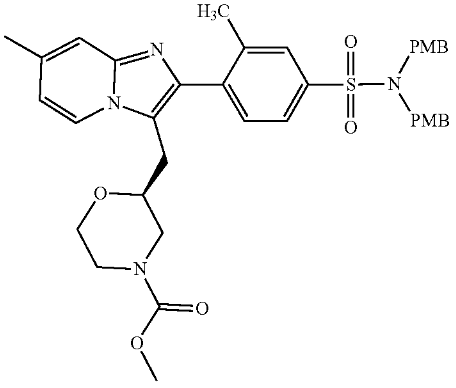

Intermediate 184-8 (450 mg, crude) and N,N'-diisopropylethylamine (325 mg, 2.53 mmol) were dissolved in anhydrous dichloromethane (5 mL) under nitrogen atmosphere. The reaction system was cooled in an ice water bath and added dropwise with a solution of methyl chloroformate in dichloromethane (10 mg/mL, 4.5 mL). After the completion of the dropwise addition, the reaction system was reacted at 0° C. for 2 h. After the reaction was completed, the reaction system was added with water (20 mL) and extracted with dichloromethane (15 mL×3). The organic phases were combined, washed with saturated brine (20 mL), dried over anhydrous sodium sulfate, filtered and concentrated by rotary evaporation to give a crude product. The crude product was purified by silica gel column chromatography to give intermediate 184-9 (150 mg, 35.4% yield) in the form of a white solid, LC-MS $[M+H]^+$=698.5.

Step (8) Preparation of methyl (S)-2-((7-methyl-2-(2-methyl-4-sulfamoylphenyl)imidazo[1,2-a]pyridin-3-yl)methyl)morpholine-4-carboxylate

184

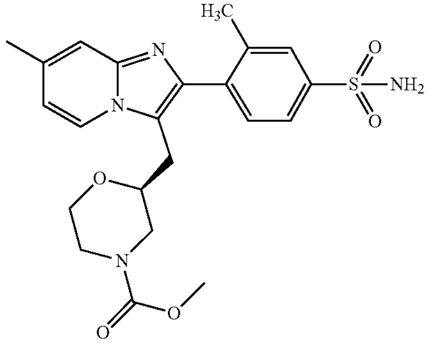

Intermediate 184-9 (150 mg, 0.21 mmol) was dissolved in anhydrous dichloromethane (1 mL), and trifluoroacetic acid (2 mL) was added. The reaction system was stirred overnight at room temperature. After the reaction was completed, the reaction system was directly concentrated by rotary evaporation and purified by preparative reverse phase chromatography to give compound 184 (17 mg, 17.3% yield) in the form of a white solid. LC-MS $[M+H]^+$=458.5.

1H NMR (400 MHZ, CDCl3) δ 8.16 (s, 1H), 7.87 (s, 1H), 7.77 (d, J=7.7 Hz, 1H), 7.56 (s, 1H), 7.42 (d, J=7.8 Hz, 1H), 6.80 (d, J=7.0 Hz, 1H), 5.53 (brs, 2H), 3.98-3.76 (m, 3H), 3.69 (s, 3H), 3.58-3.47 (m, 1H), 3.43-3.31 (m, 1H), 3.05-2.85 (m, 3H), 2.60-2.50 (m, 1H), 2.49 (s, 3H), 2.35 (s, 3H).

Example 185

185

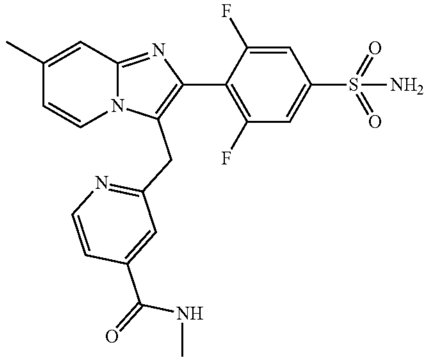

The compound was prepared according to the preparation method as described in Example 181. LC-MS: $[M+H]^+$=472.1.

Example 186
186
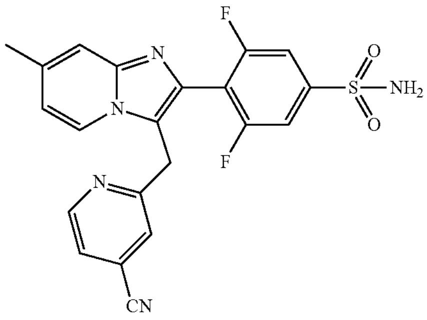
The compound was prepared according to the preparation method as described in Example 181. LC-MS: $[M+H]^+=440.2$.
Example 187
187
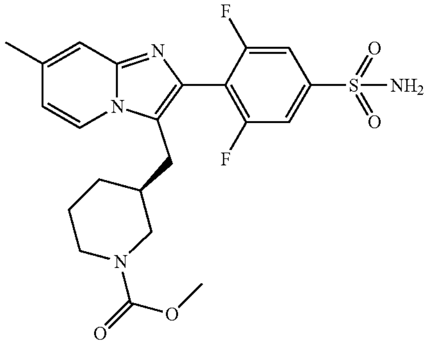
The compound was prepared according to the preparation method as described in Example 181. LC-MS: $[M+H]^+=479.1$.
Example 188
188
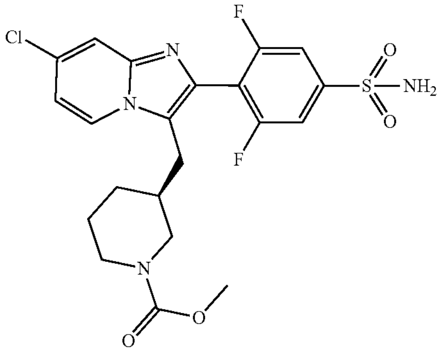
The compound was prepared according to the preparation method as described in Example 181. LC-MS: $[M+H]^+=499.1$.
Example 189
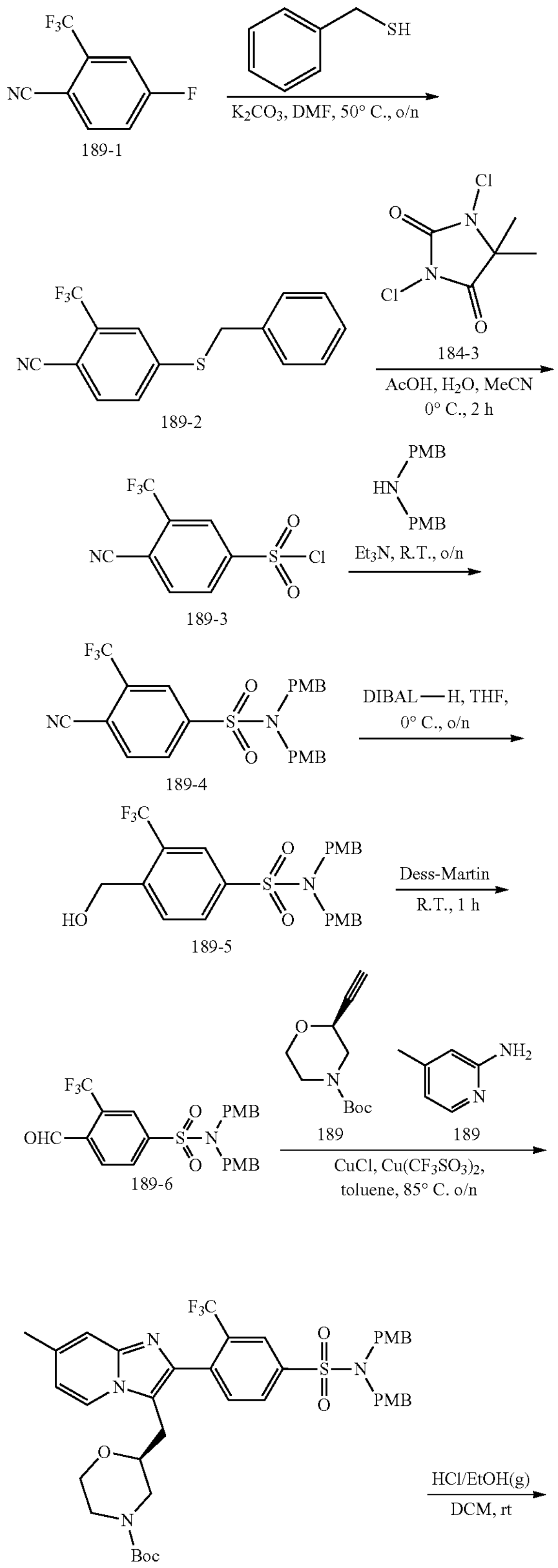
189-1
189-2
184-3
189-3
189-4
189-5
189-6
189
189
189-7

-continued

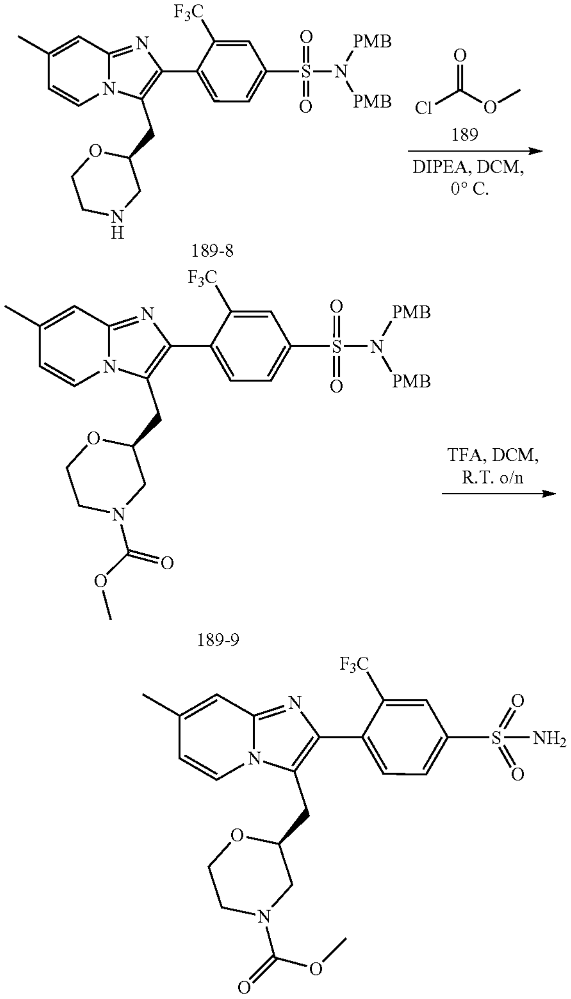

189-8

189-9

189

Step (1) Preparation of 4-(benzylthio)-2-(trifluoromethyl)benzonitrile 189-2

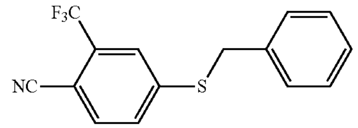

4-fluoro-2-(trifluoromethyl)benzonitrile (5.00 g, 26.44 mmol) was dissolved in N,N-dimethylformamide (30 mL) and potassium carbonate (7.50 g, 54.35 mmol) was added. The reaction system was added with benzy lmercaptan (2.80 mL), heated to 50° C. and stirred overnight. Then the reaction system was cooled to room temperature, added with water (80 mL) to quench the reaction, and extracted with ethyl acetate (40 mL×3). The organic phases were combined, dried over anhydrous sodium sulfate, filtered and concentrated. The residue was purified by silica gel column chromatography to give intermediate 189-2 (6.80 g, 83.3% yield) in the form of a yellow solid. LC-MS: $[M+H]^+$=293.7.

Step (2) Preparation of 4-cyano-3-(trifluoromethyl)benzenesulfonyl chloride 189-3

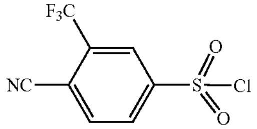

Intermediate 189-2 (6.80 g, 23.18 mmol) was dissolved in a prepared solvent (95 mL of acetonitrile, 4 mL of acetic acid, 2.5 mL of water) under nitrogen atmosphere. The reaction system was cooled to 0° C., added with 1,3-dichloro-5,5-dimethylimidazolidine-2,4-dione (9.14 g, 46.37 mmol) in portions, and reacted for 2 h. Then the reaction system was added with water (100) to quench the reaction and extracted with ethyl acetate (60 mL×3). The organic phases were combined, washed with saturated brine (50 mL), dried over anhydrous sodium sulfate, filtered and concentrated. The crude product was purified by silica gel column chromatography to give intermediate 189-3 (3.50 g, 51.5% yield) in the form of a white solid. LC-MS: $[M+H]^+$=270.2.

Step (3) Preparation of 4-cyano-N,N-bis(4-methoxybenzyl)-3-(trifluoromethyl)benzenesulfonamide 189-4

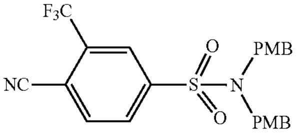

Triethylamine (3.93 g, 38.94 mmol) and bis(4-methoxybenzyl)amine (3.34 g, 12.98 mmol) were dissolved in dichloromethane (85 mL) under nitrogen atmosphere. The reaction system was cooled to 0° C., added with intermediate 189-3 (3.50 g, 12.98 mmol) in portions, warmed to room temperature and stirred overnight. Then the reaction system was added with water (50 mL) to quench the reaction. The aqueous phase was extracted with dichloromethane (50 mL×2). The organic phases were combined, washed with saturated brine (50 mL), dried over anhydrous sodium sulfate, filtered and concentrated. The crude product was purified by silica gel column chromatography to give intermediate 189-4 (5.00 g, 75.1% yield) in the form of a light yellow solid, LC-MS: $[M+H]^+$=512.7.

Step (4) Preparation of 4-(hydroxymethyl)-N,N-bis(4-methoxybenzyl)-3-(trifluoromethyl)benzenesulfonamide 189-5

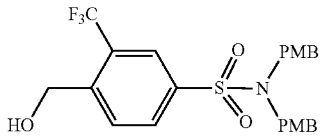

Intermediate 189-4 (4.40 g, 8.97 mmol) was dissolved in anhydrous tetrahydrofuran (80 mL). The reaction system was cooled to 0° C., added dropwise with a solution of diisobutylaluminum hydride in n-hexane (1 N, 27 mL), slowly warmed to room temperature and stirred overnight. Then the reaction system was added with diluted hydrochloric acid (80 mL, 1 N) to quench the reaction, and then filtered, and the filtrate was extracted with ethyl acetate (50 mL×3). The organic phases were combined, washed with saturated brine (50 mL), dried over anhydrous sodium sulfate, filtered and concentrated by rotary evaporation to give intermediate 189-5 (5.00 g, crude product) in the form of a white solid, which was used directly in the next step. LC-MS: $[M+H]^+$=494.6.

Step (5) Preparation of 4-formyl-N,N-bis(4-methoxybenzyl)-3-(trifluoromethyl)benzenesulfonamide 189-6

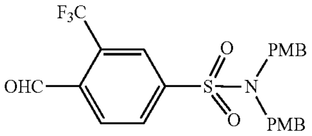

Intermediate 189-5 (5.00 g, crude product) was dissolved in anhydrous dichloromethane (70 mL), and Dess-Martin periodinane (4.85 g, 11.56 mmol) was added in portions. The reaction system was stirred at room temperature for 1.5 h. Then the reaction system was added with saturated aqueous sodium thiosulfate solution (20 mL) to quench the reaction, and then added with water (30 mL). The aqueous phase was extracted with dichloromethane (40 mL×2). The organic phases were combined, washed with saturated brine (50 mL), dried over anhydrous sodium sulfate, filtered and dried by rotary evaporation. The crude product was purified by silica gel column chromatography to give intermediate 189-6 (2.00 g, 45.2% yield over two steps) in the form of a white solid. LC-MS: $[M+H]^+$=515.5.

Step (6) Preparation of tert-butyl (S)-2-((2-(4-(N,N-bis(4-methoxybenzyl)sulfamoyl)-2-(trifluoromethyl)phenyl)-7-methylimidazo[1,2-a]pyridin-3-yl)methyl)morpholine-4-carboxylate 189-7

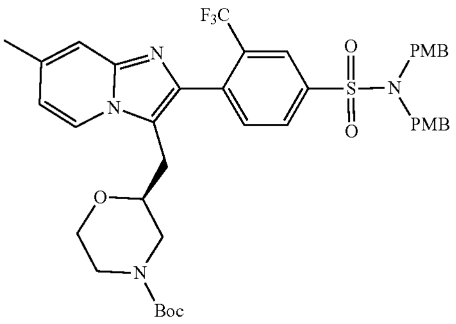

Intermediate 189-6 (500 mg, 1.01 mmol), 4-methylpyridin-2-amine (110 mg, 1.01 mmol), tert-butyl (S)-2-ethynylmorpholine-4-carboxylate (214 mg, 1.01 mmol), copper (I) chloride (30 mg, 0.30 mmol) and copper(II) trifluoromethanesulfonate (110 mg, 0.30 mmol) were dissolved in anhydrous toluene (5 mL) under nitrogen atmosphere. The reaction system was warmed to 85° C., added with 5 drops of N,N'-dimethylacetamide, and stirred at 85° C. overnight. The reaction system was cooled to room temperature and filtered, and the filtrate was concentrated. The crude product was purified by silica gel column chromatography to give intermediate 189-7 (280 mg, 34.8% yield) in the form of a colorless transparent oil, LC-MS: $[M+H]^+$=794.4.

Step (7) Preparation of (S)—N,N-bis(4-methoxybenzyl)-4-(7-methyl-3-(morpholin-2-ylmethyl)imidazo[1,2-a]pyridin-2-yl)-3-(trifluoromethyl)benzenesulfonamide 189-8

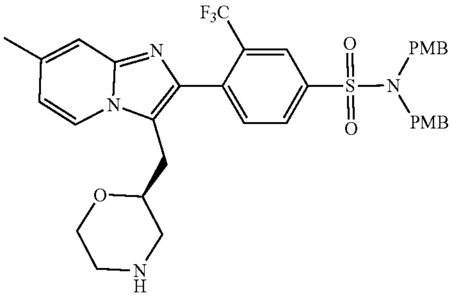

Intermediate 189-7 (280 mg, 0.35 mmol) was dissolved in anhydrous dichloromethane (5 mL), and a solution of HCl in ethanol (0.6 mL, 4 N) was added dropwise. The reaction system was stirred at room temperature for 3 h. Then the reaction system was concentrated under reduced pressure to give intermediate 189-8 (300 mg, crude product) in the form of a white solid, LC-MS: $[M+H]^+$=694.5.

Step (8) Preparation of methyl (S)-2-((2-(4-(N,N-bis(4-methoxybenzyl)sulfamoyl)-2-(trifluoromethyl)phenyl)-7-methylimidazo[1,2-a]pyridin-3-yl)methyl)morpholine-4-carboxylate 189-9

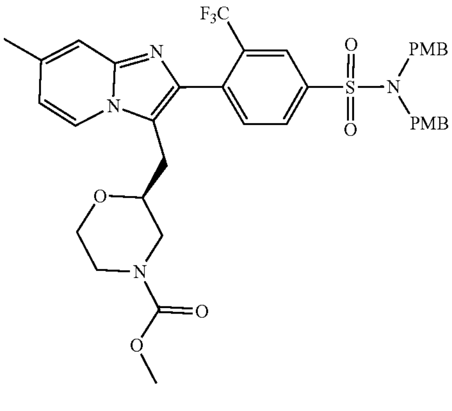

Intermediate 189-8 (300 mg, crude product) was dissolved in anhydrous dichloromethane (4 mL) under nitrogen atmosphere, and N,N'-diisopropylethylamine (225 mg, 1.75 mmol) was added under nitrogen atmosphere. The reaction system was cooled in an ice water bath, added dropwise with a solution of methyl chloroformate in dichloromethane (10 mg/mL, 3.3 mL) and then reacted at 0° C. for 4 h. Then the reaction system was added with water (20 mL) to quench the reaction and extracted with dichloromethane (10 mL×3). The organic phases were combined, washed with saturated brine (10 mL), dried over anhydrous sodium sulfate, filtered and concentrated by rotary evaporation to give a crude product. The crude product was purified by silica gel column chromatography to give intermediate 189-9 (200 mg, 74.2% yield) in the form of a white solid, LC-MS $[M+H]^+$=752.4.

Step (9) Preparation of methyl (S)-2-((7-methyl-2-(4-sulfamoyl-2-(trifluoromethyl)phenyl)imidazo[1,2-a]pyridin-3-yl)methyl)morpholine-4-carboxylate

189

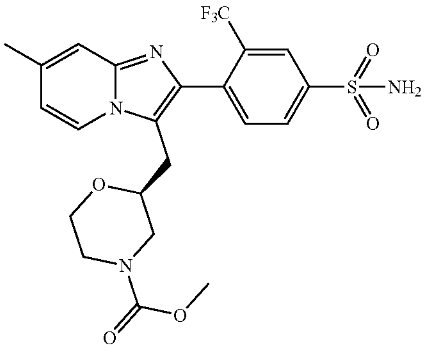

Intermediate 189-9 (200 mg, 0.26 mmol) was dissolved in dichloromethane (2 mL), and trifluoroacetic acid (2 mL) was added. The reaction system was stirred overnight at room temperature. Then the reaction system was directly concentrated by rotary evaporation and purified by preparative reverse phase chromatography to give compound 189 (51 mg, 37.5% yield) in the form of a white solid, LC-MS: $[M+H]^+$=512.6.

1H NMR (400 MHZ, CDCl3) δ 8.25 (brs, 1H), 8.13 (brs, 1H), 8.04 (brs, 1H), 7.60 (brs, 1H), 7.47 (brs, 1H), 7.00-6.65 (m, 3H), 4.00-3.70 (m, 3H), 3.38 (s, 3H), 3.52-3.28 (m, 2H), 3.00-2.77 (m, 3H), 2.62-2.50 (m, 1H), 2.49 (s, 3H).

Example 190

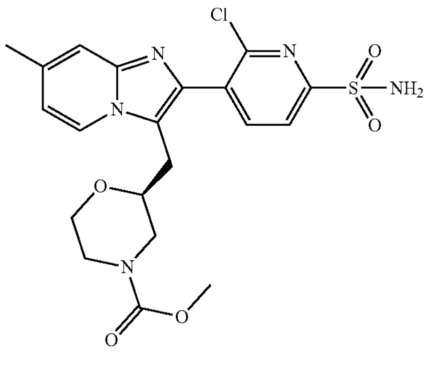 [SMILES: COC(=O)N1CCO[C@@H](Cc2c(-c3ccc(S(N)(=O)=O)nc3Cl)nc3cc(C)ccn23)C1]

The compound was prepared according to the preparation method as described in Example 181. LC-MS: $[M+H]^+$ =480.2.

Example 191

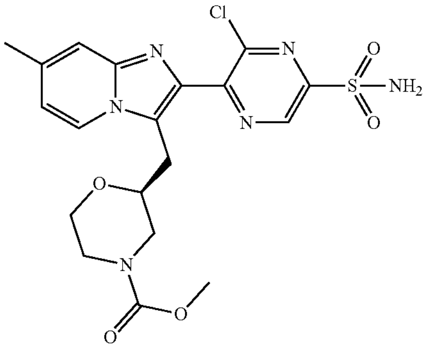 [SMILES: COC(=O)N1CCO[C@@H](Cc2c(-c3ncc(S(N)(=O)=O)nc3Cl)nc3cc(C)ccn23)C1]

The compound was prepared according to the preparation method as described in Example 181. LC-MS: $[M+H]^+$ =481.4.

Example 192

Preparation of methyl (S)-2-((2-(4-(4-cyano-1H-imidazol-1-yl)-2,6-difluorophenyl)-7-methylimidazo[1,2-a]pyridin-3-yl)methyl)morpholine-4-carboxylate

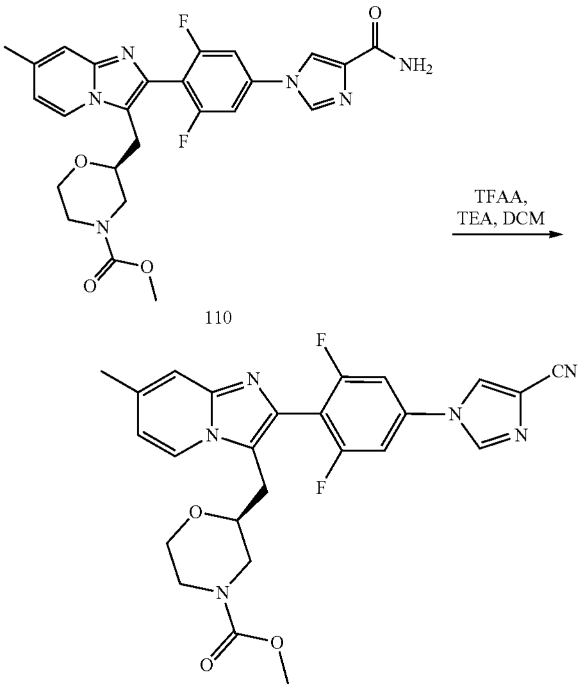

110

192

Compound 110 (100 mg, 0.2 mmol) and triethylamine (89 mg, 0.88 mmol) were dissolved in dichloromethane (5 mL), and a solution of trifluoroacetic anhydride (82 mg, 0.39 mmol) in dichloromethane (1 mL) was added dropwise under nitrogen atmosphere in an ice water bath. The reaction system was stirred overnight at room temperature. Then the reaction system was diluted with dichloromethane (30 mL), washed successively with saturated sodium bicarbonate solution (15 mL×2) and saturated brine (15 mL), dried over anhydrous sodium sulfate, filtered and concentrated by rotary evaporation. The crude product was purified by preparative chromatography to give compound 192 (30 mg, 30% yield) in the form of a white solid. LC-MS: $[M+H]^+$=492.8.

$^1H$ NMR (400 MHZ, MeOD) δ 8.83 (d, J=7.1 Hz, 1H), 8.61 (d, J=1.2 Hz, 1H), 8.54 (d, J=1.1 Hz, 1H), 7.80 (d, J=8.5 Hz, 2H), 7.72 (s, 1H), 7.39 (d, J=7.1 Hz, 1H), 4.01 (d, J=12.9 Hz, 1H), 3.83 (d, J=13.4 Hz, 1H), 3.76 (d, J=10.8 Hz, 1H), 3.71-3.67 (m, 1H), 3.69 (s, 3H), 3.37-3.35 (m, 1H), 3.28-3.25 (m, 2H), 2.97-2.85 (m, 1H), 2.82-2.67 (m, 1H), 2.64 (s, 3H).

BIOLOGICAL EXPERIMENTS

Example A: Evaluation of In Vitro Biological Activity

The antagonist property of the compounds disclosed herein was determined using the FLIPR (fluorescence imaging plate reader) method, showing that the compounds are inhibitors for the intracellular calcium increase induced by the activation of $hP2X^3$ (human purinergic P2X receptor subtype 3, Accession No. NM_002559.4) expressed in HEK293 cells (human renal epithelial cell line, ATCC).

HEK293 cells that stably express $hP2X^3$ were cultured in DMEM high glucose medium containing 10% FBS (fetal bovine serum, Gibco, 10099-141), 1% penicillin-streptomycin (Gibco, 15140-122) and 1 mg/mL G418 (Invitrogen, 10131027) in a cell incubator at 37° C., 5% humidity. Cells at 400,000 cells/mL were seeded into a 384-well plate (10,000 cells/well) 18-24 h prior to the FLIPR experiment and then incubated overnight in a cell incubator. On the day of the experiment, the medium was discarded and the cells were washed in an FLIPR buffer (each 30 mL buffer contains 0.3 mL of probenecid (Thermo, P36400), 0.6 mL of 1 M HEPES (Invitrogen, 15630080) and 29.1 mL of HBSS (Invitrogen, 14065056)). Each well was added with 20 μL of 0.5×Calcium 6 fluorescent dye (Molecular Devices, R8190) and then was subjected to dye-loading incubation at 37° C. for 1.5 h. Each well was added with 10 μL of test compound (which was dissolved in DMSO at a concentration of 10 mM and serially diluted with buffer) or vehicle, and then was left to equilibrate for 30 min at room temperature. The cell plate was then placed in the FLIPR for baseline fluorescence measurements (excitation at 485 nm and emission at 525-535 nm). An agonist (BZ-ATP (Sigma, B6396) at a final concentration of 2.5 μM) or a vehicle (ultrapure water) was then added at 10 μL/well, fluorescence values were measured for 2 min at 1-second intervals, and finally the output fluorescence counts were analyzed.

The $IC_{50}$ values obtained by the above method are shown in Table 2.

TABLE 2

$IC_{50}$ values of compounds of Examples 1-192 for P2X3 receptor

| Compound | P2X3 $IC_{50}$ (μM) |
|---|---|
| Compound 1 | D |
| Compound 2 | A |
| Compound 3 | B |
| Compound 4 | A |
| Compound 5 | A |
| Compound 6 | C |
| Compound 7 | A |
| Compound 8 | D |
| Compound 9 | D |
| Compound 10 | A |
| Compound 11 | B |
| Compound 12 | A |
| Compound 13 | B |
| Compound 14 | D |
| Compound 15 | A |
| Compound 16 | B |
| Compound 17 | B |
| Compound 18 | C |
| Compound 19 | D |
| Compound 20 | D |
| Compound 21 | D |
| Compound 22 | D |
| Compound 23 | D |
| Compound 24 | D |
| Compound 25 | A |
| Compound 26 | C |
| Compound 27 | A |
| Compound 28 | B |
| Compound 29 | A |
| Compound 30 | B |
| Compound 31 | D |
| Compound 32 | D |
| Compound 33 | D |
| Compound 34 | A |
| Compound 35 | D |
| Compound 36 | B |
| Compound 37 | A |
| Compound 38 | A |
| Compound 39 | D |
| Compound 40 | D |
| Compound 41 | D |
| Compound 42 | A |
| Compound 43 | A |
| Compound 44 | A |
| Compound 45 | D |
| Compound 46 | D |
| Compound 47 | D |
| Compound 48 | C |
| Compound 49 | A |
| Compound 50 | A |
| Compound 51 | C |
| Compound 52 | A |
| Compound 53 | A |
| Compound 54 | A |
| Compound 55 | A |
| Compound 56 | A |
| Compound 57 | A |
| Compound 58 | A |
| Compound 59 | A |
| Compound 60 | A |
| Compound 61 | A |
| Compound 62 | D |
| Compound 63 | C |
| Compound 64 | C |
| Compound 65 | C |
| Compound 66 | C |
| Compound 67 | B |
| Compound 68 | B |
| Compound 69 | B |
| Compound 70 | B |
| Compound 71 | A |
| Compound 72 | C |
| Compound 73 | C |
| Compound 74 | C |
| Compound 75 | B |
| Compound 76 | C |
| Compound 77 | A |

TABLE 2-continued

IC50 values of compounds of Examples 1-192 for P2X3 receptor

| Compound | P2X3 $IC_{50}$ (μM) |
|---|---|
| Compound 78 | B |
| Compound 79 | B |
| Compound 80 | B |
| Compound 81 | A |
| Compound 82 | B |
| Compound 83 | C |
| Compound 84 | C |
| Compound 85 | C |
| Compound 86 | B |
| Compound 87 | C |
| Compound 88 | B |
| Compound 89 | B |
| Compound 90 | B |
| Compound 91 | A |
| Compound 92 | B |
| Compound 93 | B |
| Compound 94 | C |
| Compound 95 | B |
| Compound 96 | B |
| Compound 97 | C |
| Compound 98 | B |
| Compound 97 | C |
| Compound 98 | B |
| Compound 99 | B |
| Compound 100 | B |
| Compound 101 | B |
| Compound 102 | A |
| Compound 103 | C |
| Compound 104 | C |
| Compound 105 | A |
| Compound 106 | B |
| Compound 107 | B |
| Compound 108 | D |
| Compound 109 | C |
| Compound 110 | B |
| Compound 111 | B |
| Compound 112 | D |
| Compound 113 | D |
| Compound 114 | B |
| Compound 115 | D |
| Compound 116 | B |
| Compound 117 | B |
| Compound 118 | D |
| Compound 119 | B |
| Compound 120 | A |
| Compound 121 | D |
| Compound 122 | D |
| Compound 123 | C |
| Compound 124 | A |
| Compound 124-2 | A |
| Compound 125 | A |
| Compound 126 | B |
| Compound 127 | A |
| Compound 128 | D |
| Compound 129 | B |
| Compound 130 | D |
| Compound 131 | B |
| Compound 132 | A |
| Compound 133 | B |
| Compound 134 | B |
| Compound 135 | A |
| Compound 136 | C |
| Compound 137 | B |
| Compound 138 | A |
| Compound 139 | A |
| Compound 140 | C |
| Compound 141 | B |
| Compound 142 | A |
| Compound 143 | A |
| Compound 144 | B |
| Compound 145 | C |
| Compound 146 | C |
| Compound 147 | B |
| Compound 148 | A |
| Compound 149 | A |
| Compound 150 | A |
| Compound 151 | A |
| Compound 152 | A |
| Compound 153 | C |
| Compound 154 | A |
| Compound 155 | A |
| Compound 156 | A |
| Compound 157 | A |
| Compound 158 | A |
| Compound 159 | A |
| Compound 160 | A |
| Compound 161 | B |
| Compound 162 | A |
| Compound 163 | A |
| Compound 164 | B |
| Compound 165 | A |
| Compound 166 | A |
| Compound 167 | A |
| Compound 168 | B |
| Compound 169 | A |
| Compound 170 | C |
| Compound 171 | 0.0021 |
| Compound 172 | 0.0007 |
| Compound 173 | 0.0018 |
| Compound 174 | 0.0016 |
| Compound 175 | >10 |
| Compound 176 | 0.0075 |
| Compound 177 | 0.0011 |
| Compound 178 | 0.0001 |
| Compound 179 | 0.0004 |
| Compound 180 | 0.0002 |
| Compound 181 | 0.0018 |
| Compound 182 | 0.0035 |
| Compound 183 | 0.0055 |
| Compound 184 | 0.0056 |
| Compound 185 | 0.013 |
| Compound 186 | 0.065 |
| Compound 187 | 0.050 |
| Compound 188 | 0.009 |
| Compound 189 | 0.0100 |
| Compound 190 | A |
| Compound 191 | A |
| Compound 192 | B |
| Positive compound 1 | 0.0115 |
| Positive compound 2 | 0.0522 |

A: $IC_{50}$ ≤ 10 nM,
B: 10 < $IC_{50}$ ≤ 50 nM,
C: 50 < $IC_{50}$ ≤ 200 nM,
D: 200 < $IC_{50}$ ≤ 5000 nM.

Positive Compound 1:

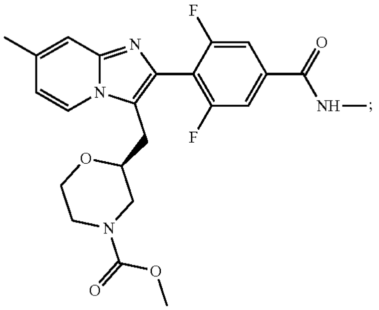

Positive Compound 2:

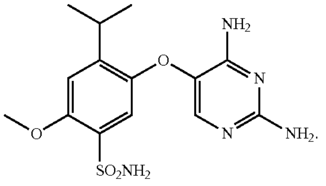 [SMILES: COc1cc(C(C)C)c(Oc2cnc(N)nc2N)cc1S(N)(=O)=O]

As can be seen from the data in Table 2, the compounds disclosed herein exhibit good inhibitory activity against $P2X^3$, wherein most of the compounds show stronger inhibitory activity than that of positive compound 2, and some of the compounds show stronger inhibitory activity than that of positive compound 1. Compounds with stronger inhibitory activity than that of positive compound 2 are preferred, and compounds with stronger inhibitory activity than that of positive compound 1 are more preferred.

Example B: Evaluation of In Vitro $P2X^{2/3}$ Receptor Selectivity

The selectivity of the compounds disclosed herein for the $P2X^{2/3}$ receptor was determined using the FLIPR (fluorescence imaging plate reader) method, showing that the compounds were inhibitors for the intracellular calcium increase induced by the activation of $hP2X^{2/3}$ (heterodimeric receptors formed by human purinergic P2X receptors subtype 2 and subtype 3, Accession No. NM_002559.4 for $P2X^2$ and Accession No. NM_002559.4 for $P2X^3$) expressed in HEK293 cells (human renal epithelial cell line, ATCC).

HEK293 cells that stably express $hP2X^{2/3}$ were cultured in DMEM high glucose medium containing 10% FBS (fetal bovine serum, Gibco, 10099-141), 1% penicillin-streptomycin (Gibco, 15140-122) and 1 mg/mL G418 (Invitrogen, 10131027) in a cell incubator at 37° C., 5% humidity. Cells at 250000 cells/mL were seeded into a 96-well plate (25000 cells/well) 18-24 h prior to the FLIPR experiment and then incubated overnight in a cell incubator. On the day of the experiment, the medium was discarded and the cells were washed in an FLIPR buffer (0.3 mL of probenecid (Thermo, P36400), 0.6 mL of 1 M HEPES (Invitrogen, 15630080) and 29.1 mL of HBSS (Invitrogen, 14065056) per 30 mL of buffer). Each well was added with 75 μL of 1 mM Fluo-4 AM fluorescent dye (Thermo, F14202) and then was subjected to dye-loading incubation at 37° C. for 1.0 h. The 96-well plate was then washed once with buffer, added with a buffer containing a test compound or a vehicle at 50 μL per well and then incubated for 30 min at room temperature. The cell plate was then placed in the FLIPR for baseline fluorescence measurements (excitation at 485 nm and emission at 525-535 nm). An agonist (BZ-ATP (Sigma, B6396) at a final concentration of 5 μM) or a vehicle (ultrapure water) was then added at 50 μL/well, fluorescence values were measured for 2 min at 1-second intervals, and finally the output fluorescence counts were analyzed.

The $IC_5\%$ values obtained by the above method are shown in Table 3.

TABLE 3

$IC_{50}$ values and folds of selectivity of some of the compounds for P2X2/3 receptors

| Compound | $IC_{50}$ | Folds of selectivity | Compound | $IC_{50}$ | Folds of selectivity |
|---|---|---|---|---|---|
| Compound 2 | >60 | A | Compound 3 | >60 | A |
| Compound 4 | 14.31 | A | Compound 5 | >60 | A |
| Compound 7 | >60 | A | Compound 10 | 37.39 | A |
| Compound 11 | 17.56 | B | Compound 12 | 12.13 | A |
| Compound 13 | 14.44 | B | Compound 15 | 21.56 | B |
| Compound 17 | 29.81 | B | Compound 25 | >60 | A |
| Compound 54 | >60 | A | Compound 58 | >60 | A |
| Compound 61 | >60 | A | Compound 138 | >60 | A |
| Compound 149 | >60 | A | Compound 151 | >60 | A |
| Compound 158 | >60 | A | Compound 159 | >60 | A |
| Compound 160 | >60 | A | Compound 161 | >60 | A |
| Compound 162 | >60 | A | Compound 163 | >60 | A |
| Compound 164 | >60 | A | Compound 165 | >60 | A |
| Compound 166 | >60 | A | Compound 167 | >60 | A |
| Compound 168 | >60 | A | Compound 169 | >60 | A |
| Compound 171 | 36.78 | 45975 | Compound 172 | >60 | >85714 |
| Compound 173 | 33.86 | 18811 | Compound 191 | >60 | A |
| Positive compound 1 | >60 | >5217 | Positive compound 2 | 0.36 | 6.9 |

A: folds of selectivity >1000, B: 200< folds of selectivity ≤1000, C: folds of selectivity ≤200.

As can be seen from the data in Table 3, the compounds disclosed herein exhibit poor inhibitory activity against $P2X^{2/3}$ heterodimeric receptor and good selectivity for $P2X^3$ and $P2X^{2/3}$. Folds of selectivity=($IC_{50}$ for $P2X^{2/3}$)/($IC_{50}$ for $P2X^3$). Compounds with the folds of selectivity of more than 200 are preferred, and compounds with the folds of selectivity of more than 1000 are more preferred.

Example C: Activity Test in Citric Acid Only Cough Models

Male Dunkin Hartley guinea pigs (300-350 g) were placed in an animal atomization box, and then the door of the atomization box was closed while the ultrasonic atomizer (Guangdong Yuehua) was turned on, 17.5% citric acid gas was introduced into the atomization box at a maximum atomization rate (about 2 mL/min) for 20 s, and coughs of the animals within 10 min were continuously observed from the time of the start of atomization. During the 10-min observation, coughs of the animals were counted manually, and the number of coughs were judged according to cough postures of the guinea pigs, such as abdominal twitching, mouth opening, and head inclining downward abruptly. The number of coughs during the first 5 min and that during 10 min were recorded, and the cough latency of the guinea pigs, namely the time from the initiation of citric acid induction to the appearance of the first cough, was also recorded.

TABLE 4

The number of coughs, cough inhibition rate and cough latency obtained in vivo for some of the compounds

| Group | | Mean number of coughs | Cough inhibition rate Vs Vehicle (%) | Cough inhibition rate Vs Baseline (%) | Mean cough latency |
|---|---|---|---|---|---|
| Vehicle group | Before administration | 17.22 | / | / | 108.44 |
| | After administration | 18.33 | | | 105.78 |
| Positive compound 1 | Before administration | 18.63 | 42.6 | 47.0 | 80.13 |
| 30 mg/kg | After administration | 9.88 | | | 226.75 |
| Compound 2 30 mg/kg | Before administration | 18.50 | 34.2 | 38.7 | 94.50 |
| | After administration | 11.33 | | | 194.83 |
| Compound 7 30 mg/kg | Before administration | 18.50 | 38.3 | 42.6 | 87.13 |
| | After administration | 10.63 | | | 177.00 |
| Compound 53 30 mg/kg | Before administration | 18.63 | 47.7 | 51.7 | 138.00 |
| | After administration | 9.00 | | | 250.13 |
| Compound 149 30 mg/kg | Before administration | 19.33 | 62.7 | 66.8 | 75.92 |
| | After administration | 6.42 | | | 229.00 |
| Compound 161 30 mg/kg | Before administration | 18.57 | 63.5 | 66.2 | 130.71 |
| | After administration | 6.29 | | | 302.43 |
| Compound 162 30 mg/kg | Before administration | 18.29 | 42.8 | 46.1 | 144.43 |
| | After administration | 9.86 | | | 278.43 |
| Compound 164 30 mg/kg | Before administration | 18.29 | 65.2 | 67.2 | 144.86 |
| | After administration | 6.00 | | | 275.14 |
| Compound 165 30 mg/kg | Before administration | 17.57 | 53.6 | 54.5 | 135.71 |
| | After administration | 8.00 | | | 190.71 |
| Compound 172 30 mg/kg | Before administration | 19.56 | 43.9 | 50.6 | 87.56 |
| | After administration | 9.67 | | | 118.89 |

The above experiment was conducted on the following representative compounds: compound 2, compound 7, compound 53, compound 149, compound 161, compound 162, compound 164, compound 165 and compound 172. The results as shown in Table 4 and FIGS. 1, 2, 3 and 4 demonstrate that compared with the blank vehicle or the condition before administration, compound 2, compound 7, compound 53, compound 149, compound 161, compound 162, compound 164, compound 165 and compound 172 at 30 mg/kg can effectively reduce the number of coughs and prolong the cough latency, and the efficacy of these compounds is not significantly different from that of positive compound 1, indicating that compound 2, compound 7, compound 53, compound 149, compound 161, compound 162, compound 164, compound 165 and compound 172 can reduce the number of coughs and improve the cough latency and their efficacy is equivalent to that of the positive compound.

Example D: Activity Test in ATP-Citric Acid Cough Models

Male Dunkin Hartley guinea pigs (300-400 g) were placed into a whole-body plethysmography box to adapt for 3-5 min, then ATP atomization is carried out for 2 min, and 3 min later, 5 min of citric acid atomization was followed, with all atomization rates being about 300 uL/min. The number of coughs and the cough latency of the animals within 10 min from the start of the citric acid atomization were recorded. During the 10-min observation, coughs of the animals were counted manually, and the coughs were judged according to cough postures of the guinea pigs, such as abdominal twitching, mouth opening, head inclining downward abruptly and the like. The number of coughs during 10 min were recorded, and the cough latency of the guinea pigs was also recorded.

The animals were divided into a vehicle group, a dextromethorphan (63 mg/kg) positive group, an AF-219 (30 mg/kg) positive group and Example 173 compound (3, 10, 30 mg/kg) administration groups, and all the compounds were orally administered. Except that dextromethorphan was administered 40 min before ATP-citric acid exposure, the remaining compounds were administered 2 h before ATP-citric acid exposure.

TABLE 5

Ratios of quinine/water intake obtained for the compounds

| Compound | | Number of coughs during 10 min | Cough inhibition ratio vs. vehicle (%) |
|---|---|---|---|
| Vehicle | | 20.83 | |
| Dextromethorphan group (63 mg/kg) | | 8.00 | 61.60 |
| AF-219 | 30 mg/kg | 11.42 | 45.20 |
| Compound 172 | 3 mg/kg | 14.42 | 30.80 |
| | 10 mg/kg | 10.17 | 51.20 |
| | 30 mg/kg | 9.83 | 52.80 |

Figure 5:
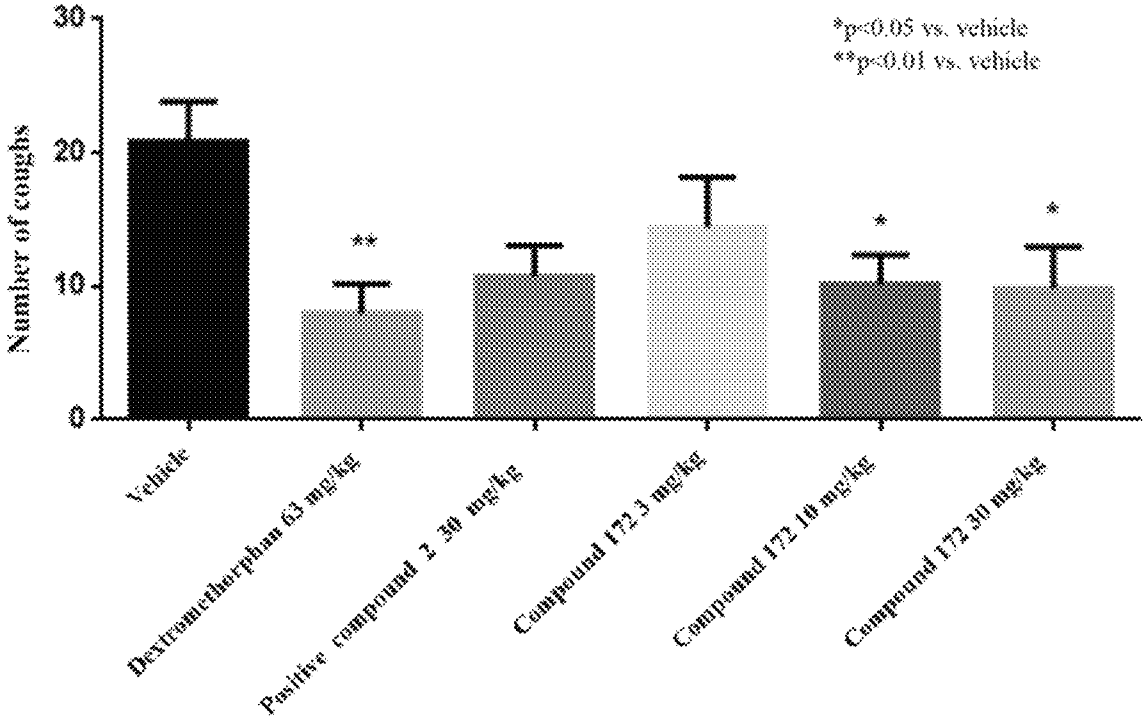
FIG. 5 shows the number of coughs for the inventive compounds in the ATP-citric acid model.
Figure 6:
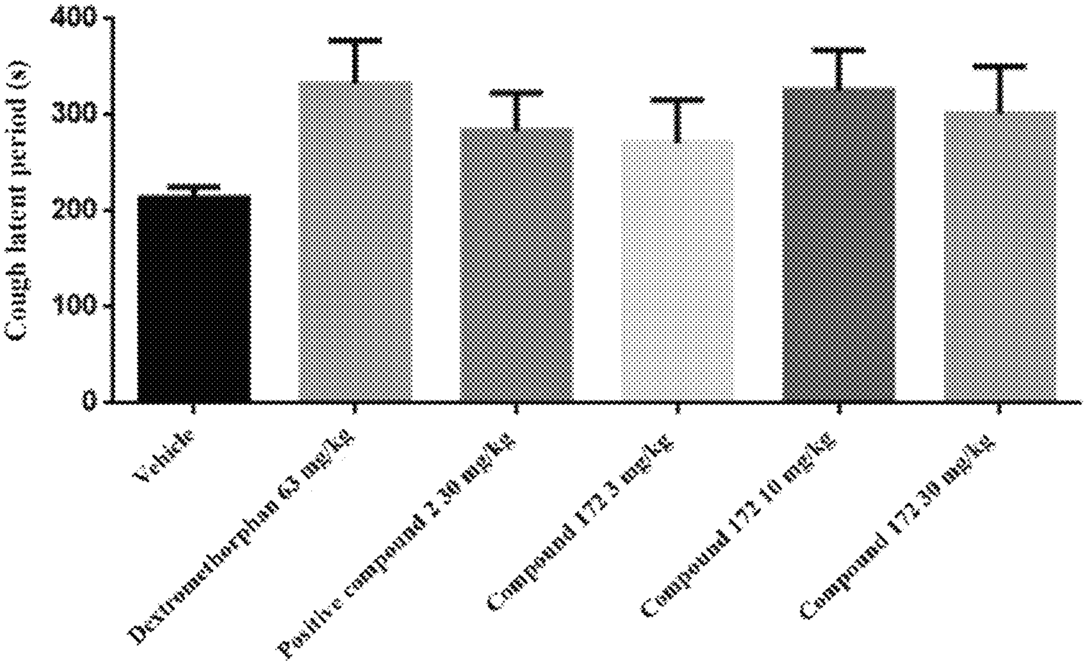
FIG. 6 shows the cough latency for the inventive compounds in the ATP-citric acid model.

As shown in Table 5 and FIGS. 5 and 6, all the compound treatment groups show a tendency of reduce in the number of coughs as compared with the vehicle group, both the dextromethorphan and compound 172 can significantly reduce the number of coughs, and compound 172 shows inhibition in a dose-dependent manner. Compound 172 exhibits stronger cough inhibition effect than positive compound 2.

Example E: In Vitro Cytotoxicity Assay

In vitro cytotoxicity assay for the compounds disclosed herein was performed in HepG2 cells using the CCK-8 method. HepG2 cells (Beina Bio) in the logarithmic growth phase were collected, the concentration of cell suspension was adjusted, and then the cells were plated on a 96-well cell culture plate at 50,000 cells/well. The cells were then incubated overnight in a cell incubator of 5% humidity at 37° C., and after 80-90% cell confluence was achieved, test compounds or vehicle (DMSO) at various concentration gradients were added after medium change. The plate was incubated in a cell incubator of 5% humidity at 37° C. for 48 h. After the treatment, the medium in the plate was discarded. The plate was washed twice with PBS, added with CCK-8 working solution (Beyotime) at 100 μL per well, and then incubated at 37° C. for 1.5 h away from light. Absorbance at OD 450 nm was measured for each well on a microplate reader, and $CC_{50}$ value of each compound was analyzed and calculated.

The $CC_{50}$ values obtained by the above method are shown in Table 6.

TABLE 6

$CC_{50}$ values obtained for some of the compounds

| Compound | HepG2 $CC_{50}$ (μM) | Compound | HepG2 $CC_{50}$ (μM) |
|---|---|---|---|
| Compound 2 | 123.5 | Compound 3 | 59.30 |
| Compound 4 | 13.21 | Compound 5 | 72.02 |
| Compound 7 | 194.6 | Compound 10 | 15.77 |
| Compound 11 | 79.44 | Compound 12 | 52.73 |
| Compound 13 | 66.48 | Compound 15 | 52.63 |
| Compound 17 | 50.95 | Compound 25 | >100 |
| Compound 26 | >100 | Compound 149 | >100 |
| Compound 158 | >100 | Compound 159 | >100 |
| Compound 160 | >100 | Compound 161 | >100 |
| Compound 162 | >100 | Compound 163 | >100 |
| Compound 164 | >100 | Compound 165 | >100 |
| Compound 166 | >100 | Compound 167 | >100 |
| Compound 168 | >100 | Compound 169 | >100 |
| Compound 171 | 200 | Compound 172 | 57.05 |
| Compound 173 | >200 | Compound 174 | >200 |
| Compound 176 | >200 | Compound 181 | 138.14 |
| Compound 182 | >200 | Compound 184 | >200 |
| Positive compound 1 | 128.4 | Positive compound 2 | >200 |

As can be seen from the data in Table 6, most of the compounds disclosed herein exhibit relatively good safety, and the $CC_{50}$ ranges are all more than 10 μM, which satisfies the requirement for in vitro cytotoxicity of general compounds. Compounds with a $CC_{50}$ value of more than 30 μM are preferred, and compounds with a $CC_{50}$ value of more than 50 μM are more preferred.

Example F: Test of In Vitro Metabolic Stability

The in vitro metabolic stability of the compounds disclosed herein was determined through incubation of liver microsomes of various species. A proper amount of test compound was added into a liver microsome reaction system (1 mg/mL liver microsome protein, 25 U/mL glucose-6 phosphate dehydrogenase, 1 mM NADP, 6 mM D-glucose 6-phosphate and 5 mM MgCl), and then the mixture was incubated in a water bath kettle at 37° C. to start the reaction. At each time point, 100 μL of the reaction mixture was added into a centrifuge tube containing 400 μL of internal standard working solution (containing a 200 ng/mL solution of dexamethasone, diclofenac, tolbutamide and labetalol in acetonitrile) precooled at 0° C. so as to terminate the reaction, and the mixture was then centrifuged at 10,000 g for 10 min at 4° C. The supernatant was collected for LC-MS assay so as to obtain the values of in vitro metabolic half-life of the test compounds in liver microsomes of various species.

The $T_{1/2}$ values obtained by the above method are shown in Table 7.

TABLE 7

$T_{1/2}$ values obtained for some of the compounds

| Compound | $T_{1/2}$ in human liver microsome min | $T_{1/2}$ in rat liver microsome min | $T_{1/2}$ in guinea pig liver microsome min |
|---|---|---|---|
| Compound 2 | 895.35 | 52.34 | 95.33 |
| Compound 3 | 260.22 | 28.72 | 50.49 |
| Compound 4 | 61.05 | 4.91 | 4.38 |
| Compound 5 | 648.70 | 37.31 | 47.62 |
| Compound 7 | 127.80 | 19.58 | 20.89 |
| Compound 10 | 222.61 | 30.80 | 13.51 |
| Compound 11 | 151.19 | 5.65 | 4.27 |
| Compound 12 | 91.92 | 7.78 | 7.56 |
| Compound 13 | 61.51 | 2.24 | 2.25 |
| Compound 15 | 190.59 | 25.39 | 16.51 |
| Compound 17 | 997.99 | 19.35 | 8.61 |
| Compound 25 | 297.97 | 227.75 | NA |
| Compound 26 | 253.12 | 80.94 | 127.80 |
| Compound 149 | 206.63 | 52.50 | 178.02 |
| Compound 168 | 522.56 | 57.59 | 29.24 |
| Compound 169 | 827.52 | 35.47 | 164.42 |
| Compound 171 | 523.3 | 8.48 | 140.1 |
| Example 172 | 824.3 | 223.4 | 410.3 |
| Example 173 | NA | 101.2 | 646.6 |
| Example 174 | NA | 398.3 | 1110.5 |
| Example 175 | >30 | >30 | >30 |
| Example 176 | 235.9 | 3.61 | 60.96 |
| Compound 177 | 324.61 | / | / |
| Compound 178 | 1233.69 | / | / |
| Compound 181 | 1400.2 | 187.65 | 234.42 |
| Compound 182 | 217.27 | 10.95 | 60.96 |
| Compound 184 | 24383.0 | 5.66 | 173.41 |
| Compound 189 | 144.57 | / | / |
| Positive compound 1 | 1454.06 | 53.42 | 112.04 |
| Positive compound 2 | NA | 1090.01 | 892.21 |

Note:
NA indicates essentially not metabolized; "/" indicates not detected.

As can be seen from the data in Table 7, the compounds disclosed herein exhibit relatively good metabolic stability in human, rat and guinea pig. As compared with positive compound 1, the compounds disclosed herein have similar metabolic half-life in human liver microsome but longer half-life in rat and guinea pig. In addition, as compared with positive compound 1, the metabolism of the compounds disclosed herein in rat and guinea pig are more close to that in human, which is beneficial to the related experimental evaluation of the compounds in rat and guinea pig. Compounds with a $T_{1/2}$>30 min in human liver microsome are preferred, and compounds with a $T_{1/2}$>90 min in human liver microsome are more preferred.

Example G: Two-Bottle Dysgeusia Test

Male SD rats (SPF grade, aged 6-8 weeks) were subjected to adaptive drinking training for 3 days after warehousing, and the specific training content was as follows: animals were fed in separate cages, and two bottles of water (both were common drinking water) were placed in each cage; during the adaptive training, drinking water was completely prohibited at night every day (drinking water bottles were removed out) and then resupplied during 8:30 am to 5:30 pm; and the operation was repeated for 3 days, the positions of the two bottles of water were changed every day, and the animals could cat freely during the whole adaptive training period. All drinking water bottles were removed out 20 h before the start of the formal experiment, and all the animals were deprived of water until the start of the experiment. In the experiment, all the animals were randomly grouped and then subjected to a single intraperitoneal injection of a test compound or a vehicle before water was resupplied. The administration time was determined according to the $T_{max}$ of the test compound. Then the animals were placed in separate cages, and two bottles of drinking water (one bottle of normal drinking water and one bottle of 0.3 mM quinine water) were provided. The water intake of the animals was observed within 15 min, statistical analysis was performed based on quinine water intake/normal water intake, and positive compound 2 was used as the dysgeusia positive control.

TABLE 8

Ratios of quinine/water intake obtained for some of the compounds

| Compound | Quinine/tap water* 100% |
|---|---|
| Vehicle | 4.54% |
| Positive compound 2 | 59.41% |
| Compound 2 | 5.49% |
| Compound 7 | 6.91% |
| Compound 53 | 7.65% |
| Compound 149 | 4.54% |
| Compound 161 | 5.03% |
| Compound 162 | 6.34% |
| Compound 164 | 6.69% |
| Compound 165 | 3.90% |

Figure 7:
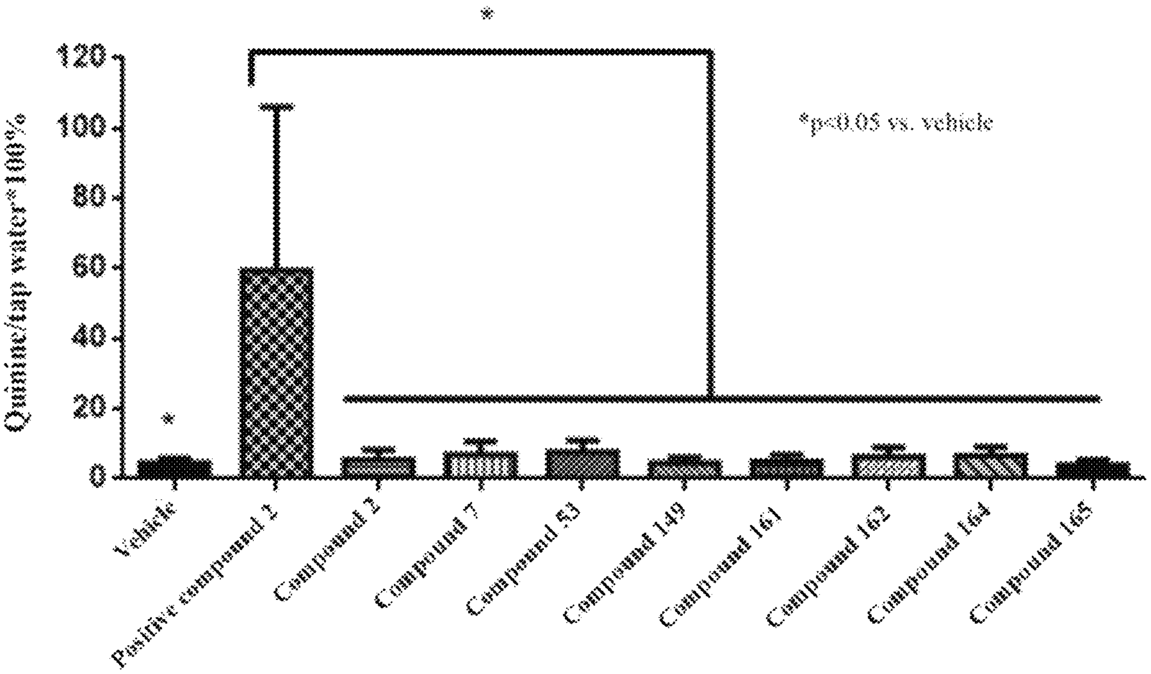
FIG. 7 shows the ratio of quinine/tap water consumed in rats after the administration of the inventive compounds.

The above experiment was conducted on the following representative compounds: compound 2, compound 7, compound 53, compound 149, compound 161, compound 162, compound 164 and compound 165. The results as shown in Table 8 and FIG. 7 demonstrate that for compound 2, compound 7, compound 53, compound 149, compound 161, compound 162, compound 164 and compound 165 at 20 mg/kg, the ratio of quinine/water intake is almost unaffected when compared with the blank vehicle while, and the ratio of quinine/water intake is remarkably reduced when compared with positive compound 2, indicating that the influence of compound 2, compound 7, compound 53, compound 149, compound 161, compound 162, compound 164 and compound 165 on animal taste is smaller,

TABLE 9

Ratios of quinine/water intake obtained for the compounds

| Compound | | Quinine/tap water* 100% |
|---|---|---|
| Vehicle | | 7.19% |
| Positive compound 2 | 10 | 18.62% |
| | 20 | 34.99% |
| Compound 172 | 5 | 7.05% |
| | 10 | 7.41% |
| | 20 | 8.66% |

Figure 8:
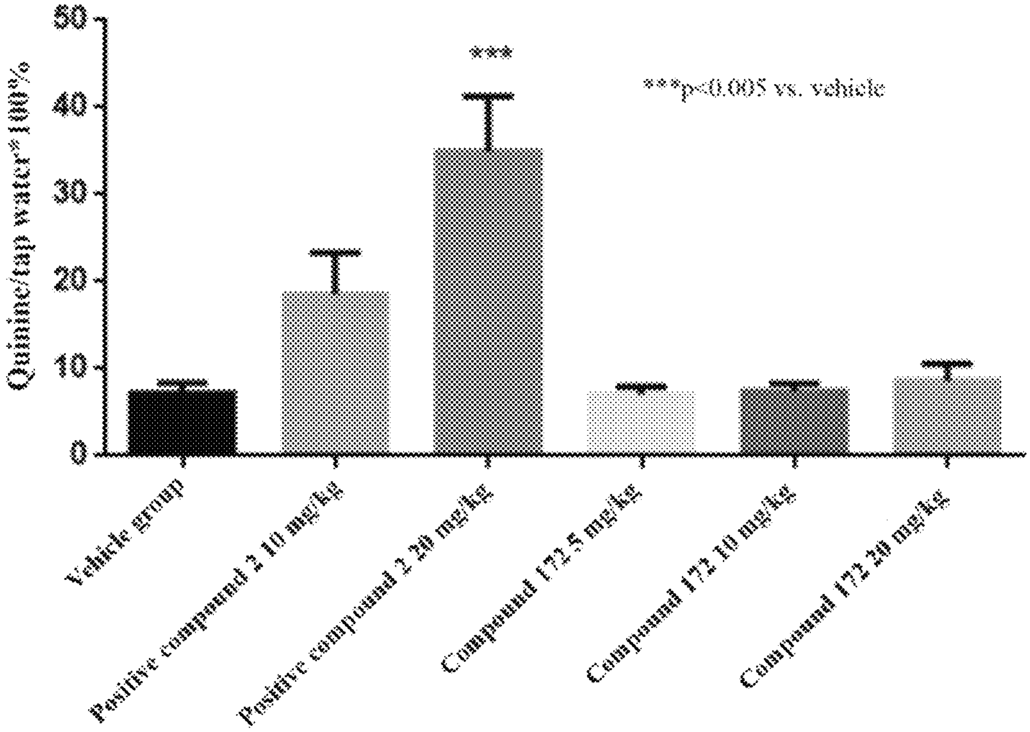
FIG. 8 shows the ratio of quinine/tap water consumed in rats after the administration of the inventive compounds at gradient concentrations.

The above experiment was conducted on the representative compound 172. The results as shown in Table 9 and FIG. 8 demonstrate that for compound 172 at 5 mg/kg, 10 mg/kg and 20 mg/kg, the ratio of quinine/water intake of rats is almost unaffected when compared with the blank vehicle, indicating that compound 172 has small influence on animal taste; as compared with the positive compound 2, the ratio of quinine/water intake is remarkably reduced, showing that the risk of causing dysgeusia by compound 172 is far lower than that by positive compound 2, and compound 172 shows better safety.

Although examples of the present invention are illustrated and described above, it will be appreciated that the above examples are exemplary and not to be construed as limiting the present invention, and that changes, modifications, substitutions and alterations can be made to the above examples by those skilled in the art within the scope of the present invention.

The invention claimed is:

1. A heterocyclic compound of formula I, a stereoisomer, or a pharmaceutically acceptable salt thereof,

I

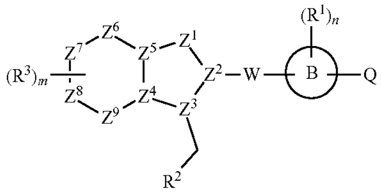

wherein,

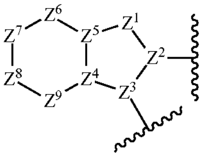

is

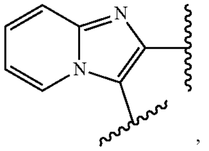

, m is 1 or 2;

each $R^3$ is independently H, halogen, or a $C_1$-$C_6$ alkyl;

W is a single bond;

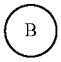

is phenyl;

n is 1 or 2;

each $R^1$ is independently H, halogen, an unsubstituted $C_1$-$C_6$ alkyl or $C_1$-$C_6$ alkyl substituted with one or more halogen;

Q is —S(═O)$_2$—N($R^{1-9}R^{1-10}$);

$R^{1-9}$ and $R^{1-10}$ are both H;

$R^2$ is

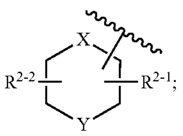

wherein $R^{2-1}$ and $R^{2-2}$ are both H;

X and Y are each independently methylene, —O—, or

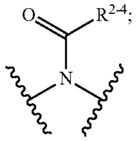

and $R^{2-4}$ is an unsubstituted $C_1$-$C_6$ alkyl or an unsubstituted $C_1$-$C_6$ alkyl-O.

2. A heterocyclic compound, a stereoisomer thereof, or a pharmaceutically acceptable salt thereof, wherein the heterocyclic compound is selected from the group consisting of:

2

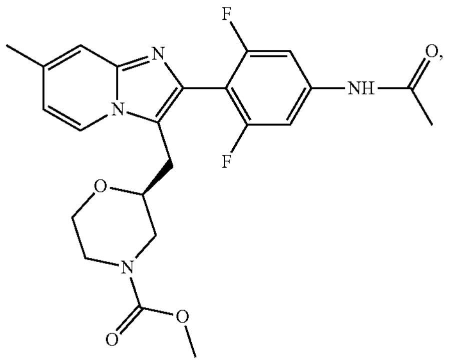

3

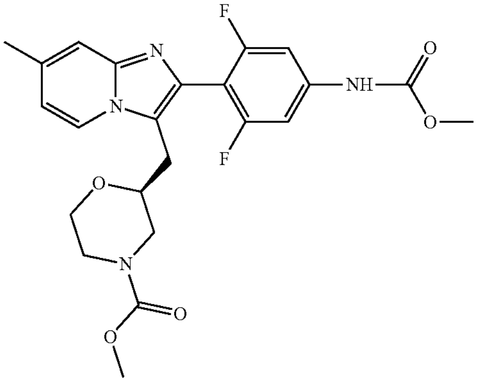

4

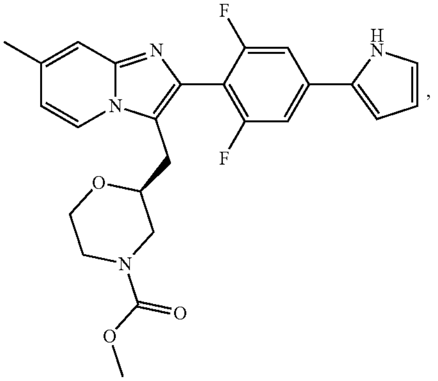

-continued
5
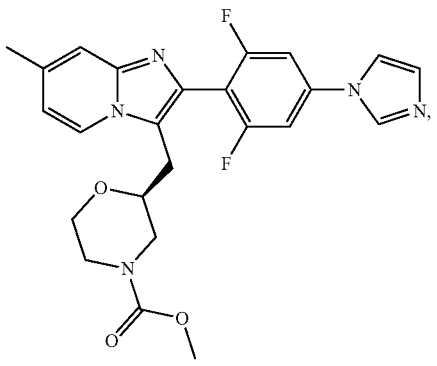
7
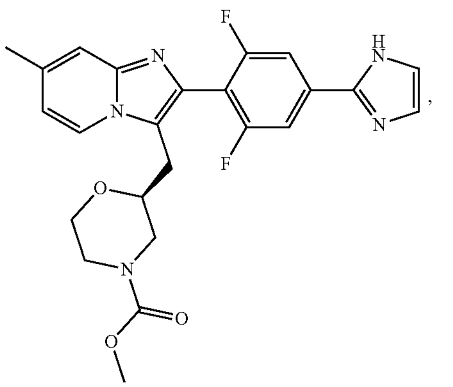
10
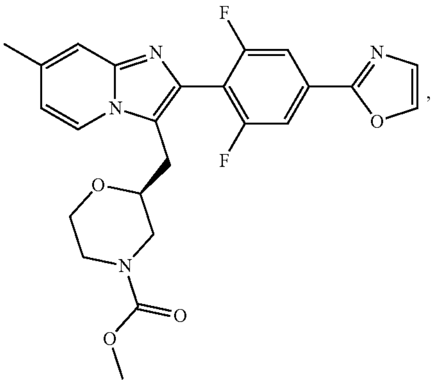
11
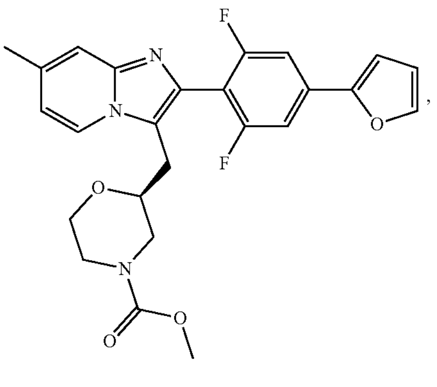
-continued
12
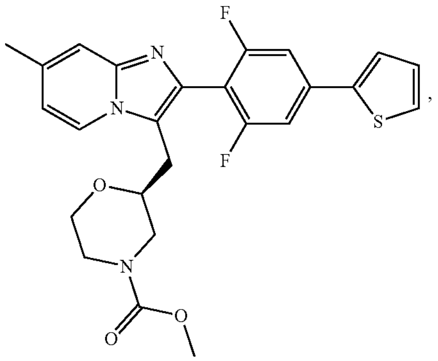
13
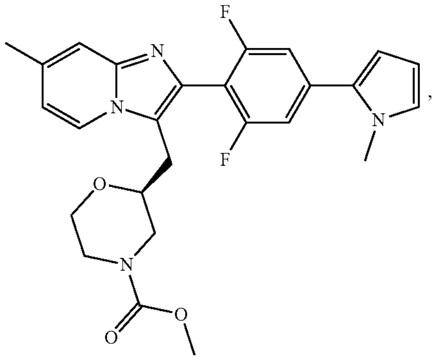
15
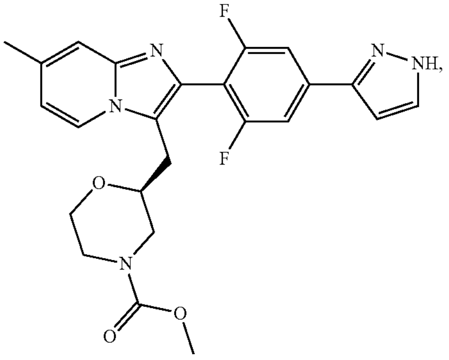
16
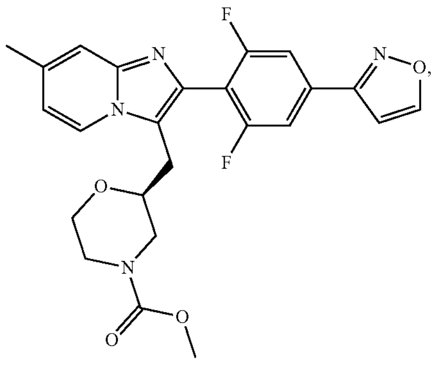

-continued
17
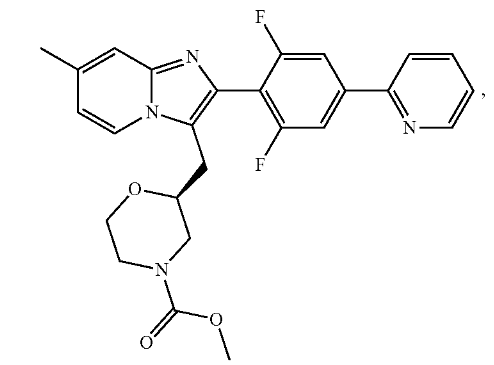
25
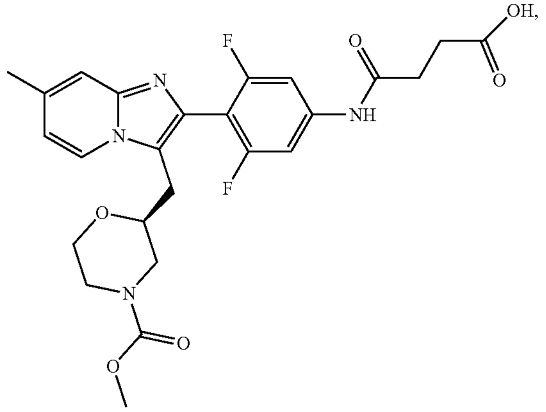
26
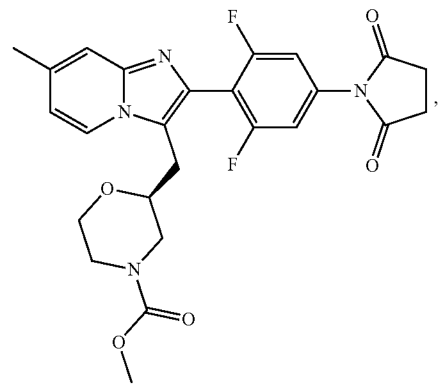
27
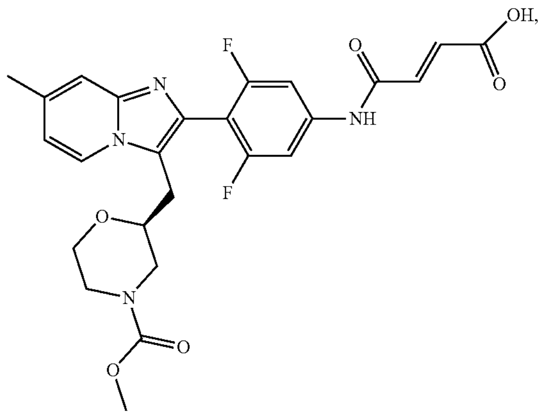
-continued
28
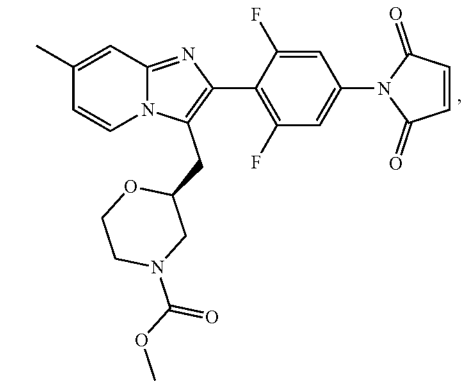
29
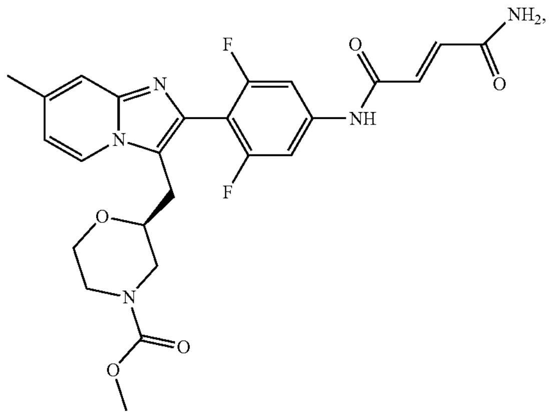
34
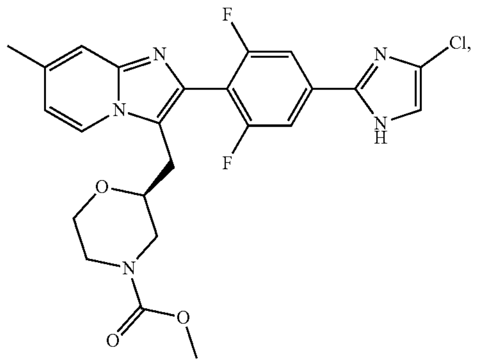
37
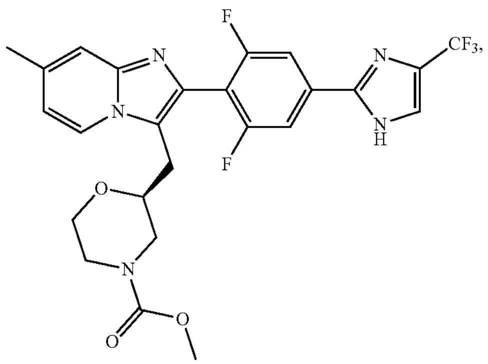

-continued
38
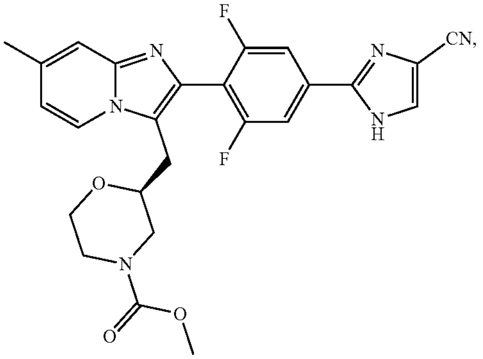
43
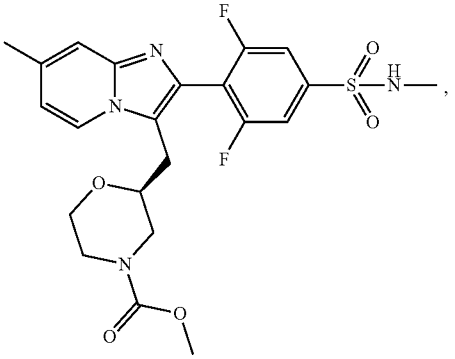
50
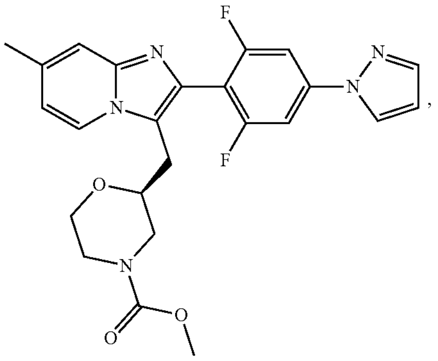
52
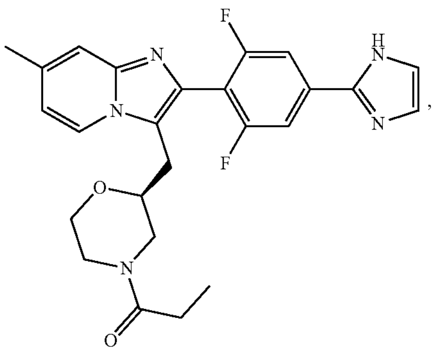
-continued
58
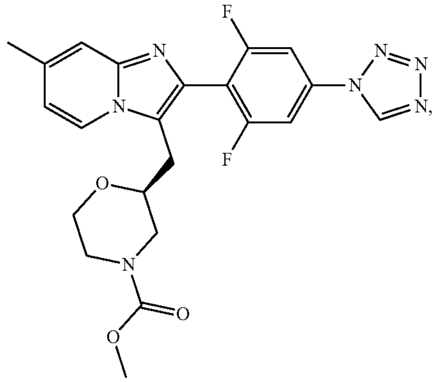
59
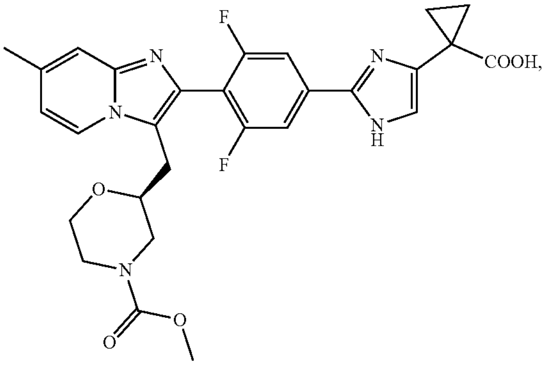
60
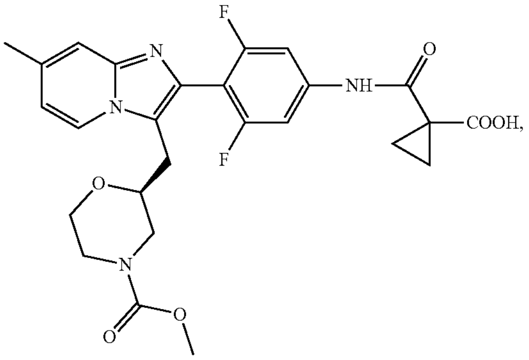
61
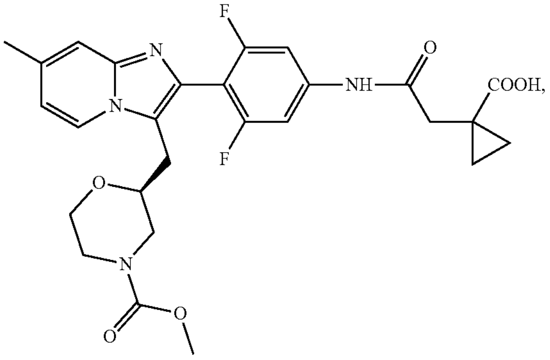

-continued
67
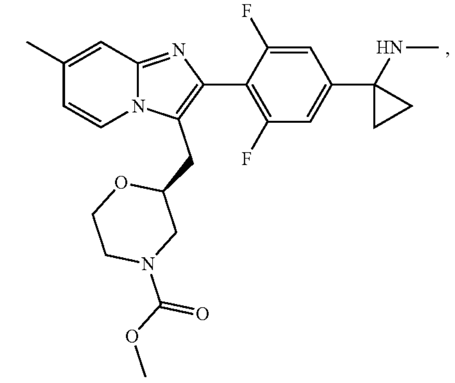
,
69
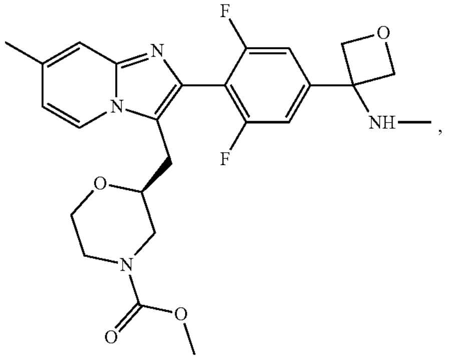
,
70
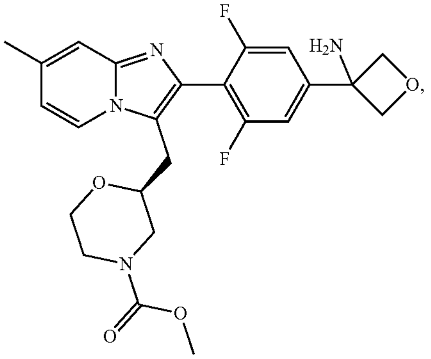
,
71
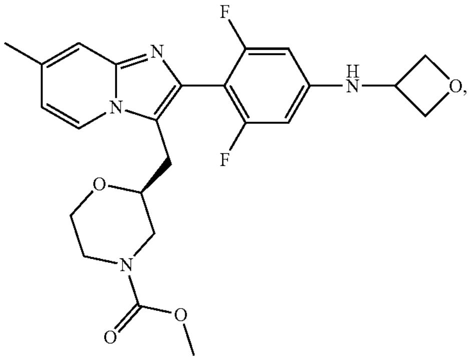
,
-continued
75
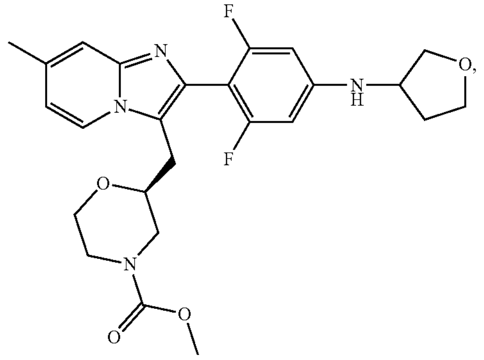
,
77
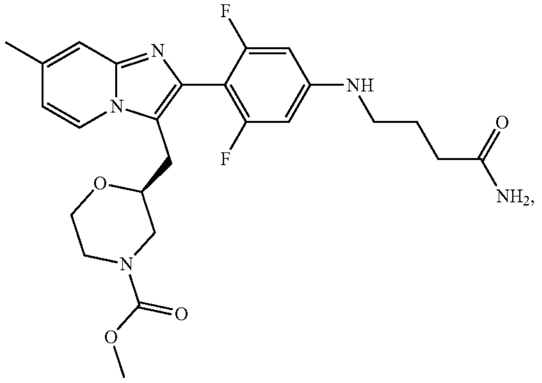
,
78
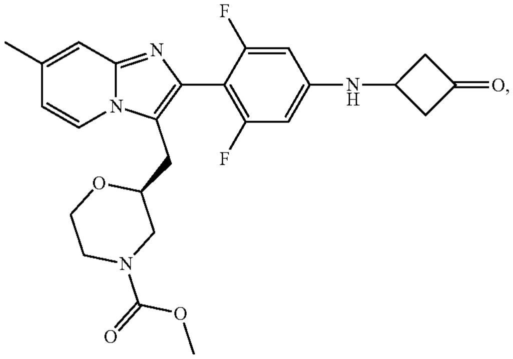
,
79
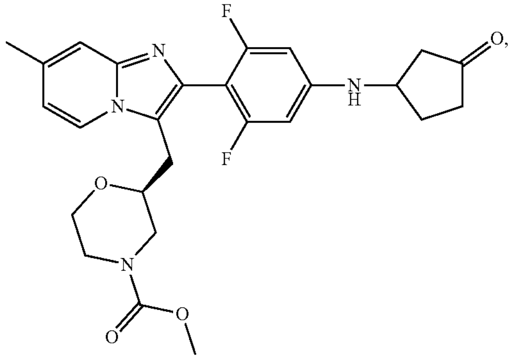
, -continued
80
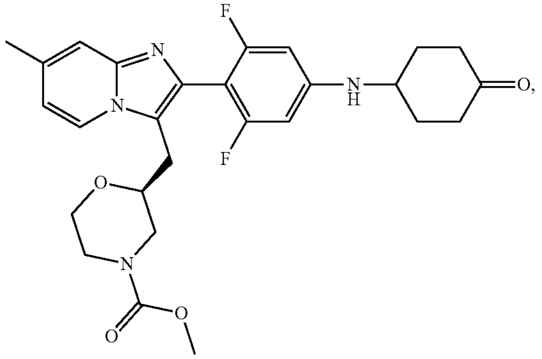
81
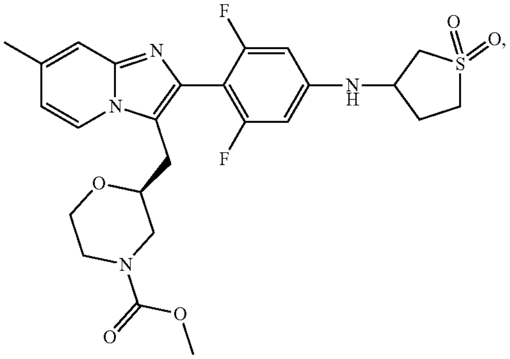
82
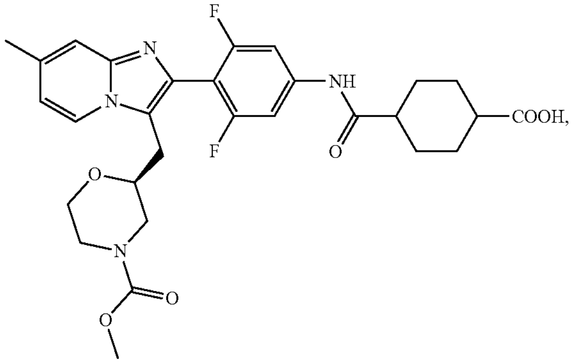
86
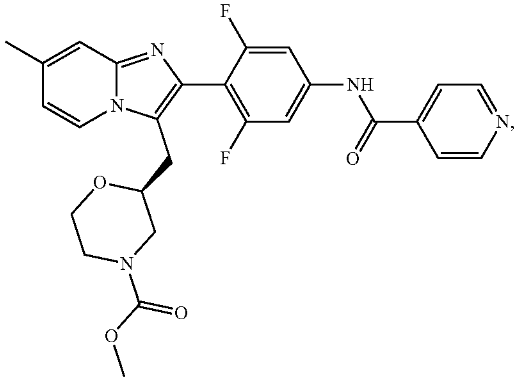
-continued
88
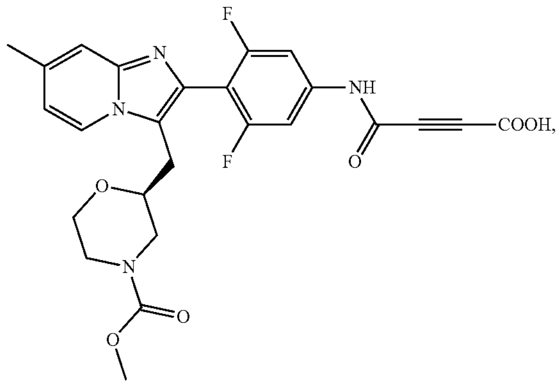
89
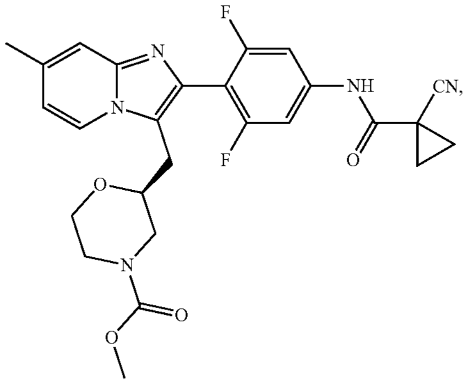
90
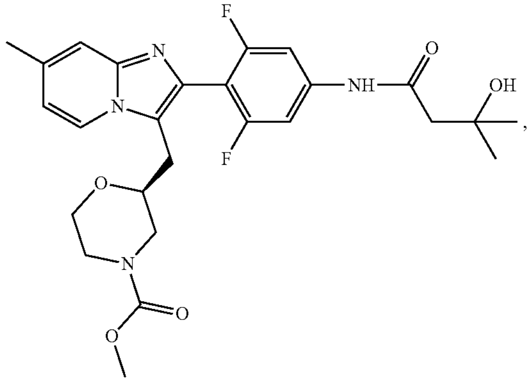
91
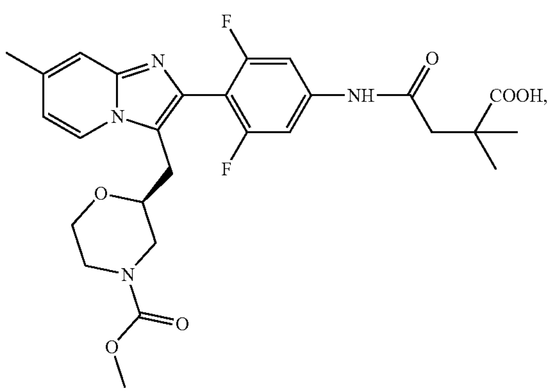

-continued
92
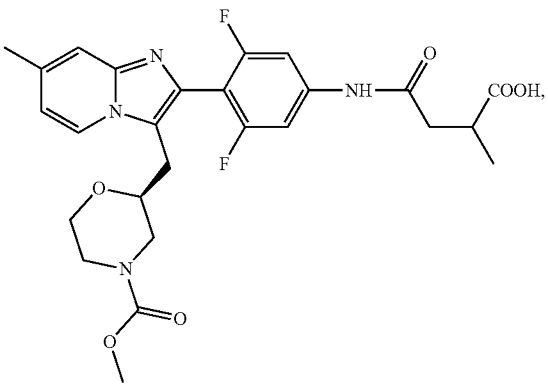
93
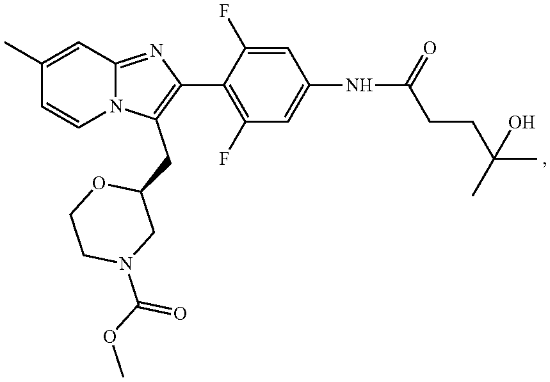
95
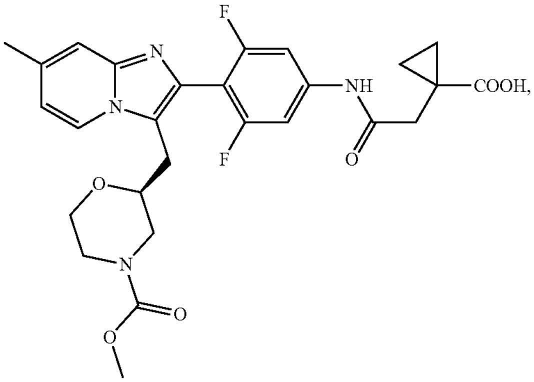
96
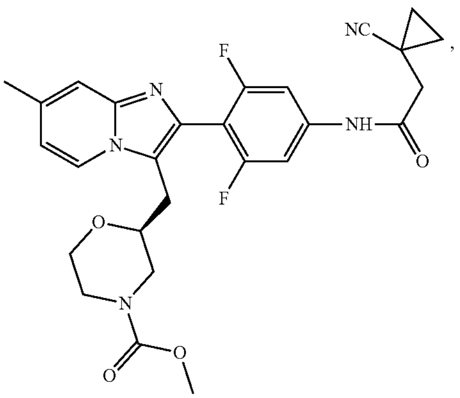
-continued
98
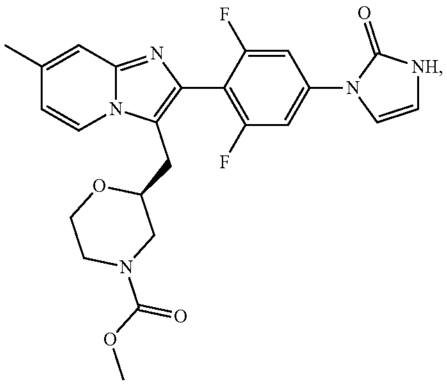
99
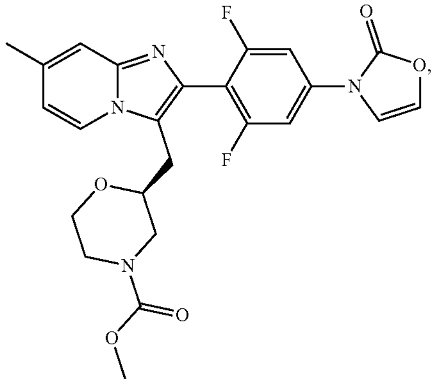
100
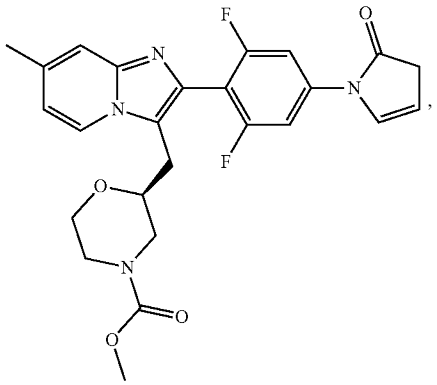
101
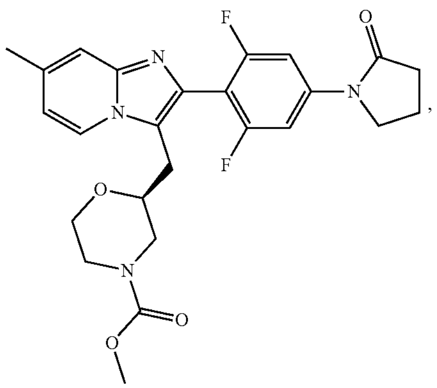

-continued
102
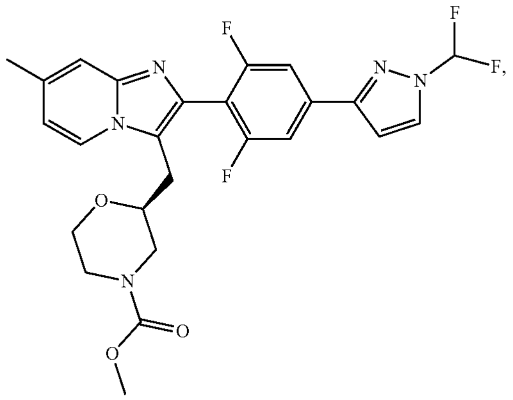
105
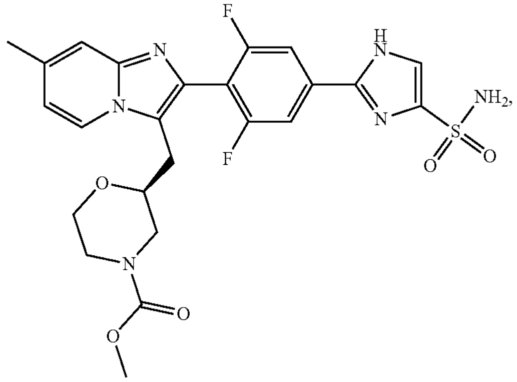
106
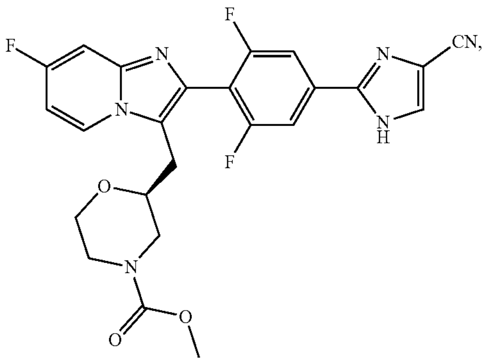
107
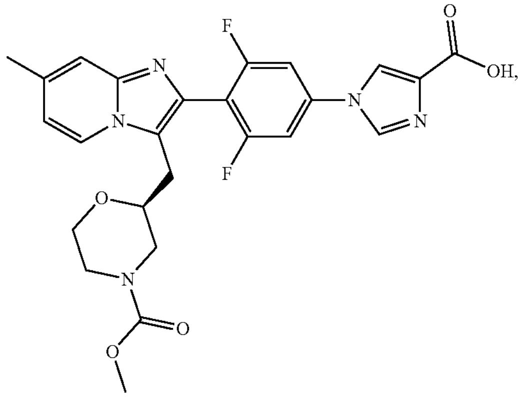
-continued
110
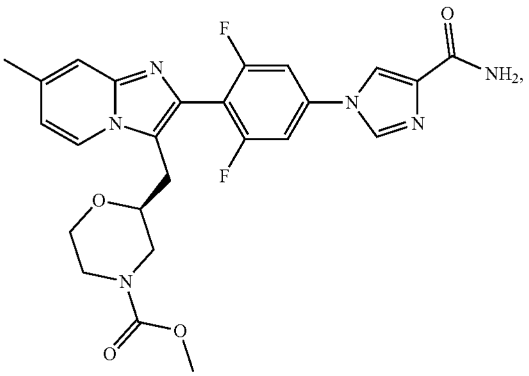
111
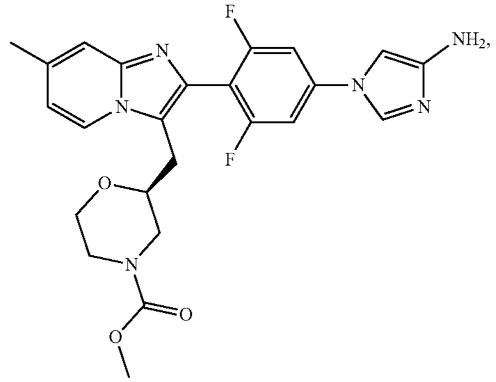
114
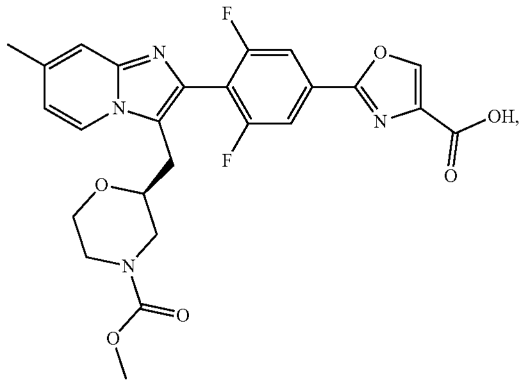
116
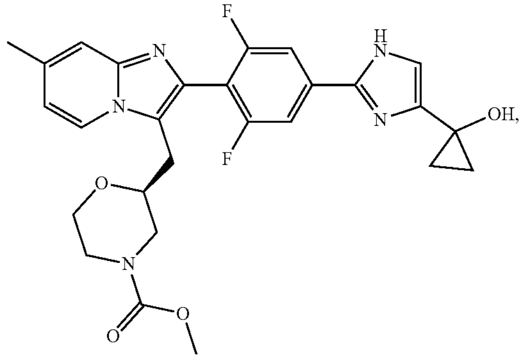

117
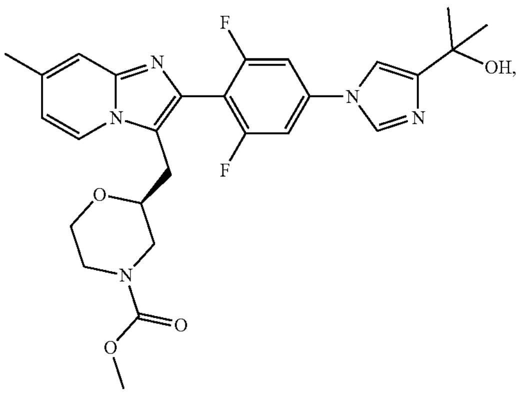
119
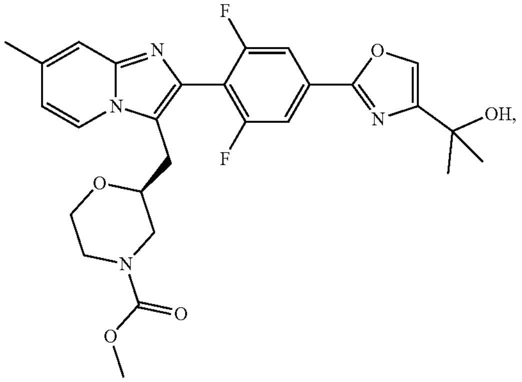
120
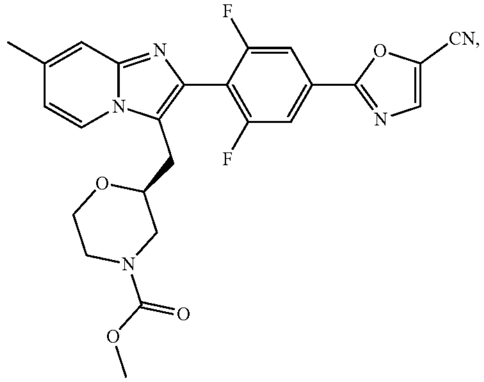
124
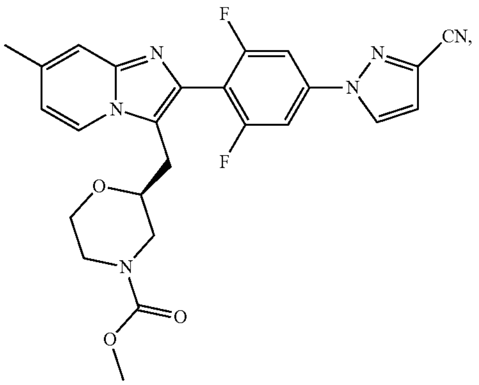
124-2
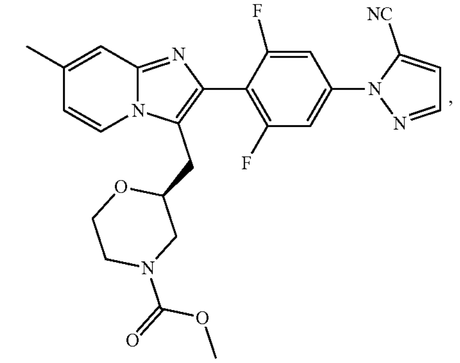
125
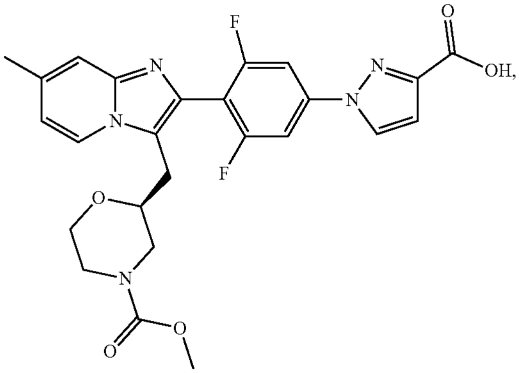
126
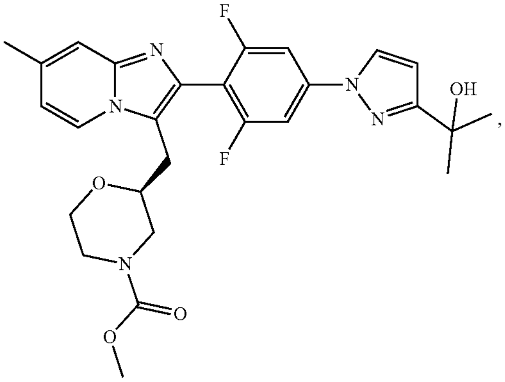
127
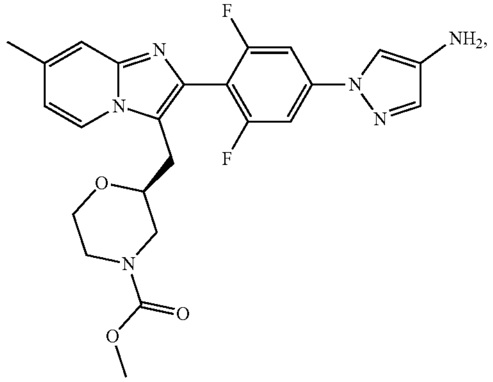

-continued
129
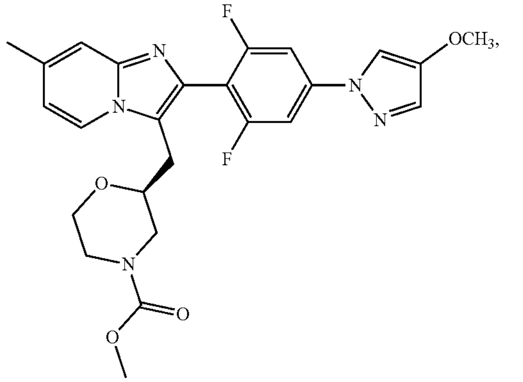
131
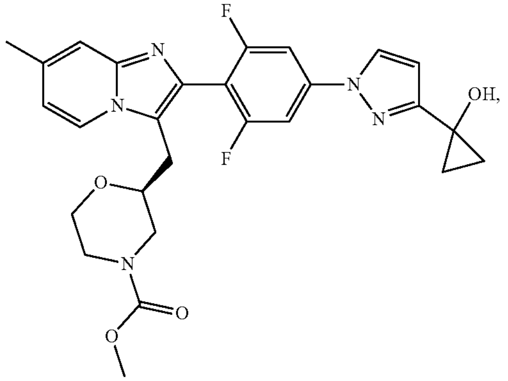
132
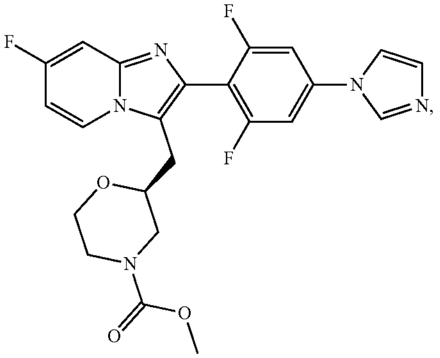
133
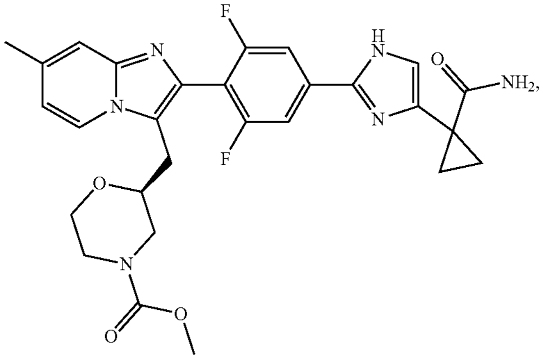
-continued
134
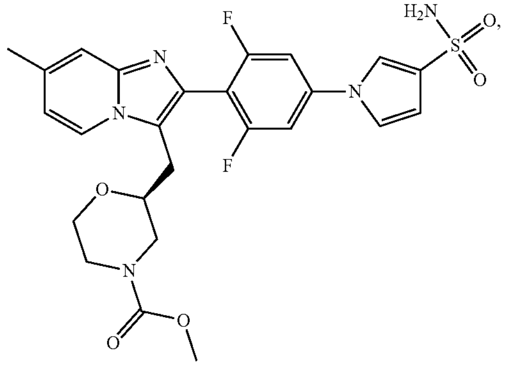
135
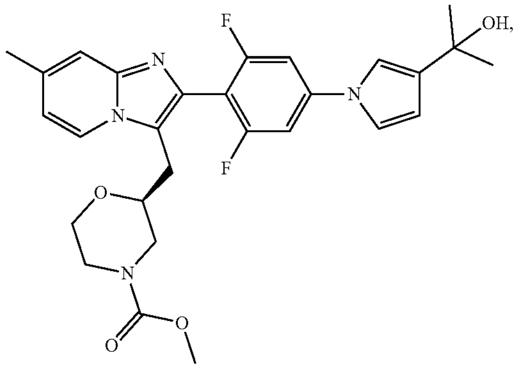
137
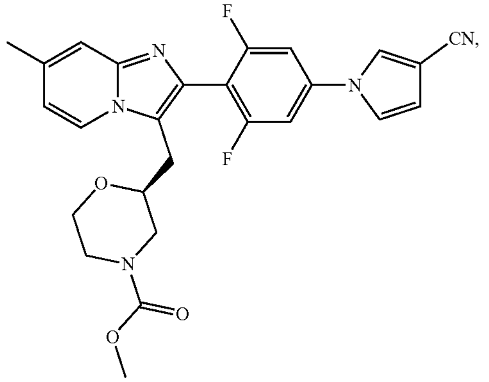
138
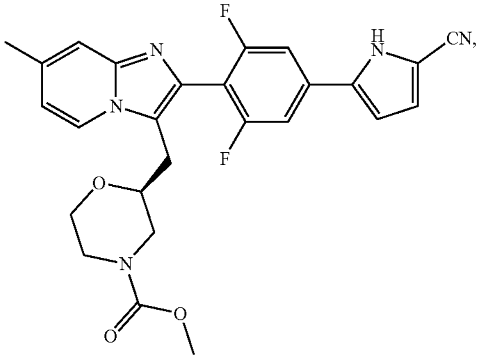

-continued
139
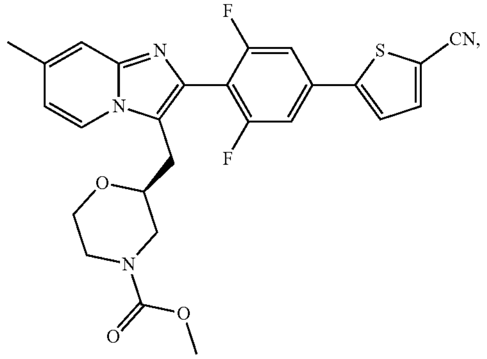
141
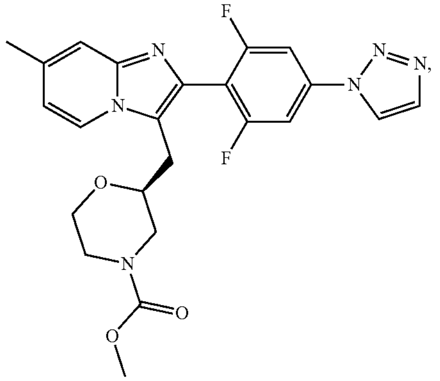
142
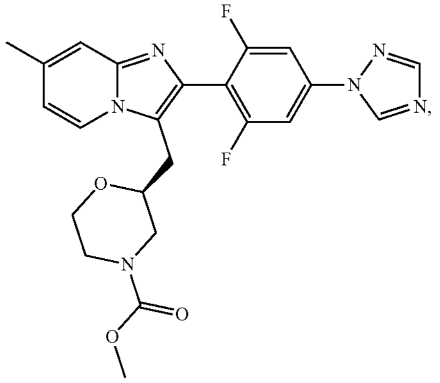
143
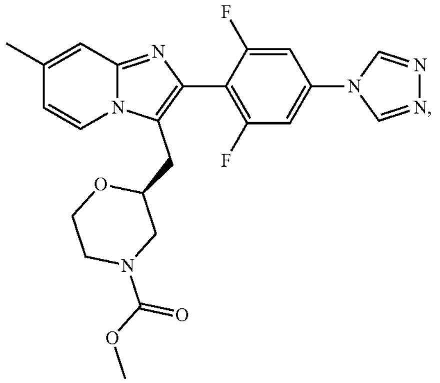
-continued
144
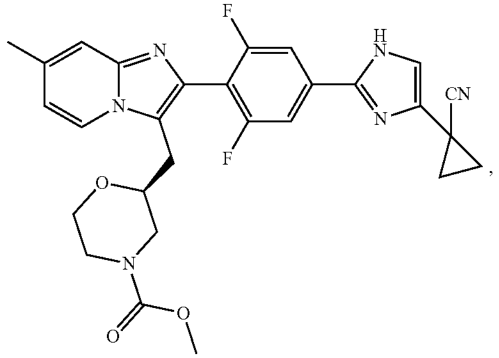
147
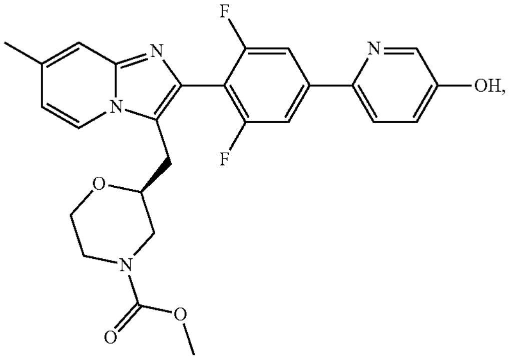
148
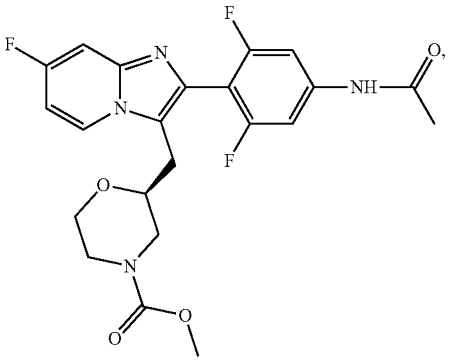
149
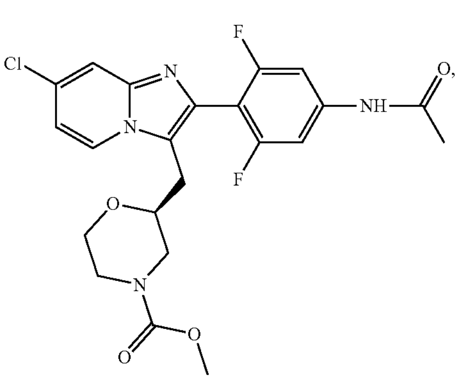

-continued
150
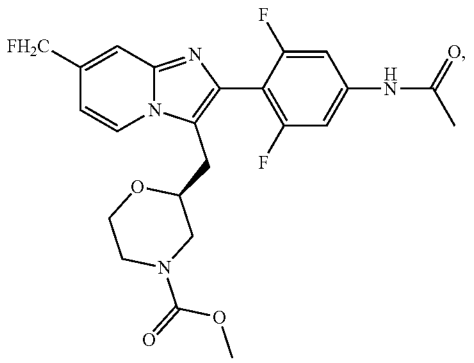
151
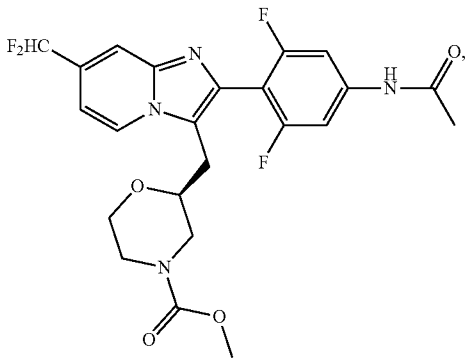
152
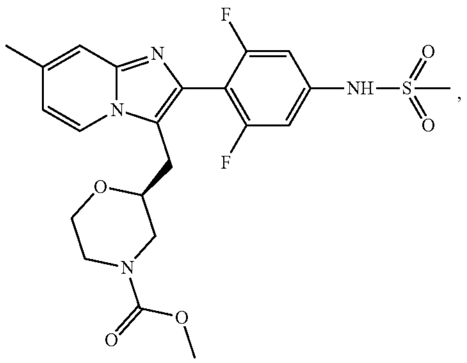
154
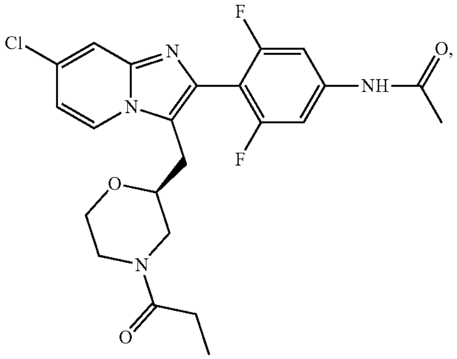
-continued
155
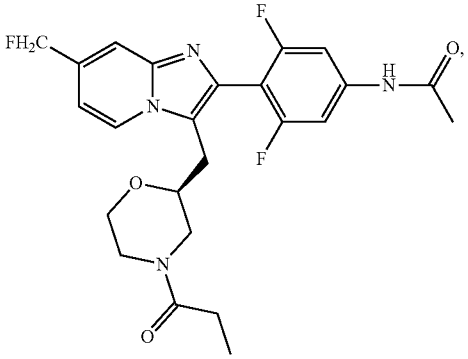
156
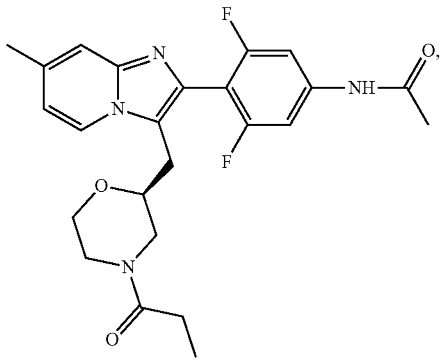
157
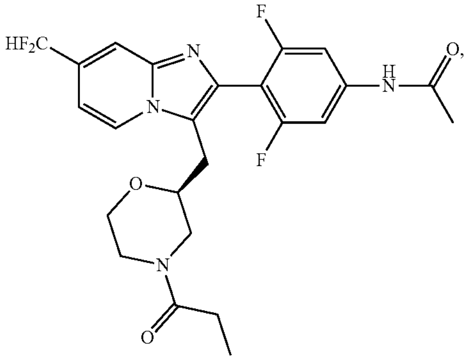
158
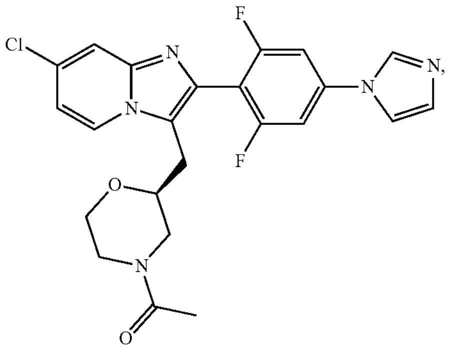

-continued
159
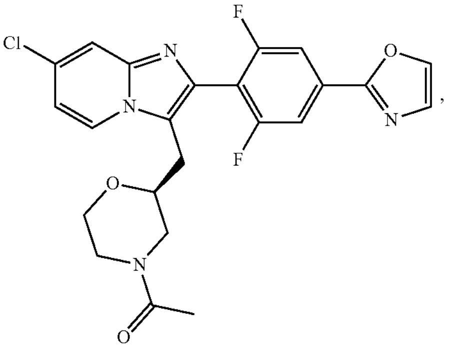
160
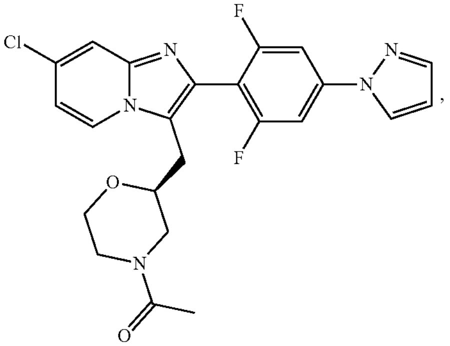
161
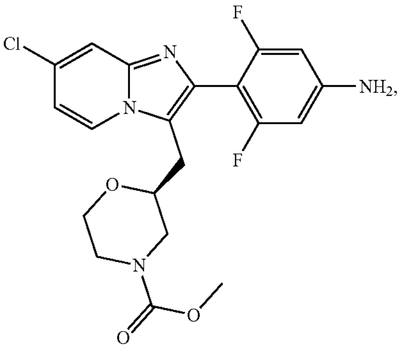
162
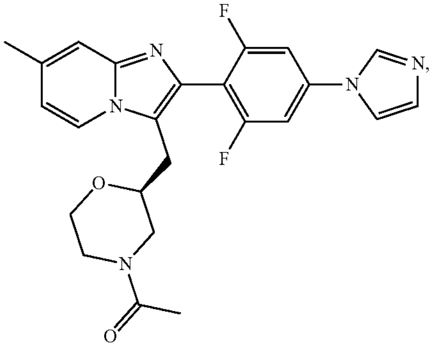
-continued
163
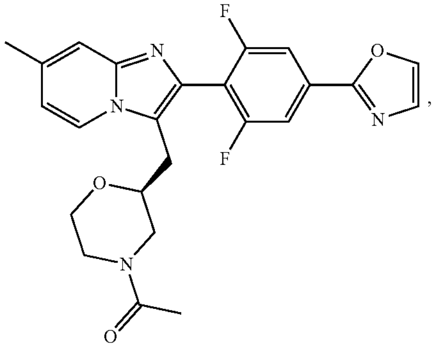
164
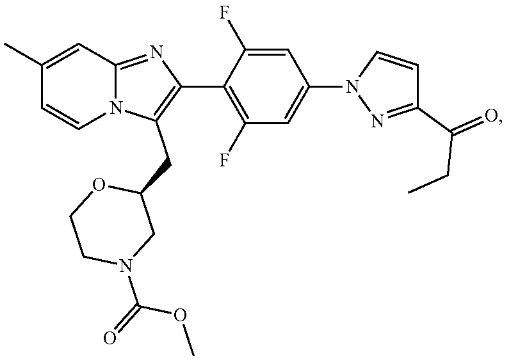
165
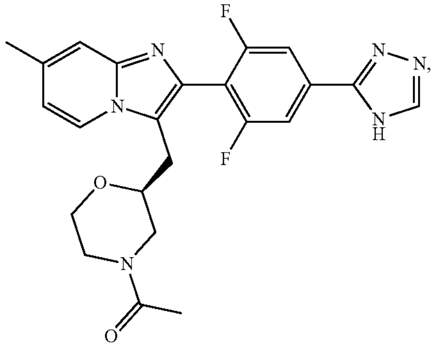
166
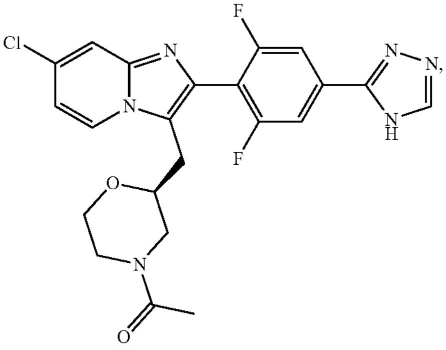

-continued
167
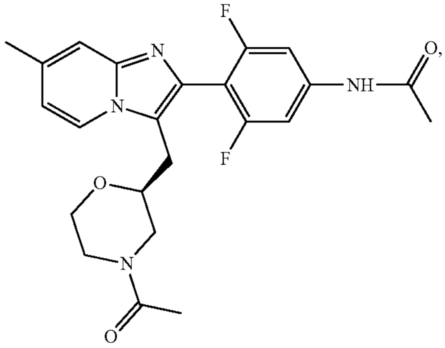
169
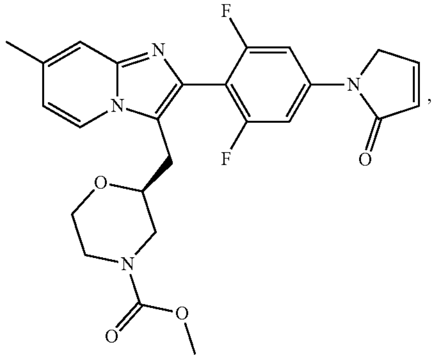
171
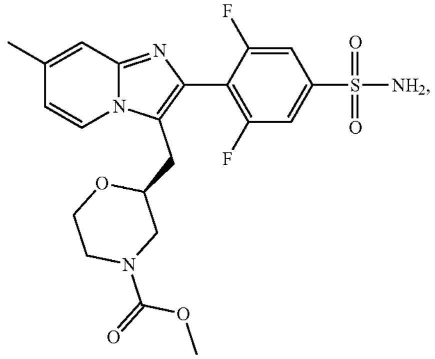
172
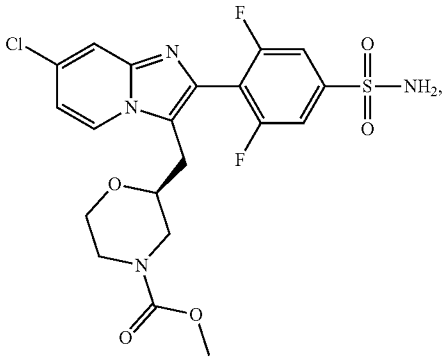
-continued
173
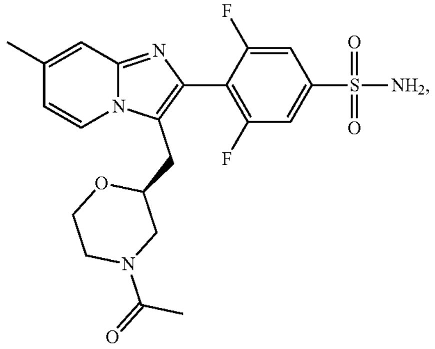
174
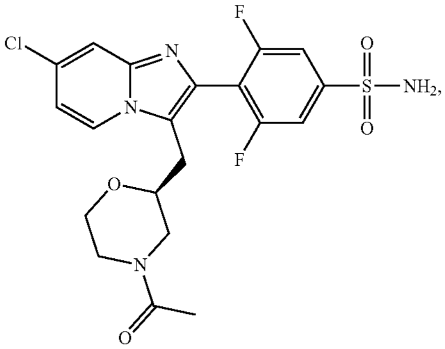
176
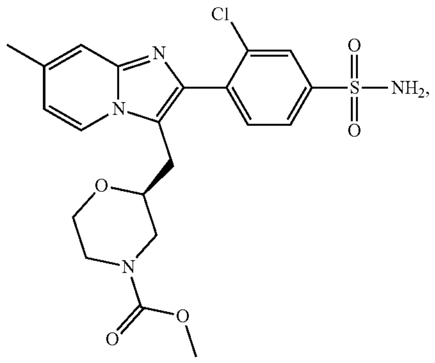
177
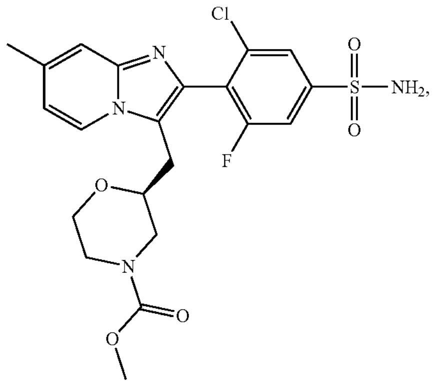

-continued
178
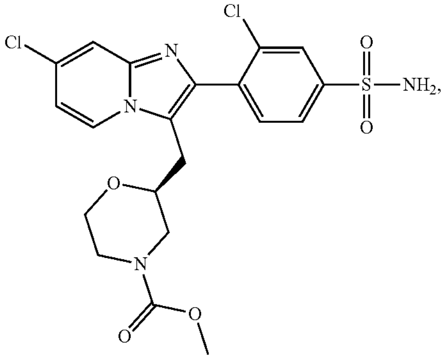
179
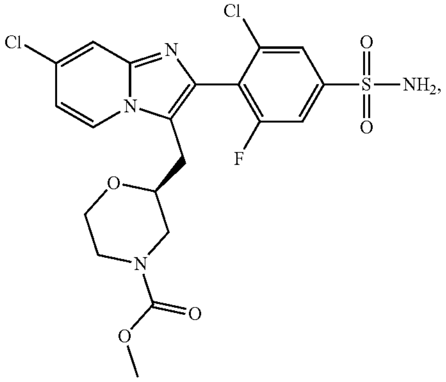
180
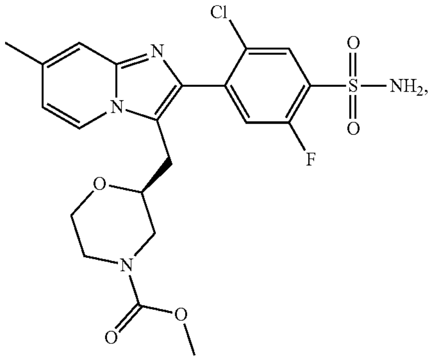
181
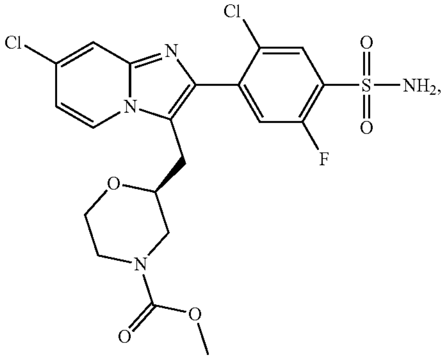
-continued
182
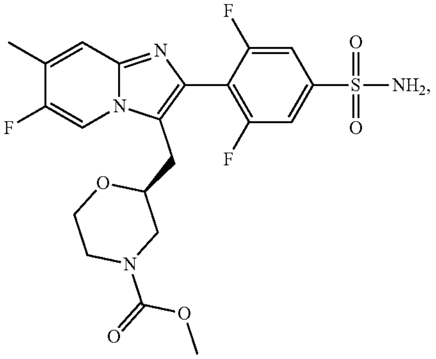
183
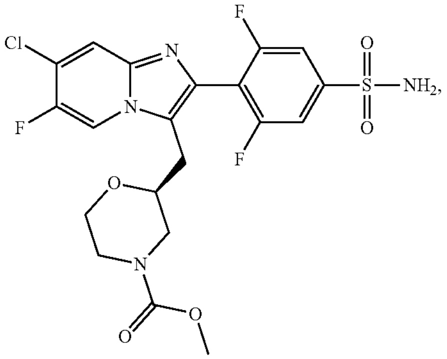
184
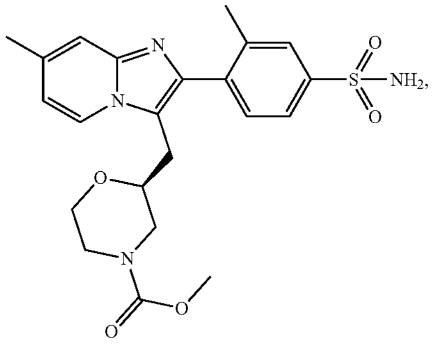
185
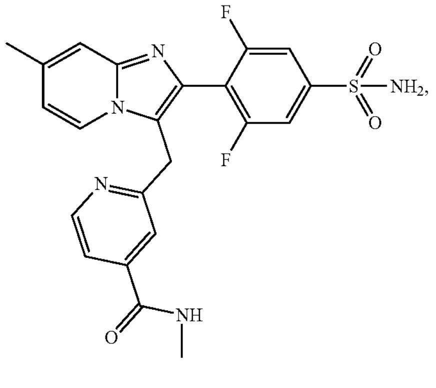

-continued

186

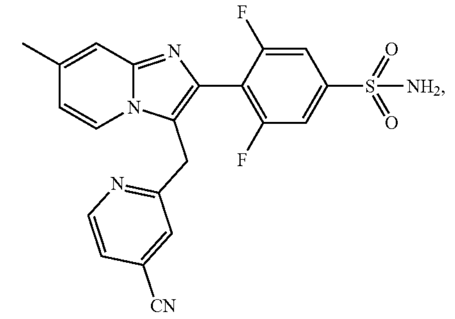

187

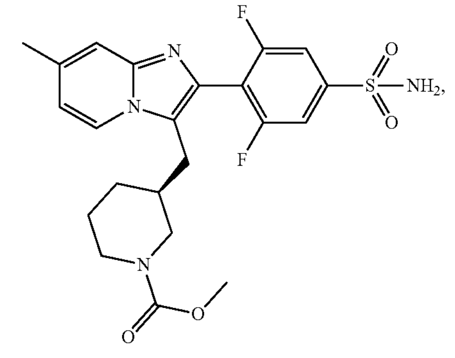

188

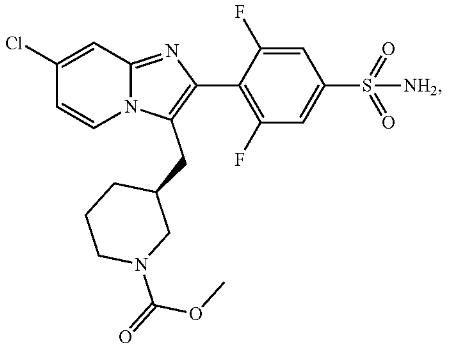

189

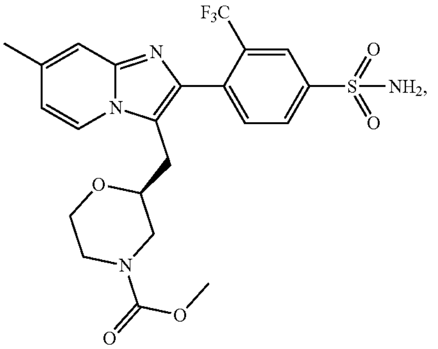

and

-continued

192

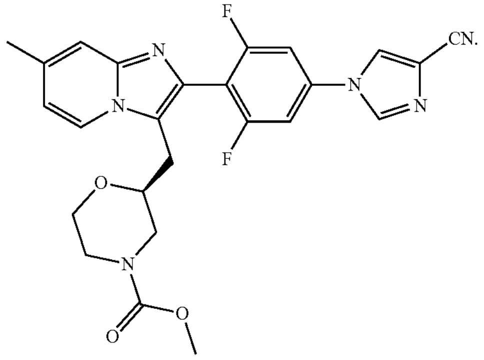

3. A preparation method of a heterocyclic compound of formula I

I

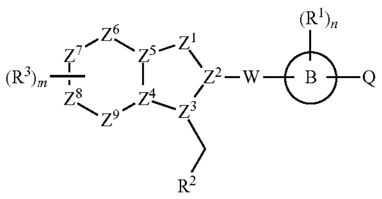

wherein,

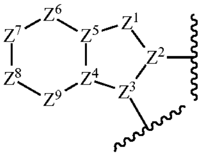

is

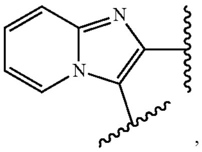

, m is 1, 2, 3 or 4;

$R^3$ is H, halogen, —OH, a $C_1$-$C_6$ haloalkyl, —CN or a $C_1$-$C_6$ alkyl; when m is not 1, $R^3$ is independently the same or different;

W is a single bond;

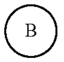

is phenyl;

n is 1, 2, 3 or 4;

$R^1$ is independently H, halogen, —OH, —CN, an unsubstituted or substituted $C_1$-$C_6$ alkyl, or an unsubstituted or substituted $C_1$-$C_6$ alkyl-O—; wherein the substituted $C_1$-$C_6$ alkyl or the substituted $C_1$-$C_6$ alkyl-O— is substituted with one or more substituents independently selected from halogen, —OH, —$CF_3$, —CN, —COOH, —C(═O)$NH_2$, a $C_1$-$C_6$ alkyl, a $C_1$-$C_6$ alkyl-O—, and ═O; when a plurality of substituents are present, they are the same or different; and when n is not 1, $R^1$ is independently the same or different;

Q is —NH—C(═O)—$R^{1-1}$, —O—C(═O)—N($R^{1-3}$ $R^{1-4}$), —S(═O)$_2$—N($R^{1-9}R^{1-10}$), —N($R^{1-14}R^{1-15}$), —NH—S(═O)$_2$—$R^{1-16}$, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, or an unsubstituted or substituted 5-10 membered heteroaryl; wherein the $C_3$-$C_9$ heterocycloalkyl contains 1-3 heteroatoms selected from one or more of O, S, and N; the $C_3$-$C_9$ heterocycloalkenyl contains 1-3 heteroatoms selected from one or more of O, S, and N; and the 5-10 membered heteroaryl contains 1-3 heteroatoms selected from one or more of O, S, and N; and the substituted $C_3$-$C_{10}$ cycloalkyl, the substituted $C_3$-$C_9$ heterocycloalkyl, the substituted $C_3$-$C_9$ heterocycloalkenyl or the substituted 5-10 membered heteroaryl is substituted with one or more substituents independently selected from halogen, —OH, —$CF_3$, —CN, —COOH, —C(═O)$NH_2$, ═O, —N($R^{1-21}R^{1-22}$), —C(═O)—N($R^{1-23}R^{1-24}$), —S(═O)$_2$—N($R^{1-25}R^{1-26}$), —C(═O)—O—$R^{1-27}$, a $C_1$-$C_6$ alkyl, a $C_1$-$C_6$ alkyl-O—, and a $C_3$-$C_6$ cycloalkyl that is unsubstituted or substituted with one or more $R^a$, wherein when a plurality of $R^a$ are present, they are the same or different, and each $R^a$ is halogen, —OH, ═O, —$CF_3$, —CN, —COOH or —C(═O)$NH_2$; and when a plurality of substituents are present, they are the same or different; wherein the —O—C(═O)—N($R^{1-3}R^{1-4}$) is —O—C(═O)—NH—$CH_3$; —N($R^{1-14}R^{1-15}$) is

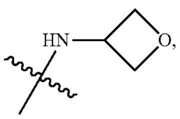

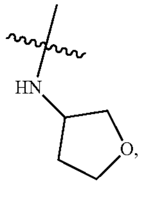

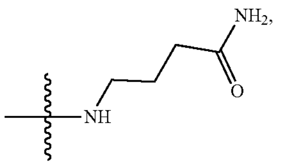

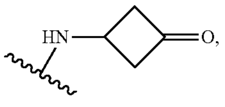

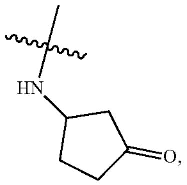

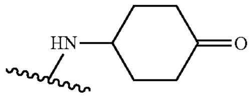

or

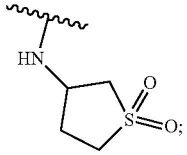

—NH—S(═O)$_2$—$R^{1-16}$ is —NH—S(═O)$_2$—$CH_3$;

$R^{1-1}$, $R^{1-9}$, $R^{1-10}$, $R^{1-21}$, $R^{1-22}$, $R^{1-23}$, $R^{1-24}$, $R^{1-25}$, $R^{1-26}$ and $R^{1-27}$ are each independently H, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_2$-$C_6$ alkynyl, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, an unsubstituted or substituted phenyl, or an unsubstituted or substituted 5-10 membered heteroaryl; wherein the $C_3$-$C_9$ heterocycloalkyl contains 1-3 heteroatoms selected from one or more of O, S, and N; the $C_3$-$C_9$ heterocycloalkenyl contains 1-3 heteroatoms selected from one or more of O, S, and N; and the 5-10 membered heteroaryl contains 1-3 heteroatoms selected from one or more of N, O, and S; and the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_2$-$C_6$ alkynyl, the substituted $C_3$-$C_{10}$ cycloalkyl, the substituted $C_3$-$C_9$ heterocycloalkyl, the substituted $C_3$-$C_9$ heterocycloalkenyl, the substituted phenyl or the substituted 5-10 membered heteroaryl is substituted with one or more substituents independently selected from halogen, —OH, —$CF_3$, —CN, —COOH, —$COOCH_3$, —$NH_2$, ═O, a $C_1$-$C_6$ alkyl, a $C_1$-$C_6$ alkyl-O—, and a $C_3$-$C_6$ cycloalkyl that is unsubstituted or substituted with one or more $R^d$, wherein when a plurality of $R^d$ are present, they are the same or different, and each $R^d$ is independently H, halogen, —OH, ═O, —$CF_3$, —CN, —COOH or —C(═O)$NH_2$; and when a plurality of substituents are present, they are the same or different; or $R^2$ is independently

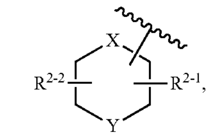

or an unsubstituted or substituted 5-6 membered heteroaryl; wherein the 5-6 membered heteroaryl contains 1-3 heteroatoms selected from one or more of N, O, and S; and the substituted 5-6 membered heteroaryl is substituted with one or more substituents independently selected from halogen, —OH, —CN, an unsubstituted or halogen-substituted $C_1$-$C_6$ alkyl, an unsubstituted or halogen-substituted $C_1$-$C_6$ alkyl-O—, —C(═O) $R^{2-7}$, and —C(═O)N($R^{2-8}R^{2-9}$), wherein when a plurality of substituents are present, they are the same or different;

wherein $R^{2-1}$ and $R^{2-2}$ are each independently H, halogen, —OH, —CN, an unsubstituted or substituted $C_1$-$C_6$ alkyl, an unsubstituted or substituted $C_1$-$C_6$ alkyl-O—, or ═O; wherein the substituted $C_1$-$C_6$ alkyl or the substituted $C_1$-$C_6$ alkyl-O— is substituted with one or more substituents independently selected from halogen, —OH, —$CF_3$, —CN, a $C_1$-$C_6$ alkyl, a $C_1$-$C_6$ alkyl-O—, and ═O, and when a plurality of substituents are present, they are the same or different;

X and Y are each independently a single bond, methylene, —O—, —N($R^{2-3}$)— or

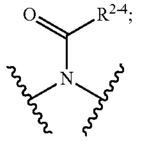

$R^{2-3}$ and $R^{2-4}$ are each independently H, an unsubstituted or substituted $C_1$-$C_6$ alkyl, an unsubstituted or substituted $C_3$-$C_8$ cycloalkyl, an unsubstituted or substituted $C_3$-$C_8$ cycloalkyl-O—or an unsubstituted or substituted $C_1$-$C_6$ alkyl-O—; wherein the substituted $C_1$-$C_6$ alkyl, the substituted $C_3$-$C_8$ cycloalkyl, the substituted $C_3$-$C_8$ cycloalkyl-O— or the substituted $C_1$-$C_6$ alkyl-O— is substituted with one or more substituents independently selected from halogen, —OH, —$CF_3$, —CN, a $C_1$-$C_6$ alkyl, a $C_1$-$C_6$ alkyl-O—, and =O, and when a plurality of substituents are present, they are the same or different;

$R^{2-7}$ is independently H, halogen, —OH, —CN, an unsubstituted or halogen-substituted $C_1$-$C_6$ alkyl, or an unsubstituted or halogen-substituted $C_1$-$C_6$ alkyl-O—; and $R^{2-8}$ and $R^{2-9}$ are each independently H, or an unsubstituted or halogen-substituted $C_1$-$C_6$ alkyl, wherein the preparation method is Scheme I, Scheme II, Scheme III, Scheme IV, Scheme V, Scheme VI, Scheme VII, or Scheme VIII, wherein Scheme I comprises the following step: performing Stille coupling reaction as shown below on a compound of formula II-1 and an organic tin reagent of formula III-1 in an organic solvent in the presence of a catalyst to give the heterocyclic compound of formula I:

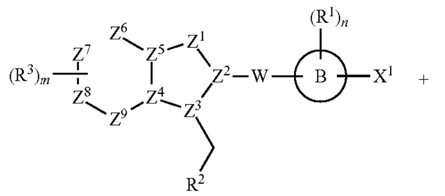

II-1

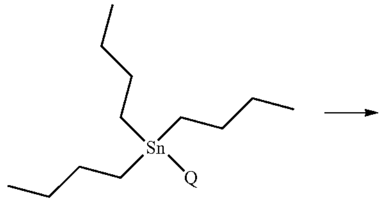

III-1

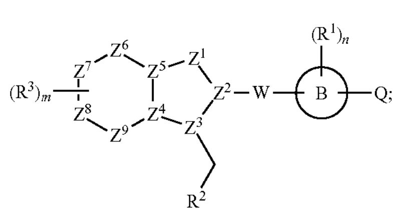

I wherein $X^1$ is Br or Cl;

Scheme II comprises the following step: performing Suzuki coupling reaction as shown below on a compound of formula II-2 and a compound of formula III-2 in a solvent in the presence of a catalyst and a basic reagent to give the heterocyclic compound of formula I:

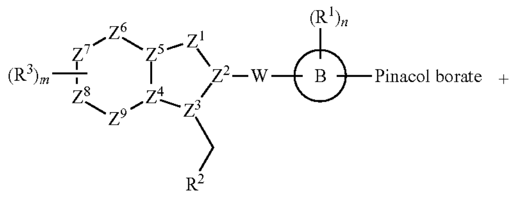

II-2

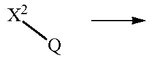

III-2

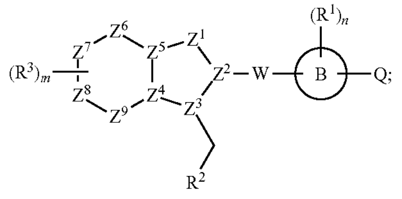

I wherein $X^2$ is Br or Cl;

Scheme III comprises the following step: performing the reaction as shown below on a compound of formula II-3, a compound of formula III-3 and formaldehyde in an organic solvent to give the heterocyclic compound of formula I:

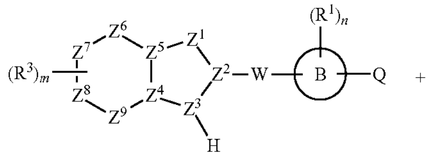

II-3

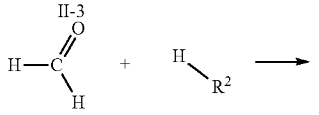

III-3

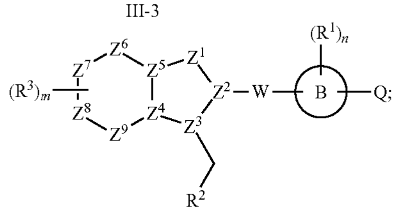

I

Scheme IV comprises the following step: performing the reaction as shown below on a compound of formula II-3 and a compound of formula III-4 in an organic solvent to give the heterocyclic compound of formula I:

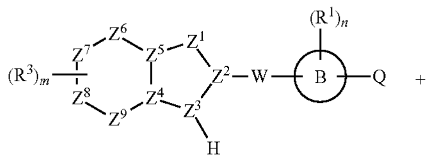

II-3

-continued

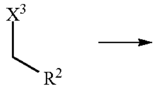

III-4

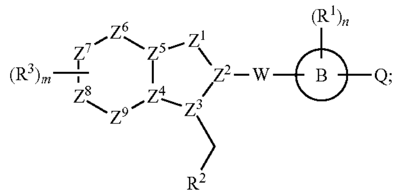

I wherein $X^3$ is a leaving group;

Scheme V comprises the following step: performing amidation reaction as shown below on a compound of formula I, wherein $R^2$ is

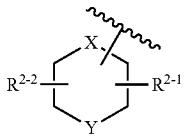

and Y is —NH—, and a compound of formula III-5 in an organic solvent in the presence of a basic reagent to give the heterocyclic compound of formula I, wherein Y is

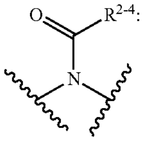

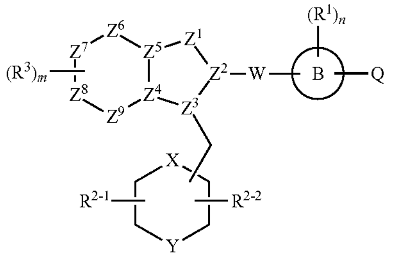

\+

I

Y is —NH—

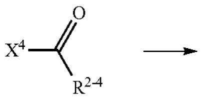

III-5

-continued

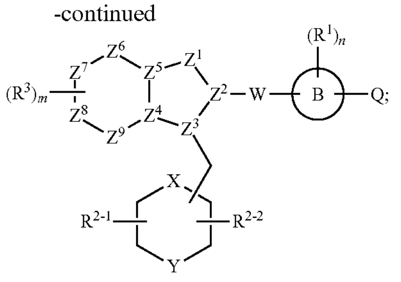

I

Y is

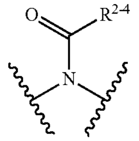

wherein $X^4$ is halogen;

Scheme VI comprises the following step: performing deprotection reaction as shown below on a compound of formula II-4 and a compound of formula III-5 in an organic solvent in the presence of an acid to give the heterocyclic compound of formula I:

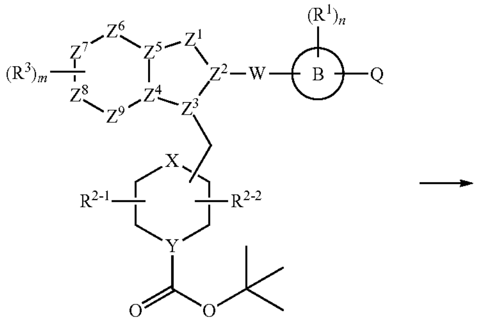

II-4

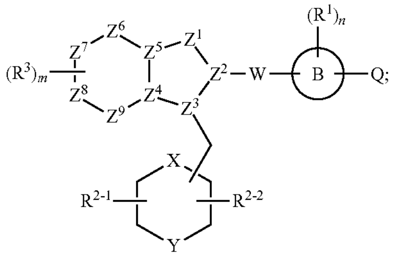

I

Y is —NH—

Scheme VII comprises the following step: performing substitution reaction as shown below on a compound of formula II-5 and $NH(R^{1-9}R^{1-10})$ in an organic solvent to give the heterocyclic compound of formula I, wherein Q is $—S(=O)_2—N(R^{1-9}R^{1-10})$:

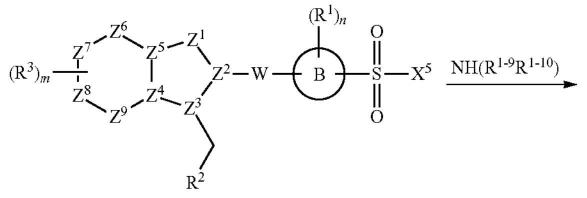

II-5

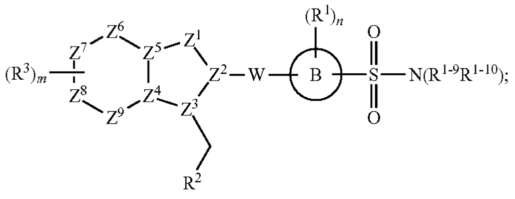

I wherein $X^5$ is Br or Cl;

and

Scheme VIII comprises the following step: performing deprotection reaction as shown below on a compound of formula II-6 or formula II-6' in an organic solvent in the presence of an acid to give the heterocyclic compound of formula I:

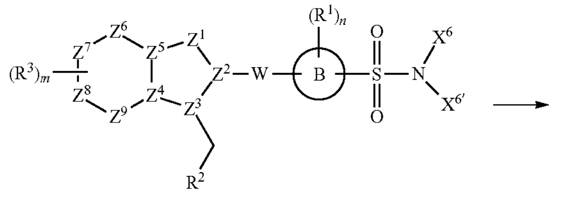

II-6

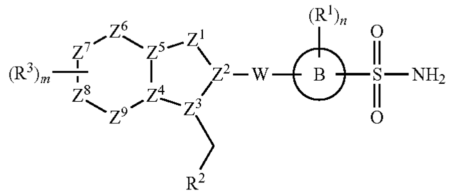

I

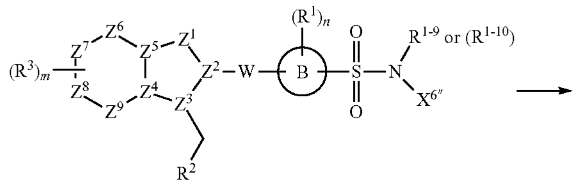

II-6'

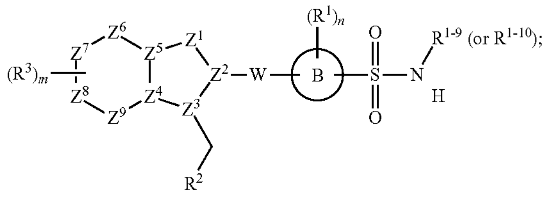

I wherein $X^6$, $X^6$ and $X^{6''}$ are N protecting groups.

4. A compound selected from the group consisting of compounds of formulae II-1, II-2, II-3, II-4, II-5, II-6, and II-6':

II-1

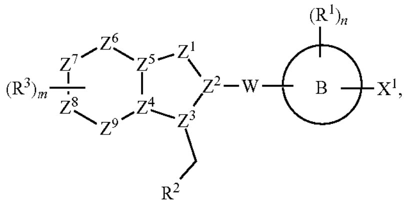

II-2

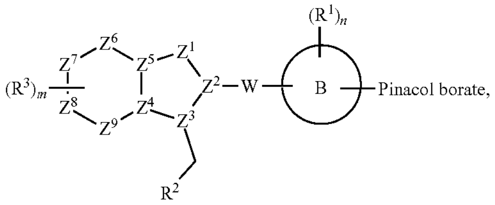

II-3

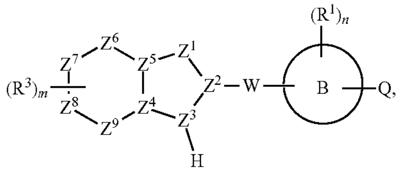

II-4

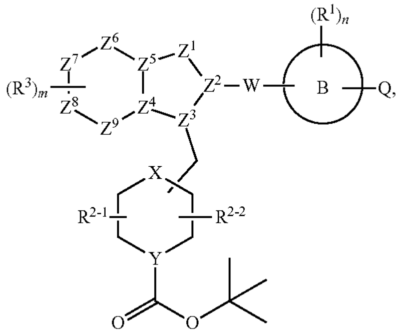

II-5

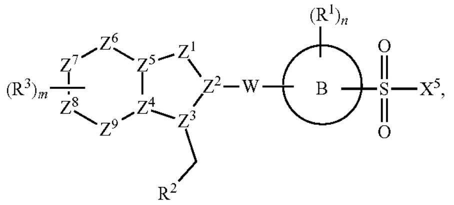

II-6

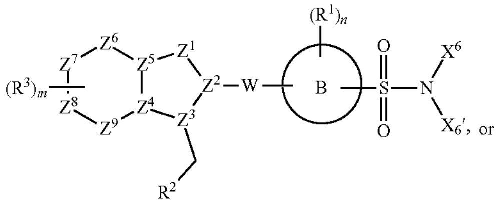

II-6'

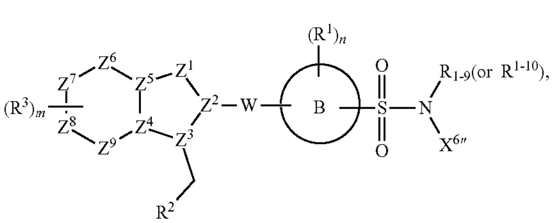

wherein,

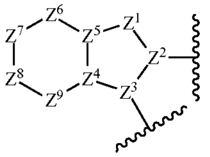

is

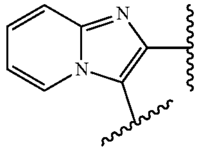

, m is 1, 2, 3 or 4;

$R^3$ is H, halogen, —OH, a $C_1$-$C_6$ haloalkyl, —CN or a $C_1$-$C_6$ alkyl; when m is not 1, $R^3$ is independently the same or different;

W is a single bond;

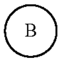

is phenyl;

n is 1, 2, 3 or 4;

$R^1$ is independently H, halogen, —OH, —CN, an unsubstituted or substituted $C_1$-$C_6$ alkyl, or an unsubstituted or substituted $C_1$-$C_6$ alkyl-O—; wherein the substituted $C_1$-$C_6$ alkyl or the substituted $C_1$-$C_6$ alkyl-O— is substituted with one or more substituents independently selected from halogen, —OH, —$CF_3$, —CN, —COOH, —C(═O)$NH_2$, a $C_1$-$C_6$ alkyl, a $C_1$-$C_6$ alkyl-O—, and ═O; when a plurality of substituents are present, they are the same or different; and when n is not 1, $R^1$ is independently the same or different;

Q is —NH—C(═O)—$R^{1-1}$, —O—C(═O)—N($R^{1-3}R^{1-4}$), —S(═O)$_2$—N($R^{1-9}R^{1-10}$), —N($R^{1-14}R^{1-15}$), —NH—S(═O)$_2$—$R^{1-16}$, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, or an unsubstituted or substituted 5-10 membered heteroaryl; wherein the $C_3$-$C_9$ heterocycloalkyl contains 1-3 heteroatoms selected from one or more of O, S, and N; the $C_3$-$C_9$ heterocycloalkenyl contains 1-3 heteroatoms selected from one or more of O, S, and N; and the 5-10 membered heteroaryl contains 1-3 heteroatoms selected from one or more of O, S, and N; and the substituted $C_3$-$C_{10}$ cycloalkyl, the substituted $C_3$-$C_9$ heterocycloalkyl, the substituted $C_3$-$C_9$ heterocycloalkenyl or the substituted 5-10 membered heteroaryl is substituted with one or more substituents independently selected from halogen, —OH, —$CF_3$, —CN, —COOH, —C(═O)$NH_2$, ═O, —N($R^{1-21}R^{1-22}$), —C(═O)—N($R^{1-23}R^{1-24}$), —S(═O)$_2$—N($R^{1-25}R^{1-26}$), —C(═O)—O—$R^{1-27}$, a $C_1$-$C_6$ alkyl, a $C_1$-$C_6$ alkyl-O—, and a $C_3$-$C_6$ cycloalkyl that is unsubstituted or substituted with one or more $R^a$, wherein when a plurality of $R^a$ are present, they are the same or different, and each $R^a$ is halogen, —OH, ═O, —$CF_3$, —CN, —COOH or —C(═O)$NH_2$; and when a plurality of substituents are present, they are the same or different; wherein the —O—C(═O)—N($R^{1-3}R^{1-4}$) is —O—C(═O)—NH—$CH_3$; —N($R^{1-14}R^{1-15}$) is

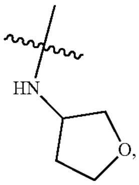

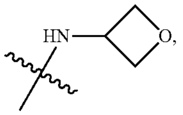

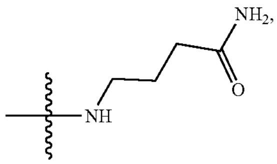

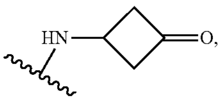

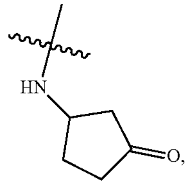

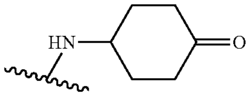

or

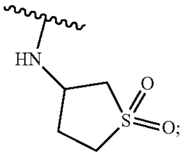

—NH—S(═O)$_2$—$R^{1-16}$ is —NH—S(═O)$_2$—$CH_3$;

$R^{1-1}$, $R^{1-9}$, $R^{1-10}$, $R^{1-21}$, $R^{1-22}$, $R^{1-23}$, $R^{1-24}$, $R^{1-25}$, $R^{1-26}$ and $R^{1-27}$ are each independently H, an unsubstituted or substituted $C_1$-$C_6$ alkyl, an unsubstituted or substituted $C_1$-$C_6$ alkyl-O—, an unsubstituted or substituted $C_2$-$C_6$ alkenyl, an unsubstituted or substituted $C_2$-$C_6$ alkenyl-O—, an unsubstituted or substituted $C_2$-$C_6$ alkynyl, an unsubstituted or substituted $C_3$-$C_{10}$ cycloalkyl, an unsubstituted or substituted $C_3$-$C_9$ heterocycloalkyl, an unsubstituted or substituted $C_3$-$C_9$ heterocycloalkenyl, an unsubstituted or substituted phenyl, or an unsubstituted or substituted 5-10 membered heteroaryl; wherein the $C_3$-$C_9$ heterocycloalkyl contains 1-3 heteroatoms selected from one or more of O, S, and N; the $C_3$-$C_9$ heterocycloalkenyl contains 1-3 heteroatoms selected from one or more of O, S, and N; and the 5-10 membered heteroaryl contains 1-3 heteroatoms selected from one or more of N, O, and S; and the substituted $C_1$-$C_6$ alkyl, the substituted $C_1$-$C_6$ alkyl-O—, the substituted $C_2$-$C_6$ alkenyl, the substituted $C_2$-$C_6$ alkenyl-O—, the substituted $C_2$-$C_6$ alkynyl, the substituted $C_3$-$C_{10}$ cycloalkyl, the substituted $C_3$-$C_9$ heterocycloalkyl, the substituted $C_3$-$C_9$ heterocycloalkenyl, the substituted phenyl or the substituted 5-10 membered heteroaryl is substituted with one or more substituents independently selected from halogen, —OH, —$CF_3$, —CN, —COOH, —$COOCH_3$, —$NH_2$, ═O, a $C_1$-$C_6$ alkyl, a $C_1$-$C_6$ alkyl-O—, and a $C_3$-$C_6$ cycloalkyl that is unsubstituted or substituted with one or more $R^d$, wherein when a plurality of $R^d$ are present, they are the same or different, and each $R^d$ is independently H, halogen, —OH, ═O, —$CF_3$, —CN, —COOH or —C(═O)$NH_2$; and when a plurality of substituents are present, they are the same or different; or

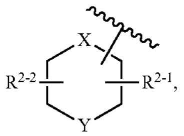

$R^2$ is independently or an unsubstituted or substituted 5-6 membered heteroaryl; wherein the 5-6 membered heteroaryl contains 1-3 heteroatoms selected from one or more of N, O, and S; and the substituted 5-6 membered heteroaryl is substituted with one or more substituents independently selected from halogen, —OH, —CN, an unsubstituted or halogen-substituted $C_1$-$C_6$ alkyl, an unsubstituted or halogen-substituted $C_1$-$C_6$ alkyl-O—, —C(═O) $R^{2-7}$, and —C(═O)N($R^{2-8}R^{2-9}$), wherein when a plurality of substituents are present, they are the same or different;

wherein $R^{2-1}$ and $R^{2-2}$ are each independently H, halogen, —OH, —CN, an unsubstituted or substituted $C_1$-$C_6$ alkyl, an unsubstituted or substituted $C_1$-$C_6$ alkyl-O—, or ═O; wherein the substituted $C_1$-$C_6$ alkyl or the substituted $C_1$-$C_6$ alkyl-O— is substituted with one or more substituents independently selected from halogen, —OH, —$CF_3$, —CN, a $C_1$-$C_6$ alkyl, a $C_1$-$C_6$ alkyl-O—, and ═O, and when a plurality of substituents are present, they are the same or different;

X and Y are each independently a single bond, methylene, —O—, —N($R^{2-3}$)— or

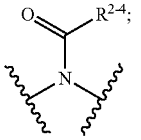

$R^{2-3}$ and $R^{2-4}$ are each independently H, an unsubstituted or substituted $C_1$-$C_6$ alkyl, an unsubstituted or substituted $C_3$-$C_8$ cycloalkyl, an unsubstituted or substituted $C_3$-$C_8$ cycloalkyl-O—, or an unsubstituted or substituted $C_1$-$C_6$ alkyl-O—; wherein the substituted $C_1$-$C_6$ alkyl, the substituted $C_3$-$C_8$ cycloalkyl, the substituted $C_3$-$C_8$ cycloalkyl-O— or the substituted $C_1$-$C_6$ alkyl-O— is substituted with one or more substituents independently selected from halogen, —OH, —$CF_3$, —CN, a $C_1$-$C_6$ alkyl, a $C_1$-$C_6$ alkyl-O—, and ═O, and when a plurality of substituents are present, they are the same or different;

$R^{2-7}$ is independently H, halogen, —OH, —CN, an unsubstituted or halogen-substituted $C_1$-$C_6$ alkyl, or an unsubstituted or halogen-substituted $C_1$-$C_6$ alkyl-O—; and $R^{2-8}$ and $R^{2-9}$ are each independently H, or an unsubstituted or halogen-substituted $C_1$-$C_6$ alkyl, and $X^1$ is Br or Cl, $X^5$ is Br or Cl, $X^6$, $X^{6'}$ and $X^{6''}$ are N protecting groups.

5. Compounds as shown below:

1-8

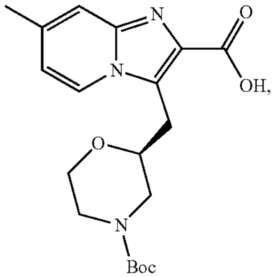

1-11

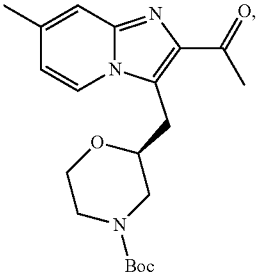

1-15

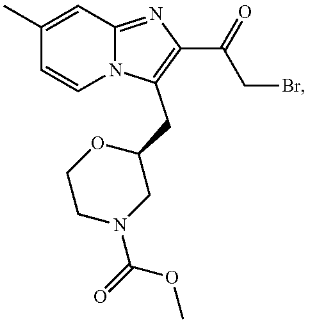

2-5

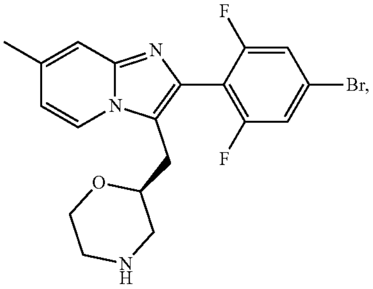

2-7

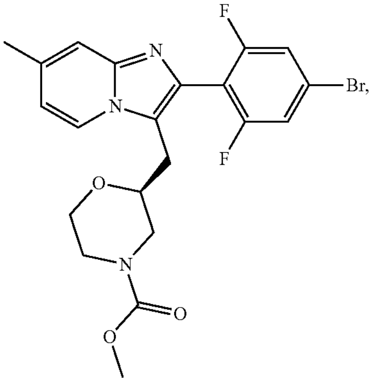

-continued
3-1
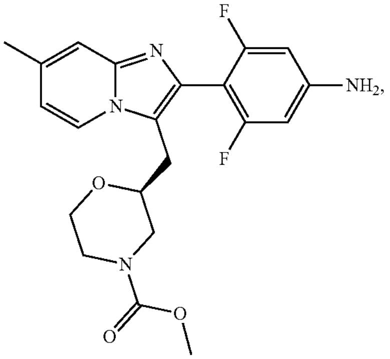
4-2
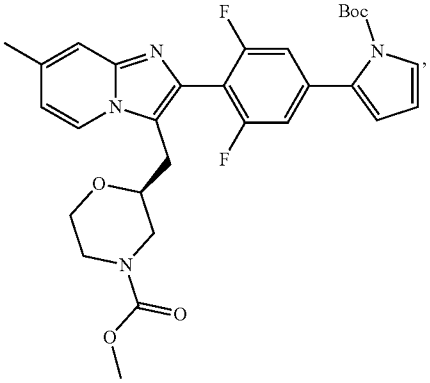
6-4
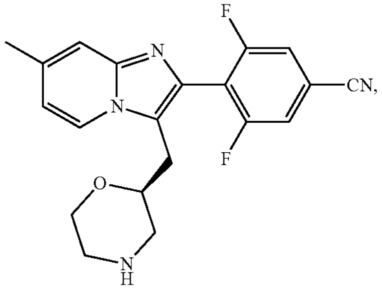
15-1
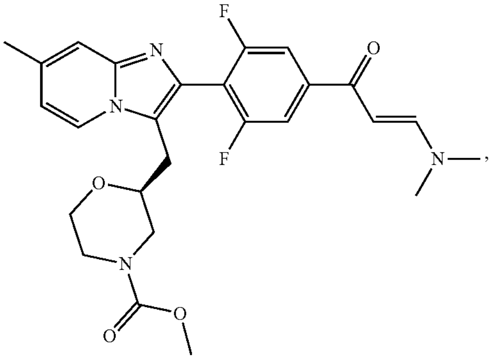
-continued
17-2
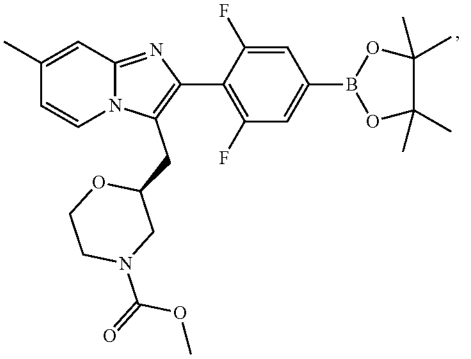
25-4
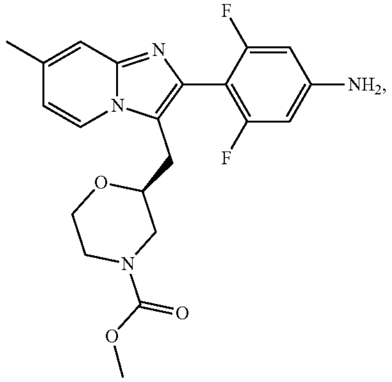
34-4
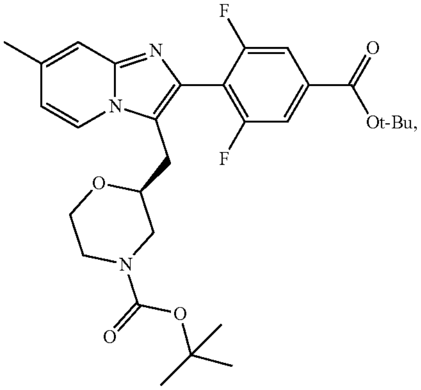
34-5
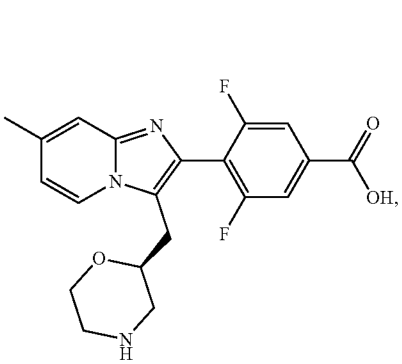

-continued
34-6
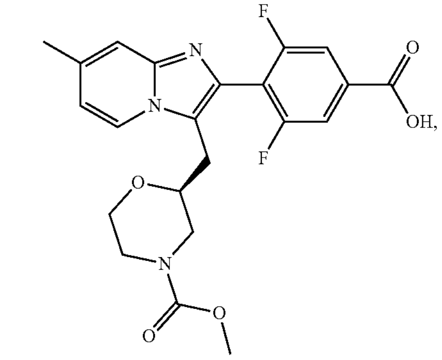
34-7
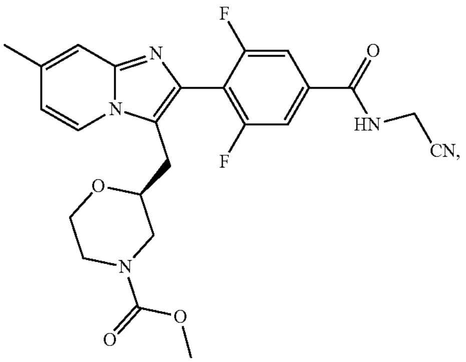
37-8
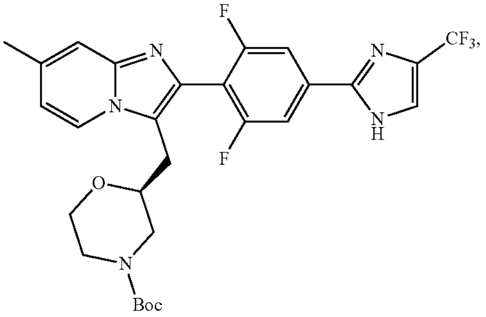
37-9
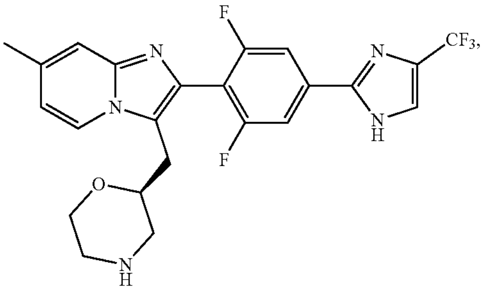
-continued
43-7
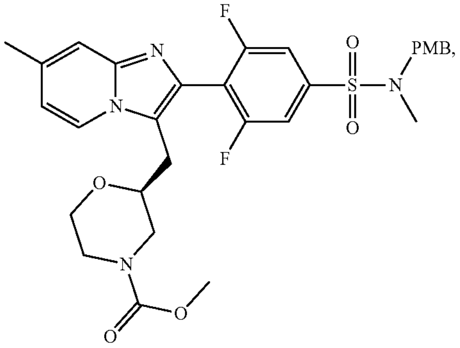
49-6
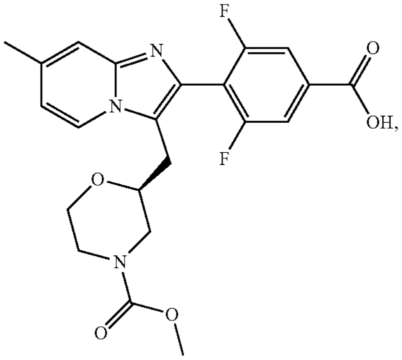
51-2
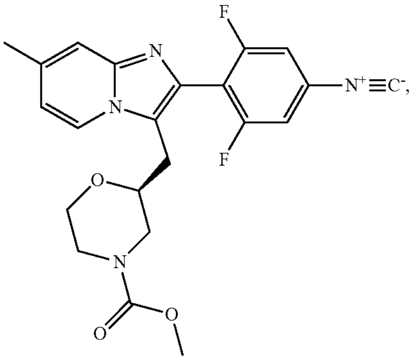
52-1
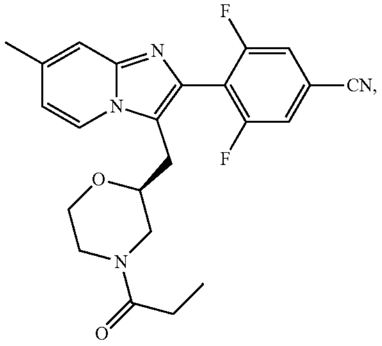

-continued
59-1
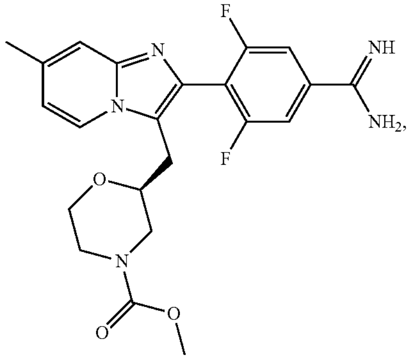
59-3
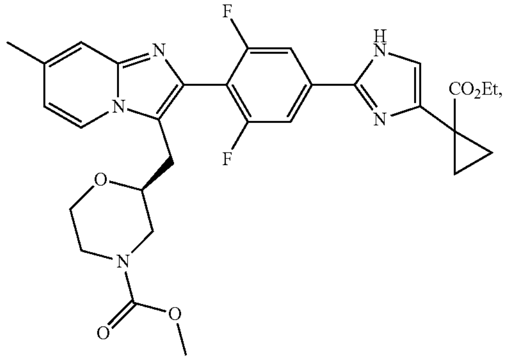
60-2
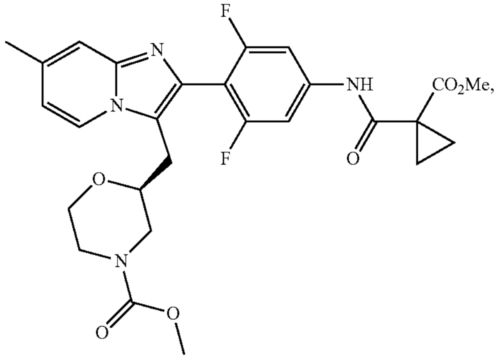
61-6
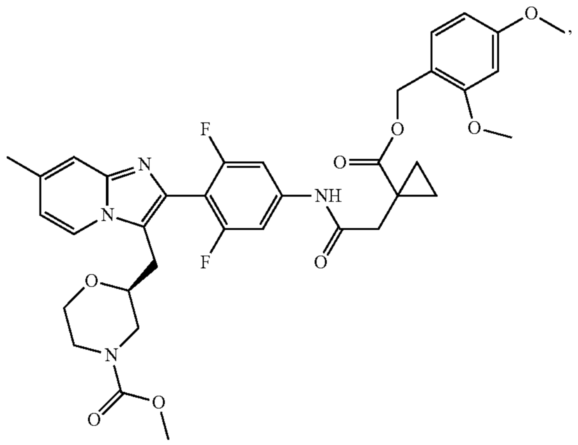
-continued
67-8
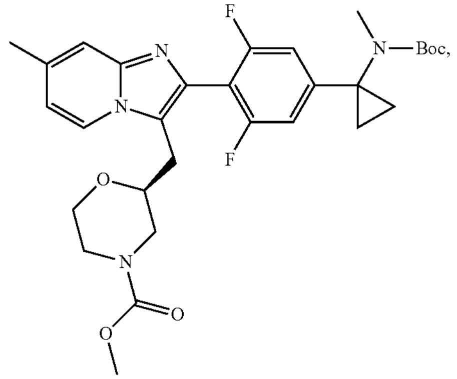
114-5
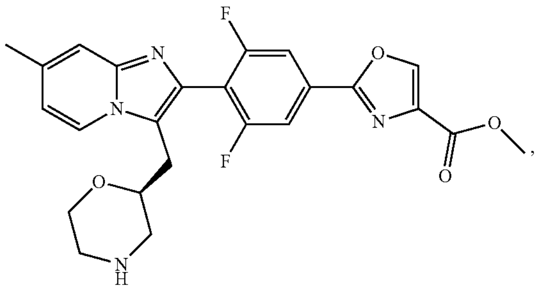
114-6
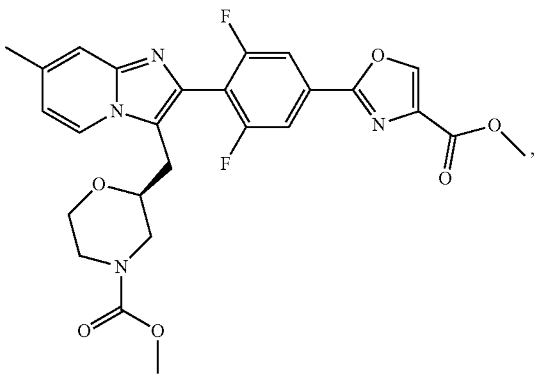
125-1
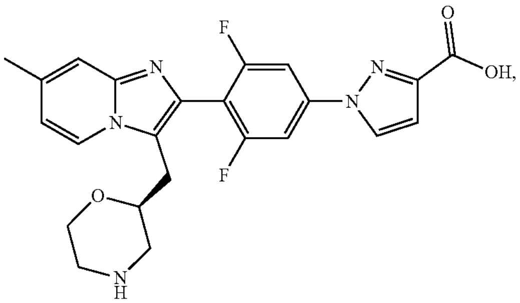

-continued
126-2
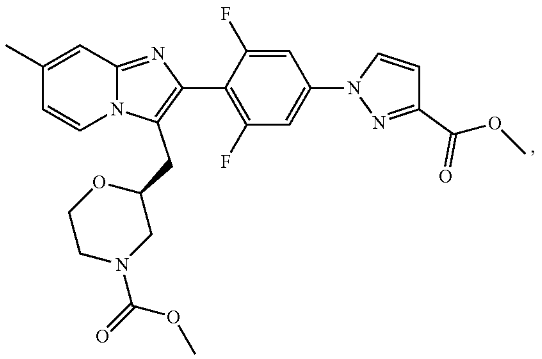
127-5
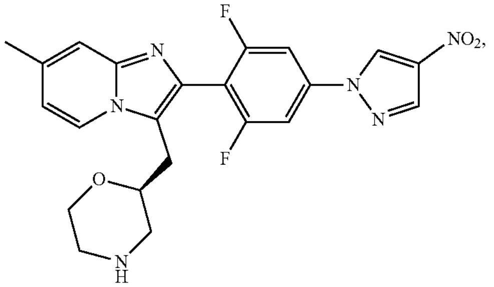
127-6
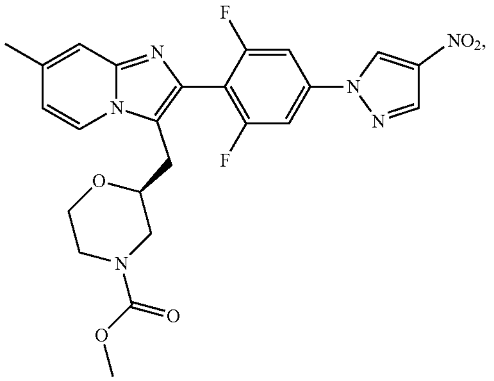
128-4
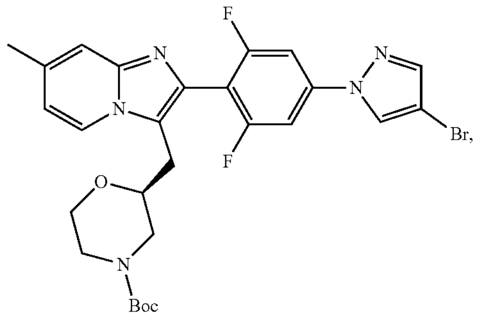
-continued
128-5
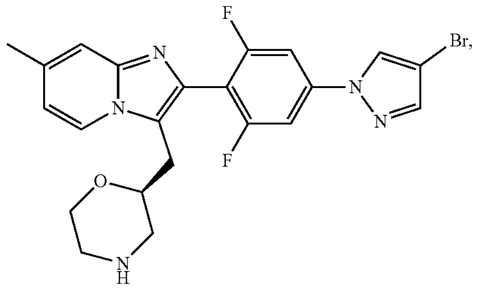
128-6
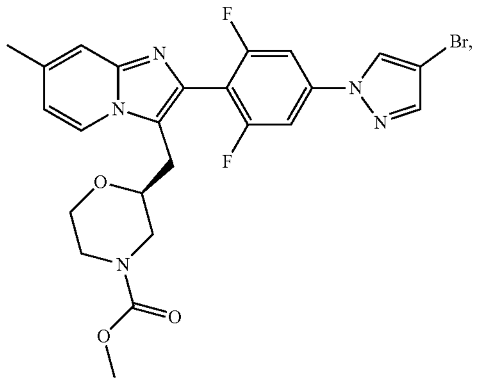
128-7
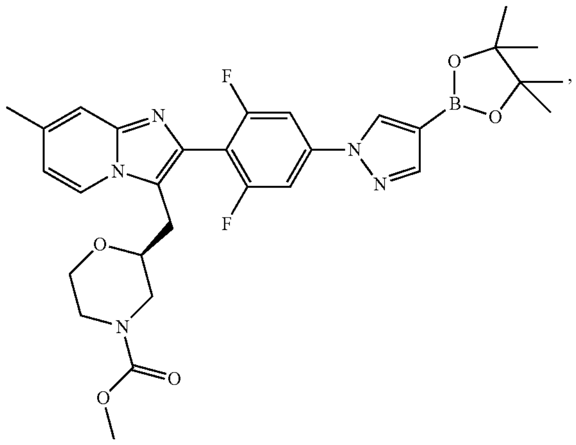
134-7
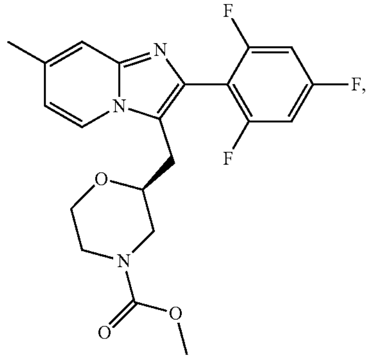

-continued
134-8
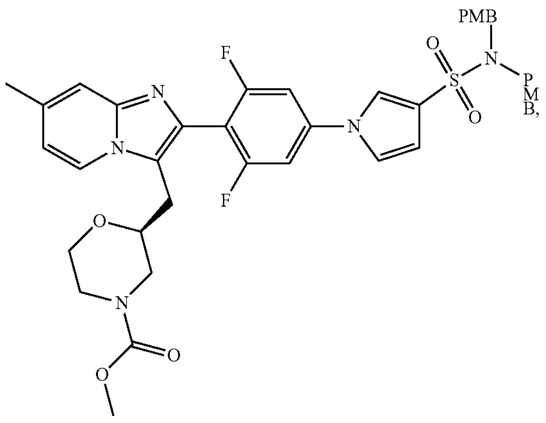
138-2
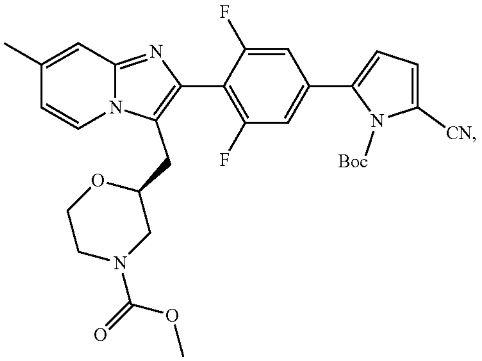
140-2
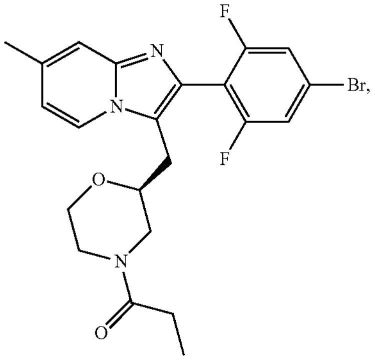
141-4
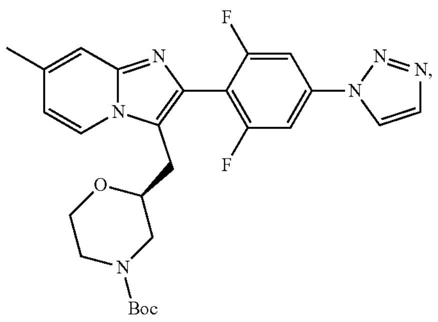
-continued
141-5
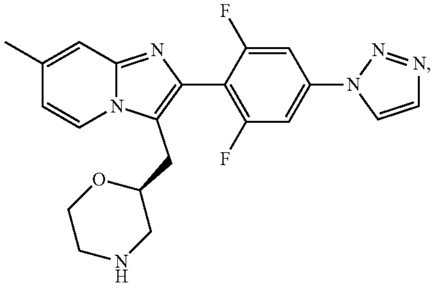
142-4
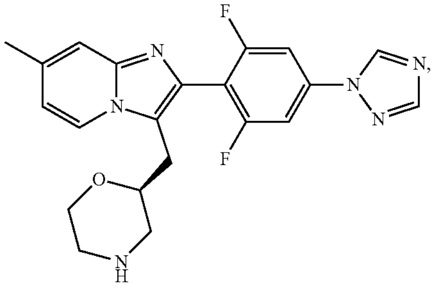
144-1
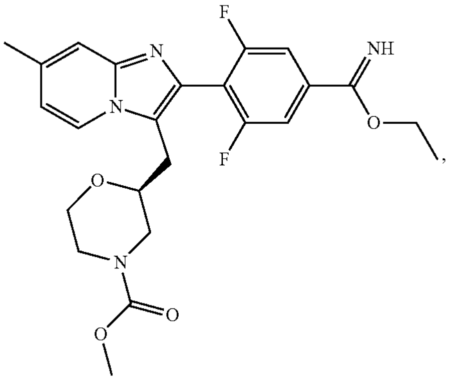
145-2
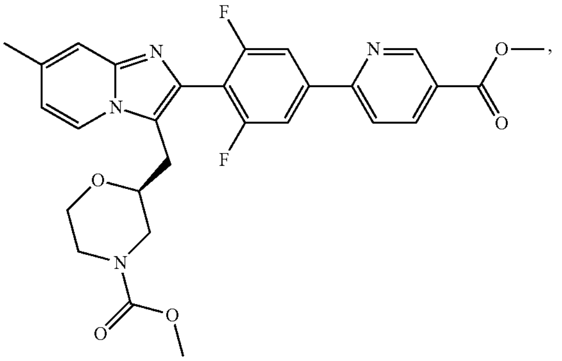

-continued
150-2
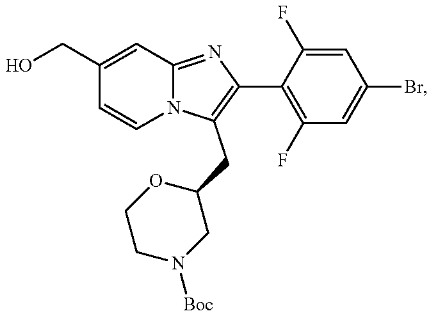
150-5
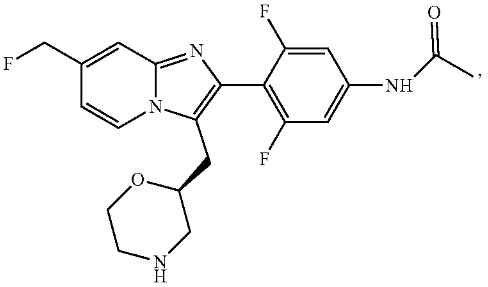
153-2
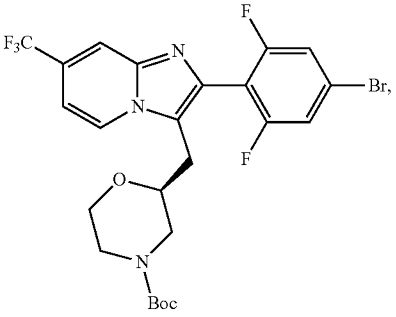
153-4
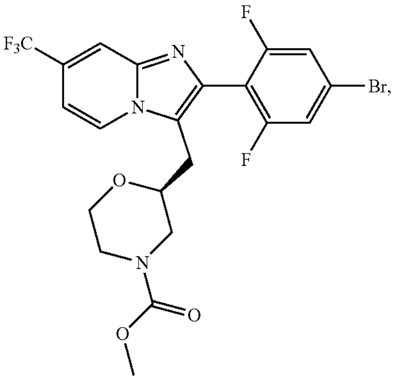
-continued
158-1
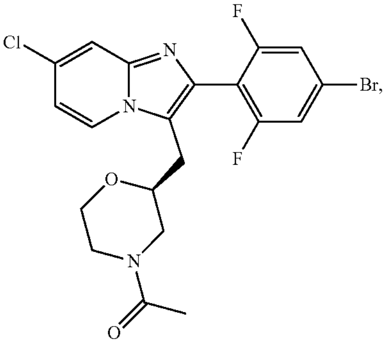
162-1
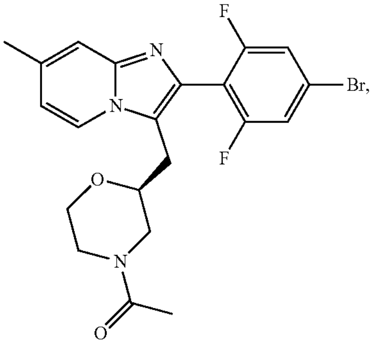
171-5
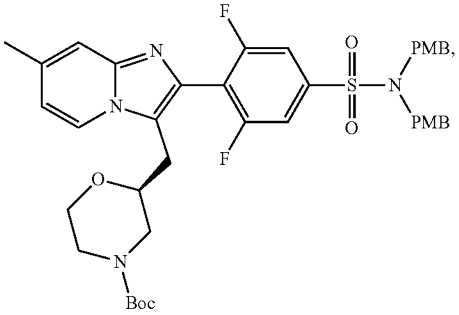
171-6
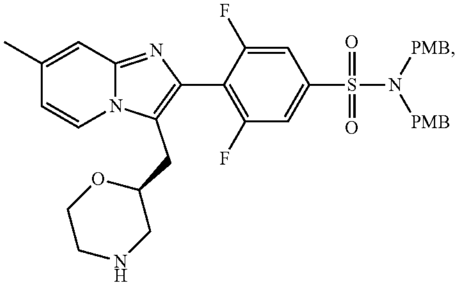

-continued
171-7
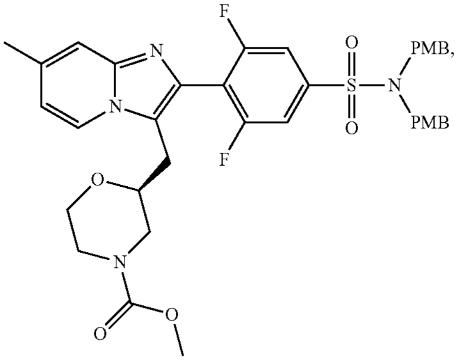
172-3
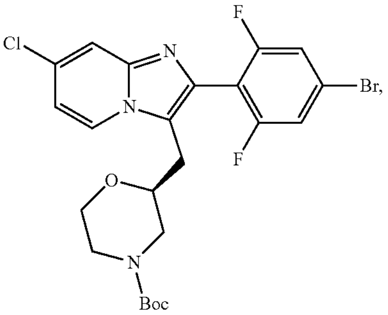
172-4
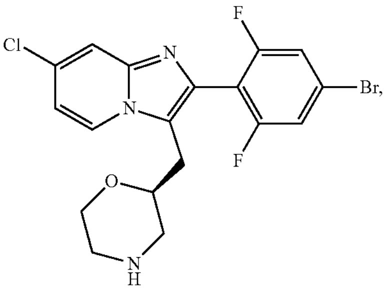
172-5
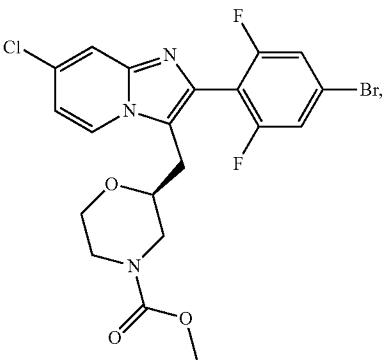
-continued
172-6
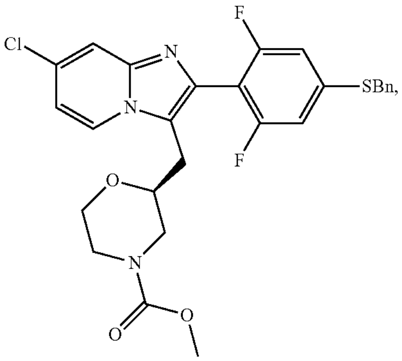
172-7
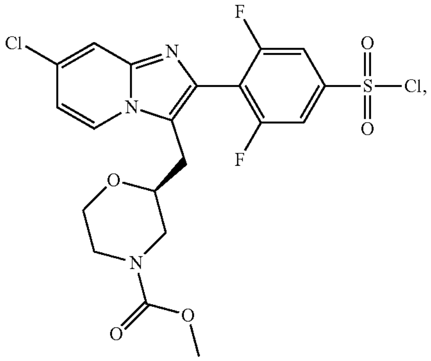
173-1
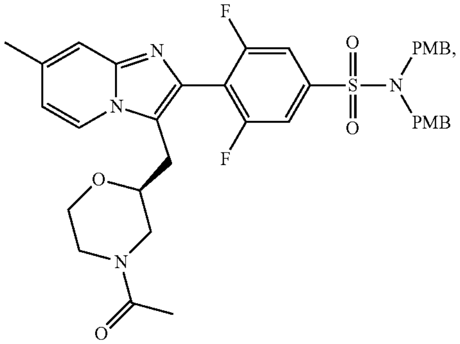
174-1
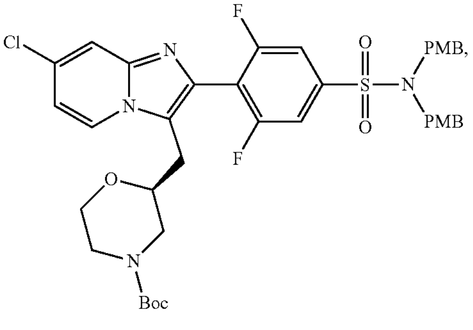

-continued
174-2
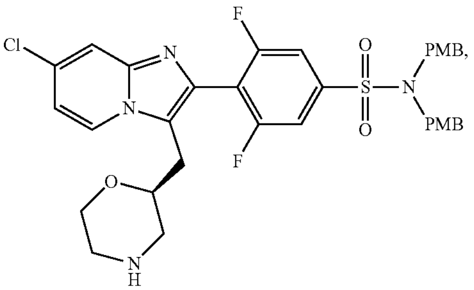
174-3
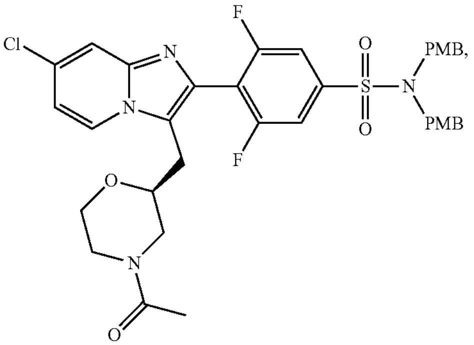
175-1
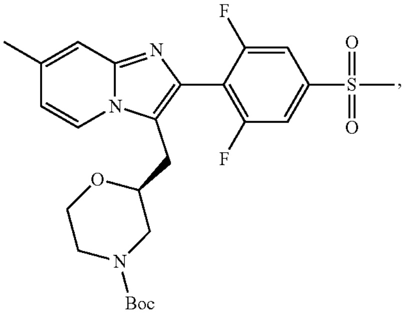
175-2
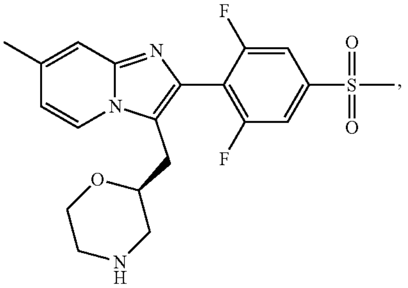
176-2
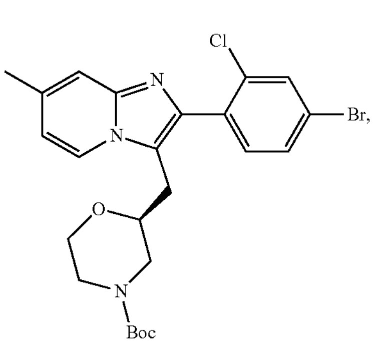
-continued
176-3
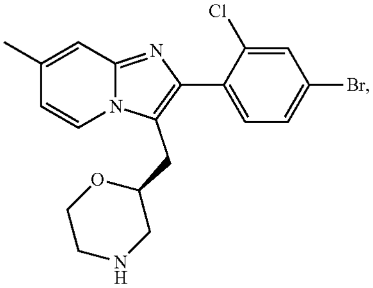
176-4
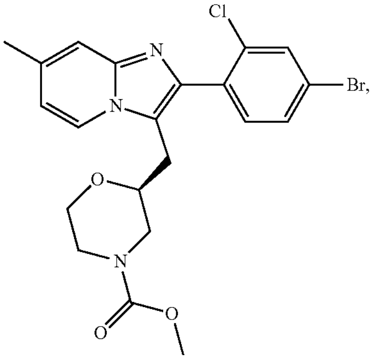
176-5
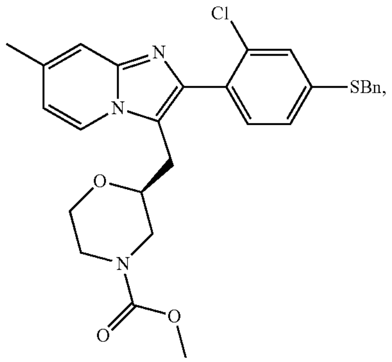
176-6
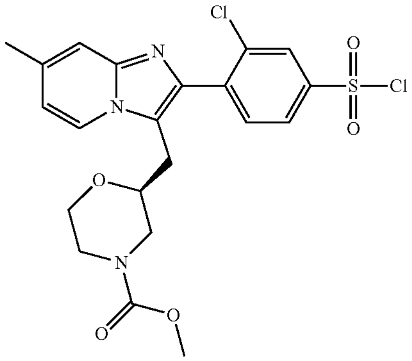

-continued
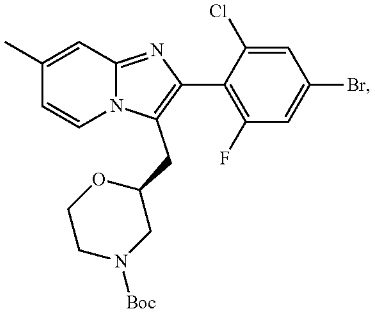
177-3
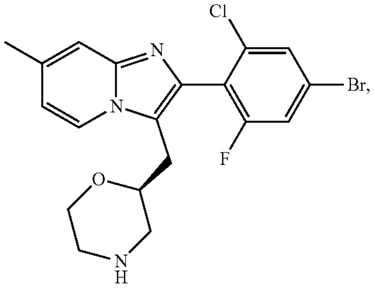
177-4
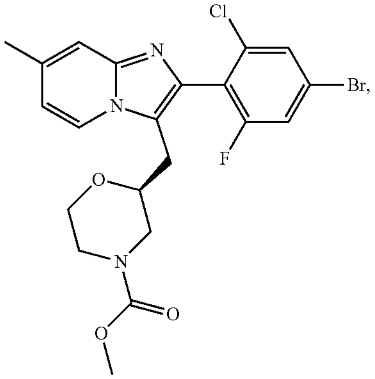
177-5
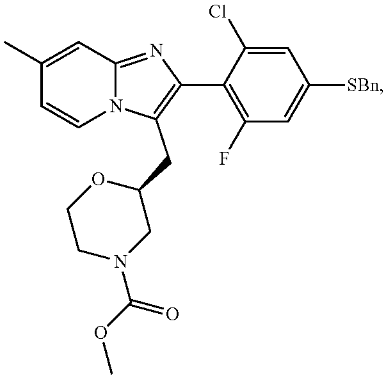
177-7
-continued
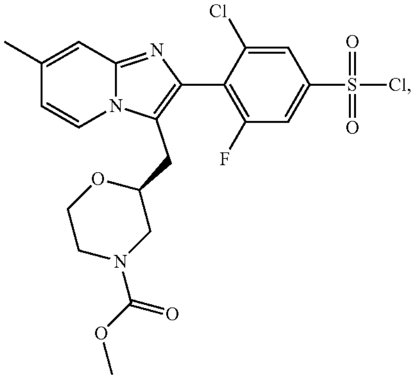
177-8
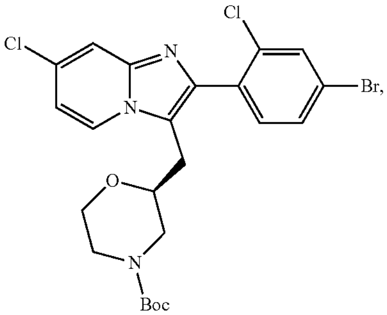
178-2
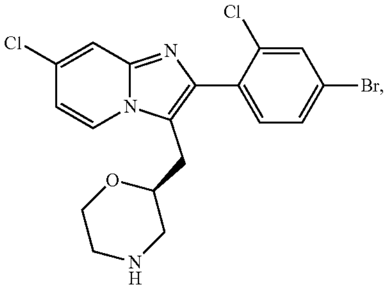
178-3
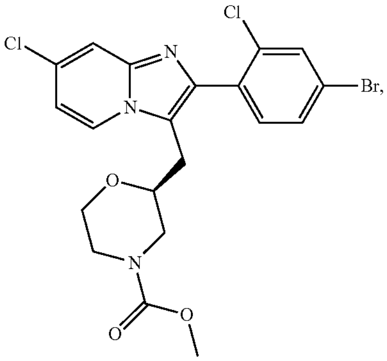
178-4

-continued
178-5
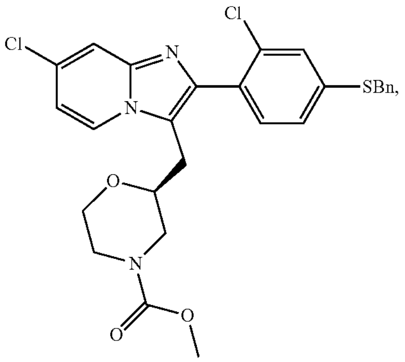
178-6
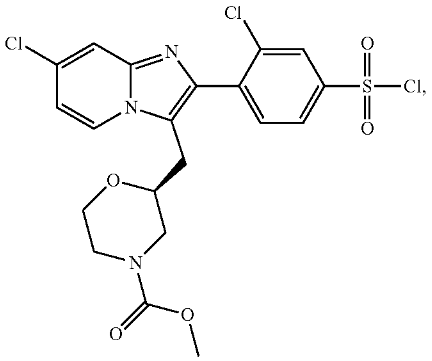
179-2
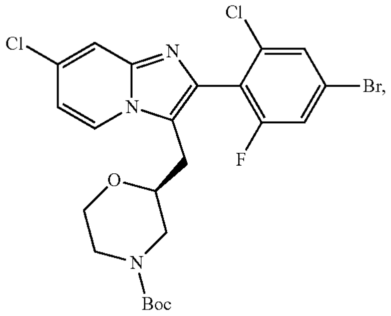
179-3
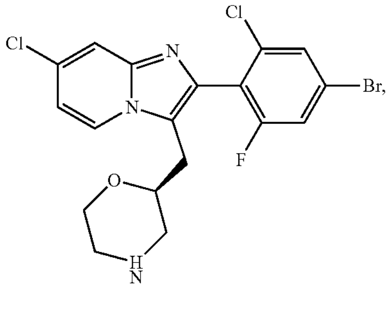
-continued
179-4
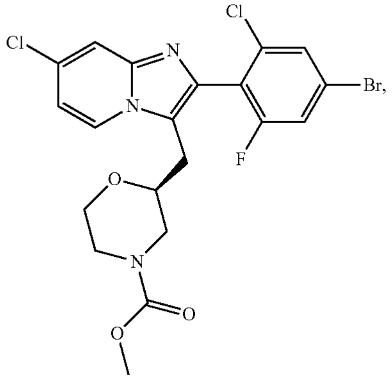
179-5
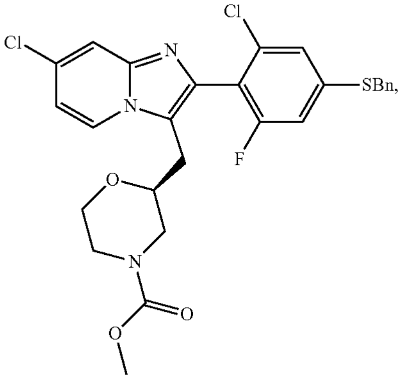
179-6
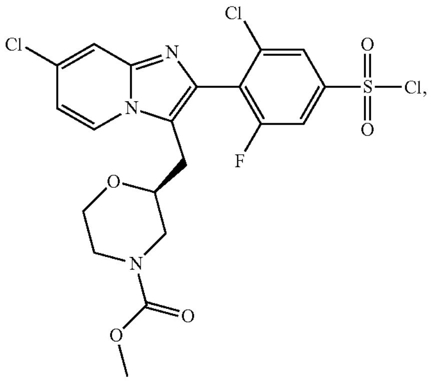
180-2
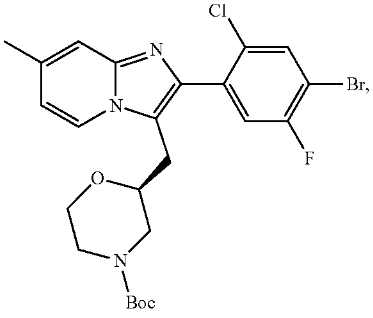

-continued
180-3
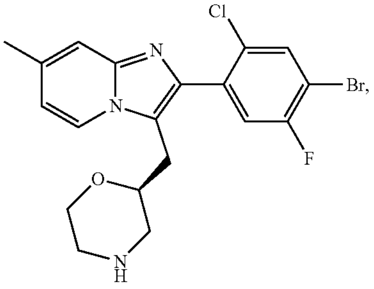
180-4
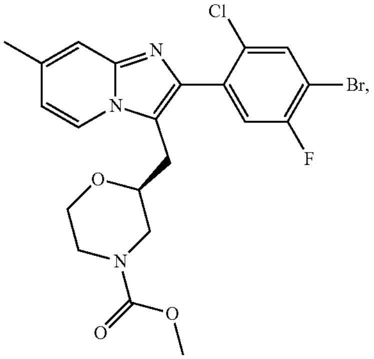
180-5
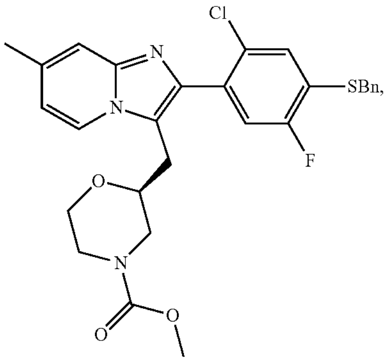
180-6
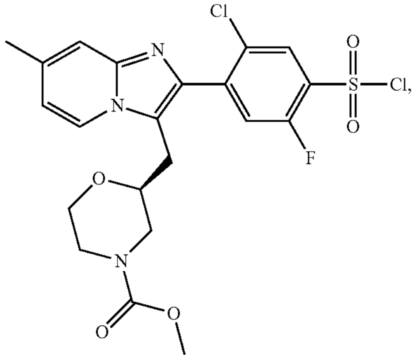
-continued
181-1
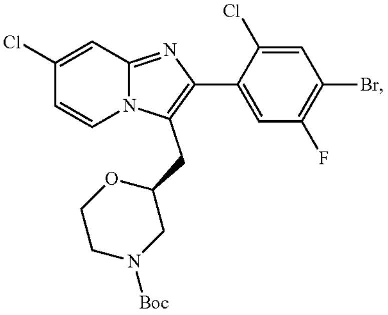
181-2
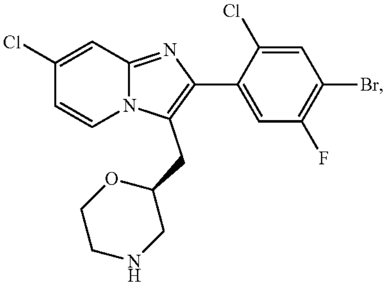
181-3
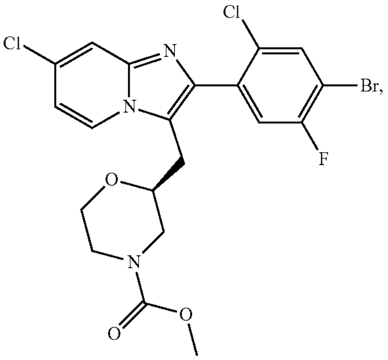
181-4
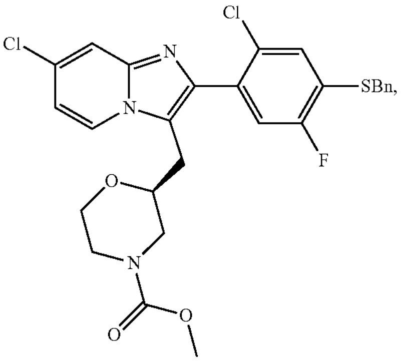

-continued
181-5
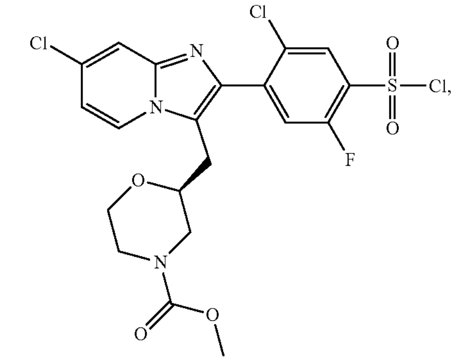
182-2
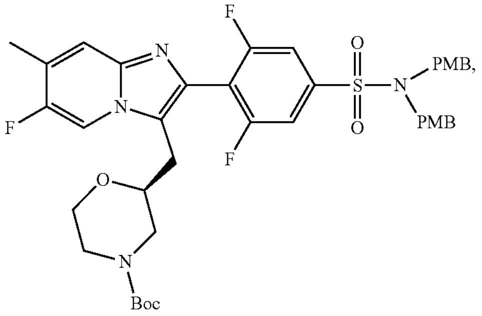
182-3
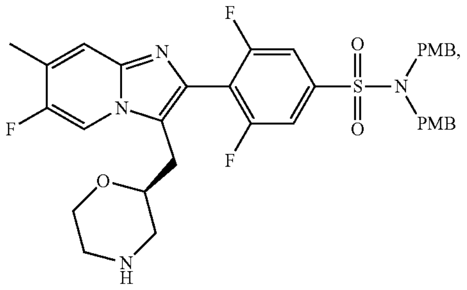
182-4
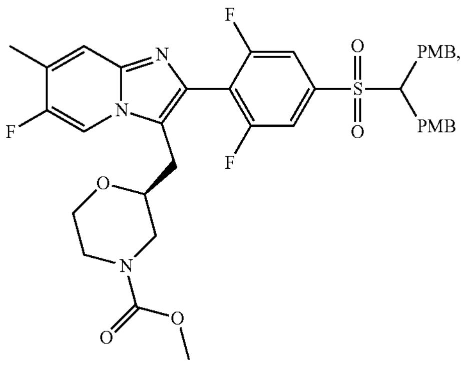
-continued
183-3
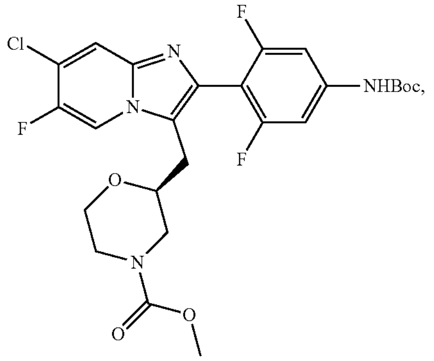
183-4
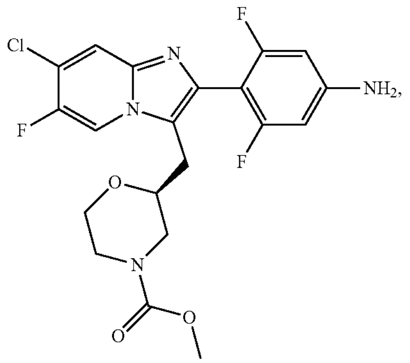
183-5
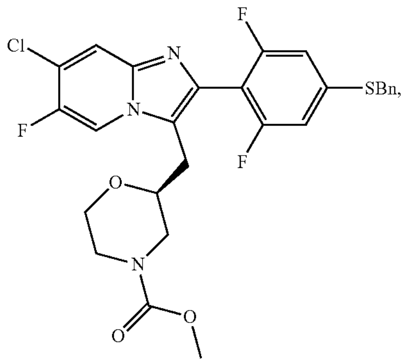
183-6
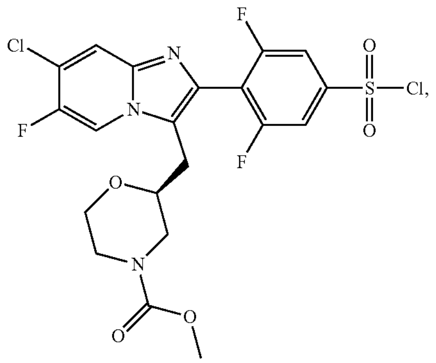

-continued 184-7

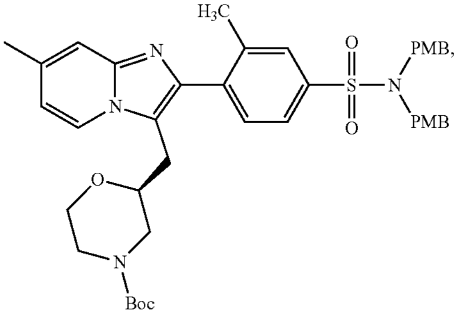

184-8

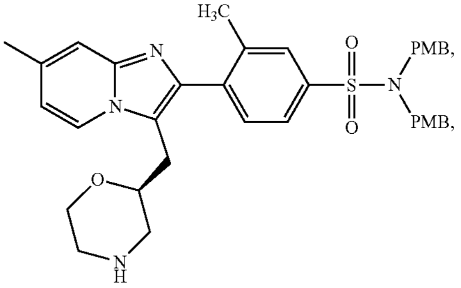

184-9

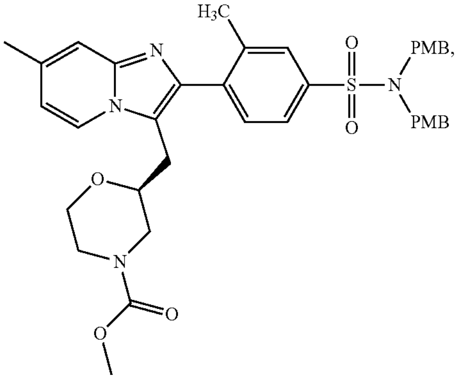

189-7

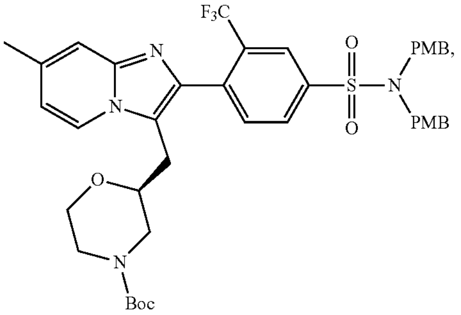

189-8

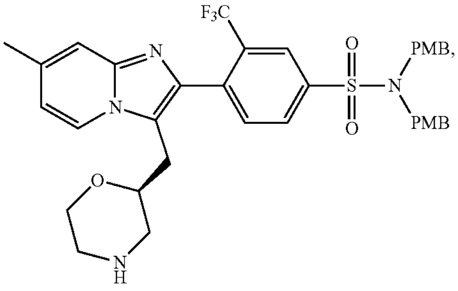

and

-continued 189-9

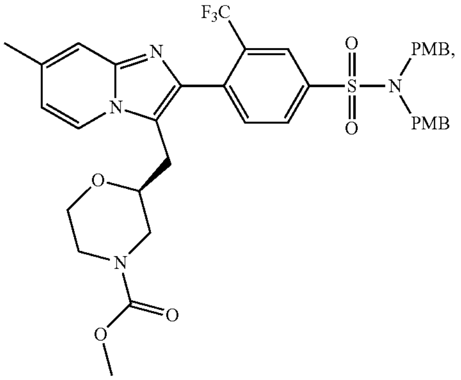

6. A pharmaceutical composition comprising the heterocyclic compound, the stereoisomer thereof, or the pharmaceutically acceptable salt thereof according to claim 1.

7. A method for treating or ameliorating a disease in a mammal mediated at least in part by $P2X^3$ or associated with $P2X^3$ activity, comprising administering the pharmaceutical composition of claim 6 to a subject in need thereof, wherein the disease is a pain, a urinary tract disease, or a respiratory disease, wherein the pain is inflammatory pain, surgical pain, visceral pain, dental pain, premenstrual pain, central pain, pain resulting from burns, migraine, or cluster headache; the urinary tract disease is urinary incontinence, overactive bladder, dysuria or cystitis; and the respiratory disease is idiopathic pulmonary fibrosis, chronic obstructive pulmonary disease, bronchospasm, or chronic cough.

8. The method according to claim 7, wherein the pain is inflammatory pain; the urinary tract disease is urinary incontinence, or overactive bladder; and the respiratory disease is chronic cough.

9. The method according to claim 7, wherein the respiratory disease is chronic cough.

10. The heterocyclic compound, the stereoisomer thereof, or the pharmaceutically acceptable salt thereof according to claim 2, wherein the heterocyclic compound is

171

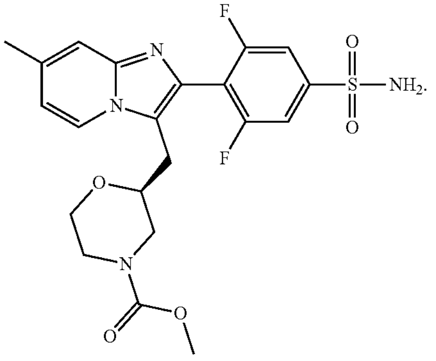

11. The heterocyclic compound, the stereoisomer thereof, or the pharmaceutically acceptable salt thereof according to claim 2, wherein the heterocyclic compound is

172

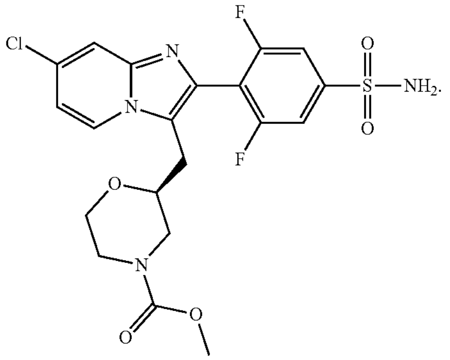

12. The heterocyclic compound, the stereoisomer thereof, or the pharmaceutically acceptable salt thereof according to claim 2, wherein the heterocyclic compound is

173

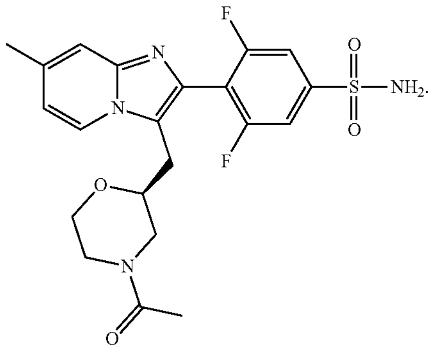

13. The heterocyclic compound, the stereoisomer thereof, or the pharmaceutically acceptable salt thereof according to claim 2, wherein the heterocyclic compound is

174

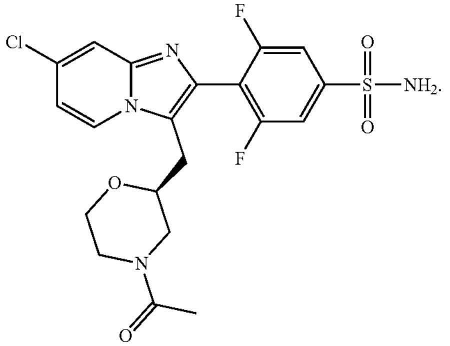

14. The heterocyclic compound, the stereoisomer thereof, or the pharmaceutically acceptable salt thereof according to claim 2, wherein the heterocyclic compound is

177

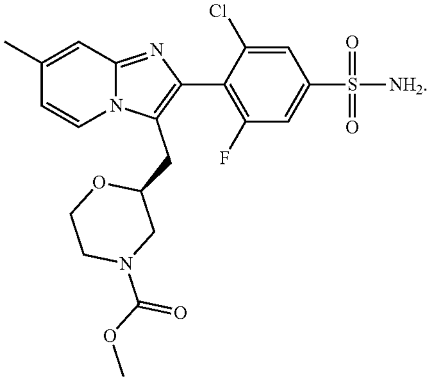

15. The heterocyclic compound, the stereoisomer thereof, or the pharmaceutically acceptable salt thereof according to claim 2, wherein the heterocyclic compound is

178

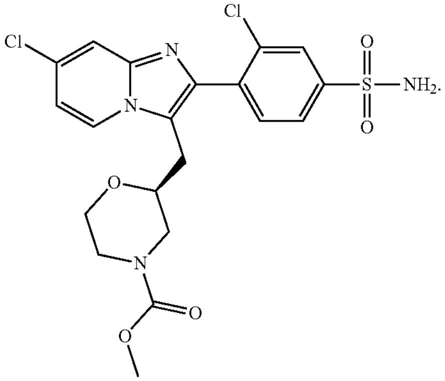

16. The heterocyclic compound, the stereoisomer thereof, or the pharmaceutically acceptable salt thereof according to claim 2, wherein the heterocyclic compound is

179

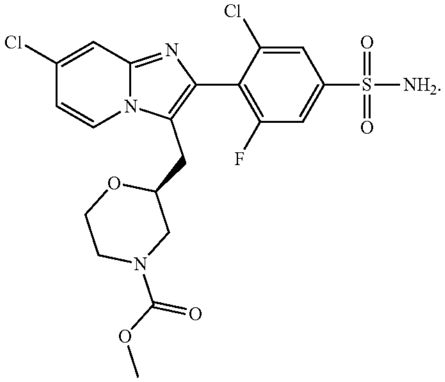

17. The heterocyclic compound, the stereoisomer thereof, or the pharmaceutically acceptable salt thereof according to claim 2, wherein the heterocyclic compound is

180

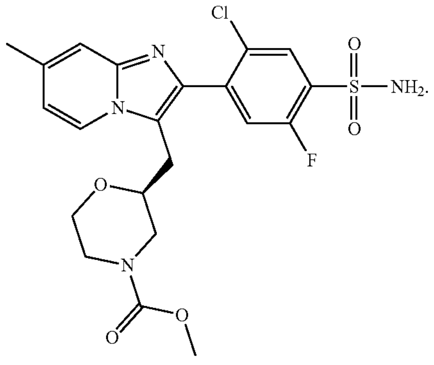

18. The heterocyclic compound, the stereoisomer thereof, or the pharmaceutically acceptable salt thereof according to claim 2, wherein the heterocyclic compound is

181

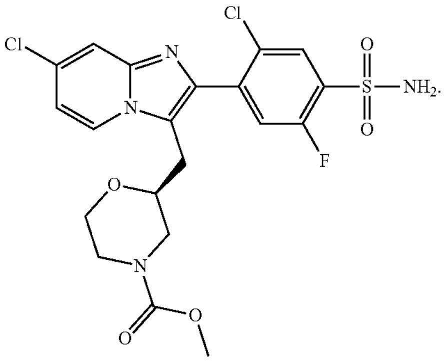

19. A pharmaceutical composition comprising the heterocyclic compound, the stereoisomer thereof, or the pharmaceutically acceptable salt thereof according to claim 2.

20. A method for treating or ameliorating a disease in a mammal mediated at least in part by $P2X^3$ or associated with $P2X^3$ activity, comprising administering the pharmaceutical composition of claim 19 to a subject in need thereof, wherein the disease is a pain, a urinary tract disease, or a respiratory disease, wherein the pain is inflammatory pain, surgical pain, visceral pain, dental pain, premenstrual pain, central pain, pain resulting from burns, migraine, or cluster headache; the urinary tract disease is urinary incontinence, overactive bladder, dysuria or cystitis; and the respiratory disease is idiopathic pulmonary fibrosis, chronic obstructive pulmonary disease, bronchospasm, or chronic cough.

21. The method according to claim 20, wherein the pain is inflammatory pain; the urinary tract disease is urinary incontinence, or overactive bladder; and the respiratory disease is chronic cough.

22. The method according to claim 20, wherein the respiratory disease is chronic cough.

* * * * *